US011608355B2

(12) United States Patent
Bowman et al.

(10) Patent No.: US 11,608,355 B2
(45) Date of Patent: Mar. 21, 2023

(54) TECHNOLOGIES FOR OLIGONUCLEOTIDE PREPARATION

(71) Applicant: WAVE LIFE SCIENCES LTD., Singapore (SG)

(72) Inventors: Keith Andrew Bowman, Stow, MA (US); Chandra Vargeese, Schwenksville, PA (US); David Charles Donnell Butler, Medford, MA (US); Pachamuthu Kandasamy, Belmont, MA (US); Mohammed Rowshon Alam, Hopkinton, MA (US); Mamoru Shimizu, Arlington, MA (US); Stephany Michelle Standley, Wakefield, MA (US); Vincent Aduda, Acton, MA (US); Gopal Reddy Bommineni, Belmont, MA (US); Snehlata Tripathi, Waltham, MA (US); Ilia Korboukh, Needham, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 8 days.

(21) Appl. No.: 16/648,146

(22) PCT Filed: Sep. 17, 2018

(86) PCT No.: PCT/US2018/051398
§ 371 (c)(1),
(2) Date: Mar. 17, 2020

(87) PCT Pub. No.: WO2019/055951
PCT Pub. Date: Mar. 21, 2019

(65) Prior Publication Data
US 2020/0231620 A1    Jul. 23, 2020

Related U.S. Application Data

(60) Provisional application No. 62/560,169, filed on Sep. 18, 2017.

(51) Int. Cl.
*C07H 21/02* (2006.01)
*C07H 21/04* (2006.01)

(52) U.S. Cl.
CPC ............. *C07H 21/02* (2013.01); *C07H 21/04* (2013.01)

(58) Field of Classification Search
CPC ......... C07H 21/02; C07H 21/04; C07H 21/00
See application file for complete search history.

(56) References Cited

U.S. PATENT DOCUMENTS

| | | |
|---|---|---|
| 5,221,736 A | 6/1993 | Coolidge et al. |
| 6,384,209 B1 | 5/2002 | Tang et al. |
| 8,470,987 B2 | 6/2013 | Wada et al. |
| 8,729,036 B2 | 5/2014 | Zamore et al. |
| 8,822,671 B2 | 9/2014 | Shimizu et al. |
| 8,859,755 B2 | 10/2014 | Wada et al. |
| 9,394,333 B2 | 7/2016 | Wada et al. |
| 9,476,044 B2 | 10/2016 | Tuschl et al. |
| 9,598,458 B2 | 3/2017 | Shimizu et al. |
| 9,605,019 B2 | 3/2017 | Verdine et al. |
| 9,617,547 B2 | 4/2017 | Gemba |
| 9,695,211 B2 | 7/2017 | Wada et al. |
| 9,744,183 B2 | 8/2017 | Verdine et al. |
| 9,982,257 B2 | 5/2018 | Butler et al. |
| 10,144,933 B2 | 12/2018 | Gemba et al. |
| 10,149,905 B2 | 12/2018 | Gemba et al. |
| 10,160,969 B2 | 12/2018 | Meena et al. |
| 10,167,309 B2 | 1/2019 | Shimizu et al. |
| 10,280,192 B2 | 5/2019 | Verdine et al. |
| 10,307,434 B2 | 6/2019 | Verdine et al. |
| 10,322,173 B2 | 6/2019 | Gemba et al. |
| 10,329,318 B2 | 6/2019 | Wada et al. |
| 10,428,019 B2 | 10/2019 | Wada et al. |
| 10,450,568 B2 | 10/2019 | Butler et al. |
| 10,479,995 B2 | 11/2019 | Vargeese et al. |
| 10,590,413 B2 | 3/2020 | Butler et al. |
| 10,696,711 B2 | 6/2020 | Shimizu et al. |
| 10,724,035 B2 | 7/2020 | Vargeese et al. |
| 10,815,482 B2 | 10/2020 | Meena et al. |
| 11,013,757 B2 | 5/2021 | Zhang et al. |
| 11,136,346 B2 | 10/2021 | Shimizu et al. |
| 11,407,775 B2 | 8/2022 | Butler et al. |
| 2013/0345462 A1 | 12/2013 | Matsuda et al. |
| 2015/0211006 A1* | 7/2015 | Butler ................... A61P 35/00 544/161 |
| 2019/0077817 A1 | 3/2019 | Butler et al. |

(Continued)

FOREIGN PATENT DOCUMENTS

| | | |
|---|---|---|
| JP | 2003-238586 A | 8/2003 |
| WO | WO-94/19363 A1 | 9/1994 |

(Continued)

OTHER PUBLICATIONS

U.S. Appl. No. 16/618,003, filed Nov. 27, 2019, Vargeese et al.
U.S. Appl. No. 16/624,896, filed Dec. 19, 2019, Butler et al.
U.S. Appl. No. 16/755,544, filed Apr. 10, 2020, Zhang et al.
U.S. Appl. No. 16/869,126, filed May 7, 2020, Vargeese et al.
U.S. Appl. No. 17/046,752, filed Oct. 9, 2020, Zhang et al.
U.S. Appl. No. 17/054,452, filed Nov. 10, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/465,238, filed Feb. 9, 2021, Shimizu et al.

(Continued)

*Primary Examiner* — Jonathan S Lau
(74) *Attorney, Agent, or Firm* — Choate, Hall & Stewart LLP; Brenda Herschbach Jarrell; Xiaodong Li

(57) ABSTRACT

Among other things, the present disclosure provides technologies for oligonucleotide preparation, particularly chirally controlled oligonucleotide preparation, which technologies provide greatly improved crude purity and yield, and significantly reduce manufacturing costs.

25 Claims, 6 Drawing Sheets

Specification includes a Sequence Listing.

(56) References Cited

U.S. PATENT DOCUMENTS

| | | |
|---|---|---|
| 2019/0127733 A1 | 5/2019 | Butler et al. |
| 2019/0249173 A1 | 8/2019 | Vargeese et al. |
| 2019/0264267 A1 | 8/2019 | Yang et al. |
| 2019/0375774 A1 | 12/2019 | Butler et al. |
| 2019/0390197 A1 | 12/2019 | Butler et al. |
| 2020/0080083 A1 | 3/2020 | Vargeese et al. |
| 2020/0157545 A1 | 5/2020 | Vargeese et al. |
| 2020/0190515 A1 | 6/2020 | Vargeese et al. |
| 2020/0231620 A1 | 7/2020 | Bowman et al. |
| 2020/0299692 A1 | 9/2020 | Frank-Kamenetsky et al. |
| 2020/0362337 A1 | 11/2020 | Dodart et al. |
| 2021/0032620 A1 | 2/2021 | Vargeese et al. |
| 2021/0115444 A1 | 4/2021 | Meena et al. |
| 2021/0130821 A1 | 5/2021 | Butler et al. |
| 2021/0198305 A1 | 7/2021 | Vargeese et al. |
| 2021/0228615 A1 | 7/2021 | Zhang et al. |
| 2021/0254062 A1 | 8/2021 | Zhang et al. |
| 2022/0098585 A1 | 3/2022 | Brown et al. |
| 2022/0127301 A1 | 4/2022 | Shimizu et al. |
| 2022/0145300 A1 | 5/2022 | Liu et al. |
| 2022/0162598 A1 | 5/2022 | Vargeese et al. |
| 2022/0186217 A1 | 6/2022 | Zhang et al. |
| 2022/0195429 A1 | 6/2022 | Vargeese et al. |
| 2022/0306573 A1 | 9/2022 | Zhang et al. |
| 2022/0307019 A1 | 9/2022 | Yokota et al. |

FOREIGN PATENT DOCUMENTS

| | | |
|---|---|---|
| WO | WO-2004/007718 A2 | 1/2004 |
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/002237 A1 | 1/2019 |
| WO | WO-2019/032607 A1 | 2/2019 |
| WO | WO-2019/032612 A1 | 2/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |
| WO | WO-2021/237223 A1 | 11/2021 |
| WO | WO-2022/046667 A1 | 3/2022 |
| WO | WO-2022/046723 A1 | 3/2022 |
| WO | WO-2022/099159 A1 | 5/2022 |

OTHER PUBLICATIONS

U.S. Appl. No. 17/605,997, filed Oct. 22, 2021, Byrne et al.
U.S. Appl. No. 17/605,998, filed Oct. 22, 2021, Byrne et al.
U.S. Appl. No. 17/609,330, filed Nov. 5, 2021, Liu et al.
Ami, E. and Ohrui, H., Lipase-catalyzed Kinetic Resolution of (±)-trans- and cis-2-Azidocycloalkanols, Biosci. Biotechnol. Biochem., 63(12):2150-2156 (1999).
Bench, B. J. et al., Proline Promoted Synthesis of Ring-Fused Homodimers: Self-Condensation of α,β-Unsaturated Aldehydes±, J. Org. Chem., 71(25):9458-9463 (2006).
Cui, H. et al., Direct aldol condensation reaction of ethyl diazoacetate with trfluoromethyl ketones, Tetra., 67(44):8470-8476 (2011).
Demir, A. S. et al., Novel Enantioselective Synthesis of Both Enantiomers of Furan-2-yl Amines and Amino Acids, Helvet. Chim. Acta, 86(1):91-105 (2003).
Gil-Av, E., Condensation Products of the Epimeric 2-Aminocyclohexanols with Carbonyl Compounds, J. Am. Chem. Soc., 81(7):1602-1606 (1959).
International Search Report for PCT/US2018/051398, 4 pages (dated Feb. 1, 2019).
Lysenko, I. L. and Kulinkovich, O. G., Stereoselective Synthesis of (7aS)-1-Methylenehexahyrdro-1/H-pyrrolizine and (-)-Heliotridane from N-Diphenylmethyl-(S)-proline Ethyl Ester, Russ. Jrnl. Org. Chem., 41:70-74 (2005).
Masui, M. and Takayuki, S., A practical method for preparation of optically pure oxazaborolidines from α-Pinene, Tetra., 51(30):8363-8370 (1995).
PUBCHEM, Compound Summary for CID 522583, Create Date: Mar. 27, 2005, 16 pages (Retrieved Aug. 23, 2018). Retrieved from the Internet: <URL: https://pubchem.ncbi.nlm.nih.gov/compound/522583>.
Written Opinion for PCT/US2018/038835, 6 pages (dated Oct. 29, 2018).
Written Opinion for PCT/US2018/051398, 16 pages (dated Feb. 1, 2019).
Xie, J. et al., Organocatalytic and direct asymmetric vinylogous Michael addition of α,α-dicyanoolefins to α,β-unsaturated aldehydes, Chem. Commun., 14:1563-1565 (2006).
U.S. Appl. No. 17/766,677, filed Apr. 5, 2022, Monian et al.
U.S. Appl. No. 17/766,680, filed Apr. 5, 2022, Liu et al.
U.S. Appl. No. 17/881,956, filed Aug. 5, 2022, Butler et al.
U.S. Appl. No. 17/907,895, filed Aug. 29, 2022, Maguire et al.
U.S. Appl. No. 17/953,292, filed Sep. 26, 2022, Monian et al.
U.S. Appl. No. 17/956,741, filed Sep. 29, 2022, Vargeese et al.
U.S. Appl. No. 17/960,090, filed Oct. 4, 2022, Vargeese et al.
Ma, M.Y. et al., Evaluation of 3-ethoxy-1,2,4-dithiazoline-5-one (EDITH) as a new sulfurizing reagent in combination with labile exocyclic amino protecting groups for solid-phase oligonucleotide synthesis, Nucleic Acids Res., 25(18):3590-3593 (1997).

\* cited by examiner

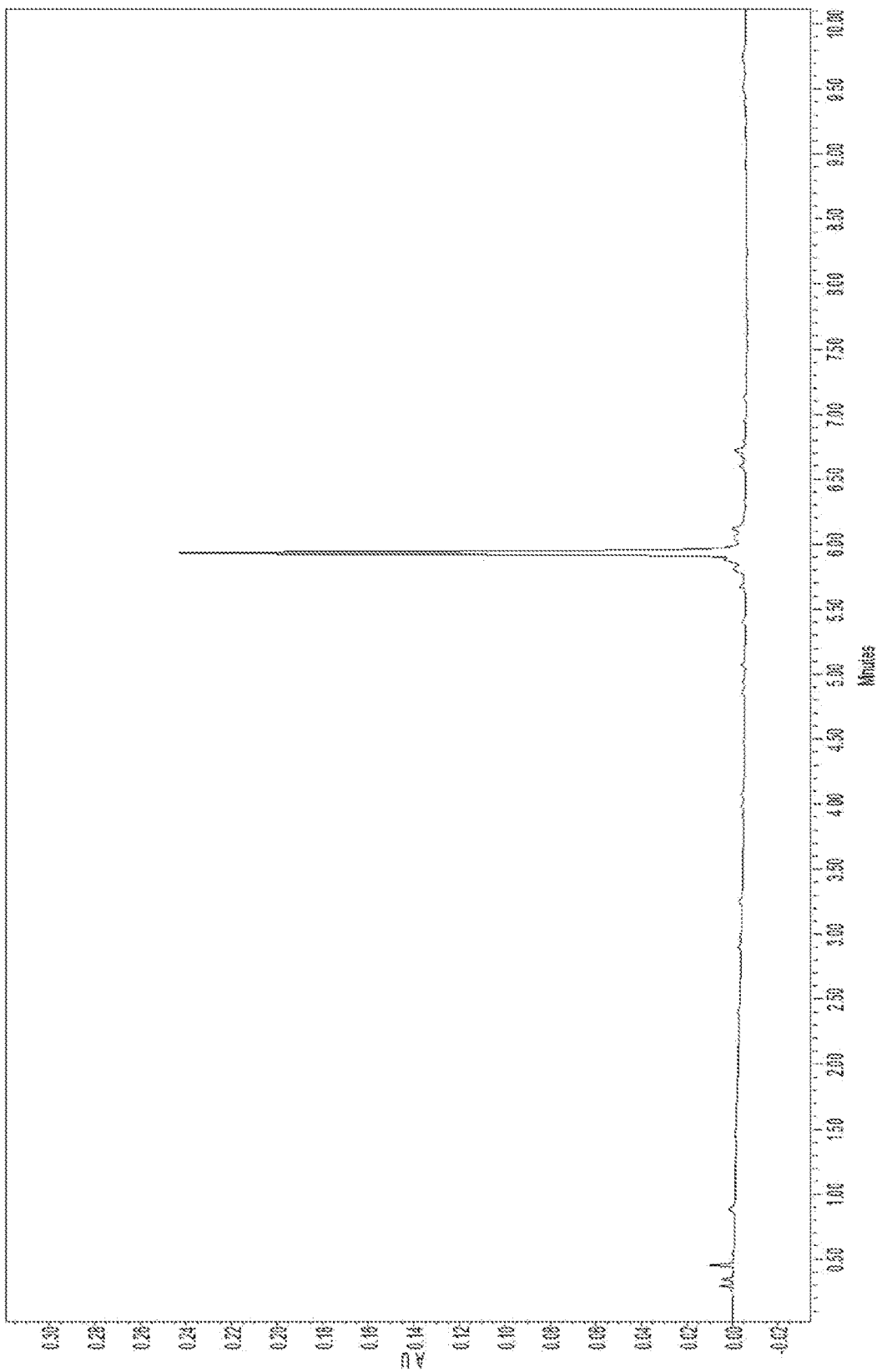
FIG. 4 (PANEL A)

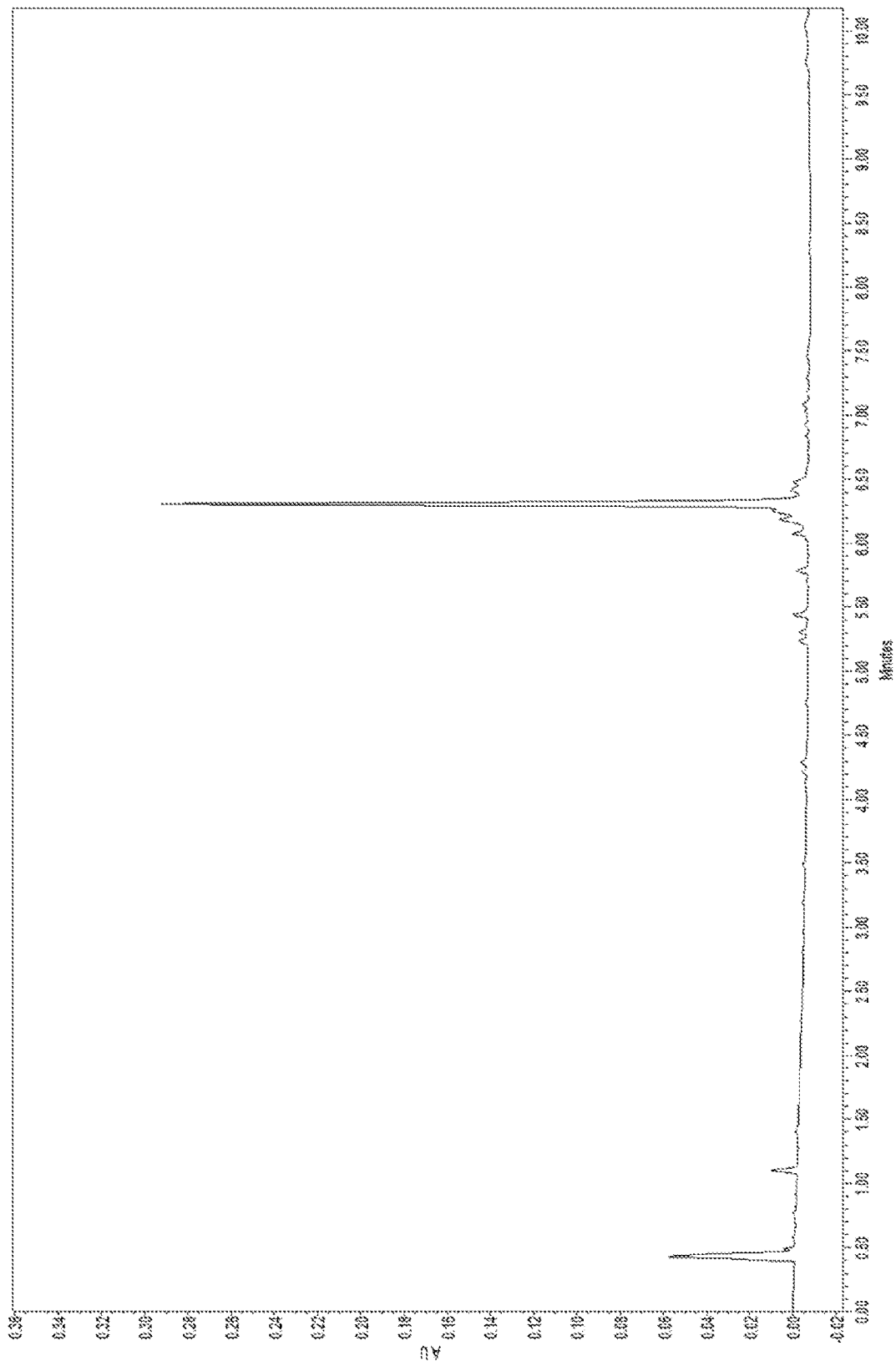
FIG. 4 (PANEL B)

TECHNOLOGIES FOR OLIGONUCLEOTIDE PREPARATION

CROSS-REFERENCE TO RELATED APPLICATIONS

This application is a U.S. National Stage Application of. International PCT Application Number PCT/US2018/051398, filed Sep. 17, 2018, which claims priority to U.S. Provisional Application No. 62/560,169, filed Sep. 18, 2017, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Mar. 30, 2019, is named SequenceListing.txt and is 847 bytes in size.

BACKGROUND

Oligonucleotides may contain a variety of modifications. Certain modifications, such as phosphorothioate internucleotidic linkages, may introduce new chiral centers into oligonucleotides.

SUMMARY

Oligonucleotides are useful for many purposes. However, natural oligonucleotides have been found to suffer disadvantages, such as low stability, low activity, etc., that can reduce or negate their usefulness as therapeutics.

Certain technologies have been developed that can improve oligonucleotide properties and usefulness. For example, certain modifications, e.g., to nucleobases, sugars, and/or internucleotidic linkages, etc., have been described that can improve oligonucleotide properties and usefulness. Moreover, technologies that permit control of stereochemistry, and/or preparation of stereocontrolled oligonucleotides have been demonstrated to provide particularly useful and effective oligonucleotide compositions. Certain exemplary useful technologies are described, for example, in one or more of: US20150211006, US20170037399, WO2017/015555, WO2017/015575, WO2017/062862, etc., each of which is incorporated herein by reference.

Particularly given the demonstrated desirability and usefulness of stereocontrolled oligonucleotide compositions, the present Applicant appreciated that developments of technologies that could improve or facilitate production of oligonucleotide compositions, particularly stereocontrolled oligonucleotide compositions, could provide significant benefits. The present disclosure describes certain such developments, and provides technologies relating to oligonucleotide compositions, particularly to stereocontrolled oligonucleotide compositions. Provided technologies may be particularly useful, for example, with respect to therapeutic oligonucleotides.

Among other things, the present disclosure encompasses the recognition that certain conditions and/or sequences of steps that have been utilized in the preparation of oligonucleotides, particularly stereocontrolled (e.g., stereopure) oligonucleotide compositions, can be associated with generation of certain impurities. In some embodiments, the present disclosure thus identifies the source of a problem with strategies that have utilized such conditions and/or steps; the present disclosure provides technologies including methods that utilize certain conditions and/or sequences of steps that are described and demonstrated to dramatically improve crude product purity and yield, in some embodiments significantly improving efficiency and/or reducing production cost. For example, as demonstrated in the Examples, in some embodiments, provided technologies can deliver chirally controlled oligonucleotide compositions with crude purity of over 70% (full-length product purity), much higher than reference technologies (crude full-length product purity of can be around 30% or lower).

Oligonucleotide synthesis typically utilizes highly efficient chemical transformations in its steps. However, despite the high efficiency, products of one or more steps often contain one or more reactive functional groups that can introduce significant impurities if uncapped, e.g., for coupling products, unreacted 5'-OH groups, and/or newly formed reactive groups (e.g., primary and/or secondary amino groups) when chiral auxiliaries are utilized for chirally controlled oligonucleotide synthesis. In many cases, such reactive functional groups are capped during oligonucleotide synthesis in order to reduce impurities from them. In some embodiments, the present disclosure encompasses the recognition of a source of problem that capping steps as those typically used in traditional phosphoramidite-based oligonucleotide synthesis can lead to generation of a significant amount of byproducts, particularly for many chirally controlled (stereocontrolled, stereoselective) oligonucleotide synthesis processes. Among other things, the present disclosure provides technologies that address the problems.

In some embodiments, the present disclosure provides methods comprising a post-modification capping step, e.g., after a modification step but before the next de-blocking and/or coupling step. In some embodiments, a post-modification capping step is after a modification step that provides a chirally controlled internucleotidic linkage but before the next de-blocking and/or coupling step.

In some embodiments, the present disclosure provides methods comprising capping steps of different chemistry strategies compared to a reference capping step in traditional oligonucleotide synthesis. For example, in some embodiments, the present disclosure provides methods comprising one or more capping steps, each of which selectively caps amino groups over hydroxyl groups (e.g., compared to a reference capping reagent system in traditional oligonucleotide synthesis). In some embodiments, provided capping steps are selective for amidation over esterification. In some embodiments, capping reagent systems for capping steps contain no or reduced levels (e.g., compared to a reference capping reagent system in traditional oligonucleotide synthesis) of strong nucleophiles and/or esterification catalysts (or reagents that can provide them when contacted with a composition to be capped), e.g., no or reduced levels of DMAP, NMI, etc. In some embodiments, the present disclosure provides methods comprising capping steps that can cap both amino groups and hydroxyl groups efficiently, e.g., capping steps that are comparable or identical to a reference capping step in traditional oligonucleotide synthesis.

In some embodiments, the present disclosure provides methods that comprise capping steps of the same or different chemistry strategies to achieve oligonucleotide synthesis and can provide various advantages, e.g., improved crude purity, improved yield, etc., particularly for chirally controlled (stereocontrolled, stereoselective) oligonucleotide synthesis. In some embodiments, the present disclosure provides methods of a pre-modification capping step (after a coupling step but before the next modification step) and a post-modification capping step (after a modification step but before the next de-blocking and/or coupling step). In some embodiments, a pre-modification capping step and post-modification capping step are different. In some embodiments, a pre-modification capping step and post-modification capping step have different chemistry strategies. In some embodiments, a pre-modification capping step caps amino groups selectively over hydroxyl groups (e.g., compared to a reference capping reagent system in traditional oligonucleotide synthesis). In some embodiments, a post-modification capping step can cap both amino and hydroxyl groups (e.g., compared to a reference capping reagent system in traditional oligonucleotide synthesis). In some embodiments, a pre-modification capping step caps amino groups selectively over hydroxyl groups (e.g., compared to a reference capping reagent system in traditional oligonucleotide synthesis). In some embodiments, a pre-modification capping step can cap both amino and hydroxyl groups (e.g., compared to a reference capping reagent system in traditional oligonucleotide synthesis).

In some embodiments, provided methods comprise two or more capping steps in an oligonucleotide synthesis cycle. In some embodiments, provided methods comprise two capping steps in an oligonucleotide synthesis cycle, wherein the two steps are separated by a modification step, e.g., oxidation, sulfurization, etc. In some embodiments, provided methods comprise a step in which a chiral modified internucleotidic linkage comprising a chiral linkage phosphorus is formed with a stereoselectivity of at least 80:20, 85:15, 90:10, 91:9, 92:8, 93:7, 94:6, 95:5, 96:4, 97:3, 98:2, or 99:1, favoring either the Rp or Sp configuration.

In some embodiments, the present disclosure provides a method comprising:

providing a chiral nucleoside phosphoramidite which comprises a chiral atom that is not the phosphorus atom or a sugar carbon atom; and a capping step immediately following a sulfurization or oxidation step.

In some embodiments, the present disclosure provides a method comprising:

providing a chiral nucleoside phosphoramidite which comprises a chiral atom that is not the phosphorus atom and is not an atom of the nucleoside unit; and a capping step immediately following a sulfurization or oxidation step.

In some embodiments, the present disclosure provides a method comprising:

providing an oligonucleotide intermediate comprising a chiral linkage phosphorus atom, which is bonded to a chiral unit which does not comprise a nucleoside unit or a part thereof; and a capping step immediately following a sulfurization or oxidation step.

In some embodiments, the present disclosure provides a method comprising:

providing an oligonucleotide intermediate comprising a chiral linkage phosphorus atom, which is bonded to a chiral unit which does not comprise an atom of a nucleoside unit; and a capping step immediately following a sulfurization or oxidation step.

In some embodiments, the present disclosure provides a method for preparing a composition comprising a plurality of oligonucleotides comprising:

a) a coupling step comprising:
contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and coupling a partner compound with the free hydroxyl groups of a plurality of de-blocked oligonucleotides or nucleosides;

wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;

b) optionally a pre-modification capping step comprising:
contacting a coupling product composition with a pre-modification capping reagent system; and capping one or more functional groups of the coupling product composition;

wherein the pre-modification capping step provides a pre-modification capping product composition comprising a plurality of pre-modification capping product oligonucleotides;

c) a modification step comprising:
contacting a coupling product composition with a modification reagent system comprising a modification reagent, and modifying one or more internucleotidic linkages of one or more coupling product oligonucleotides; or contacting a pre-modification capping product composition with a modification reagent system and modifying one or more linkages of one or more pre-modification capping product oligonucleotides;

wherein the modification step provides a modification product composition comprising a plurality of modification product oligonucleotides;

d) optionally a post-modification capping step comprising:
contacting a modification product composition with a post-modification capping reagent system; and capping one or more functional groups of a plurality of oligonucleotides of the modification product composition;

wherein the post-modification capping step provides a post-modification capping product composition comprising a plurality of post-modification capping product oligonucleotides;

e) optionally a de-blocking step comprising:
contacting a modification product composition, or a post-modification capping product composition, with a de-blocking reagent system;

wherein the deblocking step provides a de-blocking product composition comprising a plurality of de-blocking product oligonucleotides, each of which independently comprises a free hydroxyl group; and f) optionally repeating steps b) through e) a number of times.

In some embodiments, provided methods comprise one or more pre-modification capping steps. In some embodiments, provided methods comprise one or more post-modification capping steps. In some embodiments, provided methods comprise one or more pre- and post-modification capping steps. In some embodiments, provided methods comprise one or more de-blocking steps.

In some embodiments, the present disclosure provides a method for preparing a composition comprising a plurality of oligonucleotides comprising one or more cycles, each cycle independently comprises:

a) a coupling step comprising:
    contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and
    coupling a partner compound with the free hydroxyl groups of a plurality of de-blocked oligonucleotides or nucleosides;
    wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;
b) optionally a pre-modification capping step comprising:
    contacting a coupling product composition with a pre-modification capping reagent system; and
    capping one or more functional groups of the coupling product composition;
    wherein the pre-modification capping step provides a pre-modification capping product composition comprising a plurality of pre-modification capping product oligonucleotides;
c) a modification step comprising:
    contacting a coupling product composition with a modification reagent system comprising a modification reagent, and modifying one or more internucleotidic linkages of one or more coupling product oligonucleotides; or
    contacting a pre-modification capping product composition with a modification reagent system and modifying one or more linkages of one or more pre-modification capping product oligonucleotides;
    wherein the modification step provides a modification product composition comprising a plurality of modification product oligonucleotides;
d) optionally a post-modification capping step comprising:
    contacting a modification product composition with a post-modification capping reagent system; and
    capping one or more functional groups of a plurality of oligonucleotides of the modification product composition;
    wherein the post-modification capping step provides a post-modification capping product composition comprising a plurality of post-modification capping product oligonucleotides;
e) optionally a de-blocking step comprising:
    contacting a modification product composition, or a post-modification capping product composition, with a de-blocking reagent system;
    wherein the deblocking step provides a de-blocking product composition comprising a plurality of de-blocking product oligonucleotides, each of which independently comprises a free hydroxyl group.

In some embodiments, the present disclosure provides a method for preparing an oligonucleotide, comprising one or more cycles, each of which independently comprises the following steps:

(1) a coupling step;
(2) optionally a pre-modification capping step;
(3) a modification step;
(4) optionally a post-modification capping step; and
(5) a de-blocking step.

In some embodiments, a cycle comprises one or more pre-modification capping steps. In some embodiments, a cycle comprises one or more post-modification capping steps. In some embodiments, a cycle comprises one or more pre- and post-modification capping steps. In some embodiments, a cycle comprises one or more de-blocking steps.

In some embodiments, the present disclosure encompasses the recognition that traditional capping conditions when used as in traditional oligonucleotide synthesis may be a significant source of various problems under certain circumstances, and may contribute to formation of one or more by-products (impurities) and significantly lower oligonucleotide crude purity and yield, particularly for stereoselective preparation of oligonucleotides comprising one or more chiral internucleotidic linkages. Among other things, the present disclosure provides technologies comprising capping strategies that can deliver unexpectedly high crude impurity and yield compared to an appropriate reference technology, for example, through designed capping strategies in combination with other steps in oligonucleotide synthesis.

In some embodiments, a reference technology uses a traditional capping condition as in traditional phosphoramidite-based oligonucleotide synthesis, which typically is or comprises an esterification condition that acrylates hydroxyl groups, e.g., by using a mixture comprising an acylating agent (e.g., acetic anhydride), a base (e.g., 2,6-lutidine), and a catalyst (e.g., N-methylimidazole, DMAP, etc.) to contact oligonucleotides to cap hydroxyl groups (e.g., unreacted 5'-OH groups). Traditional capping conditions typically use a substantial amount of acylating agent, base and catalyst for capping, generally each independently about 5%-15% volume, and/or at least 1, 2, 3, 4, 5, 6, 7, 8, 9, 10, 20, 30, 40, 50, 60, 70, 80, 90, or 100 equivalents relative to the first nucleoside incorporated into an oligonucleotide (before any cycle forming internucleotidic linkage) or oligonucleotide loading capacity of a support (e.g., loading capacity of the support used for preparing an oligonucleotide, can be calculated by multiplying unit loading capacity of a support (e.g., umol/g) by amount of support (g)). In some embodiments, as used in traditional oligonucleotide synthesis, each synthetic cycle of a reference technology contains a single capping step. In some embodiments, a reference technology comprises no more than one capping step in each of its synthetic cycle, wherein capping is performed using an esterification condition, e.g., comprising an acylating agent (e.g., acetic anhydride), a base (e.g., 2,6-lutidine), and a catalyst (e.g., N-methylimidazole (NMI), DMAP, etc.), each independently no less than about 1%, 2%, 3%, 4%, 5%, 6%, 7%, 8%, 9%, 10%, 11%, 12%, 13%, 14%, or 15% by volume of the capping reagent solution, and/or the catalyst is no less than about 0.01, 0.02, 0.05, 0.1, 0.2, 0.5, 1, 1.1, 1.2, 1.5, or 2 equivalents relative to the acylating agent and/or the base.

In some embodiments, the present disclosure provides technologies comprising one or more capping steps, e.g., pre-modification capping steps, post-modification capping steps, etc., each of which is independently comparable or identical to a reference capping step, e.g., of traditional oligonucleotide synthesis based on phosphoramidite chemistry. In some embodiments, the present disclosure reduces by-products that may be formed in such capping steps by strategically positioning their positions (or timing) in oligonucleotide synthesis methods and/or cycles. In some embodiments, such capping steps are positioned after amino groups (typically primary and secondary) are, in many instances selectively, capped (over free hydroxyl groups, particularly, 5'-OH), either as individual separate capping steps or in combination with other capping steps (e.g., capping steps capping amino groups, in many instances selectively 5'-OH).

In some embodiments, the present disclosure provides technologies comprising one or more capping steps that each independently comprise a condition that is selective or specific for amidation over esterification. In some embodiments, the present disclosure provides technologies comprising one or more capping steps that use an amidation condition which is not an efficient and/or typical esterification condition. As readily appreciated by those skilled in the art, esterification and amidation have been extensively studied, and various conditions selective or specific for amidation over esterification, and various methods for assessing selectivity and/or specificity for amidation over esterification, are widely known in the art and can be utilized in accordance with the present disclosure. For example, a typical condition selective or specific for amidation over esterification is an anhydride and a base without a catalyst (e.g., $Ac_2O$ and 2,6-lutidine), as a corresponding efficient esterification condition typically requires an anhydride, a base, and a catalyst (e.g., $Ac_2O$, 2,6-lutidine, and NMI) as traditional capping conditions. In some embodiments, the present disclosure provides technologies that comprise one or more synthetic cycles each independently comprising a coupling step, a modification step (e.g., oxidation, sulfurization, etc.), and one or more capping steps, wherein each capping step after a coupling step and before a modification step comprising an amidation condition and no esterification condition. In some embodiments, an amidation condition comprises no more than 0.01%, 0.02%, 0.05%, 0.1%, 0.2%, 0.5%, 1%, 2%, 3%, 4%, or 5% by volume of a catalyst for esterification under an appropriate corresponding condition (having the same acylating agent and base), and/or no more than about 0.01, 0.02, 0.05, 0.1, 0.2, 0.5, 1, 1.1, or 1.2 equivalents of a catalyst for esterification under an appropriate corresponding condition (having the same acylating agent and base), relative to an acylating agent and/or relative to oligonucleotide loading capacity of a support. In some embodiments, an acylating agent is an anhydride. In some embodiments, an acylating agent is $Ac_2O$. In some embodiments, a catalyst is NMI. In some embodiments, a catalyst is DMAP. In some embodiments, a catalyst is a nucleophilic nitrogen base.

Without the intention to be limited by any theory, in some embodiments, the present disclosure encompasses the recognition of a source of a problem in oligonucleotide synthesis, that an nucleophilic agent, particularly when used in a capping step that is after a coupling step and before a modification step in stereoselective oligonucleotide preparation, may contribute to generation of byproducts and lower overall preparation efficiency and/or crude purity through, e.g., degradation of oligonucleotides, lowering performance of another step, etc. Thus, in some embodiments, the present disclosure provides capping technologies comprising greatly reduced levels of or no strong nucleophiles, e.g., catalysts used in typical capping conditions such as DMAP, NMI, etc., in contrast to traditional capping conditions which can comprise a large amount of a nucleophilic catalyst (e.g., in some cases, 5%-15% NMI by volume of capping solutions). In some embodiments, each of one or more capping steps after a coupling step and before a modification step within an oligonucleotide preparation cycle independently comprises greatly reduced levels of or no strong nucleophiles. In some embodiments, a reduced level is no more than 0.01%, 0.02%, 0.05%, 0.1%, 0.2%, 0.5%, 1%, 2%, 3%, 4%, or 5% by volume of a capping reagent solution. In some embodiments, a reduced level is no more than about 0.01, 0.02, 0.05, 0.1, 0.2, 0.5, 1, 1.1, or 1.2 equivalents relative to an acylating agent. In some embodiments, a reduced level is no more than about 0.01, 0.02, 0.05, 0.1, 0.2, 0.5, 1, 1.1, or 1.2 equivalents relative to oligonucleotide loading capacity of a support.

In some embodiments, a strong nucleophile is a nucleophilic base. In some embodiments, a nucleophilic base is a nitrogen base. In some embodiments, a nucleophilic base is a nitrogen base wherein the basic nitrogen atom (e.g., =N— or —N(-)—) has no alpha substituents. In some embodiments, a nucleophilic base is a nitrogen base wherein the basic nitrogen atom (e.g., =N— or —N(-)—) has no alpha substituent that is not part of a ring. In some embodiments, a nucleophilic base is optionally substituted 5-10 membered heteroaryl compound comprising a basic nitrogen atom=N—, wherein the nitrogen atom has less than two, or no, alpha-substituents. In some embodiments, a nucleophilic base is a nucleophilic nitrogen base. In some embodiments, a nucleophilic nitrogen base is a compound of the structure of formula B-I:

$$N(R^N)_3, \quad \text{B-I}$$

wherein each $R^N$ is independently R and the three R groups are taken together with the nitrogen atom to form an optionally substituted bicyclic or polycyclic ring as described in the present disclosure for R groups (and groups can be R), wherein the nitrogen of $\underline{N}(R^N)_3$ (underlined) is a tertiary nitrogen, and there are no substitutions at any of the positions alpha to the nitrogen atom. In some embodiments, a formed ring is saturated. In some embodiments, a nucleophilic base is DABCO (1,4-diazabicyclo[2.2.2]octane). In some embodiments, a formed ring contains one or more unsaturation.

In some embodiments, a nucleophilic nitrogen base is a base comprising =N—, wherein there are no substitutions at any of the positions alpha to the nitrogen atom. In some embodiments, a nucleophilic nitrogen base is a base comprising an aromatic moiety comprising =N—, wherein there are no substitutions at any of the positions alpha to the nitrogen atom. In some embodiments, a nucleophilic nitrogen base is a compound of the structure of formula B-II:

$$R^N-CH=N-CH=CH-R^N, \quad \text{B-II}$$

wherein each $R^N$ is independently R and the two R groups are taken together with their intervening atoms to form an optionally substituted ring as described in the present disclosure, wherein the compound comprises —CH=N—CH=. In some embodiments, a formed ring is an optionally substituted $C_{5-30}$ heteroaryl ring comprising 0-10 heteroatoms in addition to the nitrogen atom. In some embodiments, a formed ring is an optionally substituted 5-membered heteroaryl ring. In some embodiments, a formed ring is a substituted 5-membered heteroaryl ring. In some embodiments, a formed ring is a substituted imidazolyl ring. In some embodiments, a nucleophilic base is substituted imidazole. In some embodiments, a nucleophilic nitrogen base is NMI. In some embodiments, a formed ring is an optionally substituted 6-membered heteroaryl ring. In some embodiments, a formed ring is a substituted 6-membered heteroaryl ring. In some embodiments, a formed ring is a substituted pyridinyl ring. In some embodiments, a nucleophilic base is substituted pyridine. In some embodiments, a nucleophilic nitrogen base is DMAP.

As appreciated by those skilled in the art, nucleophilicity, e.g., of basic nitrogen atoms in bases, is related to several factors, e.g., steric hindrance, electron density, etc. Technologies for assessing nucleophilicity are widely known in the art and can be utilized in accordance with the present disclosure. Additionally or alternatively, bases of various levels of nucleophilicity are well-known and can be assessed and/or utilized in accordance with the present disclosure. In some embodiments, a base that can efficiently catalyze esterification reactions, e.g., a base that can be used for efficient capping of unreacted 5'-OH together with anhydride and 2,6-lutidine in traditional oligonucleotide synthesis (e.g., DMAP, NMI, etc.) is a strong nucleophilic base and should be avoided or used at reduced levels for capping steps that comprise greatly reduced levels of or no strong nucleophiles, e.g., any capping step after a coupling step and before a modification step. In some embodiments, a strong nucleophilic base is a base that can effectively replace DMAP or NMI in esterification. In some embodiments, a strong nucleophilic base is a base that can effectively replace DMAP or NMI in a capping step of traditional oligonucleotide synthesis (which typically uses phosphoramidite chemistry and does not use chiral auxiliaries and is considered non-stereoselective/non-stereocontrolled).

In some embodiments, provided methods comprise a capping step, which capping step comprises no more than 0.1, 0.2, 0.3, 0.4, 0.5, 0.5, 0.7, 0.8, 0.9, 1, 2, 3, 4, 5, 6, 7, 8, 9, or 10 equivalents of a strong nucleophilic base relative to oligonucleotides or loading capacity of a support, or no strong nucleophilic bases. In some embodiments, such a capping step is immediately followed by a non-capping step. In some embodiments, such a capping step is immediately after a non-capping step. In some embodiments, such a capping step is immediately followed by a non-capping step, and is immediately after a non-capping step. In some embodiments, a non-capping step is a coupling step. In some embodiments, a non-coupling step is a modification step. In some embodiments, a non-capping step immediately before such a capping step is a coupling modification step.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no strong nucleophile, or if it comprises one or more strong nucleophiles, level of each of the one or more strong nucleophiles is independently reduced compared to an appropriate reference capping condition.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no strong nucleophile, or if it comprises one or more strong nucleophiles, level of each of the one or more strong nucleophiles is independently no more than no more than about 0.01, 0.02, 0.05, 0.1, 0.2, 0.5, or 1 equivalents relative to the first incorporated nucleoside of the oligonucleotide.

In some embodiments, the first incorporated nucleoside of the oligonucleotide is the first nucleoside loaded to a support before the first cycle that forms an internucleotidic linkage. In some embodiments, equivalent of the first incorporated nucleoside of an oligonucleotide to oligonucleotide loading capacity of a support used for preparing the oligonucleotide is 1.

In some embodiments, a strong nucleophile is a strong nucleophile base as described in the present disclosure. In some embodiments, a strong nucleophilic base is a compound of formula B-I. In some embodiments, a strong nucleophilic base is a compound of formula B-I and can be used for efficient capping in traditional, phosphoramidite-based oligonucleotide synthesis. In some embodiments, a strong nucleophilic base is a compound of formula B-II. In some embodiments, a strong nucleophilic base is a compound of formula B-II and can be used for efficient capping in traditional, phosphoramidite-based oligonucleotide synthesis. In some embodiments, a strong nucleophilic base is DMAP. In some embodiments, a strong nucleophilic base in NMI.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst that promotes capping of 5'-OH as in an appropriate reference capping condition, or if it comprises one or more such catalysts, level of each of the one or more such catalysts is independently reduced compared to an appropriate reference capping condition.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst that promotes capping of 5'-OH as in an appropriate reference capping condition, or if it comprises one or more such catalysts, level of each of the one or more such catalysts is independently no more than 0.01, 0.02, 0.05, 0.1, 0.2, 0.5, or 1 equivalents relative to the first incorporated nucleoside of the oligonucleotide.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst for esterification, or if it comprises one or more catalysts for esterification, level of each of the one or more such catalysts is independently reduced compared to an appropriate reference capping condition.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises no catalyst for esterification, or if it comprises one or more catalysts for esterification, level of each of the one or more such catalysts is independently no more than 0.01, 0.02, 0.05, 0.1, 0.2, 0.5, or 1 equivalents relative to the first incorporated nucleoside of the oligonucleotide.

In some embodiments, a catalyst, e.g., that promotes capping of 5'-OH as in oligonucleotide synthesis, for esterification, etc., is a compound of formula B-I. In some embodiments, a catalyst is a compound of formula B-I and can be used for efficient capping in traditional, phosphoramidite-based oligonucleotide synthesis. In some embodiments, a catalyst is a compound of formula B-II. In some embodiments, a catalyst is a compound of formula B-II and can be used for efficient capping in traditional, phosphoramidite-based oligonucleotide synthesis. In some embodiments, a catalyst is DMAP. In some embodiments, a strong nucleophilic base in NMI.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises a selective condition for amidation over esterification.

In some embodiments, the present disclosure provides a method for preparing an oligonucleotide, comprising one or more cycles, wherein:

each cycle independently forms an internucleotidic linkage;

each cycle independently comprising a coupling step, one or more capping steps, and a modification step, which coupling step forms an internucleotidic linkage, and which modification step modifies the internucleotidic linkage formed in the coupling step;

wherein each capping step between the coupling step and the modification step (pre-modification capping step) comprises a selective condition for amidation over esterification, and no condition identical to or comparable to an appropriate reference condition.

In some embodiments, selective conditions for amidation over esterification comprise reduced levels of or no catalysts for esterification, e.g., no DMAP, NMI, etc. In some embodiments, a condition identical to or comparable to an appropriate reference condition can be used to replace capping conditions in traditional phosphoramidite-based oligonucleotide synthesis without significantly reducing (or with no more than 5%, 10%, 15%, 20%, 25%, 30%, 35%, 40%, 45%, or 50% of reduction of) efficiency, crude purity, and/or yield.

In some embodiments, provided methods comprise a second capping step after a modification step in one or more cycles. In some embodiments, provided methods comprise a second capping step after a modification step and before a deblocking step (which de-blocks blocked hydroxyl groups) in one or more cycles. In some embodiments, a second capping step comprises a strong nucleophile. In some embodiments, a second capping step comprises a strong nucleophile at a level comparable to a reference capping condition. In some embodiments, a second capping step comprises an esterification catalyst. In some embodiments, a second capping step comprises an esterification catalyst at a level comparable to a reference capping condition. In some embodiments, a second capping step comprises an esterification condition. In some embodiments, a second capping step comprises an esterification condition that is identical or comparable with a reference capping condition, e.g., in terms of capping unreacted 5'-OH in oligonucleotide synthesis. In some embodiments, a strong nucleophile is DMAP or NMI. In some embodiments, a strong nucleophile is DMAP. In some embodiments, a strong nucleophile is NMI. In some embodiments, an esterification catalyst is DMAP or NMI. In some embodiments, an esterification catalyst is DMAP. In some embodiments, an esterification catalyst is NMI.

In some embodiments, the present disclosure provides a method for preparing an oligonucleotide, comprising a cycle comprising steps of:
(1) a coupling step;
(2) a first capping step;
(3) a modification step;
(4) a second capping step;
(5) a de-blocking step;
wherein the cycle comprises steps in the order of (2)-(3)-(4);
wherein the cycle is repeated until the length of the oligonucleotide is achieved.

In some embodiments, the present disclosure provides a method for preparing an oligonucleotide, comprising a cycle comprising steps of:
(1) a coupling step;
(2) a first capping step;
(3) a modification step;
(4) a second capping step;
(5) a de-blocking step;
wherein the cycle comprises steps in the order of (2)-(4)-(3);
wherein the cycle is repeated until the length of the oligonucleotide is achieved.

In some embodiments, a first capping comprising no strong nucleophiles, or if any, of reduced levels, as described in the present disclosure. In some embodiments, a first capping step comprises no esterification catalysts, of if any, of reduced levels. In some embodiments, a first capping step comprises a selective condition for amidation over esterification. In some embodiments, a first capping step comprises no condition identical to or comparable to an appropriate reference condition.

In some embodiments, a first capping step is a pre-modification capping step as described in the present disclosure. In some embodiments, a first capping step utilizes a capping reagent system that is a pre-modification capping reagent system. In some embodiments, a second capping step is a post-modification capping step as described in the present disclosure. In some embodiments, a second capping step utilizes a capping reagent system that is a post-modification capping reagent system.

In some embodiments, an appropriate reference capping condition is a capping condition of traditional oligonucleotide synthesis based on phosphoramidite chemistry. An example cycle for traditional phosphoramidite-based oligonucleotide synthesis is described below:

In some embodiments, a first capping step comprises reduced levels of a strong nucleophilic base or no strong nucleophilic base. In some embodiments, a first capping step comprises a reduced level of NMI. In some embodiments, a first capping step comprises no NMI. In some embodiments, a first capping step comprises a reduced level of DMAP. In some embodiments, a first capping step comprises no DMAP.

In some embodiments, an example cycle of provided technologies is depicted below (DPSE auxiliary,

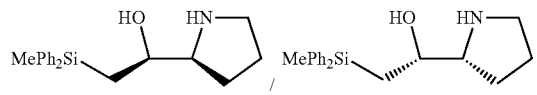

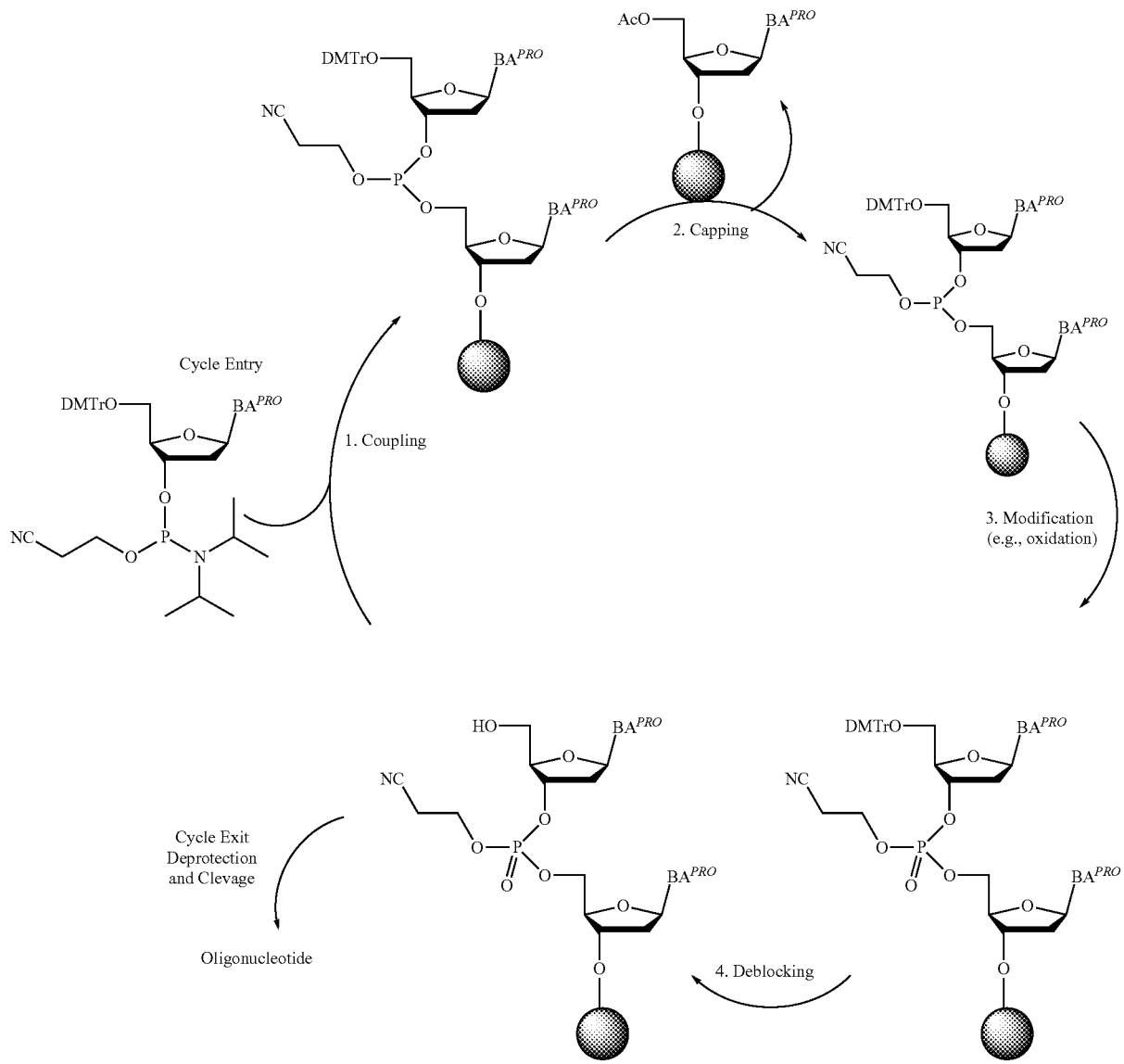

for different configurations of linkage phosphorus), wherein each $R^{LP}$ is independently —X-$L^s$-$R^5$ as described in the present disclosure, and each of BA, W, and $R^{2s}$ is independently as described in the present disclosure. In some embodiments, Capping-2 is performed after Modification. In some embodiments, Capping-1 is a pre-modification capping step. In some embodiments, Capping-2 is a post-modification capping step. In some embodiments, cycle exit is after De-blocking before the next Coupling.

In some embodiments, a reduced level of the present disclosure is no more than a percentage, e.g., 0.01%, 0.02%, 0.05%, 0.1%, 0.2%, 0.5%, 1%, 2%, 3%, 4%, 5%, etc., by volume of a capping reagent solution. In some embodiments, a percentage is 0.01%. In some embodiments, a percentage is 0.02%. In some embodiments, a percentage is 0.05%. In some embodiments, a percentage is 0.1%. In some embodiments, a percentage is 0.2%. In some embodiments, a percentage is 0.5%. In some embodiments, a percentage is

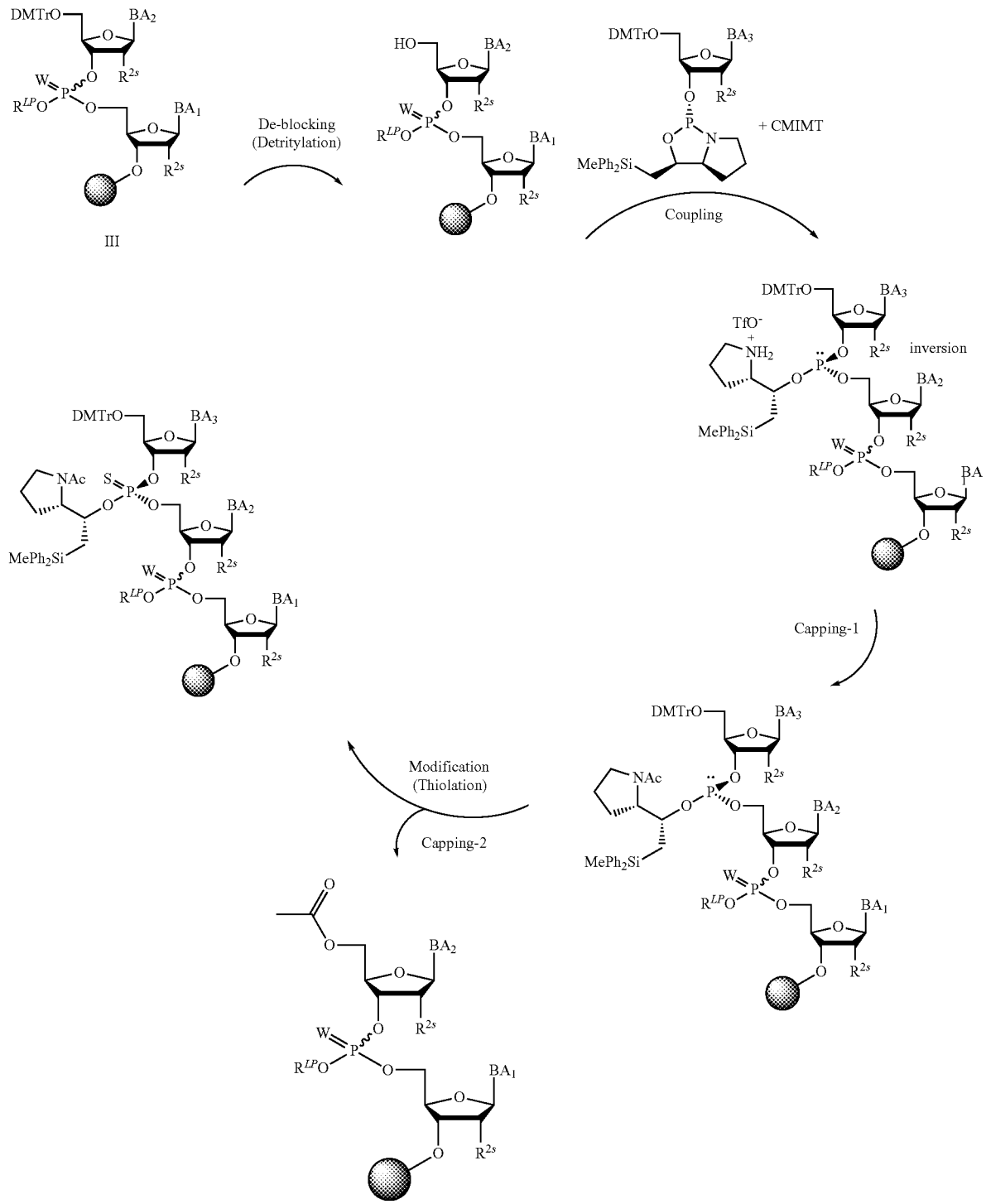

1%. In some embodiments, a percentage is 2%. In some embodiments, a percentage is 3%. In some embodiments, a percentage is 4%. In some embodiments, a percentage is 5%.

In some embodiments, a reduced level is no more than about 0.01, 0.02, 0.05, 0.1, 0.2, 0.5, 1, 1.1, or 1.2 equivalents relative to a reference agent. In some embodiments, a reference agent is an acylating agent. In some embodiments, a reference agent is a support (by oligonucleotide loading capacity). In some embodiments, a reduced level is no more than about 0.01, 0.02, 0.05, 0.1, 0.2, 0.5, 1, 1.1, or 1.2 equivalents relative to an acylating agent. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to oligonucleotide. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to the first nucleoside incorporated to an oligonucleotide. In many instances, equivalent of the first nucleoside incorporated into an oligonucleotide to oligonucleotide loading capacity of a support used to prepare the oligonucleotide is 1. In some embodiments, a reduced level is no more than about 0.01, 0.02, 0.05, 0.1, 0.2, 0.5, 1, 1.1, 1.2, 1.3, 1.4, 1.5, 2, 3, 4, 5, 6, 7, 8, 9, 10, 20, 30, 40, 50, or 100 equivalents relative to oligonucleotide loading capacity of a support. In some embodiments, a reduced level is no more than about 0.01, 0.02, 0.05, 0.1, 0.2, 0.5, 1, 1.1, 1.2, 1.3, 1.4, 1.5, 2, 3, 4, 5, or 10 equivalents relative to oligonucleotide loading capacity of a support. In some embodiments, a reduced level is no more than about 0.01, 0.02, 0.05, 0.1, 0.2, 0.5, 1, 1.1, 1.2, 1.3, 1.4, 1.5, 2, 3, 4, or 5 equivalents relative to oligonucleotide loading capacity of a support. In some embodiments, a reduced level is no more than about 0.01, 0.02, 0.05, 0.1, 0.2, 0.5, or 1 equivalent relative to oligonucleotide loading capacity of a support. In some embodiments, a reduced level is no more than about 0.01 equivalent. In some embodiments, a reduced level is no more than about 0.02 equivalent. In some embodiments, a reduced level is no more than about 0.05 equivalent. In some embodiments, a reduced level is no more than about 0.1 equivalent. In some embodiments, a reduced level is no more than about 0.2 equivalent. In some embodiments, a reduced level is no more than about 0.5 equivalent. In some embodiments, a reduced level is no more than about 1 equivalent. In some embodiments, a reduced level is no more than about 1.1 equivalents. In some embodiments, a reduced level is no more than about 1.2 equivalents.

Among other things, provided technologies are particularly useful for preparing chirally controlled oligonucleotide compositions. In some embodiments, provided technologies comprise formation of one or more chiral internucleotidic linkages each independently comprising a chiral linkage phosphorus, wherein each of the chiral linkage phosphorus chiral center is independently formed with a stereoselectivity as described in the present disclosure, e.g., of at least 80%, 85%, 90%, 91%, 92%, 93%, 94%, 95%, 96%, 97%, 98%, or 99%.

In some embodiments, provided technologies comprise use of one or more chiral auxiliary to stereoselectively form one or more chirally controlled internucleotidic linkages. In some embodiments, provided technologies comprise providing monomeric phosphoramidites of diastereomeric purity as described in the present disclosure, e.g., of at least 60%, 65%, 70%, 75%, 80%, 85%, 90%, 91%, 92%, 93%, 94%, 95%, 96%, 97%, 98%, or 99%. In many embodiments, phosphoramidites of provided diastereomeric purity comprise a chiral auxiliary moiety. In some embodiments, phosphoramidites of traditional oligonucleotide synthesis are utilized for non-chirally controlled internucleotidic linkages, and/or non-chiral internucleotidic linkages. Suitable chiral auxiliaries and phosphoramidites for chirally controlled oligonucleotide synthesis that can be utilized in accordance with the present disclosure include those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, chiral auxiliaries and phosphoramidites of each of which are independently incorporated herein by reference. In some embodiments, a chiral auxiliary is of formula I, I-a, I-a-1, I-a-2, I-b, I-c, I-d, I-e, II, II-a, II-b, III, III-a, or III-b, or a salt thereof, as described in the present disclosure. In some embodiments, a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, as described in the present disclosure.

In some embodiments, provided technologies comprising formation of an internucleotidic linkage having the structure of formula VII as described in the present disclosure.

In some embodiments, provided technologies provides oligonucleotides as intermediates and/or products. In some embodiments, a provided oligonucleotide is of formula VIII or a salt thereof as described in the present disclosure. In some embodiments, a provided oligonucleotide is one described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, oligonucleotides of each of which are independently incorporated herein by reference. In some embodiments, provided intermediates and/or products are chirally controlled oligonucleotide compositions. In some embodiments, provided intermediates and/or products are chirally controlled oligonucleotide compositions of a plurality of oligonucleotides of formula VIII or salts thereof. In some embodiments, provided intermediates and/or products are chirally controlled oligonucleotide compositions of US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, oligonucleotide compositions of each of which are independently incorporated herein by reference.

In some embodiments, the present disclosure provides a composition comprising:

the plurality of oligonucleotides is a plurality of oligonucleotides of a modification product composition;

the reagent system is a pre-modification or post-modification capping reagent system; and the post-modification capping reagent system is in contact with the plurality of oligonucleotides.

In some embodiments, the present disclosure provides a composition comprising:

a capping reagent system comprising a first compound having the structure of formula B-I or B-II, a plurality of oligonucleotides each comprising at least one internucleotidic linkage comprising a —C(O)—N(-)— moiety or a —P—S— moiety;

wherein the first compound is at a level of at least 0.1, 0.2, 0.5, 1, 2, 3, 4, 5, 6, 7, 8, 9, 10, 50, or 100 equivalents relative to the plurality of oligonucleotides.

In some embodiments, the present disclosure provides a composition comprising:

a capping reagent system comprising a first compound having the structure of formula B-I or B-II, a plurality of oligonucleotides, wherein each internucleotidic linkage of oligonucleotides of the plurality is independently an internucleotidic linkage comprising a —C(O)—N(-)— moiety and a linkage phosphorus that is tetravalent;

wherein the first compound is at a level of at least 0.1, 0.2, 0.5, 1, 2, 3, 4, 5, 6, 7, 8, 9, 10, 50, or 100 equivalents relative to the plurality of oligonucleotides.

In some embodiments, the plurality of oligonucleotides is a plurality of oligonucleotides of a modification product composition. In some embodiments:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a first compound is of formula B-I. In some embodiments, a first compound is of formula B-II. In some embodiments, a first compound is a strong nucleophile as described in the present disclosure. In some embodiments, a first compound is an esterification catalyst as described in the present disclosure. In some embodiments, a first compound is of formula B-I. In some embodiments, a first compound is of formula B-II. In some embodiments, a first compound is a base comprising =N—, wherein there are no substitutions at any alpha-positions relative to the nitrogen of =N—. In some embodiments, a first compound is a base comprising a heteroaryl moiety, which heteroaryl moiety comprises =N—, wherein there are no substitutions at any alpha-positions relative to the nitrogen of =N—.

In some embodiments, a first compound is NMI. In some embodiments, a first compound is DMAP.

In some embodiments, oligonucleotides of the plurality are attached to a support, e.g., a solid support used to prepare the oligonucleotides. In some embodiments, molar amount of the oligonucleotides of the plurality equals loading capacity of the solid support they are attached to.

In some embodiments, a plurality of oligonucleotides share 1) a common base sequence, 2) a common pattern of backbone linkages, and 3) a common pattern of backbone phosphorus modifications, wherein the plurality of oligonucleotides share the same stereochemistry at one or more chiral internucleotidic linkages. In some embodiments, a plurality of oligonucleotides share the same stereochemistry at least one internucleotidic linkage comprising a —C(O)—N(-)— moiety or a —P—S— moiety. In some embodiments, about 0.1%-100% (e.g., about 1%-100%, 5%-100%, 10%-100%, 20%-100%, 30%-100%, 40%-100%, 50%-100%, 60%-100%, 70%-100%, 80%-100%, 90%-100%, 95%-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality.

In some embodiments, oligonucleotides of a plurality are each of the structure of formula VIII or a salt thereof. In some embodiments, oligonucleotides of a plurality are oligonucleotides of US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, oligonucleotides of each of which are independently incorporated herein by reference.

In some embodiments, a level of the present disclosure is at least 0.1 equivalent. In some embodiments, a level is at least 0.2 equivalent. In some embodiments, a level is at least 0.5 equivalent. In some embodiments, a level is at least 1 equivalent. In some embodiments, a level is at least 2 equivalents. In some embodiments, a level is at least 3 equivalents. In some embodiments, a level is at least 4 equivalents. In some embodiments, a level is at least 5 equivalents. In some embodiments, a level is at least 6 equivalents. In some embodiments, a level is at least 7 equivalents. In some embodiments, a level is at least 8 equivalents. In some embodiments, a level is at least 9 equivalents. In some embodiments, a level is at least 10 equivalents. In some embodiments, a level is at least 20 equivalents. In some embodiments, a level is at least 50 equivalents. In some embodiments, a level is at least 100 equivalents.

In some embodiments, a —C(O)—N(-)— is part of a capped amino group in a chiral auxiliary moiety bonded to a linkage phosphorus, wherein the corresponding chiral auxiliary (replacing bonding to —C(O)— of —C(O)—N(-)— with —H, and replacing bonding to the linkage phosphorus with —H) is a compound of formula I, I-a, I-a-I, I-a-2, I-b, I-c, I-d, I-e, II, II-a, II-b, III, III-a, III-b, or a salt thereof.

Among other things, the present disclosure provides oligonucleotide compositions of high crude purity. In some embodiments, the present disclosure provides a crude chirally controlled oligonucleotide composition comprising a plurality of oligonucleotides, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, the present disclosure provides a crude chirally controlled oligonucleotide composition comprising a plurality of oligonucleotides, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a provided crude chirally controlled oligonucleotide composition has a crude purity of at least 40%, 45%, 50%, 55%, 60%, 65%, 70%, or 75%. In some embodiments, a crude chirally controlled oligonucleotide composition is cleaved from a support, and before any further purification. In some embodiments, crude chirally controlled oligonucleotide composition is cleaved from a support, after de-salting, and before any further purification. In some embodiments, crude chirally controlled oligonucleotide composition is before any chromatograph or gel purification. In some embodiments, a crude purity is % full-length product. In some embodiments, a crude purity is % full-length product as assessed by LC-UV monitored at UV 260 nm.

In some embodiments, DS is at least 80%, 85%, 90%, 91%, 92%, 93%, 94%, 95%, 96%, 97%, 98% or 99%. In some embodiments, DS is at least 85%. In some embodiments, DS is at least 90%. In some embodiments, DS is at least 92%. In some embodiments, DS is at least 95%. In some embodiments, DS is at least 96%. In some embodiments, DS is at least 97%. In some embodiments, DS is at least 98%. In some embodiments, DS is at least 99%. In some embodiments, DS is diastereoselectivity at, and/or diastereopurity of, a chiral linkage phosphorus of a chirally controlled internucleotidic linkage.

In some embodiments, diastereoselectivity at, and/or diastereopurity of, chiral linkage phosphorus of a chiral internucleotidic linkage in an oligonucleotide may be measured or represented through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage. For example, diastereopurity of the underlined linkage in NNNNNNNG*SGNNNNNNN can be assessed from coupling two G moieties under the same or comparable conditions, e.g., monomers, chiral auxiliaries, solvents, activators, temperatures, etc. In some embodiments, diastereopurity (and/or diastereoselectivity) of the linkage of a dimer (G*SG) is used as diastereopurity (and/or diastereoselectivity) of a corresponding linkage in an oligonucleotide (NNNNNNNG*SGNNNNNNN). In some embodiments, diastereopurity of a compound comprising multiple chiral elements is product of diastereomeric purity of all its chiral elements. In some embodiments, diastereopurity (i.e., diastereomeric purity) of a provided oligonucleotide is product of diastereomeric purity of all its chiral linkage phosphorus in its chiral internucleotidic linkages.

In some embodiments, Nc is the number of chirally controlled internucleotidic linkage and is 1-100. In some embodiments, Nc is 1-50. In some embodiments, Nc is 1-40. In some embodiments, Nc is 1-30. In some embodiments, Nc is 1-25. In some embodiments, Nc is 1-24. In some embodiments, Nc is 1-23. In some embodiments, Nc is 1-22. In some embodiments, Nc is 1-21. In some embodiments, Nc is 1-20. In some embodiments, Nc is 1-19. In some embodiments, Nc is 1-18. In some embodiments, Nc is 1-17. In some embodiments, Nc is 1-16. In some embodiments, Nc is 1-15. In some embodiments, Nc is 1-14. In some embodiments, Nc is 1-13. In some embodiments, Nc is 1-12. In some embodiments, Nc is 1-11. In some embodiments, Nc is 1-10. In some embodiments, Nc is 1-9. In some embodiments, Nc is 1-8. In some embodiments, Nc is 1-7. In some embodiments, Nc is 1-6. In some embodiments, Nc is 1-5. In some embodiments, Nc is 1. In some embodiments, Nc is 2. In some embodiments, Nc is 3. In some embodiments, Nc is 4. In some embodiments, Nc is 5. In some embodiments, Nc is 6. In some embodiments, Nc is 7. In some embodiments, Nc is 8. In some embodiments, Nc is 9. In some embodiments, Nc is 10. In some embodiments, Nc is 11. In some embodiments, Nc is 12. In some embodiments, Nc is 13. In some embodiments, Nc is 14. In some embodiments, Nc is 15. In some embodiments, Nc is 16. In some embodiments, Nc is 17. In some embodiments, Nc is 18. In some embodiments, Nc is 19. In some embodiments, Nc is 20. In some embodiments, Nc is 21. In some embodiments, Nc is 22. In some embodiments, Nc is 23. In some embodiments, Nc is 24. In some embodiments, Nc is 25.

In some embodiments, provided technologies comprising one or more modification steps that independently comprise or are sulfurization (thiolation). In some embodiments, provided intermediates and/or products comprise one or more phosphorothioate internucleotidic linkages or precursors thereof (which can be converted into phosphorothioate internucleotidic linkages upon deprotection/cleavage), optionally chirally controlled. In some embodiments, provided technologies comprising one or more modification steps that independently comprise or are oxidation. In some embodiments, provided intermediates and/or products comprise one or more natural phosphate linkages or precursors thereof (which can be converted into natural phosphate linkages upon deprotection/cleavage). In some embodiments, provided intermediates and/or products comprise one or more natural phosphate linkages and one or more phosphorothioate internucleotidic linkages.

Various supports can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc. In some embodiments, a support is a polymer. In some embodiments, a support is a solid support. In some embodiments, a solid support is a polymer, e.g., polystyrene. In some embodiments, a solid support is a Primer Support (e.g., Primer Support 5G, Primer Support 200, etc.). In some embodiments, a solid support is NittoPhase support (e.g., NittoPhase HL, NittoPhase UnyLinker, etc.). In some embodiments, a solid support is controlled-pore glass (CPG). In some embodiments, volume of a solid support, e.g., certain polystyrene based solid support, changes during oligonucleotide synthesis, e.g., at different stages of synthesis and/or when contacted with different solvent systems and/or reagents. In some embodiments, volume of a solid support, e.g., many CPG support, changes less than 25%, 20%, 15%, 10%, or 5%, or remains substantially the same during oligonucleotide synthesis. In some embodiments, the present disclosure encompasses the recognition than volume change of solid support during synthesis may cause deviations from planned reaction conditions, e.g., solvent system, reagent concentrations, contact time, etc., and may negatively impact synthesis efficiency, crude purity and/or yield. In some embodiments, solid support that does not significantly change its volume or keep substantially the same volume during oligonucleotide synthesis may provide advantages, e.g., less deviation from planned reaction conditions, higher crude purity, higher yield, etc. A support can have a number of chemical modifications for nucleoside loading, and may have various unit loading capacities (e.g., umol/g).

In oligonucleotide synthesis using a support, typically oligonucleotides are linked to a support through a linker. A number of linkers can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, etc. In some embodiments, the present disclosure provides designed linkers.

In some embodiments, a support is functionalized with amino groups. In some embodiments, a support is functionalized with —$CH_2$—($CH_2$)$_n$—$CH_2$—$NH_2$, wherein the —$CH_2$— end is connected to a support, e.g., CPG. In some embodiments, a first linker is —$CH_2$—($CH_2$)$_n$—$CH_2$—NH—, wherein the —$CH_2$— end is connected to a support, e.g., CPG, and the —NH— is connected to a nucleoside, e.g., 3'-OH, through a second linker, e.g., —C(O)—$CH_2$—$CH_2$—C(O)—, wherein n is as described in the present disclosure. In some embodiments, n is 1. In some embodiments, n is 7.

In some embodiments, a first linker is —$CH_2$—($CH_2$)$_n$—$CH_2$—NH—C(O)—X—($CH_2$)$_m$—NH—, wherein each variable is independently as described in the present disclosure. In some embodiments, a first linker is —$CH_2$—($CH_2$)$_n$—$CH_2$—NH—C(O)—X—($CH_2$)$_m$—NH—C(O)—X—($CH_2$)$_p$—NH—, wherein each variable is independently as described in the present disclosure. In some embodiments, a first linker is —$CH_2$—($CH_2$)$_n$—$CH_2$—NH—C(O)—X—$CH_2$—$CH_2$—$CH_2$—O—$CH_2$—$CH_2$—O—$CH_2$—$CH_2$—O—$CH_2$—$CH_2$—$CH_2$—NH—, wherein each variable is independently as described in the present disclosure. In some embodiments, a first linker is —$CH_2$—($CH_2$)$_n$—$CH_2$—NH—C(O)—X—$CH_2$—$CH_2$—O—$CH_2$—$CH_2$—O—($CH_2$—$CH_2$—O)$_m$—$CH_2$—$CH_2$—O—$CH_2$—$CH_2$—O—$CH_2$—$CH_2$—$CH_2$—NH—, wherein each variable is independently as described in the present disclosure. In some embodiments, a first linker is —$CH_2$—($CH_2$)$_n$—$CH_2$—NH—C(O)—X—$CH_2$—$CH_2$—$CH_2$—O—$CH_2$—$CH_2$—O—($CH_2$—$CH_2$—$CH_2$—O) m-$CH_2$—$CH_2$—$CH_2$—O—$CH_2$—$CH_2$—$CH_2$—NH—, wherein each variable is independently as described in the present disclosure. In some embodiments, the —$CH_2$— end is connected to a support, e.g., CPG, and the —NH— is connected to a nucleoside, e.g., 3'-OH, through a second linker, e.g., —C(O)—$CH_2$—$CH_2$—C(O)—.

In some embodiments, not all available amino moieties are loaded with nucleoside, e.g., through a second linker —C(O)—$CH_2$—$CH_2$—C(O)—. In some embodiments, some available amino moiety can be capped with an acyl group, e.g., —C(O)—R forming —$CH_2$—($CH_2$)$_n$—$CH_2$—NH—C(O)—R, —$CH_2$—($CH_2$)$_n$—$CH_2$—NH—C(O)—X—($CH_2$)$_m$—NH—C(O)—R, —$CH_2$—($CH_2$)$_n$—$CH_2$—NH—C(O)—X—($CH_2$)$_m$—NH—C(O)—X—($CH_2$)$_p$—NH—C(O)—R, —$CH_2$—($CH_2$)$_n$—$CH_2$—NH—C(O)—X—$CH_2$—$CH_2$—$CH_2$—O—$CH_2$—$CH_2$—O—$CH_2$—$CH_2$—O—$CH_2$—$CH_2$—$CH_2$—NH—C(O)—R, —$CH_2$—($CH_2$)$_n$—$CH_2$—NH—C(O)—X—$CH_2$—$CH_2$—O—$CH_2$—$CH_2$—O—($CH_2$—$CH_2$—O)$_m$—$CH_2$—$CH_2$—O—$CH_2$—$CH_2$—O—$CH_2$—$CH_2$—NH—C(O)—R, or —$CH_2$—($CH_2$)$_n$—$CH_2$—NH—C(O)—X—$CH_2$—$CH_2$—$CH_2$—O—$CH_2$—$CH_2$—$CH_2$—O—($CH_2$—$CH_2$—$CH_2$—O) m-$CH_2$—$CH_2$—$CH_2$—O—$CH_2$—$CH_2$—$CH_2$—NH—C(O)—R, wherein each variable is independently as described in the present disclosure, so that unit loading capacity of a support can be adjusted. In some embodiments, R is —($CH_2$)o-, wherein o is 0-20.

In some embodiments, o is 0-12. In some embodiments, o is 0. In some embodiments, o is 1. In some embodiments, o is 2. In some embodiments, o is 3. In some embodiments, o is 4. In some embodiments, o is 5. In some embodiments, o is 6. In some embodiments, o is 7. In some embodiments, o is 8. In some embodiments, o is 9. In some embodiments, o is 10. In some embodiments, o is 11. In some embodiments, o is 12. In some embodiments, o is 13. In some embodiments, o is 14. In some embodiments, o is 15.

In some embodiments, a provided support after loading of a first nucleoside having the structure of:

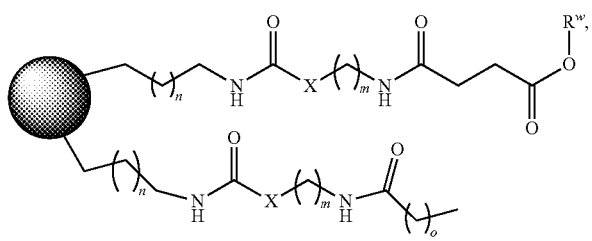

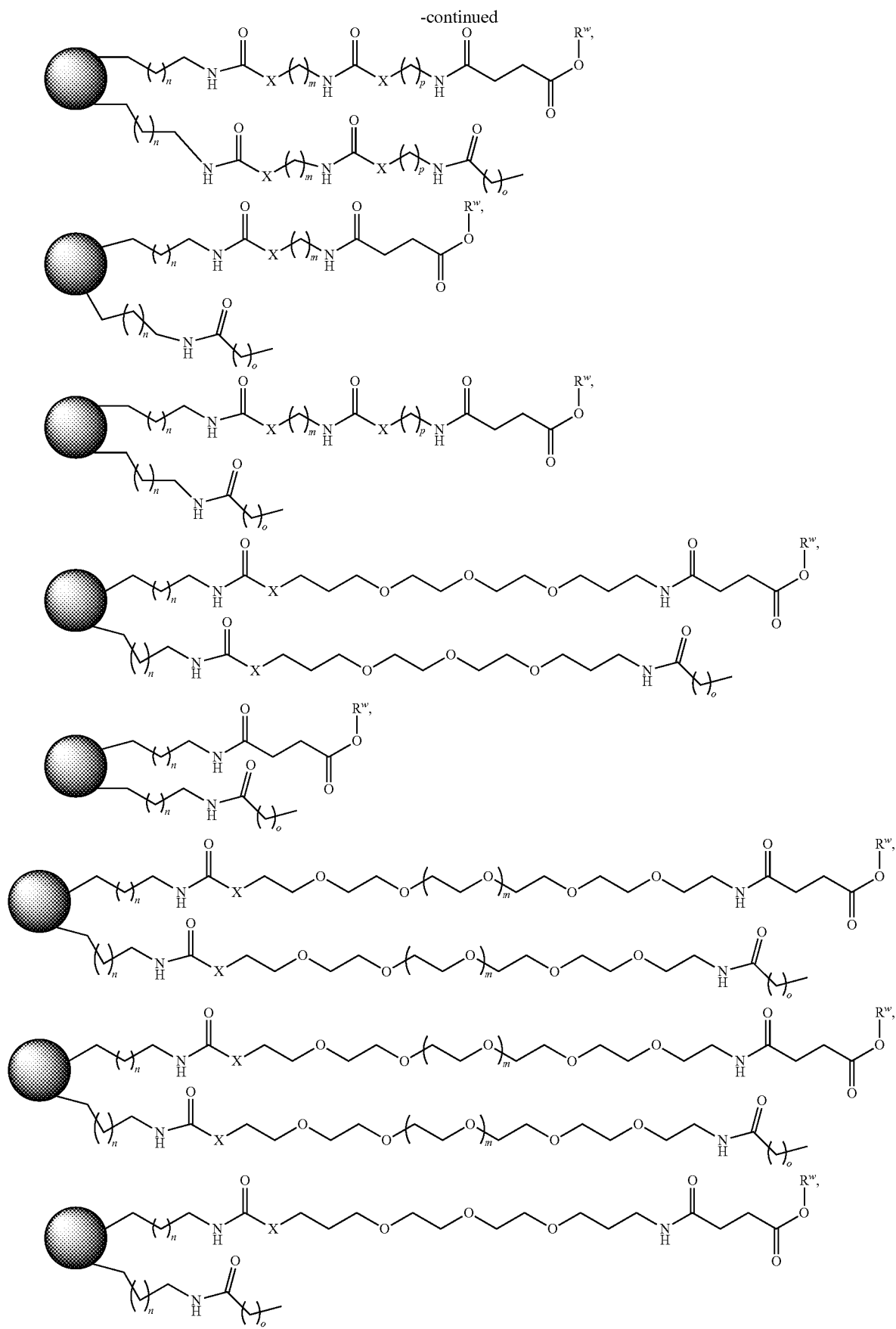

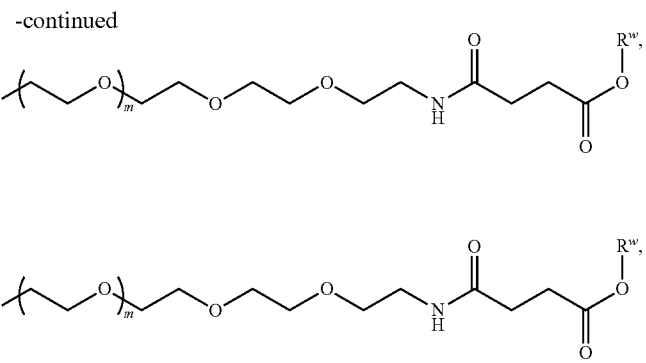

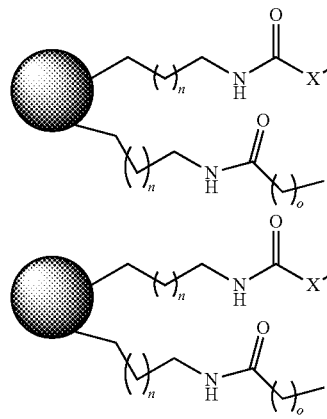

wherein —O—$R^w$ is an nucleoside moiety as described in the present disclosure, ⬤ is a support as described in the present disclosure, and each other variable is independently as described in the present disclosure. In some embodiments, In some embodiments, X is —O—, —S—, —NH—, —CH$_2$—, m is 3-15, n is 1 or 7, o is 0-12, and p is 3-15. In some embodiments, X is —O—, —S—, —NH—, —CH$_2$—, m is 0-10, n is 1 or 7, o is 0-12, and p is 3-15.

In some embodiments, —O—$R^w$ is a nucleoside moiety of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e. In some embodiments, In some embodiments, $R^W$ is

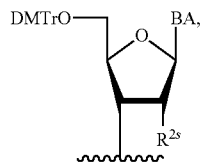

wherein $R^{2s}$ is as described in the present disclosure. In some embodiments, $R^W$ is

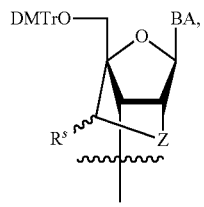

wherein each variable is as described in the present disclosure. In some embodiments, BA is a protected nucleobase selected from A, T, C, U, G and 5 mC. In some embodiments, BA is C(N-4-Ac or Bz), 5-Me-C(N-4-Ac or Bz),U, T, A(N-6-Bz), or G(N-2-iBu), $R^{2s}$ is —OH, —H, —F, —OCH$_3$, or —OCH$_2$CH$_2$OCH$_3$, Z is —O—, —S—, —CH$_2$—, and $R^s$ is —CH$_3$, —OCH$_3$, or —CH$_2$CH$_3$.

Oligonucleotide synthesis typically comprises a deblocking step, which de-blocks a blocked hydroxyl group for a next step, e.g., a coupling step, which keeps intact capped hydroxyl groups which should not participate in a next step, e.g., a coupling step. Various conditions for de-blocking can be utilized in accordance with the present disclosure, including those described in US2015100197, U.S. Pat. Nos. 9,744, 183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, and WO2018/098264. In some embodiments, de-blocking removes DMT group from DMT-protected hydroxyl (detritylation). In some embodiments, deblocking is performed by contacting oligonucleotides with an acid. In some embodiments, an acid is trichloroacetic acid or dichloroacetic acid. In some embodiments, a deblocking condition is 2% trichloroacetic acid (TCA) or 3% dichloroacetic acid (DCA), in an inert solvent (e.g., dichloromethane, toluene, etc.)

A coupling step forms an internucleotidic linkage, which adds a nucleoside unit to an existing oligonucleotide. In some embodiments, an internucleotidic linkage formed during a coupling step is a phosphite triester linkage. In some embodiments, an internucleotidic linkage can form with chirally control, e.g., as in chirally controlled oligonucleotide synthesis using diastereomerically pure phosphoramidite, typically comprising a chiral auxiliary moiety. Conditions for coupling are widely reported and many can be utilized in accordance with the present disclosure, including those described in US2015100197, U.S. Pat. Nos. 9,744, 183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264. In some embodiments, a coupling reagent system comprises a nucleoside phosphoramidite and an activator. Various phosphoramidites may be used in provided technologies, including those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403, 865, WO2017/160741, WO2017/192664, WO2017/192679, WO2017/210647, WO2018/022473, WO2018/067973, and WO2018/098264, and those having the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, as described in the present disclosure. Example activators include those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, and U.S. Pat. No. 9,403,865, activators of each of which are independently incorporated herein by reference. In some embodiments, an activator is CMPT. In some embodiments, an activator is CMIMT. In some embodiments, an activator is ETT. In some embodiments, conditions, e.g., concentrations of phosphoramidites, concentrations of activators, contact times, solvents, etc. can be optimized for each coupling to improve, e.g., crude purity, yield, etc.

In some embodiments, after a coupling step one or more capping steps are performed before a modification step. In some embodiments, each capping step after a coupling step and before a modification step is performed as described in the present disclosure, e.g., with reduced levels of or no strong nucleophiles, with reduced levels of or no catalysts for esterification, and/or under conditions selective or specific for amidation over esterification. In some embodiments, each capping step after a coupling step and before a modification step is performed to cap one or more amino groups, e.g., one or more amino groups formed after coupling in chiral auxiliaries moieties attached to linkage phosphorus atoms.

In some embodiments, after one or more capping steps as described in the present disclosure, a modification step is performed to modify a internucleotidic linkage formed after coupling, which internucleotidic linkage, in some embodiments, comprises a linkage phosphorus atom that is trivalent (e.g., as in a phosphite linkage). In some embodiments, a modification step is or comprises oxidation, e.g., converting a phosphite linkage into a tetra-coordinated phosphate triester linkage (installing an =O to a linkage phosphorus). In some embodiments, a modification step is or comprises sulfurization. In some embodiments, sulfurization converts a phosphite linkage into a tetra-coordinated internucleotidic linkage by installing an =S to a linkage phosphorus. In some embodiments, sulfurization converts a phosphite linkage into a tetra-coordinated phosphorothioate triester internucleotidic linkage (e.g., —P(=O)(S-L$^s$-R$^5$)— wherein -L$^s$-R$^5$ is not hydrogen). Example modifications and related technologies include those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, and WO2018/098264.

In some embodiments, provided technologies provide more flexibility with respect to choices of modification reagents, e.g., oxidation reagents, sulfurization reagents, etc. For example, reagents that tended to give inferior results in previously reported chirally controlled oligonucleotide synthesis can be utilized with technologies of the present disclosure to provide significantly improved, satisfactory results.

In some embodiments, after a modifying step, another capping step is performed. In some embodiments, an after-modification capping step is performed with a substantial amount of a strong nucleophile and/or an esterification catalyst (a strong nucleophile can be the same as an esterification catalyst) under an esterification condition which is comparable or identical to a capping condition in traditional oligonucleotide synthesis. In some embodiments, an after-modification capping step caps free hydroxyl groups, e.g., those residue hydroxyl groups as a result of incomplete coupling which remain intact after a modification step. After this capping step, oligonucleotides can be de-blocked to expose hydroxyl groups at sites for further chain extension, and enter another synthetic cycle.

After desired chain lengths are achieved, oligonucleotides can be fully deprotected and cleaved from support for purification and/or further uses. Various cleavage and/or deprotection technologies can be utilized in accordance with the present disclosure, including those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, and WO2018/098264. As appreciated by those skilled in the art, cleavage and/or deprotection conditions can depend on the chemistry used during oligonucleotide synthesis, e.g., properties of linkers connecting oligonucleotides to a support, properties of base and/or sugar blocking groups, properties of chiral moieties etc. In some embodiments, removal of chiral auxiliaries, e.g., DPSE-type of chiral auxiliaries, comprises use of TEA-HF. In some embodiments, the present disclosure surprisingly demonstrated that TEA-HF can be successfully utilized for oligonucleotide synthesis using CPG support.

Various types of sugars and nucleobases, including non-natural, modified sugars and nucleobases, can be utilized in provided technologies in accordance with the present disclosure, e.g., those sugar and nucleobases described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, and WO2018/098264.

In some embodiments, provided technologies are useful for large scale preparation of oligonucleotides. In some embodiments, a scale is 100 g or more. In some embodiments, a scale is 200 g or more. In some embodiments, a scale is 500 g or more. In some embodiments, a scale is at least 1000 g or more.

In some embodiments, a composition of another step being contacted in a step is a composition of the first step preceding the step. In some embodiments, a composition of another step being contacted in each step is a composition of the first step preceding the step. For example, a de-blocked composition being contacted in a coupling step is the de-blocked composition of the first de-blocking step preceding the coupling step, a coupling product composition being contacted in a pre-modification capping step is the coupling product composition of the first coupling step preceding the pre-modification capping step, a coupling product composition being contacted in a modification step is the coupling product composition of the first coupling step preceding the modification step, a pre-modification capping product composition being contacted in a modification step is the pre-modification capping product composition of the first pre-modification capping step preceding the modification step, a modification product composition being contacted in a post-modification capping step is the modification product composition of the first modification step preceding the post-modification capping step, a modification product composition being contacted in a de-blocking step is the modification product composition of the first modification step preceding the de-blocking step, a post-modification capping product composition being contacted in a de-blocking step is the post-modification capping product composition of the first post-modification capping step preceding the de-blocking step, etc.

In some embodiments, provided technologies may be generally utilized to prepare other oligomeric compounds. In some embodiments, a method for preparing a composition comprising a plurality of oligomeric compounds comprises:

a) a coupling step comprising:
  contacting a de-blocked composition comprising a plurality of de-blocked compounds, each independently comprising a de-blocked monomeric unit, which is de-blocked in that each de-blocked monomeric unit independently comprises a free connecting group, with a coupling reagent system which comprises a partner compound comprising a monomeric unit of the oligomeric compound; and
  coupling a partner compound comprising a monomeric unit of the oligomeric compound with the free connecting groups of a plurality of de-blocked compounds to provide a coupling product composition comprising a plurality of coupling products, each of which independently comprises a linkage linking the connecting group of a de-blocked monomeric unit and a monomeric unit of the partner compound;

b) optionally a pre-modification capping step comprising:
  contacting a coupling product composition with a pre-modification capping reagent system; and
  capping one or more functional groups of the coupling product composition to provide a pre-modification capping product composition comprising a plurality of pre-modification capping products;

c) a modification step comprising:
  contacting a coupling product composition and modifying one or more linkages of one or more coupling products to provide a modification step composition comprising a plurality of modification products; or
  contacting a pre-modification capping product composition and modifying one or more linkages of one or more pre-modification capping products to provide a modification product composition comprising a plurality of modification products;

d) optionally a post-modification capping step comprising:
  contacting a modification product composition with a post-modification capping reagent system; and
  capping one or more functional groups of one or more compounds of a modification product composition to provide a post-modification capping product composition comprising a plurality of post-modification capping products;

e) optionally a de-blocking step comprising:
  contacting a modification product composition, or a post-modification capping product composition, with a de-blocking reagent system to provide a de-blocked composition comprising a plurality of de-blocked products, each of which independently comprises a de-blocked monomeric unit comprising a free connecting group.

In some embodiments, a method optionally comprises repeating steps b) to e) a number of times, e.g., until a desired length is achieved. In some embodiments, a the method comprises both a pre-modification capping step and a post-modification capping step, wherein a pre-modification capping reagent system is optionally different from a post-modification reagent system, or a pre-modification capping step, wherein the pre-modification capping reagent system caps a plurality of non-connecting groups of a plurality of coupling products, and a modification step that comprises sulfurization, which sulfurization provides a modification product composition comprising a plurality of modification products, each of which independently comprises a $P=S$ moiety, or a post-modification capping step, comprising contacting a modification product composition comprising a plurality of modification products, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center, or a post-modification capping step, and a coupling reagent system comprising a chiral partner compound that comprises a monomeric unit of the oligomeric compound, wherein the chiral partner compound comprises a chiral atom that is not within the monomeric unit; or a coupling step which is immediately followed by a pre-modification capping step, which the pre-modification capping reagent system of the pre-modification capping step comprises no esterification catalyst or comprises no strong nucleophile.

As described in the present disclosure, in some embodiments, an oligomeric compound is an oligonucleotide. In some embodiments, a composition comprising a plurality of oligomeric compounds is an oligonucleotide composition comprising a plurality of oligonucleotides. In some embodiments, a coupling step is a coupling step as described in the present disclosure for oligonucleotide synthesis. In some embodiments, a de-blocked compound is a de-blocked oligonucleotide, e.g., an oligonucleotide after de-blocking step in an oligonucleotide synthesis cycle. In some embodiments, a de-blocked monomeric unit is a de-blocked 5'-end nucleoside unit. In some embodiments, a free connecting group is a free 5'-hydroxyl group. In some embodiments, a coupling reagent system is a coupling reagent system in oligonucleotide synthesis cycles. In some embodiments, a partner compound is a phosphoramidite described herein for oligonucleotide synthesis. In some embodiments, a coupling product is an oligonucleotide formed after coupling in oligonucleotide synthesis. In some embodiments, a linkage linking the connecting group of a de-blocked monomeric unit and a monomeric unit of the partner compound is an internucleotidic linkage formed during a coupling step. In some embodiments, a pre-modification capping step is a capping step in oligonucleotide synthesis as described in the present disclosure. In some embodiments, a pre-modification capping reagent system is a pre-capping reagent system in oligonucleotide synthesis as described in the present disclosure. In some embodiments, a pre-modification capping product composition is a composition after a pre-modification capping step in oligonucleotide synthesis. In some embodiments, a pre-modification capping product is a product formed after a pre-modification capping step in oligonucleotide synthesis. In some embodiments, a modification step is a modification step as used in oligonucleotide synthesis. In some embodiments, a modification step as demonstrated in oligonucleotide synthesis described in the present disclosure modifies an internucleotidic linkage. In some embodiments, a modification product composition is an oligonucleotide composition provided after a modification step in oligonucleotide synthesis. In some embodiments, a modification product is an oligonucleotide provided after a modification step in oligonucleotide synthesis. In some embodiments, a post-modification capping step is a capping step in oligonucleotide synthesis as described in the present disclosure. In some embodiments, a post-modification capping reagent system is a post-capping reagent system in oligonucleotide synthesis as described in the present disclosure. In some embodiments, a post-modification capping product composition is a composition after a post-modification capping step in oligonucleotide synthesis. In some embodiments, a post-modification capping product is a product formed after a post-modification capping step in oligonucleotide synthesis. In some embodiments, a de-blocking step is a de-blocking step as described in the present disclosure for oligonucleotide synthesis. In some embodiments, a non-connecting group is an amino group. In some embodiments, a chirally controlled chiral center is a chirally controlled linkage phosphorus center. In some embodiments, a chiral partner compound comprising a chiral atom that is not within the monomeric unit is a phosphoramidite comprising a chiral center that is not in its nucleoside unit and is not the P. In some embodiments, a reagent system comprises no esterification catalyst comprises no DMAP and no NMI.

BRIEF DESCRIPTION OF THE DRAWING

Figure J. Crude UPLC chromatogram for B6.
FIG. 4. (A) Crude UPLC chromatogram for B110 (after NAP). (B) Crude UPLC chromatogram for B110 (As was before NAP).

DETAILED DESCRIPTION OF CERTAIN EMBODIMENTS

1. Definitions

Figure 1:
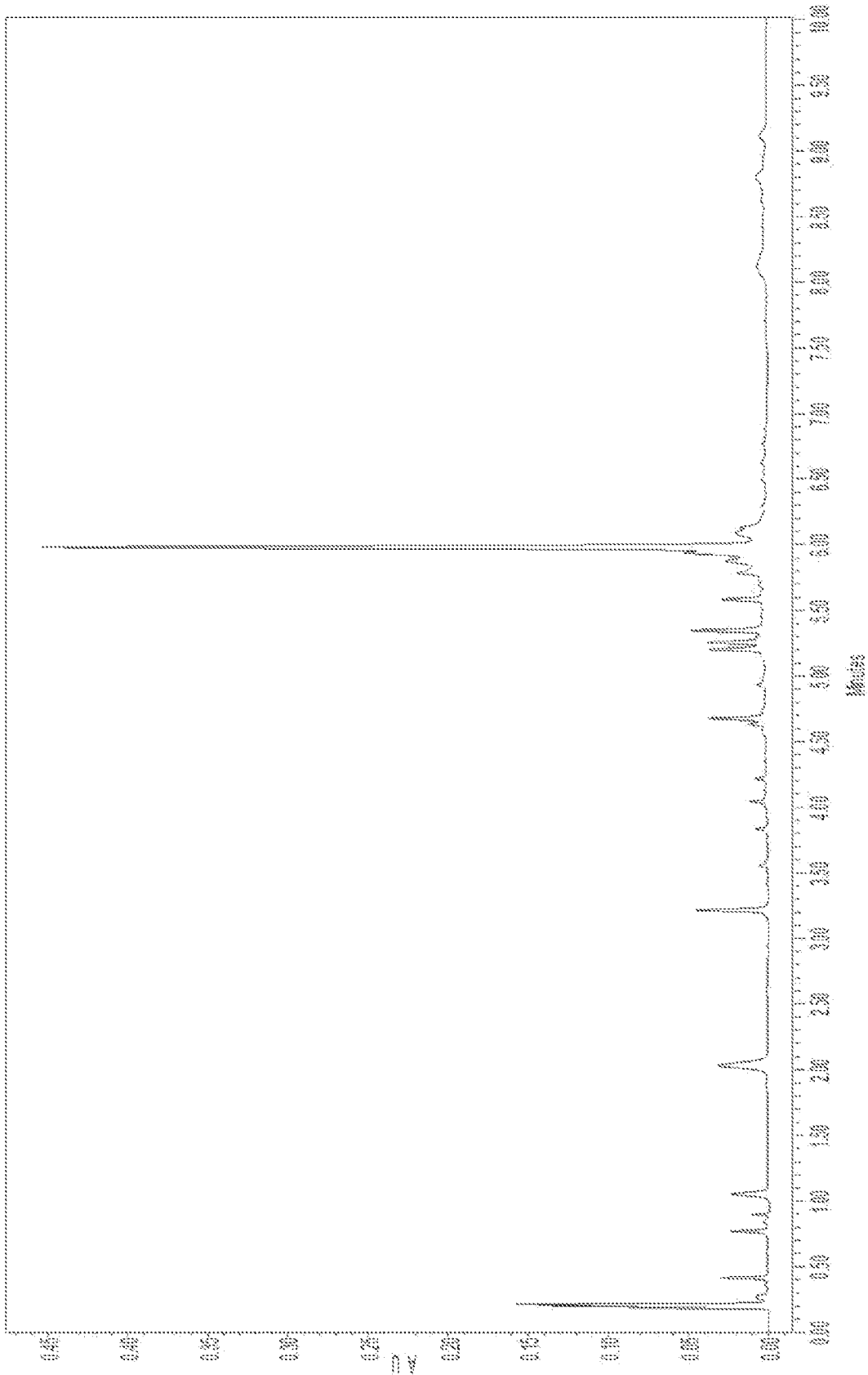

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like, where a radical or point of attachment is on an aryl ring.

Chiral control: As used herein, "chiral control" refers to control of the stereochemical designation of a chiral linkage phosphorus in a chiral internucleotidic linkage within an oligonucleotide. In some embodiments, a control is achieved through a chiral element that is absent from the sugar and base moieties of an oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same stereochemistry at one or more chiral internucleotidic linkages (chirally controlled internucleotidic linkages), and the level of the plurality of oligonucleotides (or nucleic acids) in the composition is not random/pre-determined (e.g., through chirally controlled oligonucleotide preparation to form one or more chiral internucleotidic linkages). In some embodiments, the plurality of oligonucleotides in a chirally controlled oligonucleotide composition share the same base sequence, the same, if any, nucleobase, sugar, and internucleotidic linkage modifications, and the same stereochemistry (Rp or Sp) independently at linkage phosphorus chiral centers of one or more chirally controlled internucleotidic linkages, though stereochemistry of certain linkage phosphorus chiral centers may differ. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence are oligonucleotides of the plurality. In some embodiments, about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a predetermined level is be about 0.1%-100%, (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications, are oligonucleotides of the plurality. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 0.1%-100% (e.g., about 1%-100%, 5%-100%, 10%-100%, 20%-100%, 30%-100%, 40%-100%, 50%-100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type at a predetermined level. In some embodiments, a chirally controlled oligonucleotide composition comprises more than one oligonucleotide type, each independently at a predetermined level. In some embodiments, a chirally controlled oligonucleotide composition comprises multiple oligonucleotide types, each independently at a predetermined level. In some embodiments, a chirally controlled oligonucleotide composition is a composition of oligonucleotides of an oligonucleotide type, which composition comprises a predetermined level of a plurality of oligonucleotides of the oligonucleotide type.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or NR$^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Internucleotidic linkage: As used herein, the phrase "internucleotidic linkage" refers generally to the phosphorus-containing linkage between nucleotide units of an oligonucleotide, which typically links two neighboring sugar moieties together, and is interchangeable with "inter-sugar linkage" and "phosphorus atom bridge." In some embodiments, an internucleotidic linkage is a phosphodiester linkage, as found in naturally occurring DNA and RNA molecules (a natural phosphate linkage). In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described below. In some embodiments, an internucleotidic linkage is a phosphotriester linkage, phosphorothioate diester linkage

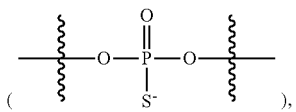 [SMILES: *OP(=O)([S-])O*]

or modified phosphorothioate triester linkage. It is understood by a person of ordinary skill in the art that the internucleotidic linkage may exist as an anion or cation at a given pH due to the existence of acid or base moieties in the linkage.

Linkage phosphorus: As defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the phosphorus of $P^L$ of Formula VII. In some embodiments, a linkage phosphorus atom is chiral. In some embodiments, a linkage phosphorus is a chiral (e.g., in natural phosphate linkage).

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—X-L-$R^5$" groups in formula VII). In some embodiments, oligonucleotides of a common designated "type" are structurally, including stereochemically, identical to one another.

Oligonucleotide: the term "oligonucleotide" refers to a polymer or oligomer of nucleotide monomers, containing any combination of nucleobases (natural or non-natural), sugars (natural or non-natural), and internucleotidic linkages (natural or non-natural). Oligonucleotides of the present disclosure can be of various lengths. In particular embodiments, oligonucleotides can range from about 2 to about 200 nucleotides in length. In various embodiments, oligonucleotides can range in length from about 4 to about 10 nucleotides, from about 10 to about 50 nucleotides, from about 20 to about 50 nucleotides, from about 15 to about 30 nucleotides, or from about 20 to about 30 nucleotides in length. In some embodiments, an oligonucleotide is from about 9 to about 39 nucleotides in length. In some embodiments, an oligonucleotide is at least 4 nucleotides in length. In some embodiments, an oligonucleotide is at least 5 nucleotides in length. In some embodiments, an oligonucleotide is at least 6 nucleotides in length. In some embodiments, an oligonucleotide is at least 7 nucleotides in length. In some embodiments, an oligonucleotide is at least 8 nucleotides in length. In some embodiments, an oligonucleotide is at least 9 nucleotides in length. In some embodiments, an oligonucleotide is at least 10 nucleotides in length. In some embodiments, an oligonucleotide is at least 11 nucleotides in length. In some embodiments, an oligonucleotide is at least 12 nucleotides in length. In some embodiments, an oligonucleotide is at least 15 nucleotides in length. In some embodiments, an oligonucleotide is at least 20 nucleotides in length. In some embodiments, an oligonucleotide is at least 25 nucleotides in length. In some embodiments, an oligonucleotide is at least 30 nucleotides in length. In some embodiments, an oligonucleotide is a duplex of complementary strands of at least 18 nucleotides in length. In some embodiments, an oligonucleotide is a duplex of complementary strands of at least 21 nucleotides in length.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., —N(R)$_3^+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Predetermined: By predetermined (or pre-determined) is meant deliberately selected, for example as opposed to randomly occurring or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. A composition that may contain certain oligonucleotides because they happen to have been generated through a process that are not controlled to intentionally generate the particular chemistry and/or stereochemistry features is not a "predetermined" composition. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5]azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)N(R^\circ)_2$; $-N(R^\circ)C(S)N(R^\circ)_2$; $-(CH_2)_{0-4}N(R^\circ)C(O)OR^\circ$; $-N(R^\circ)N(R^\circ)C(O)R^\circ$; $-N(R^\circ)N(R^\circ)C(O)N(R^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSi(R^\circ)_3$; $-(CH_2)_{0-4}OC(O)R^\circ$; $-OC(O)(CH_2)_{0-4}SR^\circ$, $-SC(S)SR^\circ$; $-(CH_2)_{0-4}SC(O)R^\circ$; $-(CH_2)_{0-4}C(O)N(R^\circ)_2$; $-C(S)N(R^\circ)_2$; $-C(S)SR^\circ$; $-SC(S)SR^\circ$, $-(CH_2)_{0-4}OC(O)N(R^\circ)_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2N(R^\circ)_2$; $-(CH_2)_{0-4}S(O)R^\circ$; $-N(R^\circ)S(O)_2N(R^\circ)_2$; $-N(R^\circ)S(O)_2R^\circ$; $-N(OR^\circ)R^\circ$; $-C(NH)N(R^\circ)_2$; $-Si(R^\circ)_3$; $-OSi(R^\circ)_3$; $-P(R^\circ)_2$; $-P(OR^\circ)_2$; $-P(R^\circ)(OR^\circ)$; $-OP(R^\circ)_2$; $-OP(OR^\circ)_2$; $-OP(R^\circ)(OR^\circ)$; $-P[N(R^\circ)_2]_2-P(R^\circ)[N(R^\circ)_2]$; $-P(OR^\circ)[N(R^\circ)_2]$; $-OP[N(R^\circ)_2]_2$; $-OP(R^\circ)[N(R^\circ)_2]$; $-OP(OR^\circ)[N(R^\circ)_2]$; $-N(R^\circ)P(R^\circ)_2$; $-N(R^\circ)P(OR^\circ)_2$; $-N(R^\circ)P(R^\circ)(OR^\circ)$; $-N(R^\circ)P[N(R^\circ)_2]_2$; $-N(R^\circ)P(R^\circ)[N(R^\circ)_2]$; $-N(R^\circ)P(OR^\circ)[N(R^\circ)_2]$; $-B(R^\circ)_2$; $-B(R^\circ)(OR^\circ)$; $-B(OR^\circ)_2$; $-OB(R^\circ)_2$; $-OB(R^\circ)(OR^\circ)$; $-OB(OR^\circ)_2$; $-P(O)(R^\circ)_2$; $-P(O)(R^\circ)(OR^\circ)$; $-P(O)(R^\circ)(SR^\circ)$; $-P(O)(R^\circ)[N(R^\circ)_2]$; $-P(O)(OR^\circ)_2$; $-P(O)(SR^\circ)_2$; $-P(O)(OR^\circ)[N(R^\circ)_2]$; $-P(O)(SR^\circ)[N(R^\circ)_2]$; $-P(O)(OR^\circ)(SR^\circ)$; $-P(O)[N(R^\circ)_2]_2$; $-OP(O)(R^\circ)_2$; $-OP(O)(R^\circ)(OR^\circ)$; $-OP(O)(R^\circ)(SR^\circ)$; $-OP(O)(R^\circ)[N(R^\circ)_2]$; $-OP(O)(OR^\circ)_2$; $-OP(O)(SR^\circ)_2$; $-OP(O)(OR^\circ)[N(R^\circ)_2]$; $-OP(O)(SR^\circ)[N(R^\circ)_2]$; $-OP(O)(OR^\circ)(SR^\circ)$; $-OP(O)[N(R^\circ)_2]_2$; $-SP(O)(R^\circ)_2$; $-SP(O)(R^\circ)(OR^\circ)$; $-SP(O)(R^\circ)(SR^\circ)$; $-SP(O)(R^\circ)[N(R^\circ)_2]$; $-SP(O)(OR^\circ)_2$; $-SP(O)(SR^\circ)_2$; $-SP(O)(OR^\circ)[N(R^\circ)_2]$; $-SP(O)(SR^\circ)[N(R^\circ)_2]$; $-SP(O)(OR^\circ)(SR^\circ)$; $-SP(O)[N(R^\circ)_2]_2$; $-N(R^\circ)P(O)(R^\circ)_2$; $-N(R^\circ)P(O)(R^\circ)(OR^\circ)$; $-N(R^\circ)P(O)(R^\circ)(SR^\circ)$; $-N(R^\circ)P(O)(R^\circ)[N(R^\circ)_2]$; $-N(R^\circ)P(O)(OR^\circ)_2$; $-N(R^\circ)P(O)(SR^\circ)_2$; $-N(R^\circ)P(O)(OR^\circ)[N(R^\circ)_2]$; $-N(R^\circ)P(O)(SR^\circ)[N(R^\circ)_2]$; $-N(R^\circ)P(O)(OR^\circ)(SR^\circ)$; $-N(R^\circ)P(O)[N(R^\circ)_2]_2$; $-P(R^\circ)_2[B(R^\circ)_3]$; $-P(OR^\circ)_2[B(R^\circ)_3]$; $-P(NR^\circ)_2[B(R^\circ)_3]$; $-P(R^\circ)(OR^\circ)[B(R^\circ)_3]$; $-P(R^\circ)[N(R^\circ)_2][B(R^\circ)_3]$; $-P(OR^\circ)[N(R^\circ)_2][B(R^\circ)_3]$; $-OP(R^\circ)_2[B(R^\circ)_3]$; $-OP(OR^\circ)_2[B(R^\circ)_3]$; $-OP(NR^\circ)_2[B(R^\circ)_3]$; $-OP(R^\circ)(OR^\circ)[B(R^\circ)_3]$; $-OP(R^\circ)[N(R^\circ)_2][B(R^\circ)_3]$; $-OP(OR^\circ)[N(R^\circ)_2][B(R^\circ)_3]$; $-N(R^\circ)P(R^\circ)_2[B(R^\circ)_3]$; $-N(R^\circ)P(OR^\circ)_2[B(R^\circ)_3]$; $-N(R^\circ)P(NR^\circ)_2[B(R^\circ)_3]$; $-N(R^\circ)P(R^\circ)(OR^\circ)[B(R^\circ)_3]$; $-N(R^\circ)P(R^\circ)[N(R^\circ)_2][B(R^\circ)_3]$; $-N(R^\circ)P(OR^\circ)[N(R^\circ)_2][B(R^\circ)_3]$; $-P(OR')[B(R')_3]-$; $-(C_{1-4}$ straight or branched)alkylene)O—N(R^\circ)_2$; or $-(C_{1-4}$ straight or branched)alkylene)C(O)O—N(R^\circ)_2$, wherein each $R^\circ$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)C(O)OR$^\bullet$, or $-SSR^\bullet$ wherein each R<sup>●</sup> is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^o$ include =O and =S.

Suitable divalent substituents are the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* are halogen, —R<sup>●</sup>, -(haloR<sup>●</sup>), —OH, —OR', —O(haloR<sup>●</sup>), —CN, —C(O)OH, —C(O)OR<sup>●</sup>, —NH$_2$, —NHR<sup>●</sup>, —NR<sup>●</sup>$_2$, or —NO$_2$, wherein each R<sup>●</sup> is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R<sup>†</sup>, —NR<sup>†</sup>$_2$, —C(O)R<sup>†</sup>, —C(O)OR<sup>†</sup>, —C(O)C(O)R<sup>†</sup>, —C(O)CH$_2$C(O)R<sup>†</sup>, —S(O)$_2$R<sup>†</sup>, —S(O)$_2$NR<sup>†</sup>$_2$, —C(S)NR<sup>†</sup>$_2$, —C(NH)NR<sup>†</sup>$_2$, or —N(R<sup>†</sup>)S(O)$_2$R<sup>†</sup>; wherein each R<sup>†</sup> is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R<sup>†</sup>, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R<sup>†</sup> are independently halogen, —R<sup>●</sup>, -(haloR<sup>●</sup>), —OH, —OR<sup>●</sup>, —O(haloR<sup>●</sup>), —CN, —C(O)OH, —C(O)OR<sup>●</sup>, —NH$_2$, —NHR<sup>●</sup>, —NR<sup>●</sup>$_2$, or —NO$_2$, wherein each R<sup>●</sup> is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

Unless otherwise specified, salts, such as pharmaceutically acceptable acid or base addition salts, stereoisomeric forms, and tautomeric forms, of provided compound are included. Unless otherwise specified, singular forms "a", "an", and "the" include the plural reference unless the context clearly indicates otherwise. Thus, for example, a reference to "a compound" may include a plurality of such compounds.

2. Detailed Description of Certain Embodiments

Among other things, the present disclosure provides technologies for preparing oligonucleotide compositions, particularly chirally controlled oligonucleotide compositions, with unexpectedly improved crude purity and yield. In some embodiments, provided technologies can dramatically reduce costs of goods, and in some embodiments, enable large production of therapeutic oligonucleotides at commercially acceptable conditions, e.g., cost, purity, yield, etc., for clinical uses and commercialization. As appreciated by those skilled in the art, provided technologies enable production of compositions of various oligonucleotides, independent of base sequences, chemical/stereochemical modifications, modes of activities, chiral auxiliaries, etc. Example embodiments of provided technologies are described herein.

Oligonucleotides and Oligonucleotide Compositions

In some embodiments, oligonucleotide compositions of provided technologies, e.g., product oligonucleotide compositions of various steps, final oligonucleotide compositions, etc., are chirally controlled oligonucleotide composition. In some embodiments, oligonucleotides of provided technologies, e.g., product oligonucleotides of various steps, final product oligonucleotides, etc., are oligonucleotides of formula VIII:

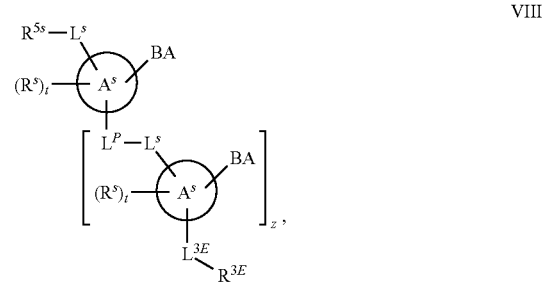

VIII or a salt thereof, wherein:

$R^{5a}$ is independently R' or —OR';

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Ring $A^s$ is independently an optionally substituted 3-20 membered monocyclic, bicyclic or polycyclic ring having 0-10 heteroatoms independently selected from oxygen, nitrogen, sulfur, phosphorus and silicon;

each $R^s$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

each t is independently 0-20;

each BA is independently an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

each $L^P$ is independently an internucleotidic linkage;

z is 1-1000;

$L^{3E}$ is -$L^s$- or -$L^s$-$L^s$-;

$R^{3E}$ is —R', -$L^s$-R', —OR', or a support;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, an oligonucleotide composition is a chirally controlled oligonucleotide composition.

In some embodiments, a chirally controlled oligonucleotide composition is an oligonucleotide composition comprising a plurality of oligonucleotides which share:

1) a common base sequence;
2) a common pattern of backbone linkages;
3) common stereochemistry independently at about 1-50 (e.g., about 5-50, about 10-50, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, etc.) chiral internucleotidic linkages ("chirally controlled internucleotidic linkages");

which composition is chirally controlled in that level of the plurality of oligonucleotides in the composition is predetermined.

In some embodiments, a chirally controlled oligonucleotide composition is an oligonucleotide composition comprising a plurality of oligonucleotides, wherein oligonucleotides of the plurality are of a particular oligonucleotide type defined by:

1) base sequence;
2) pattern of backbone linkages;
3) pattern of backbone chiral centers; and
4) pattern of backbone phosphorus modifications;

which composition is chirally controlled in that level of the plurality of oligonucleotides in the composition is predetermined.

In some embodiments, a chirally controlled oligonucleotide composition is an oligonucleotide composition comprising a plurality of oligonucleotides which share:

1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, a chirally controlled oligonucleotide composition is an oligonucleotide composition comprising a plurality of oligonucleotides, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least ((DS)Nc*100)% of all oligonucleotides sharing the same base sequence in the composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a chirally controlled oligonucleotide composition is an oligonucleotide composition comprising a plurality of oligonucleotides, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage; and wherein no less than $((DS)^{Nc}*100)\%$ of all oligonucleotides sharing the same base sequence in the composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, provided oligonucleotides comprise 1-30 non-natural internucleotidic linkages (not —O—P(O)(OH)—O— or salt forms thereof). In some embodiments, provided oligonucleotides comprise 2-30 non-natural internucleotidic linkages. In some embodiments, provided oligonucleotides comprise 5-30 non-natural internucleotidic linkages. In some embodiments, provided oligonucleotides comprise 10-30 non-natural internucleotidic linkages.

In some embodiments, provided oligonucleotides comprise 1-30 chirally controlled internucleotidic linkages. In some embodiments, provided oligonucleotides comprise 2-30 chirally controlled internucleotidic linkages. In some embodiments, provided oligonucleotides comprise 5-30 chirally controlled internucleotidic linkages. In some embodiments, provided oligonucleotides comprise 10-30 chirally controlled internucleotidic linkages. In some embodiments, provided oligonucleotides comprise 1 chirally controlled internucleotidic linkage. In some embodiments, provided oligonucleotides comprise 2 chirally controlled internucleotidic linkages. In some embodiments, provided oligonucleotides comprise 3 chirally controlled internucleotidic linkages. In some embodiments, provided oligonucleotides comprise 4 chirally controlled internucleotidic linkages. In some embodiments, provided oligonucleotides comprise 5 chirally controlled internucleotidic linkages. In some embodiments, provided oligonucleotides comprise 6 chirally controlled internucleotidic linkages. In some embodiments, provided oligonucleotides comprise 7 chirally controlled internucleotidic linkages. In some embodiments, provided oligonucleotides comprise 8 chirally controlled internucleotidic linkages. In some embodiments, provided oligonucleotides comprise 9 chirally controlled internucleotidic linkages. In some embodiments, provided oligonucleotides comprise 10 chirally controlled internucleotidic linkages. In some embodiments, provided oligonucleotides comprise 11 chirally controlled internucleotidic linkages. In some embodiments, provided oligonucleotides comprise 12 chirally controlled internucleotidic linkages. In some embodiments, provided oligonucleotides comprise 13 chirally controlled internucleotidic linkages. In some embodiments, provided oligonucleotides comprise 14 chirally controlled internucleotidic linkages. In some embodiments, provided oligonucleotides have 15 chirally controlled internucleotidic linkages. In some embodiments, provided oligonucleotides have 16 chirally controlled internucleotidic linkages. In some embodiments, provided oligonucleotides have 17 chirally controlled internucleotidic linkages. In some embodiments, provided oligonucleotides have 18 chirally controlled internucleotidic linkages. In some embodiments, provided oligonucleotides have 19 chirally controlled internucleotidic linkages. In some embodiments, provided oligonucleotides have 20 chirally controlled internucleotidic linkages. In some embodiments, about 1-100% of all internucleotidic linkages are chirally controlled internucleotidic linkages. In some embodiments, about 1-100% of all chiral internucleotidic linkages (comprising chiral linkage phosphorus) are chirally controlled internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each chiral internucleotidic linkage is chirally controlled. In some embodiments, a portion of or all of chirally controlled internucleotidic linkages in provided oligonucleotides or one or more segments thereof (e.g., 5'-wing regions, core wings, 3'-wing regions) are consecutive. In some embodiments, all chirally controlled internucleotidic linkages in provided oligonucleotides or one or more segments thereof (e.g., 5'-wing regions, core wings, 3'-wing regions) are consecutive.

In some embodiments, provided oligonucleotides comprise 1-30 natural phosphate linkages (not —O—P(O)(OH)—O— or salt forms thereof). In some embodiments, provided oligonucleotides, in addition to natural phosphate linkages, or chiral internucleotidic linkages, or chirally controlled internucleotidic linkages as described herein, further comprise 1-30 natural phosphate linkages (not —O—P(O)(OH)—O— or salt forms thereof). In some embodiments, provided oligonucleotides comprise 2-30 natural phosphate linkages. In some embodiments, provided oligonucleotides comprise 5-30 natural phosphate linkages. In some embodiments, provided oligonucleotides comprise 10-30 natural phosphate linkages. In some embodiments, provided oligonucleotides comprise 1 chirally controlled internucleotidic linkage. In some embodiments, provided oligonucleotides comprise 2 natural phosphate linkages. In some embodiments, provided oligonucleotides comprise 3 natural phosphate linkages. In some embodiments, provided oligonucleotides comprise 4 natural phosphate linkages. In some embodiments, provided oligonucleotides comprise 5 natural phosphate linkages. In some embodiments, provided oligonucleotides comprise 6 natural phosphate linkages. In some embodiments, provided oligonucleotides comprise 7 natural phosphate linkages. In some embodiments, provided oligonucleotides comprise 8 natural phosphate linkages. In some embodiments, provided oligonucleotides comprise 9 natural phosphate linkages. In some embodiments, provided oligonucleotides comprise 10 natural phosphate linkages. In some embodiments, provided oligonucleotides comprise 11 natural phosphate linkages. In some embodiments, provided oligonucleotides comprise 12 natural phosphate linkages. In some embodiments, provided oligonucleotides comprise 13 natural phosphate linkages. In some embodiments, provided oligonucleotides comprise 14 natural phosphate linkages. In some embodiments, provided oligonucleotides have 15 natural phosphate linkages. In some embodiments, provided oligonucleotides have 16 natural phosphate linkages. In some embodiments, provided oligonucleotides have 17 natural phosphate linkages. In some embodiments, provided oligonucleotides have 18 natural phosphate linkages. In some embodiments, provided oligonucleotides have 19 natural phosphate linkages. In some embodiments, provided oligonucleotides have 20 natural phosphate linkages. In some embodiments, about 1-100% of all internucleotidic linkages are natural phosphate linkages. In some embodiments, about 1-99% of all internucleotidic linkages are natural phosphate linkages, and about 1-99% of all internucleotidic linkages are non-natural internucleotidic linkages (e.g., internucleotidic linkages of formula VII, VII-a-1, VII-a-2, VII-b, VII-c, VII-d, or VII-e, or a salt form thereof and are non-natural internucleotidic linkages). In some embodiments, about 1-99% of all internucleotidic linkages are natural phosphate linkages, and about 1-99% of all internucleotidic linkages are chiral internucleotidic linkages (e.g., internucleotidic linkages of formula VII, VII-a-1, VII-a-2, VII-b, VII-c, VII-d, or VII-e, or a salt form thereof and are chiral). In some embodiments, about 1-99% of all internucleotidic linkages are natural phosphate linkages, and about 1-99% of all internucleotidic linkages are chirally controlled oligonucleotide composition internucleotidic linkages (e.g., internucleotidic linkages of formula VII, VII-a-1, VII-a-2, VII-b, VII-c, VII-d, or VII-e, or a salt form thereof and are chirally controlled). In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments, each non-natural internucleotidic linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is a non-natural internucleotidic linkage (not —O—P(O)(OH)—O— or a salt form thereof). In some embodiments, each chiral linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, each chirally controlled phosphate linkage independently has the structure of formula VII, VII-a-1, VII-a-2, VII-b, VII-c, VII-d, or VII-e, or a salt form thereof, wherein the structure of formula VII, VII-a-1, VII-a-2, VII-b, VII-c, VII-d, or VII-e, or a salt form thereof, is not a natural phosphate linkage (not —O—P(O)(OH)—O— or a salt form thereof). In some embodiments, a portion of or all of natural phosphate linkages in provided oligonucleotides or one or more segments thereof (e.g., 5'-wing regions, core wings, 3'-wing regions) are consecutive. In some embodiments, all natural phosphate linkages in provided oligonucleotides or one or more segments thereof (e.g., 5'-wing regions, core wings, 3'-wing regions) are consecutive.

In some embodiments, a non-natural internucleotidic linkage is a phosphorothioate linkage or a salt form thereof (—O—P(O)(SH)—O— or a salt form thereof). In some embodiments, a chiral internucleotidic linkage is a phosphorothioate linkage or a salt form thereof (—O—P(O)(SH)—O— or a salt form thereof). In some embodiments, a chirally controlled internucleotidic linkage is a phosphorothioate linkage or a salt form thereof (—O—P(O)(SH)—O— or a salt form thereof).

In some embodiments, provided oligonucleotides comprise 5-200, 5-150, 5-100, 5-50, 5-40, 5-35, 5-30, 5-25, 10-200, 10-150, 10-100, 10-50, 10-40, 10-35, 10-30, 10-25, 15-200, 15-150, 15-100, 15-50, 15-40, 15-35, 15-30, or 15-25 nucleobases. In some embodiments, provided oligonucleotides comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 10, 11, 12, 13, 14, 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15, 16, 17, 18, 19, 20, 21, 22, 23, 24, 25, 26, 27, 28, 29, 30, 35, 40, 45, or 50 nucleobases. In some embodiments, provided oligonucleotides comprise at least 15 nucleobases. In some embodiments, provided oligonucleotides comprise at least 16 nucleobases. In some embodiments, provided oligonucleotides comprise at least 17 nucleobases. In some embodiments, provided oligonucleotides comprise at least 18 nucleobases. In some embodiments, provided oligonucleotides comprise at least 19 nucleobases. In some embodiments, provided oligonucleotides comprise at least 20 nucleobases. In some embodiments, provided oligonucleotides comprise at least 21 nucleobases. In some embodiments, provided oligonucleotides comprise at least 22 nucleobases. In some embodiments, provided oligonucleotides comprise at least 23 nucleobases. In some embodiments, provided oligonucleotides comprise at least 24 nucleobases. In some embodiments, provided oligonucleotides comprise at least 25 nucleobases. In some embodiments, a nucleobase is optionally substituted adenine, cytosine, guanosine, thymine, or uracil, or a tautomer thereof.

In some embodiments, each chiral linkage phosphorus independently has a diastereomeric purity as described in the present disclosure. In some embodiments, a provided compound has a purity, diastereomeric purity, and/or enantiomeric purity as described in the present disclosure. In some embodiments, a provided compound has a purity as described in the present disclosure. In some embodiments, a provided compound has a diastereomeric purity as described in the present disclosure. In some embodiments, a provided compound has an enantiomeric purity as described in the present disclosure. In some embodiments, a provided compound has a diastereomeric purity and an enantiomeric purity as described in the present disclosure.

In some embodiments, provided oligonucleotides comprise or are of a 5'-wing region-core region-3'-wing region structure. In some embodiments, provided oligonucleotides comprise or are of a 5'-wing region-core region structure. In some embodiments, provided oligonucleotides comprise or are of a core region-3'-wing region structure. In some embodiments, provided oligonucleotides comprise of a 5'-wing region-core region-3'-wing region structure. In some embodiments, provided oligonucleotides comprise of a 5'-wing region-core region structure. In some embodiments, provided oligonucleotides comprise of a core region-3'-wing region structure. In some embodiments, provided oligonucleotides are of a 5'-wing region-core region-3'-wing region structure. In some embodiments, provided oligonucleotides are of a 5'-wing region-core region structure. In some embodiments, provided oligonucleotides are of a core region-3'-wing region structure. In some embodiments, a wing-core-wing (i.e., X—Y—X) motif is represented numerically as, e.g., 5-10-4, meaning 5'-wing region is 5 bases in length, the core region is 10 bases in length, and the 3'-wing region is 4-bases in length. In some embodiments, a wing-core-wing motif is any of, e.g. 2-16-2, 3-14-3, 4-12-4, 5-10-5, 2-9-6, 3-9-3, 3-9-4, 3-9-5, 4-7-4, 4-9-3, 4-9-4, 4-9-5, 4-10-5, 4-11-4, 4- 11-5, 5-7-5, 5-8-6, 8-7-5, 7-7-6, 5-9-3, 5-9-5, 5-10-4, 5-10-5, 6-7-6, 6-8-5, and 6-9-2, etc. In certain embodiments, a wing-core-wing motif is 5-10-5. In certain embodiments, a wing-core-wing motif is 7-7-6. In certain embodiments, a wing-core-wing motif is 8-7-5. In some embodiments, a wing-core motif is 5-15, 6-14, 7-13, 8-12, 9-12, etc. In some embodiments, a core-wing motif is 5-15, 6-14, 7-13, 8-12, 9-12, etc.

In some embodiments, a wing region comprises a sugar modification absent from a core region. In some embodiments, a wing region comprises a 2'-modification. In some embodiments, each nucleotide unit of a wing region independently comprises a 2'-modification. In some embodiments, each nucleotide unit of a wing region independently comprises the same 2'-modification. In some embodiments, each nucleotide unit of a 5'-wing region independently comprises the same 2'-modification. In some embodiments, each nucleotide unit of a 3'-wing region independently comprises the same 2'-modification. In some embodiments, 2'-modifications of the 5'-wing region are the same. In some embodiments, 2'-modifications of the 5'-wing region are the different. In some embodiments, a 2'-modification is 2'-OR, wherein R' is not hydrogen. In some embodiments, a 2'-modification is 2'-OR, wherein R' is optionally substituted $C_{1-6}$ aliphatic. In some embodiments, a 2'-modification is 2'-OR, wherein R' is optionally substituted $C_{1-6}$ alkyl. In some embodiments, a 2'-modification is 2'-OMe. In some embodiments, a 2'-modification is 2'-OCH$_2$CH$_2$OMe. In some embodiments, a wing region comprises one or more natural phosphate linkages as described in the present disclosure. Additionally or alternatively, in some embodiments, a wing region comprises one or more non-natural internucleotidic linkages, e.g., phosphorothioate internucleotidic linkages. In some embodiments, a core region comprises one or more natural phosphate linkages. In some embodiments, a core region comprises one or more consecutive natural phosphate linkages. In some embodiments, a core region comprises one or more chiral phosphate linkages. In some embodiments, a core region comprises one or more consecutive chiral phosphate linkages. In some embodiments, a chiral phosphate linkage is a phosphorothioate linkage. In some embodiments, a chiral phosphate linkage is a chirally controlled.

Oligonucleotides of the present disclosure may contain a pattern of backbone chiral centers. In some embodiments, a pattern of backbone chiral centers of oligonucleotides or segments thereof, e.g., core regions, provides increased stability. In some embodiments, a pattern of backbone chiral centers provides surprisingly increased activity. In some embodiments, a pattern of backbone chiral centers provides increased stability and activity. In some embodiments, a pattern of backbone chiral centers provides surprisingly increased binding to certain proteins. In some embodiments, a pattern of backbone chiral centers provides surprisingly enhanced delivery. In some embodiments, a pattern of backbone chiral centers comprises or is (Sp)m(Rp)n, (Rp)n(Sp)m, (Np)p(Rp)n(Sp)m, (Sp)p(Rp)n(Sp)m, (Sp)m(Op)n, (Op)n(Sp)m, (Np)p(Op)n(Sp)m, or (Sp)p(Op)n(Sp)m (unless otherwise specified, from 5' to 3'), wherein n is 1-10, and each of p and m is independently 0-50. In some embodiments, a pattern of backbone chiral centers comprises or is (Sp)m(Rp)n, (Rp)n(Sp)m, (Np)p(Rp)n(Sp)m, (Sp)p(Rp)n(Sp)m, (Sp)m(Op)n, (Op)n(Sp)m, (Np)p(Op)n(Sp)m, or (Sp)p(Op)n(Sp)m (unless otherwise specified, from 5' to 3'), wherein n is 1-10, and each of p and m is independently 1-50. In some embodiments, a pattern of backbone chiral centers comprises or is (Sp)m(Rp)n, (Rp)n(Sp)m, (Np)p(Rp)n(Sp)m, or (Sp)p(Rp)n(Sp)m (unless otherwise specified, from 5' to 3'), wherein n is 1-10, and each of p and m is independently 1-50. In some embodiments, a pattern of backbone chiral centers comprises (Sp)m(Rp)n, (Rp)n(Sp)m, (Np)p(Rp)n(Sp)m, or (Sp)p(Rp)n(Sp)m. In some embodiments, a pattern of backbone chiral centers comprises (Sp)m(Op)n, (Op)n(Sp)m, (Np)p(Op)n(Sp)m, or (Sp)p(Op)n(Sp)m. In some embodiments, a pattern of backbone chiral centers is (Sp)m(Rp)n, (Rp)n(Sp)m, (Np)p(Rp)n(Sp)m, or (Sp)p(Rp)n(Sp)m. In some embodiments, a pattern of backbone chiral centers is (Sp)m(Op)n, (Op)n(Sp)m, (Np)p(Op)n(Sp)m, or (Sp)p(Op)n(Sp)m. In some embodiments, a pattern of backbone chiral centers comprises or is a repeating pattern comprising or being of (Sp)m(Rp)n, (Rp)n(Sp)m, (Np)p(Rp)n(Sp)m, or (Sp)p(Rp)n(Sp)m. In some embodiments, a pattern of backbone chiral centers comprises or is a repeating pattern of (Sp)m(Rp)n, (Rp)n(Sp)m, (Np)p(Rp)n(Sp)m, or (Sp)p(Rp)n(Sp)m (from 5' to 3'). In some embodiments, a pattern of backbone chiral centers comprises or is a repeating pattern comprising or being of (Sp)m(Op)n, (Op)n(Sp)m, (Np)p(Op)n(Sp)m, or (Sp)p(Op)n(Sp)m. In some embodiments, a pattern of backbone chiral centers comprises or is a repeating pattern of (Sp)m(Op)n, (Op)n(Sp)m, (Np)p(Op)n(Sp)m, or (Sp)p(Op)n(Sp)m (from 5' to 3').

In some embodiments, a pattern of backbone chiral centers comprises or is (Rp)n(Sp)m, (Np)p(Rp)n(Sp)m, or (Sp)p(Rp)n(Sp)m, wherein m>2. In some embodiments, a pattern of backbone chiral centers comprises or is (Rp)n(Sp)m, (Np)p(Rp)n(Sp)m, or (Sp)p(Rp)n(Sp)m, wherein n is 1, p>1, and m>2. In some embodiments, m>3. In some embodiments, m>4. In some embodiments, a pattern of backbone chiral centers comprises or is (Op)n(Sp)m, (Np)p(Op)n(Sp)m, or (Sp)p(Op)n(Sp)m, wherein m>2. In some embodiments, a pattern of backbone chiral centers comprises or is (Op)n(Sp)m, (Np)p(Op)n(Sp)m, or (Sp)p(Op)n(Sp)m, wherein n is 1, p>1, and m>2. In some embodiments, m>3. In some embodiments, m>4. In some embodiments, a pattern of backbone chiral centers of an oligonucleotide or a region thereof comprises or is two or more units independently selected from (Rp)n(Sp)m, (Np)p(Rp)n(Sp)m, (Sp)p(Rp)n(Sp)m, (Op)n(Sp)m, (Np)p(Op)n(Sp)m, and (Sp)p(Op)n(Sp)m, wherein each variable is independently as described in the present disclosure. In some embodiments, n is 1. In some embodiments, n is 1 and m of each unit is independently 2 or greater as described in the present disclosure. In some embodiments, at least two m of two units are different. In some embodiments, a pattern of backbone chiral centers comprises 2, 3, 4, 5, 6, 7, 8, 9, or 10 such units. In some embodiments, a pattern of backbone chiral centers comprises 2 and no more than 2 such units. In some embodiments, a pattern of backbone chiral centers comprises 3 and no more than 3 such units. In some embodiments, a pattern of backbone chiral centers comprises 4 and no more than 4 such units. In some embodiments, a pattern of backbone chiral centers comprises 5 and no more than 5 such units. In some embodiments, a region of an oligonucleotide comprises such a pattern of backbone chiral centers. In some embodiments, such a region comprises no 2'-substitution at its sugar moieties (two 2'-H). In some embodiments, such a region is flanked by a 5'-region comprising a sugar modification as described in the present disclosure (e.g., a 2'-modification, e.g., 2'-OMe, 2'-MOE, 2'-F, etc., as described in the present disclosure), and/or a 5'-region comprising a sugar modification as described in the present disclosure (e.g., a 2'-modification, e.g., 2'-OMe, 2'-MOE, 2'-F, etc., as described in the present disclosure).

In some embodiments, a pattern of backbone chiral centers comprises or is (Rp)n(Sp)m, (Sp)p(Rp)n, (Np)p(Rp)n(Sp)m, (Sp)p(Sp)m or (Sp)p(Rp)n(Sp)m. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2% modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-F modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-OR modifications as described herein. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and the oligonucleotides comprise one or more 2'-OR modifications, wherein R is not —H. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-modifications. In some embodiments, a pattern of backbone chiral centers comprises or is (Rp)n(Sp)m, (Sp)p(Rp)n, (Np)p(Rp)n(Sp)m, or (Sp)p(Rp)n(Sp)m, and each nucleoside unit between internucleotidic linkages having the pattern of (Rp)n(Sp)m, (Sp)p(Rp)n, (Np)p(Rp)n(Sp)m, or (Sp)p(Rp)n(Sp)m comprises no 2'-substitutions (—CH$_2$— at 2'-position). In some embodiments, a pattern of backbone chiral centers comprises or is (Rp)n(Sp)m. In some embodiments, a pattern of backbone chiral centers comprises or is (Sp)p(Rp)n. In some embodiments, a pattern of backbone chiral centers comprises or is (Np)p(Rp)n(Sp)m. In some embodiments, a pattern of backbone chiral centers comprises (Rp)n(Sp)m. In some embodiments, a pattern of backbone chiral centers comprises (Sp)p(Rp)n. In some embodiments, a pattern of backbone chiral centers comprises (Np)p(Rp)n(Sp)m. In some embodiments, a pattern of backbone chiral centers is (Rp)n(Sp)m. In some embodiments, a pattern of backbone chiral centers is (Sp)p(Rp)n. In some embodiments, a pattern of backbone chiral centers is (Np)p(Rp)n(Sp)m. In some embodiments, a pattern of backbone chiral centers comprises or is (Sp)p(Sp)m, optionally with n achiral phosphate diester internucleotidic linkages and/or stereorandom (non-chirally controlled) chiral internucleotidic linkages between the section having (Sp)p and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)p(Rp)n(Sp)m.

In some embodiments, a pattern of backbone chiral centers comprises or is (Op)n(Sp)m, (Sp)p(Op)n, (Np)p(Op)n (Sp)m, (Sp)p(Sp)m or (Sp)p(Op)n(Sp)m. In some embodiments, a pattern of backbone chiral centers comprises or is (Op)n(Sp)m, (Sp)p(Op)n, (Np)p(Op)n(Sp)m, or (Sp)p(Op) n(Sp)m, and the oligonucleotides comprise one or more 2'-modifications as described herein. In some embodiments, a pattern of backbone chiral centers comprises or is (Op)n (Sp)m, (Sp)p(Op)n, (Np)p(Op)n(Sp)m, or (Sp)p(Op)n(Sp) m, and the oligonucleotides comprise one or more 2'-F modifications as described herein. In some embodiments, a pattern of backbone chiral centers comprises or is (Op)n (Sp)m, (Sp)p(Op)n, (Np)p(Op)n(Sp)m, or (Sp)p(Op)n(Sp) m, and the oligonucleotides comprise one or more 2'-OR modifications as described herein. In some embodiments, a pattern of backbone chiral centers comprises or is (Op)n (Sp)m, (Sp)p(Op)n, (Np)p(Op)n(Sp)m, or (Sp)p(Op)n(Sp) m, and the oligonucleotides comprise one or more 2'-OR modifications, wherein R is not —H. In some embodiments, a pattern of backbone chiral centers comprises or is (Op)n (Sp)m, (Sp)p(Op)n, (Np)p(Op)n(Sp)m, or (Sp)p(Op)n(Sp) m, and each nucleoside unit between internucleotidic linkages having the pattern of (Op)n(Sp)m, (Sp)p(Op)n, (Np)p (Op)n(Sp)m, or (Sp)p(Op)n(Sp)m comprises no 2'-modifications. In some embodiments, a pattern of backbone chiral centers comprises or is (Op)n(Sp)m, (Sp)p(Op)n, (Np)p(Op)n(Sp)m, or (Sp)p(Op)n(Sp)m, and each nucleoside unit between internucleotidic linkages having the pattern of (Op)n(Sp)m, (Sp)p(Op)n, (Np)p(Op)n(Sp)m, or (Sp) p(Op)n(Sp)m comprises no 2'-substitutions (—CH$_2$— at 2'-position). In some embodiments, a pattern of backbone chiral centers comprises or is (Op)n(Sp)m. In some embodiments, a pattern of backbone chiral centers comprises or is (Sp)p(Op)n. In some embodiments, a pattern of backbone chiral centers comprises or is (Np)p(Op)n(Sp)m. In some embodiments, a pattern of backbone chiral centers comprises (Op)n(Sp)m. In some embodiments, a pattern of backbone chiral centers comprises (Sp)p(Op)n. In some embodiments, a pattern of backbone chiral centers comprises (Np)p(Op)n(Sp)m. In some embodiments, a pattern of backbone chiral centers is (Op)n(Sp)m. In some embodiments, a pattern of backbone chiral centers is (Sp)p(Op)n. In some embodiments, a pattern of backbone chiral centers is (Np)p(Op)n(Sp)m. In some embodiments, a pattern of backbone chiral centers comprises or is (Sp)p(Sp)m, optionally with n achiral phosphate diester internucleotidic linkages and/or stereorandom (non-chirally controlled) chiral internucleotidic linkages between the section having (Sp)p and the section having (Sp)m. In some embodiments, there are n achiral phosphate diester internucleotidic linkages in between. In some embodiments, there are n stereorandom chiral internucleotidic linkages in between. In some embodiments, a pattern of backbone chiral centers comprises or is (Sp)p(Op)n(Sp)m.

In some embodiments, an oligonucleotide, or a region thereof, comprises a pattern, or a repeating pattern, of backbone chiral centers of (Sp)m(Rp)n, (Rp)n(Sp)m, (Np) p(Rp)n(Sp)m, or (Sp)p(Rp)n(Sp)m (structurally starting from the first, and ending at the last, internucleotidic linkage of the internucleotidic linkages which have the pattern, or the repeating pattern, of (Sp)m(Rp)n, (Rp)n(Sp)m, (Np)p (Rp)n(Sp)m, or (Sp)p(Rp)n(Sp)m, respectively; a "(repeating) (Sp)m(Rp)n region", a "(repeating) (Rp)n(Sp)m region", a "(repeating) (Np)p(Rp)n(Sp)m region", or a "(repeating) (Sp)p(Rp)n(Sp)m region", respectively, depending on repeating or not). In some embodiments, an oligonucleotide, or a region thereof, comprises a pattern, or a repeating pattern, of backbone chiral centers of (Sp)m(Op)n, (Op)n (Sp)m, (Np)p(Op)n(Sp)m, or (Sp)p(Op)n(Sp)m (structurally starting from the first, and ending at the last, internucleotidic linkage of the internucleotidic linkages which have the pattern, or the repeating pattern, of (Sp)m(Op)n, (Op)n(Sp) m, (Np)p(Op)n(Sp)m, or (Sp)p(Op)n(Sp)m, respectively; a "(repeating) (Sp)m(Rp)n region", a "(repeating) (Op)n (Sp)m region", a "(repeating) (Np)p(Op)n(Sp)m region", or a "(repeating) (Sp)p(Op)n(Sp)m region", respectively, depending on repeating or not). For example, a (Sp)p(Rp) n(Sp)m region ((Sp)7(Rp)1(Sp)3) in WV-2555: mA*SmGmCmUmU*SC*ST*T*SG*ST*SC*SC*RA* SG*SC*SmUmUmUmA*SmU (SEQ ID NO: 1)) comprises no 2'-OR sugar modifications. In some embodiments, each sugar moieties in the region is —CH$_2$— at the 2'-position. In some embodiments, each sugar moieties in the region is an unmodified, natural, 2'-deoxyribose moiety of DNA. In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-wing region, which structurally ends with a nucleoside moiety (which nucleoside moiety, at its 3'-end, is connected to the first internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m). For example, a flanking 5'-wing region in WV-2555: mA*SmGmCmUmU*SC*ST*ST*SG*ST*SC*SC*RA*SG*SC*SmUmUmUmA*SmU (SEQ ID NO: 1)). In some embodiments, a region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m is flanked by a 5'-wing region, which structurally ends with a nucleoside moiety (which nucleoside moiety, at its 3'-end, is connected to the first internucleotidic linkage of the region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m). In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 3'-wing region, which structurally starts with a nucleoside moiety (which nucleoside moiety, at its 5'-end, is connected to the last internucleotidic linkage of the region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m). For example, a flanking 3'-wing region in WV-2555: mA*SmGmCmUmU*SC*ST*ST*SG*ST*SC*SC*RA*SG*SC*SmUmUmUmA*SmU (SEQ ID NO: 1)). In some embodiments, a region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m is flanked by a 3'-wing region, which structurally starts with a nucleoside moiety (which nucleoside moiety, at its 5'-end, is connected to the last internucleotidic linkage of the region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m). In some embodiments, a region comprising a pattern, or a repeating pattern, of backbone chiral centers which comprises or is (Sp)m(Rp)n, (Rp)n(Sp)m, (Np)p(Rp)n(Sp)m, or (Sp)p(Rp)n(Sp)m is flanked by a 5'-end and a 3'-wing regions. In some embodiments, a region comprising a pattern, or a repeating pattern, of backbone chiral centers which comprises or is (Sp)m(Op)n, (Op)n(Sp)m, (Np)p(Op)n(Sp)m, or (Sp)p(Op)n(Sp)m is flanked by a 5'-end and a 3'-wing regions. In some embodiments, the flanking 5'-wing region and/or the 3'-wing region comprise a non-natural internucleotidic linkage. In some embodiments, the flanking 5'-wing region and/or the 3'-wing region comprise a chiral internucleotidic linkage. In some embodiments, the flanking 5'-wing region and/or the 3'-wing region comprise a chirally controlled internucleotidic linkage. In some embodiments, the flanking 5'-wing region and/or the 3'-wing region comprise a modified internucleotidic linkage comprising a Sp linkage phosphorus. In some embodiments, the flanking 5'-wing region and/or the 3'-wing region comprise a Sp phosphorothioate linkage. In some embodiments, the flanking 5'-wing region and/or the 3'-wing region comprise one or more natural phosphate linkages. In some embodiments, the flanking 5'-wing region and/or the 3'-wing region comprise one or more consecutive natural phosphate linkages. In some embodiments, the flanking 5'-end comprises only one modified internucleotidic linkage which is the 5'-end internucleotidic linkage, and one or more consecutive natural phosphate linkages (for example, in WV-2555: mA*SmGmCmUmU*SC*ST*ST*SG*ST*SC*SC*RA*SG*SC*SmUmUmUmA*SmU (SEQ ID NO: 1) (SOOOSSSSSSSRSSSOOOS)). In some embodiments, the flanking 3'-end comprises only one modified internucleotidic linkage which is the 3'-end internucleotidic linkage, and one or more consecutive natural phosphate linkages (for example, in WV-2555: mA*SmGmCmUmU*SC*ST*ST*SG*ST*SC*SC*RA*SG*SC*SmUmUmUmA*SmU (SEQ ID NO: 1) (SOOOSSSSSSSRSSSOOOS)). In some embodiments, the flanking 5'-wing region and/or the 3'-wing region comprise 2'-modified sugar units. In some embodiments, each sugar unit in the 5'-wing region and/or the 3'-wing region is independently modified. In some embodiments, each sugar unit in the 5'-wing region and/or the 3'-wing region independently comprises a 2'-modification (for example, m, 2'-OMe in WV-2555: mA*SmGmCmUmU*SC*ST*ST*SG*ST*SC*SC*RA*SG*SC*SmUmUmUmA*SmU (SEQ ID NO: 1)). In some embodiments, each sugar unit in the 5'-wing region and/or the 3'-wing region comprises the same 2'-modification. In some embodiments, a 2'-modification is 2'-OR, wherein R is optionally substituted $C_{1-6}$ aliphatic. In some embodiments, a 2'-modification is 2'-OMe. In some embodiments, a 2'-modification is 2'-MOE. In some embodiments, a 2'-modification is a LNA modification (which comprises a type of C2-C4 bridge).

In some embodiments, n is 1-10. In some embodiments, n is 1, 2, 3, 4, 5, 6, 7 or 8. In some embodiments, n is 1. In some embodiments, n is 2, 3, 4, 5, 6, 7 or 8. In some embodiments, n is 3, 4, 5, 6, 7 or 8. In some embodiments, n is 4, 5, 6, 7 or 8. In some embodiments, n is 5, 6, 7 or 8. In some embodiments, n is 6, 7 or 8. In some embodiments, n is 7 or 8. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is 1. In some embodiments, m is at least 2, 3, 4, 5, 6, 7, 8, 9, 10, 11, 12, 13, 14, or 15. In some embodiments, m is 2, 3, 4, 5, 6, 7, 8, 9, 10, 11, 12, 13, 14, or 15. In some embodiments, p is at least 2, 3, 4, 5, 6, 7, 8, 9, 10, 11, 12, 13, 14, or 15. In some embodiments, m is at least 2. In some embodiments, p is at least 2. In some embodiments, n is 1. In some embodiments, m is at least 2, p is at least 2, n is 1. In some embodiments, p is 2, 3, 4, 5, 6, 7, 8, 9, 10, 11, 12, 13, 14, or 15. In some embodiments, each of m and p is independently at least 2, 3, 4, 5, 6, 7, 8, 9, 10, 11, 12, 13, 14, or 15. In some embodiments, each of m and p is independently 2, 3, 4, 5, 6, 7, 8, 9, 10, 11, 12, 13, 14, or 15. In some embodiments, at least one of m and p is at least 5, 6, 7, 8, 9, 10, 11, 12, 13, 14, or 15. In some embodiments, m is at least 5, 6, 7, 8, 9, 10, 11, 12, 13, 14, or 15. In some embodiments, p is at least 5, 6, 7, 8, 9, 10, 11, 12, 13, 14, or 15.

In some embodiments, p is 0-50. In some embodiments, p is 1-50. In some embodiments, p is 1. In some embodiments, p is 2-50. In some embodiments, p is 2, 3, 4, 5, 6, 7 or 8. In some embodiments, p is 3, 4, 5, 6, 7 or 8. In some embodiments, p is 4, 5, 6, 7 or 8. In some embodiments, p is 5, 6, 7 or 8. In some embodiments, p is 6, 7 or 8. In some embodiments, p is 7 or 8. In some embodiments, p is 2. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10. In some embodiments, p is 11. In some embodiments, p is 12. In some embodiments, p is 13. In some embodiments, p is 14. In some embodiments, p is 15. In some embodiments, p is 16. In some embodiments, p is 17. In some embodiments, p is 18. In some embodiments, p is 19. In some embodiments, p is 20. In some embodiments, p is 21. In some embodiments, p is 22. In some embodiments, p is 23. In some embodiments, p is 24. In some embodiments, p is 25. In some embodiments, p is at least 2. In some embodiments, p is at least 3. In some embodiments, p is at least 4. In some embodiments, p is at least 5. In some embodiments, p is at least 6. In some embodiments, p is at least 7. In some embodiments, p is at least 8. In some embodiments, p is at least 9. In some embodiments, p is at least 10. In some embodiments, p is at least 11. In some embodiments, p is at least 12. In some embodiments, p is at least 13. In some embodiments, p is at least 14. In some embodiments, p is at least 15. In some embodiments, p is at least 16. In some embodiments, p is at least 17. In some embodiments, p is at least 18. In some embodiments, p is at least 19. In some embodiments, p is at least 20. In some embodiments, p is at least 21. In some embodiments, p is at least 22. In some embodiments, p is at least 23. In some embodiments, p is at least 24. In some embodiments, p is at least 25.

In some embodiments, m is 0-50. In some embodiments, m is 1-50. In some embodiments, m is 1. In some embodiments, m is 2-50. In some embodiments, m is 2, 3, 4, 5, 6, 7 or 8. In some embodiments, m is 3, 4, 5, 6, 7 or 8. In some embodiments, m is 4, 5, 6, 7 or 8. In some embodiments, m is 5, 6, 7 or 8. In some embodiments, m is 6, 7 or 8. In some embodiments, m is 7 or 8. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20. In some embodiments, m is 21. In some embodiments, m is 22. In some embodiments, m is 23. In some embodiments, m is 24. In some embodiments, m is 25. In some embodiments, m is at least 2. In some embodiments, m is at least 3. In some embodiments, m is at least 4. In some embodiments, m is at least 5. In some embodiments, m is at least 6. In some embodiments, m is at least 7. In some embodiments, m is at least 8. In some embodiments, m is at least 9. In some embodiments, m is at least 10. In some embodiments, m is at least 11. In some embodiments, m is at least 12. In some embodiments, m is at least 13. In some embodiments, m is at least 14. In some embodiments, m is at least 15. In some embodiments, m is at least 16. In some embodiments, m is at least 17. In some embodiments, m is at least 18. In some embodiments, m is at least 19. In some embodiments, m is at least 20. In some embodiments, m is at least 21. In some embodiments, m is at least 22. In some embodiments, m is at least 23. In some embodiments, m is at least 24. In some embodiments, m is at least 25. In some embodiments, m is at least greater than 25.

In some embodiments, at least one of m and p is greater than 2. In some embodiments, at least one of m and p is greater than 3. In some embodiments, at least one of m and p is greater than 4. In some embodiments, at least one of m and p is greater than 5. In some embodiments, at least one of m and p is greater than 6. In some embodiments, at least one of m and p is greater than 7. In some embodiments, at least one of m and p is greater than 8. In some embodiments, at least one of m and p is greater than 9. In some embodiments, at least one of m and p is greater than 10. In some embodiments, at least one of m and p is greater than 11. In some embodiments, at least one of m and p is greater than 12. In some embodiments, at least one of m and p is greater than 13. In some embodiments, at least one of m and p is greater than 14. In some embodiments, at least one of m and p is greater than 15. In some embodiments, at least one of m and p is greater than 16. In some embodiments, at least one of m and p is greater than 17. In some embodiments, at least one of m and p is greater than 18. In some embodiments, at least one of m and p is greater than 19. In some embodiments, at least one of m and p is greater than 20. In some embodiments, at least one of m and p is greater than 21. In some embodiments, at least one of m and p is greater than 22. In some embodiments, at least one of m and p is greater than 23. In some embodiments, at least one of m and p is greater than 24. In some embodiments, at least one of m and p is greater than 25.

In some embodiments, each of m and p is greater than 2. In some embodiments, each of m and p is greater than 3. In some embodiments, each of m and p is greater than 4. In some embodiments, each of m and p is greater than 5. In some embodiments, each of m and p is greater than 6. In some embodiments, each of m and p is greater than 7. In some embodiments, each of m and p is greater than 8. In some embodiments, each of m and p is greater than 9. In some embodiments, each of m and p is greater than 10. In some embodiments, each of m and p is greater than 11. In some embodiments, each of m and p is greater than 12. In some embodiments, each of m and p is greater than 13. In some embodiments, each of m and p is greater than 14. In some embodiments, each of m and p is greater than 15. In some embodiments, each of m and p is greater than 16. In some embodiments, each of m and p is greater than 17. In some embodiments, each of m and p is greater than 18. In some embodiments, each of m and p is greater than 19. In some embodiments, each of m and p is greater than 20.

In some embodiments, the sum of m and p is greater than 3. In some embodiments, the sum of m and p is greater than 4. In some embodiments, the sum of m and p is greater than 5. In some embodiments, the sum of m and p is greater than 6. In some embodiments, the sum of m and p is greater than 7. In some embodiments, the sum of m and p is greater than 8. In some embodiments, the sum of m and p is greater than 9. In some embodiments, the sum of m and p is greater than 10. In some embodiments, the sum of m and p is greater than 11. In some embodiments, the sum of m and p is greater than 12. In some embodiments, the sum of m and p is greater than 13. In some embodiments, the sum of m and p is greater than 14. In some embodiments, the sum of m and p is greater than 15. In some embodiments, the sum of m and p is greater than 16. In some embodiments, the sum of m and p is greater than 17. In some embodiments, the sum of m and p is greater than 18. In some embodiments, the sum of m and p is greater than 19. In some embodiments, the sum of m and p is greater than 20. In some embodiments, the sum of m and p is greater than 21. In some embodiments, the sum of m and p is greater than 22. In some embodiments, the sum of m and p is greater than 23. In some embodiments, the sum of m and p is greater than 24. In some embodiments, the sum of m and p is greater than 25.

In some embodiments, n is 1, and at least one of m and p is greater than 1. In some embodiments, n is 1 and each of m and p is independently greater than 1. In some embodiments, m>n and p>n. In some embodiments, (Sp)m(Rp)n (Sp)p is (Sp)$_2$Rp(Sp)$_2$. In some embodiments, (Sp)m is (Sp)$_2$Rp(Sp)$_2$. In some embodiments, (Sp)m is SpRp(Sp)$_2$. In some embodiments, (Sp)m is (Np)tRp(Sp)m. In some embodiments, n(Sp)m is (Np)$_2$Rp(Sp)m. In some embodiments, n(Sp)m is (Rp)$_2$Rp(Sp)m. In some embodiments, n(Sp)m is (Sp)$_2$Rp(Sp)m. In some embodiments, n(Sp)m is RpSpRp(Sp)m. In some embodiments, n(Sp)m is SpRpRp(Sp)m. In some embodiments, n(Sp)m is SpRpSpSp. In some embodiments, (Sp)m is (Sp)$_2$Rp(Sp)$_2$. In some embodiments, (Sp)m is (Sp)$_3$Rp(Sp)$_3$. In some embodiments, (Sp)m is (Sp)$_4$Rp(Sp)$_4$. In some embodiments, (Sp)m is (Sp)tRp(Sp)$_5$. In some embodiments, (Sp)m is SpRp(Sp)$_5$. In some embodiments, (Sp)m is (Sp)$_2$Rp(Sp)$_5$. In some embodiments, (Sp)m is (Sp)$_3$Rp(Sp)$_5$. In some embodiments, (Sp)m is (Sp)$_4$Rp(Sp)$_5$. In some embodiments, (Sp)m is (Sp)$_5$Rp(Sp)$_5$.

In some embodiments, (Sp)m(Rp)n(Sp)p is (Sp)$_2$Rp(Sp)$_2$. In some embodiments, (Sp)m(Rp)n(Sp)p is (Sp)$_3$Rp(Sp)$_3$. In some embodiments, (Sp)m(Rp)n(Sp)p is (Sp)$_4$Rp(Sp)$_4$. In some embodiments, (Sp)m(Rp)n(Sp)p is (Sp)mRp(Sp)$_5$. In some embodiments, (Sp)m(Rp)n(Sp)p is (Sp)$_2$Rp(Sp)$_5$. In some embodiments, (Sp)m(Rp)n(Sp)p is (Sp)$_3$Rp(Sp)$_5$. In some embodiments, (Sp)m(Rp)n(Sp)p is (Sp)$_4$Rp(Sp)$_5$. In some embodiments, (Sp)m(Rp)n(Sp)p is (Sp)$_5$Rp(Sp)$_5$.

In some embodiments, provided oligonucleotides are blockmers. In some embodiments, provided oligonucleotide are altmers. In some embodiments, provided oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc., or patterns thereof. Example chemical modifications, stereochemistry and patterns thereof for a block and/or an alternating unit include but are not limited to those described in this disclosure, such as those described for an oligonucleotide, etc. In some embodiments, a blockmer comprises a pattern of . . . SS . . . RR . . . SS . . . RR . . . . In some embodiments, an altmer comprises a pattern of SRSRSRSR.

In some embodiments, a provided pattern of backbone chiral centers comprises repeating (Sp)m(Rp)n, (Rp)n(Sp)m, (Np)p(Rp)n(Sp)m, or (Sp)p(Rp)n(Sp)m units. In some embodiments, a repeating unit is (Sp)m(Rp)n. In some embodiments, a repeating unit is SpRp. In some embodiments, a repeating unit is SpSpRp. In some embodiments, a repeating unit is SpRpRp. In some embodiments, a repeating unit is RpRpSp. In some embodiments, a repeating unit is (Rp)n(Sp)m. In some embodiments, a repeating unit is (Np)p(Rp)n(Sp)m. In some embodiments, a repeating unit is (Sp)p(Rp)n(Sp)m.

In some embodiments, oligonucleotides of the present disclosure comprise base sequences, base modifications, sugar modifications, pattern of backbone linkages (internucleotidic linkages), and/or pattern of backbone chiral centers (e.g., of linkage phosphorus atoms) as described in US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, each of which is independently incorporated herein by reference.

Product oligonucleotides and compositions thereof are useful for many purposes, e.g., those described in US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, etc. In some embodiments, product oligonucleotides and compositions thereof prepared by provided technologies are those described in US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, etc. In some embodiments, product oligonucleotides and compositions thereof can modulate levels and/or functions of various products of nucleic acid sequences. In some embodiments, product oligonucleotides and compositions, particularly chirally controlled oligonucleotides and compositions, are useful for treating a variety of disease. In some embodiments, the present disclosure provides pharmaceutically acceptable salts of oligonucleotides. In some embodiments, oligonucleotide compositions are pharmaceutical compositions.

In some embodiments, a final product composition is a chirally controlled oligonucleotide composition of WV-887, WV-892, WV-896, WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, or WV-3546. In some embodiments, a final product composition is a chirally controlled oligonucleotide composition of WV-2603, WV-2595, WV-1510, WV-2378, WV-2380, WV-1092, WV-1497, WV-1085, WV-1086, or WV-2623.

In some embodiments, provided technologies comprise labeling of oligonucleotides, e.g., using isotopes. In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a first plurality, comprise one or more base modifications, sugar modifications, and/or internucleotidic linkage modifications, wherein the oligonucleotides contain an enriched level of an isotope. In some embodiments, an isotope is deuterium. In some embodiments, a hydrogen in a sugar is replaced by deuterium (e.g., at the 2' position of a 2'-deoxy). In some embodiments, a hydrogen in a base is replaced by deuterium. In some embodiments, a hydrogen in an internucleotidic linkage is replaced by deuterium. In some embodiments, provided oligonucleotides are labeled with deuterium (replacing —$^1$H with —$^2$H) at one or more positions. In some embodiments, replacement of a hydrogen with deuterium can improve the stability, activity, bioavailability, easy of use, convenience, efficacy, and/or systemic exposure of an oligonucleotide. In some embodiments, one or more $^1$H of an oligonucleotide or any moiety conjugated to the oligonucleotide (e.g., a targeting moiety, lipid, etc.) is substituted with $^2$H. Such oligonucleotides can be used in any composition or method described herein. In some embodiments, an oligonucleotide which targets HTT comprises one or more isotopes. In some embodiments, an oligonucleotide which targets dystrophin comprises one or more isotopes.

Chiral Auxiliaries

In some embodiments, provided technologies are particularly useful for preparing chirally controlled oligonucleotide composition with high crude purity and/or yield. In some embodiments, in chirally controlled (stereocontrolled/stereoselective) oligonucleotide synthesis, chiral auxiliaries are typically used to control stereochemistry of a formed linkage phosphorus chiral center. In some embodiments, the present disclosure provides compounds, e.g., of formula I, I-a, I-a-I, I-a-2, I-b, I-c, I-d, I-e, II, II-a, II-b, III, III-a, or III-b, or salts thereof, that may be utilized as chiral auxiliaries for oligonucleotide synthesis.

In some embodiments, the present disclosure provides a compound having the structure of formula I:

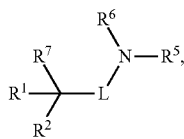

I or a salt thereof, wherein:

L is a covalent bond, or optionally substituted $C_{1-6}$ alkylene, wherein one or more methylene units are optionally and independently replaced with -L'-;

each L' is independently a covalent bond, optionally substituted bivalent $C_{1-3}$ alkylene, —$C(R^3)(R^4)$—, —$C(R^3)(R^4)$—, —$C(R^3)(R^4)$—, -Cy-, or —$C(R^3)[C(R^4)_3]$—;

each of $R^1$, $R^2$, $R^3$, $R^4$, and $R^5$ is independently —H, -$L^s$-R, halogen, —CN, —$NO_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

$R^6$ is R';

$R^7$ is —OH or —SH;

at least one of $R^1$, $R^2$, $R^3$ and $R^4$ is not —H;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, L is a covalent bond. In some embodiments, a provided compound has the structure of

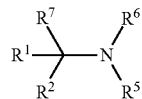

or a salt thereof. In some embodiments, $R^5$, and one or both of $R^1$ and $R^2$, are taken together with their intervening atoms to form an optionally substituted, 3-20 membered monocyclic, bicyclic or polycyclic ring having 1-5 heteroatoms. In some embodiments, one of $R^1$ and $R^2$ are taken together with $R^5$ and their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, L is —$C(R^3)(R^4)$—. In some embodiments, a provided compound has the structure of formula I-a:

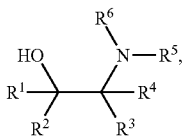

I-a or a salt thereof, wherein each variable is independently as described in the present disclosure. In some embodiments, a compound of formula I has the structure of formula I-a. In some embodiments, a provided compound has the structure of

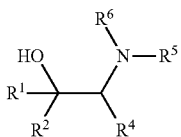

or a salt thereof, wherein each variable is independently as described in the present disclosure, wherein $R^4$ and $R^5$ are not hydrogen.

In some embodiments, a provided compound has the structure of formula (I-a-1):

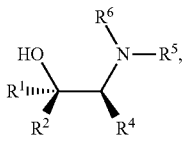

I-a-1 or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-1.

In some embodiments, a provided compound has the structure of formula (I-a-2):

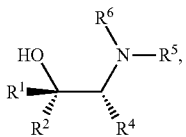

I-a-2 or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-2.

In some embodiments, $R^6$ is —H. In some embodiments, $R^6$ is —H, and $R^4$ and $R^5$ are taken together with their intervening atoms to form an optionally substituted 3-20 membered heterocyclyl ring having 1-5 heteroatoms. In some embodiments, $R^4$ and $R^5$ are taken together with their intervening atoms to form an optionally substituted 4-10 membered heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring is saturated. In some embodiments, a formed ring has no ring heteroatoms in addition to the nitrogen to which $R^5$ is attached.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is not hydrogen. In some embodiments, one of $R^1$ and $R^2$ is —H, and the other is optionally substituted $C_{1-6}$ aliphatic. In some embodiments, one of $R^1$ and $R^2$ is —H, and the other is optionally substituted $C_{1-4}$ aliphatic. In some embodiments, one of $R^1$ and $R^2$ is —H, and the other is optionally substituted $C_{1-3}$ aliphatic. In some embodiments, one of $R^1$ and $R^2$ is —H, and the other is optionally substituted $C_{1-2}$ aliphatic. In some embodiments, one of $R^1$ and $R^2$ is —H, and the other is optionally substituted $C_{1-6}$ alkenyl. In some embodiments, one of $R^1$ and $R^2$ is —H, and the other is vinyl. In some embodiments, one of $R^1$ and $R^2$ is —H, and the other is optionally substituted $C_{1-6}$ alkynyl. In some embodiments, one of $R^1$ and $R^2$ is —H, and the other is ethynyl. In some embodiments, one of $R^1$ and $R^2$ is —H, and the other is optionally substituted benzyl. In some embodiments, one of $R^1$ and $R^2$ is —H, and the other is benzyl wherein the phenyl group of the benzyl is optionally substituted. In some embodiments, R' is —H and $R^2$ is benzyl. In some embodiments, $R^1$ is —H and $R^2$ is —R, wherein R is as described in the present disclosure and is not hydrogen. In some embodiments, $R^2$ is optionally substituted $C_{1-6}$ aliphatic. In some embodiments, $R^2$ is optionally substituted —$CH_2$—$CPh_2Me$. In some embodiments, $R^2$ is —$CH_2$—$CPh_2Me$. In some embodiments, $R^2$ is optionally substituted phenyl. In some embodiments, $R^2$ is optionally substituted benzyl. In some embodiments, a provided compound is

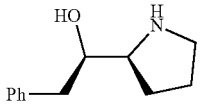

or a salt thereof.

In some embodiments, $R^1$ is not —H and $R^2$ is not —H. In some embodiments, $R^1$ and $R^2$ are independently R, wherein R is not —H. In some embodiments, $R^1$ is optionally substituted $C_{1-6}$ aliphatic, and $R^2$ is optionally substituted phenyl. In some embodiments, $R^1$ is methyl and $R^2$ is phenyl.

In some embodiments, one of $R^1$ and $R^2$ is R, wherein R comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted phenyl. In some embodiments, R is phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$ alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, one of $R^1$ and $R^2$ is optionally substituted $C_{1-6}$ alkyl, and the other is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is optionally substituted $C_{1-6}$ alkyl, and the other is optionally substituted $C_{1-6}$ alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same optionally substituted $C_{1-6}$ alkyl. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl. In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^2$ is optionally substituted benzyl. In some embodiments, $R^2$ is benzyl. In some embodiments, $R^2$ is p-$CH_3O$—$C_6H_4$—$CH_2$—. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl. In some embodiments, a provided compound is

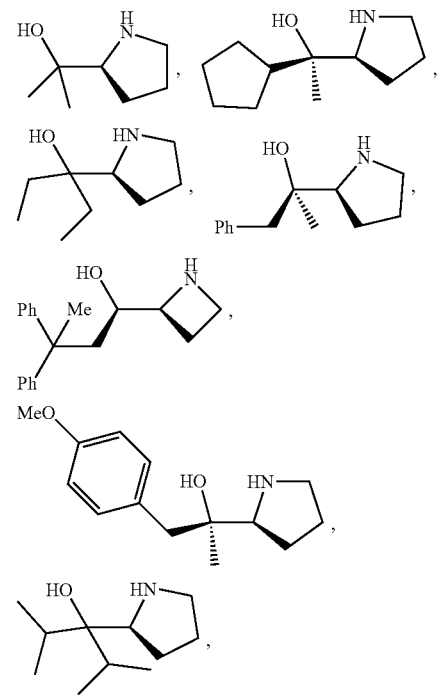

or a salt thereof. In some embodiments, a provided compound is

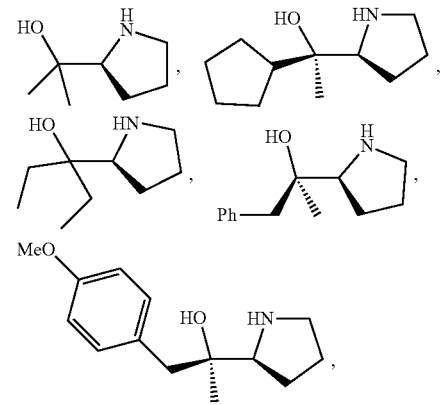

or a salt thereof. In some embodiments, a provided compound is

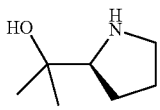

or a salt thereof. In some embodiments, a provided compound is

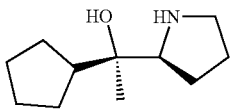

or a salt thereof. In some embodiments, a provided compound is

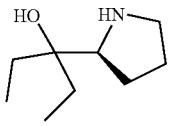

or a salt thereof. In some embodiments, a provided compound is

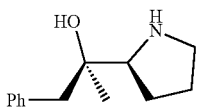

or a salt thereof. In some embodiments, a provided compound is

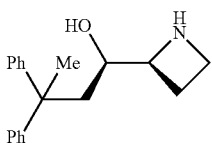

or a salt thereof. In some embodiments, a provided compound is

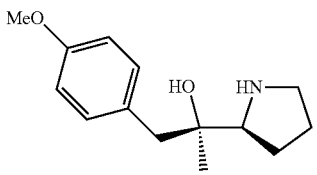 [SMILES: COc1ccc(C[C@@](C)(O)[C@@H]2CCCN2)cc1]

or a salt thereof. In some embodiments, a provided compound is

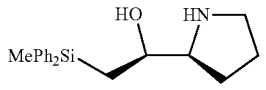

or a salt thereof. In some embodiments, a provided compound is

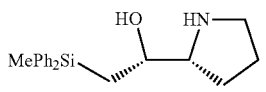

or a salt thereof. In some embodiments, a provided compound is

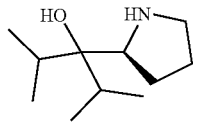

or a salt thereof.

In some embodiments, one of $R^1$ and $R^2$ is optionally substituted $C_{1-6}$ alkyl, and the other is optionally substituted phenyl. In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

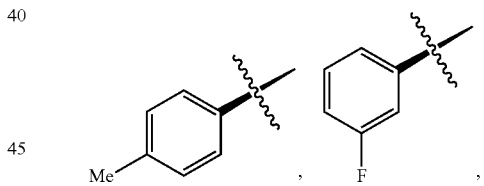

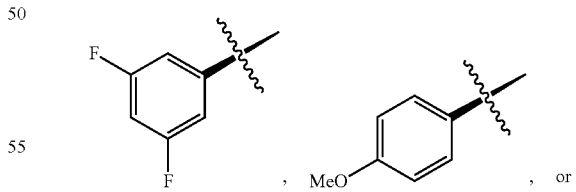

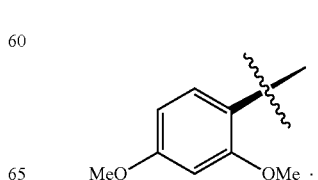

In some embodiments, a provided compound is selected from

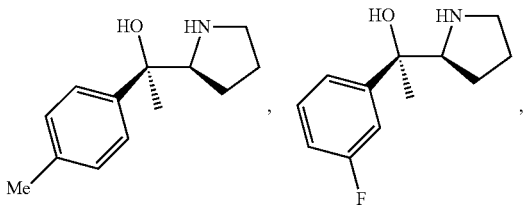

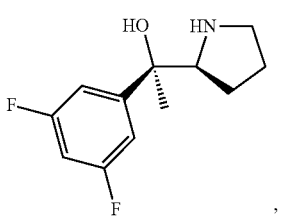

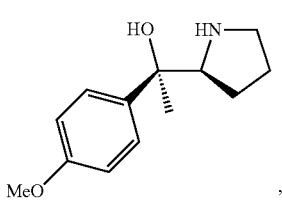

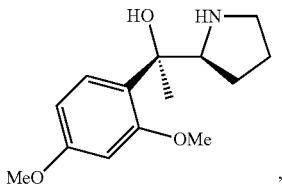

or salts thereof. In some embodiments, a provided compound is

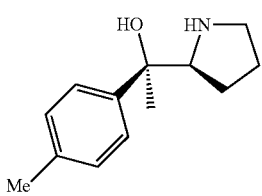

or a salt thereof. In some embodiments, a provided compound is

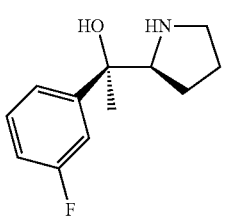

or a salt thereof. In some embodiments, a provided compound is

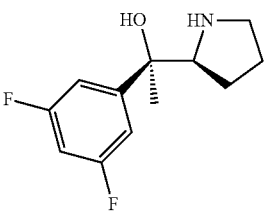 [SMILES: C[C@@](O)(c1cc(F)cc(F)c1)[C@@H]1CCCN1]

or a salt thereof. In some embodiments, a provided compound is

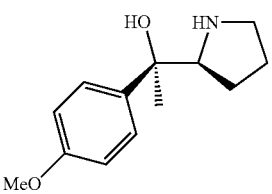 [SMILES: COc1ccc([C@@](C)(O)[C@@H]2CCCN2)cc1]

or a salt thereof. In some embodiments, a provided compound is

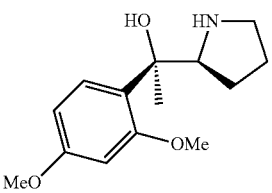 [SMILES: COc1ccc([C@@](C)(O)[C@@H]2CCCN2)c(OC)c1]

or a salt thereof.

In some embodiments, $R^1$ and $R^2$ are independently R, wherein R is an optionally substituted aryl group. In some embodiments, $R^1$ and $R^2$ are independently optionally substituted phenyl. In some embodiments, $R^1$ and $R^2$ are phenyl. In some embodiments, a provided compound is

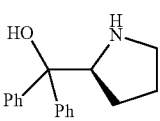

or a salt thereof.

In some embodiments, $R^1$ and $R^2$ are taken together with the carbon atom they are attached on to form an optionally substituted 3-20 membered monocyclic, bicyclic or polycyclic ring having 0-5 heteroatoms. In some embodiments, $R^1$ and $R^2$ are taken together with the carbon atom they are attached on to form an optionally substituted 3-7 membered monocyclic ring having no heteroatoms. In some embodiments, such a formed monocyclic ring is 3-membered; in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is monocyclic. In some embodiments, a formed ring is bicyclic. In some embodiments, a formed ring is polycyclic. In some embodiments, a formed ring is aliphatic.

In some embodiments, a formed ring comprises no unsaturation. In some embodiments, a formed ring is saturated, partially unsaturated, and/or partially aromatic, for example, a bicyclic or polycyclic ring comprising fused saturated, partially unsaturated, and/or aromatic moieties. In some embodiments, such a formed ring is substituted. In some embodiments, such a formed ring is not substituted. In some embodiments, the carbon to which $R^1$ and $R^2$ are attached is not chiral. In some embodiments, $R^1$ and $R^2$ are the same, and the carbon they are attached on is not chiral. In some embodiments, the ring formed by $R^1$ and $R^2$ taken together with the carbon atom they are attached on does not introduce asymmetry, and the carbon atom $R^1$ and $R^2$ attached on is not chiral. In some embodiments, $R^1$ and $R^2$ are different, and the carbon they are attached on is chiral. In some embodiments, the ring formed by $R^1$ and $R^2$ taken together with the carbon atom they are attached on introduces asymmetry, and the carbon atom $R^1$ and $R^2$ attached on is not chiral. In some embodiments, a provided compound is selected from

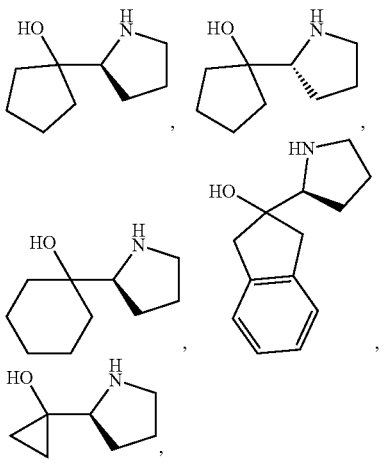

and salts thereof. In some embodiments, a provided compound is selected from

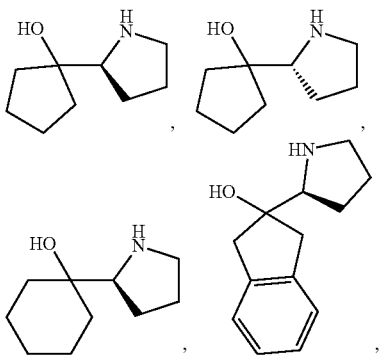

and salts thereof. In some embodiments, a provided compound is

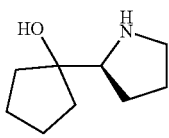

or a salt thereof. In some embodiments, a provided compound is

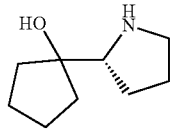 [SMILES: OC1([C@H]2CCCN2)CCCC1]

or a salt thereof. In some embodiments, a provided compound is

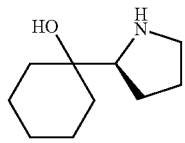 [SMILES: OC1([C@@H]2CCCN2)CCCCC1]

or a salt thereof. In some embodiments, a provided compound is

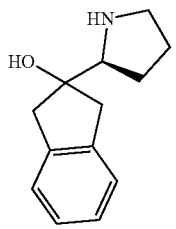 [SMILES: OC1([C@@H]2CCCN2)Cc2ccccc2C1]

or a salt thereof.

In some embodiments, $R^4$ and $R^5$ are taken together with their intervening atoms to form an optionally substituted 3-20 membered monocyclic, bicyclic or polycyclic ring having 1-5 heteroatoms. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^5$ are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are taken together with their intervening atoms to form an optionally substituted 4-7 membered monocyclic ring having a nitrogen atom (the one which $R^5$ is on). In some embodiments, $R^3$ is —H, and $R^4$ and $R^5$ are taken together with their intervening atoms to form an optionally substituted 4-membered monocyclic ring having a nitrogen atom (the one which $R^5$ is on). In some embodiments, $R^3$ is —H, and $R^4$ and $R^5$ are taken together with their intervening atoms to form an optionally substituted 5-membered monocyclic ring having a nitrogen atom (the one which $R^5$ is on). In some embodiments, $R^3$ is —H, and $R^4$ and $R^5$ are taken together with their intervening atoms to form an optionally substituted 6-membered monocyclic ring having a nitrogen atom (the one which $R^5$ is on). In some embodiments, $R^3$ is —H, and $R^4$ and $R^5$ are taken together with their intervening atoms to form an optionally substituted 7-membered monocyclic ring having a nitrogen atom (the one which $R^5$ is on). In some embodiments, $R^3$ is —H, and $R^4$ and $R^5$ are taken together with their intervening atoms to form an optionally substituted 8-membered monocyclic ring having a nitrogen atom (the one which $R^5$ is on). In some embodiments, $R^3$ is —H, and $R^4$ and $R^5$ are taken together with their intervening atoms to form an optionally substituted 9-membered monocyclic ring having a nitrogen atom (the one which $R^5$ is on). In some embodiments, $R^3$ is —H, and $R^4$ and $R^5$ are taken together with their intervening atoms to form an optionally substituted 10-membered monocyclic ring having a nitrogen atom (the one which $R^5$ is on). In some embodiments, a ring formed by $R^4$ and $R^5$ taken together with their intervening atoms is substituted. In some embodiments, a ring formed by $R^4$ and $R^5$ taken together with their intervening atoms is unsubstituted. In some embodiments, a ring formed by $R^4$ and $R^5$ taken together with their intervening atoms is monocyclic. In some embodiments, a ring formed by $R^4$ and $R^5$ taken together with their intervening atoms is bicyclic. In some embodiments, one of $R^1$ and $R^2$, and one of $R^3$ and $R^4$, are taken together with their intervening atoms to form an optionally substituted 3-20 membered monocyclic, bicyclic or polycyclic ring having 0-5 heteroatoms. In some embodiments, a formed ring is a 3-membered ring. In some embodiments, a formed ring is a 4-membered ring. In some embodiments, a formed ring is a 5-membered ring. In some embodiments, a formed ring is a 6-membered ring. In some embodiments, a formed ring is a 7-membered ring. In some embodiments, a formed ring is substituted. In some embodiments, a formed ring is unsubstituted. In some embodiments, a formed ring is monocyclic. In some embodiments, a formed ring is bicyclic. In some embodiments, a formed ring is polycyclic. In some embodiments, a formed ring has no additional heteroatoms in addition to an intervening atom. In some embodiments, a formed ring has additional ring heteroatoms in addition to an intervening atom. Example rings formed are extensively described in the present disclosure. In some embodiments, a provided compound is selected from

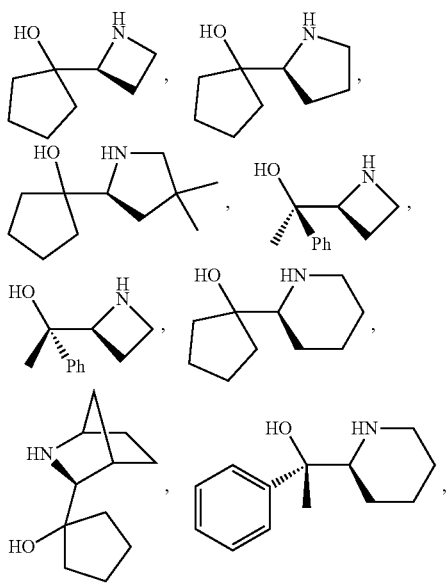

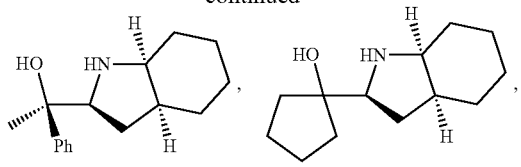

and salts thereof. In some embodiments, a provided compound is selected from

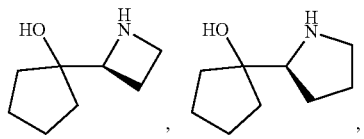

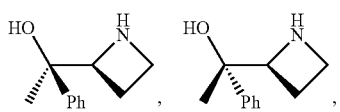

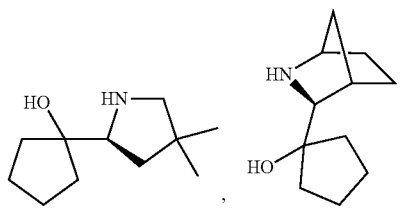

and salts thereof. In some embodiments, a provided compound is

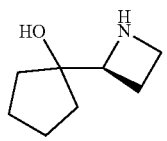

or a salt thereof. In some embodiments, a provided compound is

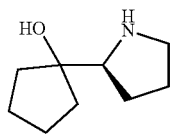

or a salt thereof. In some embodiments, a provided compound is

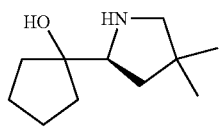

or a salt thereof. In some embodiments, a provided compound is

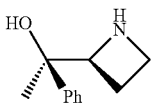

or a salt thereof. In some embodiments, a provided compound is

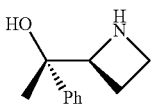

or a salt thereof. In some embodiments, a provided compound is

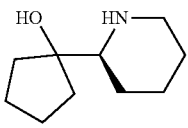 [SMILES: OC1([C@@H]2CCCCN2)CCCC1]

or a salt thereof. In some embodiments, a provided compound is

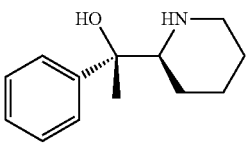

or a salt thereof. In some embodiments, a provided compound is

or a salt thereof. In some embodiments, a provided compound is

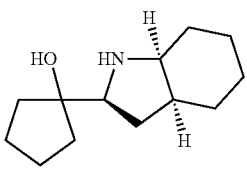 [SMILES: OC1([C@@H]2C[C@@H]3CCCC[C@@H]3N2)CCCC1]

or a salt thereof. In some embodiments, a provided compound is

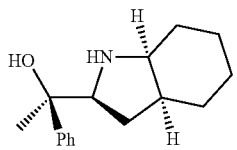 [SMILES: C[C@@](O)(c1ccccc1)[C@@H]1C[C@@H]2CCCC[C@@H]2N1]

or a salt thereof.

In some embodiments, one or two of $R^1$ and $R^2$ are taken together with one or more of $R^3$, $R^4$, and $R^5$ and the intervening atoms to form an optionally substituted 3-20 membered monocyclic, bicyclic or polycyclic ring having 0-5 heteroatoms. In some embodiments, one or two of $R^1$ and $R^2$ are taken together with one or two of $R^3$ and $R^4$ and the intervening atoms to form an optionally substituted 3-20 membered monocyclic, bicyclic or polycyclic ring having 0-5 heteroatoms. In some embodiments, one or two of $R^1$ and $R^2$ are taken together with $R^5$ and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 3-20 membered monocyclic, bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 6-20 membered bicyclic or polycyclic ring having 1-5 heteroatoms. In some embodiments, one or two of $R^1$ and $R^2$ are taken together with $R^5$, one or two of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic or polycyclic ring having 1-5 heteroatoms. In some embodiments, one of $R^1$ and $R^2$ are taken together with $R^5$, one of $R^3$ and $R^4$, and the intervening atoms to form an optionally substituted 8-20 membered bicyclic ring having 1-5 heteroatoms. In some embodiments, a formed ring is 8-membered. In some embodiments, a formed ring is 9-membered.

In some embodiments, $R^5$ is taken with one of $R^1$ and $R^2$ and their intervening atoms to form an optionally substituted 3-20 membered monocyclic, bicyclic or polycyclic ring having 1-5 heteroatoms. In some embodiments, $R^5$ is taken with one of $R^3$ and $R^4$ and their intervening atoms to form an optionally substituted 3-20 membered monocyclic, bicyclic or polycyclic ring having 1-5 heteroatoms. Example rings formed are extensively described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, $R^5$ is not taken with $R^1$, $R^2$, $R^3$, or $R^4$ to form an optionally substituted ring. In some embodiments, $R^5$ is optionally substituted $C_{1-6}$ aliphatic. In some embodiments, $R^5$ is optionally substituted $C_{1-6}$ alkyl. In some embodiments, $R^5$ is unsubstituted $C_{1-6}$ alkyl. In some embodiments, $R^5$ is methyl. In some embodiments, $R^5$ is ethyl. In some embodiments, $R^5$ is isopropyl.

In some embodiments, a provided compound is

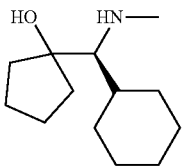

or a salt thereof. In some embodiments, a provided compound is

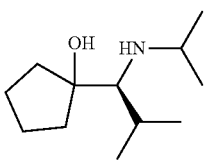

or a salt thereof. In some embodiments, a provided compound is

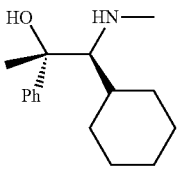 [SMILES: CN[C@@H](C1CCCCC1)[C@@](C)(O)c1ccccc1]

or a salt thereof.

In some embodiments, L is -L'-C(R$^3$)(R$^4$)—. In some embodiments, a provided compound has the structure of formula I-b:

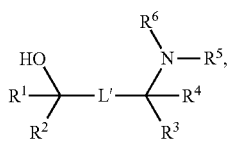

I-b or a salt thereof, wherein each variable is independently as described in the present disclosure. In some embodiments, a compound of formula I has the structure of formula I-b.

In some embodiments, L' is a covalent bond. In some embodiments, L' is —C(R$^3$)(R$^4$)—. In some embodiments, a provided compound has the structure of formula I-c:

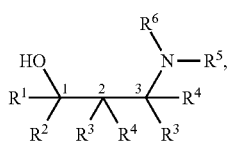

I-c or a salt thereof, wherein each variable is independently as described in the present disclosure. In some embodiments, a compound of formula I has the structure of formula I-c.

In some embodiments, one or R$^3$ and R$^4$ on C2 are taken together with R$^5$ to form with their intervening atoms to form an optionally substituted 3-20 membered monocyclic, bicyclic or polycyclic ring having a nitrogen atom (the one which R$^5$ is on). In some embodiments, one or R$^3$ and R$^4$ on C3 are taken together with R$^5$ to form with their intervening atoms to form an optionally substituted 3-20 membered monocyclic, bicyclic or polycyclic ring having a nitrogen atom (the one which R$^5$ is on). In some embodiments, one of R$^3$ and R$^4$ on C2, and one of R$^3$ and R$^4$ on C3, are taken together with their intervening atoms to form an optionally substituted 3-20 membered monocyclic, bicyclic or polycyclic ring having 0-5 heteroatoms. In some embodiments, R$^3$ and R$^4$ on the same carbon atom are taken together with the carbon atom to form an optionally substituted 3-20 membered monocyclic, bicyclic or polycyclic ring having 0-5 heteroatoms. In some embodiments, R$^3$ and R$^4$ on C2 are taken together with C2 to form an optionally substituted 3-20 membered monocyclic, bicyclic or polycyclic ring having 0-5 heteroatoms. In some embodiments, R$^3$ and R$^4$ on C3 are taken together with C3 to form an optionally substituted 3-20 membered monocyclic, bicyclic or polycyclic ring having 0-5 heteroatoms. Example such ring moieties, e.g., formed by R$^3$/R$^4$ and R$^5$, by R$^3$/R$^4$ and R$^3$/R$^4$, etc., are extensively described in the present disclosure, and can be e.g., 4-membered, 5-membered, 6-membered, 7-membered, monocyclic, bicyclic, polycyclic, substituted, unsubstituted, with additional ring heteroatoms (other than the intervening atom(s)), without additional ring heteroatoms, combinations thereof, etc.

In some embodiments, R$^3$ on C2 is hydrogen. In some embodiments, R$^4$ on C2 is hydrogen. In some embodiments, R$^3$ on C3 is hydrogen. In some embodiments, R$^4$ on C3 is hydrogen. In some embodiments, both R$^3$ and R$^4$ on C2 are hydrogen. In some embodiments, both R$^3$ and R$^4$ on C3 are hydrogen. In some embodiments, both R$^3$ and R$^4$ on C2, and one of R$^3$ and R$^4$ on C3, are hydrogen. In some embodiments, both R$^3$ and R$^4$ on C3, and one of R$^3$ and R$^4$ on C2, are hydrogen.

In some embodiments, a provided compound is

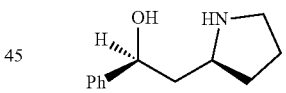

or a salt thereof.

In some embodiments, L is -Cy-. In some embodiments, a provided compound has the structure of formula I-d:

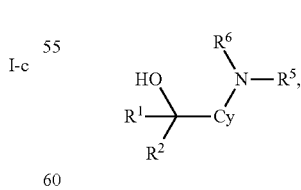

I-d or a salt thereof, wherein each variable is independently as described in the present disclosure. In some embodiments, a compound of formula I has the structure of formula I-d. In some embodiments, -Cy- is 1,2-bivalent. In some embodiments, -Cy- is optionally substituted cycloalkylene. In some embodiments, -Cy- is optionally substituted

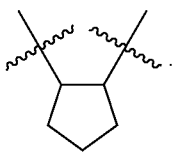 [SMILES: *C1CCCC1*]

In some embodiments, -Cy- is optionally substituted

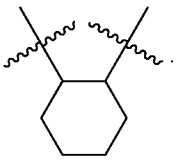 [SMILES: *C1CCCCC1*]

In some embodiments, one of $R^1$ and $R^2$, and one of $R^3$ and $R^4$, are R and are taken together with their intervening atoms to form an optionally substituted 3-20 membered ring having 1-10 heteroatoms as described in the present disclosure, e.g., Ring A as described herein. In some embodiments, a provided compound has the structure of formula I-e:

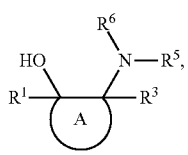

I-e or a salt thereof, wherein each variable is independently as described in the present disclosure. In some embodiments, a compound of formula I has the structure of formula I-e.

In some embodiments, one of $R^1$ and $R^2$, and $R^4$ are taken together with their intervening atoms to form an optionally substituted 3-20 membered ring having 1-5 heteroatoms. In some embodiments, $R^3$ is —H, one of $R^1$ and $R^2$, and $R^4$ are taken together with their intervening atoms to form an optionally substituted 3-20 membered ring having 1-5 heteroatoms. In some embodiments, $R^2$ and $R^4$ are taken together with their intervening atoms to form an optionally substituted ring (e.g., formula I-e). In some embodiments, a formed ring, e.g., Ring A in formula I-e, is 3, 4, 5, 6, 7, 8, 9, or 10-membered. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, a formed ring is monocyclic. In some embodiments, a formed ring is bicyclic. In some embodiments, a formed ring is polycyclic. In some embodiments, a formed ring is saturated. In some embodiments, a formed ring is partially unsaturated. In some embodiments, a formed ring has no heteroatoms. In some embodiments, a formed ring is an optionally substituted 3-membered saturated aliphatic ring. In some embodiments, a formed ring is an optionally substituted 4-membered saturated aliphatic ring. In some embodiments, a formed ring is an optionally substituted 5-membered saturated aliphatic ring. In some embodiments, a formed ring is an optionally substituted 6-membered saturated aliphatic ring. In some embodiments, a formed ring is an optionally substituted 7-membered saturated aliphatic ring. In some embodiments, a formed ring is an optionally substituted 8-membered saturated aliphatic ring. In some embodiments, a formed ring is an optionally substituted 9-membered saturated aliphatic ring. In some embodiments, a formed ring is an optionally substituted 10-membered saturated aliphatic ring.

In some embodiments, $R^3$ is —H, $R^1$ is optionally substituted $C_{1-6}$ aliphatic or phenyl, $R^5$ is optionally substituted $C_{1-6}$ aliphatic, and $R^6$ is —H. In some embodiments, $R^3$ is —H, $R^1$ and $R^5$ are taken together with their intervening atoms to form an optionally substituted ring, and $R^6$ is —H. In some embodiments, $R^3$ is —H, $R^1$ and $R^5$ are taken together with their intervening atoms to form an optionally substituted 5- or 6-membered ring, and $R^6$ is —H. In some embodiments, $R^3$ is —H, $R^1$ and $R^5$ are taken together with their intervening atoms to form an optionally substituted 5-membered saturated ring having no heteroatom in addition to the nitrogen to which $R^5$ is attached, and $R^6$ is —H. In some embodiments, $R^3$ is —H, $R^1$ and $R^5$ are taken together with their intervening atoms to form an optionally substituted 6-membered saturated ring having no heteroatom in addition to the nitrogen to which $R^5$ is attached, and $R^6$ is —H. In some embodiments, a ring formed by $R^1$ and $R^5$ taken together are unsubstituted.

In some embodiments, —OH and —N($R^5$)($R^6$) are trans. In some embodiments, —OH and —N($R^5$)($R^6$) are cis. In some embodiments, the carbon to which $R^1$ and —OH are attached is R. In some embodiments, the carbon to which $R^1$ and —OH are attached is S. In some embodiments, $R^1$ is hydrogen. In some embodiments, $R^1$ is not hydrogen. In some embodiments, $R^1$ is optionally substituted $C_{1-6}$ aliphatic or phenyl. In some embodiments, $R^1$ is methyl. In some embodiments, $R^1$ is phenyl. In some embodiments, $R^3$ is hydrogen. In some embodiments, $R^5$ is hydrogen. In some embodiments, $R^5$ is not hydrogen. In some embodiments, $R^5$ is optionally substituted $C_{1-6}$ aliphatic or phenyl. In some embodiments, $R^5$ is methyl. In some embodiments, $R^5$ is phenyl. In some embodiments, $R^6$ is hydrogen. In some embodiments, $R^6$ is not hydrogen. In some embodiments, as demonstrated by certain example data, compounds with trans —OH and —N($R^5$)($R^6$) can provide high yields and/or diastereoselectivity. In some embodiments, as demonstrated by certain example data, compounds with trans —OH and —N($R^5$)($R^6$) can provide both high yields and diastereoselectivity.

In some embodiments, a provided compound, e.g., a compound of formula I-e, is selected from

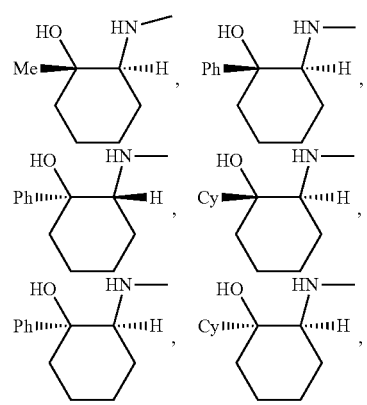

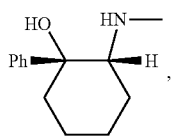

and salts thereof. In some embodiments, a provided compound is

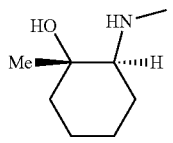

or a salt there of. In some embodiments, a provided compound is

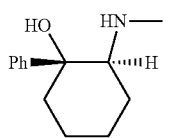

or a salt there of. In some embodiments, a provided compound is

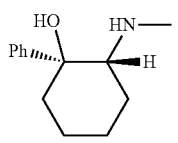

or a salt there of. In some embodiments, a provided compound is

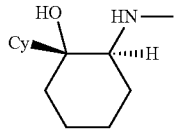

or a salt there of. In some embodiments, a provided compound is

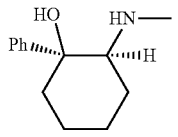

or a salt there of. In some embodiments, a provided compound is

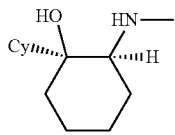

or a salt there of. In some embodiments, a provided compound is

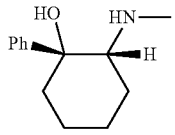

or a salt there of. In some embodiments, a provided compound is selected from

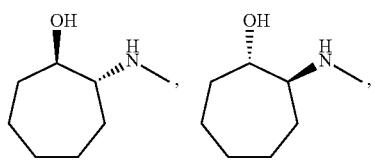

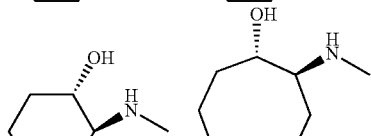

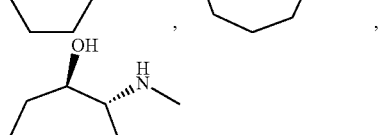

or salts thereof. In some embodiments, a provided compound is

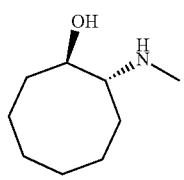

or a salt thereof. In some embodiments, a provided compound is

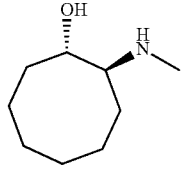

or a salt thereof. In some embodiments, a provided compound is

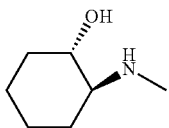

or a salt thereof. In some embodiments, a provided compound is

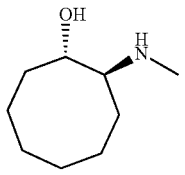

or a salt thereof. In some embodiments, a provided compound is

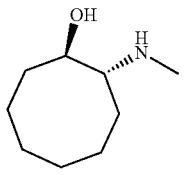

or a salt thereof.

In some embodiments, a provided compound has the structure of formula II:

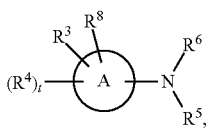

II or a salt thereof, wherein:

Ring A is an optionally substituted 3-20 membered monocyclic, bicyclic or polycyclic ring having 0-10 heteroatoms independently selected from oxygen, nitrogen, sulfur, phosphorus and silicon;

each of $R^1$, $R^2$, $R^3$, $R^4$, and $R^5$ is independently —H, -$L^s$-R, halogen, —CN, —NO$_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

t is 0-20;

$R^6$ is R';

$R^8$ is -L-$R^7$, -L-C($R^1$)($R^2$)—$R^7$, or -$L^s$-$R^7$;

$R^7$ is —OH or —SH;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula II-a:

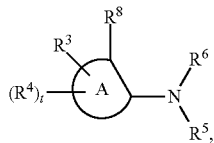

II-a or a salt thereof, wherein each variable is independently as described in the present disclosure. In some embodiments, a compound of formula II has the structure of formula II-a.

In some embodiments, a provided compound of structure II-a, has the structure of formula II-b:

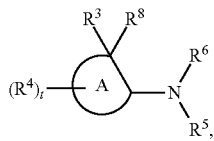

II-b or a salt thereof, wherein each variable is independently as described in the present disclosure. In some embodiments, a compound of formula II-a has the structure of formula II-b.

In some embodiments, a provided compound of structure II-a, has the structure of formula II-c:

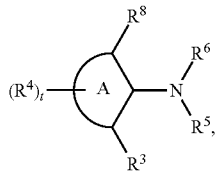

II-c or a salt thereof, wherein each variable is independently as described in the present disclosure. In some embodiments, a compound of formula II-a has the structure of formula II-c.

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A is an optionally substituted 3-20 membered monocyclic, bicyclic or polycyclic ring having 0-10 heteroatoms independently selected from oxygen, nitrogen, sulfur, phosphorus and silicon. In some embodiments, Ring A is or comprises at least one monocyclic saturated or partially unsaturated monocyclic ring moiety, optionally as part of a bicyclic or polycyclic system. In some embodiments, Ring A is monocyclic. In some embodiments, Ring A is bicyclic or polycyclic comprising at least one monocyclic saturated or partially unsaturated monocyclic ring moiety, and optionally one or more aromatic monocyclic moieties. In some embodiments, Ring A is or comprises at least one saturated monocyclic ring moiety. In some embodiments, $R^8$ is connected to a $sp^3$ ring atom of Ring A. In some embodiments, $R^8$ is connected to a $sp^3$ carbon ring atom of Ring A. In some embodiments, $R^3$ is connected to a $sp^3$ ring atom of Ring A. In some embodiments, $R^3$ is connected to a $sp^3$ carbon ring atom of Ring A. In some embodiments, —$N(R^5)(R^6)$ is connected to a $sp^3$ ring atom of Ring A. In some embodiments, —$N(R^5)(R^6)$ is connected to a $sp^3$ carbon ring atom of Ring A.

In some embodiments, Ring A is optionally substituted $C_{3-10}$ cycloalkyl. In some embodiments, Ring A is optionally substituted cyclohexyl. In some embodiments, Ring A is cyclohexyl. In some embodiments, $R^8$ and —$N(R^5)(R^6)$ are cis. In some embodiments, $R^8$ and —$N(R^5)(R^6)$ are trans. In some embodiments, a provided compound of formula II is selected from

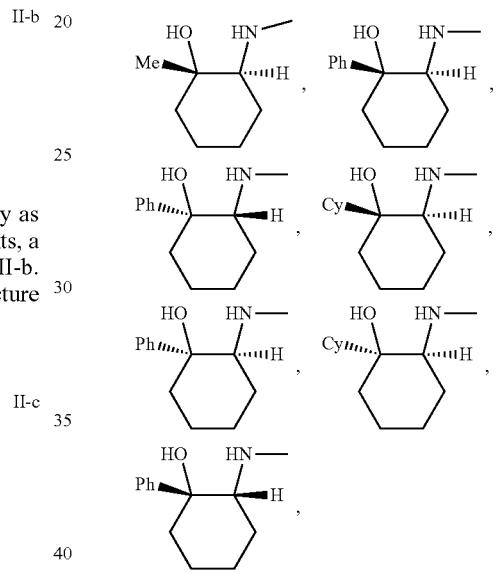

and salts thereof.

In some embodiments, a provided compound is a compound of II-c or a salt thereof. In some embodiments, $R^3$ and $R^5$ are R, and are taken together to form an optionally substituted ring as described in the present disclosure. In some embodiments, a provided compound of formula II is selected from

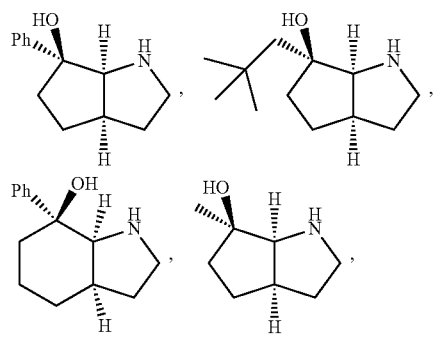

and salts thereof.

In some embodiments, a provided compound, e.g., a compound of formula I, has the structure of formula III:

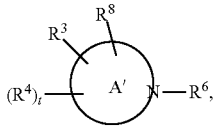

or a salt thereof, wherein:

Ring A' is an optionally substituted 3-20 membered monocyclic, bicyclic or polycyclic ring having 1-10 heteroatoms independently selected from oxygen, nitrogen, sulfur, phosphorus and silicon, wherein Ring A' comprises a —N($R^6$)— moiety;

each of $R^1$, $R^2$, $R^3$ and $R^4$ is independently —H, -$L^s$-R, halogen, —CN, —$NO_2$, -$L^s$-Si(R)$_3$, —OR, —SR, or —N(R)$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

t is 0-20;

$R^6$ is R';

$R^8$ is -L-C($R^1$)($R^2$)—$R^7$, or -$L^s$-$R^7$;

$R^7$ is —OH or —SH;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, a provided compound has the structure of formula III-a:

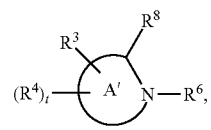

or a salt thereof, wherein each variable is independently as described in the present disclosure. In some embodiments, a compound of formula III has the structure of formula III-a.

In some embodiments, a provided compound has the structure of formula III-b:

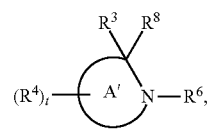

or a salt thereof, wherein each variable is independently as described in the present disclosure. In some embodiments, a compound of formula III-a has the structure of formula III-b.

In some embodiments, $R^8$ is bonded to a carbon atom ($C^2$) next to the nitrogen atom in —N($R^6$)— ($N^1$) (e.g., formula III-a, formula III-b, etc.). In some embodiments, $R^8$ is bonded to a carbon atom next to $C^2$ ($C^3$). In some embodiments, $R^8$ is bonded to a carbon atom next to $C^3$ that is not $C^2$ ($C^4$). In some embodiments, $R^8$ is bonded to a carbon atom next to $C^4$ which is not $C^3$ ($C^5$). In some embodiments, $R^8$ is bonded to a carbon atom next to $C^5$ which is not $C^4$ ($C^6$).

In some embodiments, $R^8$ is —OH. In some embodiments, $R^6$ is —H. In some embodiments, $R^5$ is optionally substituted alkyl. In some embodiments, $R^5$ is methyl. In some embodiments, t is 0. In some embodiments, $R^3$ is optionally substituted alkyl. In some embodiments, $R^3$ is methyl. In some embodiments, $R^3$ is optionally substituted phenyl. In some embodiments, $R^3$ is phenyl. In some embodiments, $R^3$ is optionally substituted $C_{3-10}$ cycloalkyl. In some embodiments, $R^3$ is optionally substituted cyclohexyl. In some embodiments, $R^3$ is cyclohexyl.

In some embodiments, Ring A' is an optionally substituted 3-20 membered monocyclic, bicyclic or polycyclic ring having 1-5 heteroatoms independently selected from oxygen, nitrogen, sulfur, phosphorus and silicon, wherein Ring A' comprises a —$N(R^6)$— moiety. In some embodiments, Ring A' is Ring A as described in the present disclosure, wherein Ring A comprises a nitrogen ring atom. In some embodiments, Ring A' is or comprises at least one monocyclic saturated or partially unsaturated monocyclic ring moiety, optionally as part of a bicyclic or polycyclic system. In some embodiments, Ring A' is monocyclic. In some embodiments, Ring A' is bicyclic or polycyclic comprising at least one monocyclic saturated or partially unsaturated monocyclic ring moiety, and optionally one or more aromatic monocyclic moieties. In some embodiments, Ring A' is or comprises at least one saturated monocyclic ring moiety. In some embodiments, $R^8$ is connected to a $sp^3$ ring atom of Ring A'. In some embodiments, $R^8$ is connected to a $sp^3$ carbon ring atom of Ring A'. In some embodiments, $R^3$ is connected to a $sp^3$ ring atom of Ring A'. In some embodiments, $R^3$ is connected to a $sp^3$ carbon ring atom of Ring A'. In some embodiments, the nitrogen to which $R^6$ is attached is $sp^3$.

In some embodiments, a provided compound of formula III is selected from

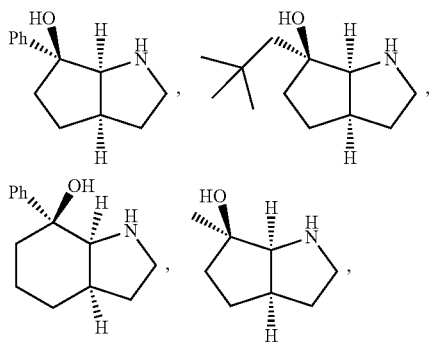

and salts thereof. In some embodiments, In some embodiments, a provided compound of formula III is selected from compounds listed in Table 4 below and salts thereof.

TABLE 1

Example compounds.

| Compound No. | Structure |
|---|---|
| WV-CA-001 | |
| WV-CA-002 | 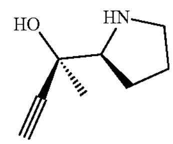 |
| WV-CA-002-S | 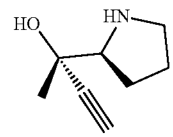 |
| WV-CA-003 | 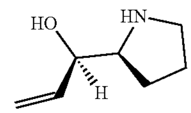 |
| WV-CA-004 | 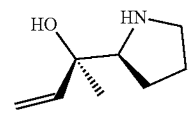 |
| WV-CA-005-D | 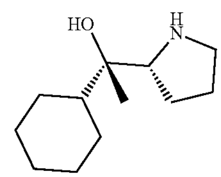 |
| WV-CA-005-L | 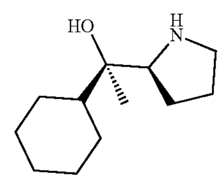 |
| WV-CA-006 | 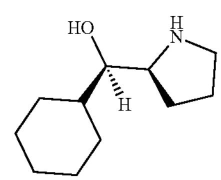 [SMILES: O[C@H](C1CCCCC1)[C@@H]1CCCN1] |
| WV-CA-011 | 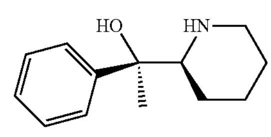 |
| WV-CA-012 | 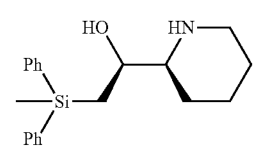 [SMILES: C[Si](C[C@@H](O)[C@@H]1CCCCN1)(c1ccccc1)c1ccccc1] |
| WV-CA-012-R | 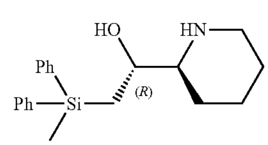 |

TABLE 1-continued

Example compounds.

| Compound No. | Structure |
|---|---|
| WV-CA-013 | 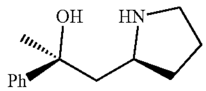 |
| WV-CA-014 | 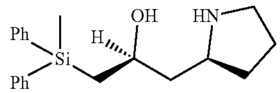 [SMILES: C[Si](C[C@@H](O)C[C@@H]1CCCN1)(c1ccccc1)c1ccccc1] |
| WV-CA-014-R | 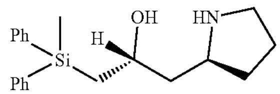 [SMILES: C[Si](C[C@H](O)C[C@@H]1CCCN1)(c1ccccc1)c1ccccc1] |
| WV-CA-015 | 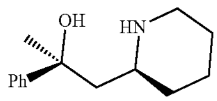 [SMILES: C[C@](O)(C[C@@H]1CCCCN1)c1ccccc1] |
| WV-CA-016 | 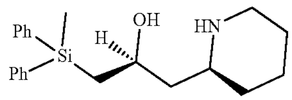 [SMILES: C[Si](C[C@@H](O)C[C@@H]1CCCCN1)(c1ccccc1)c1ccccc1] |
| WV-CA-021 | 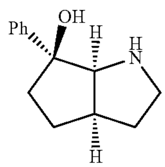 [SMILES: O[C@]1(c2ccccc2)CC[C@@H]2CCN[C@@H]21] |
| WV-CA-022 | 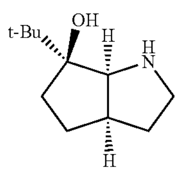 [SMILES: CC(C)(C)[C@@]1(O)CC[C@@H]2CCN[C@@H]21] |
| WV-CA-011-S | 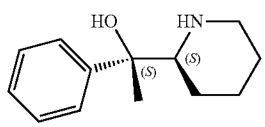 |
| WV-CA-040 | 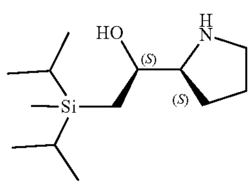 |
| WV-CA-041-D | 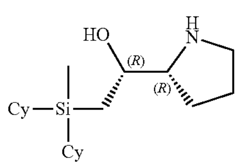 |
| WV-CA-041-L | 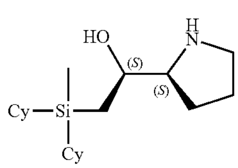 |
| WV-CA-042 | |
| WV-CA-043 | |
| WV-CA-044-R+S | |
| WV-CA-045 | |
| WV-CA-046 | |
| WV-CA-048 | |
| WV-CA-049 | |
| WV-CA-023 | |
| WV-CA-050 | |
| WV-CA-051 | |

TABLE 1-continued

Example compounds.

| Compound No. | Structure |
|---|---|
| WV-CA-052 | 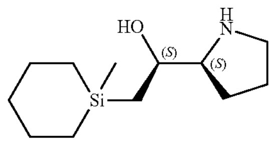 |
| WV-CA-053 | 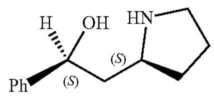 |
| WV-CA-054 | 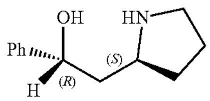 |
| WV-CA-056 | 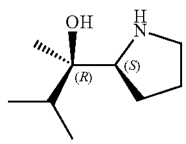 |
| WV-CA-056-S | 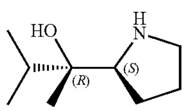 |
| WV-CA-057 | 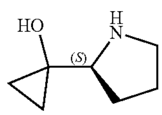 |
| WV-CA-058 | 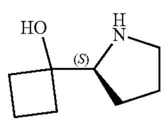 |
| WV-CA-059 | 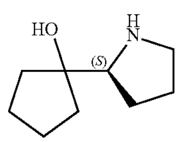 |
| WV-CA-059-R | 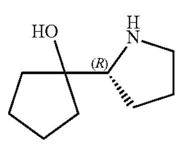 |
| WV-CA-060 | 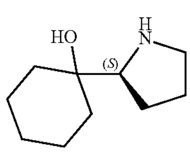 |
| WV-CA-062 | 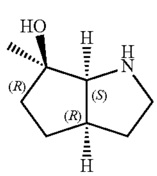 |
| WV-CA-063-S | |
| WV-CA-064-S | |
| WV-CA-065-S | |
| WV-CA-067 | |
| WV-CA-068-S | |
| WV-CA-069-S | |
| WV-CA-072-S | |
| WV-CA-082-S | |
| WV-CA-073-S | |
| WV-CA-074-M | |

TABLE 1-continued

Example compounds.

| Compound No. | Structure |
|---|---|
| WV-CA-074-R | (structure) |
| WV-CA-074-S | (structure) |
| WV-CA-076 | (structure) |
| WV-CA-077 | (structure) |
| WV-CA-078 | (structure) |
| WV-CA-079 | (structure) |
| WV-CA-080 | (structure) |
| WV-CA-081 | (structure) |
| WV-CA-097 | (structure) |
| WV-CA-083 | (structure) |
| WV-CA-084 | (structure) |
| WV-CA-088 | (structure) |
| WV-CA-089 | (structure) |
| WV-CA-090 | (structure) |
| WV-CA-091 | (structure) |
| WV-CA-093 | (structure) |
| WV-CA-094 | (structure) |
| WV-CA-096 | (structure) |
| WV-CA-106 | (structure) |
| WV-CA-107 | (structure) |

TABLE 1-continued

Example compounds.

| Compound No. | Structure |
|---|---|
| WV-CA-108 | (phenylsulfonyl)-CH2-CH(OH)(S)-pyrrolidine(S) |
| WV-CA-098 | cyclopentyl-C(OH)(R)-octahydroindole (S,S,S) |
| WV-CA-099 | Ph-C(Me)(OH)-pyrrolidine with 4,4-dimethyl |
| WV-CA-100-D | Ph-C(Me)(OH)(S)-pyrrolidine(R) |
| WV-CA-100-L | Ph-C(Me)(OH)(R)-pyrrolidine(S) |
| WV-CA-101 | Ph-C(Et)(OH)-pyrrolidine |
| WV-CA-102 | Ph-CH(OH)(R)-pyrrolidine(S) |
| WV-CA-103 | Ph-CH(OH)(S)-pyrrolidine(R) |
| WV-CA-104 | MePh2Si-CH2-CH(OH)(S)-pyrrolidine(S) |
| WV-CA-105 | MePh2Si-CH2-CH(OH)(R)-pyrrolidine(R) |
| WV-CA-117 | Ph-CH(OH)(R)-azetidine(S) |
| WV-CA-118 | Ph-C(Me)(OH)(R)-azetidine(S) |
| WV-CA-118-S | Ph-C(Me)(OH)(S)-azetidine(S) |
| WV-CA-109 | (4-tolylsulfonyl)-CH2-CH(OH)(S)-pyrrolidine(S) |
| WV-CA-109a | (methylsulfonyl)-CH2-CH(OH)(S)-pyrrolidine(S) |
| WV-CA-110 | 2,7-di-tert-butylfluorenyl-CH(OH)-pyrrolidine(S),(R) |
| WV-CA-111 | MePh2Si-CH2-CH(OH)-4,4-dimethylpyrrolidine(S) |
| WV-CA-112 | Ph2MeSi-CH2-CH(OH)(S)-octahydroindole(S,S,S) |
| WV-CA-113 | Ph-CH(OH)-azabicyclo[2.2.1]heptane |
| WV-CA-116 | MePh2Si-CH2-CH(OH)(S)-azetidine(S) |

TABLE 1-continued

Example compounds.

| Compound No. | Structure |
|---|---|
| WV-CA-126 | [2-naphthyl-C(OH)(Me)- with (S,R) stereochemistry attached to (S)-pyrrolidin-2-yl] |
| WV-CA-127 | [2,4-dimethylphenyl-C(OH)(Me)- (S,R) attached to (S)-pyrrolidin-2-yl] |
| WV-CA-128 | [2,4,6-trimethylphenyl-C(OH)(Me)- (S,R) attached to (S)-pyrrolidin-2-yl] |
| WV-CA-119 | [Ph₂MeSi-CH₂-C(OH)H- (S) attached to (S,S,S)-octahydrocyclopenta[b]pyrrol-2-yl] |
| WV-CA-120 | [Ph-CH(OH)- (R) attached to (S,S,S)-octahydrocyclopenta[b]pyrrol-2-yl] |
| WV-CA-121 | [Ph-C(OH)(Me)- (R) attached to (S,S,S)-octahydrocyclopenta[b]pyrrol-2-yl] |
| WV-CA-122 | [Ph-CH₂-CH(OH)- (R) attached to (S)-pyrrolidin-2-yl] |
| WV-CA-123 | [Ph-CH₂-C(OH)(Me)- (R) attached to (S)-pyrrolidin-2-yl] |
| WV-CA-124 | [4-MeO-phenyl-C(OH)(Me)- attached to pyrrolidin-2-yl] |
| WV-CA-125 | [1-naphthyl-C(OH)(Me)- (R) attached to (S)-pyrrolidin-2-yl] |
| WV-CA-146 | [4-methylphenyl-CH(OH)- attached to pyrrolidin-2-yl] |
| WV-CA-147 | [4-methylphenyl-C(OH)(Me)- (R) attached to (S)-pyrrolidin-2-yl] |
| WV-CA-148 | [3,5-dimethylphenyl-CH(OH)- attached to pyrrolidin-2-yl] |
| WV-CA-129 | [2,4,6-tri-tert-butylphenyl-C(OH)(Me)- (R) attached to (S)-pyrrolidin-2-yl] |
| WV-CA-130 | [2,4-di-tert-butylphenyl-C(OH)(Me)- (R) attached to (S)-pyrrolidin-2-yl] |
| WV-CA-131 | [4-tert-butylphenyl-C(OH)(Me)- (R) attached to (S)-pyrrolidin-2-yl] |
| WV-CA-132 | [2,4-dimethoxy-6-methoxyphenyl-C(OH)(Me)- (R) attached to (S)-pyrrolidin-2-yl] |
| WV-CA-133 | [CH₃-CH(OH)- (R) attached to (S)-pyrrolidin-3-yl] |
| WV-CA-134 | [(MeO)₂P(O)-CH₂-CH(OH)- attached to pyrrolidin-2-yl] |

TABLE 1-continued

Example compounds.

| Compound No. | Structure |
|---|---|
| WV-CA-145 | (hydroxy(phenyl)methyl)pyrrolidine |
| WV-CA-149 | (3,5-dimethyl-4-methoxyphenyl)(hydroxy)methyl-pyrrolidine |
| WV-CA-150 | 1-(3,5-dimethylphenyl)-1-(pyrrolidin-2-yl)ethanol |
| WV-CA-151 | 1-(3,5-dimethyl-4-methoxyphenyl)-1-(pyrrolidin-2-yl)ethanol |
| WV-CA-152 | adamantyl(hydroxy)methyl-pyrrolidine |
| WV-CA-153 | 1-adamantyl-1-(pyrrolidin-2-yl)ethanol |
| WV-CA-154 | bis(4-methoxyphenyl)(methyl)silyl-hydroxymethyl-pyrrolidine |
| WV-CA-155 | (2,4,6-trimethoxyphenyl)dimethylsilyl-hydroxymethyl-pyrrolidine |
| WV-CA-156 | bis(4-fluorophenyl)(methyl)silyl-hydroxymethyl-pyrrolidine |
| WV-CA-157 | (4-fluorophenyl)dimethylsilyl-hydroxymethyl-pyrrolidine |
| WV-CA-163 | hydroxyaziridine |
| WV-CA-164 | 9-(pyrrolidin-2-yl)-9H-fluoren-9-ol |
| WV-CA-165 | methyl(diphenyl)silyl-hydroxymethyl-pyrrolidine |

TABLE 1-continued

Example compounds.

| Compound No. | Structure |
|---|---|
| WV-CA-423 | (structure) |
| WV-CA-424 | (structure) |
| WV-CA-172 | (structure) |
| WV-CA-173 | (structure) |
| WV-CA-174 | (structure) |
| WV-CA-175 | (structure) |
| WV-CA-176 | (structure) |
| WV-CA-180 | (structure) |
| WV-CA-181 | (structure) |
| WV-CA-165 | (structure) |
| WV-CA-166 | (structure) |
| WV-CA-167 | (structure) |
| WV-CA-201 | (structure) |
| WV-CA-202 | (structure) |
| WV-CA-203 | (structure) |
| WV-CA-204 | (structure) |

TABLE 1-continued

Example compounds.

| Compound No. | Structure |
|---|---|
| WV-CA-204a | (azetidine with phenyl and hydroxycyclopentyl substituents) |
| WV-CA-206 | (pyrrolidine with 4-methoxyphenyl hydroxymethyl substituent) |
| WV-CA-209 | (pyrrolidine with hydroxyethyl substituent) |
| WV-CA-182 | (azetidine with hydroxy-tris(trimethylsilyl)silyl methyl substituent) |
| WV-CA-183 | (azetidine with hydroxy-phenylsulfonylmethyl substituent) |
| WV-CA-188 | (decahydroquinoline with OH and Ph substituents) |
| WV-CA-229 | (5,5-dimethyl-pyrrolidine (S) with hydroxycyclopentyl substituent) |
| WV-CA-231 | (pyrrolidine (S) with (R) hydroxy-(4-nitrobenzyl) substituent) |
| WV-CA-233 | (decahydroquinoline with OH) |
| WV-CA-234 | (decahydroquinoline with OH) |
| WV-CA-301 | (pyrrolidine (S) with OH) |
| WV-CA-304 | (spiro azetidine-cyclopentane with OH) |
| WV-CA-306 | (piperidine with OH and triisopropylsilylmethyl substituent) |
| WV-CA-225 | (pyrrolidine (S) with (R) hydroxy-cyclobutyl-methyl substituent) |
| WV-CA-226 | (pyrrolidine with OH and diphenylmethylsilylmethyl substituent) |
| WV-CA-227 | (pyrrolidine (S) with OH and diphenylmethylsilylmethyl substituent) |
| WV-CA-310 | (pyrrolidine (S) with hydroxy-methyl substituent) |
| WV-CA-311 | (pyrrolidine (S) with hydroxycyclopropyl substituent) |
| WV-CA-312 | (pyrrolidine (S,S) with OH and tert-butyldimethylsilylmethyl substituent) |
| WV-CA-313 | (pyrrolidine (R) with (S) hydroxyethyl substituent) |
| WV-CA-314 | (pyrrolidine (S) with (S) hydroxyethyl substituent) |

TABLE 1-continued

Example compounds.

| Compound No. | Structure |
|---|---|
| WV-CA-315 | (structure) |
| WV-CA-316 | (structure) |
| WV-CA-307 | (structure) |
| WV-CA-308 | (structure) |
| WV-CA-309 | (structure) |
| WV-CA-320 | (structure) |
| WV-CA-321 | (structure) |
| WV-CA-322 | (structure) |
| WV-CA-323 | (structure) |
| WV-CA-324 | (structure) |
| WV-CA-325 | (structure) |
| WV-CA-326 | (structure) |
| WV-CA-317 | (structure) |
| WV-CA-318 | (structure) |
| WV-CA-319 | (structure) |
| WV-CA-330 | (structure) |
| WV-CA-331 | (structure) |

TABLE 1-continued
Example compounds.
| Compound No. | Structure |
|---|---|
| WV-CA-332 | 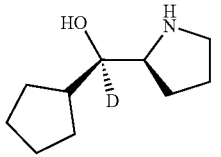 [SMILES: [2H][C@@](O)(C1CCCC1)[C@@H]1CCCN1] |
| WV-CA-333 | 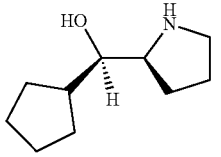 |
| WV-CA-334 | 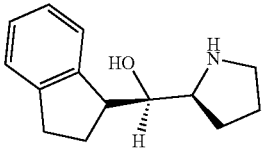 [SMILES: O[C@H](C1CCc2ccccc21)[C@@H]1CCCN1] |
| WV-CA-335 | 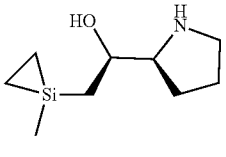 |
| WV-CA-336 | 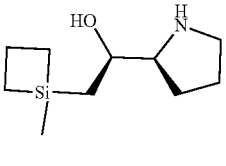 |
| WV-CA-327 | 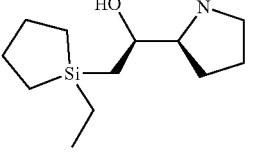 |
| WV-CA-328 | 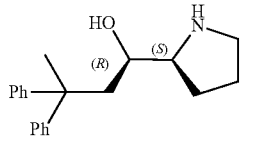 |
| WV-CA-329 | 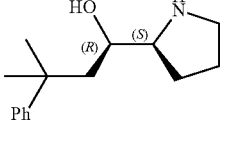 |
| WV-CA-340 | 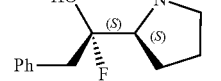 |
TABLE 1-continued
Example compounds.
| Compound No. | Structure |
|---|---|
| WV-CA-341 | 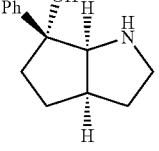 |
| WV-CA-342 | 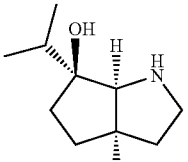 |
| WV-CA-343 | 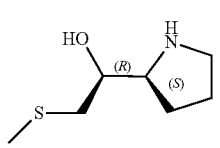 |
| WV-CA-344 | 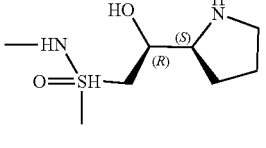 |
| WV-CA-344a | 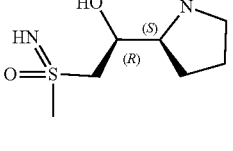 |
| WV-CA-345 | 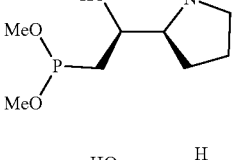 |
| WV-CA-337 | 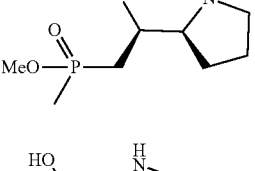 |
| WV-CA-338 | 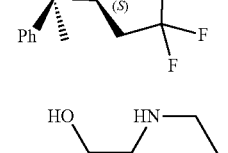 |
| WV-CA-339 | 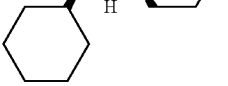 |

TABLE 1-continued

Example compounds.

| Compound No. | Structure |
|---|---|
| WV-CA-349 | 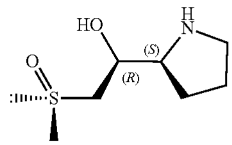 |
| WV-CA-350 | 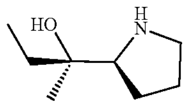 |
| WV-CA-351 | 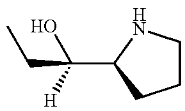 |
| WV-CA-352 | 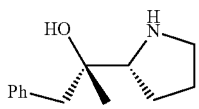 |
| WV-CA-352a | 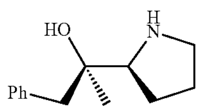 |
| WV-CA-353 | 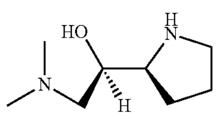 |
| WV-CA-354 | 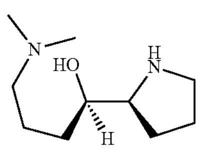 |
| WV-CA-355 | 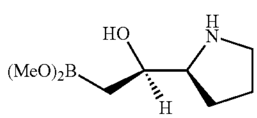 |
| WV-CA-346 | 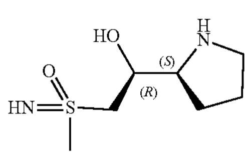 |
| WV-CA-347 | 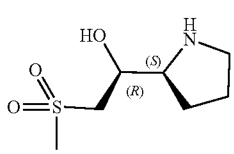 |
| WV-CA-348 | 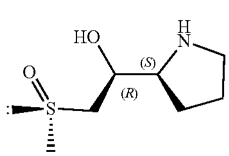 |
| WV-CA-358 | |
| WV-CA-359 | |
| WV-CA-360 | |
| WV-CA-361 | |
| WV-CA-363 | |
| WV-CA-364 | |
| WV-CA-365 | |
| WV-CA-366 | |
| WV-CA-356 | |
| WV-CA-357 | |

TABLE 1-continued

Example compounds.

| Compound No. | Structure |
|---|---|
| WV-CA-369 | (R,S)-2-(hydroxy(phenyl)methyl)-3,3-dimethyl pyrrolidine derivative |
| WV-CA-370 | (R,S)-2-(hydroxy(1-phenylcyclopropyl)methyl)pyrrolidine |
| WV-CA-371 | (R,S)-2-(hydroxy(2-fluorophenyl)methyl)pyrrolidine |
| WV-CA-372 | (R,S)-2-(hydroxy(4-fluorophenyl)methyl)pyrrolidine |
| WV-CA-373 | (R,S)-2-(hydroxy(2,3-difluorophenyl)methyl)pyrrolidine |
| WV-CA-374 | (R,S)-2-(hydroxy(2,4-difluorophenyl)methyl)pyrrolidine |
| WV-CA-375 | (R,S)-2-(hydroxy(2,5-difluorophenyl)methyl)pyrrolidine |
| WV-CA-367 | (R,S)-2-(1-hydroxy-2,2-dimethylpropyl)pyrrolidine |

TABLE 1-continued

Example compounds.

| Compound No. | Structure |
|---|---|
| WV-CA-368 | (R,S)-2-(1-fluoro-2,2-dimethyl-1-hydroxypropyl)pyrrolidine |
| WV-CA-369 | (R,S)-2-(hydroxy(phenyl)methyl)-3,3-dimethyl pyrrolidine derivative |
| WV-CA-370 | (R,S)-2-(hydroxy(1-phenylcyclopropyl)methyl)pyrrolidine |
| WV-CA-371 | (R,S)-2-(hydroxy(2-fluorophenyl)methyl)pyrrolidine |
| WV-CA-372 | (R,S)-2-(hydroxy(4-fluorophenyl)methyl)pyrrolidine |
| WV-CA-373 | (R,S)-2-(hydroxy(2,3-difluorophenyl)methyl)pyrrolidine |
| WV-CA-374 | (R,S)-2-(hydroxy(2,4-difluorophenyl)methyl)pyrrolidine |
| WV-CA-375 | (R,S)-2-(hydroxy(2,5-difluorophenyl)methyl)pyrrolidine |

TABLE 1-continued

Example compounds.

| Compound No. | Structure |
|---|---|
| WV-CA-376 | (structure: (R)-(2,6-difluorophenyl)((S)-pyrrolidin-2-yl)methanol, protonated) |
| WV-CA-377 | (structure: (R)-(3,4-difluorophenyl)((S)-pyrrolidin-2-yl)methanol) |
| WV-CA-378 | (structure: (S)-fluoro(perfluorophenyl)((S)-pyrrolidin-2-yl)methanol) |
| WV-CA-379 | (structure: (R)-(perfluorophenyl)((S)-pyrrolidin-2-yl)methanol) |
| WV-CA-380 | (structure: (R)-deutero(perfluorophenyl)((S)-pyrrolidin-2-yl)methanol) |
| WV-CA-381 | (structure: (R)-(4-fluorophenyl)methyl((S)-pyrrolidin-2-yl)methanol) |
| WV-CA-382 | (structure: (R)-phenyl(trifluoromethyl)((S)-pyrrolidin-2-yl)methanol) |
| WV-CA-383 | (structure: (S)-fluoro(perdeuterophenyl)((S)-pyrrolidin-2-yl)methanol) |
| WV-CA-376 | (structure: (R)-(2,6-difluorophenyl)((S)-pyrrolidin-2-yl)methanol) |
| WV-CA-377 | (structure: (R)-(3,4-difluorophenyl)((S)-pyrrolidin-2-yl)methanol) |
| WV-CA-378 | (structure: (S)-fluoro(perfluorophenyl)((S)-pyrrolidin-2-yl)methanol) |
| WV-CA-395 | (structure: (S)-trifluoromethyl(trideuteromethyl)((S)-pyrrolidin-2-yl)methanol) |
| WV-CA-396 | (structure: (S)-trifluoromethyl-deutero-((S)-pyrrolidin-2-yl)methanol) |
| WV-CA-397 | (structure: (S)-trifluoromethyl(methyl)((S)-pyrrolidin-2-yl)methanol) |
| WV-CA-398 | (structure: (S)-tert-butyl-((R)-pyrrolidin-2-yl)methanol) |
| WV-CA-398a | (structure: (R)-tert-butyl-((S)-pyrrolidin-2-yl)methanol) |

TABLE 1-continued

Example compounds.

| Compound No. | Structure |
|---|---|
| WV-CA-384 | (phenyl)(HO)(D₃C)C-(R)-[pyrrolidin-2-yl-(S)]-NH |
| WV-CA-385 | (2,3,4,5,6-pentadeutero-phenyl)(HO)(F)C-(R)-[pyrrolidin-2-yl-(S)]-NH |
| WV-CA-385a | (2,3,4,5,6-pentadeutero-phenyl)(HO)(F)C-(S)-[pyrrolidin-2-yl-(S)]-NH |
| WV-CA-386 | (3,5-bis(trifluoromethyl)phenyl)₂(HO)C-(S)-[pyrrolidin-2-yl]-NH |
| WV-CA-394 | (HO)(F₃C)(D)C-(S)-[pyrrolidin-2-yl-(S)]-NH |
| WV-CA-419 | Ph-C≡C-CH(OH)-CH₂-CH₂-(pyrrolidin-3-yl) |
| WV-CA-420 | (trimethylcyclopentyl)(OH)CH-(trimethylpyrrolidin-2-yl)-NH |
| WV-CA-399 | (iPr)(HO)CH-(R)-[pyrrolidin-2-yl-(S)]-NH |

TABLE 1-continued

Example compounds.

| Compound No. | Structure |
|---|---|
| WV-CA-400 | (phenyl)(CF₂)-CH(OH)-(S)-[pyrrolidin-2-yl-(S)]-NH |
| WV-CA-408 | (9,10-dihydrophenanthren-9-yl)-CH₂-CH(OH)-[pyrrolidin-2-yl]-NH |
| WV-CA-409 | (triisopropyldimethylcyclohexyl)-CH₂-CH(OH)-[pyrrolidin-2-yl]-NH |
| WV-CA-410 | (tetramethylcyclopentyl)-CH₂-CH(OH)-[pyrrolidin-2-yl]-NH |
| WV-CA-421 | Ph-C≡C-C(OH)(cyclopentyl-CH₂-pyrrolidin-3-yl) |

In some embodiments, a provided compound is an enantiomer of a compound selected from Table 1 or a salt thereof. In some embodiments, a provided compound is a diastereomer of a compound selected from Table 1 or a salt thereof.

TABLE 2

Example compounds.

| Compound No. | Structure |
|---|---|
| WV-CA-007 | Ph-CH(OH)-CH(NH-)-cyclohexyl |

TABLE 2-continued

Example compounds.

| Compound No. | Structure |
|---|---|
| WV-CA-025 | (structure) |
| WV-CA-008 | (structure) |
| WV-CA-026 | (structure) |
| WV-CA-008-S | (structure) |
| WV-CA-027 | (structure) |
| WV-CA-009 | (structure) |
| WV-CA-028 | (structure) |
| WV-CA-010 | (structure) |
| WV-CA-029 | (structure) |
| WV-CA-017 | (structure) |
| WV-CA-030 | (structure) |
| WV-CA-018 | (structure) |
| WV-CA-031 | (structure) |
| WV-CA-019 | (structure) |
| WV-CA-032 | (structure) |
| WV-CA-020 | (structure) |
| WV-CA-033 | (structure) |
| WV-CA-024 | (structure) |
| WV-CA-034 | (structure) |

TABLE 2-continued

Example compounds.

| Compound No. | Structure |
|---|---|
| WV-CA-035 | (2S,1S)-2-phenyl-1-(methylamino)-2-hydroxy-indane |
| WV-CA-070-S | (1S,2S)-1-methyl-2-(methylamino)-cyclohexan-1-ol |
| WV-CA-036 | (1S,2R)-1-phenyl-2-(methylamino)-cyclobutan-1-ol |
| WV-CA-071S | (S)-cyclohexyl(1-hydroxycyclopentyl)-N-methylmethanamine |
| WV-CA-037 | (1R,2S)-1-phenyl-2-(methylamino)-cyclobutan-1-ol |
| WV-CA-075-S | (1S,2S)-1-methyl-2-(isopropylamino)-cyclohexan-1-ol |
| WV-CA-038 | (1R,2R)-1-phenyl-2-(methylamino)-cyclobutan-1-ol |
| WV-CA-092 | (S)-1-(1-hydroxycyclopentyl)-N,2-diisopropyl ethanamine |
| WV-CA-039 | (1S,2S)-1-phenyl-2-(methylamino)-cyclobutan-1-ol |
| WV-CA-114 | (2S,3S)-1-(methyldiphenylsilyl)-3-(methylamino)-4-methylpentan-2-ol |
| WV-CA-047 | (1R,2S)-1-cyclohexyl-2-(methylamino)-cyclohexan-1-ol |
| WV-CA-115 | (2R,3S)-2-phenyl-3-(methylamino)-4,4-dimethylpentan-2-ol |
| WV-CA-055 | 1-cyclohexyl-3-(triisopropylsilyl)-1-(methylamino)-propan-2-ol |
| WV-CA-135 | cyclononane derivative with OH and NHMe |
| WV-CA-061 | (1S,2S)-1-cyclohexyl-2-(methylamino)-cyclohexan-1-ol |
| WV-CA-136 | cyclodecane derivative with OH and NHMe |
| WV-CA-066-R | (1R,2S)-1-(1-hydroxycyclopentyl)-2-(methylamino)cyclopentane |
| WV-CA-137 | cycloundecane derivative with OH and NHMe |
| WV-CA-070 | (1R,2S)-1-methyl-2-(methylamino)-cyclohexan-1-ol |
| WV-CA-138 | cyclododecane derivative with OH and NHMe |

TABLE 2-continued

Example compounds.

| Compound No. | Structure |
|---|---|
| WV-CA-139 | (cyclodecane with OH and NHMe, stereochemistry shown) |
| WV-CA-169 | (bicyclic structure with OH, methyl and NHMe) |
| WV-CA-140 | (cyclodecane with OH and NHMe) |
| WV-CA-170 | (tricyclic structure with OH, methyl and NH) |
| WV-CA-141 | (cyclodecane with OH and NHMe) |
| WV-CA-171 | (bicyclic decane with HN-Me and OH) |
| WV-CA-142 | (cyclodecane with OH and NHMe) |
| WV-CA-205 | (cyclopentane-spiro-bicyclic with HO, HN-iPr, gem-dimethyl) |
| WV-CA-158 | (thiirane-containing cyclohexane with OH, methyl, NHMe) |
| WV-CA-207 | (cyclohexane with OH and NH-Me) |
| WV-CA-159 | (piperidine-like with OH, methyl, NH, NHMe) |
| WV-CA-208 | (cyclopentane with OH and NHMe) |
| WV-CA-160 | (cyclopropyl-substituted cyclohexane with HO and HN-Me) |
| WV-CA-210 | (cubane-like with OH, methyl, NH-iPr) |
| WV-CA-161 | (cyclobutyl-substituted cyclohexane with HO and HN-Me) |
| WV-CA-211 | (cubane-like with OH, methyl, NH-O-Me) |
| WV-CA-162 | (spiro bicyclohexane with HO and HN-Me) |
| WV-CA-216 | (cyclohexane with HO, methyl, NHMe) |
| WV-CA-168 | (norbornane with methyl, OH, methyl, NH) |

TABLE 2-continued

Example compounds.

| Compound No. | Structure |
|---|---|
| WV-CA-217 | (structure) |
| WV-CA-218 | (structure) |
| WV-CA-302 | (structure) |
| WV-CA-219 | (structure) |
| WV-CA-303 | (structure) |
| WV-CA-220 | (structure) |
| WV-CA-305 | (structure) |
| WV-CA-221 | (structure) |
| WV-CA-362 | (structure) |
| WV-CA-222 | (structure) |
| WV-CA-387 | (structure) |
| WV-CA-223 | (structure) |
| WV-CA-388 | (structure) |
| WV-CA-224 | (structure) |
| WV-CA-389 | (structure) |
| WV-CA-228 | (structure) |
| WV-CA-390 | (structure) |

TABLE 2-continued

Example compounds.

| Compound No. | Structure |
|---|---|
| WV-CA-232 | *(structure)* |
| WV-CA-391 | *(structure)* |
| WV-CA-235 | *(structure)* |
| WV-CA-392 | *(structure)* |
| WV-CA-393 | *(structure)* |
| WV-CA-412 | *(structure)* |
| WV-CA-401 | *(structure)* |
| WV-CA-413 | *(structure)* |
| WV-CA-402 | *(structure)* |
| WV-CA-414 | *(structure)* |
| WV-CA-404 | *(structure)* |
| WV-CA-415 | *(structure)* |
| WV-CA-405 | *(structure)* |
| WV-CA-416 | *(structure)* |
| WV-CA-406 | *(structure)* |
| WV-CA-417 | *(structure)* |
| WV-CA-407 | *(structure)* |
| WV-CA-418 | *(structure)* |
| WV-CA-411 | *(structure)* |

In some embodiments, a provided compound is an enantiomer of a compound selected from Table 2 or a salt thereof.

In some embodiments, a provided compound is a diastereomer of a compound selected from Table 2 or a salt thereof.

TABLE 3

Example compounds.

| Compound No. | Structure |
|---|---|
| WV-CA-085 | 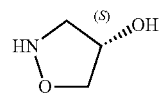 |
| WV-CA-179 | 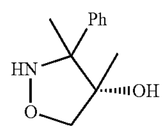 |
| WV-CA-086 | 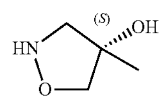 |
| WV-CA-184 | 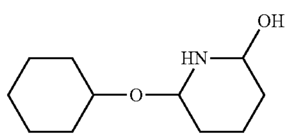 [SMILES: OC1CCCC(OC2CCCCC2)N1] |
| WV-CA-087 | 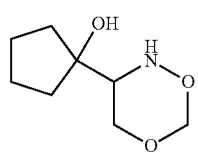 [SMILES: OC1(C2COCON2)CCCC1] |
| WV-CA-185 | 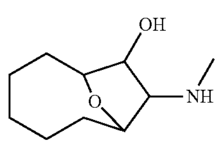 |
| WV-CA-087a | 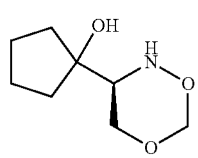 [SMILES: OC1([C@@H]2COCON2)CCCC1] |
| WV-CA-186 | 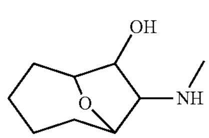 |
| WV-CA-087b | 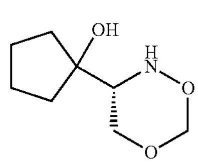 [SMILES: OC1([C@H]2COCON2)CCCC1] |
| WV-CA-187 | 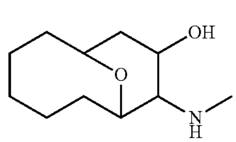 |

TABLE 3-continued

Example compounds.

| Compound No. | Structure |
|---|---|
| WV-CA-095 | 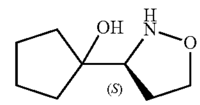 |
| WV-CA-189 | 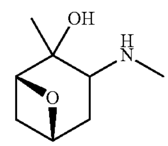 |
| WV-CA-143 | 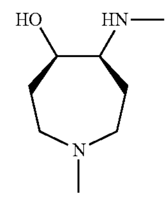 |
| WV-CA-190 | 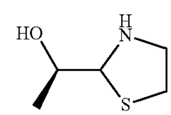 |
| WV-CA-144 | 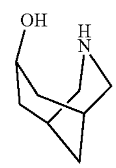 |
| WV-CA-191 | 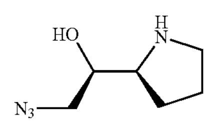 |
| WV-CA-177 | 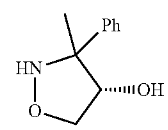 |
| WV-CA-192 | 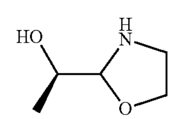 |
| WV-CA-178 | 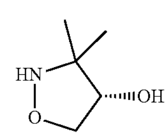 |
| WV-CA-193 | 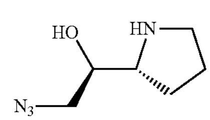 [SMILES: [N-]=[N+]=NC[C@@H](O)[C@H]1CCCN1] |
| WV-CA-194 | 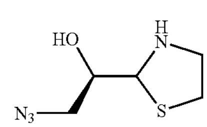 |

TABLE 3-continued

Example compounds.

| Compound No. | Structure |
|---|---|
| WV-CA-212 | (structure) |
| WV-CA-195 | (structure) |
| WV-CA-213 | (structure) |
| WV-CA-196 | (structure) |
| WV-CA-214 | (structure) |
| WV-CA-197 | (structure) |
| WV-CA-215 | (structure) |
| WV-CA-198 | (structure) |
| WV-CA-403 | (structure) |
| WV-CA-199 | (structure) |
| WV-CA-422 | (structure) |
| WV-CA-200 | (structure) |

In some embodiments, a provided compound is an enantiomer of a compound selected from Table 3 or a salt thereof. In some embodiments, a provided compound is a diastereomer of a compound selected from Table 3 or a salt thereof.

TABLE 4

Example compounds.

(structures)

TABLE 4-continued
Example compounds.
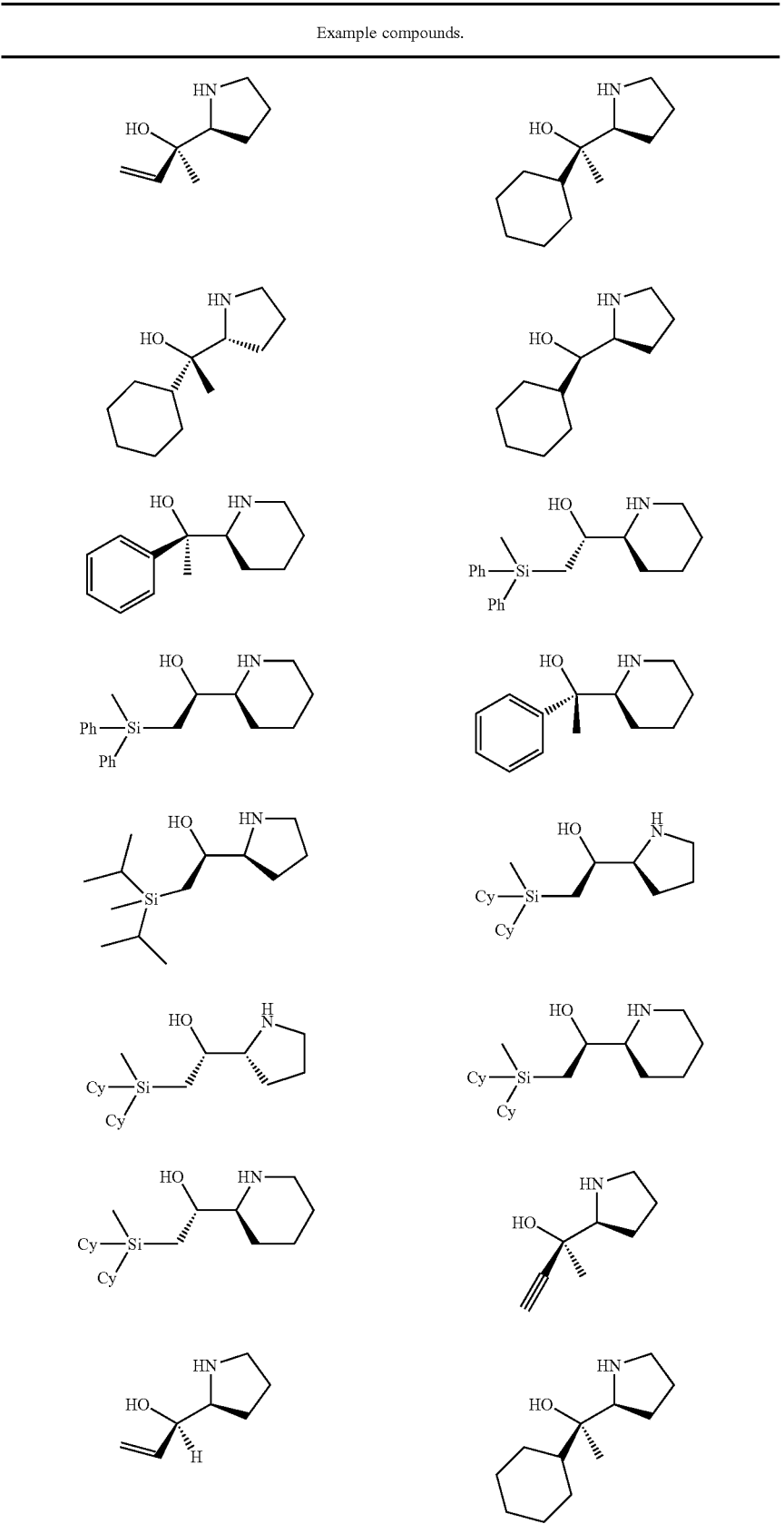

TABLE 4-continued
Example compounds.
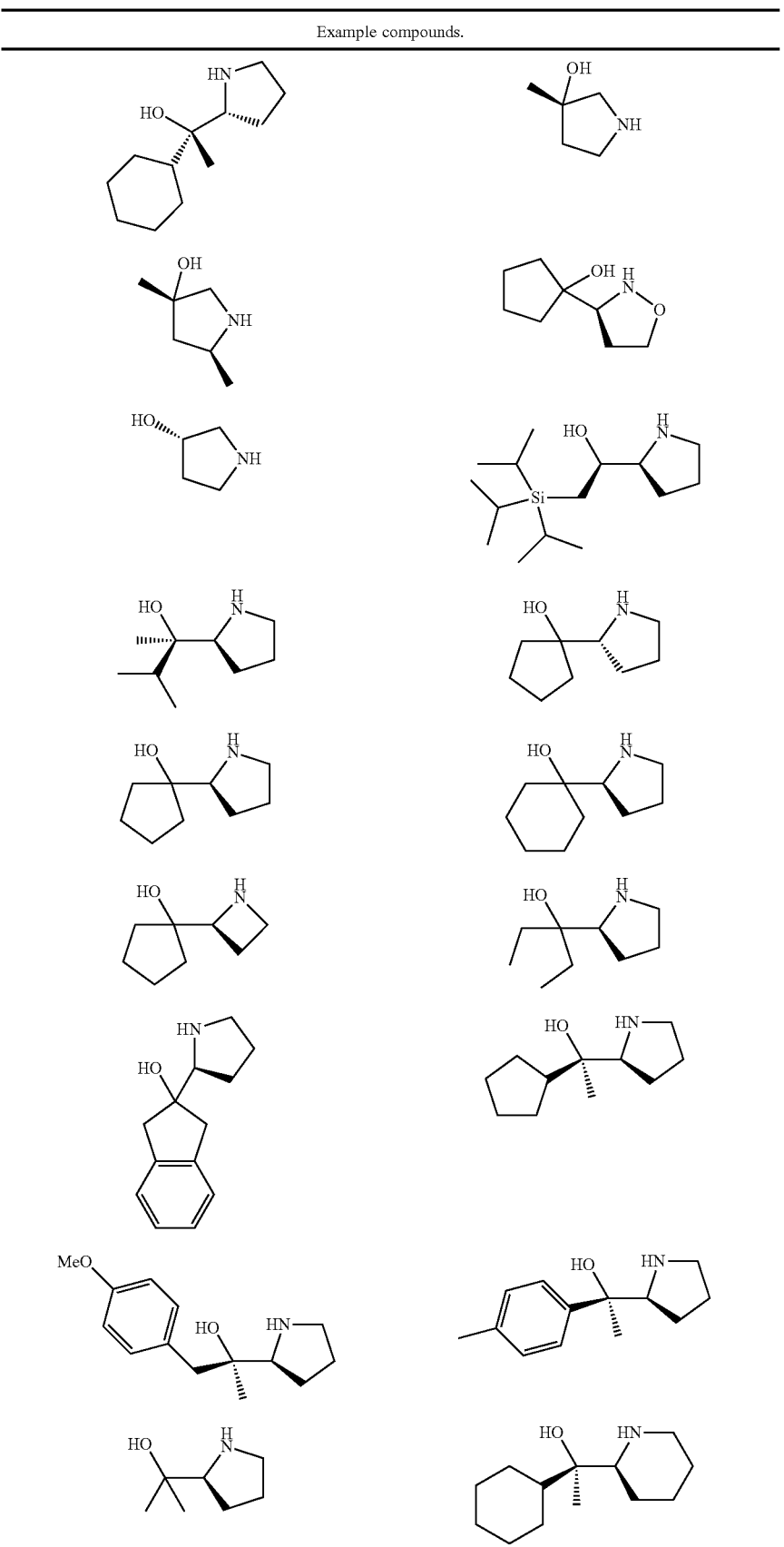

TABLE 4-continued
Example compounds.
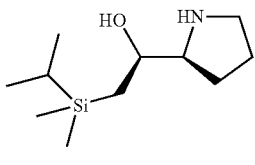 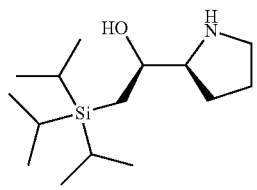 [SMILES: CC(C)[Si](C[C@@H](O)[C@@H]1CCCN1)(C(C)C)C(C)C]
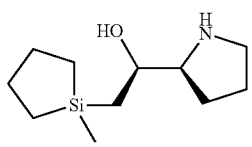 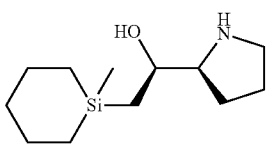
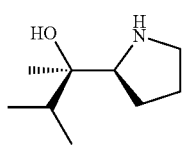 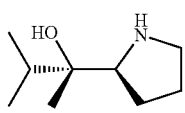
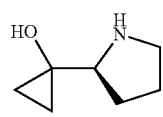 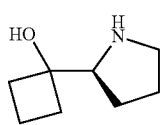
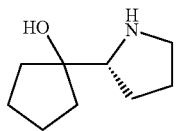 [SMILES: OC1([C@H]2CCCN2)CCCC1] 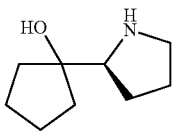 [SMILES: OC1([C@@H]2CCCN2)CCCC1]
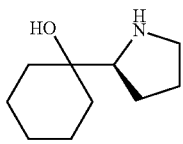 [SMILES: OC1([C@@H]2CCCN2)CCCCC1] 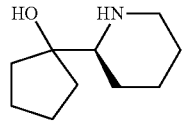 [SMILES: OC1([C@@H]2CCCCN2)CCCC1]
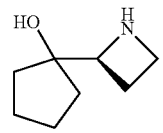 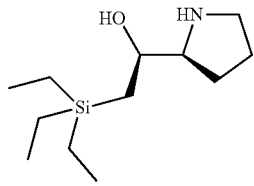
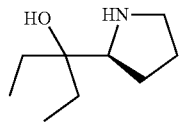 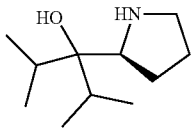
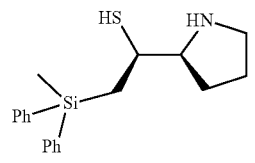 [SMILES: C[Si](C[C@@H](S)[C@@H]1CCCN1)(c1ccccc1)c1ccccc1] 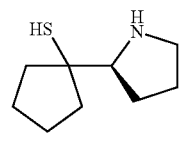 [SMILES: SC1([C@@H]2CCCN2)CCCC1]

TABLE 4-continued
Example compounds.
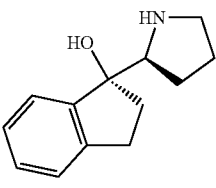 [SMILES: O[C@]1([C@@H]2CCCN2)CCc2ccccc21] 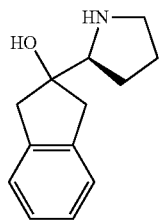 [SMILES: OC1([C@@H]2CCCN2)Cc2ccccc2C1]
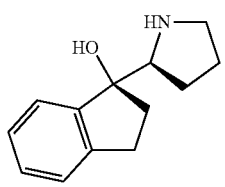 [SMILES: O[C@@]1([C@@H]2CCCN2)CCc2ccccc21] 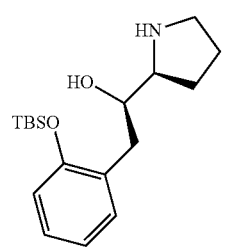 [SMILES: CC(C)(C)[Si](C)(C)Oc1ccccc1C[C@@H](O)[C@@H]1CCCN1]
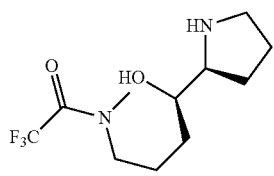 [SMILES: CN(CCC[C@@H](O)[C@@H]1CCCN1)C(=O)C(F)(F)F] 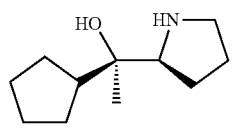
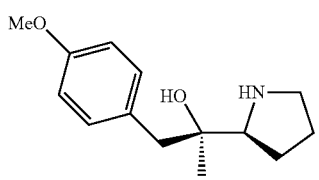 [SMILES: COc1ccc(C[C@@](C)(O)[C@@H]2CCCN2)cc1] 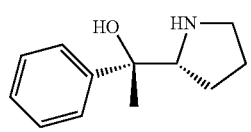
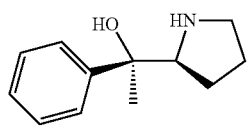 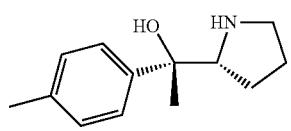
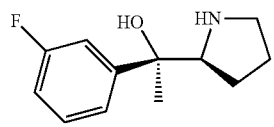 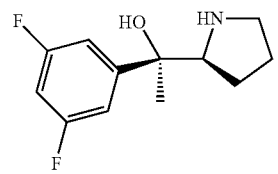 [SMILES: C[C@@](O)(c1cc(F)cc(F)c1)[C@@H]1CCCN1]
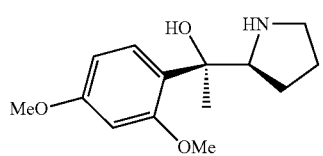 [SMILES: COc1ccc([C@@](C)(O)[C@@H]2CCCN2)c(OC)c1] 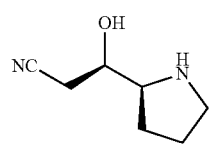
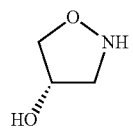 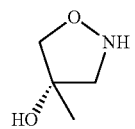

TABLE 4-continued
Example compounds.
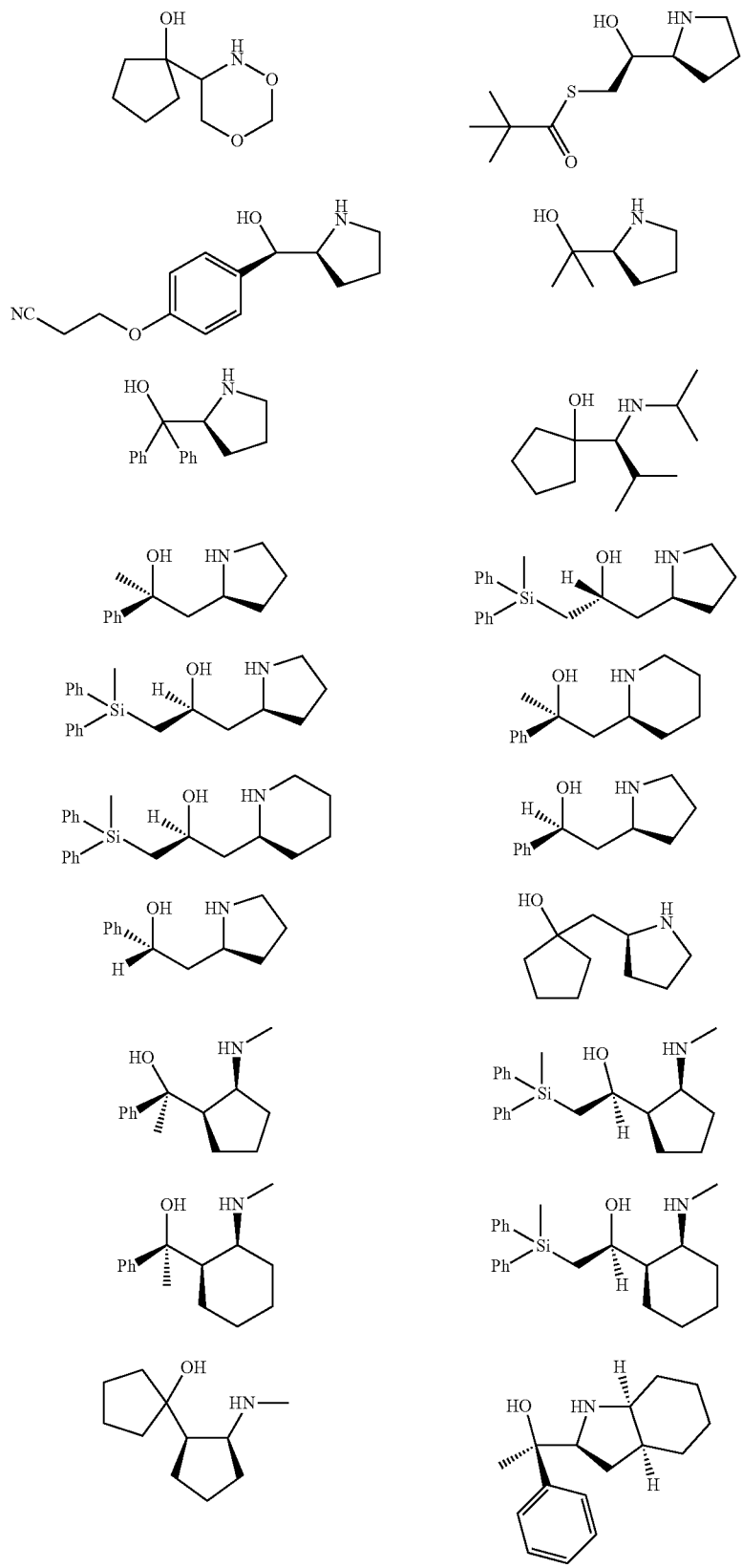

TABLE 4-continued
Example compounds.
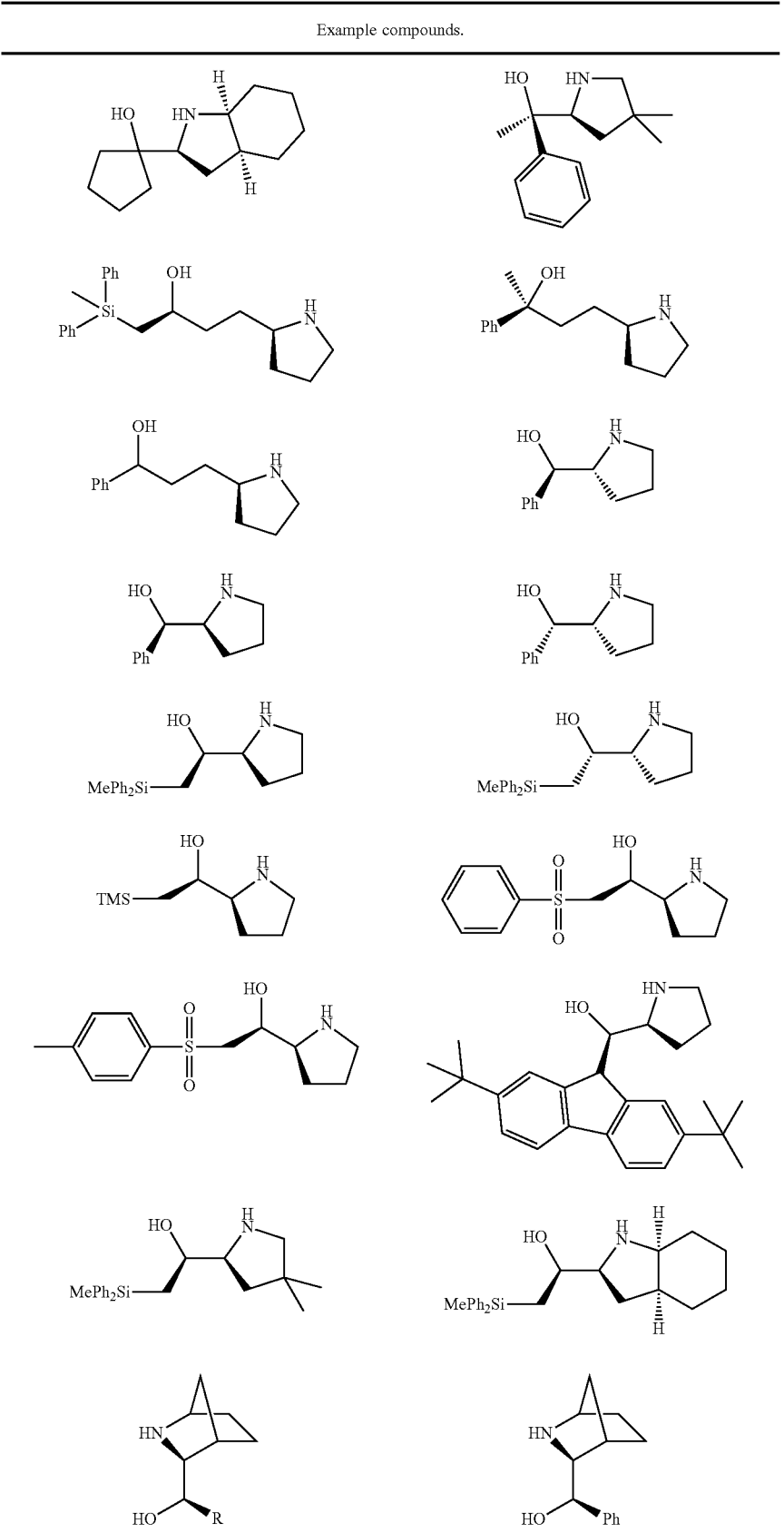

TABLE 4-continued
Example compounds.
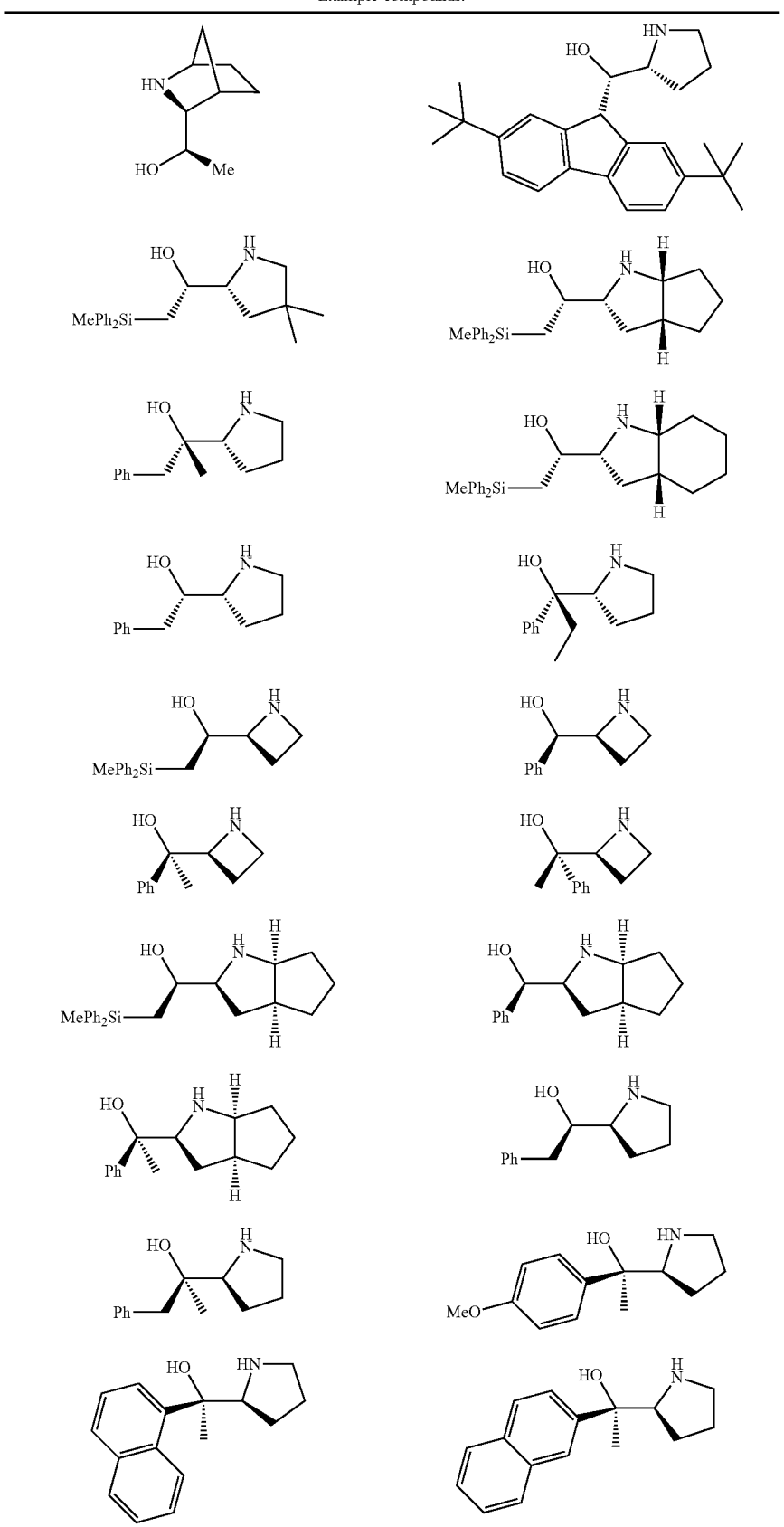

TABLE 4-continued
Example compounds.
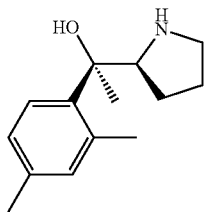 [SMILES: Cc1ccc([C@@](C)(O)[C@@H]2CCCN2)c(C)c1] 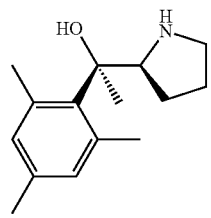 [SMILES: Cc1cc(C)c([C@@](C)(O)[C@@H]2CCCN2)c(C)c1]
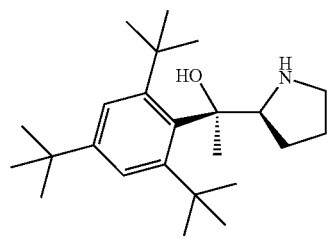 [SMILES: CC(C)(C)c1cc(C(C)(C)C)c([C@@](C)(O)[C@@H]2CCCN2)c(C(C)(C)C)c1] 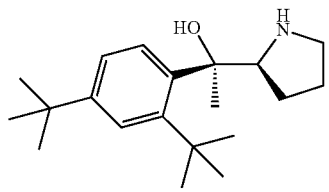 [SMILES: CC(C)(C)c1ccc([C@@](C)(O)[C@@H]2CCCN2)c(C(C)(C)C)c1]
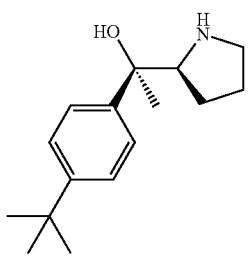 [SMILES: CC(C)(C)c1ccc([C@@](C)(O)[C@@H]2CCCN2)cc1] 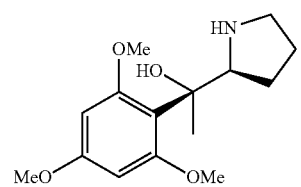 [SMILES: COc1cc(OC)c([C@@](C)(O)[C@@H]2CCCN2)c(OC)c1]
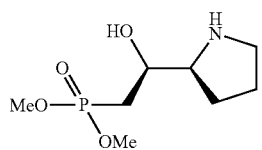 [SMILES: COP(=O)(C[C@@H](O)[C@@H]1CCCN1)OC] 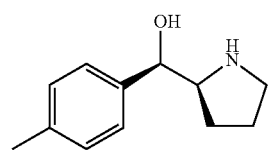
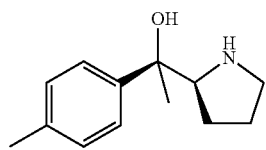 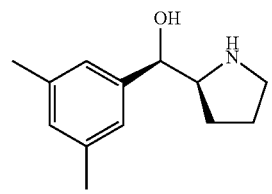
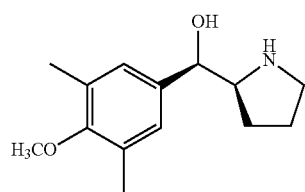 [SMILES: COc1c(C)cc([C@@H](O)[C@@H]2CCCN2)cc1C] 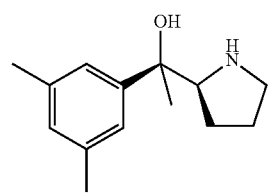 [SMILES: Cc1cc(C)cc([C@@](C)(O)[C@@H]2CCCN2)c1]
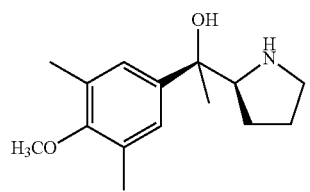 [SMILES: COc1c(C)cc([C@@](C)(O)[C@@H]2CCCN2)cc1C] 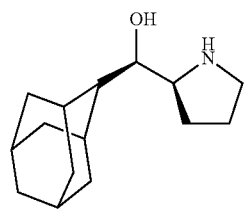 [SMILES: O[C@H](C1C2CC3CC(C2)CC1C3)[C@@H]1CCCN1]

TABLE 4-continued
Example compounds.
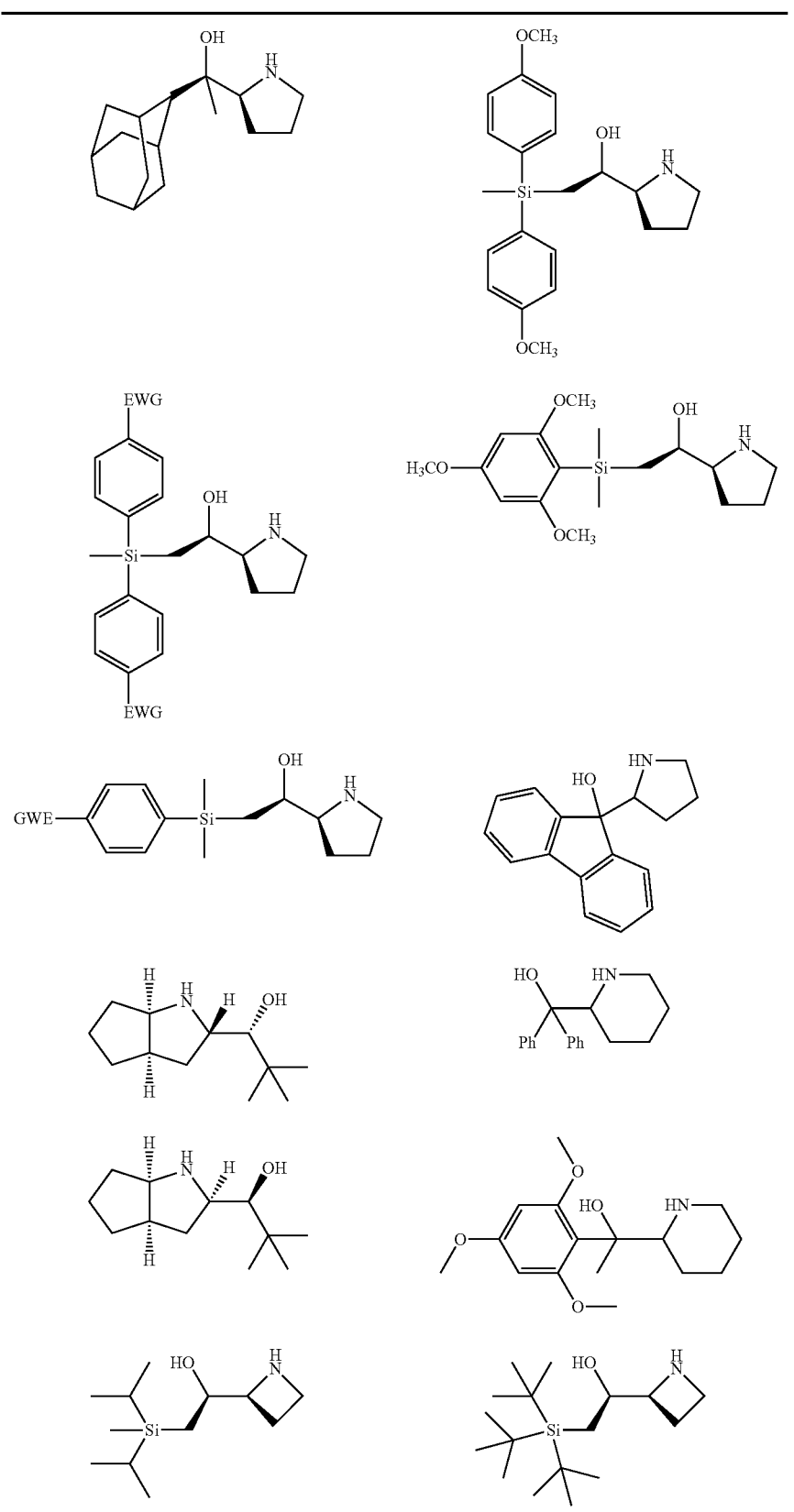

TABLE 4-continued
Example compounds.
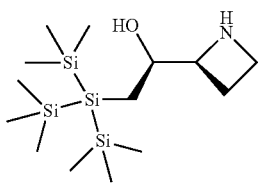 [SMILES: C[Si](C)(C)[Si](C[C@@H](O)[C@@H]1CCN1)([Si](C)(C)C)[Si](C)(C)C] 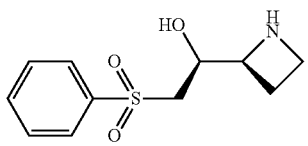 [SMILES: O=S(=O)(C[C@@H](O)[C@@H]1CCN1)c1ccccc1]
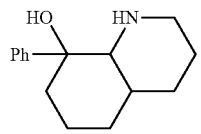 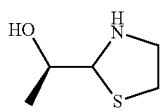
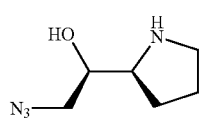 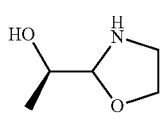
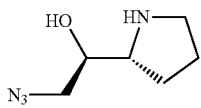 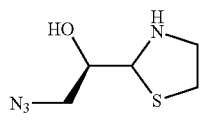
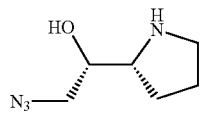 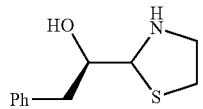 [SMILES: O[C@H](Cc1ccccc1)C1NCCS1]
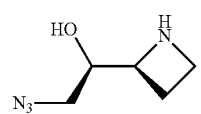 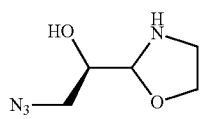
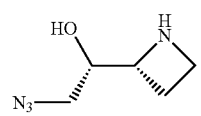 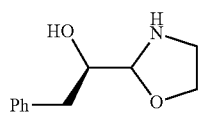
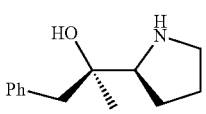 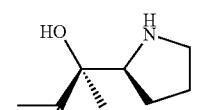
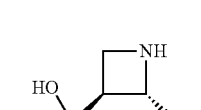 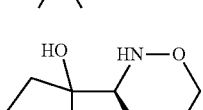
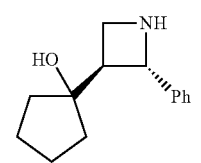 [SMILES: OC1([C@H]2CN[C@@H]2c2ccccc2)CCCC1] 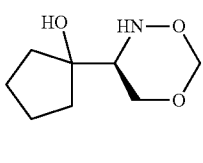
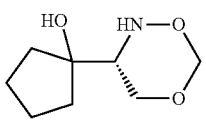 [SMILES: OC1([C@H]2COCON2)CCCC1] 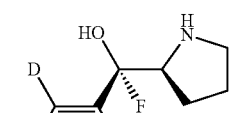
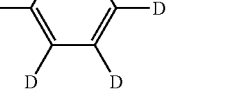 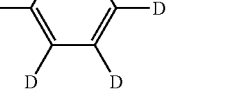

TABLE 4-continued
Example compounds.
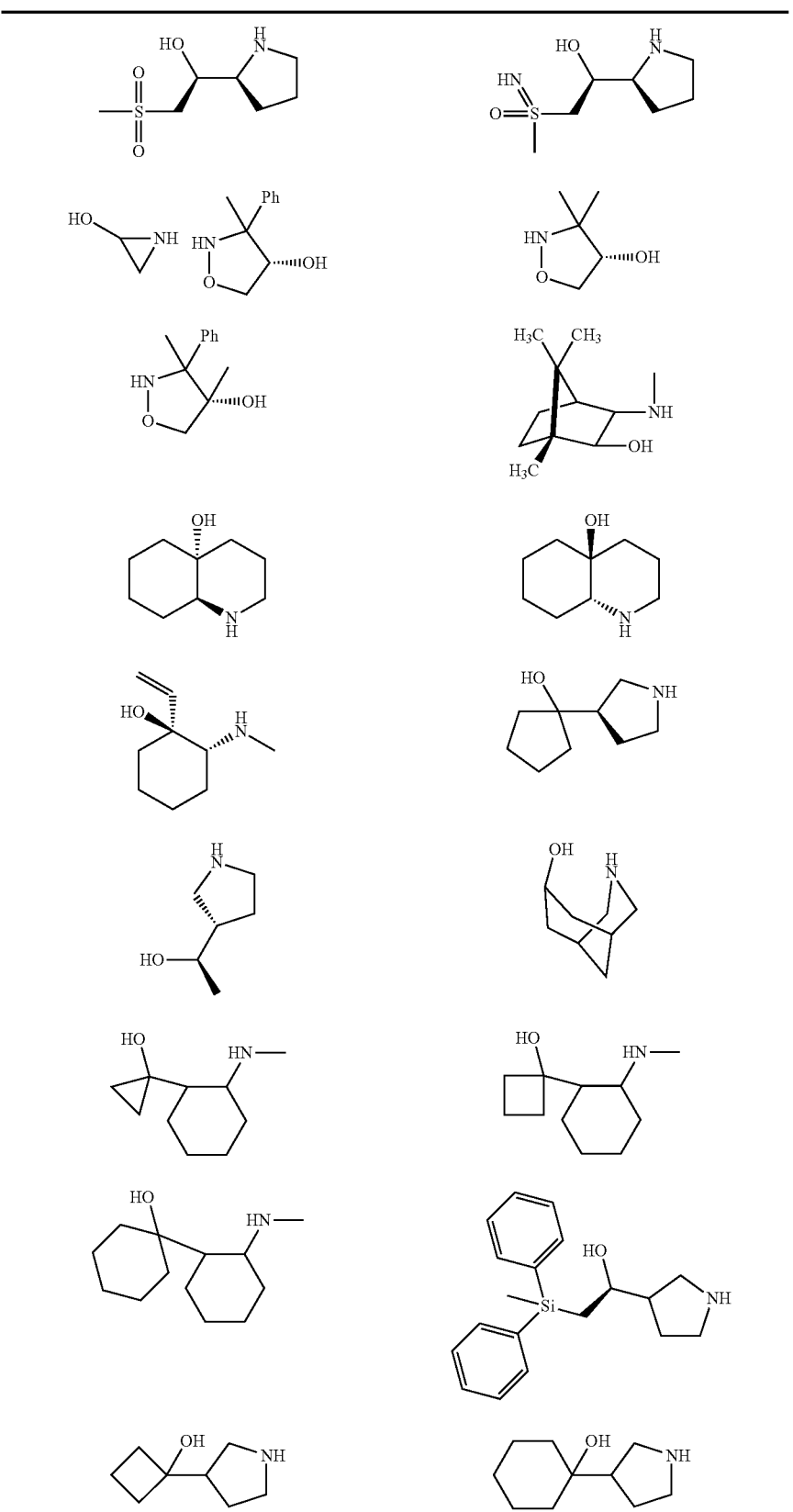

TABLE 4-continued
Example compounds.
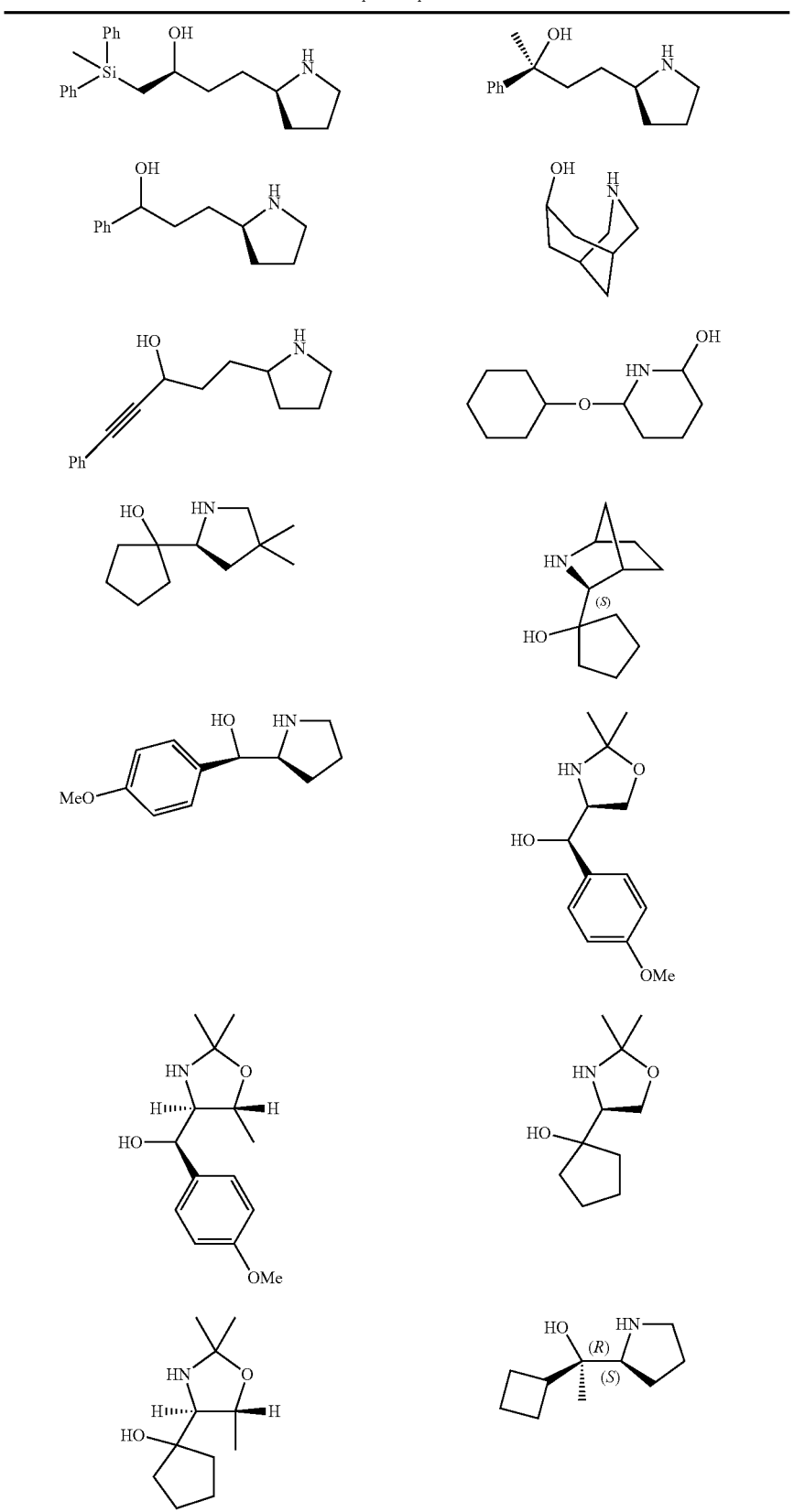

TABLE 4-continued
Example compounds.
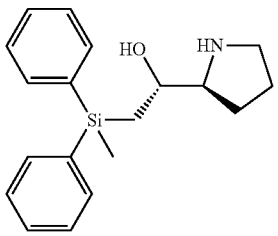 [SMILES: C[Si](C[C@H](O)[C@@H]1CCCN1)(c1ccccc1)c1ccccc1] 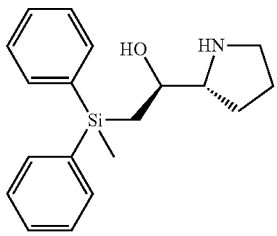 [SMILES: C[Si](C[C@@H](O)[C@H]1CCCN1)(c1ccccc1)c1ccccc1]
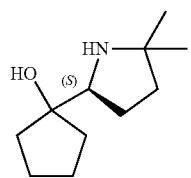 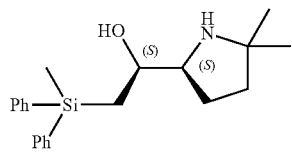
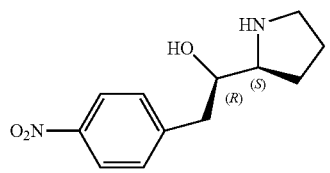 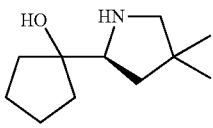
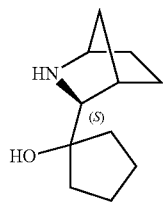 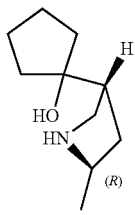
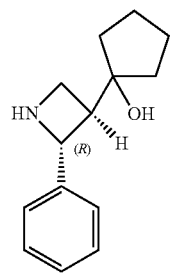 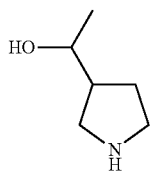
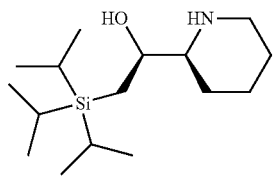 [SMILES: CC(C)[Si](C[C@@H](O)[C@@H]1CCCCN1)(C(C)C)C(C)C] 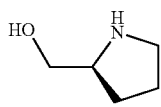
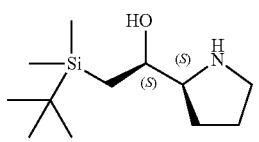 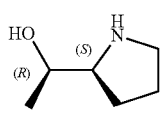

TABLE 4-continued
Example compounds.
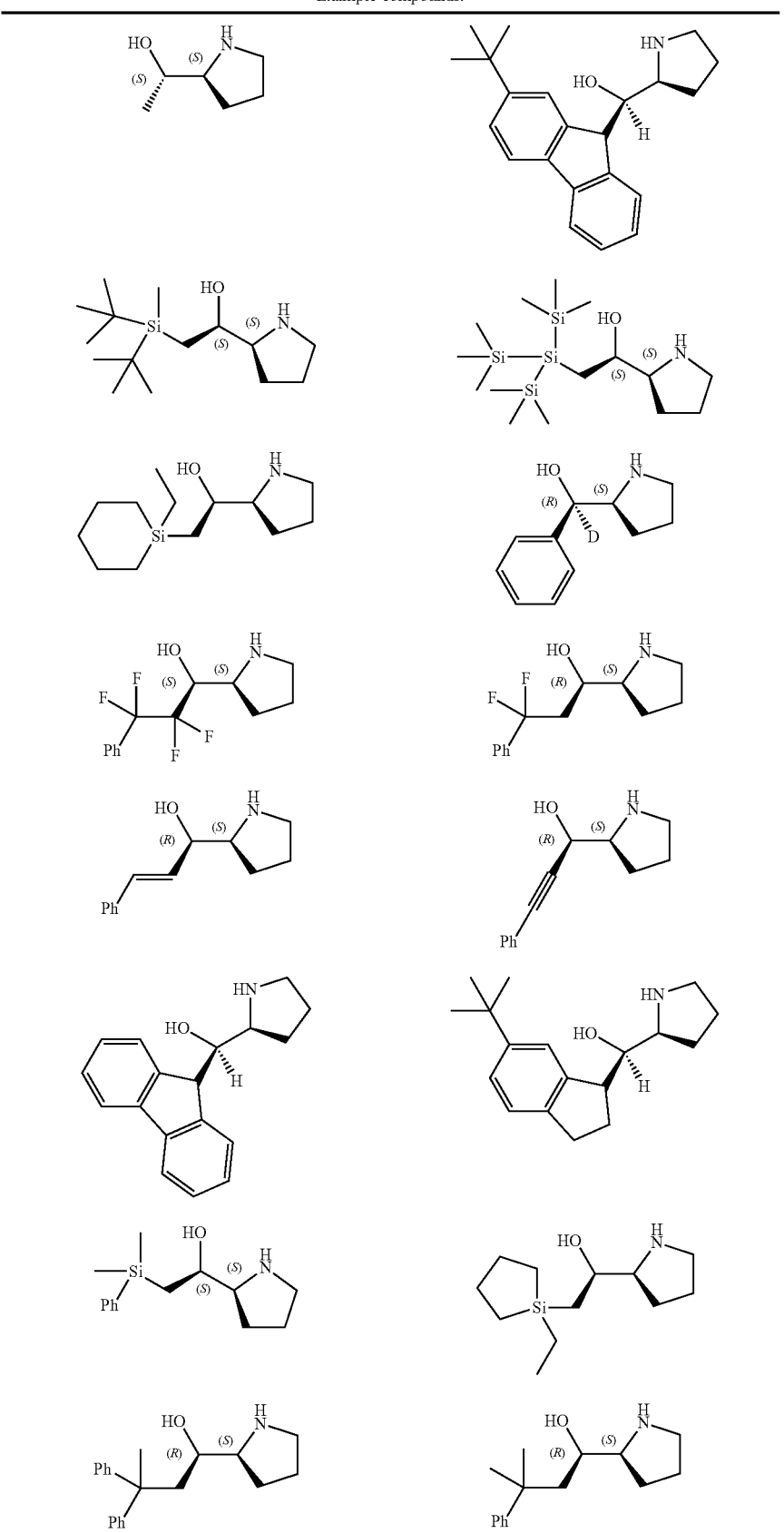

TABLE 4-continued
Example compounds.
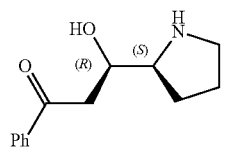 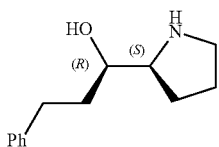
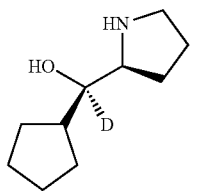 [SMILES: [2H][C@@](O)(C1CCCC1)[C@@H]1CCCN1] 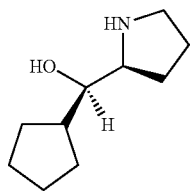 [SMILES: O[C@H](C1CCCC1)[C@@H]1CCCN1]
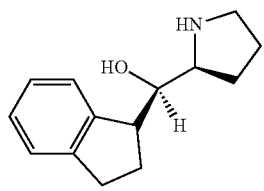 [SMILES: O[C@H](C1CCc2ccccc21)[C@@H]1CCCN1] 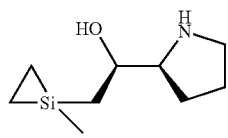
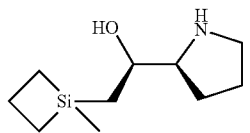 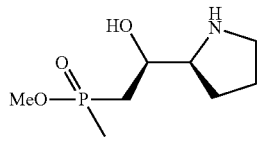
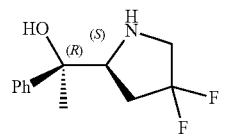 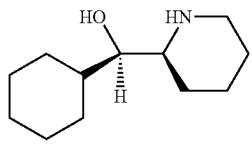 [SMILES: O[C@H](C1CCCCC1)[C@@H]1CCCCN1]
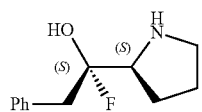 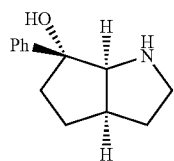
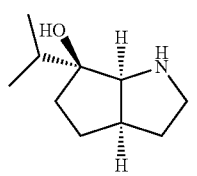 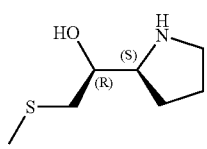
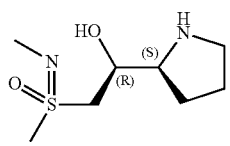 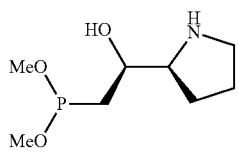 [SMILES: COP(C[C@@H](O)[C@@H]1CCCN1)OC]
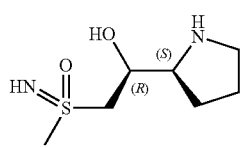 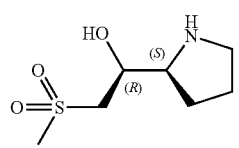

TABLE 4-continued
Example compounds.
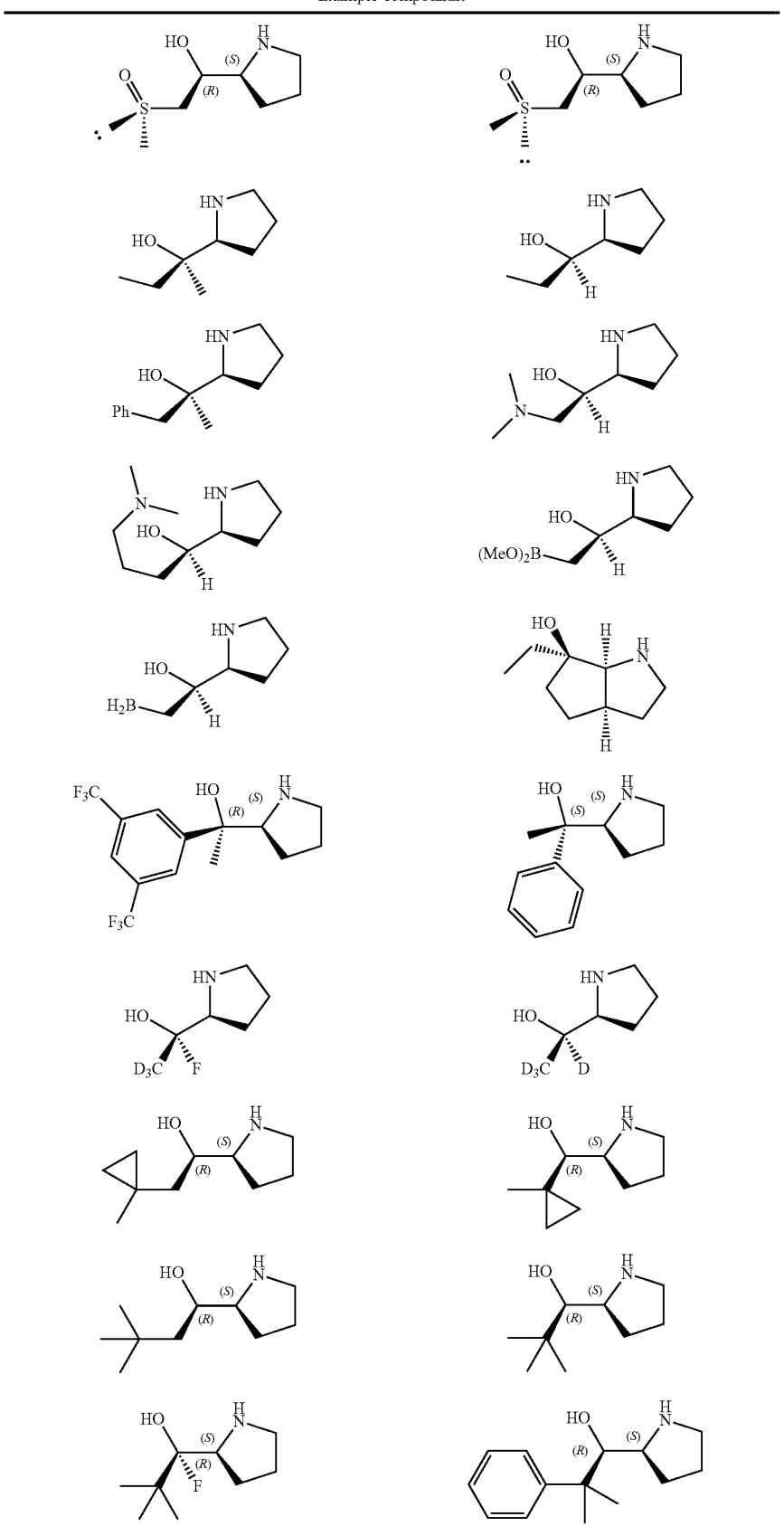

TABLE 4-continued
Example compounds.
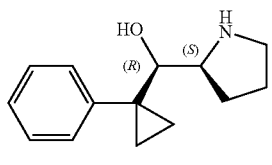 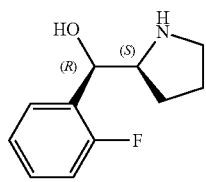
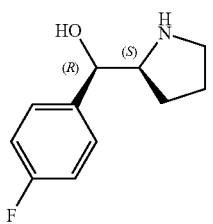 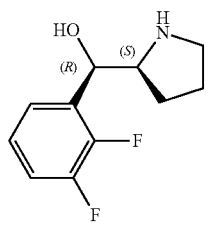
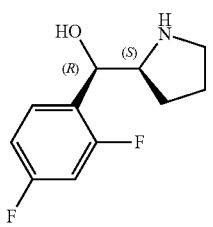 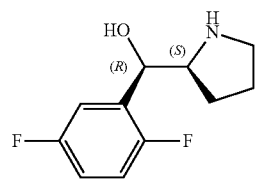
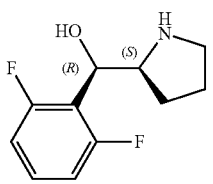 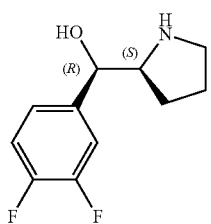
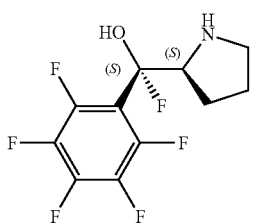 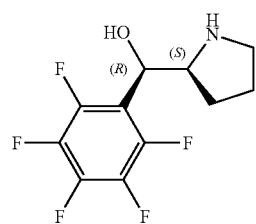
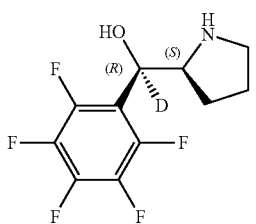 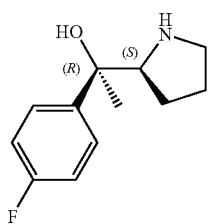
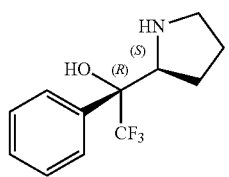 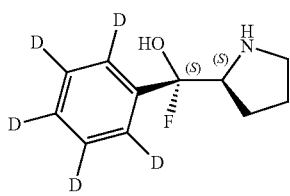

TABLE 4-continued
Example compounds.
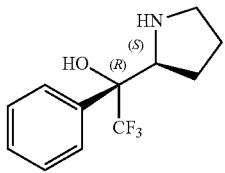 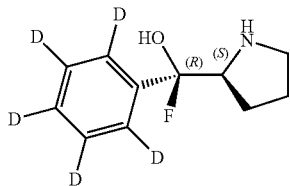
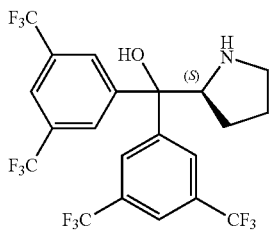 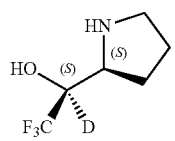
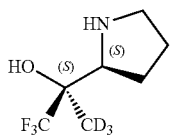 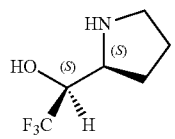
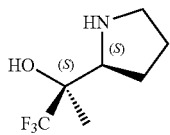 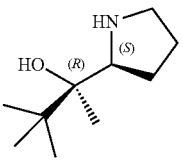
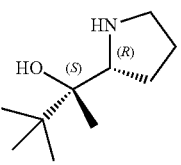 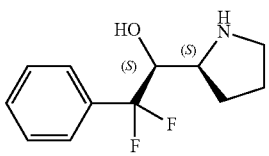
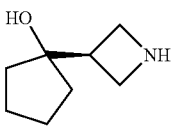 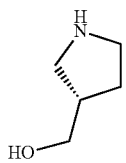
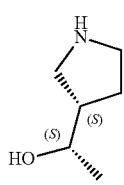 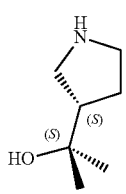
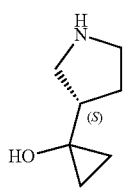 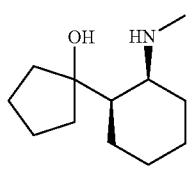

TABLE 4-continued

Example compounds.

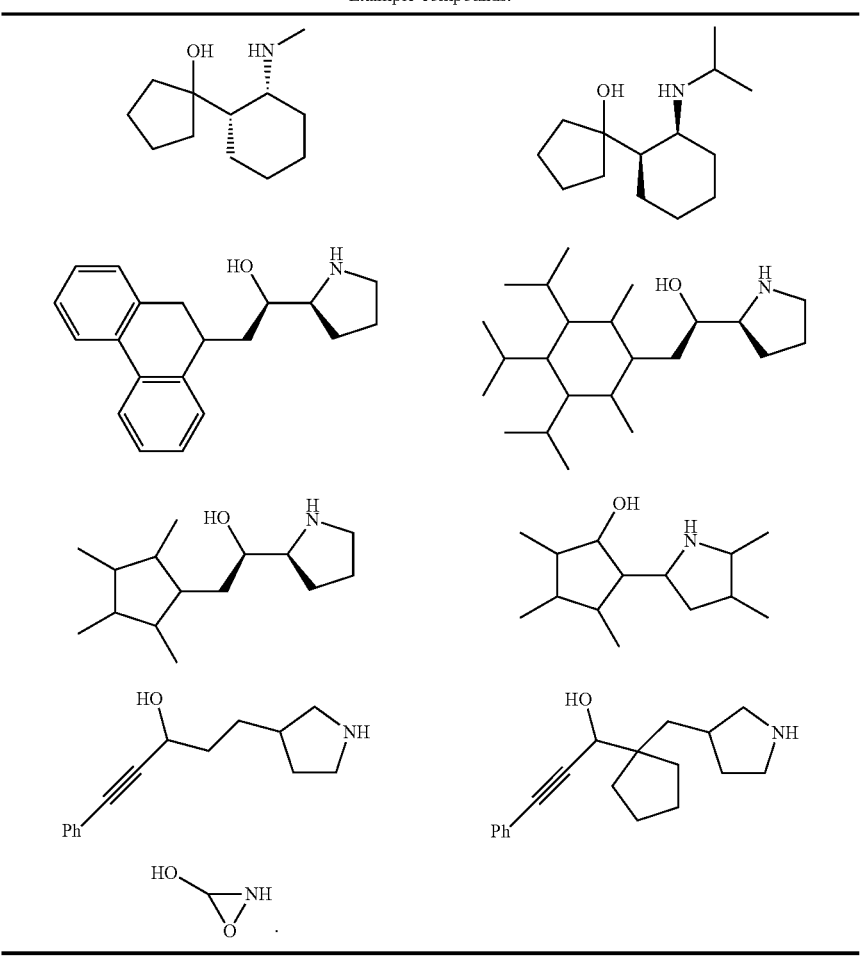

In some embodiments, a provided compound is an enantiomer of a compound selected from Table 4 or a salt thereof. In some embodiments, a provided compound is a diastereomer of a compound selected from Table 4 or a salt thereof.

In some embodiments, provided compounds, e.g., compounds of formula I, I-a, I-a-1, I-a-2, I-b, I-c, I-d, I-e, II, II-a, II-b, III, III-a, or III-b, or salts thereof, comprises one or more chiral elements. In some embodiments, provided compounds of formula I, I-a, I-a-1, I-a-2, I-b, I-c, I-d, I-e, II, II-a, II-b, III, III-a, or III-b, or salts thereof, are chiral. In some embodiments, provided chiral compounds, compounds of formula I, I-a, I-a-I, I-a-2, I-b, I-c, I-d, I-e, II, II-a, II-b, III, III-a, or III-b, or salts thereof, are of a purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a stereopurity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of a diastereomeric purity described in the present disclosure. In some embodiments, provided chiral compounds, compounds of formula I, I-a, I-a-I, I-a-2, I-b, I-c, I-d, I-e, II, II-a, II-b, III, III-a, or III-b, or salts thereof, are of a enantiomeric purity described in the present disclosure. In some embodiments, provided chiral compounds, compounds of formula I, I-a, I-a-1, I-a-2, I-b, I-c, I-d, I-e, II, II-a, II-b, III, III-a, or III-b, or salts thereof, are of diastereomeric and enantiomeric purity described in the present disclosure. In some embodiments, the present disclosure provides compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, VI-e, VIII, or salts thereof, that are made from compounds of formula I, I-a, I-a-1, I-a-2, I-b, I-c, I-d, I-e, II, II-a, II-b, III, III-a, or III-b, or salts thereof, and comprise chiral elements of compounds of formula I, I-a, I-a-1, I-a-2, I-b, I-c, I-d, I-e, II, II-a, II-b, III, III-a, or III-b.

Methods for preparing chiral auxiliary compounds are widely known in the art and can be utilized in accordance with the present disclosure. A large of compounds, including many in the tables, were prepared and characterized. Many compounds described herein, when used as chiral auxiliaries can deliver high stereoselectivity and/or purity.

Phosphoramidites

In many embodiments, chiral auxiliaries are utilized to prepare chirally pure phosphoramidites, which are used to stereoselectively form linkage phosphorus chiral centers compared to absence of chiral auxiliaries. In some embodiments, the present disclosure provides compound, e.g., of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof, that can be utilized as phosphoramidites for oligonucleotide synthesis. In some embodiments, product oligonucleotides may contain one or more natural phosphate linkages and/or non-chirally controlled chiral internucleotidic linkages, and for such linkages, phosphoramidite for traditional oligonucleotide synthesis may be readily utilized. As understand by those skilled in the art, nucleobases may be blocked in phosphoramidite for oligonucleotide synthesis, and they can be de-blocked, e.g., after synthesis cycles. Technologies for blocking and de-blocking (protecting) nucleobases are widely known in the art and can be utilized in accordance with the present disclosure. Technologies for preparing phosphoramidites can be utilized in accordance with the present disclosure. Example technologies include those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc. As illustrated, in some embodiments, a phosphoramidite is a DPSE-phosphoramidite comprising

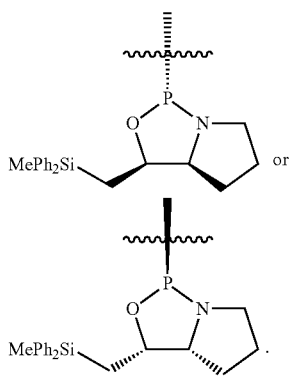

For example, in some embodiments, the present disclosure provides a compound having the structure of formula IV:

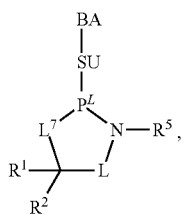

IV or a salt thereof, wherein:

$P^L$ is P(=W), P, or P→B(R')$_3$;

W is O, S or Se;

L is a covalent bond, or optionally substituted $C_{1-6}$ alkylene, wherein one or more methylene units are optionally and independently replaced with -L'-;

L' is a covalent bond, optionally substituted bivalent $C_{1-3}$ alkylene, —C(R$^3$)(R$^4$)—, —C(R$^3$)(R$^4$)—C(R$^3$)(R$^4$)—, -Cy-, or —C(R$^3$)[C(R$^4$)$_3$]—;

each of R$^1$, R$^2$, R$^3$, R$^4$, and R$^5$ is independently —H, -L$^s$-R, halogen, —CN, —NO$_2$, -L$^s$-Si(R)$_3$, —OR, —SR, or —N(R)$_2$;

each L$^s$ is independently a covalent bond, or a bivalent, optionally substituted, linear or branched group selected from a $C_{1-31}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

L$^7$ is —O— or —S—;

at least one of R', R$^2$, R$^3$ and R$^4$ is not —H; BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety;

SU is -L$^s$-O— or

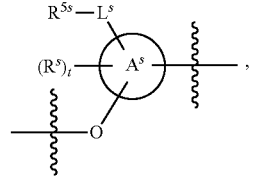

wherein SU is connected to the phosphorus atom through the oxygen atom;

each $R^s$ is independently —H, halogen, —CN, —N₃, —NO, —NO₂, -L$^s$-R', -L$^s$-Si(R)₃, -L$^s$-OR', -L$^s$-SR', -L$^s$-N(R')₂, —O-L$^s$-R', —O-L$^s$-Si(R)₃, —O-L$^s$-OR', —O-L$^s$-SR', or —O-L$^s$-N(R')₂;

t is 0-20;

Ring $A^s$ is an optionally substituted 3-20 membered monocyclic, bicyclic or polycyclic ring having 0-10 heteroatoms independently selected from oxygen, nitrogen, sulfur, phosphorus and silicon;

$R^{5s}$ is $R^s$;

each R' is independently —R, —C(O)R, —C(O)OR, or —S(O)₂R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $P^L$ is P(=W). In some embodiments, $P^L$ is P. In some embodiments, $P^L$ is P→B(R')₃. In some embodiments, P of $P^L$ is chiral. In some embodiments, P of $P^L$ is Rp. In some embodiments, P of $P^L$ is Sp.

In some embodiments, SU is -L$^s$-O—. In some embodiments, SU is

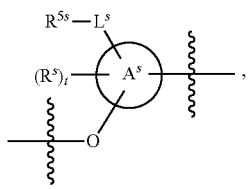

wherein each variable is independently as described in the present disclosure. In some embodiments, SU is

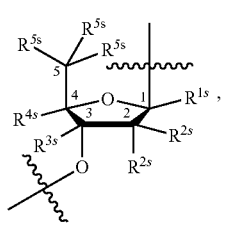

each of $R^{1s}$, $R^{2s}$, $R^{3s}$, $R^{4s}$ and $R^{5s}$ is independently $R^s$. In some embodiments, SU is

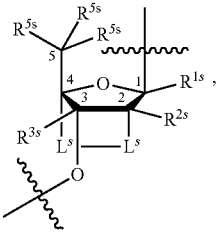

wherein each variable is independently as described in the present disclosure. In some embodiments, SU is

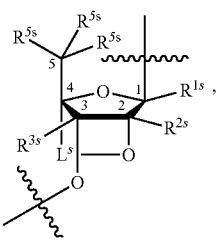

wherein each variable is independently as described in the present disclosure. In some embodiments, SU is

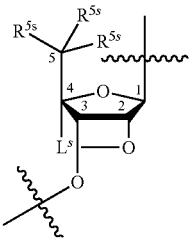

wherein each variable is independently as described in the present disclosure. In some embodiments, SU is

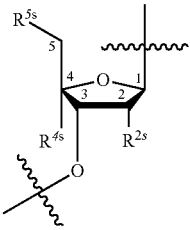

wherein each variable is independently as described in the present disclosure. In some embodiments, SU is

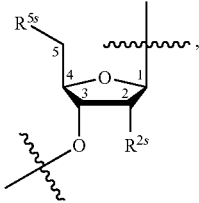

wherein each variable is independently as described in the present disclosure.

In some embodiments, a provided compound, e.g., a compound of formula IV, has the structure of formula IV-a:

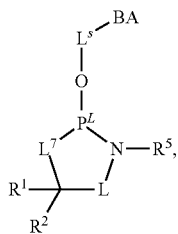

IV-a or a salt thereof, wherein each variable is independently as described in the present disclosure. In some embodiments, a provided compound of formula IV has the structure of formula IV-a. In some embodiments, $L^s$-Cy-. In some embodiments, $L^s$ is an optionally substituted monocyclic or bicyclic 3-20 membered heterocyclyl ring having 1-5 heteroatoms. In some embodiments, $L^s$ is an optionally substituted monocyclic or bicyclic 5-20 membered heterocyclyl ring having 1-5 heteroatoms, wherein at least one heteroatom is oxygen. In some embodiments, $L^s$ is an optionally substituted bivalent tetrahydrofuran ring. In some embodiments, $L^s$ is an optionally substituted furanose moiety. In some embodiments, the BA in formula IV-a is bonded to C1, and the —O— in formula IV-a is bonded to C3, of the furanose moiety.

In some embodiments, a provided compound, e.g., a compound of formula IV, has the structure of formula IV-b:

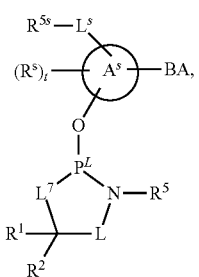

IV-b or a salt thereof, wherein each variable is independently as described in the present disclosure. In some embodiments, a provided compound of formula IV has the structure of formula IV-b.

In some embodiments, a provided compound, e.g., a compound of formula IV, has the structure of formula IV-c-1:

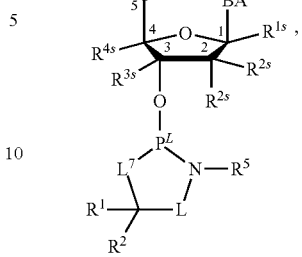

IV-c-1 or a salt thereof, wherein each variable is independently as described in the present disclosure. In some embodiments, a provided compound of formula IV has the structure of formula IV-c-1.

In some embodiments, a provided compound, e.g., a compound of formula IV, has the structure of formula IV-c-2:

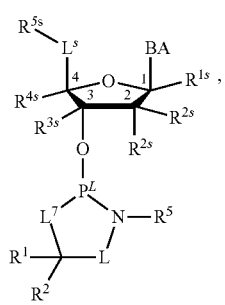

IV-c-2 or a salt thereof, wherein each variable is independently as described in the present disclosure. In some embodiments, a provided compound of formula IV has the structure of formula IV-c-2.

In some embodiments, a provided compound, e.g., a compound of formula IV, has the structure of formula IV-d:

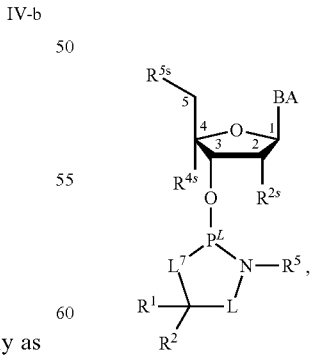

IV-d or a salt thereof, wherein each variable is independently as described in the present disclosure. In some embodiments, a provided compound of formula IV has the structure of formula IV-d.

In some embodiments, a provided compound, e.g., a compound of formula IV, has the structure of formula IV-e:

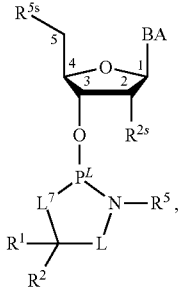
IV-e or a salt thereof, wherein each variable is independently as described in the present disclosure. In some embodiments, a provided compound of formula IV has the structure of formula IV-e.

In some embodiments, a compound of formula IV, IV-a, IV-b, IV-c-1, IV-c-2, IV-d, or IV-e, can be prepared from a compound of formula I, I-a, I-a-1, I-a-2, I-b, I-c, I-d, I-e, II, II-a, II-b, III, III-a, III-b, etc. In some embodiments,

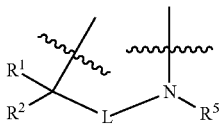

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

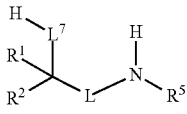

is a compound having the structure of I, I-a, I-a-1, I-a-2, I-b, I-c, I-d, or I-e, or a salt thereof.

In some embodiments, the present disclosure provides a compound having the structure of formula IVa:

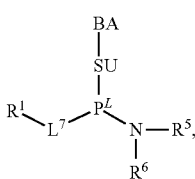
IVa or a salt thereof, wherein each variable is independently as described in the present disclosure. In some embodiments, the present disclosure provides a compound having the structure of formula IVa-a:

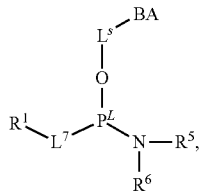
IVa-a or a salt thereof, wherein each variable is independently as described in the present disclosure. In some embodiments, a compound of formula IVa is a compound of formula IVa-a. In some embodiments, the present disclosure provides a compound having the structure of formula IVa-b:

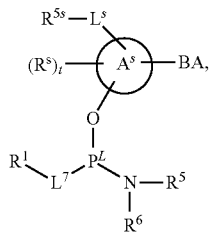
IVa-b or a salt thereof, wherein each variable is independently as described in the present disclosure. In some embodiments, a compound of formula IVa is a compound of formula IVa-b. In some embodiments, the present disclosure provides a compound having the structure of formula IVa-c-1:

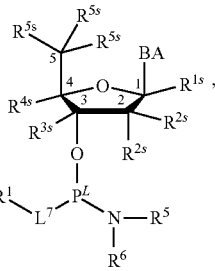
IVa-c-1 or a salt thereof, wherein each variable is independently as described in the present disclosure. In some embodiments, a compound of formula IVa is a compound of formula IVa-c-1. In some embodiments, the present disclosure provides a compound having the structure of formula IVa-c-2:

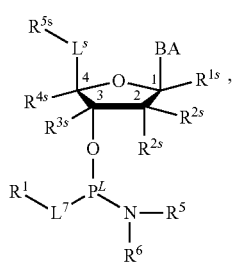
IVa-c-2 or a salt thereof, wherein each variable is independently as described in the present disclosure. In some embodiments, a compound of formula IVa is a compound of formula IVa-c-2. In some embodiments, the present disclosure provides a compound having the structure of formula IVa-d:

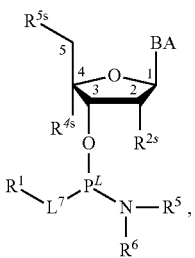

IVa-d or a salt thereof, wherein each variable is independently as described in the present disclosure. In some embodiments, a compound of formula IVa is a compound of formula IVa-d. In some embodiments, the present disclosure provides a compound having the structure of formula IVa-e:

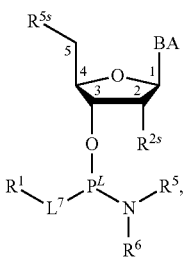

IVa-e or a salt thereof, wherein each variable is independently as described in the present disclosure. In some embodiments, a compound of formula IVa is a compound of formula IVa-e. In some embodiments, $L^7$ is —O—. In some embodiments, each of $R^1$, $R^5$ and $R^6$ is independently optionally substituted $C_{1-6}$ alkyl. In some embodiments, $R^5$ and $R^6$ are the same. In some embodiments, $P^L$ is P. In some embodiments, -$L^7$-$R^1$ contains no chiral elements. In some embodiments, —N($R^5$)($R^6$) contains no chiral elements. In some embodiments, -$L^7$-$R^1$ and —N($R^5$)($R^6$) contains no chiral elements. In some embodiments, -$L^7$-$R^1$ is —O—CH$_2$CH$_2$—CN. In some embodiments, —N($R^5$)($R^6$) is —N(i-Pr)$_2$. In some embodiments, a compound of formula IVa, IVa-a, IVa-b, IVa-c-1, IVa-c-2, IVa-d, or IVa-e, or a salt thereof, is a phosphoramidite for non-chirally controlled oligonucleotide synthesis, e.g., oligonucleotide synthesis using traditional phosphoramidite chemistry. In some embodiments, $R^1$ and $R^5$ are R and are taken together with their intervening atoms to form a ring as described in the present disclosure. In some embodiments, a formed ring contain a chiral element, and a compound of formula IVa, IVa-a, IVa-b, IVa-c-1, IVa-c-2, IVa-d, or IVa-e, or a salt thereof can be utilized for chirally controlled oligonucleotide synthesis.

In some embodiments, the present disclosure provides a compound having the structure of formula V:

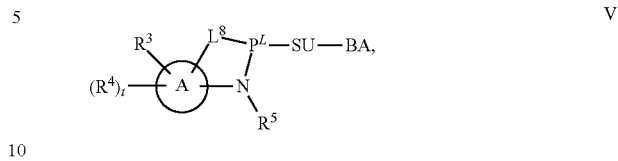

or a salt thereof, wherein:
$P^L$ is P(=W), P, or P→B(R')$_3$;
W is O, S or Se;
Ring A is an optionally substituted 3-20 membered monocyclic, bicyclic or polycyclic ring having 0-10 heteroatoms independently selected from oxygen, nitrogen, sulfur, phosphorus and silicon;
each of $R^1$, $R^2$, $R^3$, $R^4$, and $R^5$ is independently —H, -$L^s$-R, halogen, —CN, —NO$_2$, -$L^s$-Si(R)$_3$, —OR, —SR, or —N(R)$_2$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
t is 0-20;
$L^8$ is -L-O—, -L-C($R^1$)($R^2$)—O—, or -$L^s$-O—;
L is a covalent bond, or optionally substituted $C_{1-6}$ alkylene, wherein one or more methylene units are optionally and independently replaced with -L'-;
L' is a covalent bond, optionally substituted bivalent $C_{1-3}$ alkylene, —C($R^3$)($R^4$)—, —C($R^3$)($R^4$)—C($R^3$)($R^4$)—, -Cy-, or —C($R^3$)[C($R^4$)$_3$]—;
BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety; SU is -$L^s$-O— or

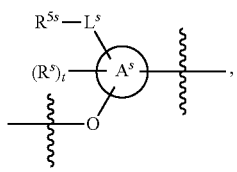

wherein SU is connected to the phosphorus atom through the oxygen atom;

$R^{5s}$ is $R^s$;

each $R^s$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R)$_2$, —O-$L^s$-R', —O-$L^s$-Si(R)$_3$, —O-$L^s$-OR', —O-$L^s$-SR', or —O-$L^s$-N(R')$_2$;

Ring $A^s$ is an optionally substituted 3-20 membered monocyclic, bicyclic or polycyclic ring having 0-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $P^L$ is P(=W). In some embodiments, $P^L$ is P. In some embodiments, $P^L$ is P→B(R')$_3$. In some embodiments, P of $P^L$ is chiral. In some embodiments, P of $P^L$ is Rp. In some embodiments, P of $P^L$ is Sp.

In some embodiments, a provided compound, e.g., a compound of formula V, has the structure of formula V-a:

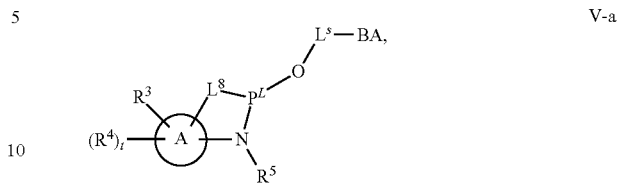

or a salt thereof, wherein each variable is independently as described in the present disclosure. In some embodiments, a provided compound of formula V has the structure of formula V-a.

In some embodiments, a provided compound, e.g., a compound of formula V, has the structure of formula V-b:

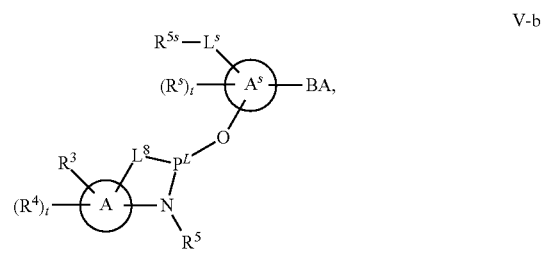

or a salt thereof, wherein each variable is independently as described in the present disclosure. In some embodiments, a provided compound of formula V has the structure of formula V-b.

In some embodiments, a provided compound, e.g., a compound of formula V, has the structure of formula V-c-1:

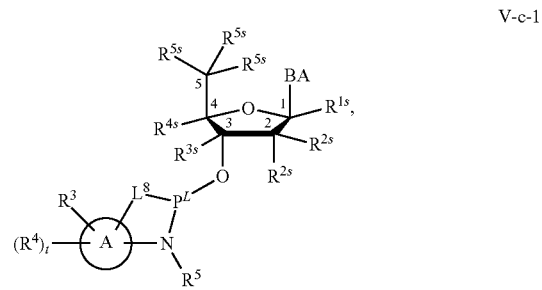

or a salt thereof, wherein each variable is independently as described in the present disclosure. In some embodiments, a provided compound of formula V has the structure of formula V-c-1.

In some embodiments, a provided compound, e.g., a compound of formula V, has the structure of formula V-c-2:

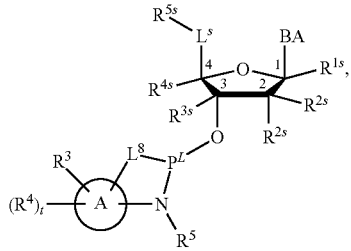

V-c-2 or a salt thereof, wherein each variable is independently as described in the present disclosure. In some embodiments, a provided compound of formula V has the structure of formula V-c-2.

In some embodiments, a provided compound, e.g., a compound of formula V, has the structure of formula V-d:

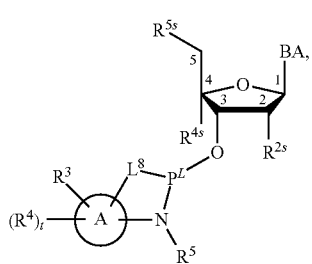

V-d or a salt thereof, wherein each variable is independently as described in the present disclosure. In some embodiments, a provided compound of formula V has the structure of formula V-d.

In some embodiments, a provided compound, e.g., a compound of formula V, has the structure of formula V-e:

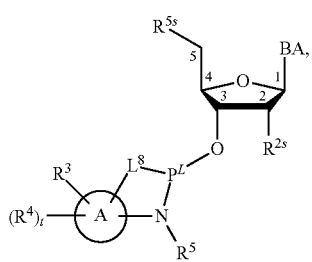

V-e or a salt thereof, wherein each variable is independently as described in the present disclosure. In some embodiments, a provided compound of formula V has the structure of formula V-e.

In some embodiments, a compound of formula V, V-a, V-b, V-c-1, V-c-2, V-d, or V-e, can be prepared from a compound of formula I, I-a, I-a-1, I-a-2, I-b, I-c, I-d, I-e, II, II-a, II-b, III, III-a, III-b, etc. In some embodiments,

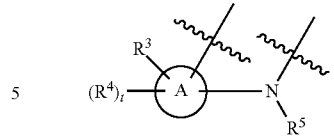

is as described for formula I, I-a, I-a-1, I-a-2, I-b, I-c, I-d, I-e, II, II-a, II-b, III, III-a, III-b, etc. In some embodiments, a compound of formula IV, IV-a, IV-b, IV-c-1, IV-c-2, IV-d, or IV-e has a structure such that

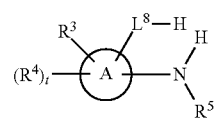

is a compound having the structure of II, II-a, or II-b.

In some embodiments, the present disclosure provides a compound having the structure of formula VI:

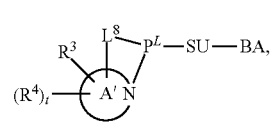

VI or a salt thereof, wherein each variable is independently as described in the present disclosure.

In some embodiments, a provided compound, e.g., a compound of formula VI, has the structure of formula VI-a:

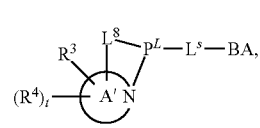

VI-a or a salt thereof, wherein Ring A' is Ring A comprising a ring nitrogen atom which is bond to P of $P^L$, and each variable is independently as described in the present disclosure. In some embodiments, a provided compound of formula VI has the structure of formula VI-a.

In some embodiments, a provided compound, e.g., a compound of formula VI, has the structure of formula VI-b:

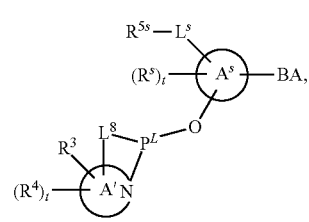

VI-b or a salt thereof, wherein each variable is independently as described in the present disclosure. In some embodiments, a provided compound of formula VI has the structure of formula VI-b.

In some embodiments, a provided compound, e.g., a compound of formula VI, has the structure of formula VI-c-1:

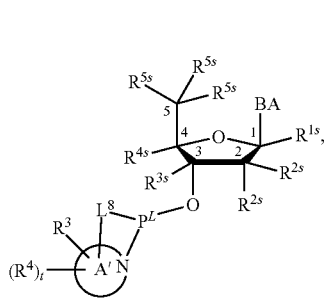

VI-c-1 or a salt thereof, wherein each variable is independently as described in the present disclosure. In some embodiments, a provided compound of formula VI has the structure of formula VI-c-1.

In some embodiments, a provided compound, e.g., a compound of formula VI, has the structure of formula VI-c-2:

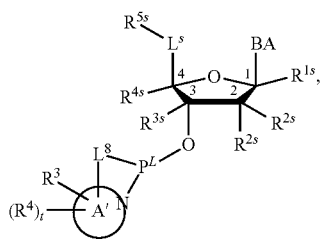

VI-c-2 or a salt thereof, wherein each variable is independently as described in the present disclosure. In some embodiments, a provided compound of formula VI has the structure of formula VI-c-2.

In some embodiments, a provided compound, e.g., a compound of formula VI, has the structure of formula VI-d:

VI-d

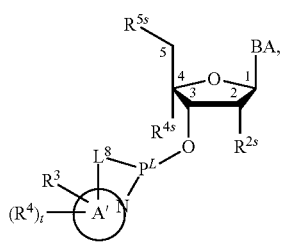

or a salt thereof, wherein each variable is independently as described in the present disclosure. In some embodiments, a provided compound of formula VI has the structure of formula VI-d.

In some embodiments, a provided compound, e.g., a compound of formula VI, has the structure of formula VI-e:

VI-e

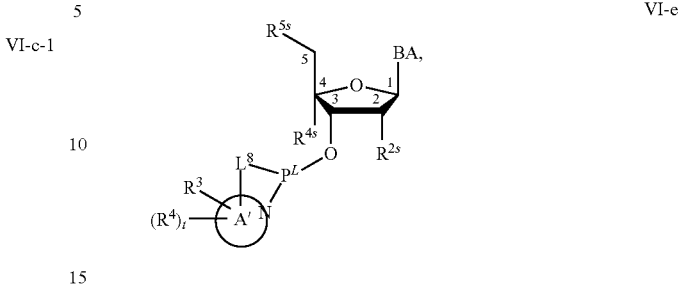

or a salt thereof, wherein each variable is independently as described in the present disclosure. In some embodiments, a provided compound of formula VI has the structure of formula VI-e.

In some embodiments, a compound of formula VI, VI-a, VI-b, VI-c-1, VI-c-2, VI-d, or VI-e, can be prepared from a compound of formula I, I-a, I-a-1, I-a-2, I-b, I-c, I-d, I-e, II, II-a, II-b, III, III-a, III-b, etc. In some embodiments,

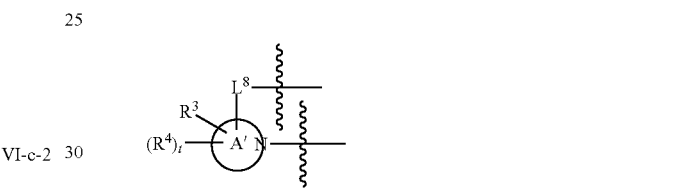

is as described for formula I, I-a, I-a-1, I-a-2, I-b, I-c, I-d, I-e, II, II-a, II-b, III, III-a, III-b, etc. In some embodiments, a compound of formula VI, VI-a, VI-b, VI-c-1, VI-c-2, VI-d, or VI-e has a structure such that

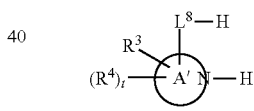

is a compound having the structure of III, III-a, or III-b.

In some embodiments, for a phosphoramidite has the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, $P^L$ is P.

In some embodiments, a phosphoramidite for non-stereocontrolled coupling is of structure

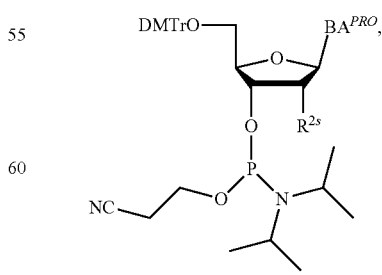

wherein each variable is independently as described in the present disclosure.

Nucleobases

In some embodiments, a nucleobase, e.g., BA, in provided oligonucleotides is a natural nucleobase (e.g., adenine, cytosine, guanosine, thymine, or uracil) or a modified nucleobase derived from a natural nucleobase, e.g., optionally substituted adenine, cytosine, guanosine, thymine, or uracil, or tautomeric forms thereof. Examples include, but are not limited to, uracil, thymine, adenine, cytosine, and guanine, and tautomeric forms thereof, having their respective amino groups protected by protecting groups, e.g., one or more of —R, —C(O)R, etc. Example protecting groups are widely known in the art and can be utilized in accordance with the present disclosure. In some embodiments, a protected nucleobase and/or derivative is selected from nucleobases with one or more acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are also disclosed in Chiu and Rana, *RNA*, 2003, 9, 1034-1048, Limbach et al. *Nucleic Acids Research*, 1994, 22, 2183-2196 and Revankar and Rao, *Comprehensive Natural Products Chemistry*, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently-selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen or sulfur;

(3) one or more double bonds in a nucleobase are independently hydrogenated; or (4) one or more optionally substituted aryl or heteroaryl rings are independently inserted into a nucleobase.

Compounds represented by the following general formulae are also contemplated as modified nucleobases:

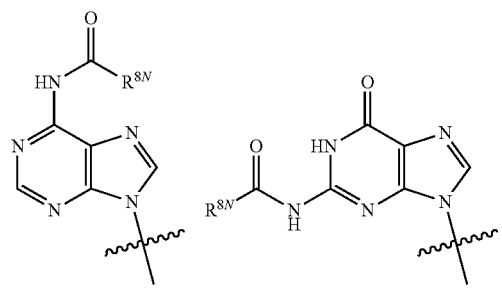

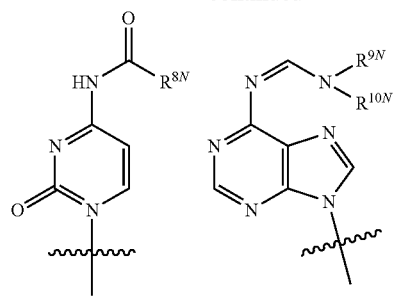

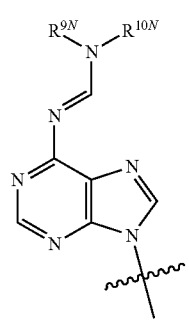

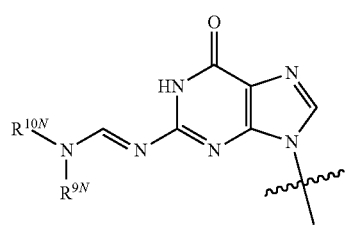

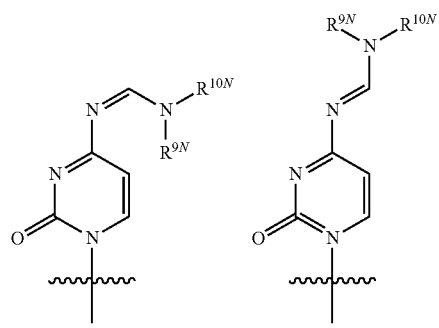

-continued

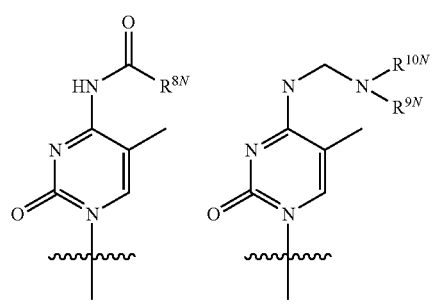

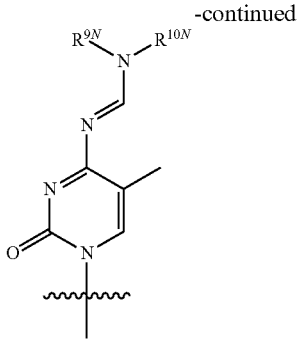

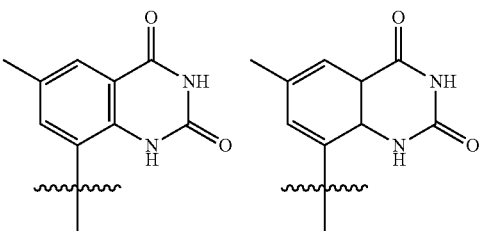

wherein $R^{8N}$ is an optionally substituted, linear or branched group selected from aliphatic, aryl, aralkyl, aryloxylalkyl, carbocyclyl, heterocyclyl and heteroaryl, each having 1 to 30 carbon atoms, and 1-10 heteroatoms if applicable, including, by way of example only, a methyl, isopropyl, phenyl, benzyl, or phenoxymethyl group; and each of $R^{9N}$ and $R^{10N}$ is independently an optionally substituted group selected from linear or branched aliphatic, carbocyclyl, aryl, heterocyclyl and heteroaryl, each having 1 to 30 carbon atoms, and 1-10 heteroatoms Modified nucleobases also include expanded-size nucleobases in which one or more aryl rings, such as phenyl rings, have been added. Nucleic base replacements described in the Glen Research catalog (www.glenresearch.com); Krueger A T et al, *Acc. Chem. Res.,* 2007, 40, 141-150; Kool, E T, *Acc. Chem. Res.,* 2002, 35, 936-943; Benner S. A., et al., *Nat. Rev. Genet.,* 2005, 6, 553-543; Romesberg, F. E., et al., *Curr. Opin. Chem. Biol.,* 2003, 7, 723-733; Hirao, I., *Curr. Opin. Chem. Biol.,* 2006, 10, 622-627, are contemplated as useful for the synthesis of certain provided compounds in the present disclosure. Some examples of these expanded-size nucleobases are shown below:

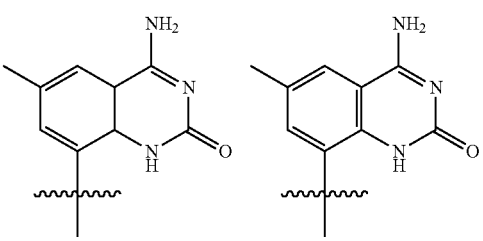

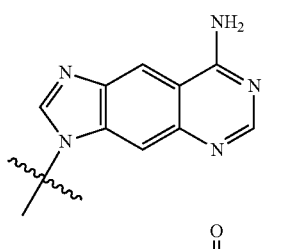

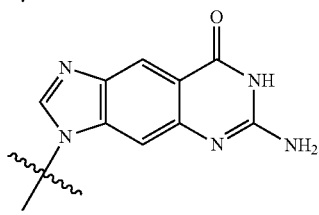

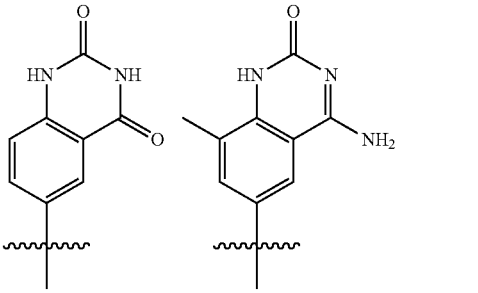

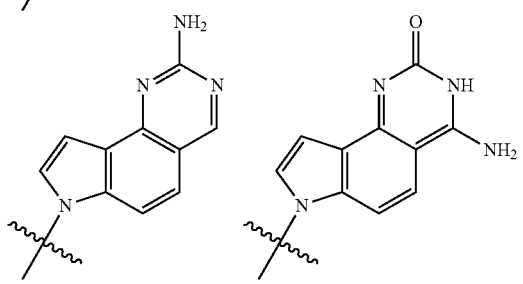

Modified nucleobases also encompass structures that are not considered typical nucleobases but are other moieties such as, but not limited to, corrin- or porphyrin-derived rings. Porphyrin-derived base replacements have been described in Morales-Rojas, H and Kool, E T, *Org. Lett.,* 2002, 4, 4377-4380. Shown below is an example of a porphyrin-derived ring which can be used as a base replacement:

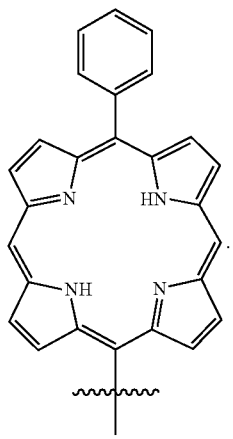 [SMILES: *c1c2nc(cc3ccc([nH]3)c(-c3ccccc3)c3nc(cc4ccc1[nH]4)C=C3)C=C2]

In some embodiments, modified nucleobases are of any one of the following structures, optionally substituted:

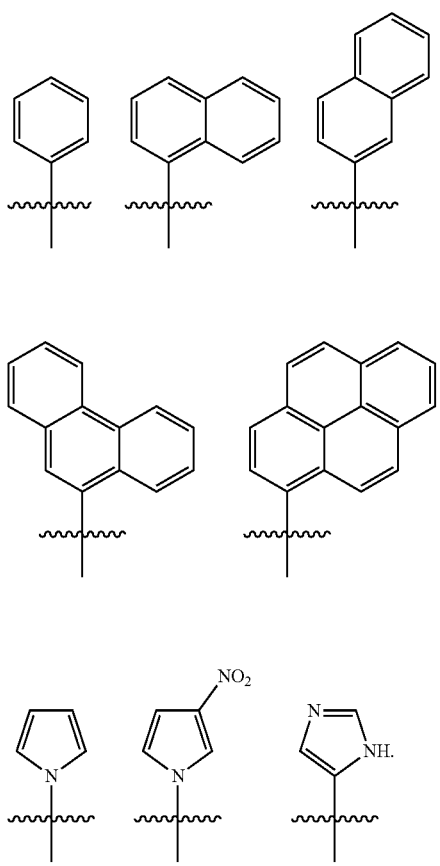

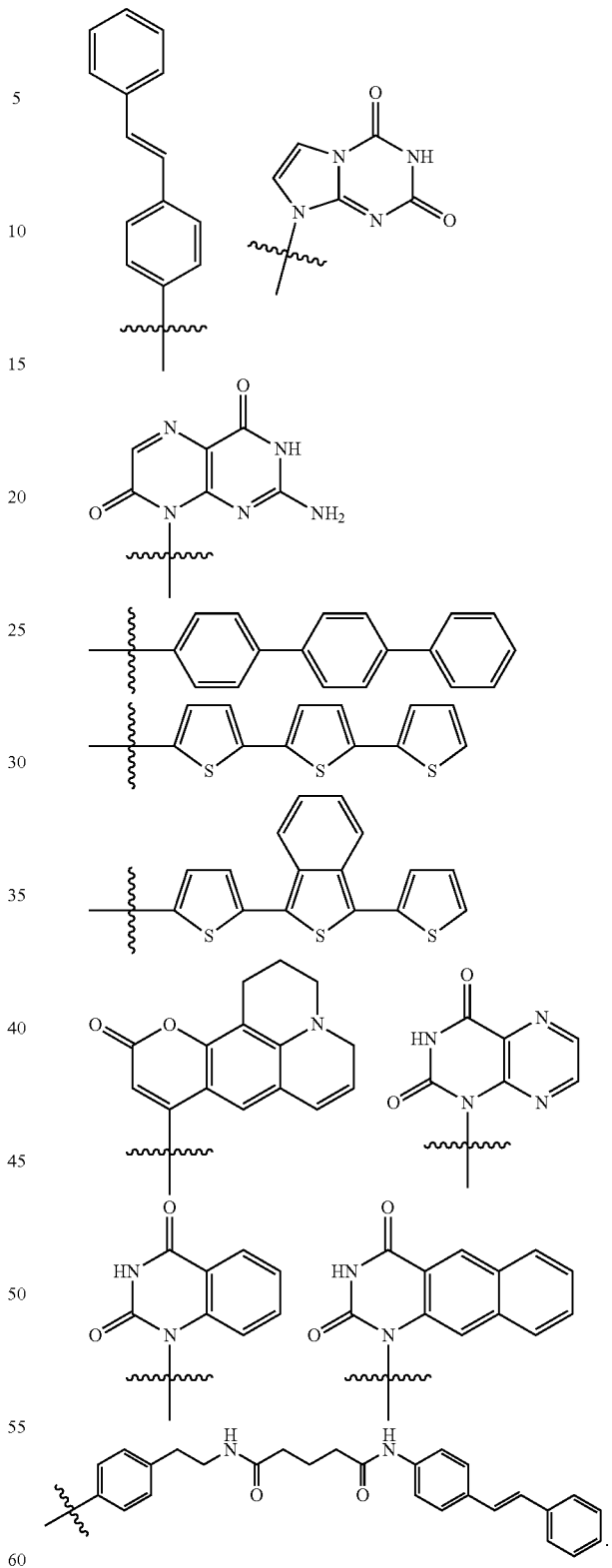

In some embodiments, a modified nucleobase is fluorescent. Examples of such fluorescent modified nucleobases include phenanthrene, pyrene, stilbene, isoxanthine, isozanthopterin, terphenyl, terthiophene, benzoterthiophene, coumarin, lumazine, tethered stilbene, benzo-uracil, and naphtho-uracil, as shown below:

In some embodiments, a modified nucleobase is unsubstituted. In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides.

In some embodiments, a modified nucleobase is a "universal base" that is not a nucleobase in the most classical sense, but that functions similarly to a nucleobase. One example of such a universal base is 3-nitropyrrole.

In some embodiments, other nucleosides can also be used in technologies disclosed in the present disclosure and may include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; M-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In some embodiments, nucleosides include 5'-modified bicyclic nucleoside analogs that have either (R) or (S)-chirality at the 5'-position and include the analogs described in US Patent Application Publication No. 20070287831.

In some embodiments, a nucleobase or modified nucleobase comprises one or more biomolecule binding moieties such as e.g., antibodies, antibody fragments, biotin, avidin, streptavidin, receptor ligands, or chelating moieties. In other embodiments, a nucleobase or modified nucleobase is 5-bromouracil, 5-iodouracil, or 2,6-diaminopurine. In some embodiments, a nucleobase or modified nucleobase is modified by substitution with a fluorescent or biomolecule binding moiety. In some embodiments, the substituent on a nucleobase or modified nucleobase is a fluorescent moiety. In some embodiments, the substituent on a nucleobase or modified nucleobase is biotin or avidin.

Representative U.S. patents that teach preparation of certain of noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, modified nucleobases, sugars, and internucleotidic linkages of each of which are incorporated by reference.

In some embodiments, a base, e.g., BA, is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)=, one or more =CH— are independently and optionally replaced with =N—, and one or more =O are independently and optionally replaced with =S, =N(-L-R$^1$), or =C(-L-R$^1$)$_2$, wherein two or more -L-R$^1$ are optionally taken together with their intervening atoms to form a 3-30 membered bicyclic or polycyclic ring having 0-10 heteroatom atoms. In some embodiments, a modified base is optionally substituted A, T, C, G or U, wherein one or more —NH$_2$ are independently and optionally replaced with —C(-L-R$^1$)$_3$, one or more —NH— are independently and optionally replaced with —C(-L-R$^1$)$_2$—, one or more =N— are independently and optionally replaced with —C(-L-R$^1$)=, one or more =CH— are independently and optionally replaced with =N—, and one or more =O are independently and optionally replaced with =S, =N(-L-R$^1$), or =C(-L-R$^1$)$_2$, wherein two or more -L-R$^1$ are optionally taken together with their intervening atoms to form a 3-30 membered bicyclic or polycyclic ring having 0-10 heteroatom atoms, wherein the modified base is different than the natural A, T, C, G and U. In some embodiments, a base is optionally substituted A, T, C, G or U. In some embodiments, a modified base is substituted A, T, C, G or U, wherein the modified base is different than the natural A, T, C, G and U.

In some embodiments, a modified nucleotide or nucleotide analog is any modified nucleotide or nucleotide analog described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630; Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; and WO 2016/079181.

Example nucleobases are also described in US 20110294124, US 20120316224, US 20140194610, US 20150211006, US 20150197540, WO 2015107425, PCT/

US2016/043542, and PCT/US2016/043598, nucleobases of each of which are incorporated herein by reference.

Sugars

In some embodiments, provided compounds, e.g., oligonucleotides, comprise one or more modified sugar moieties. In some embodiments, a sugar moiety is

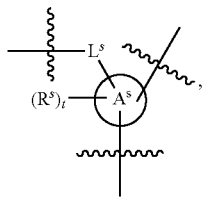

wherein each variable is independently as described in the present disclosure. In some embodiments, a sugar moiety is

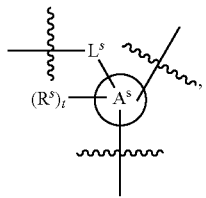

wherein $L^s$ is —C($R^{5s}$)$_2$—, wherein each $R^{5s}$ is independently as described in the present disclosure. In some embodiments, a sugar moiety has the structure of

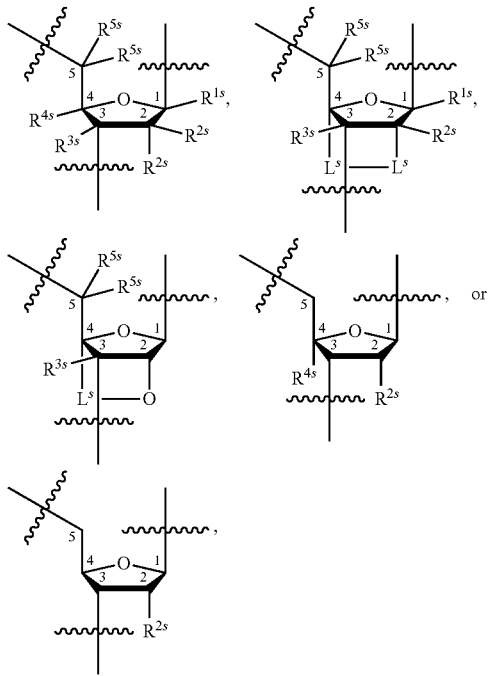

wherein each variable is independently as described in the present disclosure. In some embodiments, a sugar moiety has the structure of

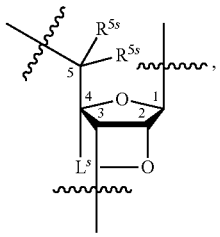

wherein each variable is independently as described in the present disclosure. In some embodiments, $L^s$ is —CH(R)—, wherein R is as described in the present disclosure. In some embodiments, R is —H. In some embodiments, R is not —H, and $L^s$ is —(R)—CH(R)—. In some embodiments, R is not —H, and $L^s$ is —(S)—CH(R)—. In some embodiments, R, as described in the present disclosure, is optionally substituted $C_{1-6}$ alkyl. In some embodiments, R is methyl.

Various types of sugar modifications are known and can be utilized in accordance with the present disclosure. In some embodiments, a sugar modification is a 2'-modification. In some embodiments, a 2'-modification is 2'-F. In some embodiments, a 2'-modification is 2'-OR, wherein R is not hydrogen. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-OMe. In some embodiments, a 2'-modification is 2'-MOE. In some embodiments, a 2'-modification is a LNA sugar modification (C2-O—CH$_2$—C4). In some embodiments, a 2'-modification is (C2-O—C(R)$_2$—C4), wherein each R is independently as described in the present disclosure. In some embodiments, a 2'-modification is (C2-O—CHR—C4), wherein R is as described in the present disclosure. In some embodiments, a 2'-modification is (C2-O—(R)—CHR—C4), wherein R is as described in the present disclosure and is not hydrogen. In some embodiments, a 2'-modification is (C2-O—(S)—CHR—C4), wherein R is as described in the present disclosure and is not hydrogen. In some embodiments, R is optionally substituted $C_{1-6}$ aliphatic. In some embodiments, R is optionally substituted $C_{1-6}$ alkyl. In some embodiments, R is unsubstituted $C_{1-6}$ alkyl. In some embodiments, R is methyl. In some embodiments, R is ethyl. In some embodiments, a 2'-modification is (C2-O—CHR—C4), wherein R is optionally substituted $C_{1-6}$ aliphatic. In some embodiments, a 2'-modification is (C2-O—CHR—C4), wherein R is optionally substituted $C_{1-6}$ alkyl. In some embodiments, a 2'-modification is (C2-O—CHR—C4), wherein R is methyl. In some embodiments, a 2'-modification is (C2-O—CHR—C4), wherein R is ethyl. In some embodiments, a 2'-modification is (C2-O—(R)—CHR—C4), wherein R is optionally substituted $C_{1-6}$ aliphatic. In some embodiments, a 2'-modification is (C2-O—(R)—CHR—C4), wherein R is optionally substituted $C_{1-6}$ alkyl. In some embodiments, a 2'-modification is (C2-O—(R)—CHR—C4), wherein R is methyl. In some embodiments, a 2'-modification is (C2-O—(R)—CHR—C4), wherein R is ethyl. In some embodiments, a 2'-modification is (C2-O—(S)—CHR—C4), wherein R is optionally substituted $C_{1-6}$ aliphatic. In some embodiments, a 2'-modification is (C2-O—(S)—CHR—C4), wherein R is optionally substituted $C_{1-6}$ alkyl. In some embodiments, a 2'-modification is (C2-O—(S)—CHR—C4), wherein R is methyl. In some embodiments, a 2'-modification is (C2-O—(S)—CHR—C4), wherein R is ethyl. In some embodiments, a 2'-modification is $C_2$—O—(R)—CH(CH$_2$CH$_3$)—C4. In some embodiments, a 2'-modification is C2-O—(S)—CH(CH$_2$CH$_3$)—C4. In some embodiments, a sugar moiety is a natural DNA sugar moiety. In some embodiments, a sugar moiety is a natural DNA sugar moiety modified at 2' (2'-modification). In some embodiments, a sugar moiety is an optionally substituted natural DNA sugar moiety. In some embodiments, a sugar moiety is an 2'-substituted natural DNA sugar moiety.

In some embodiments, linkage phosphorus in nucleotides can be linked to various positions of a sugar or modified sugar. For example, in some embodiments, linkage phosphorus can be linked to the 2', 3', 4' or 5' hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with the present disclosure.

Various types of modified sugars can be utilized in accordance with the present disclosure. In some embodiments, a modified sugar contains one or more substituents at the 2' position selected from: —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkylene)-O—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, examples of substituents include, and are not limited to, —O(CH$_2$)$_n$OCH$_3$, and —O(CH$_2$)$_n$NH$_2$, wherein n is from 1 to about 10, MOE, DMAOE, DMAEOE. In some embodiments, a modified sugar is selected from those described in WO 2001/088198; and Martin et al., *Helv. Chim. Acta*, 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of 2', 3', 4', 5', and/or 6'-positions (if any) of sugar or modified sugar moieties, including 3'-positions of a sugar moiety on a 3'-terminal nucleotide and/or 5' positions of a 5'-terminal nucleotide. In some embodiments, a RNA comprises a sugar which has, at the 2' position, a 2'-OH, or 2'-OR$^1$, wherein R$^1$ is optionally substituted C$_{1-6}$ alkyl. In some embodiments, a 2'-modification is 2'-F.

In some embodiments, the 2'-OH of a ribose is replaced with a substituent selected from: —H, —F; —CF$_3$, —CN, —N$_3$, —NO, —NO$_2$, —OR', —SR', or —N(R')$_2$, wherein each R' is independently as defined above and described herein; —O—(C$_1$-C$_{10}$ alkyl), —S—(C$_1$-C$_{10}$ alkyl), —NH—(C$_1$-C$_{10}$ alkyl), or —N(C$_1$-C$_{10}$ alkyl)$_2$; —O—(C$_2$-C$_{10}$ alkenyl), —S—(C$_2$-C$_{10}$ alkenyl), —NH—(C$_2$-C$_{10}$ alkenyl), or —N(C$_2$-C$_{10}$ alkenyl)$_2$; —O—(C$_2$-C$_{10}$ alkynyl), —S—(C$_2$-C$_{10}$ alkynyl), —NH—(C$_2$-C$_{10}$ alkynyl), or —N(C$_2$-C$_{10}$ alkynyl)$_2$; or —O—(C$_1$-C$_{10}$ alkylene)-O—(C$_1$-C$_{10}$ alkyl), —O—(C$_1$-C$_{10}$ alkylene)-NH—(C$_1$-C$_{10}$ alkyl) or —O—(C$_1$-C$_{10}$ alkylene)-NH(C$_1$-C$_{10}$ alkyl)$_2$, —NH—(C$_1$-C$_{10}$ alkyl), or —N(C$_1$-C$_{10}$ alkyl)-(C$_1$-C$_{10}$ alkylene)-O—(C$_1$-C$_{10}$ alkyl), wherein the alkyl, alkylene, alkenyl and alkynyl may be substituted or unsubstituted, and each independently contain or are of, e.g., 1-30, 1-20, 1-10, 1-9, 1-8, 1-7, 1-6, 1-5, 1-4, 1-3, 1-2, or 1, carbon. In some embodiments, a 2'-OH is replaced with —H (deoxyribose). In some embodiments, a 2'-OH is replaced with —F. In some embodiments, a 2'-OH is replaced with —OR', wherein R' is as described in the present disclosure and is not hydrogen. In some embodiments, a 2'-OH is replaced with —OMe. In some embodiments, a 2'-OH is replaced with —OCH$_2$CH$_2$OMe.

Modified sugars also include sugars of locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L$^s$- as defined herein. In some embodiments, -L$^s$- is —O—C(R)$_2$—, wherein each R is independently as described in the present disclosure. In some embodiments, -L$^s$- is —O—CHR—, wherein R is as described in the present disclosure. In some embodiments, -L$^s$- is —O—(R)—CHR—, wherein R is as described in the present disclosure. In some embodiments, -L$^s$- is —O—(S)—CHR—, wherein R is as described in the present disclosure. In some embodiments, -L$^s$- is —O—CH$_2$—, wherein —CH$_2$— is optionally substituted. In some embodiments, -L$^s$- is —O—CH$_2$—. In some embodiments, -L$^s$- is —O—CH(Et)-. In some embodiments, -L$^s$- is —O—(R)—CH(Et)-. In some embodiments, -L$^s$- is —O—(S)—CH(Et)-. In some embodiments, -L$^s$- is between C$_2$ and C$_4$ of a sugar moiety.

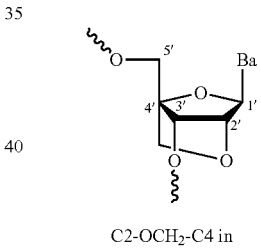

C2-OCH$_2$-C4 in e.g., LNA

In some embodiments, a modified sugar is a sugar of ENA or modified ENA (such as those described in, e.g., Seth et al., *J Am Chem Soc.* 2010 Oct. 27; 132(42): 14942-14950). In some embodiments, a modified sugar is any of those found in an XNA (xenonucleic acid), for instance, arabinose, anhydrohexitol, threose, 2' fluoroarabinose, or cyclohexene.

In some embodiments, modified sugars are sugar mimetics such as cyclobutyl or cyclopentyl moieties in place of pentofuranosyl. Representative United States patents that teach preparation of such modified sugar structures include, but are not limited to, U.S. Pat. Nos. 4,981,957; 5,118,800; 5,319,080; and 5,359,044. In some embodiments, modified sugars are sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc.).

Non-limiting examples of modified sugars include glycerol, which form glycerol nucleic acid (GNA) analogues.

One example of a GNA analogue is shown below and is described in Zhang, R et al., *J. Am. Chem. Soc.,* 2008, 130, 5846-5847; Zhang L, et al., *J. Am. Chem. Soc.,* 2005, 127, 4174-4175 and Tsai C H et al., *PNAS,* 2007, 14598-14603 (X=O⁻):

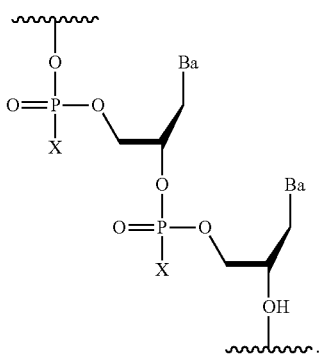

Another example of a GNA derived analogue, flexible nucleic acid (FNA) based on the mixed acetal aminal of formyl glycerol, is described in Joyce G F et al., *PNAS,* 1987, 84, 4398-4402 and Heuberger B D and Switzer C, *J. Am. Chem. Soc.,* 2008, 130, 412-413, and is shown below:

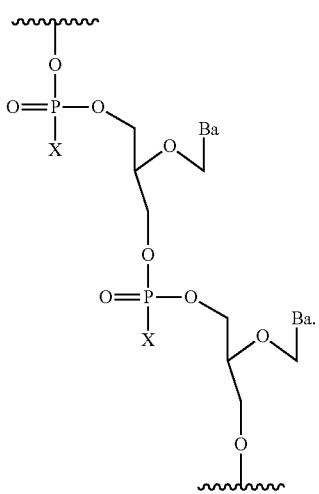

Additional non-limiting examples of modified sugars include hexopyranosyl (6' to 4'), pentopyranosyl (4' to 2'), pentopyranosyl (4' to 3'), or tetrofuranosyl (3' to 2') sugars. In some embodiments, a hexopyranosyl (6' to 4') sugar moiety is one in the following formulae:

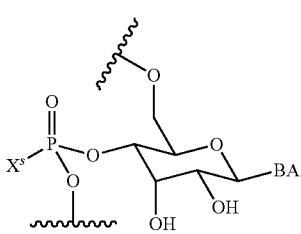

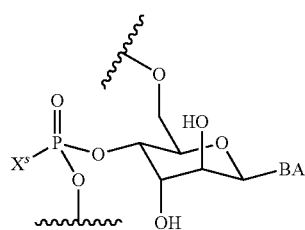

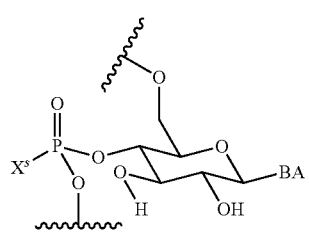

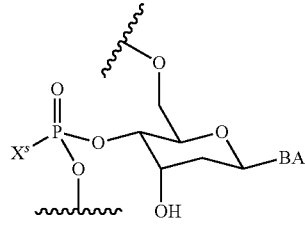

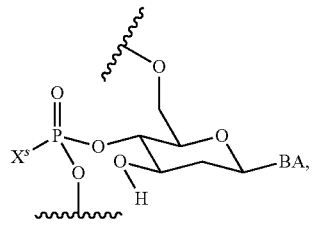

wherein $X^s$ corresponds to the P-modification group "—X-L-R⁵" described herein and BA is as defined herein.

In some embodiments, a pentopyranosyl (4' to 2') sugar moiety is one in the following formulae:

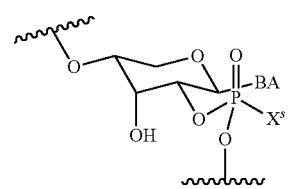

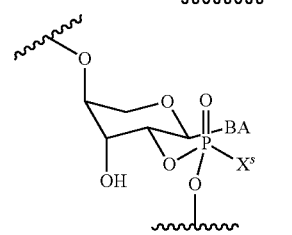

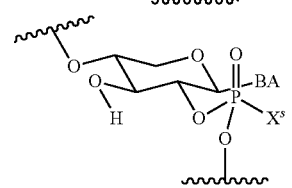

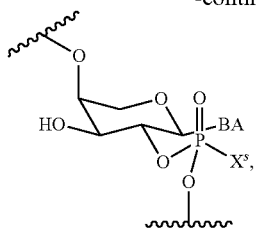

wherein $X^s$ corresponds to the P-modification group "—X-L-$R^5$" described herein and BA is as defined herein.

In some embodiments, a pentopyranosyl (4' to 3') sugar moiety is one in the following formulae:

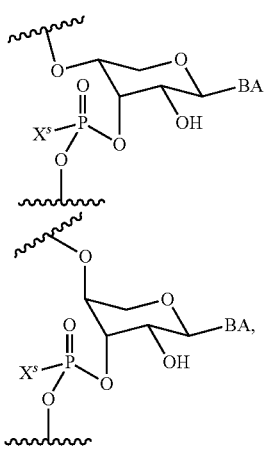

wherein $X^s$ corresponds to the P-modification group "—X-L-$R^5$" described herein and BA is as defined herein.

In some embodiments, a tetrofuranosyl (3' to 2') sugar moiety is one in the following formulae:

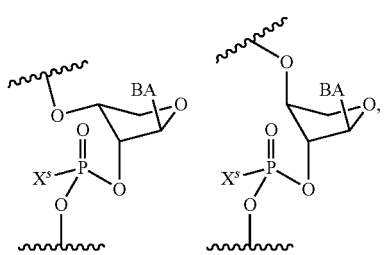

wherein $X^s$ corresponds to the P-modification group "—X-L-$R^5$" described herein and BA is as defined herein.

In some embodiments, a modified sugar moiety is one in the following formulae:

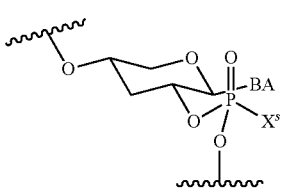
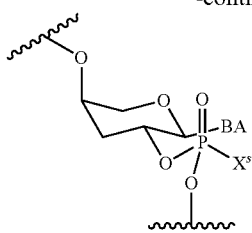
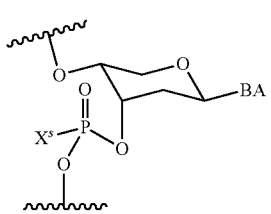
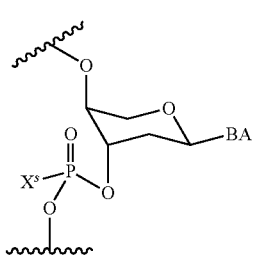
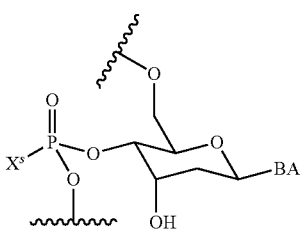
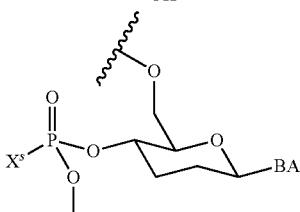
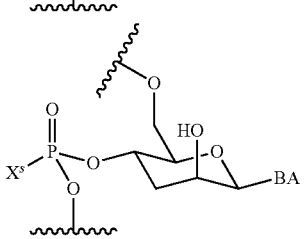
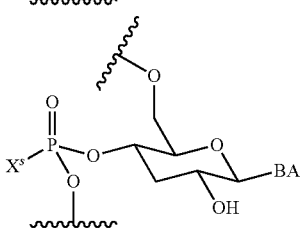

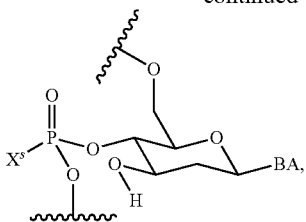

wherein $X^s$ corresponds to a P-modification group "—X-L-$R^5$" described herein and BA is as defined herein.

In some embodiments, one or more hydroxyl group in a sugar moiety is optionally and independently replaced with halogen, R'—N(R')$_2$, —OR', or —SR', wherein each R' is independently as defined above and described herein.

In some embodiments, a modified sugar moiety is one illustrated below, wherein $X^s$ corresponds to the P-modification group "—X-L-$R^5$" described herein, BA is as defined herein, and $X^1$ is selected from —S—, —Se—, —CH$_2$—, —NMe-, —NEt- or —NiPr-:

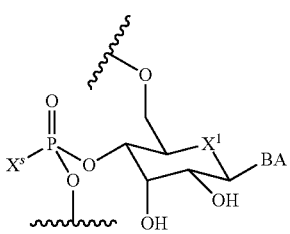

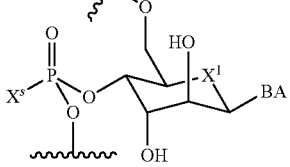

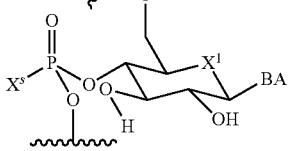

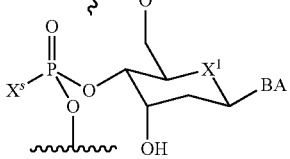

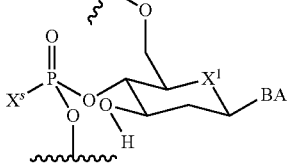

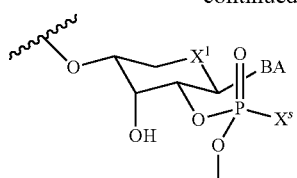

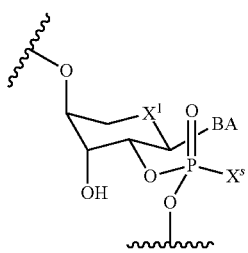

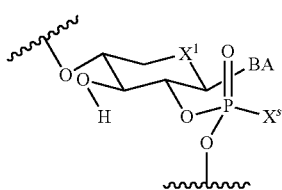

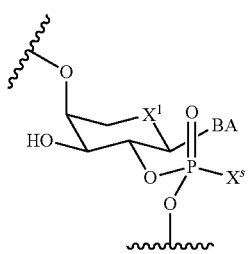

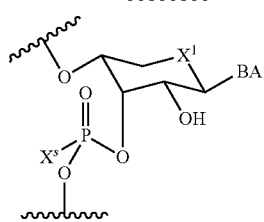

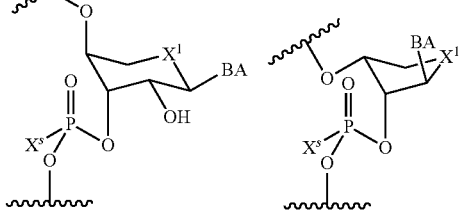

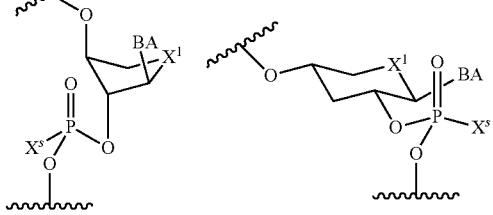

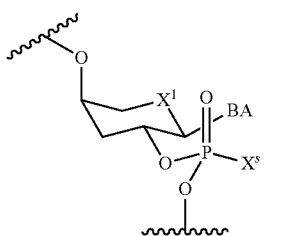
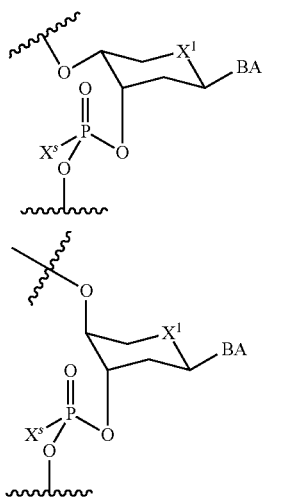
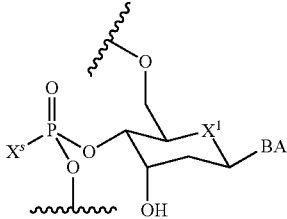
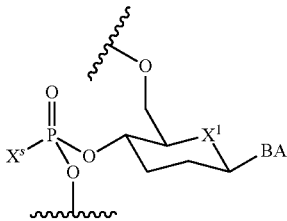
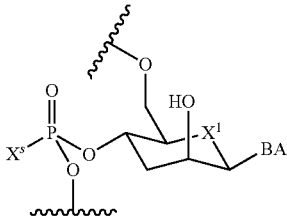
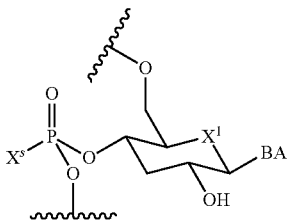

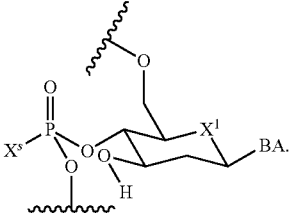

In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more (e.g., 55%, 60%, 65%, 70%, 75%, 80%, 85%, 90%, 95% or more), inclusive, of the sugars in a chirally controlled oligonucleotide composition are modified. In some embodiments, only purine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the purine residues are modified). In some embodiments, only pyrimidine residues are modified (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50% or more [e.g., 55%, 60%, 65%, 70%, 75%, 80%, 85%, 90%, 95% or more] of the pyridimine residues are modified). In some embodiments, both purine and pyrimidine residues are modified.

Modified sugars can be prepared and/or reacted with and/or incorporated into provided compounds by methods known in the art in accordance with the present disclosure, including, but not limited to: A. Eschenmoser, Science (1999), 284:2118; M. Bohringer et al, Helv. Chim. Acta (1992), 75:1416-1477; M. Egli et al, J. Am. Chem. Soc. (2006), 128(33):10847-56; A. Eschenmoser in *Chemical Synthesis: Gnosis to Prognosis*, C. Chatgilialoglu and V. Sniekus, Ed., (Kluwer Academic, Netherlands, 1996), p. 293; K.-U. Schoning et al, Science (2000), 290:1347-1351; A. Eschenmoser et al, Helv. Chim. Acta (1992), 75:218; J. Hunziker et al, Helv. Chim. Acta (1993), 76:259; G. Otting et al, Helv. Chim. Acta (1993), 76:2701; K. Groebke et al, Helv. Chim. Acta (1998), 81:375; and A. Eschenmoser, Science (1999), 284:2118. Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.*, 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310). In some embodiments, a modified sugar is any of those described in PCT Publication No. WO2012/030683. In some embodiments, a modified sugar is any modified sugar described in any of: Gryaznov, S; Chen, J.-K. J. Am. Chem. Soc. 1994, 116, 3143; Hendrix et al. 1997 Chem. Eur. J. 3: 110; Hyrup et al. 1996 Bioorg. Med. Chem. 4: 5; Jepsen et al. 2004 Oligo. 14: 130-146; Jones et al. J. Org. Chem. 1993, 58, 2983; Koizumi et al. 2003 Nuc. Acids Res. 12: 3267-3273; Koshkin et al. 1998 Tetrahedron 54: 3607-3630;

Kumar et al. 1998 Bioo. Med. Chem. Let. 8: 2219-2222; Lauritsen et al. 2002 Chem. Comm. 5: 530-531; Lauritsen et al. 2003 Bioo. Med. Chem. Lett. 13: 253-256; Mesmaeker et al. Angew. Chem., Int. Ed. Engl. 1994, 33, 226; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Nielsen et al. 1997 Chem. Soc. Rev. 73; Nielsen et al. 1997 J. Chem. Soc. Perkins Transl. 1: 3423-3433; Obika et al. 1997 Tetrahedron Lett. 38 (50): 8735-8; Obika et al. 1998 Tetrahedron Lett. 39: 5401-5404; Pallan et al. 2012 Chem. Comm. 48: 8195-8197; Petersen et al. 2003 TRENDS Biotech. 21: 74-81; Rajwanshi et al. 1999 Chem. Commun. 1395-1396; Schultz et al. 1996 Nucleic Acids Res. 24: 2966; Seth et al. 2009 J. Med. Chem. 52: 10-13; Seth et al. 2010 J. Med. Chem. 53: 8309-8318; Seth et al. 2010 J. Org. Chem. 75: 1569-1581; Seth et al. 2012 Bioo. Med. Chem. Lett. 22: 296-299; Seth et al. 2012 Mol. Ther-Nuc. Acids. 1, e47; Seth, Punit P; Siwkowski, Andrew; Allerson, Charles R; Vasquez, Guillermo; Lee, Sam; Prakash, Thazha P; Kinberger, Garth; Migawa, Michael T; Gaus, Hans; Bhat, Balkrishen; et al. From Nucleic Acids Symposium Series (2008), 52(1), 553-554; Singh et al. 1998 Chem. Comm. 1247-1248; Singh et al. 1998 J. Org. Chem. 63: 10035-39; Singh et al. 1998 J. Org. Chem. 63: 6078-6079; Sorensen 2003 Chem. Comm. 2130-2131; Ts'o et al. Ann. N. Y. Acad. Sci. 1988, 507, 220; Van Aerschot et al. 1995 Angew. Chem. Int. Ed. Engl. 34: 1338; Vasseur et al. J. Am. Chem. Soc. 1992, 114, 4006; WO 20070900071; WO 20070900071; and WO 2016/079181.

In some embodiments, a modified sugar moiety is an optionally substituted pentose or hexose moiety. In some embodiments, a modified sugar moiety is an optionally substituted pentose moiety. In some embodiments, a modified sugar moiety is an optionally substituted hexose moiety. In some embodiments, a modified sugar moiety is an optionally substituted ribose or hexitol moiety. In some embodiments, a modified sugar moiety is an optionally substituted ribose moiety. In some embodiments, a modified sugar moiety is an optionally substituted hexitol moiety.

In some embodiments, an example modified internucleotidic linkage and/or sugar moiety is selected from, e.g, those in:

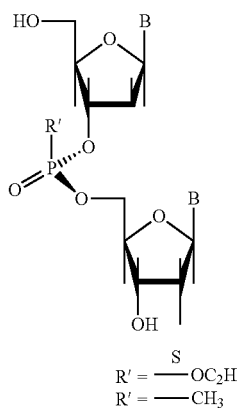
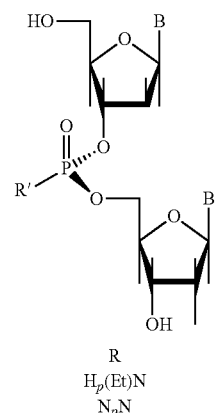

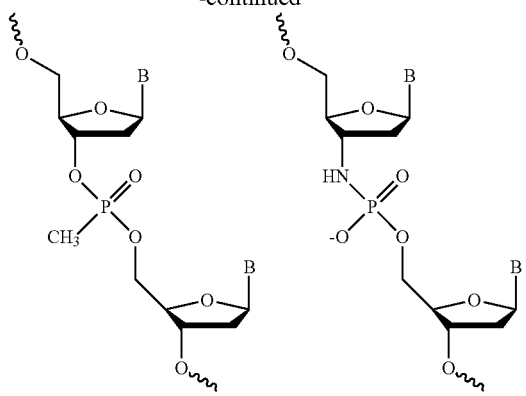

-continued

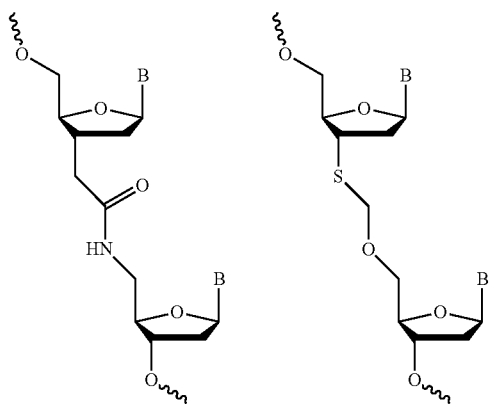

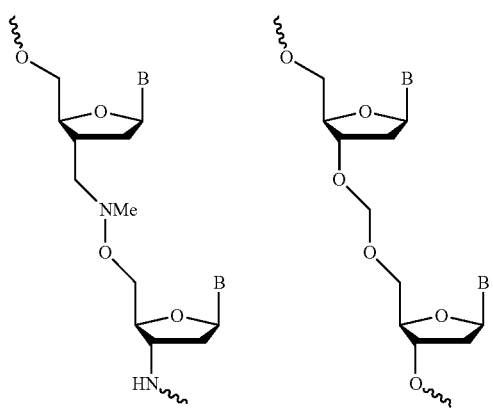

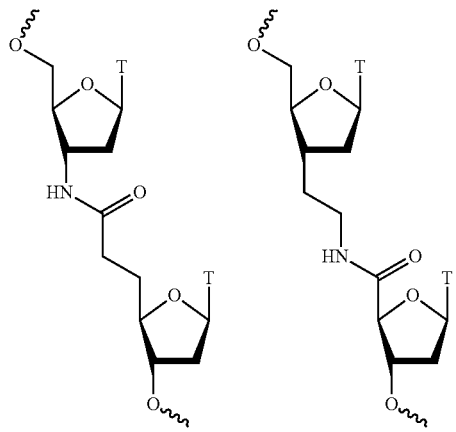

-continued
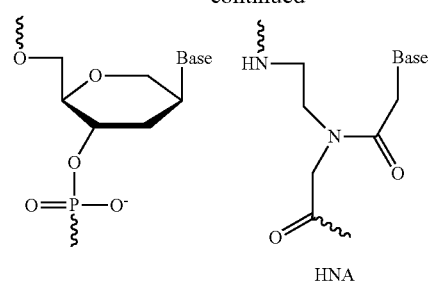
HNA
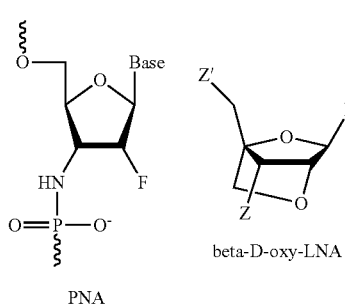
PNA    beta-D-oxy-LNA
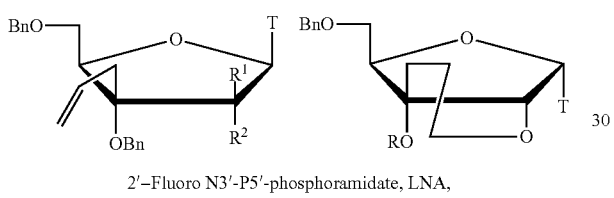
2′-Fluoro N3′-P5′-phosphoramidate, LNA,
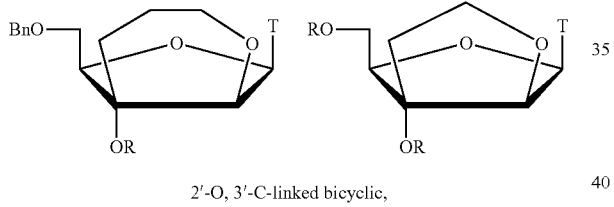
2′-O, 3′-C-linked bicyclic,
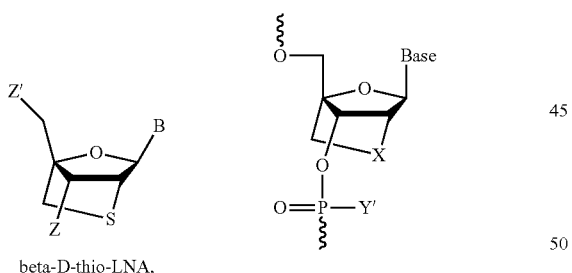
beta-D-thio-LNA,
LNA:                 X = O, Y = O
2′-Thio-LNA:         X = S, Y = O
2′-Phosphorothioate-LNA: X = O, Y = S,
PS-LNA
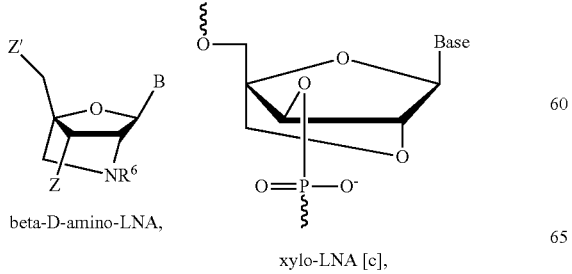
beta-D-amino-LNA,    xylo-LNA [c],
-continued
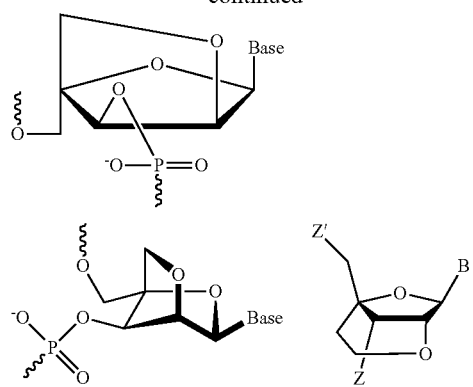
alpha-L-LNA, ENA,      beta-D-ENA,
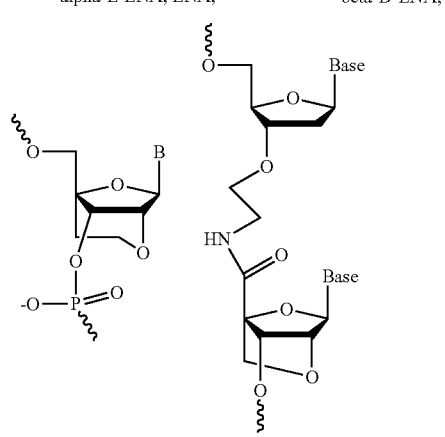
amide-linked LNA,
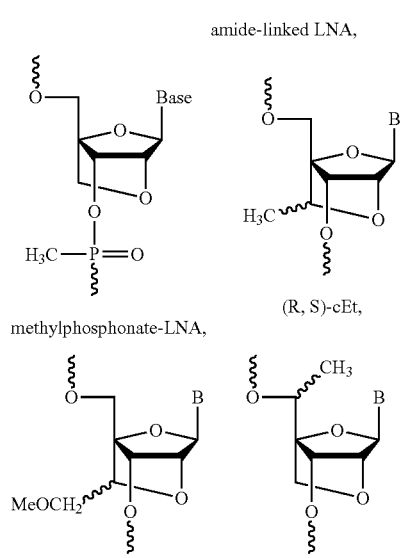
methylphosphonate-LNA,    (R, S)-cEt,
(R,S)-cMOE      (R,S)-5′-Me-LNA,
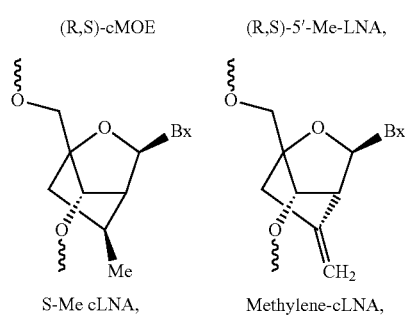
S-Me cLNA,    Methylene-cLNA,

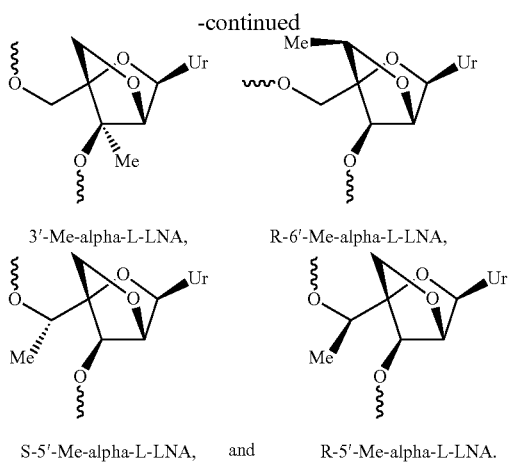

3'-Me-alpha-L-LNA, R-6'-Me-alpha-L-LNA,

S-5'-Me-alpha-L-LNA, and R-5'-Me-alpha-L-LNA.

In some embodiments, $R^1$ is R as described in the present disclosure. In some embodiments, $R^2$ is R as described in the present disclosure. In some embodiments, $R^e$ is R as described in the present disclosure. In some embodiments, $R^e$ is H, —$CH_3$, —Bn, —$COCF_3$, benzoyl, benzyl, pyren-1-ylcarbonyl, pyren-1-ylmethyl, or 2-aminoethyl. In some embodiments, an example modified internucleotidic linkage and/or sugar moiety is selected from those described in Ts'o et al. Ann. N. Y. Acad. Sci. 1988, 507, 220; Gryaznov, S.; Chen, J.-K. J. Am. Chem. Soc. 1994, 116, 3143; Mesmaeker et al. Angew. Chem., Int. Ed. Engl. 1994, 33, 226; Jones et al. J. Org. Chem. 1993, 58, 2983; Vasseur et al. J. Am. Chem. Soc. 1992, 114, 4006; Van Aerschot et al. 1995 Angew. Chem. Int. Ed. Engl. 34: 1338; Hendrix et al. 1997 Chem. Eur. J. 3: 110; Koshkin et al. 1998 Tetrahedron 54: 3607-3630; Hyrup et al. 1996 Bioorg. Med. Chem. 4: 5; Nielsen et al. 1997 Chem. Soc. Rev. 73; Schultz et al. 1996 Nucleic Acids Res. 24: 2966; Obika et al. 1997 Tetrahedron Lett. 38 (50): 8735-8; Obika et al. 1998 Tetrahedron Lett. 39: 5401-5404; Singh et al. 1998 Chem. Comm. 1247-1248; Kumar et al. 1998 Bioo. Med. Chem. Let. 8: 2219-2222; Nielsen et al. 1997 J. Chem. Soc. Perkins Transl. 1: 3423-3433; Singh et al. 1998 J. Org. Chem. 63: 6078-6079; Seth et al. 2010 J. Org. Chem. 75: 1569-1581; Singh et al. 1998 J. Org. Chem. 63: 10035-39; Sorensen 2003 Chem. Comm. 2130-2131; Petersen et al. 2003 TRENDS Biotech. 21: 74-81; Rajwanshi et al. 1999 Chem. Commun. 1395-1396; Jepsen et al. 2004 Oligo. 14: 130-146; Morita et al. 2001 Nucl. Acids Res. Supp. 1: 241-242; Morita et al. 2002 Bioo. Med. Chem. Lett. 12: 73-76; Morita et al. 2003 Bioo. Med. Chem. Lett. 2211-2226; Koizumi et al. 2003 Nuc. Acids Res. 12: 3267-3273; Lauritsen et al. 2002 Chem. Comm. 5: 530-531; Lauritsen et al. 2003 Bioo. Med. Chem. Lett. 13: 253-256; WO 20070900071; Seth et al., Nucleic Acids Symposium Series (2008), 52(1), 553-554; Seth et al. 2009 J. Med. Chem. 52: 10-13; Seth et al. 2012 Mol. Ther-Nuc. Acids. 1, e47; Pallan et al. 2012 Chem. Comm. 48: 8195-8197; Seth et al. 2010 J. Med. Chem. 53: 8309-8318; Seth et al. 2012 Bioo. Med. Chem. Lett. 22: 296-299; WO 2016/079181; U.S. Pat. Nos. 6,326,199; 6,066,500; and 6,440,739, base and sugar modifications of each of which is herein incorporated by reference.

Internucleotidic Linkages

Various internucleotidic linkages can be formed efficiently using provided technologies, in some embodiments, which high stereoselectivity (chiral control), if an internucleotidic linkage is a chiral internucleotidic linkage, for example, those of US20150211006, US20170037399, WO2017/015555, WO2017/015575, WO2017/062862, WO2017/160741, WO2017/192664, WO2017/192679, WO2017/210647, WO2018/022473, WO2018/067973, and WO2018/098264. In some embodiments, an internucleotidic linkage is a natural phosphate linkage (acid form is —O—P(O)(OH)—(O)—; can exist as various salt forms). In some embodiments, an internucleotidic linkage is a phosphorothioate linkage (acid form is —O—P(O)(SH)—(O)—; can exist as various salt forms).

In some embodiments, provided oligonucleotides comprise one or more natural phosphate linkages and one or more modified chiral internucleotidic linkages. In some embodiments, provided oligonucleotides comprise one or more natural phosphate linkages and one or more phosphorothioate internucleotidic linkages. In some embodiments, provided oligonucleotides comprise one or more natural phosphate linkages and one or more phosphorothioate internucleotidic linkages. In some embodiments, one or more modified internucleotidic linkages are chiral and are each independently chirally controlled. In some embodiments, an internucleotidic linkage is a chiral internucleotidic linkage in that it comprises a chiral linkage phosphorus.

In some embodiments, provided oligonucleotides comprise one or more chirally controlled internucleotidic linkages. In some embodiments, provided oligonucleotides comprise 1-30, e.g., 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages. In some embodiments, provided oligonucleotides comprise at least 1, 2, 3, 4, 5, 6, 7, 8, 9, 10, 11, 12, 13, 14, 15, 16, 17, 18, 19, 20, 21, 22, 23, 24, or 25, chirally controlled internucleotidic linkages.

In some embodiments, a modified internucleotidic linkage is a phosphorothioate linkage.

In some embodiments, an internucleotidic linkage has the structure of formula VII:

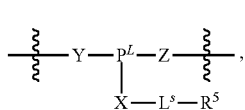

VII or a salt form thereof, wherein:
$P^L$ is P(=W), P, or P→B(R')$_3$;
W is O, S or Se;
each of $R^1$ and $R^5$ is independently —H, -$L^s$-R, halogen, —CN, —$NO_2$, -$L^s$-Si(R)$_3$, —OR, —SR, or —N(R)$_2$;
each of X, Y and Z is independently —O—, —S—, —N(-$L^s$-$R^1$)—, or $L^s$;
each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;

each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon; or H—X-L$^s$-R$^5$ has the structure of formula I, I-a, I-a-1, I-a-2, I-b, I-c, I-d, I-e, II, II-a, II-b, III, III-a, III-b, or a salt thereof.

In some embodiments, an internucleotidic linkage of formula VII is a chiral internucleotidic linkage. In some embodiments, P in P$^L$ is a chiral linkage phosphorus. In some embodiments, a chiral linkage phosphorus is Rp. In some embodiments, a chiral linkage phosphorus is Sp. In some embodiments, P$^L$ is P(=W). In some embodiments, P$^L$ is P. In some embodiments, P$^L$ is P→B(R')$_3$.

In some embodiments, an internucleotidic linkage of formula VII having the structure of formula VII-a-1:

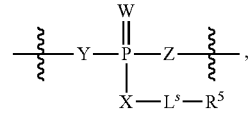
VII-a-1 or a salt form thereof, wherein each other variable is independently as described in the present disclosure.

In some embodiments, an internucleotidic linkage of formula VII or VII-a-1 having the structure of formula VII-a-2:

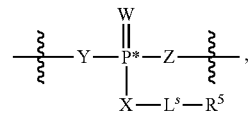
VII-a-2 or a salt form thereof, wherein P* is an asymmetric phosphorus atom, and each other variable is independently as described in the present disclosure.

In some embodiments, an internucleotidic linkage has the structure of formula VII-b:

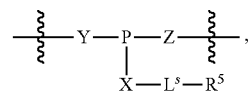
VII-b or a salt form thereof, wherein each variable is independently as described in the present disclosure. In some embodiments, an internucleotidic linkage of formula VII has the structure of formula VII-b.

In some embodiments, an internucleotidic linkage of formula VII having the structure of formula VII-c:

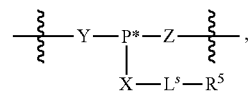
VII-c or a salt form thereof, wherein P* is an asymmetric phosphorus atom, and each other variable is independently as described in the present disclosure.

In some embodiments, an internucleotidic linkage has the structure of formula VII-d:

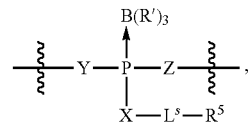
VII-d or a salt form thereof, wherein each variable is independently as described in the present disclosure.

In some embodiments, an internucleotidic linkage of formula VII-e having the structure of:

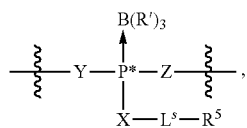

or a salt form thereof, wherein P* is an asymmetric phosphorus atom, and each other variable is independently as described in the present disclosure.

In some embodiments, the present disclosure provides oligonucleotides comprising one or more internucleotidic linkages having the structure of formula VII, VII-a-1, VII-a-2, VII-b, VII-c, VII-d, or VII-e, or a salt form thereof. In some embodiments, provided oligonucleotides comprise 1-100, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70 80, 90, 100 or more internucleotidic linkages having the structure of formula VII, VII-a-1, VII-a-2, VII-b, VII-c, VII-d, or VII-e, or a salt form thereof. In some embodiments, provided oligonucleotides comprise one or more such internucleotidic linkages. In some embodiments, provided oligonucleotides comprise two or more such internucleotidic linkages. In some embodiments, provided oligonucleotides comprise three or more such internucleotidic linkages. In some embodiments, provided oligonucleotides comprise four or more such internucleotidic linkages. In some embodiments, provided oligonucleotides comprise five or more such internucleotidic linkages. In some embodiments, provided oligonucleotides comprise six or more such internucleotidic linkages. In some embodiments, provided oligonucleotides comprise seven or more such internucleotidic linkages. In some embodiments, provided oligonucleotides comprise eight or more such internucleotidic linkages. In some embodiments, provided oligonucleotides comprise nine or more such internucleotidic linkages. In some embodiments, provided oligonucleotides comprise ten or more such internucleotidic linkages. In some embodiments, provided oligonucleotides comprise 11 or more such internucleotidic linkages. In some embodiments, provided oligonucleotides comprise 12 or more such internucleotidic linkages. In some embodiments, provided oligonucleotides comprise 13 or more such internucleotidic linkages. In some embodiments, provided oligonucleotides comprise 14 or more such internucleotidic linkages. In some embodiments, provided oligonucleotides comprise 15 or more such internucleotidic linkages. In some embodiments, provided oligonucleotides comprise 16 or more such internucleotidic linkages. In some embodiments, provided oligonucleotides comprise 17 or more such internucleotidic linkages. In some embodiments, provided oligonucleotides comprise 18 or more such internucleotidic linkages. In some embodiments, provided oligonucleotides comprise 19 or more such internucleotidic linkages. In some embodiments, provided oligonucleotides comprise 20 or more such internucleotidic linkages. In some embodiments, provided oligonucleotides comprise 21 or more such internucleotidic linkages. In some embodiments, provided oligonucleotides comprise 25 or more such internucleotidic linkages. In some embodiments, such an internucleotidic linkage is chiral. In some embodiments, as described in the present disclosure, each —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, provided oligonucleotides have the structure of formula VIII or a salt thereof.

In some embodiments, a provided oligonucleotide comprises at least two types of internucleotidic linkages, each independently having the structure of formula VII, VII-a-1, VII-a-2, VII-b, VII-c, VII-d, or VII-e, or a salt form thereof. In some embodiments, a provided oligonucleotide comprise at least two types of chiral internucleotidic linkages, each independently having the structure of formula VII, VII-a-1, VII-a-2, VII-b, VII-c, VII-d, or VII-e, or a salt form thereof. In some embodiments, the two types may have the same or different phosphorus configuration (Rp or Sp), or one or both can be stereorandom (e.g., formed not through chirally controlled synthesis). In some embodiments, a stereorandom linkage has diastereomeric purity less than 85%, 80%, 75%, 70%, 65%, 60%, or 55%. In some embodiments, P* is not stereorandom, and is either Rp or Sp. In some embodiments, in one type W is S and in the other type W is O. In some embodiments, in one type W is S and in the other type W is O, and for both types —X-$L^s$-$R^5$ is independently of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, one type is a natural phosphate linkage (—O—P(O)(OH)—O—, which may exist as —O—P(O)(O$^-$)—O—, for example, at certain pH and/or when provided as a salt), and the other is a phosphorothioate linkage (—O—P(O)(SH)—O—, which may exist as —O—P(O)(S—)—O—, for example, at certain pH and/or when provided as a salt).

In some embodiments, each $L^P$ independently has the structure of VII, VII-a-1, VII-a-2, VII-b, VII-c, VII-d, or VII-e, or a salt form thereof. In some embodiments, each $L^P$ independently has the structure of VII, VII-a-1, VII-a-2, VII-b, VII-c, VII-d, or VII-e, and in each $L^P$, —X-$L^s$-$R^5$ independently has a structure such that H—X-$L^s$-$R^5$ is a compound of formula I, I-a, I-a-1, I-a-2, I-b, I-c, I-d, I-e, II, II-a, II-b, III, III-a, or III-b, or a salt thereof.

In some embodiments, at least one $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O. In some embodiments, $L^P$ independently comprises —X-$L^s$-$R^5$ wherein H—X-$L^s$-$R^5$ has the structure of formula I, I-a, I-a-1, I-a-2, I-b, I-c, I-d, I-e, II, II-a, II-b, III, III-a, or III-b, or a salt thereof.

Cycles

As those skilled in the art readily appreciates, in some embodiments, provided methods for oligonucleotide synthesis comprise one or more cycles. Typically, in oligonucleotide synthesis, synthetic cycles are repeated until a desired oligonucleotide length is achieved.

In some embodiments, cycles of provided methods each independently comprise:
(1) a coupling step;
(2) optionally a pre-modification capping step;
(3) a modification step;
(4) optionally a post-modification capping step; and
(5) a de-blocking step.
wherein each step is independently as described in the present disclosure.

In some embodiments, a cycle comprises a pre-modification capping step. In some embodiments, a cycle comprises a post-modification capping step. In some embodiments, a cycle comprises a pre-modification capping step and a post-modification capping step. In some embodiments, steps of a cycle are performed in the order they are listed, e.g., from 1 to 5, if that given step is a step of the cycle.

In some embodiments, the present disclosure provides a method for preparing an oligonucleotide, comprising a cycle comprising steps of:
(1) a coupling step;
(2) a first capping step;
(3) a modification step;
(4) a second capping step;
(5) a de-blocking step;
wherein the cycle comprises steps in the order of (2)-(3)-(4);
wherein the cycle is repeated until the length of the oligonucleotide is achieved.

In some embodiments, the present disclosure provides a method for preparing an oligonucleotide, comprising a cycle comprising steps of:
(1) a coupling step;
(2) a first capping step;
(3) a modification step;
(4) a second capping step;
(5) a de-blocking step;
wherein the cycle comprises steps in the order of (2)-(4)-(3);
wherein the cycle is repeated until the length of the oligonucleotide is achieved.

In some embodiments, a first capping step is a pre-modification capping step as described in the present disclosure. In some embodiments, a first capping step is a post-modification capping step, but uses a condition of a pre-modification capping step as described in the present disclosure. In some embodiments, a second capping step is a post-modification capping step as described in the present disclosure. In some embodiments, a second capping is a pre-modification capping step, but uses a condition for a post-modification capping step as described in the present disclosure.

In some embodiments, cycles of a provided method comprise different number of steps. In some embodiments, cycles of a provided method comprises the same steps, but one or more or all steps of one cycle is different than those of another cycle. Those skilled in the art appreciate that conditions may be adjusted in accordance with the present disclosure.

In some embodiments, a cycle comprises no more than one of steps listed, for example, in some embodiments, a cycle comprises no more than one coupling step, no more than one pre-modification capping step, no more than one modification step, no more than one post-modification capping step, and no more than one de-blocking step. In some embodiments, a provided step, e.g., any step described for a cycle, may independently comprise two or more contacting of a reagent system with an oligonucleotide composition comprises a plurality of oligonucleotides. For example, in some embodiments, a coupling step may comprise contacting a de-blocked composition with a coupling reagent system twice or more. In some embodiments, the coupling reagent system of each contact may independently be the same as or different from the coupling reagent system of another contact. In some embodiments, a capping step may comprises contacting a composition with a capping reagent system twice or more, wherein the coupling reagent system of each contact may independently be the same as or different from the coupling reagent system of another contact; for example, in some embodiments, the first capping reagent system is selective for amino groups over hydroxyl groups (e.g., a reagent system comprising Ac$_2$O and 2,6-lutidine), which the second capping reagent system is less selective and caps both amino groups and hydroxyl groups efficiently (e.g., a reagent system comprising Ac$_2$O, 2,6-lutidine, and NMI.). Similarly, in some embodiments, a modification step and/or a de-blocking step may comprise contacting twice or more. Example steps of cycles are as described in the present disclosure.

Coupling

In some embodiments, a coupling step comprises:
contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and
coupling a partner compound with the free hydroxyl groups of a plurality of de-blocked oligonucleotides or nucleosides;
wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;

In some embodiments, a de-blocked composition is a de-blocked oligonucleotide composition comprising a plurality of de-blocked oligonucleotides, each of which independently comprises a —OH group. In some embodiments, each de-blocked oligonucleotide contains one and no more than one —OH group. In some embodiments, a —OH group is a 5'-OH group.

In some embodiments, a de-blocked composition is a de-blocked oligonucleotide composition comprising a plurality of de-blocked nucleosides, each of which independently comprises a —OH group. In some embodiments, each of the nucleosides is independently the "first" nucleoside to be incorporated into an oligonucleotide. Typically, it is the first nucleoside being linked to, e.g., a solid support optionally through a linker moiety. In some embodiments, a —OH group is a 5'-OH group.

In some embodiments, a de-blocked composition is a de-blocked oligonucleotide composition comprising a plurality of de-blocked oligonucleotides, each of which independently comprises a —OH group. In some embodiments, each de-blocked oligonucleotide contains one and no more than one —OH group. In some embodiments, a —OH group is a 5'-OH group. In some embodiments, a de-blocked composition is a chirally controlled oligonucleotide composition. In some embodiments, a de-blocked composition is a chirally controlled oligonucleotide composition comprising a plurality of de-blocked oligonucleotides, each of which is independently of formula VIII or a salt thereof.

In some embodiments, for a de-blocked oligonucleotide of formula VIII or a salt thereof, $R^{5s}$ is —OH and the only free hydroxyl. In some embodiments, $R^{5s}$ is 5'-OH. In some embodiments, each $L^P$ is independently an internucleotidic linkage of formula VII or a salt form thereof. In some embodiments, for each $L^P$, $P^L$ is not P. In some embodiments, for each $L^P$, $P^L$ is P(=O) or P(=S).

In some embodiments, each $L^P$ is an internucleotidic linkage of formula VII or a salt form thereof, wherein:
each $P^L$ is independently P(=O) or P(=S);
for each $P^L$ is P(=O), each —X-L$^s$-R$^5$ is independently -L$^7$-R$^1$, wherein L$^7$ is —O—, or —X-L$^s$-R$^5$ is independently —S-L$^s$-R$^5$; and
for each $P^L$ is P(=S), each —X-L$^s$-R$^5$ is independently of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

In some embodiments, each $L^P$ is an internucleotidic linkage of formula VII or a salt form thereof, wherein:

each $P^L$ is independently P(=O) or P(=S);

for each $P^L$ is P(=O), each —X-$L^s$-$R^5$ is independently -$L^7$-$R^1$, wherein $L^7$ is —O—, or —X-$L^s$-$R^5$ is independently —S-$L^s$-$R^5$;

for each $P^L$ is P(=S), each —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R; and each $L^P$ is independently a chirally controlled internucleotidic linkage when —X-$L^s$-$R^5$ is —S-$L^s$-$R^5$ or when $P^L$ is P(=S).

De-blocked oligonucleotides, except the de-blocked hydroxyl groups, are otherwise properly blocked, for example, amino groups of chiral auxiliary groups are properly blocked if necessary.

In some embodiments, a coupling reagent system comprises a partner compound. In some embodiments, a coupling reagent system comprises a partner compound and an activator.

In some embodiments, a partner compound is a nucleoside phosphoramidite having the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof. In some embodiments, for chirally controlled oligonucleotide synthesis, a chirally pure partner compound comprising a chiral auxiliary moiety, e.g., a chirally pure phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof is used. In some embodiments, to form an natural phosphate linkage or non-chirally controlled modified internucleotidic linkage (e.g., a stereorandom phosphorothioate linkage), non-chirally pure partner compound can be used, e.g., phosphoramidite of traditional oligonucleotide synthesis. In some embodiments, hydroxyl groups of partner compounds if any are blocked. In some embodiments, $R^{5s}$ is -ODMTr.

Various phosphoramidites can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc.

Various types of activators for promoting coupling of phosphoramidites and hydroxyl groups can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc. In some embodiments, an activator is or comprises an optionally substituted heteroaryl compound containing one or more nitrogen heteroatoms or a salt thereof. In some embodiments, the heteroaryl compound is optionally substituted tetrazole or a salt thereof.

In some embodiments, an activator is selected from:

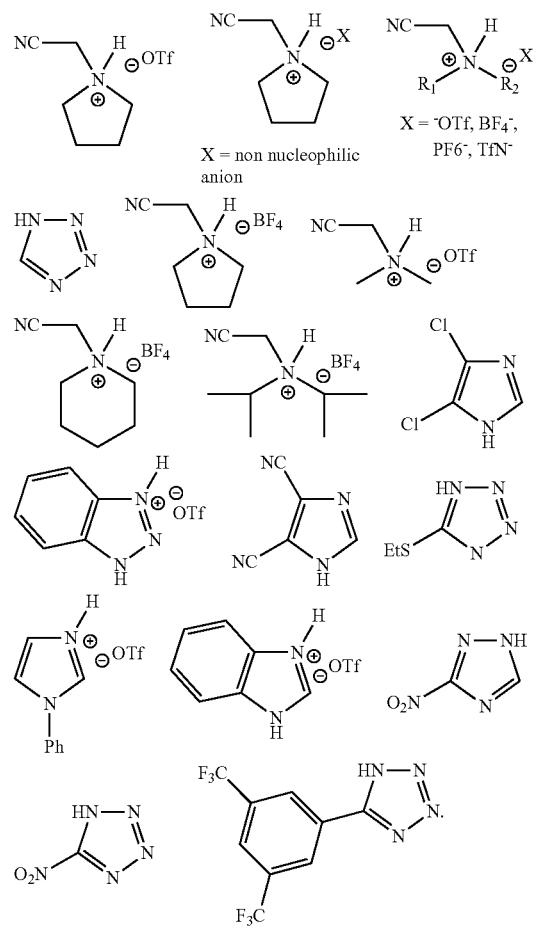

In some embodiments, an activator is selected from

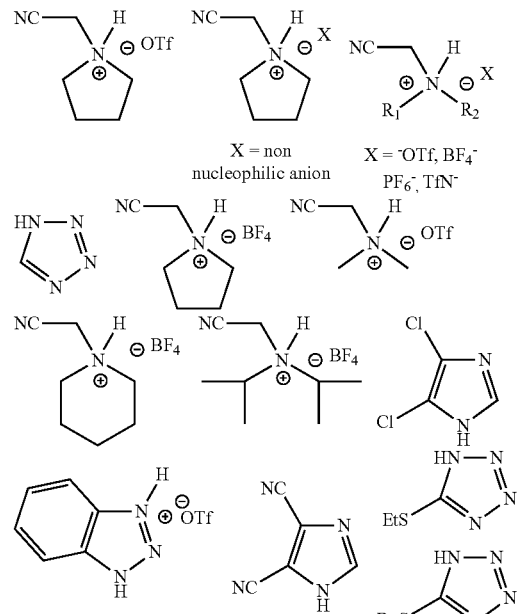

-continued

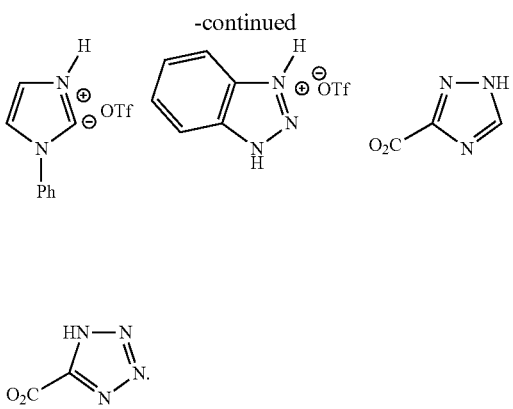

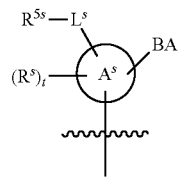

In some embodiments, an activator is selected from cyanomethyl imidazole triflate, cyanomethyl pyrrolidine triflate, ETT, phenyl(2H-tetrazol-5-yl)methanone, 2-(dimethylamino)acetonitrile/trifluorosulfonic acid(2/1), 2-(1H-imidazol-1-yl)acetonitrile/trifluorosulfonic acid(2/1), and 2-(pyrrolidin-1-yl)acetonitrile/trifluorosulfonic acid(2/1).

In some embodiments, an activator is CMIMT. In some embodiments, an activator is CMPT. In some embodiments, an activator is ETT. In some embodiments, ETT is utilized with non-chirally pure partner compounds, such as phosphoramidites of traditional oligonucleotide synthesis.

In some embodiments, each coupling product oligonucleotide is independently of formula VIII or a salt thereof. In some embodiments, a coupling product composition is a chirally controlled oligonucleotide composition. In some embodiments, internucleotidic linkage connecting a hydroxyl group of a de-blocked oligonucleotide with a nucleoside unit of a partner compound is an internucleotidic linkage of formula VII-b, or a salt form thereof. In some embodiments, each formed internucleotidic linkage is independently a chirally controlled internucleotidic linkage, wherein each chirally controlled linkage phosphorus (a linkage phosphorus of a chirally controlled internucleotidic linkage) independently has a diastereomeric purity of at least 80%, 85%, 90%, 91%, 92%, 93%, 94%, 95%, 96%, 97%, 98% or 99% within the coupling product composition.

In some embodiments, each coupling product oligonucleotide is independently of formula VIII or a salt thereof. In some embodiments, a coupling product composition is a chirally controlled oligonucleotide composition.

In some embodiments, each coupling product oligonucleotide is independently of formula VIII or a salt thereof, wherein:
the $L^P$ bonded to

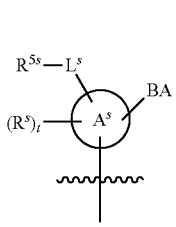

is an internucleotidic linkage of formula VII-b, or a salt form thereof;
each $L^P$ that is not bonded to

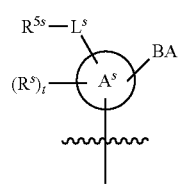

in formula VIII is independently of formula VII or a salt form thereof, wherein each $P^L$ is independently not P, wherein:
each $P^L$ that is not bonded to is independently P(=O) or P(=S);
for each $P^L$ is P(=O), each —X-$L^s$-$R^5$ is independently -$L^7$-$R^1$, wherein $L^7$ is —O—, or —X-$L^s$-$R^5$ is independently —S-$L^s$-$R^5$; and
for each $P^L$ is P(=S), each —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

In some embodiments, each coupling product oligonucleotide is independently of formula VIII or a salt thereof, wherein:
the $L^P$ bonded to is an internucleotidic linkage of formula VII-b, or a salt form thereof;
each $L^P$ that is not bonded to in formula VIII is independently of formula VII or a salt form thereof, wherein each $P^L$ is independently not P, wherein:

each $P^L$ that is not bonded to

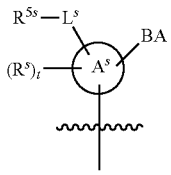

is independently P(=O) or P(=S);

each $P^L$ is independently P(=O) or P(=S);

for each $P^L$ is P(=O), each —X-$L^s$-$R^5$ is independently -$L^7$-$R^1$, wherein $L^7$ is —O—, or —X-$L^s$-$R^5$ is independently —S-$L^s$-$R^5$;

for each $P^L$ is P(=S), each —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R; and each $L^P$ is independently a chirally controlled internucleotidic linkage when —X-$L^s$-$R^5$ is —S-$L^s$-$R^5$ or when $P^L$ is P(=S).

In some embodiments, $R^{5s}$ for coupling product oligonucleotide is typical blocked —OH, e.g., -ODMTr.

In some embodiments, e.g., when an phosphoramidite comprising a chiral auxiliary moiety is used, a $L^P$ bonded to

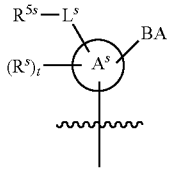

is an internucleotidic linkage of formula VII-b, or a salt form thereof, wherein —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —H. Thus, such $L^P$ groups may contain primary or secondary amino groups that need to be capped, in addition to un-coupled free hydroxyl groups of de-blocked oligonucleotide and/or nucleoside remaining in coupling product compositions. Additionally and/or alternatively, free hydroxyl group may form during coupling steps, e.g., detritylation of one or more coupling product oligonucleotide.

It is noted that when phosphoramidites of traditional oligonucleotide synthesis is used as a partner compound, typically no free amino acid group will be generated.

As appreciated by those skilled in the art, a coupling step typically adds at least one nucleoside unit to a growing oligonucleotide chain.

In some embodiments, contacting may be repeated as desired. In some embodiments, reaction conditions, such as concentrations, contact time, etc., can be adjusted in accordance with the present disclosure to improve results.

Pre-Modification Capping

As described in the present disclosure, in some embodiments, a coupling product composition may contain both amino groups and hydroxyl groups to be capped. In some embodiments, a pre-modification capping step comprises contacting a coupling product composition with a pre-modification capping reagent system, which contacting selectively caps amino over hydroxyl groups of a coupling product composition. Alternatively or additionally, in some embodiments a pre-modification capping step comprises contacting a coupling product composition with a pre-modification capping reagent system, which contacting caps both amino and hydroxyl groups of a coupling product composition. In some embodiments, when there are two contacting, typical the first one is amino-selective.

Selectivity and activity of contacting events may be tuned by pre-modification capping reagent systems. In some embodiments, a pre-modification capping reagent system is selective for amidation, e.g., capping of amino groups over esterification, e.g., capping of hydroxyl groups. In some embodiments, a pre-modification capping reagent system is efficient for both amidation and esterification, and can efficiently capping both amino and hydroxyl groups, e.g., capping reagent systems of traditional oligonucleotide synthesis (although in traditional oligonucleotide synthesis, no capping of amino groups may be needed during capping step).

Conditions and reagent systems selective for amidation over esterification, and conditions and reagent systems efficient for both amidation and esterification are well known and can be utilized in accordance with the present disclosure. In some embodiments, a selective reagent system comprises no, or greatly reduced levels of esterification catalysts and/or strong nucleophiles. In some embodiments, reagent system efficient for both amidation and esterification comprises suitable levels of esterification catalysts and/or strong nucleophiles. In some embodiments, esterification catalysts and/or strong nucleophiles are those utilized in traditional capping systems to promote capping of hydroxyl groups, e.g., DMAP, NMI, etc.

In some embodiments, in a coupling product oligonucleotide, the $L^P$ bonded to

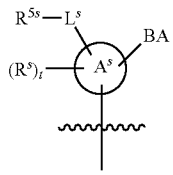

is an internucleotidic linkage of formula VII-b, or a salt form thereof, wherein —X-$L^s$-$R^5$ is independently of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —H, and a pre-modification capping step comprises converting the at least one of $R^5$ or $R^6$ which is —H into —C(O)R.

In some embodiments, a pre-modification capping reagent system comprises an acylating agent to acylate amino and/or hydroxyl groups. Various acylating agents can be utilized in accordance with the present disclosure. In some embodiments, an acylating agent is an anhydride. In some embodiments, an acylating agent is $Ac_2O$. In some embodiments, an acylating agent is a halogen-substituted acetic anhydride. In some embodiments, an acylating agent is $(Pac)_2O$. In some embodiments, a pre-modification capping reagent system further comprises a base, which among other things, may neutralize acids generated during capping. In some embodiments, for capping hydroxyl groups, an esterification catalyst, e.g., NMI, DMAP, etc. is used.

In some embodiments, a pre-modification capping reagent system comprises or is a solution of:

Pyridine/DMAP/$Ac_2O$;
2,6-Lutidine/NMI/$Ac_2O$;
2,4,6-Collidine/$Ac_2O$;

Triethylamine/Ac$_2$O;
DIEA/Ac$_2$O;
N-Methyl morpholine/Ac$_2$O;
2,6-Lutidine, then after a period of time, NMI/Ac$_2$O;
2,6-Lutidine/Ac$_2$O;
PhNCO/2,6-Lutidine;
POS;
POS then NMI/2,6-Lutidine/Ac$_2$O; or
2-(dimethylamino)acetonitrile/Ac$_2$O.

In some embodiments, a pre-modification capping reagent system comprises or is a solution of:
Pyridine (2 equiv.)/DMAP (cat.)/Ac$_2$O(4 equiv.);
2,6-Lutidine (2 equiv.)/NMI (0.25 equiv.)/Ac$_2$O(4 equiv.);
2,4,6-Collidine/Ac$_2$O(4 equiv.);
Triethylamine/Ac$_2$O(4 equiv.);
DIEA/Ac$_2$O(4 equiv.);
N-Methyl morpholine/Ac$_2$O(4 equiv.);
2,6-Lutidine (2 equiv.) then after 5 min. NMI (1 equiv.)/Ac$_2$O(4 equiv.);
2,6-Lutidine/Ac$_2$O(4 equiv.);
PhNCO/2,6-Lutidine;
POS (both oxidation and pre-capping);
POS (both oxidation and pre-capping) then NMI/2,6-Lutidine/Ac$_2$O; or
2-(dimethylamino)acetonitrile/Ac$_2$O.

In some embodiments, a pre-modification capping product composition is a chirally controlled oligonucleotide composition. In some embodiments, a pre-modification capping product oligonucleotide is an oligonucleotide of formula VIII or a salt thereof.

In some embodiments, each pre-modification capping product oligonucleotide is independently of formula VIII or a salt thereof, wherein:
the L$^P$ bonded to

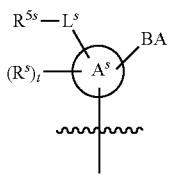

is an internucleotidic linkage of formula VII-b, or a salt form thereof, wherein —X-L$^s$-R$^5$ is of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R;
each L$^P$ that is not bonded to

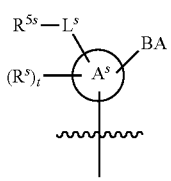

in formula VIII is independently of formula VII or a salt form thereof, wherein each P$^L$ is independently not P, wherein:
each P$^L$ that is not bonded to

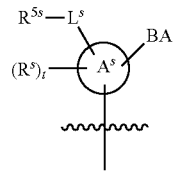

is independently P(=O) or P(=S);
for each P$^L$ is P(=O), each —X-L$^s$-R$^5$ is independently -L$^7$-R$^1$, wherein L$^7$ is —O—, or —X-L$^s$-R$^5$ is independently —S-L$^s$-R$^5$; and
for each P$^L$ is P(=S), each —X-L$^s$-R$^5$ is independently of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R.

In some embodiments, each pre-modification capping product oligonucleotide is independently of formula VIII or a salt thereof, wherein:
the L$^P$ bonded to

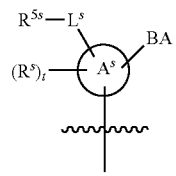

is an internucleotidic linkage of formula VII-b, or a salt form thereof, wherein —X-L$^s$-R$^5$ is of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R;
each L$^P$ that is not bonded to

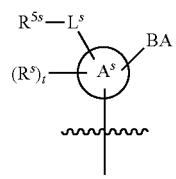

in formula VIII is independently of formula VII or a salt form thereof, wherein each P$^L$ is independently not P, wherein:
each P$^L$ that is not bonded to

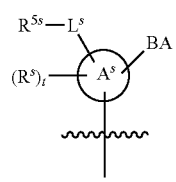

is independently P(=O) or P(=S);
for each P$^L$ is P(=O), each —X-L$^s$-R$^5$ is independently -L$^7$-R$^1$, wherein L$^7$ is —O—, or —X-L$^s$-R$^5$ is independently —S-L$^s$-R$^5$;
for each P$^L$ is P(=S), each —X-L$^s$-R$^5$ is independently of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R; and each $L^P$ is independently a chirally controlled internucleotidic linkage when —X-$L^s$-$R^5$ is —S-$L^s$-$R^5$ or when $P^L$ is P(=S) or P.

Modification

In some embodiments, a modification step modifies a trivalent (—P(-)—) linkage phosphorus and convert it into a tetravalent linkage phosphorus. As appreciated by those skilled in the art, a number of P-modifications can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, etc.

In some embodiments, a modification is sulfurization installing an O to P. In some embodiments, a modification is sulfurization. Many suitable reagents may be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, etc.

In some embodiments, an oxidation reagent is TBHP (tert-butylhydroperoxide). In some embodiments, an oxidation reagent is $I_2$/Water/Pyridine. In some embodiments, the concentration of $I_2$ is about 0.05 M.

In some embodiments, a sulfurization reagent is 3H-1,2-benzodithiol-3-one-1,1-dioxide, or the Beaucage reagent, tetraethylthiuram disulfide, phenylacetyl disulfide, dibenzoyl tetrasulfide, bis-(O,O-diisopropoxyphosphinothioyl) disulfide, benzyltriethylammonium tetrathiomolybate, bis-(p-toluenesulfonyl) disulfide, 3-ethoxy-1,2,4-dithiazoline-5-one (EDITH), 1,2,4-dithiazolidine-3,5-dione, 3-amino-1,2,4-dithiazole-5-thione, 3-methyl-1,2,4-dithiazolin-5-one, or 3-phenyl-1,2,4-dithiazoline-5-one. In some embodiments, a sulfurization reagent is 3H-1,2,4-dithiazole-3-thiones and 3H-1,2-dithiole-3-thiones, e.g., described in Guzaev, Tetrahedron Letters 52 (2011) 434-437. In some embodiments, a sulfurization reagent is POS (3-phenyl-1,2,4-dithiazolin-5-one), DDTT (((dimethylamino-methylidene)amino)-3H-1,2,4-dithiazaoline-3-thione), DTD (dimethylthiarum disulfide), xanthane hydride (XH), S-(2-cyanoethyl) methanesulfonothioate (MTS-CNE), or phenylacetyl disulfide. In some embodiments, a sulfurization reagent is POS. In some embodiments, a sulfurization reagent is DDTT. In some embodiments, a sulfurization reagent is DTD. In some embodiments, a sulfurization reagent is xanthane hydride.

In some embodiments, a thiosulfonate reagent has a structure of formula S-I:

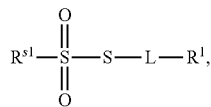

S-I wherein:

$R^{s1}$ is R; and each of R, L and $R^1$ is independently as defined and described above and herein.

In some embodiments, the sulfurizing reagent is a bis (thiosulfonate) reagent. In some embodiments, the bis(thiosulfonate) reagent has the structure of formula S-II:

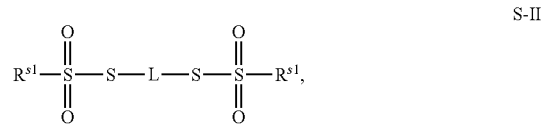

S-II wherein each variable is independently as described in the present disclosure.

As defined generally above, $R^{s1}$ is R, wherein R is as defined and described above and herein. In some embodiments, $R^{s1}$ is optionally substituted aliphatic, aryl, heterocyclyl or heteroaryl. In some embodiments, $R^{s1}$ is optionally substituted alkyl. In some embodiments, $R^{s1}$ is optionally substituted alkyl. In some embodiments, $R^{s1}$ is methyl. In some embodiments, $R^{s1}$ is cyanomethyl. In some embodiments, $R^{s1}$ is nitromethyl. In some embodiments, $R^{s1}$ is optionally substituted aryl. In some embodiments, $R^{s1}$ is optionally substituted phenyl. In some embodiments, $R^{s1}$ is phenyl. In some embodiments, $R^{s1}$ is p-nitrophenyl. In some embodiments, $R^{s1}$ is p-methylphenyl. In some embodiments, $R^{s1}$ is p-chlorophenyl. In some embodiments, $R^{s1}$ is o-chlorophenyl. In some embodiments, $R^{s1}$ is 2,4,6-trichlorophenyl. In some embodiments, $R^{s1}$ is pentafluorophenyl. In some embodiments, $R^{s1}$ is optionally substituted heterocyclyl. In some embodiments, $R^{s1}$ is optionally substituted heteroaryl.

In some embodiments, $R^{s1}$—S(O)$_2$S— is

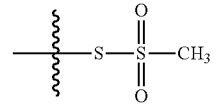 [SMILES: *SS(C)(=O)=O]

(MTS). In some embodiments, $R^{s1}$—S(O)$_2$S— is

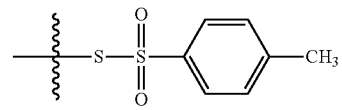 [SMILES: *SS(=O)(=O)c1ccc(C)cc1]

(TTS). In some embodiments, $R^{s1}$—S(O)$_2$S— is

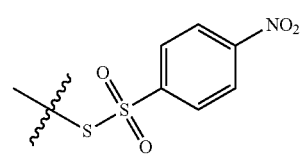 [SMILES: *SS(=O)(=O)c1ccc([N+](=O)[O-])cc1]

(NO₂PheTS). In some embodiments, $R^{s1}$—S(O)₂S— is

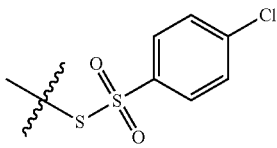 [SMILES: *SS(=O)(=O)c1ccc(Cl)cc1]

(p-ClPheTS). In some embodiments, $R^{s1}$—S(O)₂S— is

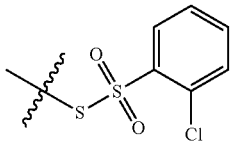 [SMILES: *SS(=O)(=O)c1ccccc1Cl]

(o-ClPheTS). In some embodiments, $R^{s1}$—S(O)₂S— is

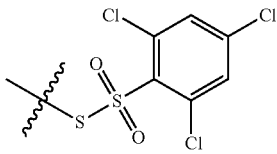 [SMILES: *SS(=O)(=O)c1c(Cl)cc(Cl)cc1Cl]

(2,4,6-TriClPheTS). In some embodiments, $R^{s1}$—S(O)₂S— is

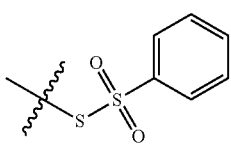 [SMILES: *SS(=O)(=O)c1ccccc1]

(PheTS). In some embodiments, $R^{s1}$—S(O)₂S— is

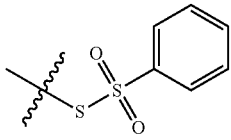 [SMILES: *SS(=O)(=O)c1ccccc1]

(PFPheTS). In some embodiments, $R^{s1}$—S(O)₂S— is

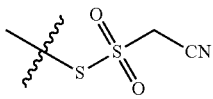 [SMILES: *SS(=O)(=O)CC#N]

(a-CNMTS). In some embodiments, $R^{s1}$—S(O)₂S— is

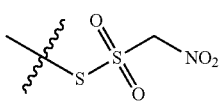

(a-NO₂MTS). In some embodiments, $R^{s1}$—S(O)₂S— is

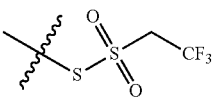 [SMILES: *SS(=O)(=O)CC(F)(F)F]

(a-CF₃MTS). In some embodiments, $R^{s1}$—S(O)₂S— is

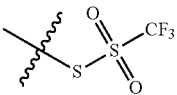

(a-CF₃TS). In some embodiments, $R^{s1}$—S(O)₂S— is

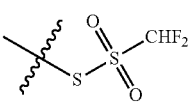 [SMILES: *SS(=O)(=O)C(F)F]

(a-CHF2TS). In some embodiments, $R^{s1}$—S(O)₂S— is

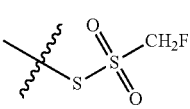

(a-CH₂FTS).

In some embodiments, the sulfurizing reagent has the structure of S-I or S-II, wherein L is optionally substituted alkylene, alkenylene, arylene or heteroarylene.

In some embodiments, a sulfurization reagent is S₈,

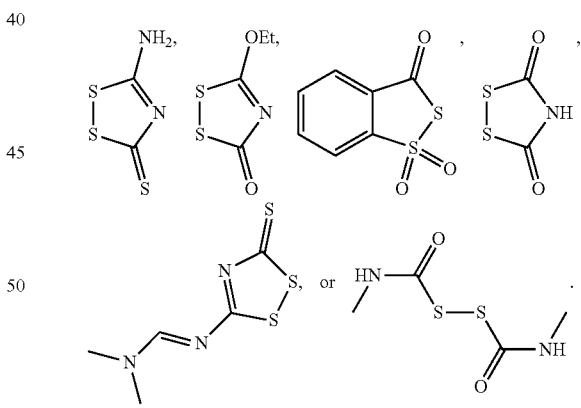

In some embodiments, the sulfurization reagent is S₈,

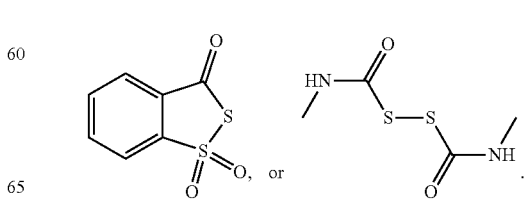

In some embodiments, the sulfurization reagent is
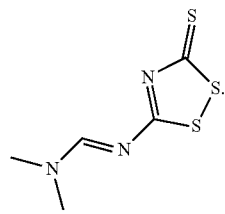
Example sulfuring reagents are depicted in below:
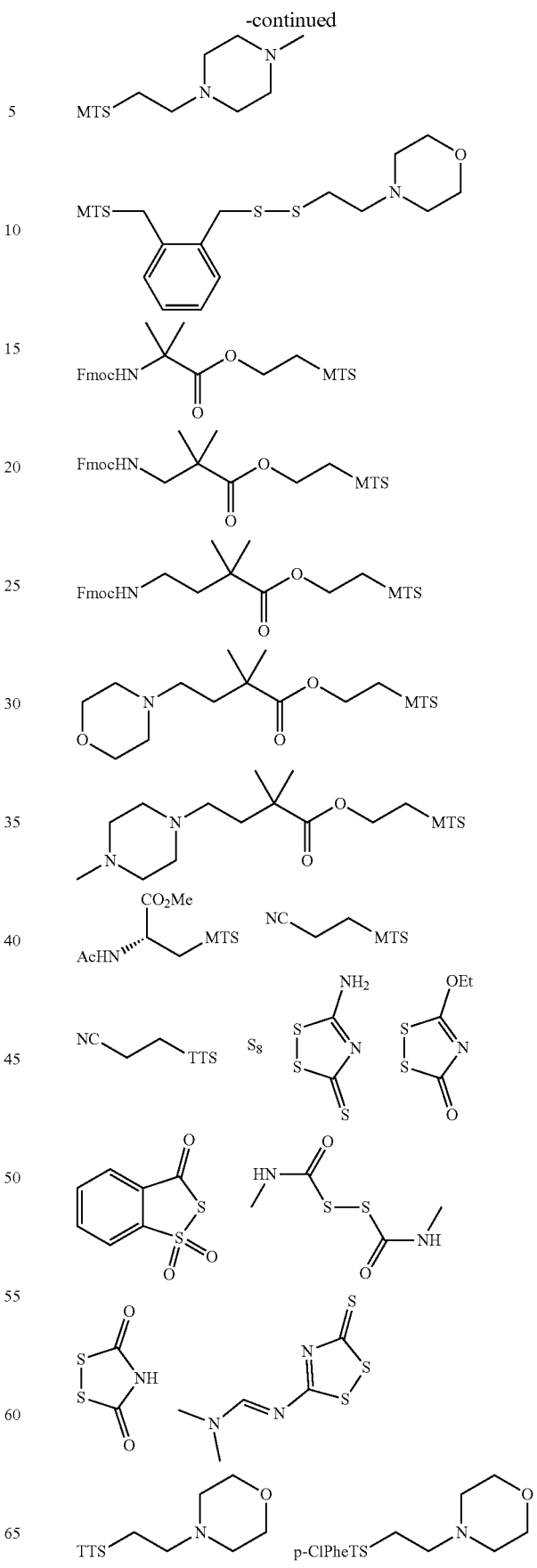

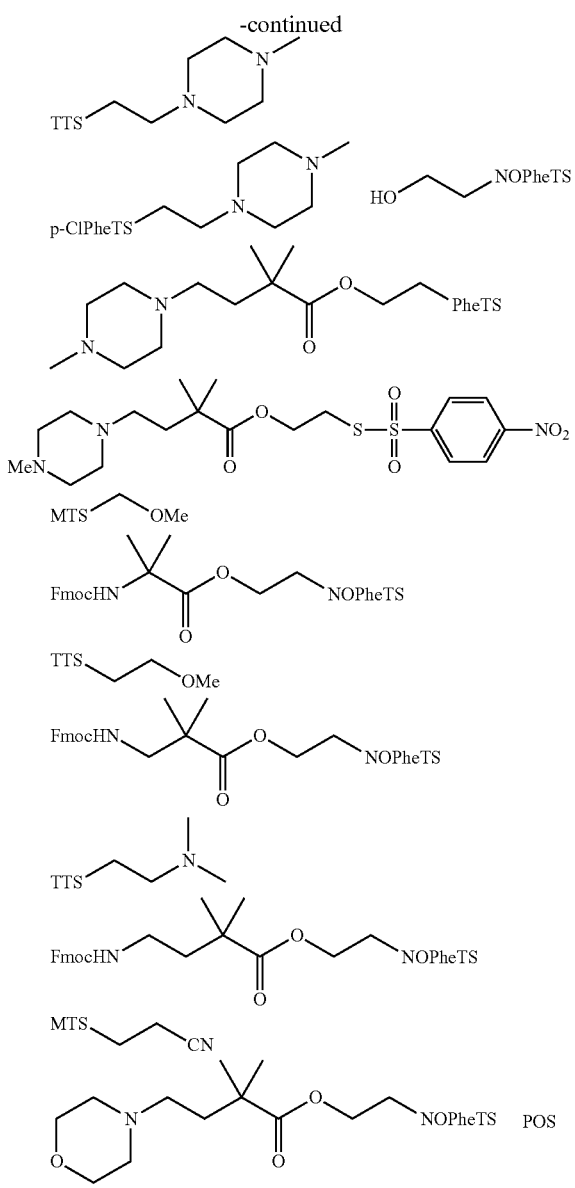

In some embodiments, a selenium electrophile is used instead of a sulfurizing reagent to introduce modification to the internucleotidic linkage. In some embodiments, a selenium electrophile is a compound having one of the following formulae:

$$Se, R^{s2}—Se—Se—R^{s3}, \text{ or } R^{s2}—Se—X^s—R^{s3},$$

wherein:

each of $R^{s2}$ and $R^{s3}$ is independently an optionally substituted group selected from aliphatic, aminoalkyl, carbocyclyl, heterocyclyl, heterocycloalkyl, aryl, heteroaryl, alkyloxy, aryloxy, heteroaryloxy, acyl, amide, imide, or thiocarbonyl; or $R^{s2}$ and $R^{s3}$ are taken together with the atoms to which they are bound to form an optionally substituted heterocyclic or heteroaryl ring;

$X^s$ is —S(O)$_2$—, —O—, or —N(R')—; and

R' is as defined and described above and herein.

In other embodiments, the selenium electrophile is a compound of Se, KSeCN,

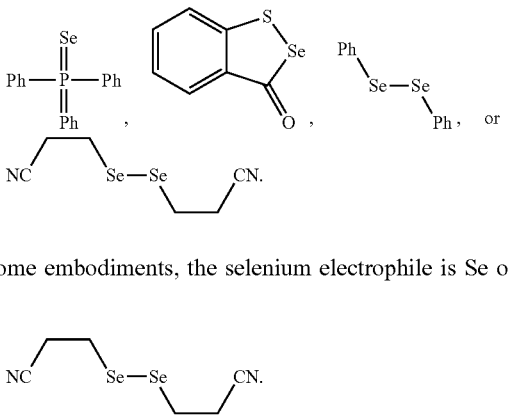

In some embodiments, the selenium electrophile is Se or

In some embodiments, a modification step is or comprises boronating of a linkage phosphorus atom. In some embodiments, a boronating reagent is a borane-amine (e.g., N,N-diisopropylethylamine (BH$_3$.DIPEA), borane-pyridine (BH$_3$.Py), borane-2-chloropyridine (BH$_3$.CPy), borane-aniline (BH$_3$.An)), a borane-ether reagent (e.g., borane-tetrahydrofuran (BH$_3$.THF)), a borane-dialkylsulfide reagent (e.g., BH$_3$.Me$_2$S), aniline-cyanoborane, or a triphenylphosphine-carboalkoxyborane. In some embodiments, an azide reagent is comprises an azide group capable of undergoing subsequent reduction to provide an amine group.

In some embodiments, a modification product composition is a chirally controlled oligonucleotide composition. In some embodiments, each modification product oligonucleotide is independently an oligonucleotide of formula VIII or a salt thereof.

In some embodiments, each pre-modification capping product oligonucleotide is independently of formula VIII or a salt thereof, wherein:

each $L^P$ is independently of formula VII or a salt form thereof, wherein each $P^L$ is independently not P, wherein:

each $L^P$ contains no free primary and no free secondary amino groups.

In some embodiments, each pre-modification capping product oligonucleotide is independently of formula VIII or a salt thereof, wherein:

each $L^P$ is independently of formula VII or a salt form thereof, wherein:

each $P^L$ is independently P(=O) or P(=S);

for each $P^L$ is P(=O), each —X-L$^s$-R$^5$ is independently -L$^7$-R$^1$, wherein L$^7$ is —O—, or —X-L$^s$-R$^5$ is independently —S-L$^s$-R$^5$, or of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R; and for each $P^L$ is P(=S), each —X-L$^s$-R$^5$ is independently of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R.

In some embodiments, each modification product oligonucleotide is independently of formula VIII or a salt thereof, wherein:

each $L^P$ is independently of formula VII or a salt form thereof, wherein:

each $P^L$ is independently P(=O) or P(=S);

for each $P^L$ is P(=O), each —X-L$^s$-R$^5$ is independently -L$^7$-R$^1$, wherein L$^7$ is —O—, or —X-L$^s$-R$^5$ is independently —S-L$^s$-R$^5$, or of such a structure that H—X-L$^s$-R$^5$ is a compound of formula I, I-a, I-a-1, I-a-2, I-b, I-c, I-d, I-e, II, II-a, 11-b, III, III-a, or III-b, wherein at least one of $R^5$ or $R^6$ is —C(O)R; and for each $P^L$ is P(=S), each —X-$L^s$-$R^5$ is independently of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R; and each $L^P$ is independently a chirally controlled internucleotidic linkage when —X-$L^s$-$R^5$ is —S-$L^s$-$R^5$ or when $P^L$ is P(=S) or P.

Post-Modification Capping

Various capping conditions, including those described for pre-modification capping steps, traditional capping steps, etc., can be utilized in accordance with the present disclosure, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc.

In some embodiments, a post-modification capping is selective for amidation over esterification. In many embodiments, a post-modification capping is efficient for both amidation and esterification, efficiently capping both amino and hydroxyl groups. In some embodiments, post-modification capping reagent systems comprise strong nucleophiles and/or esterification catalysts, e.g., DMAP, NMI, etc. at significant amount.

In some embodiments, a post-modification capping step caps various functional groups, e.g., hydroxyl groups, amino groups, that remain after, or formed during, coupling, pre-modification capping, and/or modification steps.

In some embodiments, e.g., when a modification product composition is contacted with a post-modification capping reagent system, the present disclosure provides a composition, comprising a plurality of oligonucleotides and one or more reagents of a post-modification capping reagent system, which reagents are in contact with the plurality of oligonucleotides.

In some embodiments, the present disclosure provides a composition, comprising a plurality of oligonucleotides and one or more reagents of a post-modification capping reagent system, which reagents are in contact with the plurality of oligonucleotides, wherein the plurality of oligonucleotides is a plurality of modification product oligonucleotides.

In some embodiments, the composition is a chirally controlled oligonucleotide composition. In some embodiments, a reagent is an acylating reagent, e.g., Ac$_2$O. In some embodiments, a reagent is an esterification catalyst, e.g., DMAP, NMI, etc. In some embodiments, one reagent is an anhydride, and one reagent is an esterification catalyst.

De-Blocking

In some embodiments, the step of coupling is preceded by a step of deblocking. For instance, in some embodiments, the 5' hydroxyl group of the growing oligonucleotide is blocked (i.e., protected) and is de-blocked in order to subsequently react with a nucleoside coupling partner, or before exiting the cycle.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring and or other sugar ring. In some embodiments, an acid is selected from $R^{a1}$COOH, $R^{a1}$SO$_3$H, $R^{a3}$SO$_3$H,

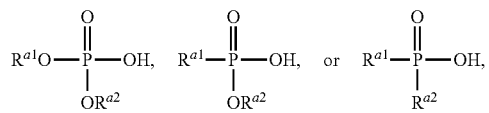

wherein each of $R^{a1}$ and $R^{a2}$ is independently hydrogen or an optionally substituted alkyl or aryl, and $R^{a3}$ is an optionally substituted alkyl or aryl.

In some embodiments, acidification is accomplished by a Lewis acid in an organic solvent. Examples of such useful Lewis acids are Zn($X^a$)$_2$ wherein $X^a$ is Cl, Br, I, or CF$_3$SO$_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10% dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is de-blocked by acidification, which comprises adding 1% trifluoroacetic acid in an organic solvent. In some embodiments, a blocking group is de-blocked by acidification, which comprises adding 3% dichloroacetic acid in an organic solvent. In some embodiments, a blocking group is de-blocked by acidification, which comprises adding 3% trichloroacetic acid in an organic solvent. In some embodiments, a blocking group is de-blocked by acidification, which comprises adding 3% trichloroacetic acid in dichloromethane.

In certain embodiments, methods of the present disclosure are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, the chiral auxiliary is removed before the deblocking step. In some embodiments, the chiral auxiliary is removed during the deblocking step.

In some embodiments, cycle exit is performed before the deblocking step. In some embodiments, cycle exit is preformed after the deblocking step.

Post-Cycle Modification/Removal of Chiral Auxiliaries

In some embodiments, prior to, concurrently with, or subsequent to cleavage from support/deprotection, a step is performed to remove a chiral auxiliary group, if one is still attached to an internucleotidic phosphorus atom. In some embodiments, for example, one or more DPSE type chiral auxiliary groups remain attached to internucleotidic phosphorus atoms during the oligonucleotide synthesis cycle. In some embodiments, chiral auxiliary groups (capped or uncapped) may be removed during a modification step. In some embodiments, chiral auxiliary groups (capped or uncapped) may be removed under acidic conditions. In some embodiments, chiral auxiliary groups (capped or uncapped) may be removed under basic conditions. In some embodiments, chiral auxiliary groups (capped or uncapped) may be removed under $F^-$ conditions. Suitable conditions for removing remaining chiral auxiliary groups are widely known in the art and can be utilized in accordance with the present disclosure, e.g., those described in e.g., US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264, etc.

In some embodiments, a condition for removing DPSE type chiral auxiliary is TBAF or HF-Et$_3$N, e.g., 0.1M TBAF in MeCN, 0.5M HF-Et$_3$N in THF or MeCN, etc. In some embodiments, the present disclosure recognizes that a linker may be cleaved during the process of removing a chiral auxiliary group. Additional example conditions are described in the present disclosure.

Cleavage/Deprotection

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., Tetrahedron, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a $C_{1-10}$ amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, the oligonucleotide is deprotected during cleavage.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C. or 100° C. In some embodiments, cleavage of oligonucleotide from solid support, or deprotection of oligonucleotide, is performed at about 30° C., 40° C., 50° C., 60° C., 70° C., 80° C. 90° C. or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Example conditions are 20% propylamine in pyridine at room temperature for about 18 hrs, and 20% propylamine in pyridine at 60° C. for about 18 hrs. Additional example conditions are described in the present disclosure.

In some embodiments, a metal chelator is utilized during cleavage/deprotection. In some embodiments, a metal chelator is EDTA. In some embodiments, After cleavage/deprotection and removal of chiral auxiliaries, provided crude oligonucleotides are typically further analyzed and purified, e.g., through various analytical and purification technologies available in the art. In some embodiments, an analytical and/or purification technology is chromatography. In some embodiments, an analytical and/or purification technology is HPLC and/or UPLC.

Supports and Linkers

Various types of supports and linkers may be utilized in accordance with the present disclosure to prepare oligonucleotides, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, U.S. Pat. No. 9,403,865, WO2017/160741, WO2017/192664, WO2017/192679, WO2017/210647, WO2018/022473, WO2018/067973, WO2018/098264, etc. In some embodiments, a support is a solid support. In some embodiments, a support is not a solid support.

In some embodiments, synthesis of provided oligonucleotides is performed on solid support. In some embodiments, reactive groups present on a solid support are protected. In some embodiments, reactive groups present on a solid support are unprotected. In some embodiments, during oligonucleotide synthesis a solid support is treated with various reagents in several synthesis cycles to achieve stepwise elongation of a growing oligonucleotide chain with individual nucleotide units. A nucleoside unit at the end of an oligonucleotide chain which is directly linked to a solid support is typically referred to as the first nucleoside linked to a solid support. In some embodiments, a first nucleoside linked to a solid support is bound to a solid support via a linker moiety, a diradical forming a bond at one end with a solid support, e.g., of a CPG, a polymer or other solid support, and at the other end with a nucleoside. In some embodiments, a linker stays intact during synthesis cycles performed to assemble the oligonucleotide chain and is cleaved after the chain assembly to liberate the oligonucleotide from the support.

As demonstrated herein, CPG in some embodiments provide improved crude purity. In some embodiments, a polystyrene support may provide high unit loading capacity.

In some embodiments, a solid support is a solid support whose volume does not change significantly during oligonucleotide synthesis, e.g., CPG. In some embodiments, such solid support may provide easier and more accurate control of reagent concentrations for oligonucleotide synthesis.

In some embodiments, a solid supports for solid-phase nucleic acid synthesis is a support described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262,530; and Koster U.S. Pat. No. 4,725,677 (reissued as RE34,069). In some embodiments, a solid support is an organic polymer support. In some embodiments, a solid support is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled pore glass (CPG), which is a silica-gel support, or aminopropyl CPG. In some embodiments, a solid support is selected from fluorous solid supports (see e.g., WO/2005/070859), and long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.,* 1983, 105, 661-663; G. R. Gough, M. J. Bruden and P. T. Gilham, *Tetrahedron Lett.,* 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to attachment of a functional group to membrane, use of a linker or spacer group attached to the membrane is also used in some embodiments to minimize steric hindrance between the membrane and the synthesized chain.

Example suitable solid supports also include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TENTAGEL® Support-an aminopolyethyleneglycol derivatized support (see, e.g., Wright, et al., *Tetrahedron Lett.,* 1993, 34, 3373), and POROS®-a copolymer of polystyrene/divinylbenzene.

Surface activated polymers have been demonstrated for use in synthesis of natural and modified nucleic acids and proteins on several solid supports mediums. In some embodiments, a solid support material is any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. In some embodiments, other materials can serve as a solid support, depending on design in accordance with the present disclosure. In some embodiments, in consideration of some designs, for example, a coated metal, in particular gold or platinum can be selected (see e.g., US publication No. 20010055761). In some embodiments, for example, a nucleoside is anchored to a solid support which is functionalized with hydroxyl or amino residues. In some embodiments, a solid support is derivatized to provide an acid labile trialkoxytrityl group, such as a trimethoxytrityl group (TMT). Without being bound by theory, it is expected that presence of a trialkoxytrityl protecting group may permit initial detritylation under conditions commonly used on DNA synthesizers. In some embodiments, for a faster release of oligonucleotide material in solution with aqueous ammonia, a diglycoate linker is optionally introduced onto the support.

In some embodiments, a provided oligonucleotide is synthesized from 3' to 5' direction. In some embodiments, a provided oligonucleotide is synthesized from 5' to 3' direction. In some embodiments, a nucleic acid is attached to a solid support through its 5' end of the growing nucleic acid, thereby presenting its 3' group for reaction, i.e. using 5'-nucleoside phosphoramidites or in an enzymatic reaction (e.g. ligation and polymerization using nucleoside 5'-triphosphates). In some embodiments, in a 5' to 3' synthesis iterative steps of the present disclosure remain unchanged (e.g. capping and modification on the chiral phosphorus).

In some embodiments, a linking moiety or linker is optionally used to connect a solid support to a first nucleoside linked to a solid support, or a compound comprising a free nucleophilic moiety. In some embodiments, suitable linkers are known such as short moieties which serve to connect a solid support to functional groups (e.g., hydroxyl groups) of initial nucleoside molecules in solid phase synthetic techniques, and can be utilized in accordance with the present disclosure. In some embodiments, a linking moiety is a succinamic acid linker, or a succinate linker (—CO—CH$_2$—CH$_2$—CO—), or an oxalyl linker (—CO—CO—). In some embodiments, a linker is a succinamic acid linker. In some embodiments, a linker is a succinate linker. In some embodiments, a linker is an oxalyl linker. In some embodiments, a linking moiety and a nucleoside are bonded together through an ester bond. In some embodiments, a linking moiety and a nucleoside are bonded together through an amide bond. In some embodiments, a linking moiety connects a nucleoside to another nucleotide or nucleic acid.

Example suitable linkers are disclosed in, for example, *Oligonucleotides And Analogues A Practical Approach*, Ekstein, F. Ed., IRL Press, N.Y., 1991, Chapter 1 and Solid-Phase Supports for Oligonucleotide Synthesis, Pon, R. T., *Curr. Prot. Nucleic Acid Chem.*, 2000, 3.1.1-3.1.28.

In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attach a nucleoside, nucleotide, oligonucleotide and/or nucleic acid to a solid support (Ravikumar et al., *Org. Process Res. Dev.*, 2008, 12 (3), 399-410). In some embodiments, other universal linkers are used (Pon, R. T., *Curr. Prot. Nucleic Acid Chem.*, 2000, 3.1.1-3.1.28). In some embodiments, various orthogonal linkers (such as disulfide linkers) are used (Pon, R. T., *Curr. Prot. Nucleic Acid Chem.*, 2000, 3.1.1-3.1.28).

Among other things, the present disclosure recognizes that a linker can be chosen or designed to be compatible with a set of reaction conditions employed in synthesis. In some embodiments, to avoid degradation of oligonucleotides and to avoid desulfurization, auxiliary groups are selectively removed before de-protection. In some embodiments, DPSE group can selectively be removed by F. In some embodiments, the present disclosure provides linkers that are stable under a DPSE de-protection condition, e.g., 0.1M TBAF in MeCN, 0.5M HF-Et$_3$N in THF or MeCN, etc. In some embodiments, a linker is a SP linker. In some embodiments, a linker is succinyl linker. In some embodiments, a linker is Q-linker. In some embodiments, a linker is oxalyl linker. Example use of certain linkers are depicted below:

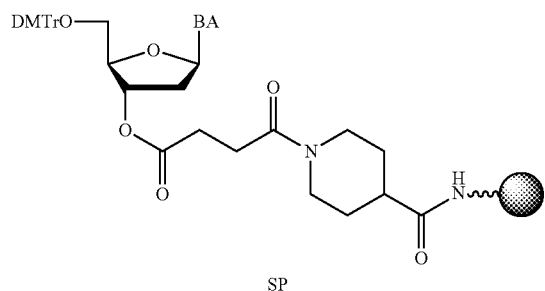

SP

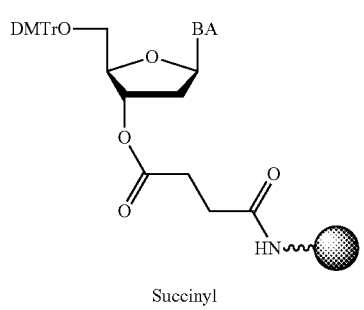

Succinyl

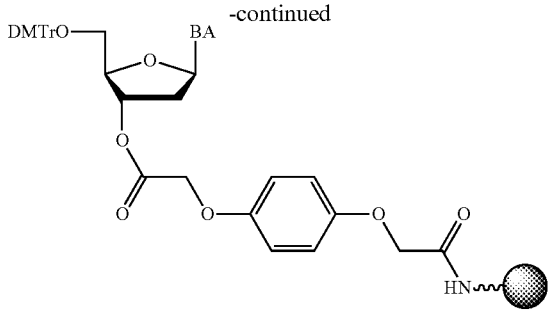

Q-linker

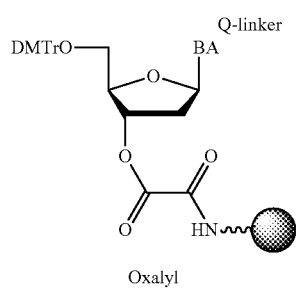

Oxalyl

In some embodiments, the present disclosure provides supports and linkers useful for oligonucleotide synthesis (in some cases, loaded with a first nucleoside for oligonucleotide synthesis). In some embodiments, a support is functionalized with amino groups. In some embodiments, a support is functionalized with —CH$_2$—(CH$_2$)$_n$—CH$_2$—NH$_2$, wherein the —CH$_2$— end is connected to a support, e.g., CPG. In some embodiments, a first linker is —CH$_2$—(CH$_2$)$_n$—CH$_2$—NH—, wherein the —CH$_2$— end is connected to a support, e.g., CPG, and the —NH— is connected to a nucleoside, e.g., 3'-OH, through a second linker, e.g., —C(O)—CH$_2$—CH$_2$—C(O)—, wherein n is as described in the present disclosure. In some embodiments, n is 1. In some embodiments, n is 7.

In some embodiments, a first linker is —CH$_2$—(CH$_2$)$_n$—CH$_2$—NH—C(O)—X—(CH$_2$)$_m$—NH—, wherein each variable is independently as described in the present disclosure. In some embodiments, a first linker is —CH$_2$—(CH$_2$)$_n$—CH$_2$—NH—C(O)—X—(CH$_2$)$_m$—NH—C(O)—X—(CH$_2$)$_p$—NH—, wherein each variable is independently as described in the present disclosure. In some embodiments, a first linker is —CH$_2$—(CH$_2$)$_n$—CH$_2$—NH—C(O)—X—CH$_2$—CH$_2$—CH$_2$—O—CH$_2$—CH$_2$—O—CH$_2$—CH$_2$—O—CH$_2$—CH$_2$—CH$_2$—NH—, wherein each variable is independently as described in the present disclosure. In some embodiments, a first linker is —CH$_2$—(CH$_2$)$_n$—CH$_2$—NH—C(O)—X—CH$_2$—CH$_2$—O—CH$_2$—CH$_2$—O—(CH$_2$—CH$_2$—O)$_m$—CH$_2$—CH$_2$—O—CH$_2$—CH$_2$—O—CH$_2$—CH$_2$—NH—, wherein each variable is independently as described in the present disclosure. In some embodiments, a first linker is —CH$_2$—(CH$_2$)$_n$—CH$_2$—NH—C(O)—X—CH$_2$—CH$_2$—CH$_2$—O—CH$_2$—CH$_2$—CH$_2$—O—(CH$_2$—CH$_2$—CH$_2$—O) m-CH$_2$—CH$_2$—CH$_2$—O—CH$_2$—CH$_2$—CH$_2$—NH—, wherein each variable is independently as described in the present disclosure. In some embodiments, the —CH$_2$— end is connected to a support, e.g., CPG, and the —NH— is connected to a nucleoside, e.g., 3'-OH, through a second linker, e.g., —C(O)—CH$_2$—CH$_2$—C(O)—.

In some embodiments, not all available amino moieties are loaded with nucleoside, e.g., through a second linker —C(O)—CH$_2$—CH$_2$—C(O)—. In some embodiments, some available amino moiety can be capped with an acyl group, e.g., —C(O)—R forming —CH$_2$—(CH$_2$)$_n$—CH$_2$—NH—C(O)—R, —CH$_2$—(CH$_2$)$_n$—CH$_2$—NH—C(O)—X—(CH$_2$)$_m$—NH—C(O)—R, —CH$_2$—(CH$_2$)$_n$—CH$_2$—NH—C(O)—X—(CH$_2$)$_m$—NH—C(O)—X—(CH$_2$)$_p$—NH—C(O)—R, —CH$_2$—(CH$_2$)$_n$—CH$_2$—NH—C(O)—X—CH$_2$—CH$_2$—CH$_2$—O—CH$_2$—CH$_2$—O—CH$_2$—CH$_2$—CH$_2$—O—CH$_2$—CH$_2$—CH$_2$—NH—C(O)—R, —CH$_2$—(CH$_2$)$_n$—CH$_2$—NH—C(O)—X—CH$_2$—CH$_2$—O—CH$_2$—CH$_2$—O—(CH$_2$—CH$_2$—O)$_m$—CH$_2$—CH$_2$—O—CH$_2$—CH$_2$—O—CH$_2$—CH$_2$—NH—C(O)—R, or —CH$_2$—(CH$_2$)$_n$—CH$_2$—NH—C(O)—X—CH$_2$—CH$_2$—CH$_2$—O—CH$_2$—CH$_2$—CH$_2$—O—(CH$_2$—CH$_2$—CH$_2$—O) m-CH$_2$—CH$_2$—CH$_2$—O—CH$_2$—CH$_2$—CH$_2$—NH—C(O)—R, wherein each variable is independently as described in the present disclosure, so that unit loading capacity of a support can be adjusted. In some embodiments, R is —(CH$_2$)o-, wherein o is 0-20.

In some embodiments, o is 0-12. In some embodiments, o is 0. In some embodiments, o is 1. In some embodiments, o is 2. In some embodiments, o is 3. In some embodiments, o is 4. In some embodiments, o is 5. In some embodiments, o is 6. In some embodiments, o is 7. In some embodiments, o is 8. In some embodiments, o is 9. In some embodiments, o is 10. In some embodiments, o is 11. In some embodiments, o is 12. In some embodiments, o is 13. In some embodiments, o is 14. In some embodiments, o is 15.

In some embodiments, a provided support after loading of a first nucleoside having the structure of:

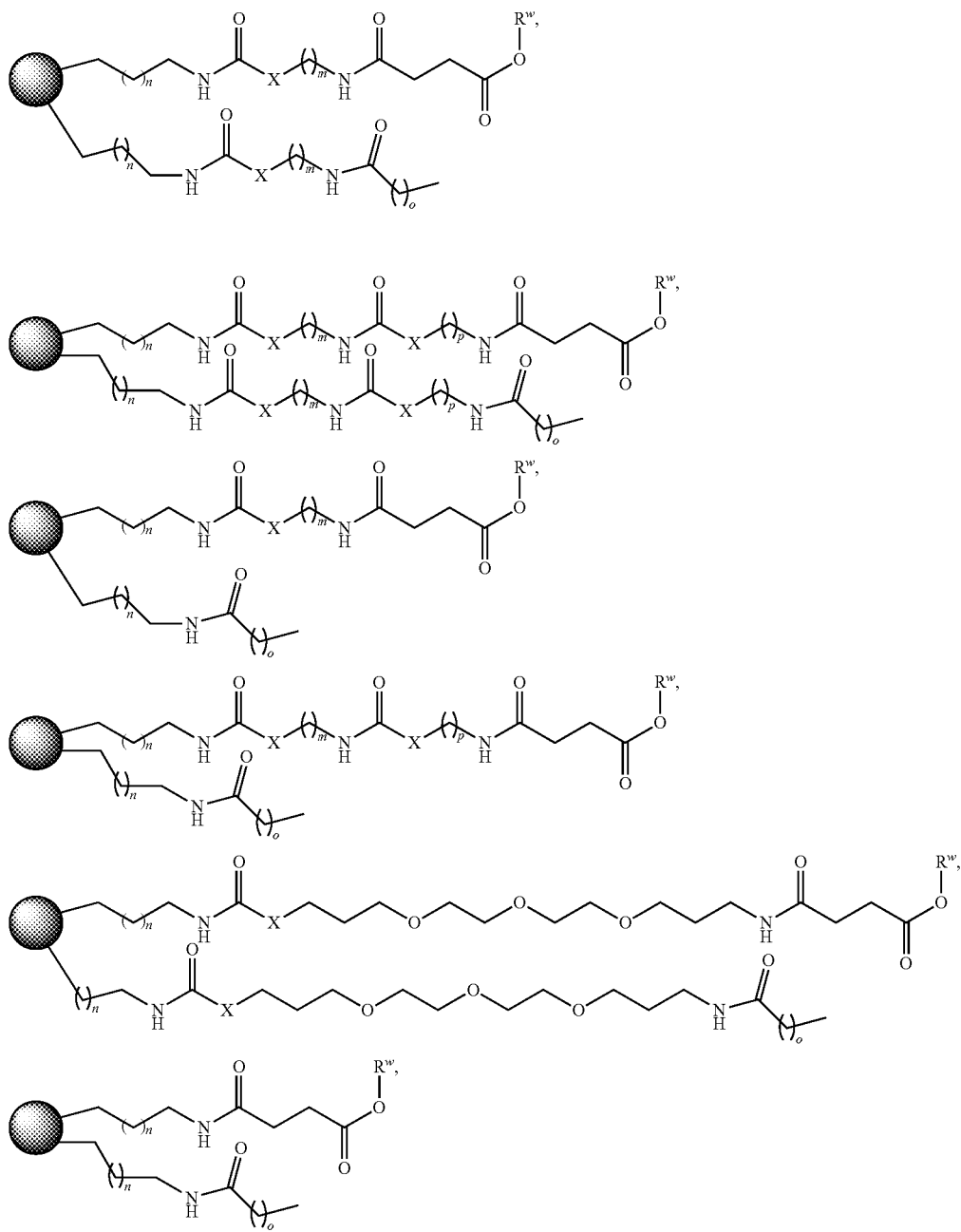

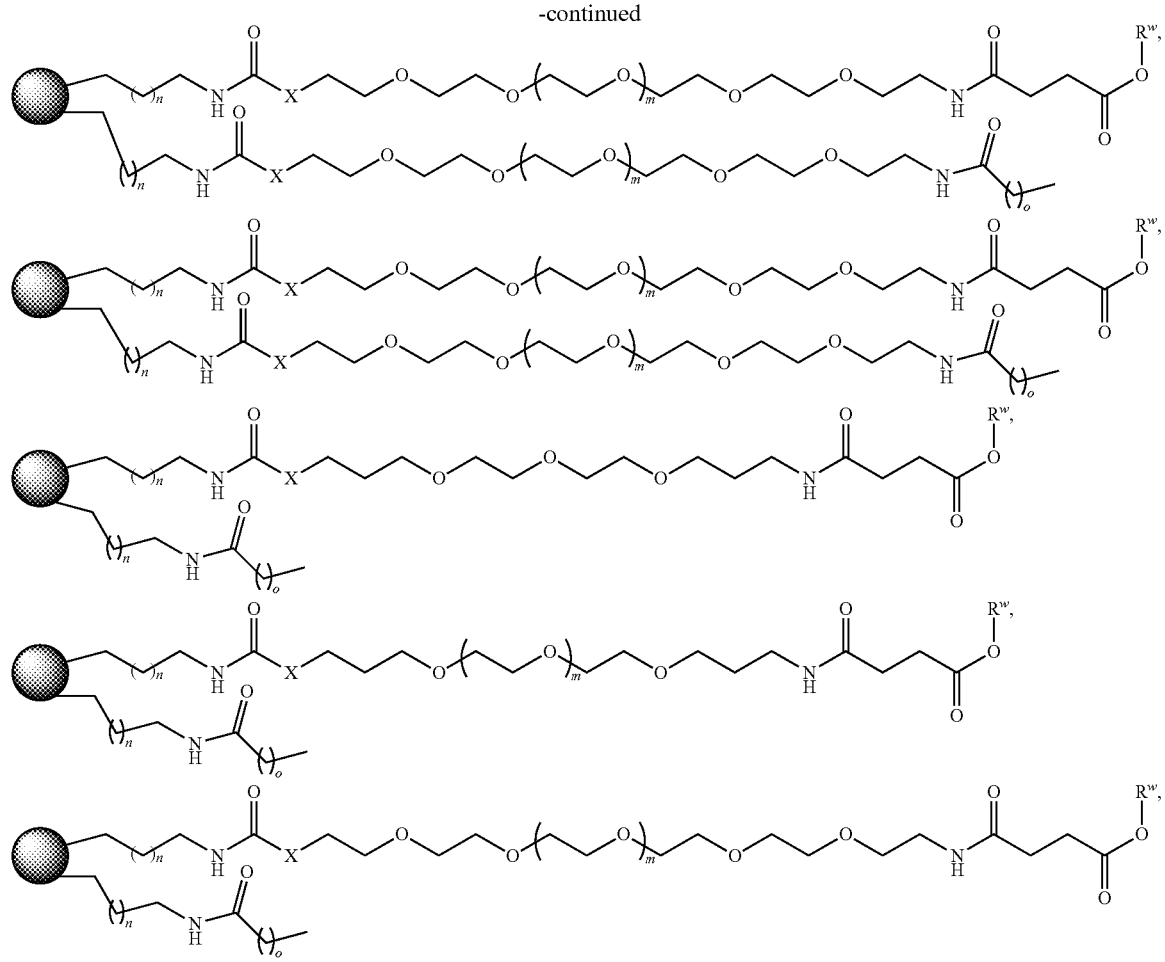

wherein —O—R$^w$ is an nucleoside moiety as described in the present disclosure, ⬤ is a support as described in the present disclosure, and each other variable is independently as described in the present disclosure. In some embodiments, In some embodiments, X is —O—, —S—, —NH—, —CH$_2$—, m is 3-15, n is 1 or 7, o is 0-12, and p is 3-15. In some embodiments, X is —O—, —S—, —NH—, —CH$_2$—, m is 0-10, n is 1 or 7, o is 0-12, and p is 3-15.

In some embodiments, —O—R$^w$ is a nucleoside moiety of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e. In some embodiments, In some embodiments, R$^W$ is

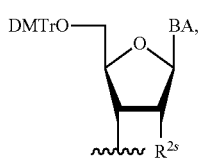

wherein R$^{2s}$ is as described in the present disclosure. In some embodiments, R$^W$ is

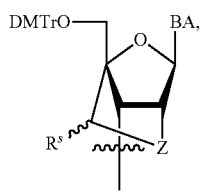

wherein each variable is as described in the present disclosure. In some embodiments, BA is a protected nucleobase selected from A, T, C, U, G and 4 mC. In some embodiments, BA is C(N-4-Ac or Bz), 5-Me-C(N-4-Ac or Bz),U, T, A(N-6-Bz), or G(N-2-iBu), R$^{2s}$ is —OH, —H, —F, —OCH$_3$, or —OCH$_2$CH$_2$OCH$_3$, Z is —O—, —S—, —CH$_2$—, and R$^s$ is —CH$_3$, —OCH$_3$, or —CH$_2$CH$_3$.

In some embodiments, the present disclosure provides technologies to tune properties of support and/or linker, e.g., chemical compatibility, stability, unit loading capacities, distance to solid core, etc. for oligonucleotide synthesis.

Additional example supports and linkers are described in the Examples.

Improved Results

Provided technologies provide a number of advantages. Among other things, as demonstrated in the present disclosure, provided technologies can greatly improve oligonucleotide synthesis crude purity and yield, particularly for modified and/or chirally pure oligonucleotides that provide a number of properties and activities that are critical for therapeutic purposes. With the capability to provide unexpectedly high crude purity and yield for therapeutically important oligonucleotides, provided technologies can significantly reduce manufacturing costs (through, e.g., simplified purification, greatly improved overall yields, etc.). In some embodiments, provided technologies can be readily scaled up to produce oligonucleotides in sufficient quantities and qualities for clinical purposes.

In some embodiments, provided technologies provides improved reagents compatibility. For example, as demonstrated in the present disclosure, provided technologies provide flexibility to use different reagent systems for oxidation and/or sulfurization, particularly for chirally controlled oligonucleotide synthesis.

Among other things, the present disclosure provides oligonucleotide compositions of high crude purity. In some embodiments, the present disclosure provides chirally controlled oligonucleotide composition of high crude purity.

In some embodiments, the present disclosure provides a crude chirally controlled oligonucleotide composition comprising a plurality of oligonucleotides which share:
1) a common base sequence;
2) a common pattern of backbone linkages;
3) common stereochemistry independently at about 1-50 (e.g., about 5-50, about 10-50, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, etc.) chiral internucleotidic linkages ("chirally controlled internucleotidic linkages");
which composition is chirally controlled in that level of the plurality of oligonucleotides in the composition is predetermined.

In some embodiments, the present disclosure provides a crude chirally controlled oligonucleotide composition comprising a plurality of oligonucleotides, wherein oligonucleotides of the plurality are of a particular oligonucleotide type defined by:
1) base sequence;
2) pattern of backbone linkages;
3) pattern of backbone chiral centers; and
4) pattern of backbone phosphorus modifications;
which composition is chirally controlled in that level of the plurality of oligonucleotides in the composition is predetermined.

In some embodiments, the present disclosure provides a crude chirally controlled oligonucleotide composition comprising a plurality of oligonucleotides which share:
1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, the present disclosure provides a crude chirally controlled oligonucleotide composition comprising a plurality of oligonucleotides, wherein:
oligonucleotides of the plurality share the same base sequence;
oligonucleotides of the plurality share the same pattern of backbone linkages; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)$% of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, the present disclosure provides a crude chirally controlled oligonucleotide composition comprising a plurality of oligonucleotides, wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)$% of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

In some embodiments, a provided crude chirally controlled oligonucleotide composition has a crude purity of at least 40%, 45%, 50%, 55%, 60%, 65%, 70%, or 75%. In some embodiments, a crude chirally controlled oligonucleotide composition is cleaved from a support, and before any further purification. In some embodiments, crude chirally controlled oligonucleotide composition is cleaved from a support, after de-salting, and before any further purification. In some embodiments, crude chirally controlled oligonucleotide composition is before any chromatograph or gel purification. In some embodiments, a crude purity is % full-length product. In some embodiments, a crude purity is % full-length product as assessed by LC-UV monitored at UV 260 nm.

In some embodiments, technologies of the present disclosure provide highly efficient oligonucleotide synthesis. In some embodiments, provided technologies are robust, versatile, and flexible (e.g., in terms of yield, purity, reaction conditions, etc.) and can be performed at various scales and/or in parallel (e.g., synthesizing multiple oligonucleotides at the same time (e.g., multiple columns, plate format, microarray, etc.) to provide highly efficient synthesis of multiple oligonucleotides, optionally with control of all structural elements of each oligonucleotide (e.g., chemical modifications of sugars, nucleobases, internucleotidic linkages, etc.; stereochemistry of linkage phosphorus, etc.). In some embodiments, the present disclosure provides technologies for highly efficient preparation of a collection of oligonucleotides, the chemistry and/or stereochemistry of each of which can be individually and independently designed and controlled at each nucleobase, sugar, and/or internucleotidic linkage (e.g., as in chirally controlled oligonucleotide compositions described in the present disclosure). As those skilled in the art appreciate, development of useful oligonucleotides, e.g., oligonucleotides for therapeutic purposes, often comprises assessment of a number of oligonucleotides. The present disclosure, among other things, provides collections of oligonucleotides, in some embodiments, chirally controlled ones, and technologies for preparing such collections. In some embodiments, oligonucleotides, e.g., those of collections of oligonucleotides, are prepared in plate formats for, e.g., storage, screening, etc. In some embodiments, the present disclosure provides technologies for preparing oligonucleotides at various scales, including scales for various formats of plates (e.g., 6, 12, 24, 48, 60, 72, 96, or 384-well plate). In some embodiments, oligonucleotides are provided on microarrays. In some embodiments, the present disclosure provides microarrays of oligonucleotides, each of which is optionally and independently chirally controlled. In some embodiments, the present disclosure provides technologies for synthesizing oligonucleotides on chips to provide oligonucleotide microarrays, with independent control of chemistry and/or stereochemistry of each oligonucleotide if desired. Various microarray technologies (e.g., chips, formats, processes, etc.) can be utilized in accordance with the present disclosure, e.g., those of Twist, Affymetrix, Agilent, etc. Among other things, chemical technologies of the present disclosure (e.g., processes, reagents, conditions, etc.) are robust, versatile, and flexible; in combination with various microarray/chip technologies they are particularly powerful for preparing microarrays of oligonucleotides, e.g., those with chemical modifications and/or stereochemistry control described in the present disclosure. In some embodiments, each oligonucleotide of a provided microarray is independently and optionally chirally controlled. In some embodiments, at least one oligonucleotide of a provided microarray comprises at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5% of the oligonucleotides of a microarray independently comprise at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, each oligonucleotide of a microarray independently comprises at least one chirally controlled internucleotidic linkage. Microarrays are powerful tools for many applications. Among other things, provided microarrays can be utilized in screenings against various types of agents, e.g., proteins, nucleic acids, small molecules. In some embodiments, differential binding to stereochemical motifs and/or patterns of screened agents are assessed. As appreciated by those skilled in the art, oligonucleotide compositions prepared at a certain scale can be optionally and alternatively provided in many formats as desired. In some embodiments, the present disclosure provides technologies that are particularly useful for preparing collections of oligonucleotides at scales, e.g., for various plate and/or microarray formats.

In some embodiments, technologies of the present disclosure provide highly efficient oligonucleotide synthesis. In some embodiments, provided technologies are robust, versatile, and flexible (e.g., in terms of yield, purity, reaction conditions, etc.) and can be performed at various scales and/or in parallel (e.g., synthesizing multiple oligonucleotides at the same time (e.g., multiple columns, plate format, microarray, etc.) to provide highly efficient synthesis of multiple oligonucleotides, optionally with control of all structural elements of each oligonucleotide (e.g., chemical modifications of sugars, nucleobases, internucleotidic linkages, etc.; stereochemistry of linkage phosphorus, etc.). In some embodiments, the present disclosure provides technologies for highly efficient preparation of a collection of oligonucleotides, the chemistry and/or stereochemistry of each of which can be individually and independently designed and controlled at each nucleobase, sugar, and/or internucleotidic linkage (e.g., as in chirally controlled oligonucleotide compositions described in the present disclosure). As those skilled in the art appreciate, development of useful oligonucleotides, e.g., oligonucleotides for therapeutic purposes, often comprises assessment of a number of oligonucleotides. The present disclosure, among other things, provides collections of oligonucleotides, in some embodiments, chirally controlled ones, and technologies for preparing such collections. In some embodiments, oligonucleotides, e.g., those of collections of oligonucleotides, are prepared in plate formats for, e.g., storage, screening, etc. In some embodiments, the present disclosure provides technologies for preparing oligonucleotides at various scales, including scales for various formats of plates (e.g., 6, 12, 24, 48, 60, 72, 96, or 384-well plate). In some embodiments, oligonucleotides are provided on microarrays. In some embodiments, the present disclosure provides microarrays of oligonucleotides, each of which is optionally and independently chirally controlled. In some embodiments, the present disclosure provides technologies for synthesizing oligonucleotides on chips to provide oligonucleotide microarrays, with independent control of chemistry and/or stereochemistry of each oligonucleotide if desired. Various microarray technologies (e.g., chips, formats, processes, etc.) can be utilized in accordance with the present disclosure, e.g., those of Twist, Affymetrix, Agilent, etc. Among other things, chemical technologies of the present disclosure (e.g., processes, reagents, conditions, etc.) are robust, versatile, and flexible; in combination with various microarray/chip technologies they are particularly powerful for preparing microarrays of oligonucleotides, e.g., those with chemical modifications and/or stereochemistry control described in the present disclosure. In some embodiments, each oligonucleotide of a provided microarray is independently and optionally chirally controlled. In some embodiments, at least one oligonucleotide of a provided microarray comprises at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5% of the oligonucleotides of a microarray independently comprise at least one chirally controlled internucleotidic linkage as described herein (e.g., 1, 2, 3, 4, 5, 6, 7, 8, 9, 10, 11, 12, 13, 14, 15, 16, 17, 18, 19, 20, 21, 22, 23, 24, 25 or more; or at least 5%, 10%, 15%, 20%, 25%, 30%, 35%, 40%, 45%, 50%, 55%, 60%, 65%, 70%, 75%, 80%, 85%, 90%, 95% or more of an oligonucleotide; or each chiral internucleotidic linkage is independently chirally controlled). In some embodiments, each oligonucleotide of a microarray independently comprises at least one chirally controlled internucleotidic linkage. Microarrays are powerful tools for many applications. Among other things, provided microarrays can be utilized in screenings against various types of agents, e.g., proteins, nucleic acids, small molecules. In some embodiments, differential binding to stereochemical motifs and/or patterns of screened agents are assessed. As appreciated by those skilled in the art, oligonucleotide compositions prepared at a certain scale can be optionally and alternatively provided in many formats as desired. In some embodiments, the present disclosure provides technologies that are particularly useful for preparing collections of oligonucleotides at scales, e.g., for various plate and/or microarray formats.

In some embodiments, provided technologies are performed at large scale (e.g., at least about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 450, 500, mmol, etc.). In some embodiments, a scale is at least about 10 mmol. In some embodiments, a scale is at least about 20 mmol. In some embodiments, a scale is at least about 30 mmol. In some embodiments, a scale is at least about 40 mmol. In some embodiments, a scale is at least about 50 mmol. In some embodiments, a scale is at least about 75 mmol. In some embodiments, a scale is at least about 100 mmol. In some embodiments, a scale is at least about 125 mmol. In some embodiments, a scale is at least about 150 mmol. In some embodiments, a scale is at least about 200 mmol. In some embodiments, a scale is at least about 250 mmol. In some embodiments, a scale is at least about 300 mmol. In some embodiments, a scale is at least about 350 mmol. In some embodiments, a scale is at least about 400 mmol. In some embodiments, a scale is at least about 450 mmol. In some embodiments, a scale is at least about 500 mmol. In some embodiments, the present disclosure provides technologies that are particularly useful for large scale synthesis. For example, in some embodiments, the present disclosure provides technologies for performing certain procedures that are typically performed off-column in traditional oligonucleotide synthesis, e.g., chiral auxiliary removal, product cleavage, etc. on column, which can significantly simplify operation and/or lower cost.

Synthetic technologies (e.g., methods, reagents, conditions, etc.) and oligonucleotide compositions are compatible with and can be utilized in combination with various technologies for purification, formulation, enrichment, etc. Such technologies are routinely used to process (e.g., to purity, to concentrate, to dilute, to change solvent/buffer for) oligonucleotides (e.g., after cleavage/deprotection; before or after certain purification, etc.). In some embodiments, ultrafiltration is utilized to increase concentration of a product, e.g., an oligonucleotide, to a desired concentration to, e.g., at least 10, 20, 30, 40, 50, 60, 70, 80, 90, or 100 mg/mL. In some embodiments, diafiltration is utilized to remove a salt and/or change solvent for a solution, e.g., an oligonucleotide product solution. In some embodiments, diafiltration maintains product concentration (e.g., oligonucleotide concentration) of a solution subjected to diafiltration, or does not significantly change product concentration (e.g., less than 100%, 90%, 80%, 75%, 70%, 60%, 50%, 40%, 30%, 25%, 20%, 15%, 10%, 5%, 1% decrease; less than 100%, 90%, 80%, 75%, 70%, 60%, 50%, 40%, 30%, 25%, 20%, 15%, 10%, 5%, 1% increase, etc.). In some embodiments, ultrafiltration and/or diafiltration is utilized to formulate a product in its final form, e.g., after chromatography or other purification steps. In some embodiments, ultrafiltration and/or diafiltration is performed after crude product is obtained and certain purification. In some embodiments, it may be desirable to remove one or more component in a crude product (e.g., fluoride, base, etc.) to protect one or more instruments/equipment to extend life, improve results (e.g., yield, purity, etc.), save reagents, and/or lower cost.

Various purification technologies, e.g., chromatography technologies such as various types of HPLC, UPLC, etc., optionally with various of other technologies such as UV, MS, etc., can be utilized in accordance with the present disclosure. In some embodiments, provided technologies comprise one or more HPLC processes. In some embodiments, provided technologies comprise cartridge purification. Various cartridge purification technologies can be utilized in accordance with the present disclosure. For example, in some embodiments, a cartridge purification is a reverse-phase purification. In some embodiments, a cartridge is a C18 cartridge. In some embodiments, a 5'-protection group, such as DMT, is kept on when performing cartridge purification of an oligonucleotide, e.g., when using C18 cartridge purification. Among other things, the present disclosure provides synthesis technologies that are compatible with various purification technologies. For example, in some embodiments, to keep the 5'-DMT protecting group on for C18 cartridge purification, pH of cleavage conditions can be adjusted, in some cases, increased. Those skilled in the art will appreciate that one or more parameters of provided technologies (e.g., reagents, conditions, reaction times, etc.) can be adjusted to achieve desired results in accordance with the present disclosure. An example procedure for preparing oligonucleotides at a scale useful for plate formats is described in Example 5.

Provided products, e.g., various oligonucleotides as described in the present disclosure, can be formulated in various formats as described in the present disclosure. For example, in some embodiments, provided products are lyophilized (with low temperature and/or pressure) and dried. In some embodiments, products are provided as solids, e.g., of oligonucleotides or salts thereof (e.g., sodium salts or other pharmaceutically acceptable salts), as powders, tablets, etc. In some embodiments, products in solid form are dissolved with a desired solvent, e.g., water, a salt solution, a buffer, etc., before administration to a subject. In some embodiments, products are provided as high-concentration solutions, e.g., in water, a salt solution, a buffer (e.g., PBS, DPBS, etc.). As appreciated by those skilled in the art, such high-concentration solutions can be readily diluted by a suitable solvent, e.g., water, a salt solution, a buffer, etc. to a suitable concentration before administration to a subject. Typically products are stored at low temperature. For example, solutions may be frozen at low temperature for storage. In some embodiments, a form of formulation and/or storage process (e.g., ultrafiltration and/or diafiltration and high-concentration solutions) may provide better results than another form of formulation and/or storage process (e.g., lyophilization and solid forms) (e.g., higher purity, shorter time for preparation before administration, etc.)

Among other things, the present disclosure contains a number of variables for, e.g., structures, formulae, etc. Unless otherwise specified, an embodiment for a variable may be optionally combined with embodiments of any other variables.

In some embodiments, $R^1$ is —H, -$L^s$-R, halogen, —CN, —NO$_2$, -$L^s$-Si(R)$_3$, —OR, —SR, or —N(R)$_2$. In some embodiments, $R^1$ is —H. In some embodiments, $R^1$ is -$L^s$-R, wherein each of $L^s$ and R is independently as described in the present disclosure. In some embodiments, $R^1$ is R, for example, an R embodiment as described in the present disclosure. In some embodiments, $R^1$ is halogen. In some embodiments, $R^1$ is —F. In some embodiments, $R^1$ is —Cl. In some embodiments, $R^1$ is —Br. In some embodiments, $R^1$ is —I. In some embodiments, $R^1$ is —CN. In some embodiments, $R^1$ is —NO$_2$. In some embodiments, $R^1$ is -$L^s$-Si(R)$_3$, wherein each of $L^s$ and R is independently as described in the present disclosure. In some embodiments, $R^1$ is —CH$_2$—Si(R)$_3$, wherein the —CH$_2$— group is optionally substituted, and each R is independently as described in the present disclosure. In some embodiments, $R^1$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, at least one R of —Si(R)$_3$ is optionally substituted $C_{1-6}$ alkyl, and at least one R of —Si(R)$_3$ is optionally substituted phenyl. In some embodiments, two R of —Si(R)$_3$ are independently optionally substituted $C_{1-6}$ alkyl, and one R of —Si(R)$_3$ is optionally substituted phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^1$ is —OR, wherein R is as described in the present disclosure. In some embodiments, $R^1$ is —SR wherein R is as described in the present disclosure. In some embodiments, $R^1$ is —N(R)$_2$, wherein each R is independently as described in the present disclosure.

In some embodiments, $R^2$ is —H, -$L^s$-R, halogen, —CN, —NO$_2$, -$L^s$-Si(R)$_3$, —OR, —SR, or —N(R)$_2$. In some embodiments, $R^2$ is —H. In some embodiments, $R^2$ is -$L^s$-R, wherein each of $L^s$ and R is independently as described in the present disclosure. In some embodiments, $R^2$ is R, for example, an R embodiment as described in the present disclosure. In some embodiments, $R^2$ is halogen. In some embodiments, $R^2$ is —F. In some embodiments, $R^2$ is —Cl. In some embodiments, $R^2$ is —Br. In some embodiments, $R^2$ is —I. In some embodiments, $R^2$ is —CN. In some embodiments, $R^2$ is —NO$_2$. In some embodiments, $R^2$ is -$L^s$-Si(R)$_3$, wherein each of $L^s$ and R is independently as described in the present disclosure. In some embodiments, $R^2$ is —CH$_2$—Si(R)$_3$, wherein the —CH$_2$— group is optionally substituted, and each R is independently as described in the present disclosure. In some embodiments, $R^2$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^2$ is —OR, wherein R is as described in the present disclosure. In some embodiments, $R^2$ is —SR wherein R is as described in the present disclosure. In some embodiments, $R^2$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$ and $R^2$ is not hydrogen. In some embodiments, $R^1$ is hydrogen and $R^2$ is not hydrogen. In some embodiments, $R^1$ is not hydrogen and $R^2$ is hydrogen. In some embodiments, neither of $R^1$ and $R^2$ is hydrogen.

In some embodiments, one of $R^1$ and $R^2$ is —H, and the other is R, wherein R is as described in the present disclosure and is not hydrogen. In some embodiments, one of $R^1$ and $R^2$ is —H, and the other is R, wherein R is optionally substituted $C_{1-6}$ aliphatic as described in the present disclosure. In some embodiments, one of $R^1$ and $R^2$ is —H, and the other is R, wherein R is optionally substituted $C_{1-4}$ aliphatic. In some embodiments, one of $R^1$ and $R^2$ is —H, and the other is R, wherein R is optionally substituted $C_{1-3}$ aliphatic. In some embodiments, one of $R^1$ and $R^2$ is —H, and the other is R, wherein R is optionally substituted $C_{1-2}$ aliphatic. In some embodiments, one of $R^1$ and $R^2$ is —H, and the other is R, wherein R is optionally substituted $C_{1-6}$ alkenyl. In some embodiments, one of $R^1$ and $R^2$ is —H, and the other R, wherein R is vinyl. In some embodiments, one of $R^1$ and $R^2$ is —H, and the other is R, wherein R is optionally substituted $C_{1-6}$ alkynyl. In some embodiments, one of $R^1$ and $R^2$ is —H, and the other is R, wherein R is ethynyl. In some embodiments, one of $R^1$ and $R^2$ is —H, and the other is R, wherein R is optionally substituted benzyl. In some embodiments, one of $R^1$ and $R^2$ is —H, and the other is R, wherein R is benzyl wherein the phenyl group of the benzyl is optionally substituted. In some embodiments, $R^1$ is —H and $R^2$ is benzyl. In some embodiments, a provided compound is

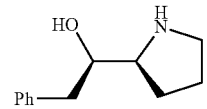 [SMILES: O[C@H](Cc1ccccc1)[C@@H]1CCCN1]

or a salt thereof. In some embodiments, a provided compound is a diastereomer of

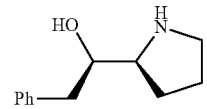 [SMILES: O[C@H](Cc1ccccc1)[C@@H]1CCCN1]

or a salt thereof. In some embodiments, a provided compound is an enantiomer of

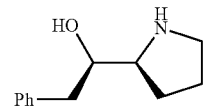 [SMILES: O[C@H](Cc1ccccc1)[C@@H]1CCCN1]

or a salt thereof.

In some embodiments, one of $R^1$ and $R^2$ is R, wherein R is as described in the present disclosure and comprises a ring moiety. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, sulfur, phosphorus and silicon. In some embodiments, R is an optionally substituted group selected from $C_{3-20}$ cycloaliphatic, $C_{6-20}$ aryl, 5-20 membered heteroaryl having 1-5 heteroatoms, and 3-20 membered heterocyclyl having 1-5 heteroatoms, wherein each heteroatom is independently selected from nitrogen, oxygen, and sulfur. In some embodiments, R is optionally substituted $C_{3-20}$ cycloaliphatic. In some embodiments, R is optionally substituted $C_{3-10}$ cycloaliphatic. In some embodiments, R is optionally substituted $C_{3-10}$ cycloalkyl. In some embodiments, R is optionally substituted $C_{4-10}$ cycloalkyl. In some embodiments, R is optionally substituted cyclopropyl. In some embodiments, R is optionally substituted cyclobutyl. In some embodiments, R is optionally substituted cyclopentyl. In some embodiments, R is optionally substituted cyclohexyl. In some embodiments, R is optionally substituted cycloheptyl. In some embodiments, R is cyclopropyl. In some embodiments, R is cyclobutyl. In some embodiments, R is cyclopentyl. In some embodiments, R is cyclohexyl. In some embodiments, R is cycloheptyl. In some embodiments, R is optionally substituted $C_{6-20}$ aryl. In some embodiments, R is optionally substituted phenyl. In some embodiments, R is phenyl. In some embodiments, R is optionally substituted 5-20 membered heteroaryl having 1-5 heteroatoms. In some embodiments, R is optionally substituted 5-membered heteroaryl having 1-5 heteroatoms. In some embodiments, R is optionally substituted 6-membered heteroaryl having 1-5 heteroatoms. In some embodiments, R is optionally substituted 3-20 membered heterocyclyl having 1-5 heteroatoms. In some embodiments, the other of $R^1$ and $R^2$ is R wherein R is not hydrogen. In some embodiments, R is optionally substituted $C_{1-6}$ aliphatic. In some embodiments, R is optionally substituted $C_{1-6}$ alkyl. In some embodiments, R is $C_{1-6}$ alkyl. In some embodiments, R is methyl. In some embodiments, R is substituted methyl. In some embodiments, R is ethyl. In some embodiments, R is substituted ethyl. In some embodiments, one of $R^1$ and $R^2$ is R comprising a cyclic moiety as described in the present disclosure, and the other is an alkyl group as described in the present disclosure.

In some embodiments, one of $R^1$ and $R^2$ is R, wherein R is optionally substituted $C_{1-6}$ alkyl, and the other is R, wherein R is optionally substituted $C_{1-6}$ alkenyl. In some embodiments, one of $R^1$ and $R^2$ is optionally substituted methyl or ethyl, and the other is vinyl. In some embodiments, one of $R^1$ and $R^2$ is methyl, and the other is vinyl.

In some embodiments, one of $R^1$ and $R^2$ is R, wherein R is optionally substituted $C_{1-6}$ alkyl, and the other is R, wherein R is optionally substituted $C_{1-6}$ alkynyl. In some embodiments, one of $R^1$ and $R^2$ is optionally substituted methyl or ethyl, and the other is ethynyl. In some embodiments, one of $R^1$ and $R^2$ is methyl, and the other is ethynyl.

In some embodiments, each of $R^1$ and $R^2$ is independently R, wherein R is optionally substituted $C_{1-20}$ aliphatic. In some embodiments, R is unsubstituted $C_{1-20}$ aliphatic. In some embodiments, R is optionally substituted $C_{1-20}$ alkyl. In some embodiments, R is optionally substituted $C_{1-6}$ alkyl. In some embodiments, R is linear $C_{1-6}$ alkyl. In some embodiments, one of $R^1$ and $R^2$ is optionally substituted $C_{1-6}$ alkyl, and the other is optionally substituted $C_{1-6}$ alkyl. In some embodiments, $R^1$ and $R^2$ are the same. In some embodiments, $R^1$ and $R^2$ are different.

In some embodiments, each of $R^1$ and $R^2$ is independently R, wherein R is optionally substituted $C_{1-6}$ alkyl. In some embodiments, $R^1$ and $R^2$ are the same. Among other things, the present disclosure demonstrates that compounds with $R^1$ and $R^2$ being the same, or phosphoramidites prepared therefrom, can deliver high stereoselectivity, yields and/or purity when utilized in chirally controlled oligonucleotide preparation. In some embodiments, $R^1$ and $R^2$ are the same optionally substituted $C_{1-2}$ alkyl, and $R^1$ and $R^2$ comprise no more than two carbon atoms. In some embodiments, both $R^1$ and $R^1$ are methyl. In some embodiments, both $R^1$ and $R^1$ are ethyl. In some embodiments, both $R^1$ and $R^1$ are isopropyl.

In some embodiments, one of $R^1$ and $R^2$ is optionally substituted $C_{1-3}$ linear alkyl, and the other is optionally substituted $C_{3-10}$ cycloalkyl. In some embodiments, one of $R^1$ and $R^2$ is optionally substituted $C_{1-3}$ linear alkyl, and the other is optionally substituted $C_{5-6}$ cycloalkyl. In some embodiments, $R^1$ is methyl. In some embodiments, $R^2$ is cyclopentyl. In some embodiments, $R^2$ is cyclohexyl. In some embodiments, one of $R^1$ and $R^2$ is optionally substituted $C_{1-3}$ linear alkyl, and the other is optionally substituted benzyl. In some embodiments, $R^1$ is methyl and $R^2$ is optionally substituted benzyl. In some embodiments, $R^2$ is benzyl. In some embodiments, $R^2$ is p-$CH_3O$—$C_6H_4$—$CH_2$—. In some embodiments, $R^1$ is selected from methyl, ethyl, cyclohexyl, and benzyl which is optionally substituted at the phenyl. In some embodiments, $R^2$ is selected from methyl, ethyl, cyclohexyl, and benzyl which is optionally substituted at the phenyl. In some embodiments, each of $R^1$ and $R^2$ is independently selected from methyl, ethyl, cyclohexyl, and benzyl which is optionally substituted at the phenyl.

In some embodiments, a provided compound is

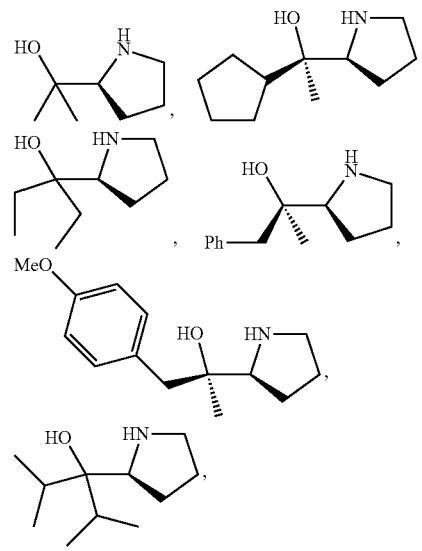

or a salt thereof. In some embodiments, a provided compound is a diastereomer of

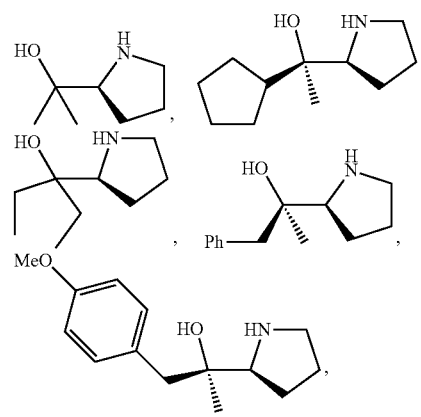

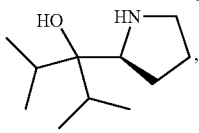
, or a salt thereof. In some embodiments, a provided compound is an enantiomer of

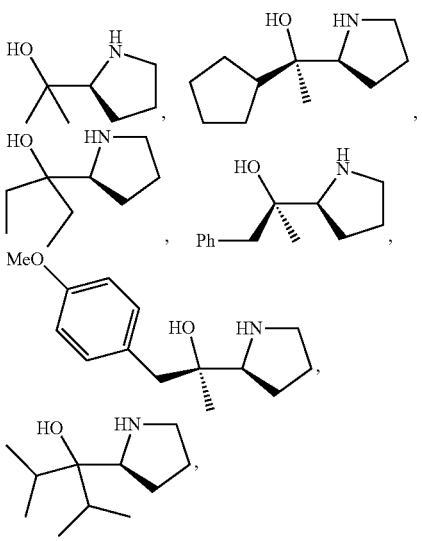

or a salt thereof. In some embodiments, a provided compound is a diastereomer of

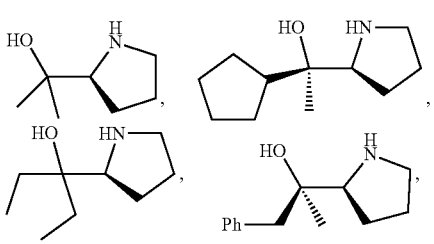

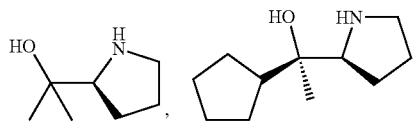
, or a salt thereof. In some embodiments, a provided compound is an enantiomer of

or a salt thereof. In some embodiments, a provided compound is

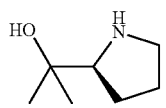

or a salt thereof. In some embodiments, a provided compound is

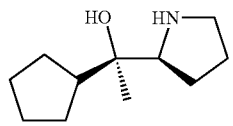

or a salt thereof. In some embodiments, a provided compound is

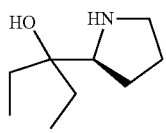

or a salt thereof. In some embodiments, a provided compound is

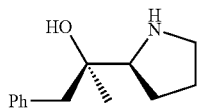

or a salt thereof. In some embodiments, a provided compound is

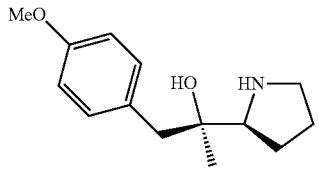

or a salt thereof. In some embodiments, a provided compound is

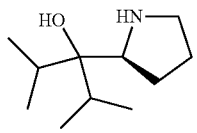

or a salt thereof. In some embodiments, a provided compound is a diastereomer of

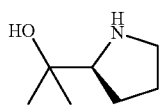

or a salt thereof. In some embodiments, a provided compound is a diastereomer of

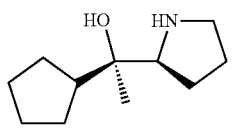

or a salt thereof. In some embodiments, a provided compound is a diastereomer of

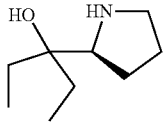

or a salt thereof. In some embodiments, a provided compound is a diastereomer of

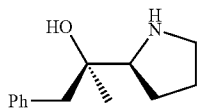

or a salt thereof. In some embodiments, a provided compound is a diastereomer of

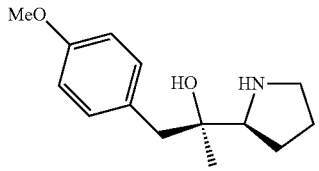 [SMILES: COc1ccc(C[C@@](C)(O)[C@@H]2CCCN2)cc1]

or a salt thereof. In some embodiments, a provided compound is a diastereomer of

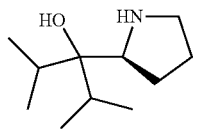

or a salt thereof. In some embodiments, a provided compound is an enantiomer of

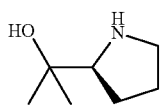

or a salt thereof. In some embodiments, a provided compound is an enantiomer of

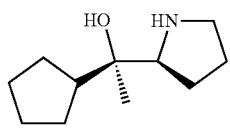

or a salt thereof. In some embodiments, a provided compound is an enantiomer of

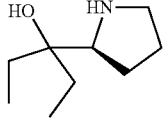

or a salt thereof. In some embodiments, a provided compound is an enantiomer of

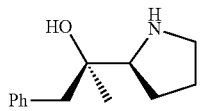

or a salt thereof. In some embodiments, a provided compound is an enantiomer of

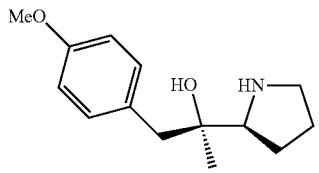 [SMILES: COc1ccc(C[C@@](C)(O)[C@@H]2CCCN2)cc1]

or a salt thereof. In some embodiments, a provided compound is an enantiomer of

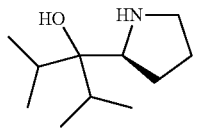

or a salt thereof.

In some embodiments, one of $R^1$ and $R^2$ is R, wherein R is optionally substituted $C_{1-6}$ alkyl, and the other is R, wherein R is an optionally substituted group selected from $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, one of $R^1$ and $R^2$ is R, wherein R is optionally substituted $C_{1-6}$ alkyl, and the other is R, wherein R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is an optionally substituted group selected from $C_{6-20}$ aryl, and 5-20 membered heteroaryl having 1-10 heteroatoms independently selected from oxygen, nitrogen, and sulfur. In some embodiments, one of $R^1$ and $R^2$ is R, wherein R is optionally substituted $C_{1-6}$ alkyl, and the other is R, wherein R is optionally substituted $C_{6-20}$ aryl. In some embodiments, one of $R^1$ and $R^2$ is R, wherein R is optionally substituted $C_{1-6}$ alkyl, and the other is R, wherein R is optionally substituted phenyl. In some embodiments, R as optionally substituted $C_{1-6}$ alkyl is methyl. In some embodiments, R as optionally substituted phenyl is

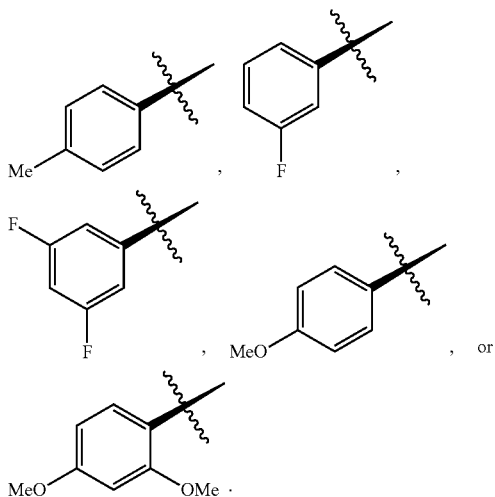

In some embodiments, $R^1$ is methyl, and $R^2$ is optionally substituted phenyl. In some embodiments, $R^1$ is methyl, and $R^2$ is phenyl. In some embodiments, $R^1$ is methyl, and $R^2$ is

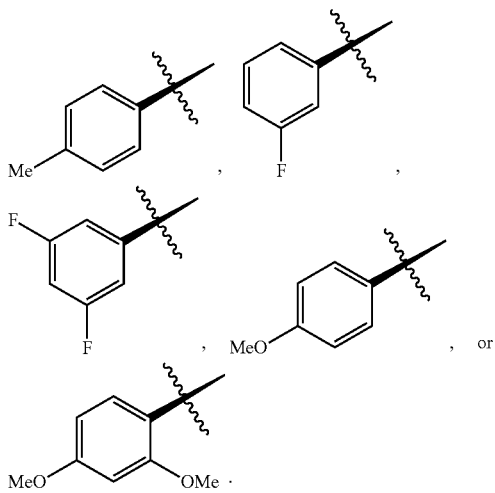

In some embodiments, a provided compound is selected from

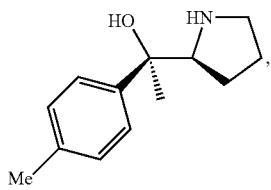

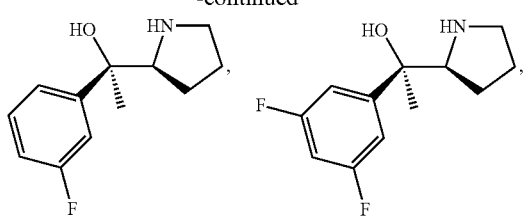

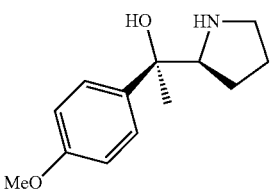

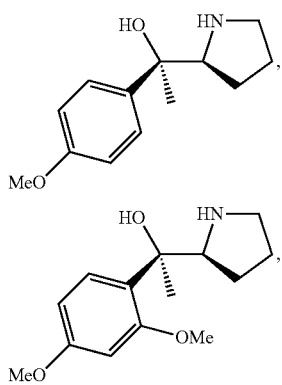

or salts thereof. In some embodiments, a provided compound is

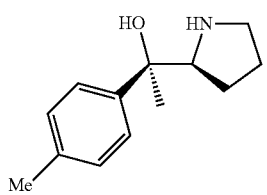

or a salt thereof. In some embodiments, a provided compound is

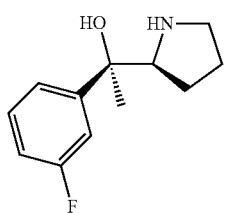

or a salt thereof. In some embodiments, a provided compound is

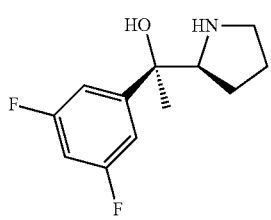

or a salt thereof. In some embodiments, a provided compound is

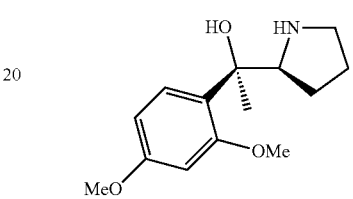

or a salt thereof. In some embodiments, a provided compound is

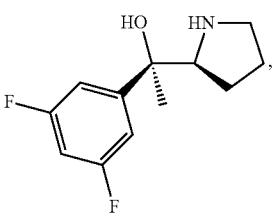

or a salt thereof. In some embodiments, a provided compound is a diastereomer of

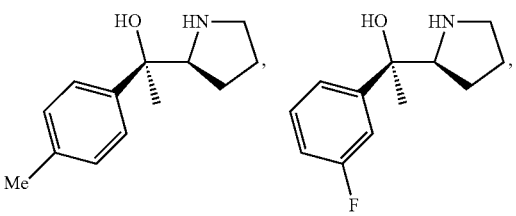

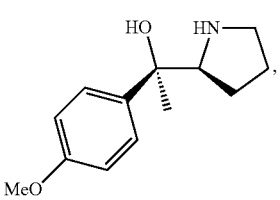

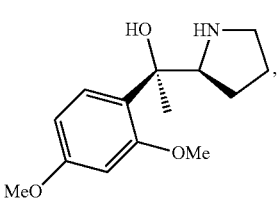

or a salt thereof. In some embodiments, a provided compound is a diastereomer of

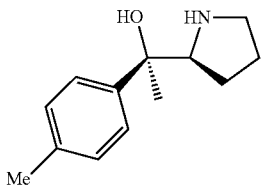

or a salt thereof. In some embodiments, a provided compound is a diastereomer of

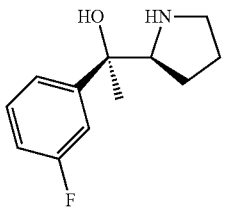

or a salt thereof. In some embodiments, a provided compound is a diastereomer of

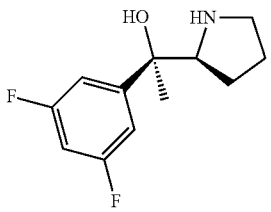 [SMILES: C[C@@](O)(c1cc(F)cc(F)c1)[C@@H]1CCCN1]

or a salt thereof. In some embodiments, a provided compound is a diastereomer of

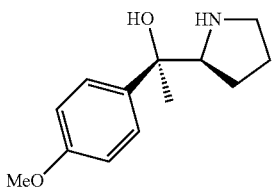 [SMILES: COc1ccc([C@@](C)(O)[C@@H]2CCCN2)cc1]

or a salt thereof. In some embodiments, a provided compound is a diastereomer of

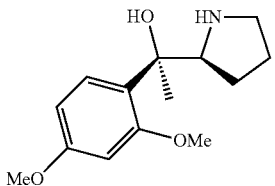 [SMILES: COc1ccc([C@@](C)(O)[C@@H]2CCCN2)c(OC)c1]

or a salt thereof. In some embodiments, a provided compound is an enantiomer of

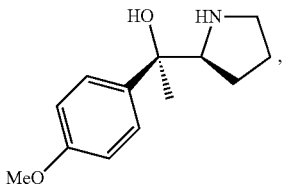

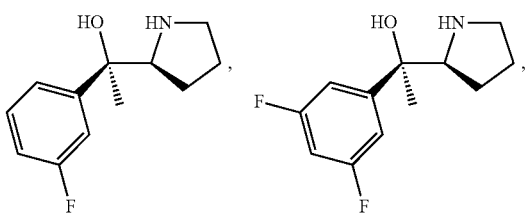

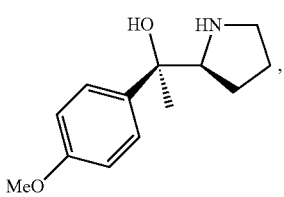

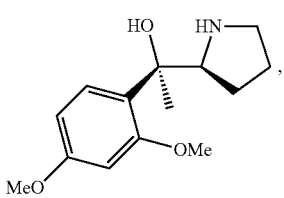

or a salt thereof. In some embodiments, a provided compound is an enantiomer of

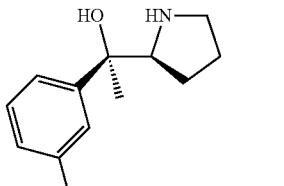

or a salt thereof. In some embodiments, a provided compound is an enantiomer of

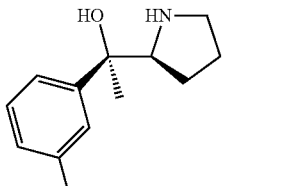

or a salt thereof. In some embodiments, a provided compound is an enantiomer of

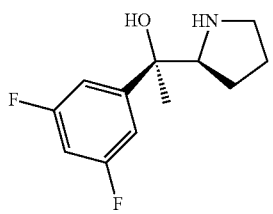 [SMILES: C[C@@](O)(c1cc(F)cc(F)c1)[C@@H]1CCCN1]

or a salt thereof. In some embodiments, a provided compound is an enantiomer of

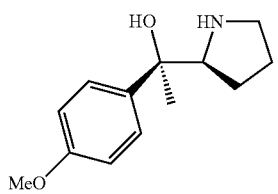 [SMILES: COc1ccc([C@@](C)(O)[C@@H]2CCCN2)cc1]

or a salt thereof. In some embodiments, a provided compound is an enantiomer of

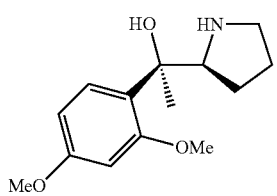 [SMILES: COc1ccc([C@@](C)(O)[C@@H]2CCCN2)c(OC)c1]

or a salt thereof.

In some embodiments, $R^1$ and $R^2$ are independently R, wherein R is as described in the present disclosure. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is an optionally substituted group selected from $C_{3-20}$ cycloaliphatic, $C_{6-20}$ aryl, 5-20 membered heteroaryl having 1-10 heteroatoms independently selected from oxygen, nitrogen, and sulfur, and 3-20 membered heterocyclyl having 1-10 heteroatoms independently selected from oxygen, nitrogen, and sulfur. In some embodiments, R is an optionally substituted group selected from $C_{3-20}$ cycloaliphatic, and 3-20 membered heterocyclyl having 1-10 heteroatoms independently selected from oxygen, nitrogen, sulfur, phosphorus and silicon. In some embodiments, R is an optionally substituted group selected from $C_{6-20}$ aryl, and 5-20 membered heteroaryl having 1-10 heteroatoms independently selected from oxygen, nitrogen, sulfur, phosphorus and silicon. In some embodiments, R is an optionally substituted group selected from $C_{3-20}$ cycloaliphatic and $C_{6-20}$ aryl. In some embodiments, R is an optionally substituted group selected from 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon. In some embodiments, R is optionally substituted $C_{3-20}$ cycloaliphatic. In some embodiments, R is optionally substituted $C_{3-20}$ cycloalkyl. In some embodiments, R is optionally substituted $C_{1-20}$ heteroaliphatic having 1-10 heteroatoms independently selected from oxygen, nitrogen, sulfur, phosphorus and silicon. In some embodiments, R is optionally substituted $C_{6-20}$ aryl. In some embodiments, R is optionally substituted 5-20 membered heteroaryl having 1-10 heteroatoms independently selected from oxygen, nitrogen, sulfur, phosphorus and silicon. In some embodiments, R is optionally substituted 3-20 membered heterocyclyl having 1-10 heteroatoms independently selected from oxygen, nitrogen, sulfur, phosphorus and silicon. In some embodiments, R is optionally substituted phenyl. In some embodiments, R is phenyl. In some embodiments, $R^1$ and $R^2$ are optionally substituted phenyl. In some embodiments, $R^1$ and $R^2$ are phenyl. In some embodiments, a provided compound is

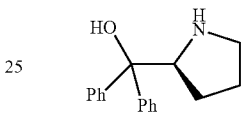

or a salt thereof. In some embodiments, a provided compound is a diastereomer of

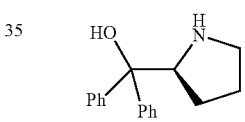

or a salt thereof. In some embodiments, a provided compound is an enantiomer of

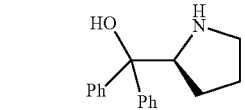

or a salt thereof.

In some embodiments, the carbon atom to which $R^1$ and $R^2$ are attached is not chiral. In some embodiments, $R^1$ and $R^2$ are the same. In some embodiments, $R^1$ and $R^2$ are the same and neither are hydrogen. In some embodiments, $R^1$ and $R^2$ are methyl. In some embodiments, $R^1$ and $R^2$ are ethyl. In some embodiments, $R^1$ and $R^2$ are optionally substituted phenyl. In some embodiments, $R^1$ and $R^2$ are phenyl. In some embodiments, $R^1$ and $R^2$ are R, wherein the two R groups are taken together to form an optionally substituted ring as described in the present disclosure. In some embodiments, a formed ring does not contain any chiral elements. In some embodiments, a formed ring is an optionally substituted 5-membered cycloaliphatic ring. In some embodiments, a formed ring is optionally substituted In some embodiments, a formed ring is

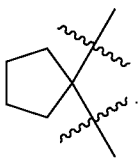 [SMILES: *C1(*)CCCC1]

In some embodiments, a formed ring is optionally substituted

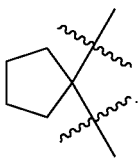 [SMILES: *C1(*)CCCC1]

In some embodiments, a formed ring is

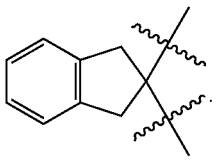 [SMILES: *C1(*)Cc2ccccc2C1]

In some embodiments, a formed ring is

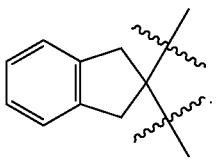 [SMILES: *C1(*)Cc2ccccc2C1]

In some embodiments, a formed ring is an optionally substituted 6-membered cycloaliphatic ring. In some embodiments, a formed ring is optionally substituted

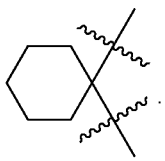 [SMILES: *C1(*)CCCCC1]

In some embodiments, a formed ring is

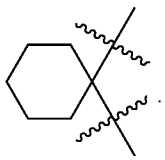 [SMILES: *C1(*)CCCCC1]

Among other things, the present disclosure demonstrated that provided compounds in which the carbon atom to which $R^1$ and $R^2$ are attached is not chiral can provide surprisingly high stereoselectivity when they are used in chirally controlled oligonucleotide synthesis. In some embodiments, such compounds provides high yields.

In some embodiments, $R^3$ is —H, $-L^s$-R, halogen, —CN, —NO$_2$, $-L^s$-Si(R)$_3$, —OR, —SR, or —N(R)$_2$. In some embodiments, $R^3$ is —H. In some embodiments, $R^3$ is $-L^s$-R, wherein each of $L^s$ and R is independently as described in the present disclosure. In some embodiments, $R^3$ is R, for example, an R embodiment as described in the present disclosure. In some embodiments, $R^3$ is halogen. In some embodiments, $R^3$ is —F. In some embodiments, $R^3$ is —Cl. In some embodiments, $R^3$ is —Br. In some embodiments, $R^3$ is —I. In some embodiments, $R^3$ is —CN. In some embodiments, $R^3$ is —NO$_2$. In some embodiments, $R^3$ is $-L^s$-Si(R)$_3$, wherein each of $L^s$ and R is independently as described in the present disclosure. In some embodiments, $R^3$ is —CH$_2$—Si(R)$_3$, wherein the —CH$_2$— group is optionally substituted, and each R is independently as described in the present disclosure. In some embodiments, $R^3$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from C$_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^3$ is —OR, wherein R is as described in the present disclosure. In some embodiments, $R^3$ is —SR wherein R is as described in the present disclosure. In some embodiments, $R^3$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, $R^4$ is —H, $-L^s$-R, halogen, —CN, —NO$_2$, $-L^s$-Si(R)$_3$, —OR, —SR, or —N(R)$_2$. In some embodiments, $R^4$ is —H. In some embodiments, $R^4$ is $-L^s$-R, wherein each of $L^s$ and R is independently as described in the present disclosure. In some embodiments, $R^4$ is R, for example, an R embodiment as described in the present disclosure. In some embodiments, $R^4$ is halogen. In some embodiments, $R^4$ is —F. In some embodiments, $R^4$ is —Cl. In some embodiments, $R^4$ is —Br. In some embodiments, $R^4$ is —I. In some embodiments, $R^4$ is —CN. In some embodiments, $R^4$ is —NO$_2$. In some embodiments, $R^4$ is $-L^s$-Si(R)$_3$, wherein each of $L^s$ and R is independently as described in the present disclosure. In some embodiments, $R^4$ is —CH$_2$—Si(R)$_3$, wherein the —CH$_2$— group is optionally substituted, and each R is independently as described in the present disclosure. In some embodiments, $R^4$ is —CH$_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from C$_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^4$ is —OR, wherein R is as described in the present disclosure. In some embodiments, $R^4$ is —SR wherein R is as described in the present disclosure. In some embodiments, $R^4$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, at least one of $R^1$, $R^2$, $R^3$ and $R^4$ is not —H. In some embodiments, a provided compound of formula I, I-a, I-a-1, I-a-2, I-b, I-c, I-d, or I-e comprises one or more chiral elements. In some embodiments, $R^3$ and $R^4$ are not —H, and the carbon to which they are attached is a chiral center. In some embodiments, at least one of $R^1$ and $R^2$ is not hydrogen, and $R^1$ and $R^2$ are different, and the carbon to which they are attached is a chiral center. In some embodiments, at least one of $R^1$ and $R^2$ is not hydrogen, and $R^1$ and $R^2$ are the same, and the carbon to which they are attached is not a chiral center. Among other things, the present disclosure demonstrates that provided compounds, in which the carbon atoms to which $R^1$ and $R^2$ are attached are not chiral, can deliver surprisingly high stereoselectivity when used as chiral auxiliaries in oligonucleotide synthesis.

In some embodiments, $R^5$ is —H, -$L^s$-R, halogen, —CN, —$NO_2$, -$L^s$-Si(R)$_3$, —OR, —SR, or —N(R)$_2$. In some embodiments, $R^5$ is —H. In some embodiments, $R^5$ is -$L^s$-R, wherein each of $L^s$ and R is independently as described in the present disclosure. In some embodiments, $R^5$ is R, for example, an R embodiment as described in the present disclosure. In some embodiments, $R^5$ is halogen. In some embodiments, $R^5$ is —F. In some embodiments, $R^5$ is —Cl. In some embodiments, $R^5$ is —Br. In some embodiments, $R^5$ is —I. In some embodiments, $R^5$ is —CN. In some embodiments, $R^5$ is —$NO_2$. In some embodiments, $R^5$ is -$L^s$-Si(R)$_3$, wherein each of $L^s$ and R is independently as described in the present disclosure. In some embodiments, $R^5$ is —$CH_2$—Si(R)$_3$, wherein the —$CH_2$— group is optionally substituted, and each R is independently as described in the present disclosure. In some embodiments, $R^5$ is —$CH_2$—Si(R)$_3$, wherein each R is independently as described in the present disclosure. In some embodiments, each R of —Si(R)$_3$ is not —H. In some embodiments, each R of —Si(R)$_3$ is independently an optionally substituted group selected from $C_{1-6}$ alkyl and phenyl. In some embodiments, —Si(R)$_3$ is —Si(Ph)$_2$Me. Other non-hydrogen embodiments of R are extensively described in the present disclosure and may be used in —Si(R)$_3$. In some embodiments, $R^5$ is —OR, wherein R is as described in the present disclosure. In some embodiments, $R^5$ is —SR wherein R is as described in the present disclosure. In some embodiments, $R^5$ is —N(R)$_2$, wherein each R is independently as described in the present disclosure. In some embodiments, $R^2$ is the same or different from $R^1$, and is a group selected from any groups described for $R^1$ in the present disclosure.

In some embodiments, $R^5$, and one or both of $R^1$ and $R^2$, are R and are taken together with their intervening atoms to form an optionally substituted, 3-20 membered monocyclic, bicyclic or polycyclic ring having 1-5 heteroatoms. In some embodiments, $R^5$ and $R^1$ are R and are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R and are taken together with their intervening atoms to form an optionally substituted, 3-20 membered monocyclic, bicyclic or polycyclic ring having 1-5 heteroatoms. As extensively described in the present disclosure, a formed ring by two R groups taken together can be of various sizes, monocyclic, bicyclic or polycyclic, and contain various numbers of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a formed ring contains no ring heteroatom in addition to the nitrogen to which $R^5$ is attached. In some embodiments, a ring is a saturated ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, two or more of $R^1$, $R^2$, $R^3$, $R^4$, and $R^5$ are independently R, and the R groups are optionally and independently taken together to form rings as described in the present disclosure. In some embodiments, $R^1$ and $R^2$ are R, and the two R groups are taken together to form an optionally substituted ring as described in the present disclosure. In some embodiments, one of $R^1$ and $R^2$, and one of $R^3$ and $R^4$, are R, and the two R groups are taken together to form an optionally substituted ring as described in the present disclosure. In some embodiments, one of $R^3$ and $R^4$, and $R^5$, are R, and the two R groups are taken together to form an optionally substituted ring as described in the present disclosure.

In some embodiments, a formed ring, e.g., by $R^1$ and $R^2$, or one of $R^1$ and $R^2$ and one of $R^3$ and $R^4$, is an optionally substituted 3-20 membered monocyclic, bicyclic or polycyclic ring having 0-5 heteroatoms. In some embodiments, a formed ring is monocyclic. In some embodiments, a formed ring is bicyclic. In some embodiments, a formed ring is polycyclic. In some embodiments, a formed ring is aliphatic. In some embodiments, a formed ring comprises no unsaturation. In some embodiments, a formed ring is partially unsaturated. In some embodiments, a formed ring comprises one or more saturated monocyclic ring moieties. In some embodiments, a formed ring comprises one or more monocyclic partially unsaturated ring moieties. In some embodiments, a formed ring comprises one or more monocyclic aromatic ring moieties. In some embodiments, a formed ring comprises one or more saturated, partially unsaturated, and/or aromatic ring moieties, for example, a bicyclic or polycyclic ring comprising fused saturated, partially unsaturated, and/or aromatic monocyclic moieties. In some embodiments, a formed ring is optionally substituted. In some embodiments, a formed ring is substituted. In some embodiments, a formed ring is not substituted. In some embodiments, a formed ring comprises no chiral elements. In some embodiments, a formed ring comprises one or more chiral elements. In some embodiments, a formed ring comprises one or more chiral elements and is chiral. In some embodiments, a chiral element is a chiral center. In some embodiments, a formed ring is an optionally substituted 3-10 membered monocyclic ring having no heteroatoms. In some embodiments, a formed monocyclic ring is 3-membered; in some embodiments, 4-membered; in some embodiments, 5-membered; in some embodiments, 6-membered; in some embodiments 7-membered; in some embodiments, 8-membered; in some embodiments 9-membered; and in some embodiments 10-membered. In some embodiments, a formed ring is a 3-membered saturated cycloaliphatic ring. In some embodiments, a formed ring is an optionally substituted 5-membered saturated cycloaliphatic ring. In some embodiments, a formed ring is an optionally substituted 5-membered saturated cycloaliphatic ring containing no chiral elements. In some embodiments, a formed ring is an unsubstituted 5-membered saturated cycloaliphatic ring containing no chiral elements. In some embodiments, a 5-membered ring described herein is fused to another optionally substituted ring, which can be saturated, partially unsaturated or aryl. In some embodiments, a 5-membered ring described herein is fused to an optionally substituted aryl ring. In some embodiments, a 5-membered ring described herein is fused to an optionally substituted phenyl ring. In some embodiments, a 5-membered ring described herein is fused to a phenyl ring. In some embodiments, fusion is at C3 and C4 (C1 being the carbon atom to which $R^1$ and $R^2$ are attached). In some embodiments, a formed ring is optionally substituted

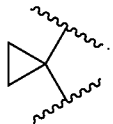

In some embodiments, a formed ring is

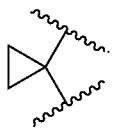

In some embodiments, a formed ring is optionally substituted

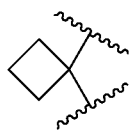

In some embodiments, a formed ring is

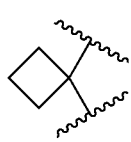

In some embodiments, a formed ring is optionally substituted

In some embodiments, a formed ring is

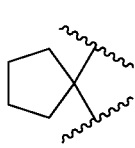

In some embodiments, a formed ring is optionally substituted

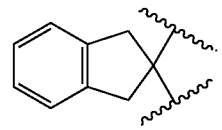 [SMILES: *C1(*)Cc2ccccc2C1]

In some embodiments, a formed ring is

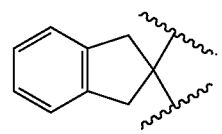 [SMILES: *C1(*)Cc2ccccc2C1]

In some embodiments, a formed ring is an optionally substituted 6-membered saturated cycloaliphatic ring. In some embodiments, a formed ring is an optionally substituted 6-membered saturated cycloaliphatic ring containing no chiral elements. In some embodiments, a formed ring is an unsubstituted 6-membered saturated cycloaliphatic ring containing no chiral elements. In some embodiments, one or more ring moieties may be fused to the 6-membered ring, for example, as described above for the 5-membered ring. Ring embodiments described herein are applicable to other variables two of which can be R and can be taken together to form an optionally substituted ring. In some embodiments, a formed ring is optionally substituted

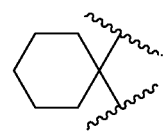

In some embodiments, a formed ring is

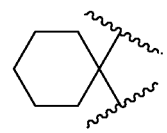 [SMILES: *C1(*)CCCCC1]

In some embodiments, a provided compound is

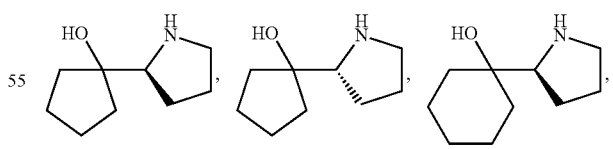

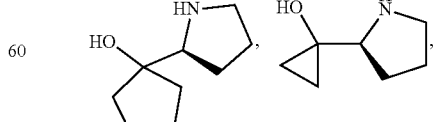

or a salt thereof. In some embodiments, a provided compound is selected from

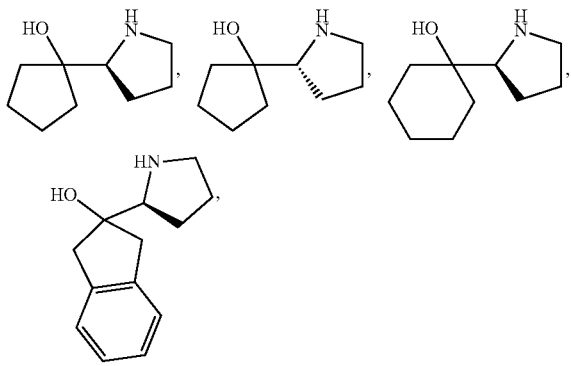

and salts thereof. In some embodiments, a provided compound is

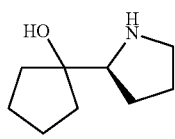

or a salt thereof. In some embodiments, a provided compound is

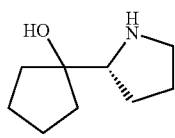 [SMILES: OC1([C@H]2CCCN2)CCCC1]

or a salt thereof. In some embodiments, a provided compound is

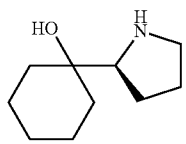 [SMILES: OC1([C@@H]2CCCN2)CCCCC1]

or a salt thereof. In some embodiments, a provided compound is

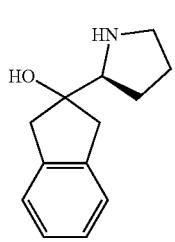 [SMILES: OC1([C@@H]2CCCN2)Cc2ccccc2C1]

or a salt thereof. In some embodiments, a provided compound is a diastereomer of

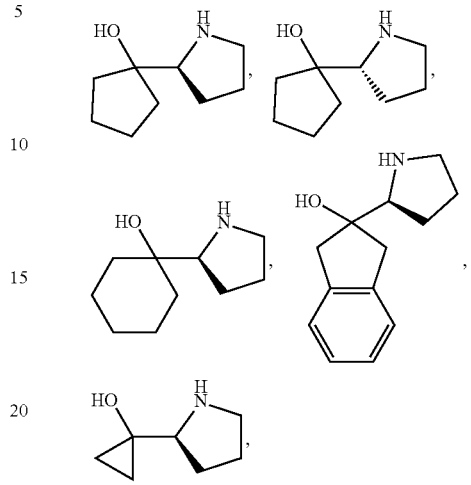

or a salt thereof. In some embodiments, a provided compound is a diastereomer of selected from

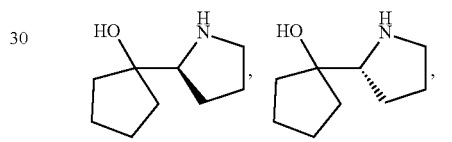

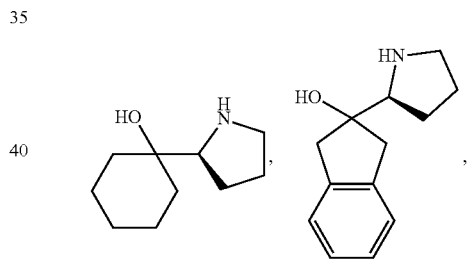

and salts thereof. In some embodiments, a provided compound is a diastereomer of

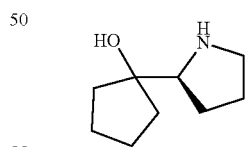

or a salt thereof. In some embodiments, a provided compound is a diastereomer of

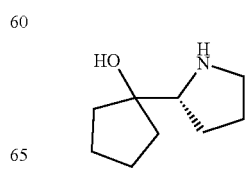

or a salt thereof. In some embodiments, a provided compound is a diastereomer of

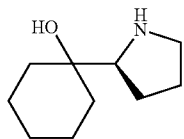 [SMILES: OC1([C@@H]2CCCN2)CCCCC1]

or a salt thereof. In some embodiments, a provided compound is a diastereomer of

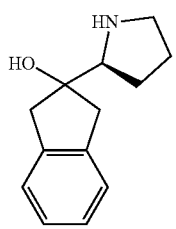 [SMILES: OC1([C@@H]2CCCN2)Cc2ccccc2C1]

or a salt thereof. In some embodiments, a provided compound is an enantiomer of

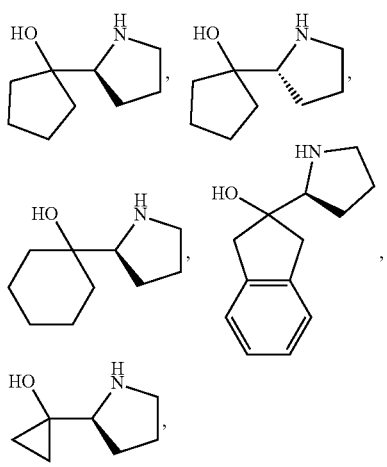

or a salt thereof. In some embodiments, a provided compound is an enantiomer of selected from

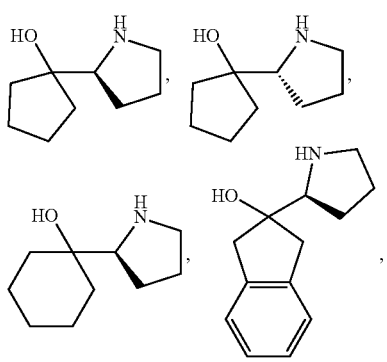

and salts thereof. In some embodiments, a provided compound is an enantiomer of

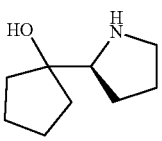 [SMILES: OC1([C@@H]2CCCN2)CCCC1]

or a salt thereof. In some embodiments, a provided compound is an enantiomer of

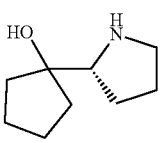 [SMILES: OC1([C@H]2CCCN2)CCCC1]

or a salt thereof. In some embodiments, a provided compound is an enantiomer of

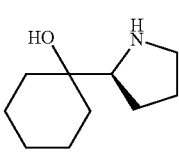

or a salt thereof. In some embodiments, a provided compound is an enantiomer of

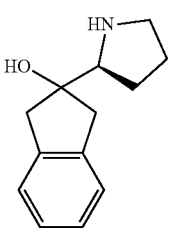 [SMILES: OC1([C@@H]2CCCN2)Cc2ccccc2C1]

or a salt thereof.

In some embodiments, one of $R^1$ and $R^2$, and one of $R^3$ and $R^4$, are R, (e.g., one of $R^1$ and $R^2$, and one of $R^3$ and $R^4$, of formula I-a) and the two R groups are taken together to form an optionally substituted ring as described in the present disclosure. In some embodiments, $R^1$ and $R^3$ are R, and the two R groups are taken together to form an optionally substituted ring as described in the present disclosure. In some embodiments, $R^1$ and $R^4$ are R, and the two R groups are taken together to form an optionally substituted ring as described in the present disclosure. In some embodiments, $R^2$ and $R^3$ are R and the two R groups are taken together to form an optionally substituted ring as described in the present disclosure. In some embodiments, $R^2$ and $R^4$ are R, and the two R groups are taken together to form an optionally substituted ring as described in the present disclosure. In some embodiments, a provided compound has the structure of formula I-e or a salt thereof. As described in the present disclosure, in some embodiments, a formed ring is an optionally substituted $C_{3-20}$ cycloaliphatic ring. In some embodiments, a formed ring is an optionally substituted $C_{3-10}$ cycloaliphatic ring. In some embodiments, a formed ring is an optionally substituted $C_{5-7}$ cycloaliphatic ring. In some embodiments, a formed ring is an optionally substituted $C_5$ cycloaliphatic ring. In some embodiments, a formed ring is an optionally substituted $C_6$ cycloaliphatic ring. In some embodiments, a formed ring is an optionally substituted $C_7$ cycloaliphatic ring. In some embodiments, a formed ring is an optionally substituted $C_8$ cycloaliphatic ring. In some embodiments, a formed ring is an optionally substituted $C_9$ cycloaliphatic ring. In some embodiments, a formed ring is an optionally substituted $C_{10}$ cycloaliphatic ring. As described in the present disclosure, in some embodiments, a formed ring can be monocyclic, bicyclic, or polycyclic, and can comprise one or more saturated, partially saturated and/or aromatic monocyclic moieties. In some embodiments, a formed ring is an optionally substituted $C_{3-20}$ saturated, monocyclic cycloaliphatic ring. In some embodiments, a formed ring is an optionally substituted $C_{3-10}$ saturated, monocyclic cycloaliphatic ring. In some embodiments, a formed ring is an optionally substituted $C_{5-7}$ saturated, monocyclic cycloaliphatic ring. In some embodiments, a formed ring is an optionally substituted $C_5$ saturated, monocyclic cycloaliphatic ring. In some embodiments, a formed ring is an optionally substituted $C_6$ saturated, monocyclic cycloaliphatic ring. In some embodiments, a formed ring is an optionally substituted $C_7$ saturated, monocyclic cycloaliphatic ring. In some embodiments, a formed ring is an optionally substituted $C_8$ saturated, monocyclic cycloaliphatic ring. In some embodiments, a formed ring is an optionally substituted $C_9$ saturated, monocyclic cycloaliphatic ring. In some embodiments, a formed ring is an optionally substituted $C_{10}$ saturated, monocyclic cycloaliphatic ring. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-20}$ aliphatic; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is an optionally substituted $C_{1-6}$ alkyl; $R^6$ is —H; and $R^7$ is —OH. In some embodiments, one of $R^1$ and $R^2$, and one of $R^3$ and $R^4$, are R, and the two R groups are taken together to form an optionally substituted ring as described in the present disclosure; $R^5$ is R, wherein R is methyl; $R^6$ is —H; and $R^7$ is —OH. Among other things, the present disclosure demonstrated that provided compounds, wherein the N atom to which $R^5$ and $R^6$ are attached is not within a ring, can provide surprisingly high stereoselectivity and/or yield when used in chirally controlled preparation of oligonucleotides.

In some embodiments, a provided compound, e.g., a compound of formula I-e, is

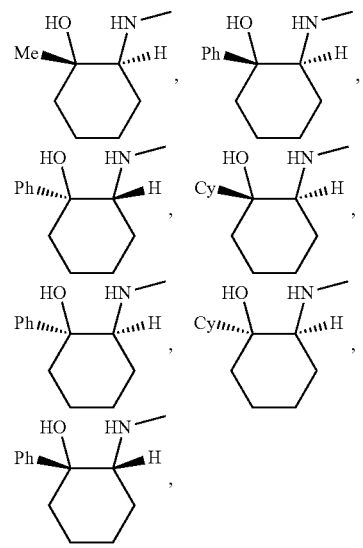

and thereof. In some embodiments, a provided compound is

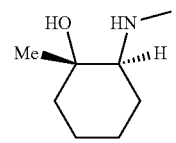

or a salt there of. In some embodiments, a provided compound is

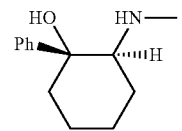

or a salt there of. In some embodiments, a provided compound is

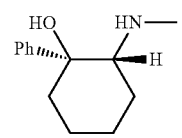

or a salt there of. In some embodiments, a provided compound is

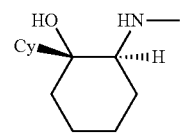

or a salt there of. In some embodiments, a provided compound is

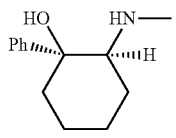

or a salt there of. In some embodiments, a provided compound is

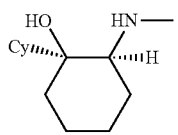

or a salt there of. In some embodiments, a provided compound is

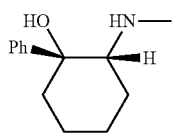

or a salt there of. In some embodiments, a provided compound is

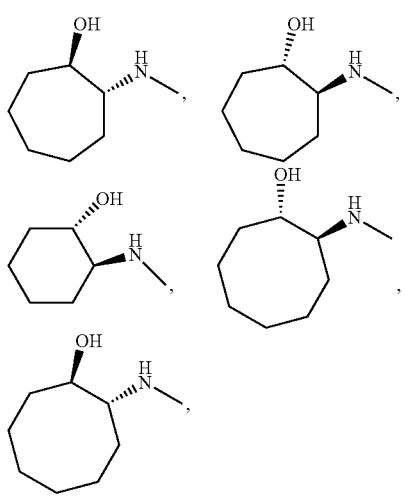

or a salt thereof. In some embodiments, a provided compound is

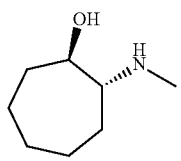

or a salt thereof. In some embodiments, a provided compound is

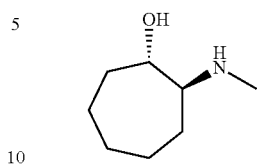

or a salt thereof. In some embodiments, a provided compound is

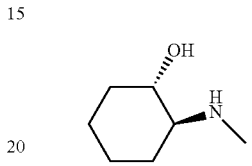

or a salt thereof. In some embodiments, a provided compound is

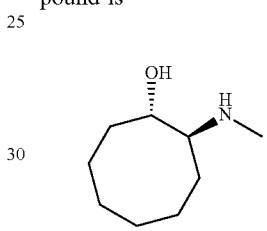

or a salt thereof. In some embodiments, a provided compound is

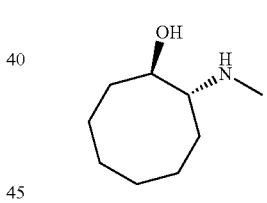

or a salt thereof.

In some embodiments, a provided compound, e.g., a compound of formula I-e, is

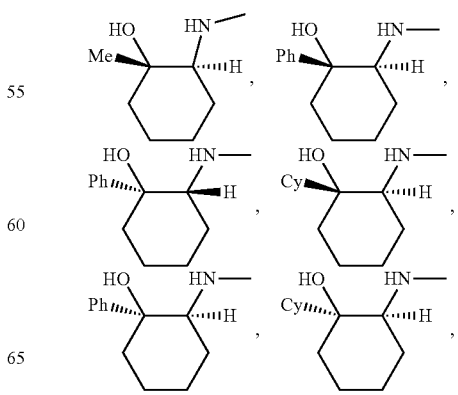

-continued

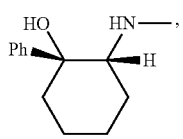

and thereof. In some embodiments, a provided compound is a diastereomer of

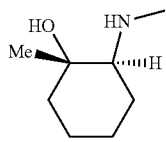

or a salt there of. In some embodiments, a provided compound is a diastereomer of

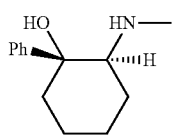

or a salt there of. In some embodiments, a provided compound is a diastereomer of

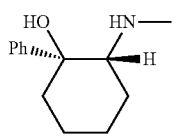

or a salt there of. In some embodiments, a provided compound is a diastereomer of

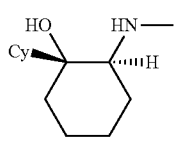

or a salt there of. In some embodiments, a provided compound is a diastereomer of

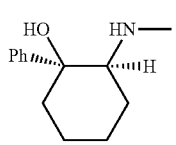

or a salt there of. In some embodiments, a provided compound is a diastereomer of

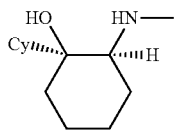

or a salt there of. In some embodiments, a provided compound is a diastereomer of

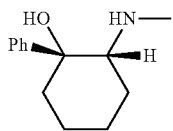

or a salt there of. In some embodiments, a provided compound is a diastereomer of

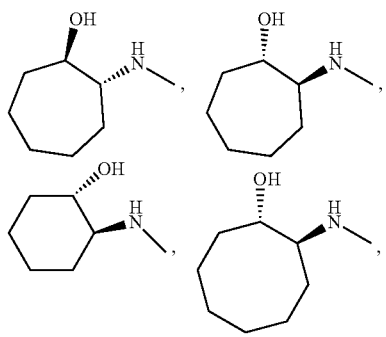

or a salt thereof. In some embodiments, a provided compound is a diastereomer of

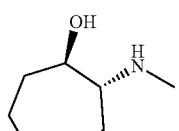

or a salt thereof. In some embodiments, a provided compound is a diastereomer of

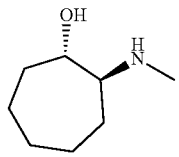

or a salt thereof. In some embodiments, a provided compound is a diastereomer of

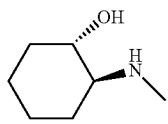

or a salt thereof. In some embodiments, a provided compound is a diastereomer of

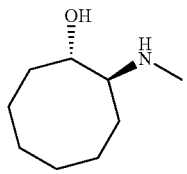

or a salt thereof. In some embodiments, a provided compound is a diastereomer of

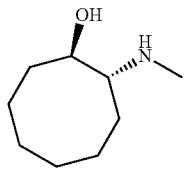

or a salt thereof.

In some embodiments, a provided compound, e.g., a compound of formula I-e, is

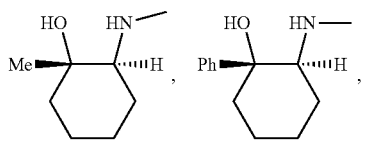

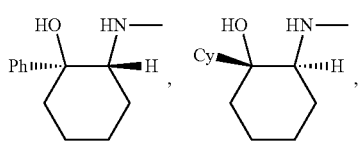

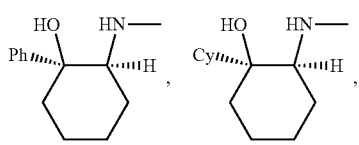

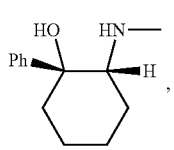

and thereof. In some embodiments, a provided compound is an enantiomer of

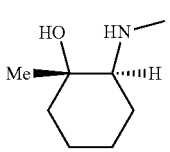

or a salt there of. In some embodiments, a provided compound is an enantiomer of

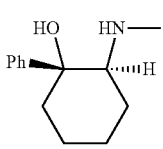

or a salt there of. In some embodiments, a provided compound is an enantiomer of

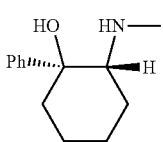

or a salt there of. In some embodiments, a provided compound is an enantiomer of

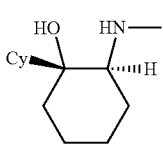

or a salt there of. In some embodiments, a provided compound is an enantiomer of

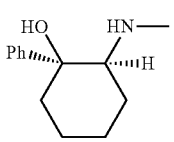

or a salt there of. In some embodiments, a provided compound is an enantiomer of

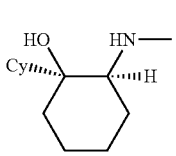

or a salt there of. In some embodiments, a provided compound is an enantiomer of

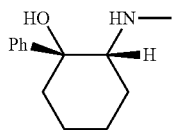

or a salt there of. In some embodiments, a provided compound is an enantiomer of

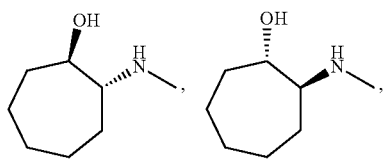

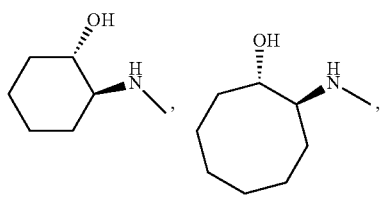

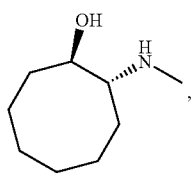

or a salt thereof. In some embodiments, a provided compound is an enantiomer of

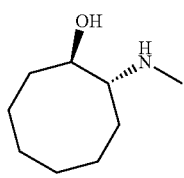

or a salt thereof. In some embodiments, a provided compound is an enantiomer of

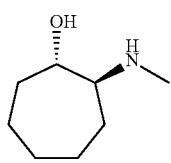

or a salt thereof. In some embodiments, a provided compound is an enantiomer of

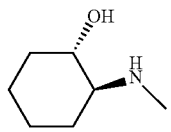

or a salt thereof. In some embodiments, a provided compound is an enantiomer of

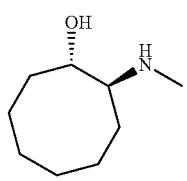

or a salt thereof. In some embodiments, a provided compound is an enantiomer of

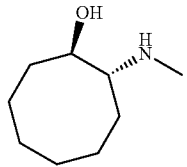

or a salt thereof.

In some embodiments, $R^3$ and $R^4$ are R, and the two R groups are taken together to form an optionally substituted ring as described in the present disclosure.

In some embodiments, $R^3$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure. In some embodiments, $R^4$ and $R^5$ are R, and the two R groups are taken together to form an optionally substituted ring as described in the present disclosure; $R^6$ is —H; and $R^7$ is —OH.

In some embodiments, a formed ring is an optionally substituted 3-20 membered monocyclic, bicyclic or polycyclic ring having 1-5 heteroatoms. In some embodiments, a formed ring is an optionally substituted 4-6 membered monocyclic ring having no more than one heteroatom. In some embodiments, a formed ring is an optionally substituted 4-6 membered saturated monocyclic ring having only one ring heteroatom, which only ring heteroatom is the nitrogen to which $R^5$ is attached. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is 8-membered. In some embodiments, a formed ring is 9-membered. In some embodiments, a formed ring is 10-membered. In some embodiments, $R^3$ is —H, and $R^4$ and $R^5$ are R, which are taken together with their intervening atoms to form an optionally substituted 3-20 membered monocyclic, bicyclic or polycyclic ring having 1-5 heteroatoms. In some embodiments, $R^3$ is —H, and $R^4$ and $R^5$ are R, which are taken together with their intervening atoms to form an optionally substituted 3-20 membered monocyclic, bicyclic or polycyclic ring having a nitrogen atom (the one which $R^5$ is on). In some embodiments, $R^3$ is —H, and $R^4$ and $R^5$ are R, which are taken together with their intervening atoms to form an optionally substituted 4-7 membered monocyclic ring having a nitrogen atom (the one which $R^5$ is on). In some embodiments, $R^3$ is —H, and $R^4$ and $R^5$ are R, which are taken together with their intervening atoms to form an optionally substituted 4-membered monocyclic ring having a nitrogen atom (the one which $R^5$ is on). In some embodiments, $R^3$ is —H, and $R^4$ and $R^5$ are R, which are taken together with their intervening atoms to form an optionally substituted 5-membered monocyclic ring having a nitrogen atom (the one which $R^5$ is on). In some embodiments, $R^3$ is —H, and $R^4$ and $R^5$ are R, which are taken together with their intervening atoms to form an optionally substituted 6-membered monocyclic ring having a nitrogen atom (the one which $R^5$ is on). In some embodiments, $R^3$ is —H, and $R^4$ and $R^5$ are R, which are taken together with their intervening atoms to form an optionally substituted 7-membered monocyclic ring having a nitrogen atom (the one which $R^5$ is on). In some embodiments, $R^3$ is —H, and $R^4$ and $R^5$ are R, which are taken together with their intervening atoms to form an optionally substituted 8-membered monocyclic ring having a nitrogen atom (the one which $R^5$ is on). In some embodiments, $R^3$ is —H, and $R^4$ and $R^5$ are R, which are taken together with their intervening atoms to form an optionally substituted 9-membered monocyclic ring having a nitrogen atom (the one which $R^5$ is on). In some embodiments, $R^3$ is —H, and $R^4$ and $R^5$ are R, which are taken together with their intervening atoms to form an optionally substituted 10-membered monocyclic ring having a nitrogen atom (the one which $R^5$ is on). In some embodiments, a formed ring is substituted. In some embodiments, a formed ring is unsubstituted. In some embodiments, formed ring is monocyclic. In some embodiments, a formed ring is bicyclic. In some embodiments, a formed ring has no additional heteroatoms in addition to an intervening atom. In some embodiments, a formed ring has additional ring heteroatoms in addition to an intervening atom. In some embodiments, a formed ring is an optionally substituted saturated, monocyclic, 4-membered ring having no more than one ring heteroatom, wherein the only ring heteroatom is nitrogen. In some embodiments, a formed ring is an optionally substituted saturated, monocyclic, 5-membered ring having no more than one ring heteroatom, wherein the only ring heteroatom is nitrogen. In some embodiments, a formed ring is an optionally substituted saturated, monocyclic, 6-membered ring having no more than one ring heteroatom, wherein the only ring heteroatom is nitrogen. In some embodiments, a formed ring is an optionally substituted saturated, monocyclic, 7-membered ring having no more than one ring heteroatom, wherein the only ring heteroatom is nitrogen. In some embodiments, a formed ring is an optionally substituted saturated, monocyclic, 8-membered ring having no more than one ring heteroatom, wherein the only ring heteroatom is nitrogen. In some embodiments, a formed ring is an optionally substituted saturated, monocyclic, 9-membered ring having no more than one ring heteroatom, wherein the only ring heteroatom is nitrogen. In some embodiments, a formed ring is an optionally substituted saturated, monocyclic, 10-membered ring having no more than one ring heteroatom, wherein the only ring heteroatom is nitrogen. In some embodiments, a formed ring is of such a structure that

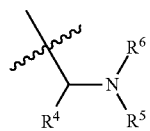

($R^6$ is —H), is, in some embodiments,

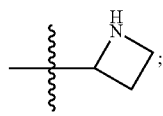 [SMILES: *C1CCN1]

in some embodiments,

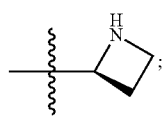 [SMILES: *[C@@H]1CCN1]

in some embodiments,

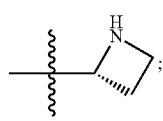 [SMILES: *[C@H]1CCN1]

in some embodiments,

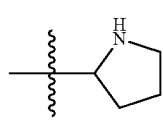

in some embodiments,

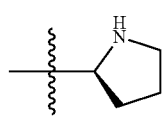

in some embodiments,

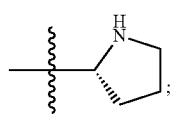

in some embodiments,

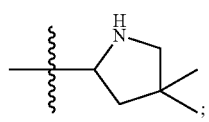 [SMILES: *C1CC(C)(C)CN1]

in some embodiments,
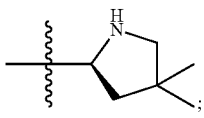 [SMILES: *[C@@H]1CC(C)(C)CN1];
in some embodiments,
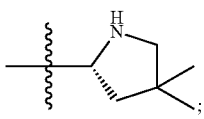;
in some embodiments,
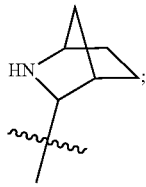 [SMILES: *C1NC2CCC1C2];
in some embodiments,
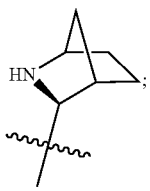 [SMILES: *[C@H]1NC2CCC1C2];
in some embodiments,
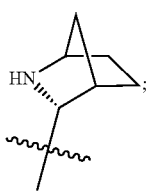 [SMILES: *[C@@H]1NC2CCC1C2];
in some embodiments,
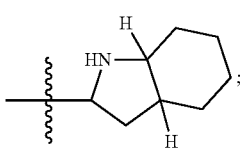 [SMILES: *C1CC2CCCCC2N1];
in some embodiments,
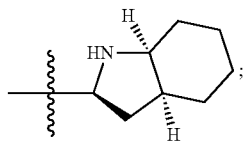 [SMILES: *[C@@H]1C[C@@H]2CCCC[C@@H]2N1];
in some embodiments,
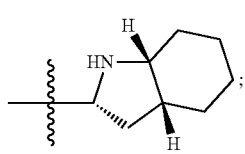 [SMILES: *[C@H]1C[C@H]2CCCC[C@H]2N1];
in some embodiments,
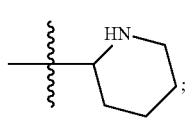 [SMILES: *C1CCCCN1];
in some embodiments,
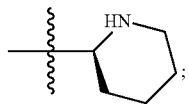 [SMILES: *[C@@H]1CCCCN1];
in some embodiments,
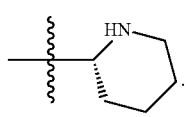.
In some embodiments, a provided compound is
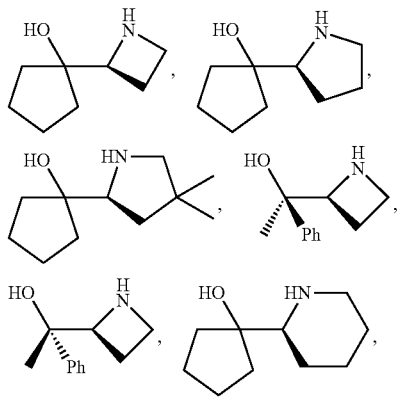

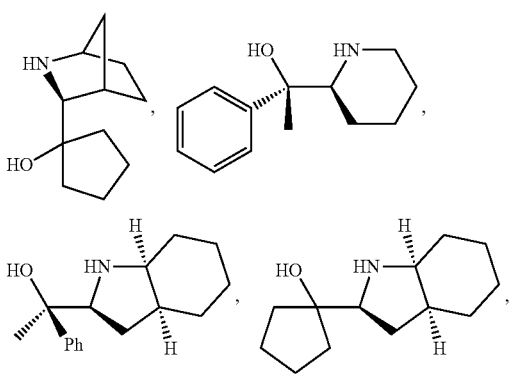

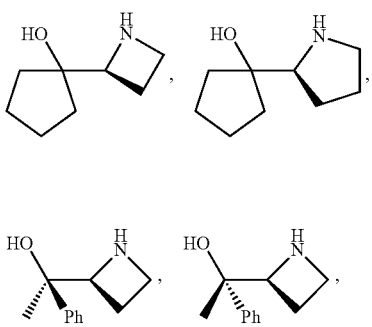

or a salt thereof. In some embodiments, a provided compound is

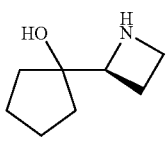

or a salt thereof. In some embodiments, a provided compound is

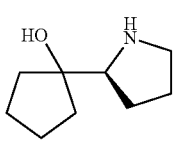

or a salt thereof. In some embodiments, a provided compound is

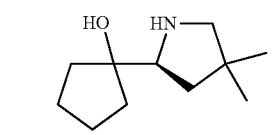

or a salt thereof. In some embodiments, a provided compound is

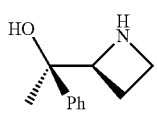

or a salt thereof. In some embodiments, a provided compound is

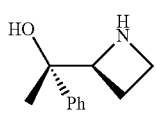

or a salt thereof. In some embodiments, a provided compound is

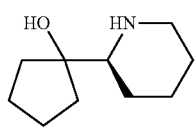 [SMILES: OC1([C@@H]2CCCCN2)CCCC1]

or a salt thereof. In some embodiments, a provided compound is

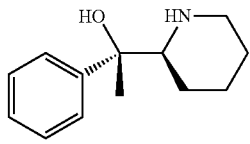

or a salt thereof. In some embodiments, a provided compound is

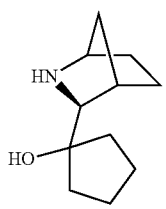 [SMILES: OC1([C@H]2NC3CCC2C3)CCCC1]

or a salt thereof. In some embodiments, a provided compound is

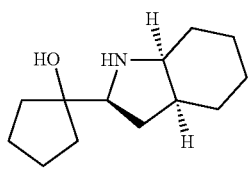 [SMILES: OC1([C@@H]2C[C@@H]3CCCC[C@@H]3N2)CCCC1]

or a salt thereof. In some embodiments, a provided compound is

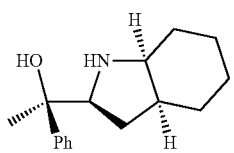

or a salt thereof.

In some embodiments, a provided compound is a diastereomer of

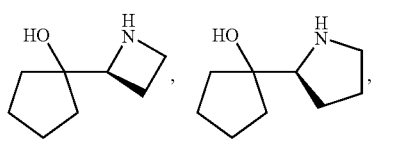

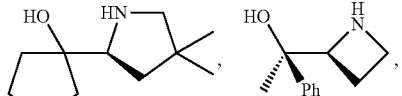

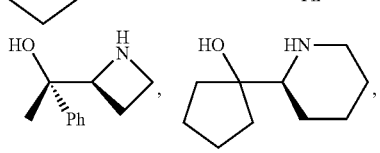

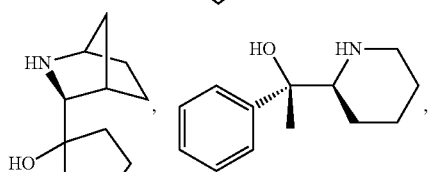

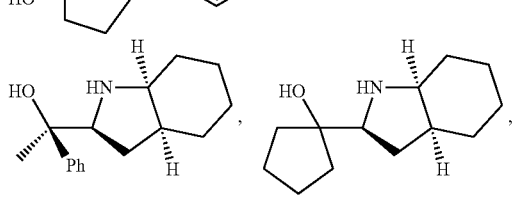

or a salt thereof. In some embodiments, a provided compound is a diastereomer of

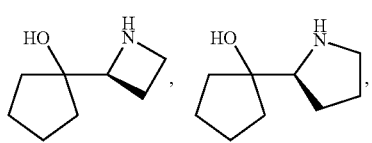

-continued

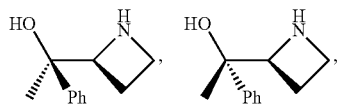

or a salt thereof. In some embodiments, a provided compound is a diastereomer of

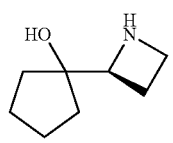

or a salt thereof. In some embodiments, a provided compound is a diastereomer of

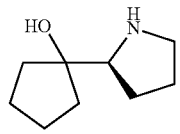

or a salt thereof. In some embodiments, a provided compound is a diastereomer of

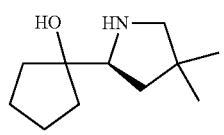

or a salt thereof. In some embodiments, a provided compound is a diastereomer of

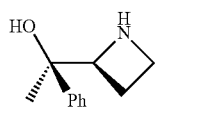

or a salt thereof. In some embodiments, a provided compound is a diastereomer of

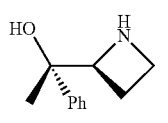

or a salt thereof. In some embodiments, a provided compound is a diastereomer of

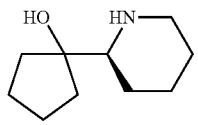 [SMILES: OC1([C@@H]2CCCCN2)CCCC1]

or a salt thereof. In some embodiments, a provided compound is a diastereomer of

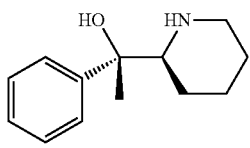

or a salt thereof. In some embodiments, a provided compound is a diastereomer of

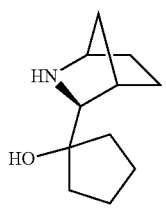

or a salt thereof. In some embodiments, a provided compound is a diastereomer of

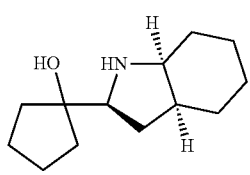 [SMILES: OC1([C@@H]2C[C@@H]3CCCC[C@@H]3N2)CCCC1]

or a salt thereof. In some embodiments, a provided compound is a diastereomer of

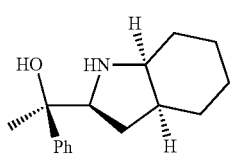 [SMILES: C[C@@](O)(c1ccccc1)[C@@H]1C[C@@H]2CCCC[C@@H]2N1]

or a salt thereof.

In some embodiments, a provided compound is an enantiomer of

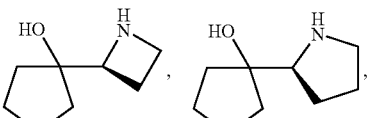

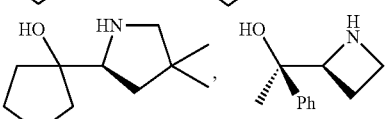

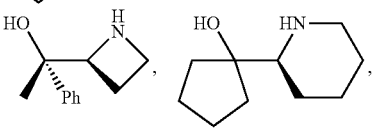

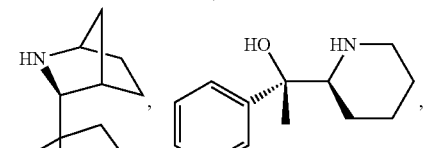

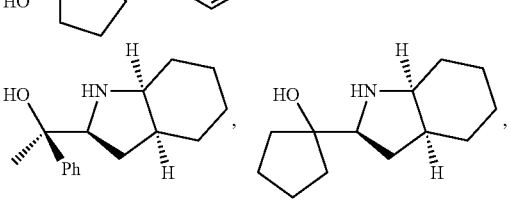

or a salt thereof. In some embodiments, a provided compound is an enantiomer of

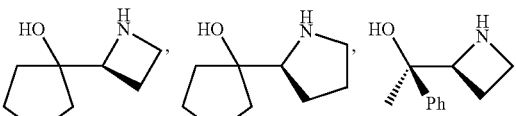

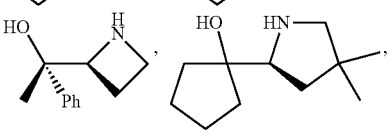

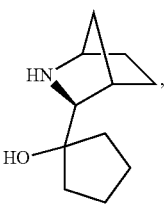

or a salt thereof. In some embodiments, a provided compound is an enantiomer of

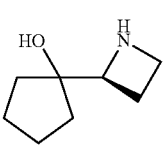

or a salt thereof. In some embodiments, a provided compound is an enantiomer of

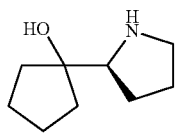

or a salt thereof. In some embodiments, a provided compound is an enantiomer of

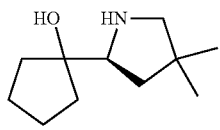

or a salt thereof. In some embodiments, a provided compound is an enantiomer of

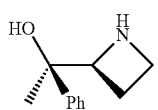

or a salt thereof. In some embodiments, a provided compound is an enantiomer of

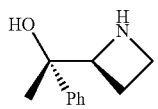

or a salt thereof. In some embodiments, a provided compound is an enantiomer of

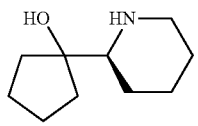 [SMILES: OC1([C@@H]2CCCCN2)CCCC1]

or a salt thereof. In some embodiments, a provided compound is an enantiomer of

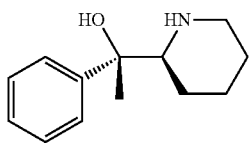

or a salt thereof. In some embodiments, a provided compound is an enantiomer of

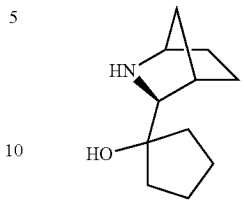

or a salt thereof. In some embodiments, a provided compound is an enantiomer of

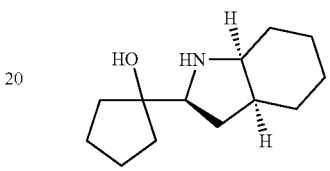

or a salt thereof. In some embodiments, a provided compound is an enantiomer of

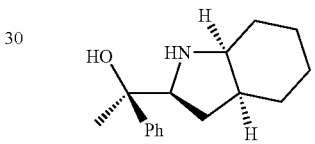

or a salt thereof.

In some embodiments, $R^5$, and one or both of $R^1$ and $R^2$, are R, which are taken together with their intervening atoms to form an optionally substituted, 3-20 membered monocyclic, bicyclic or polycyclic ring having 1-5 heteroatoms. In some embodiments, one of $R^1$ and $R^2$, and $R^5$, are R, and the R groups are taken together with their intervening atoms to form an optionally substituted, 3-20 membered monocyclic, bicyclic or polycyclic ring having 1-5 heteroatoms. As extensively described in the present disclosure, a formed ring can be of various sizes, monocyclic, bicyclic or polycyclic, and contain various numbers and/or types of heteroatoms. In some embodiments, a ring is a 3-membered ring. In some embodiments, a ring is a 4-membered ring. In some embodiments, a ring is a 5-membered ring. In some embodiments, a ring is a 6-membered ring. In some embodiments, a ring is monocyclic. In some embodiments, a ring contains additional ring heteroatoms other than the intervening heteroatoms. In some embodiments, a ring is a 3-membered ring containing one ring heteroatom. In some embodiments, a ring is a 3-membered ring containing two ring heteroatoms. In some embodiments, a ring is a 3-membered ring containing one carbon, one nitrogen, and one oxygen ring atom.

In some embodiments, $R^6$ is R', wherein R' is as described in the present disclosure. In some embodiments, $R^6$ is —H, for example, when a provided compound has the structure of I, I-a, I-a-1, I-a-2, I-b, I-c, I-d, I-e, II, II-a, II-b, III, III-a, or III-b, or a salt thereof. In some embodiments, $R^6$ is a suitable capping group used in oligonucleotide synthesis, many of which are widely known and can be utilized in accordance with the present disclosure. In some embodiments, $R^6$ is —C(O)R, wherein R is as described in the present disclosure. In some embodiments, $R^6$ is a capping group when in a provided structure in oligonucleotide synthesis, for example, structure of formula VII, or VIII, or a salt thereof. In some embodiments, a capping group has the structure of —C(O)R, wherein R is as described in the present disclosure. In some embodiments, $R^6$ is —C(O)R, wherein R is as described in the present disclosure. In some embodiments, R is methyl. In some embodiments, R is —$CF_3$.

In some embodiments, $R^6$ is —H. In some embodiments, $R^6$ is —H, and $R^4$ and $R^5$ are R, and the R groups are taken together with their intervening atoms to form an optionally substituted 3-20 membered heterocyclyl ring having 1-5 heteroatoms as described in the present disclosure. In some embodiments, $R^6$ is —H, and $R^4$ and $R^5$ are R, and the R groups are taken together with their intervening atoms to form an optionally substituted 4-6 membered heterocyclyl ring having 1-5 heteroatoms as described in the present disclosure. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered.

In some embodiments, le is —OH. In some embodiments, $R^7$ is —SH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^1$ is —OH. In some embodiments, the present disclosure provides a compound of formula I, I-a, I-a-1, I-a-2, I-b, I-c, I-d, I-e, II, II-a, II-b, III, III-a, or III-b, or a salt thereof, wherein $R^7$ is —SH.

In some embodiments, $R^8$ is -L-$R^7$, -L-C($R^1$)($R^2$)—$R^7$, or -$L^s$-$R^7$, wherein each variable is independently as described in the present disclosure. In some embodiments, $R^8$ is $R^7$ as described in the present disclosure. In some embodiments, $R^8$ is —OH. In some embodiments, $R^8$ is —SH. In some embodiments, $R^8$ is -L-$R^7$, wherein each of L and $R^7$ is independently as described in the present disclosure. In some embodiments, $R^8$ is -L-OH, wherein $L^s$ is as described in the present disclosure. In some embodiments, $R^8$ is -L-SH, wherein $L^s$ is as described in the present disclosure. In some embodiments, $R^8$ is -L-C($R^1$)($R^2$)—$R^7$, wherein each variable is independently as described in the present disclosure. In some embodiments, $R^8$ is —C($R^1$)($R^2$)—$R^7$, wherein each variable is independently as described in the present disclosure. In some embodiments, $R^8$ is —$CH_2$—$R^7$, wherein $R^7$ is as described in the present disclosure. In some embodiments, $R^8$ is —$CH_2$OH. In some embodiments, $R^8$ is —$CH_2$SH. In some embodiments, $R^8$ is -$L^s$-$R^7$, wherein each variable is independently as described in the present disclosure. In some embodiments, $R^8$ is -$L^s$-OH, wherein $L^s$ is as described in the present disclosure. In some embodiments, $R^8$ is -$L^s$-SH, wherein $L^s$ is as described in the present disclosure.

In some embodiments, $R^4$ and $R^5$ are R, which are taken together with their intervening atoms to form an optionally substituted 4-10 membered heterocyclyl ring with the intervening nitrogen atom as the only ring heteroatom. In some embodiments, $R^4$ and $R^5$ are R, which are taken together with their intervening atoms to form an optionally substituted 4-10 membered saturated monocyclic heterocyclyl ring with the intervening nitrogen atom as the only ring heteroatom. In some embodiments, $R^4$ and $R^5$ are R, which are taken together with their intervening atoms to form an optionally substituted 4-10 membered saturated bicyclic heterocyclyl ring with the intervening nitrogen atom as the only ring heteroatom. In some embodiments, a formed ring is 3-membered. In some embodiments, a formed ring is 4-membered. In some embodiments, a formed ring is 5-membered. In some embodiments, a formed ring is 6-membered. In some embodiments, a formed ring is 7-membered. In some embodiments, a formed ring is an optionally substituted pyrrolidine moiety. In some embodiments, $R^7$ is —OH. In some embodiments, $R^7$ is —SH.

In some embodiments, a provided compound of formula I, I-a, I-a-I, I-a-2, I-b, I-c, I-d, I-e, II, II-a, II-b, III, III-a, or III-b comprises no more than one chiral elements. In some embodiments, a provided compound of formula I, I-a, I-a-I, I-a-2, I-b, I-c, I-d, I-e, II, II-a, II-b, III, III-a, or III-b comprises no more than one chiral elements, wherein the only one chiral element is chiral carbon atom. In some embodiments, a provided compound of formula I, I-a, I-a-I, I-a-2, I-b, I-c, I-d, I-e, II, II-a, II-b, III, III-a, or III-b comprises no more than one chiral elements, wherein the only one chiral element is chiral carbon atom to which $R^3$ and $R^4$ are attached. In some embodiments, $R^1$ and $R^2$ are the same. In some embodiments, $R^1$ and $R^2$ are the same, and are optionally substituted straight chain $C_{1-3}$ alkyl. In some embodiments, $R^1$ and $R^2$ are the same, and are optionally substituted straight chain $C_{1-3}$ alkyl wherein no substituent comprises a carbon atom. In some embodiments, $R^1$ and $R^2$ are the same, and are optionally substituted straight chain $C_{1-2}$ alkyl. In some embodiments, $R^1$ and $R^2$ are the same, and are optionally substituted straight chain $C_{1-2}$ alkyl wherein no substituent comprises a carbon atom. In some embodiments, $R^1$ and $R^2$ are methyl. In some embodiments, $R^1$ and $R^2$ are ethyl. In some embodiments, $R^1$ and $R^2$ are n-propyl. In some embodiments, $R^1$ and $R^2$ are taken together to form an optionally substituted ring as described in the present disclosure. In some embodiments, $R^1$ and $R^2$ are taken together to form an optionally substituted ring where the ring contains no chiral elements.

In some embodiments, L is a covalent bond, or optionally substituted $C_{1-6}$ alkylene, wherein one or more methylene units are optionally and independently replaced with -L'-, wherein L' is as described in the present disclosure. In some embodiments, L is a covalent bond. In some embodiments, L is optionally substituted $C_{1-6}$ alkylene, wherein one or more methylene units are optionally and independently replaced with -L'-, wherein L' is as described in the present disclosure. In some embodiments, L is optionally substituted $C_{1-6}$ alkylene, wherein one or more methylene units are independently replaced with -L'-, wherein each L' is independently as described in the present disclosure.

In some embodiments, L is a covalent bond. In some embodiments, a provided compound, e.g., a compound of formula I, has the structure of

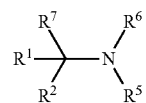

or a salt thereof.

In some embodiments, L is —C($R^3$)($R^4$)—. In some embodiments, a provided compound has the structure of formula I-a:

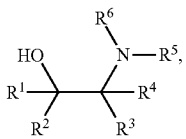

I-a or a salt thereof, wherein each variable is independently as described in the present disclosure. In some embodiments, a compound of formula I has the structure of formula I-a. In some embodiments, a provided compound has the structure of

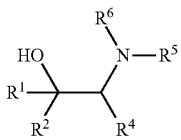

or a salt thereof, wherein each variable is independently as described in the present disclosure, and wherein $R^4$ and $R^5$ are not hydrogen. In some embodiments, a provided compound has the structure of

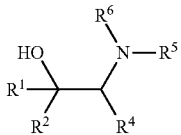

or a salt thereof, wherein each variable is independently as described in the present disclosure, and wherein $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-1):

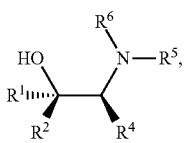

I-a-1 or a salt thereof, wherein each variable is independently as described in the present disclosure, and wherein $R^4$ and $R^5$ are not hydrogen, and $R^2$ has a larger size than $R^1$. In some embodiments, a compound of formula I-a has the structure of formula I-a-1. In some embodiments, $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, a provided compound has the structure of formula (I-a-2):

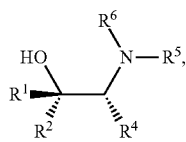

I-a-2 or a salt thereof, wherein each variable is independently as described in the present disclosure, and wherein $R^4$ and $R^5$ are not hydrogen, and $R^2$ has a larger size than R'. In some embodiments, a compound of formula I-a has the structure of formula I-a-2. In some embodiments, $R^4$ and $R^5$ are R and are taken together to form an optionally substituted ring as described in the present disclosure. In some embodiments, $R^1$ and $R^2$ are different. In some embodiments, $R^1$ and $R^2$ are the same. In some embodiments, $R^1$ and $R^2$ are the same and are hydrogen. In some embodiments, $R^1$ and $R^2$ are the same and are not hydrogen. In some embodiments, $R^1$ and $R^2$ are the same and are optionally substituted $C_{1-6}$ aliphatic. In some embodiments, $R^1$ and $R^2$ are the same and are optionally substituted $C_{1-6}$ alkyl.

In some embodiments, L is -L'-C($R^3$)($R^4$)—, wherein each variable is independently as described in the present disclosure. In some embodiments, a provided compound has the structure of formula I-b:

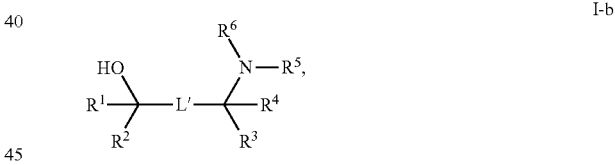

I-b or a salt thereof, wherein each variable is independently as described in the present disclosure. In some embodiments, a compound of formula I has the structure of formula I-b.

In some embodiments, L' is a covalent bond. In some embodiments, L' is optionally substituted bivalent $C_{1-3}$ alkylene. In some embodiments, L' is —C($R^3$)($R^4$)—, wherein each of $R^3$ and $R^4$ is independently as described in the present disclosure. In some embodiments, L' is —C($R^3$)($R^4$)—C($R^3$)($R^4$)—, wherein each of $R^3$ and $R^4$ is independently as described in the present disclosure. In some embodiments, L' is -Cy- as described in the present disclosure. In some embodiments, L' is —C($R^3$)[C($R^4$)$_3$]—, wherein each of $R^3$ and $R^4$ is independently as described in the present disclosure.

In some embodiments, L' is a covalent bond. In some embodiments, L' is optionally substituted bivalent $C_{1-3}$ alkylene. In some embodiments, L' is —C($R^3$)($R^4$)—. In some embodiments, a provided compound has the structure of formula I-c:

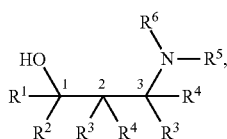

I-c or a salt thereof, wherein each variable is independently as described in the present disclosure. In some embodiments, a compound of formula I has the structure of formula I-c, or a salt thereof. In some embodiments, a compound of formula I-b has the structure of formula I-c, or a salt thereof. In some embodiments, each of $R^1$ and $R^2$ is independently R, wherein R is as described in the present disclosure. In some embodiments, one of $R^1$ and $R^2$ is —H, and the other is R, wherein R is as described in the present disclosure and is not —H. In some embodiments, each of $R^1$ and $R^2$ is independently R, wherein R is as described in the present disclosure and is not —H. In some embodiments, each of $R^1$ and $R^2$ is independently R, wherein the two R groups are taken together to form an optionally substituted ring as described in the present disclosure. In some embodiments, one of $R^1$ and $R^2$ is —H, and the other is optionally substituted phenyl. In some embodiments, one of $R^1$ and $R^2$ is —H, and the other is phenyl. In some embodiments, each of $R^3$ and $R^4$ attached to C2 in formula I-c is independently R, wherein R is as described in the present disclosure. In some embodiments, each of $R^3$ and $R^4$ attached to C2 is —H. In some embodiments, each of $R^3$ and $R^4$ attached to C3 is independently R, wherein R is as described in the present disclosure. In some embodiments, one of $R^3$ and $R^4$ attached to C3 is hydrogen. In some embodiments, one of $R^3$ and $R^4$ attached to C3 R, $R^5$ is R, and the two R groups are taken together to form an optionally substituted ring as described in the present disclosure.

In some embodiments, a formed ring is an optionally substituted heterocyclyl moiety as described in the present disclosure. In some embodiments, a formed ring is an optionally substituted, monocyclic, and saturated 4, 5, or 6-membered heterocyclyl ring having one nitrogen ring atom and no more than one heteroatom as described in the present disclosure. In some embodiments, a formed ring is an optionally substituted trivalent azetidinyl moiety as described in the present disclosure. In some embodiments, a formed ring is an optionally substituted trivalent pyrrolidinyl moiety as described in the present disclosure. In some embodiments, a formed ring is an optionally substituted trivalent piperidinyl moiety as described in the present disclosure. In some embodiments, one of $R^3$ and $R^4$ attached to $C_2$ is R, one of $R^3$ and $R^4$ attached to $C_3$ is R, and the two R groups are taken together to form an optionally substituted ring as described in the present disclosure. In some embodiments, a formed ring is an optionally substituted cycloaliphatic ring. In some embodiments, a formed ring an optionally substituted saturated cycloaliphatic ring. In some embodiments, a formed ring is 3, 4, 5, 6, 7, 8, 9, or 10-membered. In some embodiments, a formed ring is an optionally substituted 5-membered, saturated, monocyclic cycloaliphatic ring. In some embodiments, a provided compound is

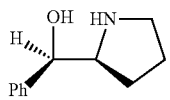

or a salt thereof. In some embodiments, a provided compound is a diastereomer of

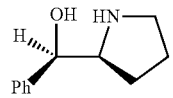

or a salt thereof. In some embodiments, a provided compound is an enantiomer of

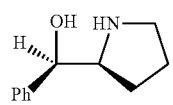

or a salt thereof. In some embodiments, a provided compound is

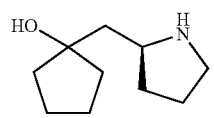

or a salt thereof. In some embodiments, a provided compound is a diastereomer of

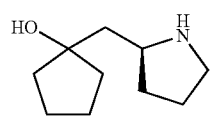

or a salt thereof. In some embodiments, a provided compound is an enantiomer of

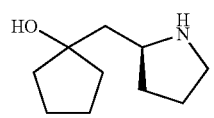 [SMILES: OC1(C[C@@H]2CCCN2)CCCC1]

or a salt thereof. In some embodiments, a provided compound is

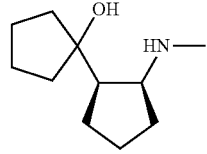

or a salt thereof. In some embodiments, a provided compound is a diastereomer of

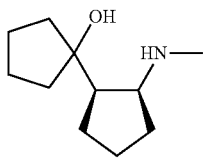

or a salt thereof. In some embodiments, a provided compound is an enantiomer of

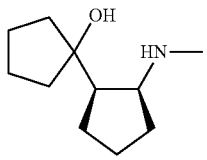

or a salt thereof.

In some embodiments, L' is —C(R$^3$)(R$^4$)—C(R$^3$)(R$^4$)—, wherein each variable is independently as described in the present disclosure. In some embodiments, L' is -Cy-. In some embodiments, L' is —C(R$^3$)[C(R$^4$)$_3$]—.

In some embodiments, each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, -Cy- is an optionally substituted ring as described in the present disclosure, for example, for R and Cy$^L$, but is bivalent.

In some embodiments, -Cy- is monocyclic. In some embodiments, -Cy- is bicyclic. In some embodiments, -Cy- is polycyclic. In some embodiments, -Cy- is saturated. In some embodiments, -Cy- is partially unsaturated. In some embodiments, -Cy- is aromatic. In some embodiments, -Cy-comprises a saturated cyclic moiety. In some embodiments, -Cy-comprises a partially unsaturated cyclic moiety. In some embodiments, -Cy- comprises an aromatic cyclic moiety. In some embodiments, -Cy-comprises a combination of a saturated, a partially unsaturated, and/or an aromatic cyclic moiety. In some embodiments, -Cy- is 3-membered. In some embodiments, -Cy- is 4-membered. In some embodiments, -Cy- is 5-membered. In some embodiments, -Cy- is 6-membered. In some embodiments, -Cy- is 7-membered. In some embodiments, -Cy- is 8-membered. In some embodiments, -Cy- is 9-membered. In some embodiments, -Cy- is 10-membered. In some embodiments, -Cy- is 11-membered. In some embodiments, -Cy- is 12-membered. In some embodiments, -Cy- is 13-membered. In some embodiments, -Cy- is 14-membered. In some embodiments, -Cy- is 15-membered. In some embodiments, -Cy- is 16-membered. In some embodiments, -Cy- is 17-membered. In some embodiments, -Cy- is 18-membered. In some embodiments, -Cy- is 19-membered. In some embodiments, -Cy- is 20-membered.

In some embodiments, -Cy- is an optionally substituted bivalent C$_{3-20}$ cycloaliphatic ring. In some embodiments, -Cy- is an optionally substituted bivalent, saturated C$_{3-20}$ cycloaliphatic ring. In some embodiments, -Cy- is an optionally substituted bivalent, partially unsaturated C$_{3-20}$ cycloaliphatic ring. In some embodiments, -Cy-comprises an aromatic moiety. In some embodiments, -Cy- is optionally substituted

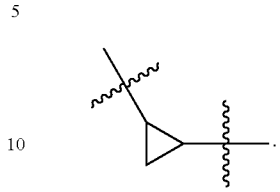

In some embodiments, -Cy- is optionally substituted

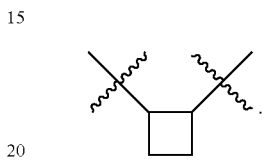

In some embodiments, -Cy- is optionally substituted

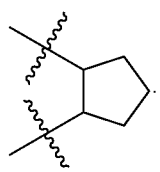 [SMILES: *C1CCCC1*]

In some embodiments, -Cy- is optionally substituted

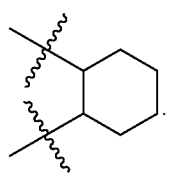 [SMILES: *C1CCCCC1*]

In some embodiments, -Cy- is optionally substituted

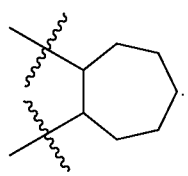 [SMILES: *C1CCCCCC1*]

In some embodiments, -Cy- is optionally substituted

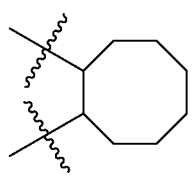

In some embodiments, -Cy-H is optionally substituted cycloaliphatic as described in the present disclosure, for example, cycloaliphatic embodiments for R.

In some embodiments, -Cy- is an optionally substituted $C_{6-20}$ aryl ring. In some embodiments, -Cy- is optionally substituted phenylene. In some embodiments, -Cy- is optionally substituted 1,2-phenylene. In some embodiments, -Cy- is optionally substituted 1,3-phenylene. In some embodiments, -Cy- is optionally substituted 1,4-phenylene. In some embodiments, -Cy- is an optionally substituted bivalent naphthalene ring. In some embodiments, -Cy-H is optionally substituted aryl as described in the present disclosure, for example, aryl embodiments for R.

In some embodiments, -Cy- is an optionally substituted bivalent 5-20 membered heteroaryl ring having 1-10 heteroatoms independently selected from oxygen, nitrogen, sulfur, phosphorus and silicon. In some embodiments, -Cy- is an optionally substituted bivalent 5-20 membered heteroaryl ring having 1-10 heteroatoms independently selected from oxygen, nitrogen, and sulfur. In some embodiments, -Cy- is an optionally substituted bivalent 5-6 membered heteroaryl ring having 1-4 heteroatoms independently selected from oxygen, nitrogen, sulfur. In some embodiments, -Cy- is an optionally substituted bivalent 5-6 membered heteroaryl ring having 1-3 heteroatoms independently selected from oxygen, nitrogen, sulfur. In some embodiments, -Cy- is an optionally substituted bivalent 5-6 membered heteroaryl ring having 1-2 heteroatoms independently selected from oxygen, nitrogen, sulfur. In some embodiments, -Cy- is an optionally substituted bivalent 5-6 membered heteroaryl ring having one heteroatom independently selected from oxygen, nitrogen, sulfur. In some embodiments, -Cy-H is optionally substituted heteroaryl as described in the present disclosure, for example, heteroaryl embodiments for R.

In some embodiments, -Cy- is an optionally substituted bivalent 3-20 membered heterocyclyl ring having 1-10 heteroatoms independently selected from oxygen, nitrogen, sulfur, phosphorus and silicon. In some embodiments, -Cy- is an optionally substituted bivalent 3-20 membered heterocyclyl ring having 1-10 heteroatoms independently selected from oxygen, nitrogen, and sulfur. In some embodiments, -Cy- is an optionally substituted bivalent 3-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-3 heteroatoms independently selected from oxygen, nitrogen, sulfur. In some embodiments, -Cy- is an optionally substituted bivalent 5-6 membered heterocyclyl ring having 1-2 heteroatoms independently selected from oxygen, nitrogen, sulfur. In some embodiments, -Cy- is an optionally substituted bivalent 5-6 membered heterocyclyl ring having one heteroatom independently selected from oxygen, nitrogen, sulfur. In some embodiments, -Cy- is an optionally substituted saturated bivalent heterocyclyl group. In some embodiments, -Cy- is an optionally substituted partially unsaturated bivalent heterocyclyl group. In some embodiments, -Cy-H is optionally substituted heterocyclyl as described in the present disclosure, for example, heterocyclyl embodiments for R.

In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N (R')—, —N(R')C(O)O—, —S(O)—, —S(O)$_2$—, —S(O)$_2$N (R')—, —C(O)S—, —C(O)O—, —P(O)(OR')—, —P(O) (SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP (NR')O—, —OP(R')O—, or —OP(OR')[B(R')$_3$]O—, and one or more carbon atoms are optionally and independently replaced with $Cy^L$.

In some embodiments, $L^s$ is a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$. In some embodiments, $L^s$ is a covalent bond, or a bivalent, optionally substituted, linear or branched $C_{1-30}$ aliphatic group, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)

(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L$^s$ is a covalent bond, or a bivalent, optionally substituted, linear or branched C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C— a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, -S-, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$. In some embodiments, L$^s$ is a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—, and one or more carbon atoms are optionally and independently replaced with Cy$^L$. In some embodiments, L$^s$ is a covalent bond, or a bivalent, optionally substituted, linear or branched group selected from a C$_{1-10}$ aliphatic group and a C$_{1-10}$ heteroaliphatic group having 1-5 heteroatoms independently selected from oxygen, nitrogen, sulfur, phosphorus and silicon, wherein one or more methylene units are optionally and independently replaced by an optionally substituted group selected from —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, and —C(O)O—.

In some embodiments, L$^s$ is a covalent bond. In some embodiments, L$^s$ is optionally substituted bivalent C$_{1-30}$ aliphatic. In some embodiments, L$^s$ is optionally substituted bivalent C$_{1-30}$ heteroaliphatic having 1-10 heteroatoms independently selected from boron, oxygen, nitrogen, sulfur, phosphorus and silicon.

In some embodiments, aliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc. In some embodiments, heteroaliphatic moieties, e.g. those of L$^s$, R, etc., either monovalent or bivalent or multivalent, and can contain any number of carbon atoms (before any optional substitution) within its range, e.g., C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, C$_{16}$, C$_{17}$, C$_{18}$, C$_{19}$, C$_{20}$, C$_{21}$, C$_{22}$, C$_{23}$, C$_{24}$, C$_{25}$, C$_{26}$, C$_{27}$, C$_{28}$, C$_{29}$, C$_{30}$, etc.

In some embodiments, a methylene unit is replaced with -Cy-, wherein -Cy- is as described in the present disclosure. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —O—. In some embodiments, a methylene unit is replaced with —S—. In some embodiments, a methylene unit is replaced with —N(R')—. In some embodiments, a methylene unit is replaced with —C(O)—. In some embodiments, a methylene unit is replaced with —S(O)—. In some embodiments, a methylene unit is replaced with —S(O)$_2$—. In some embodiments, a methylene unit is replaced with —P(O)(OR')—. In some embodiments, a methylene unit is replaced with —P(O)(SR')—. In some embodiments, a methylene unit is replaced with —P(O)(R')—. In some embodiments, a methylene unit is replaced with —P(O)(NR')—. In some embodiments, a methylene unit is replaced with —P(S)(OR')—. In some embodiments, a methylene unit is replaced with —P(S)(SR')—. In some embodiments, a methylene unit is replaced with —P(S)(R')—. In some embodiments, a methylene unit is replaced with —P(S)(NR')—. In some embodiments, a methylene unit is replaced with —P(R')—. In some embodiments, a methylene unit is replaced with —P(OR')—. In some embodiments, a methylene unit is replaced with —P(SR')—. In some embodiments, a methylene unit is replaced with —P(NR')—. In some embodiments, a methylene unit is replaced with —P(OR')[B(R')$_3$]—. In some embodiments, one or more methylene unit is optionally and independently substituted with —O—, —S—, —N(R')—, —C(O)—, —S(O)—, —S(O)$_2$—, —P(O)(OR')—, —P(O)(SR')—, —P(S)(OR')—, or —P(S)(OR')—. In some embodiments, a methylene unit is replaced with —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, each of which may independently be an internucleotidic linkage.

In some embodiments, L$^s$, e.g., when connected to R$^s$, is —CH$_2$—. In some embodiments, L$^s$ is —C(R)$_2$—, wherein at least one R is not hydrogen. In some embodiments, L$^s$ is —CHR—. In some embodiments, R is hydrogen. In some embodiments, L$^s$ is —CHR—, wherein R is not hydrogen. In some embodiments, C of —CHR— is chiral. In some embodiments, L$^s$ is —(R)—CHR—, wherein C of —CHR— is chiral. In some embodiments, L$^s$ is —(S)—CHR—, wherein C of —CHR— is chiral. In some embodiments, R is optionally substituted $C_{1-6}$ aliphatic. In some embodiments, R is optionally substituted $C_{1-6}$ alkyl. In some embodiments, R is optionally substituted $C_{1-5}$ aliphatic. In some embodiments, R is optionally substituted $C_{1-5}$ alkyl. In some embodiments, R is optionally substituted $C_{1-4}$ aliphatic. In some embodiments, R is optionally substituted $C_{1-4}$ alkyl. In some embodiments, R is optionally substituted $C_{1-3}$ aliphatic. In some embodiments, R is optionally substituted $C_{1-3}$ alkyl. In some embodiments, R is optionally substituted $C_2$ aliphatic. In some embodiments, R is optionally substituted methyl. In some embodiments, R is $C_{1-6}$ aliphatic. In some embodiments, R is $C_{1-6}$ alkyl. In some embodiments, R is $C_{1-5}$ aliphatic. In some embodiments, R is $C_{1-5}$ alkyl. In some embodiments, R is $C_{1-4}$ aliphatic. In some embodiments, R is $C_{1-4}$ alkyl. In some embodiments, R is $C_{1-3}$ aliphatic. In some embodiments, R is $C_{1-3}$ alkyl. In some embodiments, R is $C_2$ aliphatic. In some embodiments, R is methyl. In some embodiments, R is $C_{1-6}$ haloaliphatic. In some embodiments, R is $C_{1-6}$ haloalkyl. In some embodiments, R is $C_{1-5}$ haloaliphatic. In some embodiments, R is $C_{1-5}$ haloalkyl. In some embodiments, R is $C_{1-4}$ haloaliphatic. In some embodiments, R is $C_{1-4}$ haloalkyl. In some embodiments, R is $C_{1-3}$ haloaliphatic. In some embodiments, R is $C_{1-3}$ haloalkyl. In some embodiments, R is $C_2$ haloaliphatic. In some embodiments, R is methyl substituted with one or more halogen. In some embodiments, R is —$CF_3$. In some embodiments, $L^s$ is optionally substituted —CH=CH—. In some embodiments, $L^s$ is optionally substituted (E)-CH=CH—. In some embodiments, $L^s$ is optionally substituted (Z)—CH=CH—. In some embodiments, $L^s$ is —C≡C—.

In some embodiments, $L^s$ comprises at least one phosphorus atom. In some embodiments, at least one methylene unit of $L^s$ is replaced with —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—.

In some embodiments, $L^s$ is -Cy-. In some embodiments, -Cy- is optionally substituted monocyclic or bicyclic 3-20 membered heterocyclyl ring having 1-5 heteroatoms. In some embodiments, -Cy- is optionally substituted monocyclic or bicyclic 5-20 membered heterocyclyl ring having 1-5 heteroatoms, wherein at least one heteroatom is oxygen. In some embodiments, -Cy- is optionally substituted bivalent tetrahydrofuran ring. In some embodiments, -Cy- is an optionally substituted furanose moiety.

In some embodiments, $Cy^L$ is an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon.

In some embodiments, $Cy^L$ is monocyclic. In some embodiments, $Cy^L$ is bicyclic. In some embodiments, $Cy^L$ is polycyclic.

In some embodiments, $Cy^L$ is saturated. In some embodiments, $Cy^L$ is partially unsaturated. In some embodiments, $Cy^L$ is aromatic. In some embodiments, $Cy^L$ is or comprises a saturated ring moiety. In some embodiments, $Cy^L$ is or comprises a partially unsaturated ring moiety. In some embodiments, $Cy^L$ is or comprises an aromatic ring moiety.

In some embodiments, $Cy^L$ is an optionally substituted $C_{3-20}$ cycloaliphatic ring as described in the present disclosure (for example, those described for R but tetravalent). In some embodiments, a ring is an optionally substituted saturated $C_{3-20}$ cycloaliphatic ring. In some embodiments, a ring is an optionally substituted partially unsaturated $C_{3-20}$ cycloaliphatic ring. A cycloaliphatic ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. In some embodiments, a ring is an optionally substituted cyclopropyl moiety. In some embodiments, a ring is an optionally substituted cyclobutyl moiety. In some embodiments, a ring is an optionally substituted cyclopentyl moiety. In some embodiments, a ring is an optionally substituted cyclohexyl moiety. In some embodiments, a ring is an optionally substituted cycloheptyl moiety. In some embodiments, a ring is an optionally substituted cyclooctanyl moiety. In some embodiments, a cycloaliphatic ring is a cycloalkyl ring. In some embodiments, a cycloaliphatic ring is monocyclic. In some embodiments, a cycloaliphatic ring is bicyclic. In some embodiments, a cycloaliphatic ring is polycyclic. In some embodiments, a ring is a cycloaliphatic moiety as described in the present disclosure for R with more valences.

In some embodiments, $Cy^L$ is an optionally substituted 6-20 membered aryl ring. In some embodiments, a ring is an optionally substituted tetravalent phenyl moiety. In some embodiments, a ring is a tetravalent phenyl moiety. In some embodiments, a ring is an optionally substituted naphthalene moiety. A ring can be of different size as described in the present disclosure. In some embodiments, an aryl ring is 6-membered. In some embodiments, an aryl ring is 10-membered. In some embodiments, an aryl ring is 14-membered. In some embodiments, an aryl ring is monocyclic. In some embodiments, an aryl ring is bicyclic. In some embodiments, an aryl ring is polycyclic. In some embodiments, a ring is an aryl moiety as described in the present disclosure for R with more valences.

In some embodiments, $Cy^L$ is an optionally substituted 5-20 membered heteroaryl ring having 1-10 heteroatoms independently selected from oxygen, nitrogen, sulfur, phosphorus and silicon. In some embodiments, $Cy^L$ is an optionally substituted 5-20 membered heteroaryl ring having 1-10 heteroatoms independently selected from oxygen, nitrogen, and sulfur. In some embodiments, as described in the present disclosure, heteroaryl rings can be of various sizes and contain various numbers and/or types of heteroatoms. In some embodiments, a heteroaryl ring contains no more than one heteroatom. In some embodiments, a heteroaryl ring contains more than one heteroatom. In some embodiments, a heteroaryl ring contains no more than one type of heteroatom. In some embodiments, a heteroaryl ring contains more than one type of heteroatoms. In some embodiments, a heteroaryl ring is 5-membered. In some embodiments, a heteroaryl ring is 6-membered. In some embodiments, a heteroaryl ring is 8-membered. In some embodiments, a heteroaryl ring is 9-membered. In some embodiments, a heteroaryl ring is 10-membered. In some embodiments, a heteroaryl ring is monocyclic. In some embodiments, a heteroaryl ring is bicyclic. In some embodiments, a heteroaryl ring is polycyclic. In some embodiments, a heteroaryl ring is a nucleobase moiety, e.g., A, T, C, G, U, etc. In some embodiments, a ring is a heteroaryl moiety as described in the present disclosure for R with more valences.

In some embodiments, $Cy^L$ is a 3-20 membered heterocyclyl ring having 1-10 heteroatoms independently selected from oxygen, nitrogen, sulfur, phosphorus and silicon. In some embodiments, $Cy^L$ is a 3-20 membered heterocyclyl ring having 1-10 heteroatoms independently selected from oxygen, nitrogen, and sulfur. In some embodiments, a heterocyclyl ring is saturated. In some embodiments, a heterocyclyl ring is partially unsaturated. A heterocyclyl ring can be of various sizes as described in the present disclosure. In some embodiments, a ring is 3, 4, 5, 6, 7, 8, 9, or 10-membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is 9-membered. In some embodiments, a ring is 10-membered. Heterocyclyl rings can contain various numbers and/or types of heteroatoms. In some embodiments, a heterocyclyl ring contains no more than one heteroatom. In some embodiments, a heterocyclyl ring contains more than one heteroatom. In some embodiments, a heterocyclyl ring contains no more than one type of heteroatom. In some embodiments, a heterocyclyl ring contains more than one type of heteroatoms. In some embodiments, a heterocyclyl ring is monocyclic. In some embodiments, a heterocyclyl ring is bicyclic. In some embodiments, a heterocyclyl ring is polycyclic. In some embodiments, a ring is a heterocyclyl moiety as described in the present disclosure for R with more valences.

As readily appreciated by a person having ordinary skill in the art, many suitable ring moieties are extensively described in and can be used in accordance with the present disclosure, for example, those described for R (which may have more valences for $Cy^L$).

In some embodiments, $Cy^L$ is a sugar moiety in a nucleic acid. In some embodiments, $Cy^L$ is an optionally substituted furanose moiety. In some embodiments, $Cy^L$ is a pyranose moiety. In some embodiments, $Cy^L$ is an optionally substituted furanose moiety found in DNA. In some embodiments, $Cy^L$ is an optionally substituted furanose moiety found in RNA. In some embodiments, $Cy^L$ is an optionally substituted 2'-deoxyribofuranose moiety. In some embodiments, $Cy^L$ is an optionally substituted ribofuranose moiety. In some embodiments, substitutions provide sugar modifications as described in the present disclosure. In some embodiments, an optionally substituted 2'-deoxyribofuranose moiety and/or an optionally substituted ribofuranose moiety comprise substitution at a 2'-position. In some embodiments, a 2'-position is a 2'-modification as described in the present disclosure. In some embodiments, a 2'-modification is —F. In some embodiments, a 2'-modification is —OR, wherein R is as described in the present disclosure. In some embodiments, R is not hydrogen. In some embodiments, $Cy^L$ is a modified sugar moiety, such as a sugar moiety in LNA. In some embodiments, $Cy^L$ is a modified sugar moiety, such as a sugar moiety in ENA. In some embodiments, $Cy^L$ is a terminal sugar moiety of an oligonucleotide, connecting an internucleotidic linkage and a nucleobase. In some embodiments, $Cy^L$ is a terminal sugar moiety of an oligonucleotide, for example, when that terminus is connected to a solid support optionally through a linker. In some embodiments, $Cy^L$ is a sugar moiety connecting two internucleotidic linkages and a nucleobase. Example sugars and sugar moieties are extensively described in the present disclosure.

In some embodiments, $Cy^L$ is a nucleobase moiety. In some embodiments, a nucleobase is a natural nucleobase, such as A, T, C, G, U, etc. In some embodiments, a nucleobase is a modified nucleobase. In some embodiments, $Cy^L$ is optionally substituted nucleobase moiety selected from A, T, C, G, U, and 5 mC. Example nucleobases and nucleobase moieties are extensively described in the present disclosure.

In some embodiments, two $Cy^L$ moieties are bonded to each other, wherein one $Cy^L$ is a sugar moiety and the other is a nucleobase moiety. In some embodiments, such a sugar moiety and nucleobase moiety forms a nucleoside moiety. In some embodiments, a nucleoside moiety is natural. In some embodiments, a nucleoside moiety is modified. In some embodiments, $Cy^L$ is an optionally substituted natural nucleoside moiety selected from adenosine, 5-methyluridine, cytidine, guanosine, uridine, 5-methylcytidine, 2'-deoxyadenosine, thymidine, 2'-deoxycytidine, 2'-deoxyguanosine, 2'-deoxyuridine, and 5-methyl-2'-deoxycytidine. Example nucleosides and nucleosides moieties are extensive described in the present disclosure.

In some embodiments, for example in $L^s$, $Cy^L$ is an optionally substituted nucleoside moiety bonded to an internucleotidic linkage, for example, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, —OP(OR')[B(R')$_3$]O—, etc., which may form an optionally substituted nucleotidic unit. Example nucleotides and nucleosides moieties are extensive described in the present disclosure.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is —(CH$_2$)$_2$CN.

In some embodiments, R is optionally substituted C$_{3-30}$ cycloaliphatic. In some embodiments, R is optionally substituted C$_{3-20}$ cycloaliphatic. In some embodiments, R is optionally substituted C$_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted C$_{1-30}$ heteroaliphatic having 1-10 heteroatoms independently selected from oxygen, nitrogen, sulfur, phosphorus and silicon. In some embodiments, R is optionally substituted C$_{1-20}$ heteroaliphatic having 1-10 heteroatoms. In some embodiments, R is optionally substituted C$_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted C$_{1-30}$ heteroaliphatic comprising 1-10 groups independently selected from

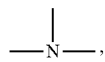

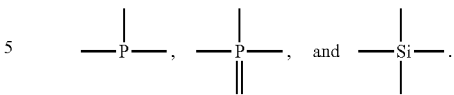

In some embodiments, R is optionally substituted C$_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydropyranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, $P^L$ is $P(=W)$. In some embodiments, $P^L$ is P. In some embodiments, $P^L$ is $P \to B(R')_3$. In some embodiments, P of $P^L$ is chiral. In some embodiments, P of $P^L$ is Rp. In some embodiments, P of $P^L$ is Sp. In some embodiments, a linkage of formula VII is a phosphate linkage or a salt form thereof. In some embodiments, a linkage of formula VII is a phosphorothioate linkage or a salt form thereof.

In some embodiments, $L^7$ is —O— or —S—. In some embodiments, $L^7$ is —O—. In some embodiments, $L^7$ is —S—.

In some embodiments, $L^8$ is -L-O—, -L-C($R^1$)($R^2$)—O—, or -$L^s$-O—, wherein each variable is independently as described in the present disclosure. In some embodiments, $L^8$ is -L-O, wherein L is as described in the present disclosure. In some embodiments, $L^8$ is -L-C($R^1$)($R^2$)—O—, wherein each variable is independently as described in the present disclosure. In some embodiments, $L^8$ is -$L^s$-O—, wherein $L^s$ is as described in the present disclosure.

In some embodiments, provided compounds, e.g., compounds of formula I, I-a, I-a-1, I-a-2, I-b, I-c, I-d, I-e, II, II-a, II-b, III, III-a, or III-b, or salts thereof, may be utilized to prepare other compounds which incorporate their chiral elements. In some embodiments, provide compounds of formula I, I-a, I-a-1, I-a-2, I-b, I-c, I-d, I-e, II, II-a, II-b, III, III-a, or III-b, or salts thereof, are incorporated into other compounds, e.g., compounds of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof, as chiral auxiliaries so that such other compounds can be further utilized for stereoselective synthesis of, e.g., oligonucleotides (e.g., of formula VIII) comprising internucleotidic linkages having the structure of formula VII, VII-a-1, VII-a-2, VII-b, VII-c, VII-d, or VII-e, or a salt form thereof. In some embodiments, provided compounds, e.g., compounds of formula I, I-a, I-a-1, I-a-2, I-b, I-c, I-d, I-e, II, II-a, II-b, III, III-a, or III-b, or salts thereof, optionally activated, react with nucleosides or derivatives thereof to provide phosphoramidites for oligonucleotide preparation. In some embodiments, provided phosphoramidites have the structure of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof. In some embodiments, provided phosphoramidites have the structure of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof. In some embodiments, provided compounds, e.g., phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof have purifies, diastereopurities, and/or enantiopurities as described in the present disclosure. In some embodiments, provided compounds, e.g., phosphoramidites of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or salts thereof have purities, diastereopurities, and/or enantiopurities as described in the present disclosure.

In some embodiments, BA is an optionally substituted group selected from $C_{3-30}$ cycloaliphatic, $C_{6-30}$ aryl, $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, $C_{3-30}$ heterocyclyl having 1-10 heteroatoms independently selected from oxygen, nitrogen, sulfur, phosphorus and silicon, a natural nucleobase moiety, and a modified nucleobase moiety. In some embodiments, BA is an optionally substituted group selected from $C_{5-30}$ heteroaryl having 1-10 heteroatoms independently selected from oxygen, nitrogen, sulfur, phosphorus and silicon, a natural nucleobase moiety, and a modified nucleobase moiety. In some embodiments, BA is optionally substituted $C_{5-30}$ heteroaryl having 1-10 heteroatoms independently selected from oxygen, nitrogen, and sulfur. In some embodiments, BA is optionally substituted natural nucleobases and tautomers thereof. In some embodiments, BA is protected natural nucleobases and tautomers thereof. Various nucleobase protecting groups for oligonucleotide synthesis are known and can be utilized in accordance with the present disclosure. In some embodiments, BA is an optionally substituted nucleobase selected from adenine, cytosine, guanosine, thymine, and uracil, and tautomers thereof. In some embodiments, BA is an optionally protected nucleobase selected from adenine, cytosine, guanosine, thymine, and uracil, and tautomers thereof.

In some embodiments, BA is optionally substituted $C_{3-30}$ cycloaliphatic. In some embodiments, BA is optionally substituted $C_{6-30}$ aryl. In some embodiments, BA is optionally substituted $C_{3-30}$ heterocyclyl. In some embodiments, BA is optionally substituted $C_{5-30}$ heteroaryl. In some embodiments, BA is an optionally substituted natural base moiety. In some embodiments, BA is an optionally substituted modified base moiety. BA is an optionally substituted group selected from $C_{3-30}$ cycloaliphatic, $C_{6-30}$ aryl, $C_{3-30}$ heterocyclyl, and $C_{5-30}$ heteroaryl. In some embodiments, BA is an optionally substituted group selected from $C_{3-30}$ cycloaliphatic, $C_{6-30}$ aryl, $C_{3-30}$ heterocyclyl, $C_{5-30}$ heteroaryl, and a natural nucleobase moiety.

In some embodiments, BA is connected to SU through an aromatic ring. In some embodiments, BA is connected to SU through a heteroatom. In some embodiments, BA is connected to SU through a ring heteroatom of an aromatic ring. In some embodiments, BA is connected to SU through a ring nitrogen atom of an aromatic ring.

In some embodiments, BA is a natural nucleobase moiety. In some embodiments, BA is an optionally substituted natural nucleobase moiety. In some embodiments, BA is a substituted natural nucleobase moiety. In some embodiments, BA is natural nucleobase A, T, C, U, or G. In some embodiments, BA is an optionally substituted group selected from natural nucleobases A, T, C, U, and G.

In some embodiments, BA is an optionally substituted group, which group is formed by removing a —H from

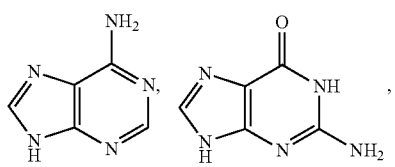

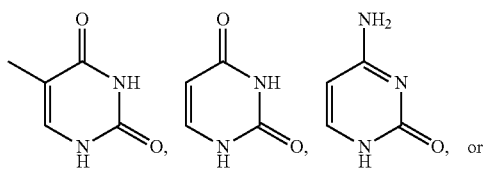

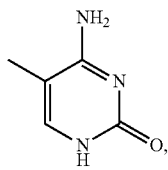

or a tautomer thereof. In some embodiments, BA is an optionally substituted group, which group is formed by removing a —H from

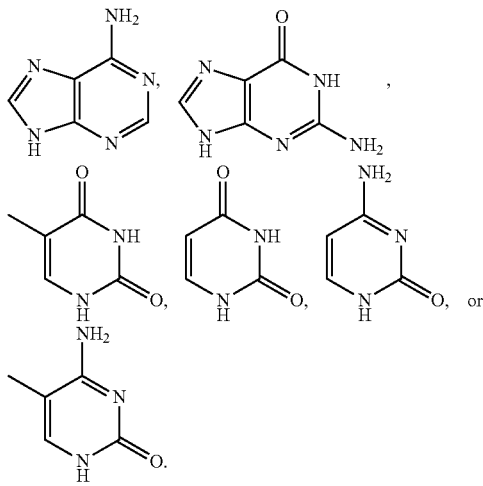

In some embodiments, BA is an optionally substituted group which group is selected from

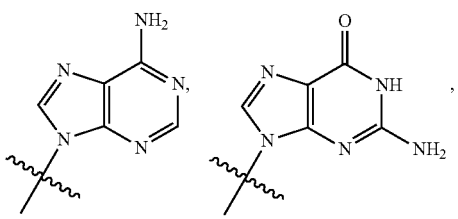

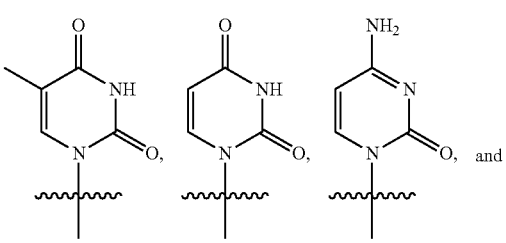

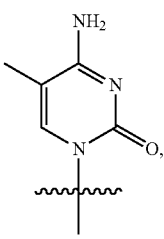

and tautomeric forms thereof. In some embodiments, BA is an optionally substituted group which group is selected from

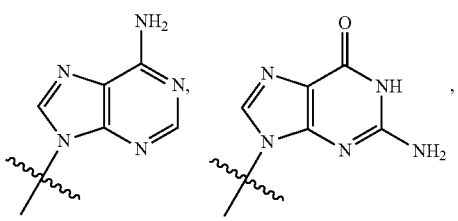

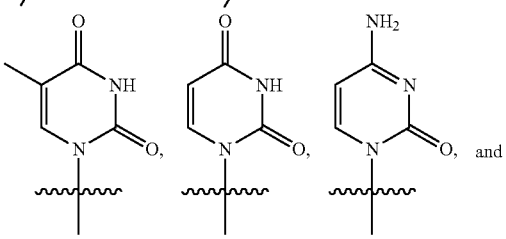

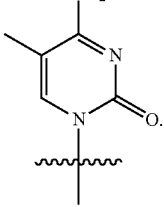

In some embodiments, BA is an optionally substituted group, which group is formed by removing a —H from

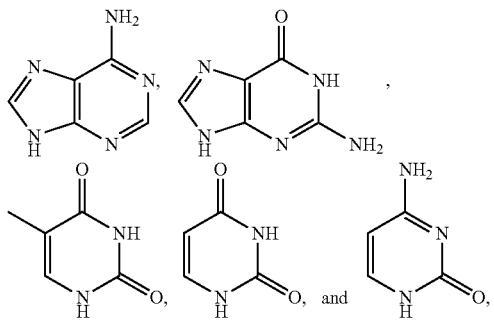

and tautomers thereof. In some embodiments, BA is an optionally substituted group, which group is formed by removing a —H from

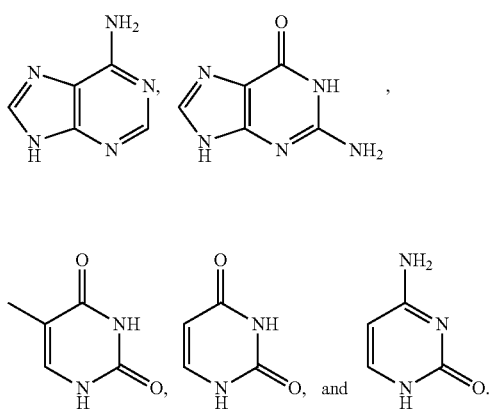

In some embodiments, BA is an optionally substituted group which group is selected from

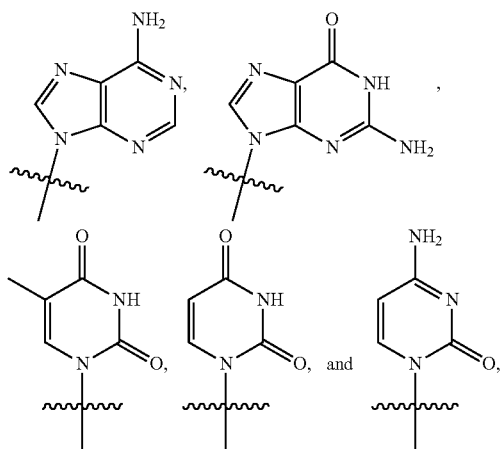

and tautomeric forms thereof. In some embodiments, BA is an optionally substituted group which group is selected from

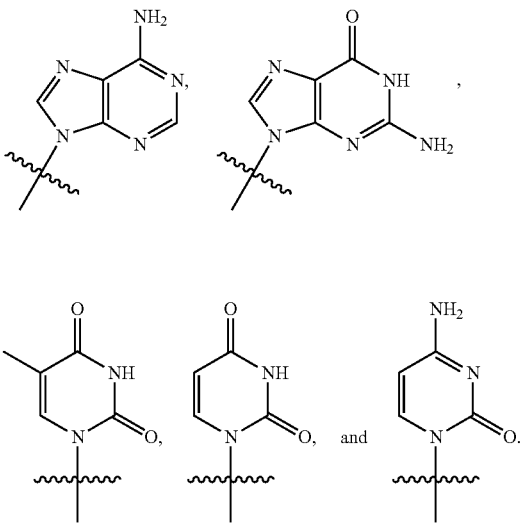

In some embodiments, BA is optionally substituted

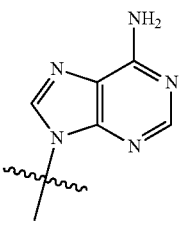

or a tautomeric form thereof. In some embodiments, BA is optionally substituted

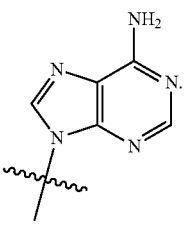 [SMILES: *n1cnc2c(N)ncnc21]

In some embodiments, BA is optionally substituted

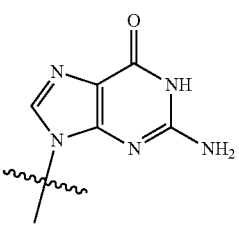 [SMILES: *n1cnc2c(=O)[nH]c(N)nc21]

or a tautomeric form thereof. In some embodiments, BA is optionally substituted

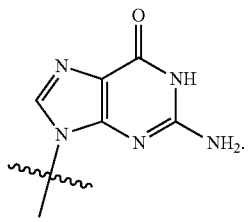 [SMILES: *n1cnc2c(=O)[nH]c(N)nc21]

In some embodiments, BA is optionally substituted

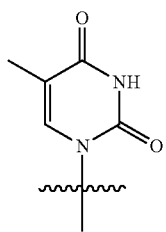 [SMILES: *n1cc(C)c(=O)[nH]c1=O]

or a tautomeric form thereof. In some embodiments, BA is optionally substituted

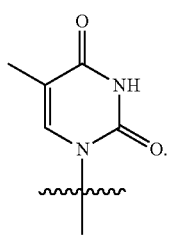 [SMILES: *n1cc(C)c(=O)[nH]c1=O]

In some embodiments, BA is optionally substituted

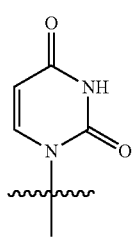 [SMILES: *n1ccc(=O)[nH]c1=O]

or a tautomeric form thereof. In some embodiments, BA is optionally substituted

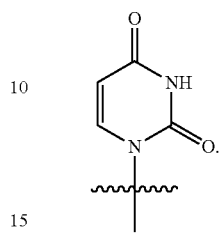

In some embodiments, BA is optionally substituted

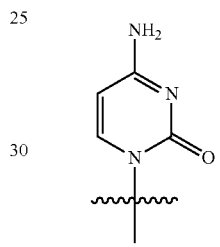

or a tautomeric form thereof. In some embodiments, BA is optionally substituted

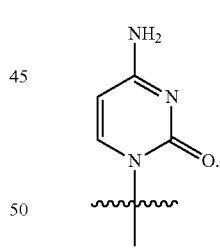

In some embodiments, BA is

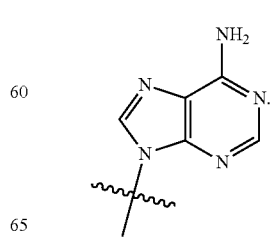

In some embodiments, BA is

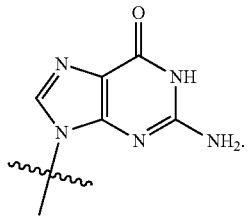

In some embodiments, BA is

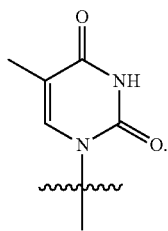

In some embodiments, BA is

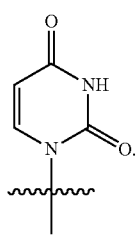 [SMILES: *n1ccc(=O)[nH]c1=O]

In some embodiments, BA is

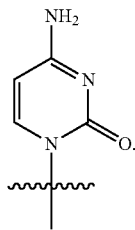 [SMILES: *n1ccc(N)nc1=O]

In some embodiments, BA of the 5'-end nucleoside unit of a provided oligonucleotide, e.g., an oligonucleotide of formula VIII, is an optionally substituted group, which group is formed by removing a —H from

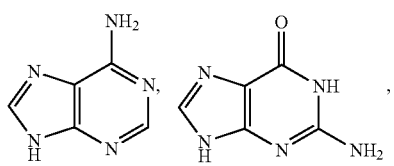

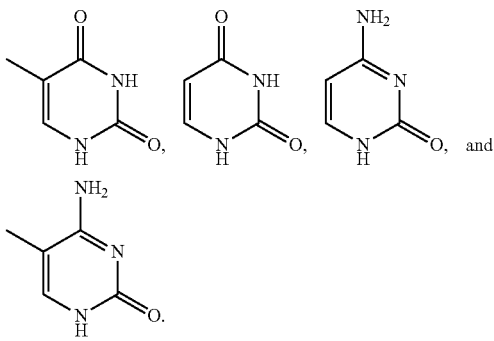

In some embodiments, BA of the 5'-end nucleoside unit is an optionally substituted group which group is selected from

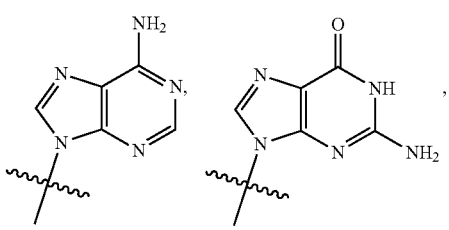

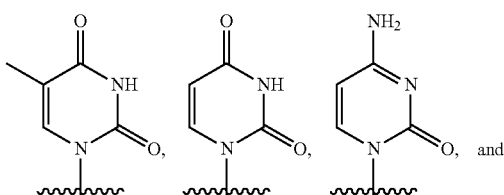

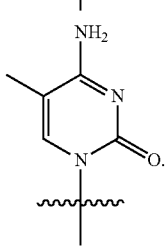

In some embodiments, BA of the 5'-end nucleoside unit is an optionally substituted group, which group is formed by removing a —H from

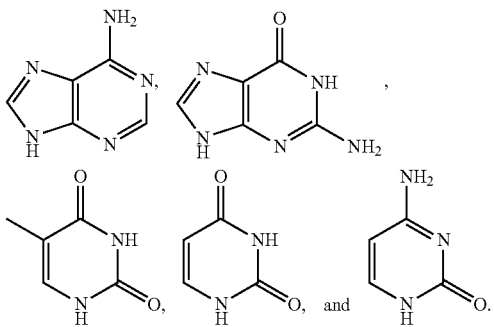

In some embodiments, BA of the 5'-end nucleoside unit is an optionally substituted group which group is selected from

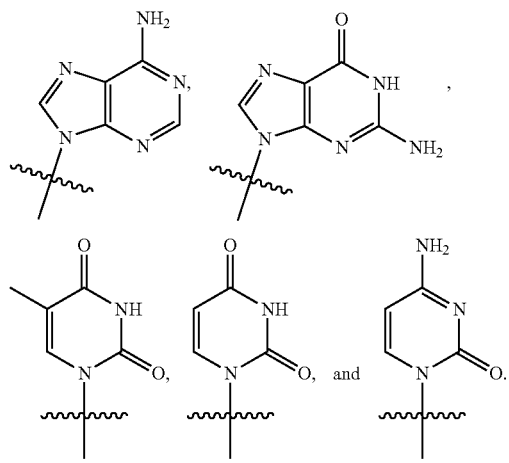

In some embodiments, BA of the 5'-end nucleoside unit is optionally substituted

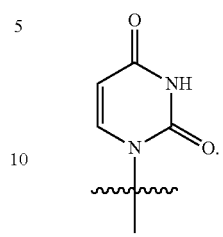

In some embodiments, BA of the 5'-end nucleoside unit is optionally substituted

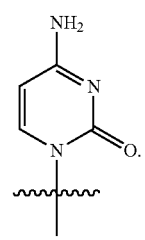

In some embodiments, BA of the 5'-end nucleoside unit is optionally substituted

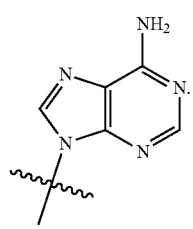 [SMILES: *n1cnc2c(N)ncnc21]

In some embodiments, BA of the 5'-end nucleoside unit is optionally substituted

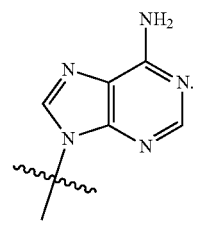 [SMILES: *n1cnc2c(N)ncnc21]

In some embodiments, BA of the 5'-end nucleoside unit is

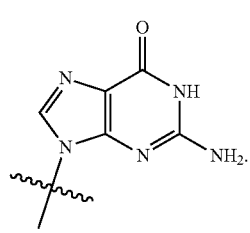 [SMILES: *n1cnc2c(=O)[nH]c(N)nc21]

In some embodiments, BA of the 5'-end nucleoside unit is optionally substituted

In some embodiments, BA of the 5'-end nucleoside unit is

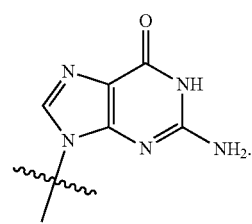

In some embodiments, BA of the 5'-end nucleoside unit is

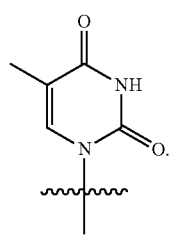 [SMILES: *n1cc(C)c(=O)[nH]c1=O]

In some embodiments, BA of the 5'-end nucleoside unit is

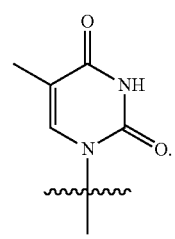

In some embodiments, BA of the 5'-end nucleoside unit is
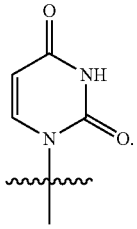
In some embodiments, BA of the 5'-end nucleoside unit is
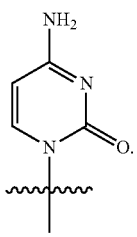
In some embodiments, BA is
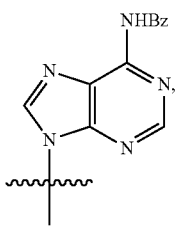 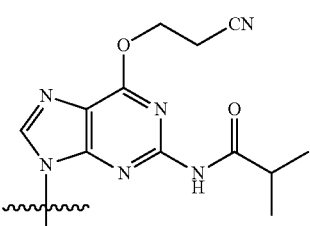,
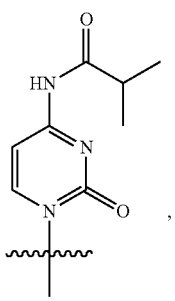 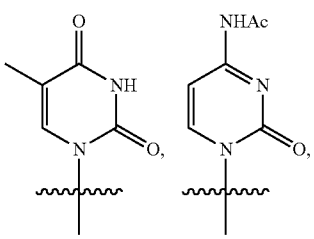
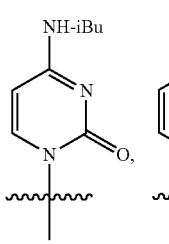 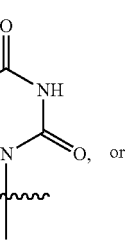 or
-continued
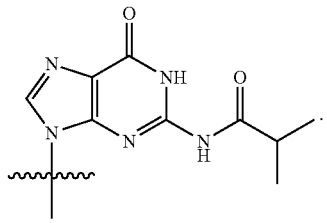
In some embodiments, BA is
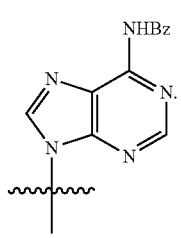
In some embodiments, BA is
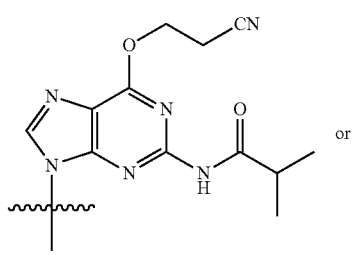 or
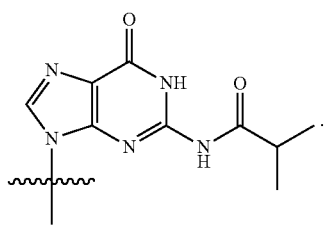
In some embodiments, BA is
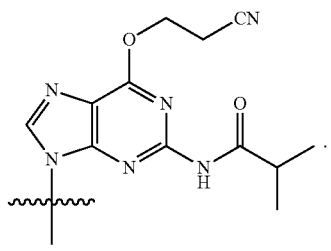 [SMILES: *n1cnc2c(OCCC#N)nc(NC(=O)C(C)C)nc21]

In some embodiments, BA is

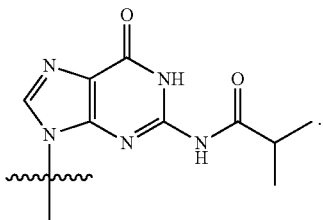 [SMILES: *n1cnc2c(=O)[nH]c(NC(=O)C(C)C)nc21]

In some embodiments, BA is

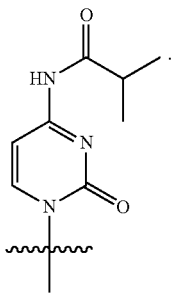 [SMILES: *n1ccc(NC(=O)C(C)C)nc1=O]

In some embodiments, BA is

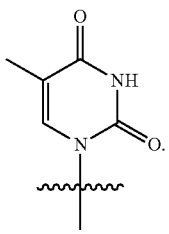 [SMILES: *n1cc(C)c(=O)[nH]c1=O]

In some embodiments, BA is

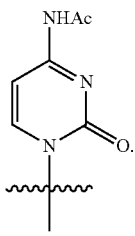

In some embodiments, BA is

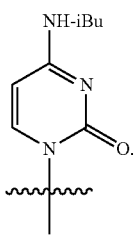

In some embodiments, BA is

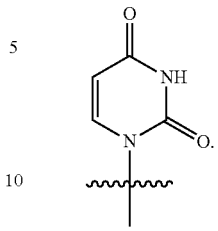

In some embodiments, a protection group is —Ac. In some embodiments, a protection group is —Bz. In some embodiments, a protection group is -iBu for nucleobase.

In some embodiments, BA is an optionally substituted purine base residue. In some embodiments, BA is a protected purine base residue. In some embodiments, BA is an optionally substituted adenine residue. In some embodiments, BA is a protected adenine residue. In some embodiments, BA is an optionally substituted guanine residue. In some embodiments, BA is a protected guanine residue. In some embodiments, BA is an optionally substituted cytosine residue. In some embodiments, BA is a protected cytosine residue. In some embodiments, BA is an optionally substituted thymine residue. In some embodiments, BA is a protected thymine residue. In some embodiments, BA is an optionally substituted uracil residue. In some embodiments, BA is a protected uracil residue. In some embodiments, BA is an optionally substituted 5-methylcytosine residue. In some embodiments, BA is a protected 5-methylcytosine residue.

In some embodiments, BA is a protected base residue as used in oligonucleotide preparation. In some embodiments, BA is a base residue illustrated in US 2011/0294124, US 2015/0211006, US 2015/0197540, and WO 2015/107425, each of which is incorporated herein by reference.

Those skilled in the art appreciate that a variety of modified nucleobases are suitable for use in accordance with the present disclosure in, for example, compounds of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, VI-e, or VIII, or salts thereof. Example modified bases include but are not limited to those limited in WO/2011/005761, WO/2013/012758, WO/2014/012081, WO/2015/107425, WO/2010/064146, WO/2014/010250, WO/2011/108682, WO/2012/039448, and WO/2012/073857, modified nucleobases of each of which are hereby incorporated by reference.

In some embodiments, BA is a substituted/protected nucleobase so that the phosphoramidite is properly protected with one or more protecting groups and can be used for oligonucleotide synthesis. Suitable protecting groups for nucleobases are widely known, including those useful for oligonucleotide synthesis, and can be utilized in accordance with the present disclosure. In some embodiments, a protecting group is acetyl (Ac), phenylacetyl, benzoyl (Bz), isobutyryl (iBu), phenoxyacetyl (Pac), isopropyl-Pac, tert-butyl-Pac, alkyl-Pac, dimethylformamidine (DMF), or dialkylformamidine. In some embodiments, a protecting group is phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). For additional suitable protecting groups, see Green and Wuts, Protective Groups in Organic Synthesis, 2nd Ed., John Wiley & Sons, New York, 1991, and WO/2011/005761, WO/2013/012758, WO/2014/012081, WO/2015/107425, WO/2010/064146, WO/2014/010250, WO/2011/108682, WO/2012/039448, and WO/2012/073857.

In some embodiments, SU is $-L^s-O-$ or

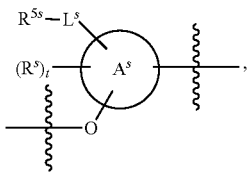

wherein SU is connected to the phosphorus atom through the oxygen atom. In some embodiments, SU is sugar moiety. In some embodiments, SU is a sugar moiety as used in oligonucleotides. In some embodiments, SU is a modified sugar moiety as used in oligonucleotides.

In some embodiments, SU is a sugar moiety or modified sugar moiety in natural or unnatural nucleosides, nucleotides, and/or oligonucleotides.

In some embodiments, SU is $-L^s-O-$, wherein SU is connected to the phosphorus atom through the oxygen atom.

In some embodiments, SU is $-L^s-O-$. In some embodiments, $L^s$ is -Cy-. In some embodiments, $L^s$ is optionally substituted 3-30 membered carbocyclylene. In some embodiments, $L^s$ is optionally substituted 6-30 membered arylene. In some embodiments, $L^s$ is optionally substituted 5-30 membered heteroarylene having 1-10 heteroatoms independently selected from oxygen, nitrogen and sulfur. In some embodiments, $L^s$ is optionally substituted 5-30 membered heteroarylene having 1-5 heteroatoms independently selected from oxygen, nitrogen and sulfur. In some embodiments, $L^s$ is optionally substituted 3-30 membered heterocyclylene having 1-10 heteroatoms independently selected from oxygen, nitrogen, sulfur, phosphorus and silicon. In some embodiments, $L^s$ is optionally substituted 3-30 membered heterocyclylene having 1-5 heteroatoms independently selected from oxygen, nitrogen, sulfur, phosphorus and silicon. In some embodiments, $L^s$ is optionally substituted 5-30 membered heterocyclylene having 1-10 heteroatoms independently selected from oxygen, nitrogen, sulfur, phosphorus and silicon. In some embodiments, $L^s$ is optionally substituted 5-30 membered heterocyclylene having 1-5 heteroatoms independently selected from oxygen, nitrogen, sulfur, phosphorus and silicon. In some embodiments, $L^s$ is optionally substituted 5-10 membered heterocyclylene having one oxygen atom. In some embodiments, $L^s$ is optionally substituted 5-membered heterocyclylene having one oxygen atom. In some embodiments, $L^s$ is optionally substituted 6-membered heterocyclylene having one oxygen atom. In some embodiments, $L^s$ is optionally substituted 5-10 membered bicyclic heterocyclylene having one or two oxygen atoms. In some embodiments, $L^s$ is optionally substituted 7-10 membered bicyclic heterocyclylene having one or two oxygen atoms. In some embodiments, $L^s$ is optionally substituted 7-10 membered bicyclic heterocyclylene having two oxygen atoms. In some embodiments, $L^s$ is optionally substituted 7-membered bicyclic heterocyclylene having two oxygen atoms.

In some embodiments, SU is a sugar moiety used in oligonucleotide synthesis. A person of ordinary skill in the art understands that phosphoramidites with a variety of sugar moieties can benefit from improved yields and/or purity when provided technologies are utilized for their preparation. In some embodiments, SU is an optionally substituted saturated monocyclic, bicyclic or polycyclic saturated aliphatic ring wherein one or more methylene units are replaced with $-O-$. In some embodiments, SU is a ribose or deoxyribose moiety found in natural DNA or RNA molecules.

In some embodiments, SU is

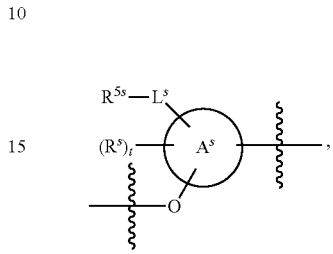

wherein each variable is independently as described in the present disclosure, and wherein SU is connected to the phosphorus atom through the oxygen atom.

In some embodiments, Ring $A^s$ is

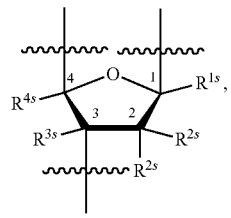

BA is connected at C1, and each of $R^{1s}$, $R^{2s}$, $R^{3s}$, $R^{4s}$ and $R^{5s}$ is independently $R^5$. In some embodiments, Ring $A^s$ is

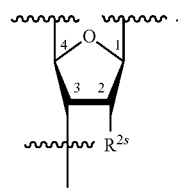

In some embodiments, Ring $A^s$ is

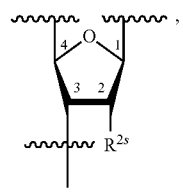

wherein $R^{2s}$ is not —OH. In some embodiments, Ring $A^s$ is

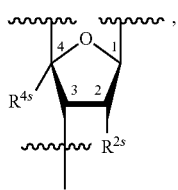

wherein $R^{2s}$ and $R^{4s}$ are R, and the two R groups are taken together with their intervening atoms to form an optionally substituted ring. In some embodiments, Ring $A^s$ is optionally substituted

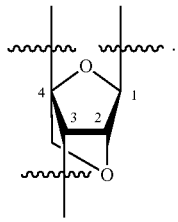 [SMILES: *[C@@H]1O[C@@]2(*)COC1[C@H]2*]

In some embodiments, Ring $A^s$ is

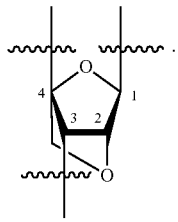 [SMILES: *[C@@H]1O[C@@]2(*)COC1[C@H]2*]

In some embodiments, Ring $A^s$ is

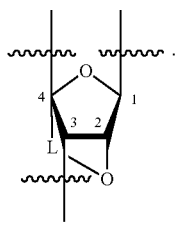

In some embodiments, SU is

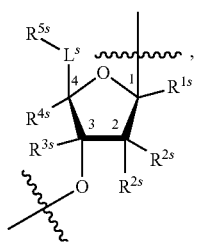

wherein each variable is independently as described in the present disclosure. In some embodiments, SU is

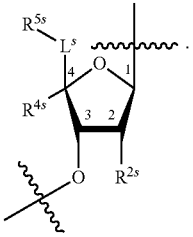

In some embodiments, SU is

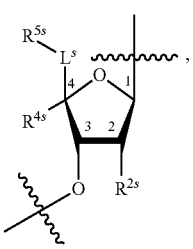

wherein $R^{4s}$ and $R^{2s}$ are taken together to form an optionally substituted ring. In some embodiments, SU is

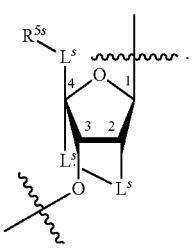

In some embodiments, SU is

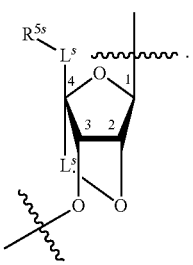

In some embodiments, SU is

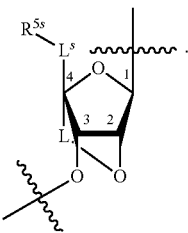

In some embodiments, SU is

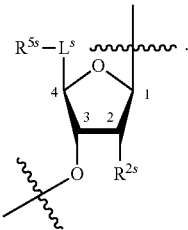

In some embodiments, $L^s$ is optionally substituted —O—CH$_2$—. In some embodiments, $L^s$ is optionally substituted —O—CH$_2$—, wherein the oxygen atom connects to les. In some embodiments, $L^s$ is optionally substituted —O—C(R)$_2$—, wherein the oxygen atom connects to $R^{5s}$. In some embodiments, $L^s$ is optionally substituted —O—CHR—, wherein the oxygen atom connects to $R^{5s}$. In some embodiments, SU is

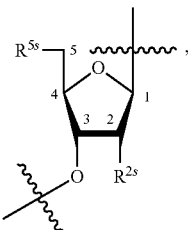

In some embodiments, SU is a modified sugar having the structure of:

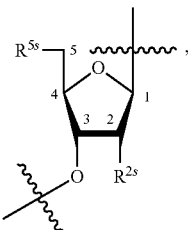

wherein $R^{5s}$ is —OR'; and $R^{2s}$ is —F, —CN, —N$_3$, —NO, —NO$_2$, —R', —OR', —SR', —N(R')$_2$, —O-L-OR', —O-L-SR', or —O-L-N(R')$_2$. In some embodiments, $R^{2s}$ and $R^{4s}$ are taken together to form an optionally substituted ring, and -$L^s$-connects C2 with C1, C2, C3, C4 or C5. In some embodiments, $R^{2s}$ is —H. In some embodiments, $R^{2s}$ is —F.

In some embodiments, $R^{2s}$ is —OMe. In some embodiments, $R^{2s}$ is —OCH$_2$CH$_2$OMe.

In some embodiments, SU is

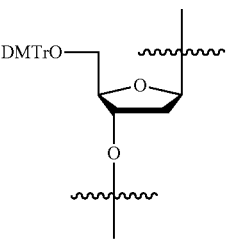

In some embodiments, SU is

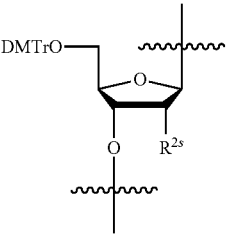

In some embodiments, SU is

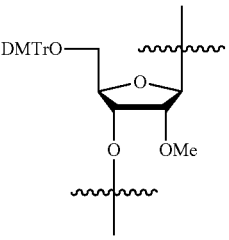

In some embodiments, SU is

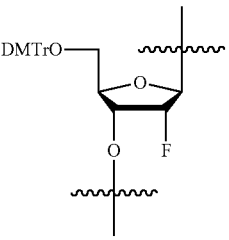

In some embodiments, SU is

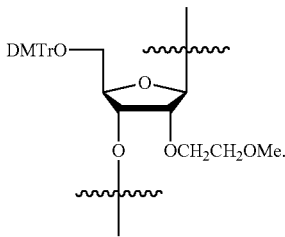

In some embodiments, a sugar moiety in a provided compound, e.g., a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or salts thereof, an oligonucleotide of formula VIII or a salt thereof, is a modified sugar moiety as described in the present disclosure.

In some embodiments, one or more hydroxyl group in a sugar moiety is optionally and independently replaced with halogen, —R'—N(R')$_2$, —OR', or —SR', wherein each R' is independently as defined above and described herein.

In some embodiments, each $R^s$ is independently —H, halogen, —CN, —N$_3$, —NO, —NO$_2$, -L$^s$-R', -L$^s$-Si(R)$_3$, -L$^s$-OR', -L$^s$-SR', -L$^s$-N(R')$_2$, —O-L$^s$-Si(R)$_3$, —O-L$^s$-OR', —O-L$^s$-SR', or —O-L$^s$-N(R')$_2$.

In some embodiments, $R^s$ is R'. In some embodiments, $R^s$ is R. In some embodiments, $R^s$ is optionally substituted C$_{1-30}$ heteroaliphatic. In some embodiments, $R^s$ comprises one or more silicon atoms. In some embodiments, $R^s$ is —CH$_2$Si(Ph)$_2$CH$_3$.

In some embodiments, $R^s$ is -L$^s$-R'. In some embodiments, $R^s$ is -L$^s$-R' wherein -L$^s$- is a bivalent, optionally substituted C$_{1-30}$ heteroaliphatic group. In some embodiments, $R^s$ is —CH$_2$Si(Ph)$_2$CH$_3$.

In some embodiments, $R^s$ is —F. In some embodiments, $R^s$ is —Cl. In some embodiments, $R^s$ is —Br. In some embodiments, $R^s$ is —I. In some embodiments, $R^s$ is —CN. In some embodiments, $R^s$ is —N$_3$. In some embodiments, $R^s$ is —NO. In some embodiments, $R^s$ is —NO$_2$. In some embodiments, $R^s$ is -L$^s$-Si(R)$_3$. In some embodiments, $R^s$ is —Si(R)$_3$. In some embodiments, $R^s$ is -L$^s$-R'. In some embodiments, $R^s$ is —R'. In some embodiments, $R^s$ is -L$^s$-OR'. In some embodiments, $R^s$ is —OR'. In some embodiments, $R^s$ is -L$^s$-SR'. In some embodiments, $R^s$ is —SR'. In some embodiments, $R^s$ is -L$^s$-N(R')$_2$. In some embodiments, $R^s$ is —N(R')$_2$. In some embodiments, $R^s$ is —O-L$^s$-R'. In some embodiments, $R^s$ is —O-L$^s$-Si(R)$_3$. In some embodiments, $R^s$ is —O-L$^s$-OR'. In some embodiments, $R^s$ is —O-L$^s$-SR'. In some embodiments, $R^s$ is —O-L$^s$-N(R')$_2$. In some embodiments, $R^s$ is a 2'-modification as described in the present disclosure. In some embodiments, $R^s$ is —OR, wherein R is as described in the present disclosure. In some embodiments, $R^s$ is —OR, wherein R is optionally substituted C$_{1-6}$ aliphatic. In some embodiments, $R^s$ is —OMe. In some embodiments, $R^s$ is —OCH$_2$CH$_2$OMe.

In some embodiments, t is 0-20. In some embodiments, t is 1-20. In some embodiments, t is 1-5. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, each of $R^{1s}$, $R^{2s}$, $R^{3s}$, $R^{4s}$, and $R^{5s}$ is independently $R^s$, wherein $R^s$ is as described in the present disclosure.

In some embodiments, $R^{1s}$ is $R^s$ at a 1'-position (BA is at 1'-position). In some embodiments, $R^s$ at a 1'-position is —F. In some embodiments, $R^s$ at a 1'-position is —Cl. In some embodiments, $R^s$ at a 1'-position is —Br. In some embodiments, $R^s$ at a 1'-position is —I. In some embodiments, $R^s$ at a 1'-position is —CN. In some embodiments, $R^s$ at a 1'-position is —N$_3$. In some embodiments, $R^s$ at a 1'-position is —NO. In some embodiments, $R^s$ at a 1'-position is —NO$_2$. In some embodiments, $R^s$ at a 1'-position is -L-R'. In some embodiments, $R^s$ at a 1'-position is —R'. In some embodiments, $R^s$ at a 1'-position is -L-OR'. In some embodiments, $R^s$ at a 1'-position is —OR'. In some embodiments, $R^s$ at a 1'-position is -L-SR'. In some embodiments, $R^s$ at a 1'-position is —SR'. In some embodiments, $R^s$ at a 1'-position is L-L-N(R')$_2$. In some embodiments, $R^s$ at a 1'-position is —N(R')$_2$. In some embodiments, $R^s$ at a 1'-position is —OR', wherein R' is optionally substituted C$_{1-6}$ aliphatic. In some embodiments, $R^s$ at a 1'-position is —OR', wherein R' is optionally substituted C$_{1-6}$ alkyl. In some embodiments, $R^s$ at a 1'-position is —OMe. In some embodiments, $R^s$ at a 1'-position is -MOE. In some embodiments, $R^s$ at a 1'-position is hydrogen. In some embodiments, $R^s$ at one 1'-position is hydrogen, and $R^s$ at the other 1'-position is not hydrogen as described herein. In some embodiments, $R^s$ at both 1'-positions are hydrogen. In some embodiments, $R^s$ at one 1'-position is hydrogen, and the other 1'-position is connected to an internucleotidic linkage. In some embodiments, $R^{1s}$ is —F. In some embodiments, $R^{1s}$ is —Cl. In some embodiments, $R^{1s}$ is —Br. In some embodiments, $R^s$ is —I. In some embodiments, $R^{1s}$ is —CN. In some embodiments, $R^{1s}$ is —N$_3$. In some embodiments, $R^{1s}$ is —NO. In some embodiments, $R^{1s}$ is —NO$_2$. In some embodiments, $R^{1s}$ is -L-R'. In some embodiments, $R^{1s}$ is —R'. In some embodiments, $R^{1s}$ is -L-OR'. In some embodiments, $R^{1s}$ is —OR'. In some embodiments, $R^{1s}$ is -L-SR'. In some embodiments, $R^{1s}$ is —SR'. In some embodiments, $R^{1'}$ is -L-N(R')$_2$. In some embodiments, $R^{1s}$ is —N(R')$_2$. In some embodiments, $R^{1s}$ is —OR', wherein R' is optionally substituted C$_{1-6}$ aliphatic. In some embodiments, $R^{1s}$ is —OR', wherein R' is optionally substituted C$_{1-6}$ alkyl. In some embodiments, $R^{1s}$ is —OH. In some embodiments, $R^{1s}$ is —OMe. In some embodiments, $R^{1s}$ is -MOE. In some embodiments, $R^{1s}$ is hydrogen. In some embodiments, one $R^{1s}$ at a 1'-position is hydrogen, and the other $R^{1s}$ at the other 1'-position is not hydrogen as described herein. In some embodiments, $R^{1s}$ at both 1'-positions are hydrogen. In some embodiments, $R^{1s}$ is —O-L$^s$-OR'. In some embodiments, $R^{1s}$ is —O-L$^s$-OR', wherein L$^s$ is optionally substituted C$_{1-6}$ alkylene, and R' is optionally substituted C$_{1-6}$ aliphatic. In some embodiments, $R^{1s}$ is —O-(optionally substituted C$_{1-6}$ alkylene)-OR'. In some embodiments, $R^{1s}$ is —O-(optionally substituted C$_{1-6}$ alkylene)-OR', wherein R' is optionally substituted C$_{1-6}$ alkyl. In some embodiments, $R^{1s}$ is —OCH$_2$CH$_2$OMe.

In some embodiments, $R^{2s}$ is $R^s$ at a 2'-position (BA is at 1'-position). In some embodiments, $R^s$ at a 2'-position is —F. In some embodiments, $R^s$ at a 2'-position is —Cl. In some embodiments, $R^s$ at a 2'-position is —Br. In some embodiments, $R^s$ at a 2'-position is —I. In some embodiments, $R^s$ at a 2'-position is —CN. In some embodiments, $R^s$ at a 2'-position is —N$_3$. In some embodiments, $R^s$ at a 2'-position is —NO. In some embodiments, $R^s$ at a 2'-position is —NO$_2$. In some embodiments, $R^s$ at a 2'-position is -L-R'. In some embodiments, $R^s$ at a 2'-position is —R'. In some embodiments, $R^s$ at a 2'-position is -L-OR'. In some embodiments, $R^s$ at a 2'-position is —OR'. In some embodiments, $R^s$ at a 2'-position is -L-SR'. In some embodiments, $R^s$ at a 2'-position is —SR'. In some embodiments, $R^s$ at a 2'-position is L-L-N(R')$_2$. In some embodiments, $R^s$ at a 2'-position is —N(R')$_2$. In some embodiments, $R^s$ at a 2'-position is —OR', wherein R' is optionally substituted C$_{1-6}$ aliphatic. In some embodiments, $R^s$ at a 2'-position is —OR', wherein R' is optionally substituted C$_{1-6}$ alkyl. In some embodiments, $R^s$ at a 2'-position is —OMe. In some embodiments, $R^s$ at a 2'-position is -MOE. In some embodiments, $R^s$ at a 2'-position is hydrogen. In some embodiments, $R^s$ at one 2'-position is hydrogen, and $R^s$ at the other 2'-position is not hydrogen as described herein. In some embodiments, $R^s$ at both 2'-positions are hydrogen. In some embodiments, $R^s$ at one 2'-position is hydrogen, and the other 2'-position is connected to an internucleotidic linkage. In some embodiments, $R^{2s}$ is —F. In some embodiments, $R^{2s}$ is —Cl. In some embodiments, $R^{2s}$ is —Br. In some embodiments, $R^{2s}$ is —I. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is -L-R'. In some embodiments, $R^{2s}$ is —R'. In some embodiments, $R^{2s}$ is -L-OR'. In some embodiments, $R^{2s}$ is —OR'. In some embodiments, $R^{2s}$ is -L-SR'. In some embodiments, $R^{2s}$ is —SR'. In some embodiments, $R^{2s}$ is -L-N(R')$_2$. In some embodiments, $R^{2s}$ is —N(R')$_2$. In some embodiments, $R^{2s}$ is —OR', wherein R' is optionally substituted C$_{1-6}$ aliphatic. In some embodiments, $R^{2s}$ is —OR', wherein R' is optionally substituted C$_{1-6}$ alkyl. In some embodiments, $R^{2s}$ is —OH. In some embodiments, $R^{2s}$ is —OMe. In some embodiments, $R^{2s}$ is -MOE. In some embodiments, $R^{2s}$ is hydrogen. In some embodiments, one $R^{2s}$ at a 2'-position is hydrogen, and the other $R^{2s}$ at the other 2'-position is not hydrogen as described herein. In some embodiments, $R^{2s}$ at both 2'-positions are hydrogen. In some embodiments, $R^{2s}$ is —O-L$^s$-OR'. In some embodiments, $R^{2s}$ is —O-L$^s$-OR', wherein L$^s$ is optionally substituted C$_{1-6}$ alkylene, and R' is optionally substituted C$_{1-6}$ aliphatic. In some embodiments, $R^{2s}$ is —O-(optionally substituted C$_{1-6}$ alkylene)-OR'. In some embodiments, $R^{2s}$ is —O-(optionally substituted C$_{1-6}$ alkylene)-OR', wherein R' is optionally substituted C$_{1-6}$ alkyl. In some embodiments, $R^{2s}$ is —OCH$_2$CH$_2$OMe.

In some embodiments, $R^{3s}$ is $R^s$ at a 3'-position (BA is at 1'-position). In some embodiments, $R^s$ at a 3'-position (BA is at 1'-position) is —F. In some embodiments, $R^s$ at a 3'-position is —Cl. In some embodiments, $R^s$ at a 3'-position is —Br. In some embodiments, $R^s$ at a 3'-position is —I. In some embodiments, $R^s$ at a 3'-position is —CN. In some embodiments, $R^s$ at a 3'-position is —N$_3$. In some embodiments, $R^s$ at a 3'-position is —NO. In some embodiments, $R^s$ at a 3'-position is —NO$_2$. In some embodiments, $R^s$ at a 3'-position is -L-R'. In some embodiments, $R^s$ at a 3'-position is —R'. In some embodiments, $R^s$ at a 3'-position is -L-OR'. In some embodiments, $R^s$ at a 3'-position is —OR'. In some embodiments, $R^s$ at a 3'-position is -L-SR'. In some embodiments, $R^s$ at a 3'-position is —SR'. In some embodiments, $R^s$ at a 3% position is -L-N(R')$_2$. In some embodiments, $R^s$ at a 3'-position is —N(R')$_2$. In some embodiments, $R^s$ at a 3'-position is —OR', wherein R' is optionally substituted C$_{1-6}$ aliphatic. In some embodiments, $R^s$ at a 3'-position is —OR', wherein R' is optionally substituted C$_{1-6}$ alkyl. In some embodiments, $R^s$ at a 3'-position is —OMe. In some embodiments, $R^s$ at a 3'-position is -MOE. In some embodiments, $R^s$ at a 3'-position is hydrogen. In some embodiments, $R^s$ at one 3'-position is hydrogen, and $R^s$ at the other 3'-position is not hydrogen as described herein. In some embodiments, $R^s$ at both 3'-positions are hydrogen. In some embodiments, $R^s$ at one 3'-position is hydrogen, and the other 3'-position is connected to an internucleotidic linkage. In some embodiments, $R^{3s}$ is —F. In some embodiments, $R^{3s}$ is —Cl. In some embodiments, $R^{3s}$ is —Br. In some embodiments, $R^{3s}$ is —I. In some embodiments, $R^{3s}$ is —CN. In some embodiments, $R^{3s}$ is —N$_3$. In some embodiments, $R^{3s}$ is —NO. In some embodiments, $R^{3s}$ is —NO$_2$. In some embodiments, $R^{3s}$ is -L-R'. In some embodiments, $R^{3s}$ is —R'. In some embodiments, $R^{3s}$ is -L-OR'. In some embodiments, $R^{3s}$ is —OR'. In some embodiments, $R^{3s}$ is -L-SR'. In some embodiments, $R^{3s}$ is —SR'. In some embodiments, $R^{3s}$ is L-L-N(R')$_2$. In some embodiments, $R^{3s}$ is —N(R')$_2$. In some embodiments, $R^{3s}$ is —OR', wherein R' is optionally substituted C$_{1-6}$ aliphatic. In some embodiments, $R^{3s}$ is —OR', wherein R' is optionally substituted C$_{1-6}$ alkyl. In some embodiments, $R^{3s}$ is —OH. In some embodiments, $R^{3s}$ is —OMe. In some embodiments, $R^{3s}$ is -MOE. In some embodiments, $R^{3s}$ is hydrogen.

In some embodiments, $R^{4s}$ is $R^s$ at a 4'-position (BA is at 1'-position). In some embodiments, $R^s$ at a 4'-position (BA is at 1'-position) is —F. In some embodiments, $R^s$ at a 4'-position is —Cl. In some embodiments, $R^s$ at a 4'-position is —Br. In some embodiments, $R^s$ at a 4'-position is —I. In some embodiments, $R^s$ at a 4'-position is —CN. In some embodiments, $R^s$ at a 4'-position is —N$_3$. In some embodiments, $R^s$ at a 4'-position is —NO. In some embodiments, $R^s$ at a 4'-position is —NO$_2$. In some embodiments, $R^s$ at a 4'-position is -L-R'. In some embodiments, $R^s$ at a 4'-position is —R'. In some embodiments, $R^s$ at a 4'-position is -L-OR'. In some embodiments, $R^s$ at a 4'-position is —OR'. In some embodiments, $R^s$ at a 4'-position is -L-SR'. In some embodiments, $R^s$ at a 4'-position is —SR'. In some embodiments, $R^s$ at a 4'-position is -L-N(R')$_2$. In some embodiments, $R^s$ at a 4'-position is —N(R')$_2$. In some embodiments, $R^s$ at a 4'-position is —OR', wherein R' is optionally substituted C$_{1-6}$ aliphatic. In some embodiments, $R^s$ at a 4'-position is —OR', wherein R' is optionally substituted C$_{1-6}$ alkyl. In some embodiments, $R^s$ at a 4'-position is —OMe. In some embodiments, $R^s$ at a 4'-position is -MOE. In some embodiments, $R^s$ at a 4'-position is hydrogen. In some embodiments, $R^s$ at one 4'-position is hydrogen, and $R^s$ at the other 4'-position is not hydrogen as described herein. In some embodiments, $R^s$ at both 4'-positions are hydrogen. In some embodiments, $R^s$ at one 4'-position is hydrogen, and the other 4'-position is connected to an internucleotidic linkage. In some embodiments, $R^{4s}$ is —F. In some embodiments, $R^{4s}$ is —Cl. In some embodiments, $R^{4s}$ is —Br. In some embodiments, $R^{4s}$ is —I. In some embodiments, $R^{4s}$ is —CN. In some embodiments, $R^{4s}$ is —N$_3$. In some embodiments, $R^{4s}$ is —NO. In some embodiments, $R^{4s}$ is —NO$_2$. In some embodiments, $R^{4s}$ is -L-R'. In some embodiments, $R^{4s}$ is —R'. In some embodiments, $R^{4s}$ is -L-OR'. In some embodiments, $R^{4s}$ is —OR'. In some embodiments, $R^{4s}$ is -L-SR'. In some embodiments, $R^{4s}$ is —SR'. In some embodiments, $R^{4s}$ is L-L-N(R')$_2$. In some embodiments, $R^{4s}$ is —N(R')$_2$. In some embodiments, $R^{4s}$ is —OR', wherein R' is optionally substituted C$_{1-6}$ aliphatic. In some embodiments, $R^{4s}$ is —OR', wherein R' is optionally substituted C$_{1-6}$ alkyl. In some embodiments, $R^{4s}$ is —OH. In some embodiments, $R^{4s}$ is —OMe. In some embodiments, $R^{4s}$ is -MOE. In some embodiments, $R^{4s}$ is hydrogen.

In some embodiments, $R^{5s}$ is R'. In some embodiments, $R^{5s}$ is —F. In some embodiments, $R^{5s}$ is —Cl. In some embodiments, $R^{5s}$ is —Br. In some embodiments, $R^{5s}$ is —I. In some embodiments, $R^{5s}$ is —CN. In some embodiments, $R^{5s}$ is —$N_3$. In some embodiments, $R^{5s}$ is —NO. In some embodiments, $R^{5s}$ is —$NO_2$. In some embodiments, $R^{5s}$ is -L-R'. In some embodiments, $R^{5s}$ is —R'. In some embodiments, $R^{5s}$ is -L-OR'. In some embodiments, $R^{5s}$ is —OR'. In some embodiments, $R^{5s}$ is -L-SR'. In some embodiments, $R^{5s}$ is —SR'. In some embodiments, $R^{5s}$ is L-L-N(R')$_2$. In some embodiments, $R^{5s}$ is —N(R')$_2$. In some embodiments, $R^{5s}$ is —OR', wherein R' is optionally substituted $C_{1-6}$ aliphatic. In some embodiments, $R^{5s}$ is —OR', wherein R' is optionally substituted $C_{1-6}$ alkyl. In some embodiments, $R^{5s}$ is —OH. In some embodiments, $R^{5s}$ is —OMe. In some embodiments, $R^{5s}$ is -MOE. In some embodiments, $R^{5s}$ is hydrogen.

In some embodiments, $R^{5s}$ is optionally substituted

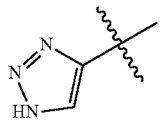

In some embodiments, $R^{5s}$ is optionally substituted

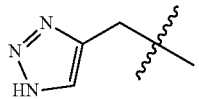

In some embodiments, $R^{5s}$ is a protected hydroxyl group suitable for oligonucleotide synthesis. In some embodiments, $R^{5s}$ is —OR', wherein R' is optionally substituted $C_{1-6}$ aliphatic. In some embodiments, $R^{5s}$ is DMTrO-. Example protecting groups are widely known for use in accordance with the present disclosure. For additional examples, see Greene, T. W.; Wuts, P. G. M. Protective Groups in Organic Synthesis, 2nd ed.; Wiley: New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, protecting groups of each of which are hereby incorporated by reference.

In some embodiments, -$L^s$-$R^{4s}$ is $R^E$. In some embodiments, —C($R^{5s}$)$_3$ is $R^E$. In some embodiments, provided oligonucleotides, e.g., oligonucleotides comprising one or more internucleotidic linkages each independently of formula VII, VII-a-1, VII-a-2, VII-b, VII-c, VII-d, or VII-e, or a salt form thereof, oligonucleotides of formula VIII or salts thereof, etc. comprise $R^E$. In some embodiments, 5'-end nucleoside comprise $R^E$. In some embodiments, the present disclosure encompasses the recognition that incorporation of $R^E$ may significantly improve properties and/or activities of oligonucleotides, for example, in RNAi.

In some embodiments, $R^E$ is R. In some embodiments, $R^E$ is —H. In some embodiments, $R^E$ is —OR'. In some embodiments, $R^E$ is —OH. In some embodiments, $R^E$ is —OR', wherein R' is optionally substituted $C_{1-6}$ aliphatic. In some embodiments, $R^E$ is —OR', wherein R' is optionally substituted $C_{1-6}$ alkyl. In some embodiments, R' is methyl. In some embodiments, R' is ethyl. In some embodiments, R' is n-propyl. In some embodiments, $R^E$ is —$CH_2OCH_3$. In some embodiments, $R^E$ is —$CH_2F$. In some embodiments, $R^E$ is —$CH_2OH$.

In some embodiments, $R^E$ is —$CH_2OP(O)(OR)_2$ or a salt form thereof, wherein each R is independently as described in the present disclosure. In some embodiments, $R^E$ is —$CH_2OP(O)(OH)_2$ or a salt form thereof. In some embodiments, $R^E$ is —$CH_2OP(O)(OR)(SR)$ or a salt form thereof, wherein each R is independently as described in the present disclosure. In some embodiments, $R^E$ is —$CH_2OP(O)(SH)(OH)$ or a salt form thereof. In some embodiments, $R^E$ is —CH=CHP(O)(OR)$_2$ or a salt form thereof, wherein each R is independently as described in the present disclosure. In some embodiments, $R^E$ is -(E)-CH=CHP(O)(OR)$_2$ or a salt form thereof, wherein each R is independently as described in the present disclosure. In some embodiments, $R^E$ is -(E)-CH=CHP(O)(OH)$_2$.

In some embodiments, $R^E$ is —CH(R)—OR'. In some embodiments, $R^E$ is —(R)—CH(R)—OR'. In some embodiments, $R^E$ is —(S)—CH(R)—OR'. In some embodiments, R is not hydrogen. In some embodiments, R is optionally substituted $C_{1-6}$ aliphatic. In some embodiments, R is optionally substituted $C_{1-6}$ alkyl. In some embodiments, R is optionally substituted $C_{1-3}$ aliphatic. In some embodiments, R is optionally substituted $C_{1-3}$ alkyl. In some embodiments, R is linear. In some embodiments, R is unsubstituted. In some embodiments, R is substituted. In some embodiments, R is unsubstituted linear $C_{1-3}$ alkyl. In some embodiments, R is linear $C_{1-3}$ haloalkyl. In some embodiments, R is methyl. In some embodiments, R is ethyl. In some embodiments, R' is a hydroxyl protecting group. In some embodiments, R' is —C(O)R. In some embodiments, R' is DMTr.

In some embodiments, $R^E$ is —CH(R')—OH, wherein R' is as described in the present disclosure. In some embodiments, $R^E$ is —CH(R')—OP(O)(R)$_2$ or a salt form thereof, wherein each R' and R is independently as described in the present disclosure. In some embodiments, $R^E$ is —CH(R')—OP(O)(OR)$_2$ or a salt form thereof, wherein each R' and R is independently as described in the present disclosure. In some embodiments, $R^E$ is —CH(R')—OP(O)(OH)$_2$ or a salt form thereof. In some embodiments, $R^E$ is —CH(R')—OP(O)(OR)(SR) or a salt form thereof. In some embodiments, $R^E$ is —CH(R')—OP(O)(OH)(SH) or a salt form thereof. In some embodiments, $R^E$ is —(R)—CH(R')—OH, wherein R' is as described in the present disclosure. In some embodiments, $R^E$ is —(R)—CH(R')—OP(O)(R)$_2$ or a salt form thereof, wherein each R' and R is independently as described in the present disclosure. In some embodiments, $R^E$ is —(R)—CH(R')—OP(O)(OR)$_2$ or a salt form thereof, wherein each R' and R is independently as described in the present disclosure. In some embodiments, $R^E$ is —(R)—CH(R')—OP(O)(OH)$_2$ or a salt form thereof. In some embodiments, $R^E$ is —(R)—CH(R')—OP(O)(OR)(SR) or a salt form thereof. In some embodiments, $R^E$ is —(R)—CH(R')—OP(O)(OH)(SH) or a salt form thereof. In some embodiments, $R^E$ is —(S)—CH(R')—OH, wherein R' is as described in the present disclosure. In some embodiments, $R^E$ is —(S)—CH(R')—OP(O)(R)$_2$ or a salt form thereof, wherein each R' and R is independently as described in the present disclosure. In some embodiments, $R^E$ is —(S)—CH(R')—OP(O)(OR)$_2$ or a salt form thereof, wherein each R' and R is independently as described in the present disclosure. In some embodiments, $R^E$ is —(S)—CH(R')—OP(O)(OH)$_2$ or a salt form thereof. In some embodiments, $R^E$ is —(S)—CH(R')—OP(O)(OR)(SR) or a salt form thereof. In some embodiments, $R^E$ is —(S)—CH(R')—OP(O)(OH)(SH) or a salt form thereof. In some embodiments, R' is optionally substituted $C_1$, $C_2$, $C_3$, or $C_4$ aliphatic. In some embodiments, R' is $C_1$, $C_2$, $C_3$, or $C_4$ aliphatic or haloaliphatic. In some embodiments, R' is optionally substituted —$CH_3$. In some embodiments, R' is —$CH_3$.

In some embodiments, $R^E$ is -$L^s$-P(O)(XR)$_2$ or a salt form thereof, wherein each X is independently —O—, —S—, or —N(R')—. In some embodiments, $R^E$ is -$L^s$-P(O)(XR)$_2$ or a salt form thereof, wherein each X is independently —O—, —S—, or a covalent bond. In some embodiments, $R^E$ is -$L^s$-P(O)(OR)$_2$ or a salt form thereof. In some embodiments, $R^E$ is -$L^s$-P(O)(OR)(SR) or a salt form thereof. In some embodiments, $R^E$ is -$L^s$-P(O)(OR)(R) or a salt form thereof. In some embodiments, $L^s$ is a covalent bond, or a bivalent, optionally substituted, linear or branched $C_{1-6}$ aliphatic, wherein one or more methylene units are optionally and independently replaced with —O—, —S— or —N(R')—. In some embodiments, $R^E$ is —X-$L^s$-R. In some embodiments, $R^E$ is —X-$L^s$-$R^5$. In some embodiments, $R^5$ is optionally substituted 5-20 membered heteroaryl having 1-5 heteroatoms. In some embodiments, $R^5$ is optionally substituted 5-membered heteroaryl having 1-4 hetereoatoms. In some embodiments, $R^E$ is optionally substituted

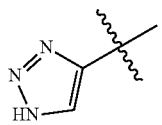

In some embodiments, $R^E$ is

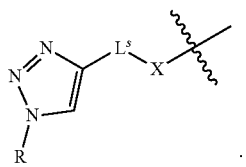

In some embodiments, $R^E$ is

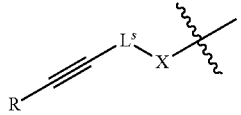

or a salt form thereof. In some embodiments, $R^E$ is

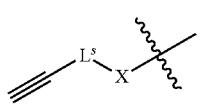

In some embodiments, X in $R^E$ is —C(R)$_2$—. In some embodiments, X is —O—. In some embodiments, X is —S—. In some embodiments, X is —N(R)—. In some embodiments, $L^s$ comprises an optionally substituted, bivalent or multivalent

group. In some embodiments, $L^s$ comprises an optionally substituted

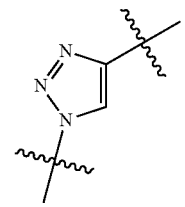 [SMILES: *c1cn(*)nn1]

group. In some embodiments, $L^s$ comprises a

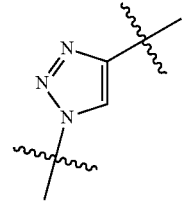 [SMILES: *c1cn(*)nn1]

group. In some embodiments, R is independently —H, or an optionally substituted group selected from $C_{1-10}$ alkyl, $C_{1-10}$ allyl, and $C_{6-14}$ aryl. In some embodiments, R is —H. In some embodiments, $R^E$ is optionally substituted

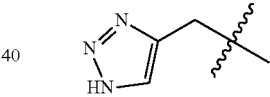

In some embodiments, $R^E$ is

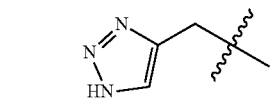

In some embodiments, $R^E$ is —CHR—O—$R^s$, wherein R is —H or optionally substituted $C_{1-4}$ aliphatic, and $R^s$ is hydroxyl protecting group. In some embodiments, R is methyl and $R^s$ is DMTr. In some embodiments, $R^E$ is —(R)—CH(Me)-ODMTr. In some embodiments, $R^E$ is —(S)—CH(Me)-ODMTr. In some embodiments, $R^E$ is -$L^s$-P(O)(OR)$_2$. In some embodiments, $R^E$ is -$L^s$-P(O)(OR)$_2$, wherein each R is independently optionally substituted $C_{1-6}$ aliphatic. In some embodiments, -$L^s$- is -(E)-CH=CH—. In some embodiments, $R^E$ is -(E)-CH=CH—P(O)(OR)$_2$.

In some embodiments, $R^E$ is -(E)-CH=CH—P(O)(OR)$_2$, wherein each R is independently optionally substituted $C_{1-6}$ aliphatic. In some embodiments, $R^E$ is -(E)-CH=CH—P(O)(OMe)$_2$.

In some embodiments, an internucleotidic linkage of formula VII, VII-a-1, VII-a-2, VII-b, VII-c, VII-d, or VII-e, or a salt form thereof, is a chiral internucleotidic linkage. In some embodiments, P in $P^L$ is a chiral linkage phosphorus. In some embodiments, a chiral linkage phosphorus is Rp. In some embodiments, a chiral linkage phosphorus is Sp. In some embodiments, $P^L$ is P(=W). In some embodiments, $P^L$ is P(=O). In some embodiments, $P^L$ is P(=S). In some embodiments, $P^L$ is P. In some embodiments, $P^L$ is P→B (R')$_3$.

In some embodiments, Y is —O— and Z is —O—, and X is —O— or —S—. In some embodiments, X and Y and Z are —O—. In some embodiments, X is —S—, and Y and Z are —O—.

In some embodiments, W is O. In some embodiments, W is O, and X and Y and Z are —O—. In some embodiments, W is O, X is —S—, and Y and Z are —O—. In some embodiments, W is S. In some embodiments, W is S, and X and Y and Z are —O—. In some embodiments, W is S, X is —S—, and Y and Z are —O—.

In some embodiments, as described in the present disclosure, —X-$L^s$-$R^5$ is of such structure that H—X-$L^s$-$R^5$ has the structure of formula I, I-a, I-a-I, I-a-2, I-b, I-c, I-d, I-e, II, II-a, II-b, III, III-a, III-b, or a salt thereof.

In some embodiments, —X-$L^s$-$R^5$ is —OR. In some embodiments, —X-$L^s$-$R^5$ is —OH. In some embodiments, —X-$L^s$-$R^5$ is —OR, wherein R is not hydrogen. In some embodiments, W is O and —X-$L^s$-$R^5$ is —OR. In some embodiments, W is O and —X-$L^s$-$R^5$ is —OH. In some embodiments, W is O and —X-$L^s$-$R^5$ is —OR, wherein R is not hydrogen.

In some embodiments, —X-$L^s$-$R^5$ is —SR. In some embodiments, —X-$L^s$-$R^5$ is —SH. In some embodiments, —X-$L^s$-$R^5$ is —SR, wherein R is not hydrogen. In some embodiments, W is O and —X-$L^s$-$R^5$ is —SR. In some embodiments, W is O and —X-$L^s$-$R^5$ is —SH. In some embodiments, W is O and —X-$L^s$-$R^5$ is —SR, wherein R is not hydrogen.

In some embodiments, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof. In some embodiments, $R^7$ is —OH, and $R^6$ is —H or —R. In some embodiments, $R^6$ is —H. In some embodiments, $R^6$ is —R, wherein R is not hydrogen. In some embodiments, R is a capping group. Suitable capping groups for oligonucleotide synthesis are well known by a personal having ordinary skill in the art, for example, those described in US/2015/0211006, US/2017/0037399, WO/2017/015555, WO/2017/062862, WO2017/160741, WO2017/192664, WO2017/192679, WO2017/210647, WO2018/022473, WO2018/067973, and WO2018/098264, each of which is incorporated herein by reference. In some embodiments, $R^6$ is —C(O)R. As described in the present disclosure, in some embodiments, immediately after coupling, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is —H in formula I, 1-a, I-a-1, I-a-2, I-b, I-c, I-d, I-e, II, II-a, II-b, III, III-a, or III-b, and a linkage may have the structure of formula VII, VII-a-1, VII-a-2, VII-b, VII-c, VII-d, or VII-e, or a salt form thereof. In some embodiments, after capping, —X-$L^s$-$R^5$ is of such a structure that H—X-$L^s$-$R^5$ has the structure of formula I, I-a, I-a-1, I-a-2, I-b, I-c, I-d, I-e, II, II-a, II-b, III, III-a, or III-b, or a salt thereof, wherein $R^6$ is a capping group, for example, a group having the structure of —C(O) R, and a linkage may have the structure of formula VII, VII-a-1, VII-a-2, VII-b, VII-c, VII-d, or VII-e, or a salt form thereof. In some embodiments, the nitrogen atom to which $R^5$ is attached is capped with a R—C(O)— group, forming a group of —N($R^5$)(—C(O)—R). In some embodiments, a capping group is —C(O)—$CH_3$. In some embodiments, a capping group is —C(O)—$CF_3$. In some embodiments, after additional chemical modification steps, a linkage may have the structure of formula VII, VII-a-1, VII-a-2, VII-b, VII-c, VII-d, or VII-e, or a salt form thereof.

In some embodiments, each $L^P$ is independently an internucleotidic linkage. In some embodiments, each $L^P$ independently has the structure of formula VII, VII-a-1, VII-a-2, VII-b, VII-c, VII-d, or VII-e, or a salt form thereof. In some embodiments, each $L^P$ independently has the structure of formula VII, VII-a-1, VII-a-2, VII-b, VII-c, VII-d, or VII-e, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof. In some embodiments, each $L^P$ independently has the structure of formula VII, VII-a-1, or VII-a-2, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof, and W is O or S. In some embodiments, each $L^P$ independently has the structure of formula VII, VII-a-1, or VII-a-2, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof, and W is O or S, and X is O. In some embodiments, each $L^P$ independently has the structure of formula VII, VII-a-1, or VII-a-2, or a salt form thereof, wherein each —X-$L^s$-$R^5$ is independently of a structure that H—X-$L^s$-$R^5$ is a compound of formula I, I-a, I-a-1, I-a-2, I-b, I-c, I-d, I-e, II, II-a, II-b, III, III-a, or III-b, or a salt thereof, and W is O or S, and X and Y and Z are —O—. In some embodiments, $L^P$ has the structure of formula VII or a salt thereof. In some embodiments, $L^P$ has the structure of formula VII or a salt thereof, wherein W is O or S, and X and Y and Z are —O—. In some embodiments, $L^P$ has the structure of formula VII-a-1 or a salt thereof. In some embodiments, $L^P$ has the structure of formula VII-a-1 or a salt thereof, wherein W is O or S, and X and Y and Z are —O—. In some embodiments, $L^P$ has the structure of formula VII-a-2 or a salt thereof. In some embodiments, $L^P$ has the structure of formula VII-a-2 or a salt thereof, wherein W is O or S, and X and Y and Z are —O—. In some embodiments, $L^P$ has the structure of formula VII-b or a salt thereof. In some embodiments, $L^P$ has the structure of formula VII-b or a salt thereof, wherein X and Y and Z are —O—. In some embodiments, $L^P$ has the structure of formula VII-c or a salt thereof. In some embodiments, $L^P$ has the structure of formula VII-c or a salt thereof, wherein X and Y and Z are —O—. In some embodiments, $L^P$ has the structure of formula VII-d or a salt thereof. In some embodiments, $L^P$ has the structure of formula VII-d or a salt thereof, wherein X and Y and Z are —O—. In some embodiments, $L^P$ has the structure of formula VII-e or a salt thereof. In some embodiments, $L^P$ has the structure of formula VII-e or a salt thereof, wherein X and Y and Z are —O—. In some embodiments, L is natural phosphate linkage. In some embodiments, L is a phosphorothioate linkage or a salt form thereof. In some embodiments, each L is independently a natural phosphate linkage or a phosphorothioate linkage, or a salt thereof.

In some embodiments, at least one $L^P$ comprises W, wherein W is S. In some embodiments, about 1-20 $L^P$ comprises W, wherein W is S. In some embodiments, at least 2, 3, 4, 5, 6, 7, 8, 9, 10, 11, 12, 13, 14, 15, 16, 17, 18, 19, 20 $L^P$ comprises W, wherein W is S. In some embodiments, at least one $L^P$ comprises W, wherein W is O. In some embodiments, about 1-20 $L^P$ comprises W, wherein W is O. In some embodiments, at least 2, 3, 4, 5, 6, 7, 8, 9, 10, 11, 12, 13, 14, 15, 16, 17, 18, 19, 20 $L^P$ comprises W, wherein W is O.

In some embodiments, z is 1. In some embodiments, z is 2. In some embodiments, z is 3. In some embodiments, z is 4. In some embodiments, z is 5. In some embodiments, z is 6. In some embodiments, z is 7. In some embodiments, z is 8. In some embodiments, z is 9. In some embodiments, z is 10. In some embodiments, z is 11. In some embodiments, z is 12. In some embodiments, z is 13. In some embodiments, z is 14. In some embodiments, z is 15. In some embodiments, z is 16. In some embodiments, z is 17. In some embodiments, z is 18. In some embodiments, z is 19. In some embodiments, z is 20. In some embodiments, z is 21. In some embodiments, z is 22. In some embodiments, z is 23. In some embodiments, z is 24. In some embodiments, z is 25. In some embodiments, z is 26. In some embodiments, z is 27. In some embodiments, z is 28. In some embodiments, z is 29. In some embodiments, z is 30. In some embodiments, z is at least 2. In some embodiments, z is at least 3. In some embodiments, z is at least 4. In some embodiments, z is at least 5. In some embodiments, z is at least 6. In some embodiments, z is at least 7. In some embodiments, z is at least 8. In some embodiments, z is at least 9. In some embodiments, z is at least 10. In some embodiments, z is at least 11. In some embodiments, z is at least 12. In some embodiments, z is at least 13. In some embodiments, z is at least 14. In some embodiments, z is at least 15. In some embodiments, z is at least 16. In some embodiments, z is at least 17. In some embodiments, z is at least 18. In some embodiments, z is at least 19. In some embodiments, z is at least 20. In some embodiments, z is at least 21. In some embodiments, z is at least 22. In some embodiments, z is at least 23. In some embodiments, z is at least 24. In some embodiments, z is at least 25. In some embodiments, z is at least 26. In some embodiments, z is at least 27. In some embodiments, z is at least 28. In some embodiments, z is at least 29. In some embodiments, z is at least 30.

In some embodiments, $L^{3E}$ is -$L^s$- or -$L^s$-$L^s$-. In some embodiments, $L^{3E}$ is -$L^s$-. In some embodiments, $L^{3E}$ is -$L^s$-$L^s$-. In some embodiments, $L^{3E}$ is a covalent bond. In some embodiments, $L^{3E}$ is a linker used in oligonucleotide synthesis. In some embodiments, $L^{3E}$ is a linker used in solid phase oligonucleotide synthesis. Various types of linkers are known and can be utilized in accordance with the present disclosure. In some embodiments, a linker is a succinate linker (—O—C(O)—CH$_2$—CH$_2$—C(O)—). In some embodiments, a linker is an oxalyl linker (—O—C(O)—C(O)—). In some embodiments, $L^{3E}$ is a succinyl-piperidine linker (SP) linker. In some embodiments, $L^{3E}$ is a succinyl linker. In some embodiments, $L^{3E}$ is a Q-linker.

In some embodiments, $R^{3E}$ is —R', -$L^s$-R', —OR', or a solid support. In some embodiments, $R^{3E}$ is —R'. In some embodiments, $R^{3E}$ is -$L^s$-R'. In some embodiments, $R^{3E}$ is —OR'. In some embodiments, $R^{3E}$ is a solid support. In some embodiments, $R^{3E}$ is —H. In some embodiments, -$L^3$-$R^{3E}$ is —H. In some embodiments, $R^{3E}$ is —OH. In some embodiments, -$L^3$-$R^{3E}$ is —OH. In some embodiments, $R^{3E}$ is optionally substituted $C_{1-6}$ aliphatic. In some embodiments, $R^{3E}$ is optionally substituted $C_{1-6}$ alkyl. In some embodiments, $R^{3E}$ is —OR'. In some embodiments, $R^{3E}$ is —OH. In some embodiments, $R^{3E}$ is —OR', wherein R' is not hydrogen. In some embodiments, $R^{3E}$ is —OR', wherein R' is optionally substituted $C_{1-6}$ alkyl. In some embodiments, $R^{3E}$ is a 3'-end cap (e.g., those used in RNAi technologies).

In some embodiments, $R^{3E}$ is a solid support. In some embodiments, $R^{3E}$ is a solid support for oligonucleotide synthesis. Various types of solid support are known and can be utilized in accordance with the present disclosure. In some embodiments, a solid support is HCP. In some embodiments, a solid support is CPG.

In some embodiments, s is 0-20. In some embodiments, s is 1-20. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11. In some embodiments, s is 12. In some embodiments, s is 13. In some embodiments, s is 14. In some embodiments, s is 15. In some embodiments, s is 16. In some embodiments, s is 17. In some embodiments, s is 18. In some embodiments, s is 19. In some embodiments, s is 20.

In some embodiments, each Ring $A^s$ is independently an optionally substituted 3-20 membered monocyclic, bicyclic or polycyclic ring having 0-10 heteroatoms independently selected from oxygen, nitrogen, sulfur, phosphorus and silicon. In some embodiments, Ring A is an optionally substituted ring, which ring is as described in the present disclosure. In some embodiments, a ring is

In some embodiments, a ring is

In some embodiments, Ring A is or comprises a ring of a sugar moiety. In some embodiments, Ring A is or comprises a ring of a modified sugar moiety.

In some embodiments, provided compounds comprise one or more bivalent or multivalent optionally substituted rings, e.g., Ring A, Ring $A^s$, Ring A', -Cy-, $Cy^L$, those formed by two or more R groups (R and (combinations of) variables that can be R) taken together, etc. In some embodiments, a ring is a cycloaliphatic, aryl, heteroaryl, or heterocyclyl group as described for R but bivalent or multivalent. As appreciated by those skilled in the art, ring moieties described for one variable, e.g., Ring A, can also be applicable to other variables, e.g., Ring A', -Cy-, $Cy^L$, etc., if requirements of the other variables, e.g., number of heteroatoms, valence, etc., are satisfied. Example rings are extensively described in the present disclosure.

In some embodiments, a ring, e.g., in Ring A, Ring $A^s$, R, etc. which is optionally substituted, is a 3-20 membered monocyclic, bicyclic or polycyclic ring having 0-10 heteroatoms independently selected from oxygen, nitrogen, sulfur, phosphorus and silicon. In some embodiments, a ring is a 3-20 membered monocyclic, bicyclic or polycyclic ring having 1-10 heteroatoms independently selected from oxygen, nitrogen, sulfur, phosphorus and silicon, wherein the ring comprises a —N($R^6$)— moiety.

In some embodiments, a ring can be of any size within its range, e.g., 3, 4, 5, 6, 7, 8, 9, 10, 11, 12, 13, 14, 15, 16, 17, 18, 19, or 20-membered.

In some embodiments, a ring is monocyclic. In some embodiments, a ring is saturated and monocyclic. In some embodiments, a ring is monocyclic and partially saturated. In some embodiments, a ring is monocyclic and aromatic.

In some embodiments, a ring is bicyclic. In some embodiments, a ring is polycyclic. In some embodiments, a bicyclic or polycyclic ring comprises two or more monocyclic ring moieties, each of which can be saturated, partially saturated, or aromatic, and each which can contain no or 1-10 heteroatoms. In some embodiments, a bicyclic or polycyclic ring comprises a saturated monocyclic ring. In some embodiments, a bicyclic or polycyclic ring comprises a saturated monocyclic ring containing no heteroatoms. In some embodiments, a bicyclic or polycyclic ring comprises a saturated monocyclic ring comprising one or more heteroatoms. In some embodiments, a bicyclic or polycyclic ring comprises a partially saturated monocyclic ring. In some embodiments, a bicyclic or polycyclic ring comprises a partially saturated monocyclic ring containing no heteroatoms. In some embodiments, a bicyclic or polycyclic ring comprises a partially saturated monocyclic ring comprising one or more heteroatoms. In some embodiments, a bicyclic or polycyclic ring comprises an aromatic monocyclic ring. In some embodiments, a bicyclic or polycyclic ring comprises an aromatic monocyclic ring containing no heteroatoms. In some embodiments, a bicyclic or polycyclic ring comprises an aromatic monocyclic ring comprising one or more heteroatoms. In some embodiments, a bicyclic or polycyclic ring comprises a saturated ring and a partially saturated ring, each of which independently contains one or more heteroatoms. In some embodiments, a bicyclic ring comprises a saturated ring and a partially saturated ring, each of which independently comprises no, or one or more heteroatoms. In some embodiments, a bicyclic ring comprises an aromatic ring and a partially saturated ring, each of which independently comprises no, or one or more heteroatoms. In some embodiments, a polycyclic ring comprises a saturated ring and a partially saturated ring, each of which independently comprises no, or one or more heteroatoms. In some embodiments, a polycyclic ring comprises an aromatic ring and a partially saturated ring, each of which independently comprises no, or one or more heteroatoms. In some embodiments, a polycyclic ring comprises an aromatic ring and a saturated ring, each of which independently comprises no, or one or more heteroatoms. In some embodiments, a polycyclic ring comprises an aromatic ring, a saturated ring, and a partially saturated ring, each of which independently comprises no, or one or more heteroatoms. In some embodiments, a ring comprises at least one heteroatom. In some embodiments, a ring comprises at least one nitrogen atom. In some embodiments, a ring comprises at least one oxygen atom. In some embodiments, a ring comprises at least one sulfur atom.

As appreciated by those skilled in the art in accordance with the present disclosure, a ring is typically optionally substituted. In some embodiments, a ring is unsubstituted. In some embodiments, a ring is substituted. In some embodiments, a ring is substituted on one or more of its carbon atoms. In some embodiments, a ring is substituted on one or more of its heteroatoms. In some embodiments, a ring is substituted on one or more of its carbon atoms, and one or more of its heteroatoms. In some embodiments, two or more substituents can be located on the same ring atom. In some embodiments, all available ring atoms are substituted. In some embodiments, not all available ring atoms are substituted. In some embodiments, in provided structures where rings are indicated to be connected to other structures (e.g., Ring $A^s$ in

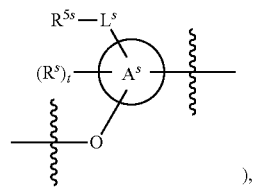

),

"optionally substituted" is to mean that, besides those structures already connected, remaining substitutable ring positions, if any, are optionally substituted (e.g., in

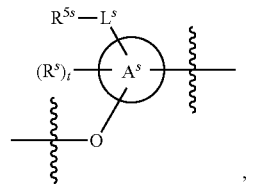

,

Ring $A^s$ may optionally have one or more substituents besides $R^{5s}$-$L^s$-, t $R^s$, —O—, and —).

In some embodiments, a ring is a bivalent or multivalent $C_{3-30}$ cycloaliphatic ring. In some embodiments, a ring is a bivalent or multivalent $C_{3-20}$ cycloaliphatic ring. In some embodiments, a ring is a bivalent or multivalent $C_{3-10}$ cycloaliphatic ring. In some embodiments, a ring is a bivalent or multivalent 3-30 membered saturated or partially unsaturated carbocyclic ring. In some embodiments, a ring is a bivalent or multivalent 3-7 membered saturated or partially unsaturated carbocyclic ring. In some embodiments, a ring is a bivalent or multivalent 3-membered saturated or partially unsaturated carbocyclic ring. In some embodiments, a ring is a bivalent or multivalent 4-membered saturated or partially unsaturated carbocyclic ring. In some embodiments, a ring is a bivalent or multivalent 5-membered saturated or partially unsaturated carbocyclic ring. In some embodiments, a ring is a bivalent or multivalent 6-membered saturated or partially unsaturated carbocyclic ring. In some embodiments, a ring is a bivalent or multivalent 7-membered saturated or partially unsaturated carbocyclic ring. In some embodiments, a ring is a bivalent or multivalent cyclohexyl ring. In some embodiments, a ring is a bivalent or multivalent cyclopentyl ring. In some embodiments, a ring is a bivalent or multivalent cyclobutyl ring. In some embodiments, a ring is a bivalent or multivalent cyclopropyl ring.

In some embodiments, a ring is a bivalent or multivalent $C_{6-30}$ aryl ring. In some embodiments, a ring is a bivalent or multivalent phenyl ring.

In some embodiments, a ring is a bivalent or multivalent 8-10 membered bicyclic saturated, partially unsaturated or aryl ring. In some embodiments, a ring is a bivalent or multivalent 8-10 membered bicyclic saturated ring. In some embodiments, a ring is a bivalent or multivalent 8-10 membered bicyclic partially unsaturated ring. In some embodiments, a ring is a bivalent or multivalent 8-10 membered bicyclic aryl ring. In some embodiments, a ring is a bivalent or multivalent naphthyl ring.

In some embodiments, a ring is a bivalent or multivalent 5-30 membered heteroaryl ring having 1-10 heteroatoms independently selected from oxygen, nitrogen, sulfur, phosphorus and silicon. In some embodiments, a ring is a bivalent or multivalent 5-30 membered heteroaryl ring having 1-10 heteroatoms independently selected from oxygen, nitrogen, and sulfur. In some embodiments, a ring is a bivalent or multivalent 5-30 membered heteroaryl ring having 1-5 heteroatoms independently selected from oxygen, nitrogen, sulfur, phosphorus and silicon. In some embodiments, a ring is a bivalent or multivalent 5-30 membered heteroaryl ring having 1-5 heteroatoms independently selected from oxygen, nitrogen, and sulfur.

In some embodiments, a ring is a bivalent or multivalent 5-6 membered monocyclic heteroaryl ring having 1-4 heteroatoms independently selected from nitrogen, oxygen, and sulfur. In some embodiments, a ring is a bivalent or multivalent 5-6 membered monocyclic heteroaryl ring having 1-3 heteroatoms independently selected from nitrogen, sulfur, and oxygen.

In some embodiments, a ring is a bivalent or multivalent 5-membered monocyclic heteroaryl ring having 1-4 heteroatoms independently selected from nitrogen, oxygen or sulfur. In some embodiments, a ring is a bivalent or multivalent 6-membered monocyclic heteroaryl ring having 1-4 heteroatoms independently selected from nitrogen, oxygen, and sulfur.

In some embodiments, a ring is a bivalent or multivalent 5-membered monocyclic heteroaryl ring having one heteroatom selected from nitrogen, oxygen, and sulfur. In some embodiments, a ring is a bivalent or multivalent pyrrolyl, furanyl, or thienyl ring.

In some embodiments, a ring is a bivalent or multivalent 5-membered heteroaryl ring having two heteroatoms independently selected from nitrogen, oxygen, and sulfur. In certain embodiments, a ring is a bivalent or multivalent 5-membered heteroaryl ring having one nitrogen atom, and an additional heteroatom selected from sulfur or oxygen. In some embodiments, a ring is a bivalent or multivalent pyrazolyl, imidazolyl, thiazolyl, isothiazolyl, oxazolyl or isoxazolyl ring.

In some embodiments, a ring is a bivalent or multivalent 5-membered heteroaryl ring having three heteroatoms independently selected from nitrogen, oxygen, and sulfur. In some embodiments, a ring is a bivalent or multivalent triazolyl, oxadiazolyl or thiadiazolyl ring.

In some embodiments, a ring is a bivalent or multivalent 5-membered heteroaryl ring having four heteroatoms independently selected from nitrogen, oxygen, and sulfur. In some embodiments, a ring is a bivalent or multivalent tetrazolyl, oxatriazolyl and thiatriazolyl ring.

In some embodiments, a ring is a bivalent or multivalent 6-membered heteroaryl ring having 1-4 nitrogen atoms. In some embodiments, a ring is a bivalent or multivalent 6-membered heteroaryl ring having 1-3 nitrogen atoms. In other embodiments, a ring is a bivalent or multivalent 6-membered heteroaryl ring having 1-2 nitrogen atoms. In some embodiments, a ring is a bivalent or multivalent 6-membered heteroaryl ring having four nitrogen atoms. In some embodiments, a ring is a bivalent or multivalent 6-membered heteroaryl ring having three nitrogen atoms. In some embodiments, a ring is a bivalent or multivalent 6-membered heteroaryl ring having two nitrogen atoms. In certain embodiments, a ring is a bivalent or multivalent 6-membered heteroaryl ring having one nitrogen atom. In some embodiments, a ring is a bivalent or multivalent pyridinyl, pyrimidinyl, pyrazinyl, pyridazinyl, triazinyl, or tetrazinyl ring.

In certain embodiments, a ring is a bivalent or multivalent 8-10 membered bicyclic heteroaryl ring having 1-4 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having 1 heteroatom independently selected from nitrogen, oxygen, and sulfur. In some embodiments, a ring is a bivalent or multivalent indolyl ring. In some embodiments, a ring is a bivalent or multivalent azabicyclo[3.2.1]octanyl ring. In certain embodiments, a ring is a bivalent or multivalent 5,6-fused heteroaryl ring having 2 heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having 3 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 5,6-fused heteroaryl ring having three heteroatoms independently selected from nitrogen, oxygen, and sulfur. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring.

In certain embodiments, a ring is a bivalent or multivalent 6,6-fused heteroaryl ring having 1-4 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having 1 heteroatom independently selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having 2 heteroatoms independently selected from nitrogen, oxygen, and sulfur. In some embodiments, a ring is a bivalent or multivalent quinazoline or a quinoxaline.

In some embodiments, a ring is a bivalent or multivalent 3-30 membered heterocyclic ring having 1-10 heteroatoms independently selected from oxygen, nitrogen, sulfur, phosphorus and silicon. In some embodiments, a ring is a bivalent or multivalent 3-30 membered heterocyclic ring having 1-10 heteroatoms independently selected from oxygen, nitrogen, and sulfur. In some embodiments, a ring is a bivalent or multivalent 3-30 membered heterocyclic ring having 1-5 heteroatoms independently selected from oxygen, nitrogen, sulfur, phosphorus and silicon. In some embodiments, a ring is a bivalent or multivalent 3-30 membered heterocyclic ring having 1-5 heteroatoms independently selected from oxygen, nitrogen, and sulfur.

In some embodiments, a ring is a bivalent or multivalent 3-7 membered saturated or partially unsaturated heterocyclic ring having 1-3 heteroatoms independently selected from nitrogen, oxygen, and sulfur. In some embodiments, a ring is a bivalent or multivalent a substituted 3-7 membered saturated or partially unsaturated heterocyclic ring having 1-3 heteroatoms independently selected from nitrogen, oxygen, and sulfur. In some embodiments, a ring is a bivalent or multivalent an unsubstituted 3-7 membered saturated or partially unsaturated heterocyclic ring having 1-3 heteroatoms independently selected from nitrogen, oxygen, and sulfur. In certain embodiments, a ring is a bivalent or multivalent 5-7 membered partially unsaturated monocyclic ring having 1-3 heteroatoms independently selected from nitrogen, oxygen, and sulfur. In certain embodiments, a ring is a bivalent or multivalent 5-6 membered partially unsaturated monocyclic ring having 1-3 heteroatoms independently selected from nitrogen, oxygen, and sulfur. In certain embodiments, a ring is a bivalent or multivalent 5-membered partially unsaturated monocyclic ring having 1-3 heteroatoms independently selected from nitrogen, oxygen, and sulfur. In certain embodiments, a ring is a bivalent or multivalent 6-membered partially unsaturated monocyclic ring having 1-3 heteroatoms independently selected from nitrogen, oxygen, and sulfur. In certain embodiments, a ring is a bivalent or multivalent 7-membered partially unsaturated monocyclic ring having 1-3 heteroatoms independently selected from nitrogen, oxygen, and sulfur. In some embodiments, a ring is a bivalent or multivalent 3-membered heterocyclic ring having one heteroatom selected from nitrogen, oxygen or sulfur. In some embodiments, a ring is a bivalent or multivalent 4-membered heterocyclic ring having 1-3 heteroatoms independently selected from nitrogen, oxygen, and sulfur. In some embodiments, a ring is a bivalent or multivalent 5-membered heterocyclic ring having 1-3 heteroatoms independently selected from nitrogen, oxygen, and sulfur. In some embodiments, a ring is a bivalent or multivalent 6-membered heterocyclic ring having 1-3 heteroatoms independently selected from nitrogen, oxygen, and sulfur. In some embodiments, a ring is a bivalent or multivalent 7-membered heterocyclic ring having 1-3 heteroatoms independently selected from nitrogen, oxygen, and sulfur.

In some embodiments, a ring is a bivalent or multivalent 3-membered saturated or partially unsaturated heterocyclic ring having 1-2 heteroatoms independently selected from nitrogen, oxygen, and sulfur. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 7-membered saturated or partially unsaturated heterocyclic ring having 1-2 heteroatoms independently selected from nitrogen, oxygen, and sulfur.

In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms. In some embodiments, a ring is a bivalent or multivalent 4-membered saturated or partially unsaturated heterocyclic ring having 1-2 heteroatoms independently selected from nitrogen, oxygen, and sulfur. In some embodiments, a ring is a bivalent or multivalent 4-membered partially unsaturated heterocyclic ring having 2 heteroatoms independently selected from nitrogen, oxygen, and sulfur. In some embodiments, a ring is a bivalent or multivalent 4-membered partially unsaturated heterocyclic ring having no more than 1 heteroatom. In some embodiments, a ring is a bivalent or multivalent 4-membered partially unsaturated heterocyclic ring having no more than 1 heteroatom, wherein the heteroatom is nitrogen. In some embodiments, a ring is a bivalent or multivalent 4-membered partially unsaturated heterocyclic ring having no more than 1 heteroatom, wherein the heteroatom is oxygen. In some embodiments, a ring is a bivalent or multivalent 4-membered partially unsaturated heterocyclic ring having no more than 1 heteroatom, wherein the heteroatom is sulfur. In some embodiments, a ring is a bivalent or multivalent 4-membered partially unsaturated heterocyclic ring having 2 oxygen atoms. In some embodiments, a ring is a bivalent or multivalent 4-membered partially unsaturated heterocyclic ring having 2 nitrogen atoms.

In some embodiments, a ring is a bivalent or multivalent 5-membered saturated or partially unsaturated heterocyclic ring having 1-2 heteroatoms independently selected from nitrogen, oxygen, and sulfur. In some embodiments, a ring is a bivalent or multivalent 5-membered partially unsaturated heterocyclic ring having 2 heteroatoms independently selected from nitrogen, oxygen, and sulfur. In some embodiments, a ring is a bivalent or multivalent 5-membered partially unsaturated heterocyclic ring having no more than 1 heteroatom. In some embodiments, a ring is a bivalent or multivalent 5-membered partially unsaturated heterocyclic ring having no more than 1 heteroatom, wherein the heteroatom is nitrogen. In some embodiments, a ring is a bivalent or multivalent 5-membered partially unsaturated heterocyclic ring having no more than 1 heteroatom, wherein the heteroatom is oxygen. In some embodiments, a ring is a bivalent or multivalent 5-membered partially unsaturated heterocyclic ring having no more than 1 heteroatom, wherein the heteroatom is sulfur. In some embodiments, a ring is a bivalent or multivalent 5-membered partially unsaturated heterocyclic ring having 2 oxygen atoms. In some embodiments, a ring is a bivalent or multivalent 5-membered partially unsaturated heterocyclic ring having 2 nitrogen atoms.

In some embodiments, a ring is a bivalent or multivalent 6-membered saturated or partially unsaturated heterocyclic ring having 1-2 heteroatoms independently selected from nitrogen, oxygen, and sulfur. In some embodiments, a ring is a bivalent or multivalent 6-membered partially unsaturated heterocyclic ring having 2 heteroatoms independently selected from nitrogen, oxygen, and sulfur. In some embodiments, a ring is a bivalent or multivalent 6-membered partially unsaturated heterocyclic ring having no more than 1 heteroatom. In some embodiments, a ring is a bivalent or multivalent 6-membered partially unsaturated heterocyclic ring having no more than 1 heteroatom, wherein the heteroatom is nitrogen. In some embodiments, a ring is a bivalent or multivalent 6-membered partially unsaturated heterocyclic ring having no more than 1 heteroatom, wherein the heteroatom is oxygen. In some embodiments, a ring is a bivalent or multivalent 6-membered partially unsaturated heterocyclic ring having no more than 1 heteroatom, wherein the heteroatom is sulfur. In some embodiments, a ring is a bivalent or multivalent 6-membered partially unsaturated heterocyclic ring having 2 oxygen atoms. In some embodiments, a ring is a bivalent or multivalent 6-membered partially unsaturated heterocyclic ring having 2 nitrogen atoms.

In certain embodiments, a ring is a bivalent or multivalent a 3-7 membered saturated or partially unsaturated heterocyclic ring having 1-2 heteroatoms independently selected from nitrogen, oxygen, and sulfur. In certain embodiments, a ring is a bivalent or multivalent oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl ring.

In certain embodiments, a ring is a bivalent or multivalent 5-6 membered partially unsaturated monocyclic ring having 1-2 heteroatoms independently selected from nitrogen, oxygen, and sulfur. In certain embodiments, a ring is a bivalent or multivalent tetrahydropyridinyl, dihydrothiazolyl, dihydrooxazolyl, or oxazolinyl group.

In some embodiments, a ring is a bivalent or multivalent 7-10 membered bicyclic saturated or partially unsaturated heterocyclic ring having 1-5 heteroatoms independently selected from nitrogen, oxygen, and sulfur. In some embodiments, a ring is a bivalent or multivalent indolinyl ring. In some embodiments, a ring is a bivalent or multivalent isoindolinyl ring. In some embodiments, a ring is a bivalent or multivalent 1, 2, 3, 4-tetrahydroquinolinyl ring. In some embodiments, a ring is a bivalent or multivalent 1, 2, 3, 4-tetrahydroisoquinolinyl ring. In some embodiments, a ring is a bivalent or multivalent azabicyclo[3.2.1]octanyl ring.

In some embodiments, a ring is a bivalent or multivalent 8-10 membered bicyclic heteroaryl ring having 1-5 heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In some embodiments, a ring is a bivalent or multivalent 5,6-fused heteroaryl ring having 1-4 heteroatoms independently selected from nitrogen, oxygen, and sulfur. In some embodiments, a ring is a bivalent or multivalent 5,6-fused heteroaryl ring having 1-3 heteroatoms independently selected from nitrogen, oxygen, and sulfur. In some embodiments, a ring is a bivalent or multivalent 5,6-fused heteroaryl ring having two heteroatoms independently selected from nitrogen, oxygen, and sulfur. In some embodiments, a ring is a bivalent or multivalent 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl ring. In some embodiments, a ring is a bivalent or multivalent 5,6-fused heteroaryl ring having three heteroatoms independently selected from nitrogen, oxygen, and sulfur. In some embodiments, a ring is a bivalent or multivalent dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl ring. In some embodiments, a ring is a bivalent or multivalent 5,6-fused heteroaryl ring having four heteroatoms independently selected from nitrogen, oxygen, and sulfur. In some embodiments, a ring is a bivalent or multivalent 5,6-fused heteroaryl ring having five heteroatoms independently selected from nitrogen, oxygen, and sulfur.

In some embodiments, a ring is a bivalent or multivalent 5,6-fused heteroaryl ring having 1-5 heteroatoms independently selected from nitrogen, oxygen, and sulfur. In other embodiments, a ring is a bivalent or multivalent 5,6-fused heteroaryl ring having 1-2 heteroatoms independently selected from nitrogen, oxygen, and sulfur. In certain embodiments, a ring is a bivalent or multivalent 5,6-fused heteroaryl ring having one heteroatom independently selected from nitrogen, oxygen, and sulfur. In some embodiments, a ring is a bivalent or multivalent indolyl ring. In some embodiments, a ring is a bivalent or multivalent benzofuranyl ring. In some embodiments, a ring is a bivalent or multivalent benzo[b]thienyl ring. In certain embodiments, a ring is a bivalent or multivalent 5,6-fused heteroaryl ring having two heteroatoms independently selected from nitrogen, oxygen, and sulfur. In some embodiments, a ring is a bivalent or multivalent azaindolyl ring. In some embodiments, a ring is a bivalent or multivalent benzimidazolyl ring. In some embodiments, a ring is a bivalent or multivalent benzothiazolyl ring. In some embodiments, a ring is a bivalent or multivalent benzoxazolyl ring. In some embodiments, a ring is a bivalent or multivalent indazolyl ring. In certain embodiments, a ring is a bivalent or multivalent 5,6-fused heteroaryl ring having three heteroatoms independently selected from nitrogen, oxygen, and sulfur. In some embodiments, a ring is a bivalent or multivalent oxazolopyridiyl, thiazolopyridinyl or imidazopyridinyl ring. In certain embodiments, a ring is a bivalent or multivalent 5,6-fused heteroaryl ring having four heteroatoms independently selected from nitrogen, oxygen, and sulfur. In some embodiments, a ring is a bivalent or multivalent purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl ring. In certain embodiments, a ring is a bivalent or multivalent 5,6-fused heteroaryl ring having five heteroatoms independently selected from nitrogen, oxygen, and sulfur.

In certain embodiments, a ring is a bivalent or multivalent 6,6-fused heteroaryl ring having 1-5 heteroatoms independently selected from nitrogen, oxygen, and sulfur. In some embodiments, a ring is a bivalent or multivalent 6,6-fused heteroaryl ring having 1-2 heteroatoms independently selected from nitrogen, oxygen, and sulfur. In other embodiments, a ring is a bivalent or multivalent 6,6-fused heteroaryl ring having one heteroatom selected from nitrogen, oxygen, and sulfur. In some embodiments, a ring is a bivalent or multivalent quinolinyl ring. In some embodiments, a ring is a bivalent or multivalent isoquinolinyl ring. In some embodiments, a ring is a bivalent or multivalent 6,6-fused heteroaryl ring having two heteroatoms independently selected from nitrogen, oxygen, and sulfur. In some embodiments, a ring is a bivalent or multivalent quinazolinyl, phthalazinyl, quinoxalinyl or naphthyridinyl ring. In some embodiments, a ring is a bivalent or multivalent 6,6-fused heteroaryl ring having three heteroatoms independently selected from nitrogen, oxygen, and sulfur. In some embodiments, a ring is a bivalent or multivalent pyridopyrimidinyl, pyridopyridazinyl, pyridopyrazinyl, or benzotriazinyl ring. In some embodiments, a ring is a bivalent or multivalent 6,6-fused heteroaryl ring having four heteroatoms independently selected from nitrogen, oxygen, and sulfur. In some embodiments, a ring is a bivalent or multivalent pyridotriazinyl, pteridinyl, pyrazinopyrazinyl, pyrazinopyridazinyl, pyridazinopyridazinyl, pyrimidopyridazinyl or pyrimidopyrimidinyl ring. In some embodiments, a ring is a bivalent or multivalent 6,6-fused heteroaryl ring having five heteroatoms independently selected from nitrogen, oxygen, and sulfur.

In some embodiments, a ring formed by two or more groups taken together, which is typically optionally substituted, is a monocyclic saturated 5-7 membered ring having no additional heteroatoms in addition to intervening heteroatoms, if any. In some embodiments, a ring formed by two or more groups taken together is a monocyclic saturated 5-membered ring having no additional heteroatoms in addition to intervening heteroatoms, if any. In some embodiments, a ring formed by two or more groups taken together is a monocyclic saturated 6-membered ring having no additional heteroatoms in addition to intervening heteroatoms, if any. In some embodiments, a ring formed by two or more groups taken together is a monocyclic saturated 7-membered ring having no additional heteroatoms in addition to intervening heteroatoms, if any.

In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a bicyclic, saturated, partially unsaturated, or aryl 5-30 membered ring having, in addition to the intervening heteroatoms, if any, 0-10 heteroatoms independently selected from oxygen, nitrogen, and sulfur. In some embodiments, a ring formed by two or more groups taken together is a bicyclic and saturated 8-10 membered bicyclic ring having no additional heteroatoms in addition to intervening heteroatoms, if any. In some embodiments, a ring formed by two or more groups taken together is a bicyclic and saturated 8-membered bicyclic ring having no additional heteroatoms in addition to intervening heteroatoms, if any. In some embodiments, a ring formed by two or more groups taken together is a bicyclic and saturated 9-membered bicyclic ring having no additional heteroatoms in addition to intervening heteroatoms, if any. In some embodiments, a ring formed by two or more groups taken together is a bicyclic and saturated 10-membered bicyclic ring having no additional heteroatoms in addition to intervening heteroatoms, if any. In some embodiments, a ring formed by two or more groups taken together is bicyclic and comprises a 5-membered ring fused to a 5-membered ring. In some embodiments, a ring formed by two or more groups taken together is bicyclic and comprises a 5-membered ring fused to a 6-membered ring. In some embodiments, the 5-membered ring comprises one or more intervening nitrogen, phosphorus and oxygen atoms as ring atoms. In some embodiments, a ring formed by two or more groups taken together comprises a ring system having the backbone structure of

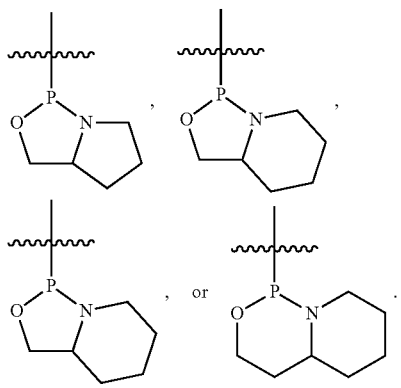

In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, sulfur, phosphorus and silicon. In some embodiments, a ring formed by two or more groups taken together is a polycyclic, saturated, partially unsaturated, or aryl 3-30 membered ring having, in addition to the intervening heteroatoms, if any, 0-10 heteroatoms independently selected from oxygen, nitrogen, and sulfur.

In some embodiments, a ring formed by two or more groups taken together is monocyclic, bicyclic or polycyclic and comprises a 5-10 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-9 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-8 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-7 membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 5-6 membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 6-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 7-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 8-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 9-membered monocyclic ring whose ring atoms comprise one or more intervening nitrogen, phosphorus and/or oxygen atoms. In some embodiments, a ring formed by two or more groups taken together is monocyclic, bicyclic or polycyclic and comprises a 10-membered monocyclic ring whose ring atoms comprise one or more intervening nitrogen, phosphorus and/or oxygen atoms.

In some embodiments, a ring formed by two or more groups taken together is monocyclic, bicyclic or polycyclic and comprises a 5-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 6-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 7-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 8-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 9-membered ring whose ring atoms consist of carbon atoms and the intervening nitrogen, phosphorus and oxygen atoms. In some embodiments, a ring formed by two or more groups taken together is monocyclic, bicyclic or polycyclic and comprises a 10-membered ring whose ring atoms consist of carbon atoms and the intervening nitrogen, phosphorus and oxygen atoms.

In some embodiments, a ring formed by two or more groups taken together comprises a ring system having the backbone structure of

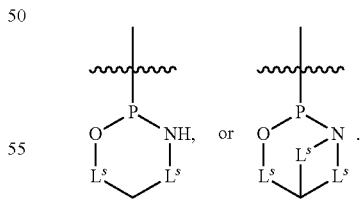

In some embodiments, rings described herein are unsubstituted. In some embodiments, rings described herein are substituted. In some embodiments, substituents are selected from those described in example compounds provided in the present disclosure.

In some embodiments, provided features, e.g., purity (e.g., overall purity, diastereomeric purity, enantiomeric purity, etc.), selectivity (e.g., overall selectivity, region-selectivity, diastereomeric selectivity, enantiomeric selectivity, etc.), levels (e.g., predetermined levels (of oligonucleotides, chiral auxiliaries, etc.), levels of activities, etc.), etc., are described as percentages or ranges of percentages. A percentage can be any percentage within provided ranges. For example, in some embodiments, depending on the ranges if any, a percentage is about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, depending on the ranges if any, a percentage is at least 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99%. In some embodiments, a percentage is at least 1%. In some embodiments, a percentage is at least 2%. In some embodiments, a percentage is at least 3%. In some embodiments, a percentage is at least 4%. In some embodiments, a percentage is at least 5%. In some embodiments, a percentage is at least 10%. In some embodiments, a percentage is at least 15%. In some embodiments, a percentage is at least 20%. In some embodiments, a percentage is at least 25%. In some embodiments, a percentage is at least 30%. In some embodiments, a percentage is at least 35%. In some embodiments, a percentage is at least 40%. In some embodiments, a percentage is at least 45%. In some embodiments, a percentage is at least 50%. In some embodiments, a percentage is at least 55%. In some embodiments, a percentage is at least 60%. In some embodiments, a percentage is at least 65%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 91%. In some embodiments, a percentage is at least 92%. In some embodiments, a percentage is at least 93%. In some embodiments, a percentage is at least 94%. In some embodiments, a percentage is at least 95%. In some embodiments, a percentage is at least 96%. In some embodiments, a percentage is at least 97%. In some embodiments, a percentage is at least 98%. In some embodiments, a percentage is at least 99%. In some embodiments, a percentage is about 1%. In some embodiments, a percentage is about 2%. In some embodiments, a percentage is about 3%. In some embodiments, a percentage is about 4%. In some embodiments, a percentage is about 5%. In some embodiments, a percentage is about 10%. In some embodiments, a percentage is about 15%. In some embodiments, a percentage is about 20%. In some embodiments, a percentage is about 25%. In some embodiments, a percentage is about 30%. In some embodiments, a percentage is about 35%. In some embodiments, a percentage is about 40%. In some embodiments, a percentage is about 45%. In some embodiments, a percentage is about 50%. In some embodiments, a percentage is about 55%. In some embodiments, a percentage is about 60%. In some embodiments, a percentage is about 65%. In some embodiments, a percentage is about 70%. In some embodiments, a percentage is about 75%. In some embodiments, a percentage is about 80%. In some embodiments, a percentage is about 85%. In some embodiments, a percentage is about 90%. In some embodiments, a percentage is about 91%. In some embodiments, a percentage is about 92%. In some embodiments, a percentage is about 93%. In some embodiments, a percentage is about 94%. In some embodiments, a percentage is about 95%. In some embodiments, a percentage is about 96%. In some embodiments, a percentage is about 97%. In some embodiments, a percentage is about 98%. In some embodiments, a percentage is about 99%. In some embodiments, a percentage is less than 1%. In some embodiments, a percentage is less than 2%. In some embodiments, a percentage is less than 3%. In some embodiments, a percentage is less than 4%. In some embodiments, a percentage is less than 5%. In some embodiments, a percentage is less than 10%. In some embodiments, a percentage is less than 15%. In some embodiments, a percentage is less than 20%. In some embodiments, a percentage is less than 25%. In some embodiments, a percentage is less than 30%. In some embodiments, a percentage is less than 35%. In some embodiments, a percentage is less than 40%. In some embodiments, a percentage is less than 45%. In some embodiments, a percentage is less than 50%. In some embodiments, a percentage is less than 55%. In some embodiments, a percentage is less than 60%. In some embodiments, a percentage is less than 65%. In some embodiments, a percentage is less than 70%. In some embodiments, a percentage is less than 75%. In some embodiments, a percentage is less than 80%. In some embodiments, a percentage is less than 85%. In some embodiments, a percentage is less than 90%. In some embodiments, a percentage is less than 91%. In some embodiments, a percentage is less than 92%. In some embodiments, a percentage is less than 93%. In some embodiments, a percentage is less than 94%. In some embodiments, a percentage is less than 95%. In some embodiments, a percentage is less than 96%. In some embodiments, a percentage is less than 97%. In some embodiments, a percentage is less than 98%. In some embodiments, a percentage is less than 99%.

Provided methods may comprise use of a temperature higher and/or lower than room temperature. In some embodiments, provided methods, e.g., in a reaction forming a phosphoramidite, comprise use of a lowered temperature, such as a temperature equal to or lower than about −78, -75, -70, -65, -60, -55, -50, -45, -40, -35, -30, -25, -20, -15, -10, -5, 0, 5, 10, 15, or 20° C. In some embodiments, provided methods, e.g., in a reaction forming a phosphoramidite, comprise use of an elevated temperature, such as a temperature equal to or more than about 25, 30, 35, 40, 45, 50, 55, 60, 65, 70, 75, 80, 85, 90, 95, 100, 110, 120, 130, 140 or 150° C. In some embodiments, provided methods comprise a temperature increase from a lowered temperature to another lowered temperature. In some embodiments, provided methods comprise a temperature increase from a lowered temperature to room temperature. In some embodiments, provided methods comprise a temperature increase from room temperature to an elevated temperature. In some embodiments, provided methods comprise a temperature increase from a lowered temperature to an elevated temperature. In some embodiments, provided methods comprise a temperature decrease from an elevated temperature to another elevated temperature. In some embodiments, provided methods comprise a temperature decrease from an elevated temperature to room temperature. In some embodiments, provided methods comprise a temperature decrease from room temperature to a lowered temperature. In some embodiments, provided methods comprise a temperature decrease from an elevated temperature to a lowered temperature.

Various solvents are suitable for use in provided methods. In some embodiments, reactions for forming phosphoramidites are performed in a solvent comprising ether. In some embodiments, reactions for forming phosphoramidites are performed in a solvent comprising THF. In some embodiments, reactions for forming phosphoramidites are performed in THF. Suitable solvents are widely known (e.g., those in US/2011/0294124, US/2015/0211006, US/2017/0037399, WO/2017/015555, WO/2017/062862, WO/2017/160741, WO/2017/192664, WO/2017/192679, WO/2017/210647, WO2018/022473, WO2018/067973, and WO2018/098264, solvents of each of which are incorporated herein by reference) and can be utilized in accordance with the present disclosure.

In some embodiments, one or more steps are performed under an inert gas. In some embodiments, formation of phosphoramidites is performed under an inert gas. In some embodiments, one or more steps of oligonucleotide synthesis cycle is performed under an inert gas. In some embodiments, an inert gas is argon. In some embodiments, an inert gas is nitrogen.

In some embodiments, one or more steps are performed under increased pressure. In some embodiments, one or more steps are performed under vacuum. In some embodiments, filtration is performed under vacuum.

In some embodiments, a provided compound, e.g., a compound of formula I, I-a, I-a-1, I-a-2, I-b, I-c, I-d, I-e, II, II-a, II-b, III, III-a, or III-b, or a salt thereof, a compound of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or a salt thereof, or an oligonucleotide of formula VIII or salt thereof, etc., has a purity which is about or more than 50%, 60%, 70%, 75%, 80%, 85%, 90%, 91%, 92%, 93%, 94%, 95%, 96%, 97%, 98%, or 99%. In some embodiments, a purity is about 50% or more. In some embodiments, a purity is about 55% or more. In some embodiments, a purity is about 60% or more. In some embodiments, a purity is about 65% or more. In some embodiments, a purity is about 70% or more. In some embodiments, a purity is about 75% or more. In some embodiments, a purity is about 80% or more. In some embodiments, a purity is about 85% or more. In some embodiments, a purity is about 90% or more. In some embodiments, a purity is about 91% or more. In some embodiments, a purity is about 92% or more. In some embodiments, a purity is about 93% or more. In some embodiments, a purity is about 94% or more. In some embodiments, a purity is about 95% or more. In some embodiments, a purity is about 96% or more. In some embodiments, a purity is about 97% or more. In some embodiments, a purity is about 98% or more. In some embodiments, a purity is about 99% or more. In some embodiments, a purity is about 99.5% or more.

In some embodiments, a provided compound, e.g., a chiral auxiliary, a phosphoramidite, an oligonucleotide, etc., has a diastereomeric purity of at least 60%, 65%, 70%, 75%, 80%, 85%, 90%, 91%, 92%, 93%, 94%, 95%, 96%, 97%, 98%, or 99%. In some embodiments, a provided compound has a diastereomeric purity of at least 60%. In some embodiments, a provided compound has a diastereomeric purity of at least 70%. In some embodiments, a provided compound has a diastereomeric purity of at least 80%. In some embodiments, a provided compound has a diastereomeric purity of at least 85%. In some embodiments, a provided compound has a diastereomeric purity of at least 90%. In some embodiments, a provided compound has a diastereomeric purity of at least 91%. In some embodiments, a provided compound has a diastereomeric purity of at least 92%. In some embodiments, a provided compound has a diastereomeric purity of at least 93%. In some embodiments, a provided compound has a diastereomeric purity of at least 94%. In some embodiments, a provided compound has a diastereomeric purity of at least 95%. In some embodiments, a provided compound has a diastereomeric purity of at least 96%. In some embodiments, a provided compound has a diastereomeric purity of at least 97%. In some embodiments, a provided compound has a diastereomeric purity of at least 98%. In some embodiments, a provided compound has a diastereomeric purity of at least 99%. In some embodiments, a provided compound has a diastereomeric purity of at least 99.5%.

In some embodiments, a chiral element, e.g., a chiral center (carbon, phosphorus, etc.) of a provided compound has a diastereomeric purity of 60%-100%. In some embodiments, a chiral element, e.g., a chiral center (carbon, phosphorus, etc.) of a provided compound has a diastereomeric purity of at least 60%, 65%, 70%, 75%, 80%, 85%, 90%, 91%, 92%, 93%, 94%, 95%, 96%, 97%, 98%, or 99%. In some embodiments, a chiral element is a chiral carbon. In some embodiments, a chiral element is a chiral phosphorus (e.g., a linkage phosphorus atom in a chiral internucleotidic linkage). In some embodiments, a chiral element has a diastereomeric purity of at least 60%. In some embodiments, a chiral center has a diastereomeric purity of at least 70%. In some embodiments, a chiral center has a diastereomeric purity of at least 80%. In some embodiments, a chiral center has a diastereomeric purity of at least 85%. In some embodiments, a chiral center has a diastereomeric purity of at least 90%. In some embodiments, a chiral center has a diastereomeric purity of at least 91%. In some embodiments, a chiral center has a diastereomeric purity of at least 92%. In some embodiments, a chiral center has a diastereomeric purity of at least 93%. In some embodiments, a chiral center has a diastereomeric purity of at least 94%. In some embodiments, a chiral center has a diastereomeric purity of at least 95%. In some embodiments, a chiral center has a diastereomeric purity of at least 96%. In some embodiments, a chiral center has a diastereomeric purity of at least 97%. In some embodiments, a chiral center has a diastereomeric purity of at least 98%. In some embodiments, a chiral center has a diastereomeric purity of at least 99%. In some embodiments, a chiral center has a diastereomeric purity of at least 99.5%.

In some embodiments, the present disclosure provides methods, e.g., methods for preparing chiral auxiliaries, phosphoramidites, oligonucleotides, etc., with high stereoselectivity. In some embodiments, the present disclosure provides methods with high diastereoselectivity. In some embodiments, the present disclosure provides methods with high enantioselectivity. In some embodiments, the present disclosure provides methods with both high diastereoselectivity and high enantioselectivity. In some embodiments, a selectivity is about 60%-100%. In some embodiments, a selectivity is at least 60%, 65%, 70%, 75%, 80%, 85%, 90%, 91%, 92%, 93%, 94%, 95%, 96%, 97%, 98%, or 99%. In some embodiments, a diastereoselectivity is at least 60%, 65%, 70%, 75%, 80%, 85%, 90%, 91%, 92%, 93%, 94%, 95%, 96%, 97%, 98%, or 99%. In some embodiments, a enantioselectivity is at least 60%, 65%, 70%, 75%, 80%, 85%, 90%, 91%, 92%, 93%, 94%, 95%, 96%, 97%, 98%, or 99%. In some embodiments, both a diastereoselectivity and an enantioselectivity are at least 60%, 65%, 70%, 75%, 80%, 85%, 90%, 91%, 92%, 93%, 94%, 95%, 96%, 97%, 98%, or 99%. In some embodiments, a selectivity is at least 60%. In some embodiments, a selectivity is at least 70%. In some embodiments, a selectivity is at least 80%. In some embodiments, a selectivity is at least 85%. In some embodiments, a selectivity is at least 90%. In some embodiments, a selectivity is at least 91%. In some embodiments, a selectivity is at least 92%. In some embodiments, a selectivity is at least 93%. In some embodiments, a selectivity is at least 94%. In some embodiments, a selectivity is at least 95%. In some embodiments, a selectivity is at least 96%. In some embodiments, a selectivity is at least 97%. In some embodiments, a selectivity is at least 98%. In some embodiments, a selectivity is at least 99%. In some embodiments, a selectivity is at least 99.5%.

As demonstrated herein, provided technologies can surprisingly improve yields and/or purity. In some embodiments, the absolute improvement is about 5%, 10%, 15%, 20%, 25%, 30%, 35%, 40%, 45%, 50%, 55%, 60%, 65%, 70%, 75%, 80%, 85%, 90%, 95% or more. In some embodiments, the absolute improvement is greater than about 5%, 10%, 15%, 20%, 25%, 30%, 35%, 40%, 45%, 50%, 55%, 60%, 65%, 70%, 75%, 80%, 85%, 90%, 95% or more. In some embodiments, yield from a provided technology is greater than about 80%, while yield from a corresponding technology is less than about 60% (corresponding to an absolute improvement of greater than 20%). In some embodiments, the improvement relative to a corresponding technology is greater than about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900% or more.

In some embodiments, as readily appreciated by a person having ordinary skill in the art, in provided oligonucleotide compositions oligonucleotides may exist as salts. In some embodiments, provided oligonucleotide compositions are pharmaceutical compositions. In some embodiments, provided oligonucleotides exist as pharmaceutically acceptable salts.

In some embodiments, one or more lipid moieties, one or more targeting moieties, and/or one or more carbohydrate moieties may be independently and optionally incorporated into oligonucleotides. In some embodiments, provided oligonucleotides comprise one or more lipid moieties, one or more targeting moieties, and/or one or more carbohydrate moieties. Example lipid moieties, targeting moieties, and carbohydrate moieties are widely known (e.g., those in US/2015/0211006, US/2017/0037399, WO/2017/015555, WO/2017/062862, WO/2017/160741, WO2017/192664, WO2017/192679, WO2017/210647, WO2018/022473, WO2018/067973, and WO2018/098264, lipid moieties, targeting moieties, and carbohydrate moieties of each of which are incorporated herein by reference) and can be utilized in accordance with the present disclosure.

In some embodiments, the present disclosure provides multimers of provided oligonucleotides. In some embodiments, the present disclosure provides multimers of provided oligonucleotides, each of which independently has the structure of formula VIII or a salt thereof. In some embodiments, provided multimers are of oligonucleotides of the same structure. In some embodiments, provided multimers are of oligonucleotides of different structures.

Unless otherwise stated, structures depicted herein are also meant to include all isomeric (e.g., enantiomeric, diastereomeric, and geometric (or conformational)) forms of the structures. Unless otherwise stated, all tautomeric forms of compounds of the present disclosure are included. Additionally, unless otherwise stated, structures depicted herein are also meant to include compounds that differ only in the presence of one or more isotopically enriched atoms. For example, compounds having present structures except for replacement of hydrogen with deuterium and/or tritium, or replacement of carbon by $^{11}C$, $^{13}C$, and/or $^{14}C$ are included. Such compounds are useful, for example, as analytical tools or probes in biological assays. Unless otherwise specified, compounds, e.g., oligonucleotides, etc. include salts thereof.

In some embodiments, provided compounds are isotope labelled. In some embodiments, labeled compounds are useful for diagnosis, detection, modulation of one or more properties, modulation of activities, etc. In some embodiments, an isotope label is selected from $^2H$, $^3H$, $^{11}C$, $^{13}C$, $^{14}C$, $^{15}N$, $^{18}O$, $^{32}P$, $^{35}S$, etc. In some embodiments, an isotope label is selected from $^2H$, $^3H$, $^{11}C$, $^{13}C$, $^{14}C$, $^{15}N$, $^{18}O$, $^{32}P$, and $^{35}S$. In some embodiments, an isotope is a stable isotope. In some embodiments, an isotope is selected from $^2H$, $^{13}C$, $^{15}N$, and $^{18}O$. In some embodiments, an isotope is radioactive. In some embodiments, an isotope is selected from $^3H$, $^{32}P$, and $^{35}S$. In some embodiments, a provided compound comprises a $^2H$ label. In some embodiments, a provided compound comprises a $^3H$ label. In some embodiments, a provided compound comprises a $^{11}C$ label. In some embodiments, a provided compound comprises a $^{13}C$ label. In some embodiments, a provided compound comprises a $^{14}C$ label. In some embodiments, a provided compound comprises a $^{15}N$ label. In some embodiments, a provided compound comprises a $^{18}O$ label. In some embodiments, a provided compound comprises a $^{32}P$ label. In some embodiments, a provided compound comprises a $^{35}S$ label. In some embodiments, a provided compound comprises one and no more than one type of isotope label. In some embodiments, a provided compound comprises two or more types of isotope labels. In some embodiments, a provided compound comprises one or more types of isotope labels, each of which is independently enriched at least 1.5, 2, 3, 4, 5, 6, 7, 8, 9, 10, 50, 100, 1,000, 5,000, 10,000 or more folds or natural level. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, a label is of an atom % of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 99.5%. In some embodiments, essentially all atoms at one or more position are labelled (atom % greater than 99%).

Various methods described herein or known in the art can be utilized for confirming or identifying the stereochemistry pattern of the backbone of an oligonucleotide and/or stereochemistry of particular internucleotidic linkages, and/or determining the diastereoselectivity of one or more chiral internucleotidic linkages. Useful technologies include, as non-limiting examples: NMR (e.g., 1D (one-dimensional) and/or 2D (two-dimensional)$^1H$-$^{31}P$ HETCOR (heteronuclear correlation spectroscopy)), HPLC, RP—HPLC, mass spectrometry, LC-MS, and/or stereospecific nucleases. In some embodiments, stereospecific nucleases include: benzonase, micrococcal nuclease, and svPDE (snake venome phosphodiesterase), which are specific for internucleotidic linkages in the Rp configuration (e.g., a PS in the Rp configuration); and nuclease P1, mung bean nuclease, and nuclease S1, which are specific for internucleotidic linkages in the Sp configuration (e.g., a PS in the Sp configuration). Without wishing to be bound by any particular theory, the present disclosure notes that, in at least some cases, stereospecificity of a particular nuclease may be altered by a modification (e.g., 2'-modification) of a sugar, by a base sequence, or by a stereochemical context. For example, in at least some cases, benzonase and micrococcal nuclease, which are specific for Rp internucleotidic linkages, were both unable to cleave an isolated PS Rp internucleotidic linkage flanked by PS Sp internucleotidic linkages.

Among other things, the present disclosure provides the following Example Embodiments:

1. A method for preparing a composition comprising a plurality of oligonucleotides comprising:
- a) a coupling step comprising:
  - contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and
  - coupling a partner compound with the free hydroxyl groups of a plurality of de-blocked oligonucleotides or nucleosides;
  - wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;
- b) optionally a pre-modification capping step comprising:
  - contacting a coupling product composition with a pre-modification capping reagent system; and
  - capping one or more functional groups of the coupling product composition;
  - wherein the pre-modification capping step provides a pre-modification capping product composition comprising a plurality of pre-modification capping product oligonucleotides;
- c) a modification step comprising:
  - contacting a coupling product composition with a modification reagent system comprising a modification reagent, and modifying one or more internucleotidic linkages of one or more coupling product oligonucleotides; or
  - contacting a pre-modification capping product composition with a modification reagent system and modifying one or more linkages of one or more pre-modification capping product oligonucleotides;
  - wherein the modification step provides a modification product composition comprising a plurality of modification product oligonucleotides;
- d) optionally a post-modification capping step comprising:
  - contacting a modification product composition with a post-modification capping reagent system; and
  - capping one or more functional groups of a plurality of oligonucleotides of the modification product composition;
  - wherein the post-modification capping step provides a post-modification capping product composition comprising a plurality of post-modification capping product oligonucleotides;
- e) optionally a de-blocking step comprising:
  - contacting a modification product composition, or a post-modification capping product composition, with a de-blocking reagent system;
  - wherein the deblocking step provides a de-blocking product composition comprising a plurality of de-blocking product oligonucleotides, each of which independently comprises a free hydroxyl group; and
- f) optionally repeating steps b) through e) a number of times.

2. A method for preparing a composition comprising a plurality of oligonucleotides comprising one or more cycles, each cycle independently comprises:
- a) a coupling step comprising:
  - contacting a de-blocked composition comprising a plurality of de-blocked oligonucleotides (a de-blocked oligonucleotide composition) or nucleosides, which is de-blocked in that each independently comprises a free hydroxyl group, with a coupling reagent system comprising a partner compound which comprises a nucleoside unit; and
  - coupling a partner compound with the free hydroxyl groups of a plurality of de-blocked oligonucleotides or nucleosides;
  - wherein the coupling step provides a coupling product composition comprising a plurality of coupling product oligonucleotides, each of which independently comprises an internucleotidic linkage connecting a hydroxyl group of a de-blocked oligonucleotide with a nucleoside unit of a partner compound;
- b) optionally a pre-modification capping step comprising:
  - contacting a coupling product composition with a pre-modification capping reagent system; and
  - capping one or more functional groups of the coupling product composition;
  - wherein the pre-modification capping step provides a pre-modification capping product composition comprising a plurality of pre-modification capping product oligonucleotides;
- c) a modification step comprising:
  - contacting a coupling product composition with a modification reagent system comprising a modification reagent, and modifying one or more internucleotidic linkages of one or more coupling product oligonucleotides; or
  - contacting a pre-modification capping product composition with a modification reagent system and modifying one or more linkages of one or more pre-modification capping product oligonucleotides;
  - wherein the modification step provides a modification product composition comprising a plurality of modification product oligonucleotides;
- d) optionally a post-modification capping step comprising:
  - contacting a modification product composition with a post-modification capping reagent system; and
  - capping one or more functional groups of a plurality of oligonucleotides of the modification product composition;
  - wherein the post-modification capping step provides a post-modification capping product composition comprising a plurality of post-modification capping product oligonucleotides;
- e) optionally a de-blocking step comprising:
  - contacting a modification product composition, or a post-modification capping product composition, with a de-blocking reagent system;
  - wherein the deblocking step provides a de-blocking product composition comprising a plurality of de-blocking product oligonucleotides, each of which independently comprises a free hydroxyl group.

3. The method of any one of the preceding embodiments, wherein:
the method comprises both a pre-modification capping step and a post-modification capping step, wherein there are no steps other than modification steps between the pre-modification capping and post-modification capping steps, wherein a post-modification capping step comprises contacting a modification product composition comprising a plurality of modification product oligonucleotides, each of which independently comprises a linkage phosphorus bonded to an atom that is not oxygen; or the method comprises both a pre-modification capping step and a post-modification capping step, wherein there are no steps other than modification steps between the pre-modification capping and post-modification capping steps, wherein a pre-modification capping reagent system is different from a post-modification reagent system; or the method comprises a pre-modification capping step, wherein the pre-modification capping reagent system caps a plurality of non-hydroxyl groups of a plurality of coupling product oligonucleotides, and a modification step that comprises sulfurization, which sulfurization provides a modification product composition comprising a plurality of modification product oligonucleotides, each of which independently comprises a P=S moiety; or the method comprises a post-modification capping step, comprising contacting a modification product composition comprising a plurality of modification product oligonucleotides, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center; or the method comprises a post-modification capping step, and a coupling reagent system comprising a chiral partner compound that comprises a monomeric unit of the oligomeric compound, wherein the chiral partner compound comprises a chiral atom that is not within the monomeric unit; or the method comprises a coupling step, a modification step, and one or more pre-modification capping steps between the coupling step and the modification step, wherein for each pre-modification capping step between the coupling step and the modification step, its pre-modification capping reagent system comprises no esterification catalyst, and no agent that is converted into an esterification catalyst when the pre-modification capping reagent system contacts a plurality of oligonucleotides to be capped;

the method comprises a coupling step, a modification step, and one or more pre-modification capping steps between the coupling step and the modification step, wherein for each pre-modification capping step between the coupling step and the modification step, the pre-modification capping step caps amino groups selectively over hydroxyl groups.

4. The method of any one of the preceding embodiments, wherein the method comprises both a pre-modification capping step and a post-modification capping step, wherein there are no steps other than modification steps between the pre-modification capping and post-modification capping steps, wherein a post-modification capping step comprises contacting a modification product composition comprising a plurality of modification product oligonucleotides, each of which independently comprises a linkage phosphorus bonded to an atom that is not oxygen.

5. The method of any one of the preceding embodiments, wherein the method comprises both a pre-modification capping step and a post-modification capping step, wherein there are no steps other than modification steps between the pre-modification capping and post-modification capping steps, wherein a pre-modification capping reagent system is different from a post-modification reagent system.

6. The method of any one of the preceding embodiments, wherein the method comprises a pre-modification capping step, wherein the pre-modification capping reagent system caps a plurality of non-hydroxyl groups of a plurality of coupling product oligonucleotides, and a modification step that comprises sulfurization, which sulfurization provides a modification product composition comprising a plurality of modification product oligonucleotides, each of which independently comprises a P=S moiety.

7. The method of any one of the preceding embodiments, wherein the method comprises a post-modification capping step, comprising contacting a modification product composition comprising a plurality of modification product oligonucleotide, each of which independently comprises a linkage that comprises at least one chirally controlled chiral center in that at least 80%, 85%, 90%, 95%, 96%, 97%, 98% or 99% oligomeric compounds within the modification product composition comprising the chiral center and having the same constitution share the same stereochemical configuration at the chiral center.

8. The method of any one of the preceding embodiments, wherein the method comprises a post-modification capping step, and a coupling reagent system comprising a chiral partner compound that comprises a monomeric unit of the oligomeric compound, wherein the chiral partner compound comprises a chiral atom that is not within the monomeric unit.

9. The method of any one of the preceding embodiments, wherein the method comprises a coupling step, a modification step, and one or more pre-modification capping steps between the coupling step and the modification step, wherein for each pre-modification capping step between the coupling step and the modification step, its pre-modification capping reagent system comprises no esterification catalyst, and no agent that is converted into an esterification catalyst when the pre-modification capping reagent system contacts a plurality of oligonucleotides to be capped.

10. The method of any one of the preceding embodiments, wherein the method comprises a coupling step, a modification step, and one or more pre-modification capping steps between the coupling step and the modification step, wherein for each pre-modification capping step between the coupling step and the modification step, the pre-modification capping step caps amino groups selectively over hydroxyl groups.

11. A method for preparing an oligonucleotide, comprising:
providing a chiral nucleoside phosphoramidite which comprises a chiral atom that is not the phosphorus atom or a sugar carbon atom; and
a post-modification capping step after a modification step but before the next de-blocking step or the next coupling step.

12. A method for preparing an oligonucleotide, comprising one or more cycles, each of which independently comprises:
a pre-modification capping step immediately before a modification step, which comprises sulfurization or oxidation, and a post-modification capping step immediately after a modification step.

13. A method for preparing an oligonucleotide, comprising:
providing an oligonucleotide intermediate comprising a chiral linkage phosphorus atom, which is bonded to a chiral center which is not within a nucleoside unit; and
a post-modification capping step after a modification step but before the next de-blocking step or the next coupling step.

14. The embodiment of any one of embodiments 11-13, wherein the post-modification capping step is a post-modification capping step of embodiment 1.

15. The embodiment of any one of embodiments 11-14, comprising a coupling step.

16. The embodiment of any one of embodiments 11-14, comprising a coupling step of embodiment 1.

17. The embodiment of any one of embodiments 11-16, comprising a pre-modification capping step.

18. The embodiment of any one of embodiments 11-16, comprising a pre-modification capping step of embodiment 1.

19. The embodiment of any one of embodiments 11-18, comprising a modification step.

20. The embodiment of any one of embodiments 11-18, comprising a modification step of embodiment 1.

21. The embodiment of any one of embodiments 11-20, comprising a de-blocking step.

22. The embodiment of any one of embodiments 11-20, comprising a de-blocking step of embodiment 1.

23. A method for preparing an oligonucleotide, comprising one or more cycles, each of which independently comprises the following steps:
    (1) coupling;
    (2) optionally a pre-modification capping;
    (3) a modification step;
    (4) optionally a post-modification capping; and
    (5) de-blocking.

24. The method of embodiment 23, wherein the coupling step is a coupling step of embodiment 1.

25. The method of any one of embodiments 23-24, comprising a pre-modification capping step wherein the pre-modification capping step is a pre-modification capping step of embodiment 1.

26. The method of any one of embodiments 23-25, comprising a modification step wherein the modification step is a pre-modification capping step of embodiment 1.

27. The method of any one of embodiments 23-24, comprising a post-modification capping step wherein the post-modification capping step is a pre-modification capping step of embodiment 1.

28. The method of any one of embodiments 23-24, comprising a post-modification de-blocking step wherein the de-blocking step is a pre-modification capping step of embodiment 1.

29. A method for oligonucleotide synthesis, comprising:
    one or more pre-modification capping steps after a coupling step and before the next modification step,
    wherein the capping condition of each pre-modification capping step after a coupling step and before the next modification step is independently selective or specific for amidation over esterification.

30. A method for oligonucleotide synthesis, comprising:
    one or more pre-modification capping steps that are after a coupling step and before the next modification step,
    wherein each pre-modification capping step after a coupling step and before the next modification step independently comprises no strong nucleophile, or if it comprises one or more strong nucleophiles, the level of each of the one or more strong nucleophiles is independently reduced compared to an appropriate reference capping condition.

31. A method for oligonucleotide synthesis, comprising:
    one or more pre-modification capping steps after a coupling step and before the next modification step,
    wherein each pre-modification capping step after a coupling step and before the next modification step independently comprises no strong nucleophile, or if it comprises one or more strong nucleophiles, the level of each of the one or more strong nucleophiles is independently no more than no more than about 0.01, 0.02, 0.05, 0.1, 0.2, 0.5, or 1 equivalents relative to the first incorporated nucleoside of the oligonucleotide.

32. A method for oligonucleotide synthesis, comprising:
    one or more pre-modification capping steps after a coupling step and before the next modification step,
    wherein each pre-modification capping step after a coupling step and before the next modification step independently comprises no esterification catalyst, or if it comprises one or more esterification catalysts, the level of each of the one or more esterification catalysts is independently reduced compared to an appropriate reference capping condition.

33. A method for oligonucleotide synthesis, comprising:
    one or more pre-modification capping steps after a coupling step and before the next modification step,
    wherein each pre-modification capping step after a coupling step and before the next modification step independently comprises no esterification catalyst, or if it comprises one or more esterification catalysts, the level of each of the one or more esterification catalysts is independently no more than no more than about 0.01, 0.02, 0.05, 0.1, 0.2, 0.5, or 1 equivalents relative to the first incorporated nucleoside of the oligonucleotide.

34. The embodiment of any one of embodiments 29-33, wherein the pre-modification capping step is a pre-modification capping step of embodiment 1.

35. The embodiment of any one of embodiments 29-34, wherein the coupling step is a coupling step of embodiment 1.

36. The embodiment of any one of embodiments 29-35, wherein the modification step is a modification step of embodiment 1.

37. The embodiment of any one of embodiments 29-36, comprising a post-modification capping step.

38. The embodiment of any one of embodiments 29-37, comprising a post-modification capping step of embodiment 1.

39. The embodiment of any one of embodiments 29-38, comprising a de-blocking step.

40. The embodiment of any one of embodiments 29-39, comprising a de-blocking step of embodiment 1.

41. The method of any one of the preceding embodiments, comprising a coupling step wherein the plurality of the de-blocked oligonucleotides or nucleosides is loaded on a support.

42. The method of any one of the preceding embodiments, wherein for each coupling step, the plurality of the de-blocked oligonucleotides or nucleosides is loaded on a support.

43. The method of any one of the preceding embodiments, wherein each oligonucleotide of the plurality of the de-blocked oligonucleotides independently has the structure of formula VIII or a salt thereof.

44. The method of any one of the preceding embodiments, wherein for each coupling step, each oligonucleotide of the plurality of the de-blocked oligonucleotides independently has the structure of formula VIII.

45. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each $P^L$ is not P.

46. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each $P^L$ is independently P(=W), wherein W is O or S.

47. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each —X-$L^s$-$R^5$ independently contains no free amino group.

48. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each —X-$L^s$-$R^5$ is independently -$L^7$-$R^1$.

49. The method of embodiment 48, wherein at least one of $R^5$ or $R^6$ is —C(O)CH$_3$.

50. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each X is independently —O— or —S—.

51. The method of any one of the preceding embodiments, wherein each oligonucleotide of the plurality of the de-blocked oligonucleotides independently has the structure of formula VIII or a salt thereof, wherein each $L^P$ is independently of formula VII or a salt form thereof, wherein each of Y and Z is —O—.

52. The method of any one of the preceding embodiments, wherein each oligonucleotide of the plurality of the de-blocked oligonucleotides independently has the structure of formula VIII or a salt thereof, wherein each —X-$L^s$-$R^5$ independently contains no free amino group.

53. The method of any one of the preceding embodiments, wherein each oligonucleotide of the plurality of the de-blocked oligonucleotides independently has the structure of formula VIII or a salt thereof, wherein each $R^{5S}$ is —OH.

54. The method of any one of the preceding embodiments, wherein a de-blocked oligonucleotide composition comprising a plurality of de-blocked oligonucleotides is a chirally controlled oligonucleotide composition.

55. The method of any one of the preceding embodiments, wherein a de-blocked oligonucleotide composition comprising a plurality of de-blocked oligonucleotides is a chirally controlled oligonucleotide composition, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage; and wherein no less than ((DS)$^{Nc}$*100)% of all oligonucleotides sharing the same base sequence in the de-blocked product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

56. The method of any one of the preceding embodiments, a free hydroxyl group of a de-blocked oligonucleotide or nucleoside is a 5'-OH.

57. The method of any one of the preceding embodiments, wherein a partner compound is a nucleoside phosphoramidite, wherein each —OH of a sugar unit is independently blocked.

58. The method of any one of the preceding embodiments, wherein a partner compound comprises a nucleoside unit having the structure of

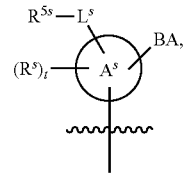

wherein $R^{5s}$ is —OR, wherein R is not —H.

59. The method of any one of the preceding embodiments, wherein a partner compound comprises a nucleoside unit having the structure of

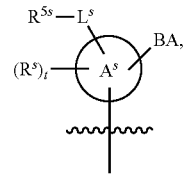

wherein $R^{5s}$ is —OR, wherein R is DMTr.

60. The method of any one of the preceding embodiments, wherein a partner compound is of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof.

61. The method of any one of the preceding embodiments, wherein a partner compound is a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, wherein $P^L$ is P.

62. The method of any one of the preceding embodiments, wherein for each coupling step, a partner compound is a phosphoramidite of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c-1, VI-c-2, VI-d, or VI-e, or a salt thereof, wherein $P^L$ is P.

63. The method of any one of the preceding embodiments, wherein a coupling reagent system comprises a partner compound and an activator.

64. The method of any one of the preceding embodiments, wherein an activator is an optionally substituted tetrazole.

65. The method of any one of embodiments 1-61, wherein an activator is selected from cyanomethyl imidazole triflate, cyanomethyl pyrrolidine triflate, ETT, phenyl(2H-tetrazol-5-yl)methanone, 2-(dimethylamino)acetonitrile/trifluorosulfonic acid(2/1), 2-(1H-imidazol-1-yl)acetonitrile/trifluorosulfonic acid(2/1), and 2-(pyrrolidin-1-yl)acetonitrile/trifluorosulfonic acid(2/1).

66. The method of any one of the preceding embodiments, wherein an activator is CMIMT.

67. The method of any one of the preceding embodiments, comprising a coupling step in which an activator is CMIMT, and a partner is of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.

68. The method of any one of the preceding embodiments, comprising a coupling step in which an activator is CMIMT, and a partner compound is diastereomerically pure.

69. The method of any one of the preceding embodiments, wherein for each coupling step in which a partner compound is diastereomerically pure, an activator is CMIMT.

70. The method of any one of the preceding embodiments, wherein an activator is CMPT.

71. The method of any one of the preceding embodiments, comprising a coupling step in which an activator is CMPT, and a partner is of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.

72. The method of any one of embodiments 1-71, comprising a coupling step in which an activator is CMPT, and a partner compound is diastereomerically pure.

73. The method of any one of the preceding embodiments, wherein an activator is ETT.

74. The method of any one of the preceding embodiments, comprising a coupling step in which an activator is ETT, and a partner is of formula IV, IV-a, IV-b, IV-c-1, IV-c-2, IV-d, IV-e, V, V-a, V-b, V-c-1, V-c-2, V-d, V-e, VI, VI-a, VI-b, VI-c-1, VI-c-2, VI-d, or VI-e, or a salt thereof.

75. The method of any one of the preceding embodiments, comprising a coupling step in which an activator is ETT, and a partner compound is of formula IVa, IVa-a, IVa-b, IVa-c-1, IVa-c-2, IVa-d, or IVa-e, or a salt thereof.

76. The method of any one of the preceding embodiments, wherein each coupling step independently forms an internucleotidic linkage of formula VII-b, or a salt form thereof.

77. The method of any one of the preceding embodiments, wherein one or more coupling steps each independently forms a chirally controlled internucleotidic linkage.

78. The method of any one of the preceding embodiments, wherein one or more coupling steps each independently forms a chirally controlled internucleotidic linkage, wherein each chirally controlled linkage phosphorus (a linkage phosphorus of a chirally controlled internucleotidic linkage) independently has a diastereomeric purity of at least 80%, 85%, 90%, 91%, 92%, 93%, 94%, 95%, 96%, 97%, 98% or 99% within the coupling product composition.

79. The method of any one of the preceding embodiments, wherein one or more coupling steps each independently forms a non-chirally controlled internucleotidic linkage.

80. The method of any one of the preceding steps, wherein a coupling step provides a coupling product composition comprising a plurality of coupling product oligonucleotides, wherein each coupling product oligonucleotide is independently an oligonucleotide of formula VIII or a salt thereof.

81. The method of any one of the preceding steps, wherein each coupling step provides a coupling product composition comprising a plurality of coupling product oligonucleotides, wherein each coupling product oligonucleotide is independently an oligonucleotide of formula VIII or a salt thereof.

82. The method of any one of embodiments 80-81, wherein for a coupling step, z of formula VIII for a coupling product oligonucleotide ($z^{CP}$) is greater than z of formula VIII for a corresponding de-blocked oligonucleotide ($z^{DB}$).

83. The method of any one of embodiments 80-81, wherein for a coupling step $z^{CP}=z^{DB}+1$.

84. The method of any one of the preceding steps, wherein a coupling product composition comprises a plurality of coupling product oligonucleotides, each of which is independently of formula VIII or a salt thereof, wherein each $L^P$ bonded to

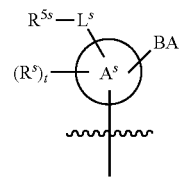

in formula VIII is independently an internucleotidic linkage of formula VII-b, or a salt form thereof.

85. The method of any one of the preceding embodiments, wherein a coupling product composition comprises a plurality of coupling product oligonucleotides, each of which is independently of formula VIII or a salt thereof, wherein each $L^P$ that is not bonded to

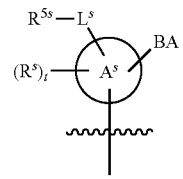

in formula VIII is independently of formula VII or a salt form thereof, wherein each $P^L$ is independently not P.

86. The method of any one of the preceding embodiments, wherein a coupling product composition comprises a plurality of coupling product oligonucleotides, each of which is independently of formula VIII or a salt thereof, wherein each $L^P$ that is not bonded to

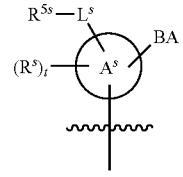

in formula VIII is independently of formula VII or a salt form thereof, wherein each $P^L$ is independently P(=W), wherein W is O or S.

87. The method of any one of the preceding embodiments, wherein a coupling product composition comprises a plurality of coupling product oligonucleotides, each of which is independently of formula VIII or a salt thereof, wherein each $L^P$ that is bonded to

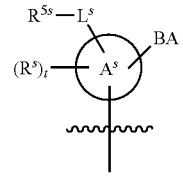

in formula VIII is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —H.

88. The method of any one of the preceding embodiments, wherein for at least one coupling step, a plurality of coupling product oligonucleotides are oligonucleotide of formula VIII or a salt thereof, wherein the $L^P$ that is bonded to

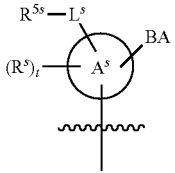

in formula VIII is independently of formula VII or a salt form thereof, wherein each —X-$L^s$-$R^5$ is independently -$L^7$-$R^1$.

89. The method of any one of the preceding embodiments, wherein for at least one coupling step, a plurality of coupling product oligonucleotides are oligonucleotide of formula VIII or a salt thereof, wherein the $L^P$ that is bonded to

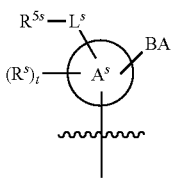

in formula VIII is independently of formula VII or a salt form thereof, wherein each —X-$L^s$-$R^5$ is independently of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —H.

90. The method of any one of the preceding embodiments, wherein a coupling product composition comprises a plurality of coupling product oligonucleotides, each of which is independently of formula VIII or a salt thereof, wherein each $L^P$ that is not bonded to

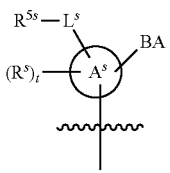

in formula VIII is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

91. The method of any one of the preceding embodiments, wherein a coupling product composition comprises a plurality of coupling product oligonucleotides, each of which is independently of formula VIII or a salt thereof, wherein each $L^P$ that is not bonded to

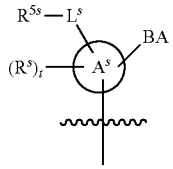

in formula VIII is independently of formula VII or a salt form thereof and contains no free primary or secondary amino groups.

92. The method of embodiment 90, wherein at least one of $R^5$ or $R^6$ is —C(O)CH$_3$.

93. The method of any one of the preceding embodiments, wherein a coupling product composition comprises a plurality of coupling product oligonucleotides, each of which is independently of formula VIII or a salt thereof, wherein each $L^P$ is independently of formula VII or a salt form thereof, wherein each X is independently —O— or —S—.

94. The method of any one of the preceding embodiments, wherein a coupling product composition comprises a plurality of coupling product oligonucleotides, each of which is independently of formula VIII or a salt thereof, wherein each $L^P$ is independently of formula VII or a salt form thereof, wherein each of Y and Z is —O—.

95. The method of any one of the preceding embodiments, comprising a coupling step wherein the coupling step provides a coupling product composition comprises a plurality of coupling product oligonucleotides, wherein each of the coupling product is independently an oligonucleotide loaded on a support.

96. The method of any one of the preceding embodiments, wherein each coupling step independently provides a coupling product composition comprises a plurality of coupling product oligonucleotides, wherein each of the coupling product is independently an oligonucleotide loaded on a support.

97. The method of any one of the preceding embodiments, wherein a coupling product composition is a chirally controlled oligonucleotide composition.

98. The method of any one of the preceding embodiments, wherein a coupling product composition comprising a plurality of coupling product oligonucleotides, and the coupling product composition comprising the plurality of oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least ((DS)$^{Nc}$*100)% of all oligonucleotides sharing the same base sequence in the coupling product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

99. The method of any one of the preceding embodiments, wherein a coupling product composition comprises a plurality of oligonucleotides, each of which independently comprises a free —OH.

100. The method of any one of the preceding embodiments, wherein each coupling product composition comprises a plurality of oligonucleotides, each of which independently comprises a free —OH.
101. The method of any one of the preceding embodiments, wherein a coupling product composition comprises a plurality of de-blocked oligonucleotides or nucleosides, each of which independently comprises a free —OH.
102. The method of any one of the preceding embodiments, wherein each coupling product composition comprises a plurality of de-blocked oligonucleotides or nucleosides, each of which independently comprises a free —OH.
103. The method of any one of embodiments 99-102, wherein the free —OH is a free 5'-OH.
104. The method of any one of the preceding embodiments, wherein contact time of the coupling reagent system with the de-blocked composition of one coupling step is different from the other.
105. The method of any one of the preceding embodiments, wherein a coupling step comprising repeating the contacting, each time independently with the same or different coupling reagent systems.
106. The method of any one of the preceding embodiments, wherein a pre-modification capping reagent system comprises an acylating agent.
107. The method of any one of the preceding embodiments, wherein a pre-modification capping reagent system comprises an acylating agent, wherein the acylating agent is of formula R'—C(O)-$L^s$-$R^s$.
108. The method of any one of the preceding embodiments, wherein a pre-modification capping reagent system comprises an acylating agent, wherein the acylating agent is of formula R'—C(O)-$L^s$-$R^s$, wherein R'—C(O)— is bonded to a heteroatom of -$L^s$-$R^s$.
109. The method of any one of the preceding embodiments, wherein a pre-modification capping reagent system comprises an acylating agent, wherein the acylating agent is of formula R'—C(O)-$L^s$-$R^s$, wherein R'—C(O)— is bonded to an oxygen, nitrogen, halogen, or sulfur, of -$L^s$-$R^s$.
110. The method of any one of the preceding embodiments, wherein a pre-modification capping reagent system comprises an acylating agent, wherein the acylating agent is an anhydride.
111. The method of any one of the preceding embodiments, wherein a pre-modification capping reagent system comprises an acylating agent, wherein the acylating agent is R—NCO.
112. The method of any one of the preceding embodiments, wherein a pre-modification capping reagent system comprises an acylating agent, wherein the acylating agent is Ph-NCO.
113. The method of any one of the preceding embodiments, wherein a pre-modification capping reagent system comprises POS, which optionally modifies an internucleotidic linkage and caps.
114. The method of any one of the preceding embodiments, wherein a pre-modification capping reagent system comprises a base.
115. The method of embodiment 111, wherein a base is of formula N($R^3$), wherein the nitrogen atom has no alpha-substitution.
116. The method of embodiment 111, wherein a base is optionally substituted pyridine.
117. The method of embodiment 111, wherein a base is substituted pyridine, comprising substituents at 2'- and 6'-positions.
118. The method of embodiment 111, wherein a base is pyridine.
119. The method of embodiment 111, wherein a base is 2,6-lutidine.
120. The method of embodiment 111, wherein a base is 2,6-lutidine.
121. The method of embodiment 111, wherein a base is triethylamine.
122. The method of embodiment 111, wherein a base is DIEA.
123. The method of embodiment 111, wherein a base is N-methyl morpholine.
124. The method of embodiment 111, wherein a base is 2-(dimethylamino)acetonitrile.
125. The method of any one of the preceding embodiments, wherein a pre-modification capping reagent system comprises no strong nucleophile, and no reagent that when contacted with a coupling product composition, can provide a strong nucleophile.
126. The method of any one of the preceding embodiments, wherein a pre-modification capping reagent system comprises no esterification catalyst, and no reagent that when contacted with a coupling product composition, can provide an esterification catalyst.
127. The method of any one of the preceding embodiments, wherein a strong nucleophile or an esterification catalyst is DMAP or NMI.
128. The method of any one of the preceding embodiments, wherein a strong nucleophile or an esterification catalyst is NMI.
129. The method of any one of the preceding embodiments, wherein a strong nucleophile or an esterification catalyst is DMAP.
130. The method of any one of the preceding embodiments, wherein a pre-modification capping reagent system comprises a strong nucleophile, or a reagent that when contacted with a coupling product composition, can provide a strong nucleophile.
131. The method of any one of the preceding embodiments, wherein a pre-modification capping reagent system comprises an esterification catalyst, or a reagent that when contacted with a coupling product composition, can provide a strong nucleophile.
132. The method of any one of the preceding embodiments, wherein a strong nucleophile or an esterification catalyst is DMAP or NMI.
133. The method of any one of the preceding embodiments, wherein a strong nucleophile or an esterification catalyst is NMI.
134. The method of any one of the preceding embodiments, wherein a strong nucleophile or an esterification catalyst is DMAP.
135. The method of any one of embodiments 130-134, wherein the pre-modification capping reagent system comprises reduced level of each strong nucleophile, each reagent that when contacted with a coupling product composition can provide a strong nucleophile, each esterification catalyst, and each reagent that when contacted with a coupling product composition can provide an esterification catalyst, which reduced level is independently no more than 0.01, 0.02, 0.05, 0.1, 0.2, 0.5, 1, 1.1, 1.2, 1.5, or 2 equivalents relative to the acylating agent, the base, or the plurality of product oligonucleotides of the coupling product composition.
136. The method of embodiment 135, wherein reduced level is independently no more than 0.01, 0.02, 0.05, 0.1, 0.2, or 0.5 equivalents relative to all acylating agents of the pre-modification capping reagent system.

137. The method of embodiment 135, wherein reduced level is independently no more than 0.01, 0.02, 0.05, 0.1, 0.2, or 0.5 equivalents relative to all bases of the pre-modification capping reagent system.

138. The method of embodiment 135, wherein reduced level is independently no more than 0.01, 0.02, 0.05, 0.1, 0.2, or 0.5 equivalents relative to the plurality of product oligonucleotides of the coupling product composition.

139. The method of any one of the preceding embodiments, wherein a pre-modification capping step is selective for amidation over esterification.

140. The method of any one of the preceding embodiments, wherein a pre-modification capping step is selective for capping of primary and secondary amino groups over esterification capping of free hydroxyl groups.

141. The method of any one of the preceding embodiments, wherein a pre-modification capping step is selective for capping of primary and secondary amino groups over capping of free hydroxyl groups in that in a system comprising:
a plurality of coupling product oligonucleotides wherein each coupling product is independently an oligonucleotide comprising one or more internucleotidic linkages of formula VII, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —H;
and a plurality of oligonucleotides each of which independently comprises a free 5'-OH group;
when at least 80%, 85%, 90%, 91%, 92%, 93%, 94%, 95%, 96%, 97%, 98%, or 99% —X-$L^s$-$R^5$ groups, wherein —X-$L^s$-$R^5$ is of such a structure that H—X-$L^s$-$R^5$ is a compound of formula I, I-a, I-a-1, I-a-2, I-b, I-c, I-d, I-c, II, II-a, II-b, III, III-a, or III-b, wherein at least one of $R^5$ or $R^6$ is —H, in internucleotidic linkages of formula VII is converted into corresponding —X-$L^s$-$R^5$ groups, wherein —X-$L^s$-$R^5$ is of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R via amidation, no more than 1%, 5%, 10%, 20%, 30%, 40%, 50%, 60%, 70%, 80%, 85%, 90%, 91%, 92%, 93%, 94%, 95%, 96%, 97%, 98%, or 99% of free hydroxyl groups is converted into —O—C(O)R.

142. The method of embodiment 141, wherein no more than 1%, 5%, 10%, 20%, 30%, 40%, or 50% of free hydroxyl groups is converted into —O—C(O)R.

143. The method of any one of embodiments 1-138, wherein a pre-modification capping step caps at least 90%, 91%, 92%, 93%, 94%, 95%, 96%, 97%, 98%, or 99% of free hydroxyl groups of a coupling product composition.

144. The method of any one of embodiments 1-138, wherein a pre-modification capping step caps at least 90%, 91%, 92%, 93%, 94%, 95%, 96%, 97%, 98%, or 99% of free 5-OH of oligonucleotides of a coupling product composition.

145. The method of any one of the preceding embodiments, wherein the pre-modification capping step caps one or more amino groups.

146. The method of any one of the preceding embodiments, wherein a pre-modification capping step caps at least 90%, 91%, 92%, 93%, 94%, 95%, 96%, 97%, 98%, or 99% of free primary and secondary amino groups of a coupling product composition.

147. The method of any one of the preceding embodiments, wherein the pre-modification capping step caps one or more amino groups of a plurality of coupling product oligonucleotides, each of which is independently an oligonucleotide of a coupling product composition.

148. The method of any one of the preceding embodiments, wherein a pre-modification capping step comprises:
contacting a coupling product composition with a first pre-modification capping system; and
contacting a coupling product composition with a second pre-modification capping system.

149. The method of embodiment 148, wherein the first and second pre-modification capping systems are different.

150. The method of embodiment 148, wherein the first pre-modification capping reagent system is selective for capping of amino groups over hydroxyl groups, and the second pre-modification capping reagent system caps both amino and hydroxyl groups efficiently.

151. The method of any one of the preceding embodiments, wherein a pre-modification capping reagent system is a solution of:
Pyridine/DMAP/$Ac_2O$;
2,6-Lutidine/NMI/$Ac_2O$;
2,4,6-Collidine/$Ac_2O$;
Triethylamine/$Ac_2O$;
DIEA/$Ac_2O$;
N-Methyl morpholine/$Ac_2O$;
2,6-Lutidine, then after a period of time, NMI/$Ac_2O$;
2,6-Lutidine/$Ac_2O$;
PhNCO/2,6-Lutidine;
POS;
POS then NMI/2,6-Lutidine/$Ac_2O$; or
2-(dimethylamino)acetonitrile/$Ac_2O$.

152. The method of any one of the preceding embodiments, wherein a pre-modification capping reagent system is a solution of:
Pyridine (2 equiv.)/DMAP (cat.)/$Ac_2O$(4 equiv.);
2,6-Lutidine (2 equiv.)/NMI (0.25 equiv.)/$Ac_2O$(4 equiv.);
2,4,6-Collidine/$Ac_2O$(4 equiv.);
Triethylamine/$Ac_2O$(4 equiv.);
DIEA/$Ac_2O$(4 equiv.);
N-Methyl morpholine/$Ac_2O$(4 equiv.);
2,6-Lutidine (2 equiv.) then after 5 min. NMI (1 equiv.)/$Ac_2O$(4 equiv.);
2,6-Lutidine/$Ac_2O$(4 equiv.);
PhNCO/2,6-Lutidine;
POS (both oxidation and pre-capping);
POS (both oxidation and pre-capping) then NMI/2,6-Lutidine/$Ac_2O$; or
2-(dimethylamino)acetonitrile/$Ac_2O$.

153. The method of any one of the preceding embodiments, wherein a pre-modification capping reagent system is a solution of 2,6-Lutidine/$Ac_2O$.

154. The method of any one of embodiments 151-153, wherein a pre-modification capping reagent system is a solution in acetonitrile.

155. The method of any one of the preceding steps, wherein a pre-modification capping step provides a pre-modification capping composition comprising a plurality of pre-modification capping product oligonucleotides, wherein each pre-modification capping product is independently an oligonucleotide of formula VIII or a salt thereof.

156. The method of any one of the preceding steps, wherein each pre-modification capping step provides a pre-modification capping product composition comprising a plurality of pre-modification capping product oligonucleotides, wherein each pre-modification capping product is independently an oligonucleotide of formula VIII or a salt thereof.

157. The method of any one of embodiments 155-156, wherein for a pre-modification capping step, z of formula VIII for a pre-modification capping product oligonucleotide ($z^{PR}$) is the same as z of formula VIII for a corresponding coupling product oligonucleotide ($z^{CP}$).

158. The method of any one of the preceding steps, wherein a pre-modification capping product composition comprises a plurality of pre-modification capping product oligonucleotides, each of which is independently of formula VIII or a salt thereof, wherein each $L^P$ bonded to

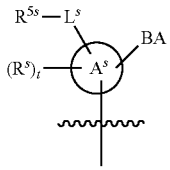

in formula VIII is independently an internucleotidic linkage of formula VII-b, or a salt form thereof.

159. The method of any one of the preceding embodiments, wherein a pre-modification capping product composition comprises a plurality of pre-modification capping product oligonucleotides, each of which is independently of formula VIII or a salt thereof, wherein each $L^P$ that is not bonded to

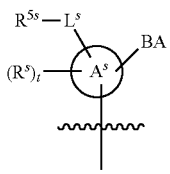

in formula VIII is independently of formula VII or a salt form thereof, wherein each $P^L$ is independently not P.

160. The method of any one of the preceding embodiments, wherein a pre-modification capping product composition comprises a plurality of pre-modification capping product oligonucleotides, each of which is independently of formula VIII or a salt thereof, wherein each $L^P$ that is not bonded to

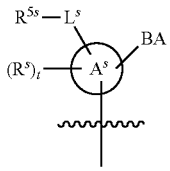

in formula VIII is independently of formula VII or a salt form thereof, wherein each $P^L$ is independently P(=W), wherein W is O or S.

161. The method of any one of the preceding embodiments, wherein a pre-modification capping product composition comprises a plurality of pre-modification capping product oligonucleotides, each of which is independently of formula VIII or a salt thereof, wherein each $L^P$ that is bonded to

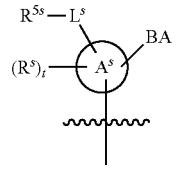

in formula VIII is independently of formula VII or a salt form thereof, wherein each $-X-L^s-R^5$ is independently $-L^7-R^1$, or of such a structure that $H-X-L^s-R^5$ is a compound of formula I, I-a, I-a-I, I-a-2, I-b, I-c, I-d, I-e, II, II-a, II-b, III, III-a, or III-b, wherein at least one of $R^5$ or $R^6$ is $-C(O)R$.

162. The method of any one of the preceding embodiments, wherein for at least one pre-modification capping step, a plurality of pre-modification capping product oligonucleotides are oligonucleotide of formula VIII or a salt thereof, wherein the $L^P$ that is bonded to

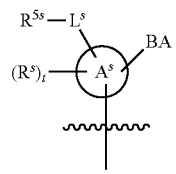

in formula VIII is independently of formula VII or a salt form thereof, wherein each $-X-L^s-R^5$ is independently $-L^7-R^1$.

163. The method of any one of the preceding embodiments, wherein for at least one pre-modification capping step, a plurality of pre-modification capping product oligonucleotides are oligonucleotide of formula VIII or a salt thereof, wherein the $L^P$ that is bonded to

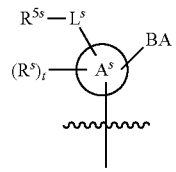

in formula VIII is independently of formula VII or a salt form thereof, wherein each $-X-L^s-R^5$ is independently of such a structure that $H-X-L^s-R^5$ is a compound of formula I, I-a, I-a-I, I-a-2, I-b, I-c, I-d, I-e, II, II-a, II-b, III, III-a, or III-b, wherein at least one of $R^5$ or $R^6$ is $-C(O)R$.

164. The method of any one of the preceding embodiments, wherein a pre-modification capping product composition comprises a plurality of pre-modification capping product oligonucleotides, each of which is independently of formula VIII or a salt thereof, wherein each $L^P$ that is not bonded to

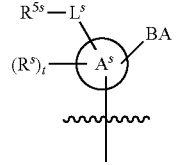

in formula VIII is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-1, I-a-2, I-b, I-c, I-d, I-e, II, II-a, II-b, III, III-a, or III-b, wherein at least one of $R^5$ or $R^6$ is —C(O)R.

165. The method of any one of the preceding embodiments, wherein a pre-modification capping product composition comprises a plurality of pre-modification capping product oligonucleotides, each of which is independently of formula VIII or a salt thereof, wherein each $L^P$ that is not bonded to

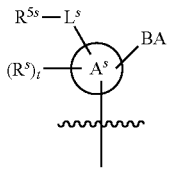

in formula VIII is independently of formula VII or a salt form thereof and contains no free primary or secondary amino groups.

166. The method of embodiment 90, wherein at least one of $R^5$ or $R^6$ is —C(O)CH$_3$.

167. The method of any one of the preceding embodiments, wherein a pre-modification capping product composition comprises a plurality of pre-modification capping product oligonucleotides, each of which is independently of formula VIII or a salt thereof, wherein each $L^P$ is independently of formula VII or a salt form thereof, wherein each X is independently —O— or —S—.

168. The method of any one of the preceding embodiments, wherein a pre-modification capping product composition comprises a plurality of pre-modification capping product oligonucleotides, each of which is independently of formula VIII or a salt thereof, wherein each $L^P$ is independently of formula VII or a salt form thereof, wherein each of Y and Z is —O—.

169. The method of any one of the preceding embodiments, wherein the pre-modification capping step provides a pre-modification capping product composition comprises a plurality of pre-modification capping product oligonucleotides, wherein each of the pre-modification capping product is independently an oligonucleotide loaded on a support.

170. The method of any one of the preceding embodiments, wherein each pre-modification capping step independently provides a pre-modification capping product composition comprises a plurality of pre-modification capping product oligonucleotides, wherein each of the pre-modification capping product is independently an oligonucleotide loaded on a support.

171. The method of any one of the preceding embodiments, wherein a pre-modification capping product composition comprising a plurality of pre-modification capping product oligonucleotides is a chirally controlled oligonucleotide composition.

172. The method of any one of the preceding embodiments, wherein a pre-modification capping product composition comprising a plurality of pre-modification capping product oligonucleotides is a chirally controlled oligonucleotide composition wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least (($DS)^{Nc}*100$)% of all oligonucleotides sharing the same base sequence in the pre-modification capping product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

173. The method of any one of the preceding embodiments, wherein a pre-modification capping product composition comprises a plurality of oligonucleotides, each of which independently comprises a free —OH.

174. The method of any one of the preceding embodiments, wherein each pre-modification capping product composition comprises a plurality of oligonucleotides, each of which independently comprises a free —OH.

175. The method of any one of the preceding embodiments, wherein a pre-modification capping product composition comprises a plurality of de-blocked oligonucleotides or nucleosides, each of which independently comprises a free —OH.

176. The method of any one of the preceding embodiments, wherein each pre-modification capping product composition comprises a plurality of de-blocked oligonucleotides or nucleosides, each of which independently comprises a free —OH.

177. The method of any one of embodiments 173-176, wherein the free —OH is a free 5'-OH.

178. The method of any one of the preceding embodiments, wherein a pre-modification capping step comprising repeating the contacting, each time independently with the same or different pre-modification capping reagent systems.

179. The method of any one of the preceding embodiments, wherein a modification step comprises contacting a coupling product composition and modifying one or more internucleotidic linkages of one or more coupling product oligonucleotides to provide a modification product composition comprising a plurality of modification product oligonucleotides.

180. The method of any one of the preceding embodiments, wherein a modification step comprises contacting a coupling product composition and modifying one or more internucleotidic linkages of one or more coupling product oligonucleotides to provide a modification product composition comprising a plurality of modification product oligonucleotides.

181. The method of any one of the preceding embodiments, wherein a modification step comprises modifying an internucleotidic linkage formed in the immediate preceding coupling step.

182. The method of any one of the preceding embodiments, wherein a modification step comprises modifying a 5'-end internucleotidic linkage.

183. The method of any one of the preceding embodiments, wherein a modification step comprises modifying an internucleotidic linkage whose linkage phosphorus is —P(–)—.

184. The method of any one of the preceding embodiments, wherein a modification step comprises modifying an internucleotidic linkage of formula VII or a salt form thereof, wherein $P^L$ is P.

185. The method of any one of the preceding embodiments, wherein a modification step comprises modifying an internucleotidic linkage of formula VII or a salt thereof, wherein $P^L$ is P to form an internucleotidic linkage of formula VII or a salt form thereof, wherein $P^L$ is not P.

186. The method of any one of the preceding embodiments, wherein a modification step comprises modifying an internucleotidic linkage of formula VII or a salt thereof, wherein $P^L$ is P to form an internucleotidic linkage of formula VII or a salt form thereof, wherein $P^L$ is P(=O) or (P=S).

187. The method of any one of the preceding embodiments, wherein a modification step comprises modifying an internucleotidic linkage of formula VII or a salt form thereof in an oligonucleotide of formula VIII or a salt thereof.

188. The method of any one of the preceding embodiments, wherein a modification step comprises modifying an internucleotidic linkage of formula VII or a salt form thereof in an oligonucleotide of formula VIII or a salt thereof, wherein the internucleotidic linkage of formula VII or a salt is $L^P$ bonded to

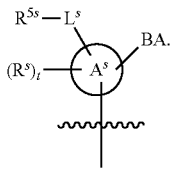

189. The method of any one of the preceding embodiments, wherein a modification step comprises:

modifying a coupling product composition comprising a plurality of coupling product oligonucleotides, or a pre-modification capping product composition comprising a plurality of pre-modification capping product oligonucleotides, each of which is independently an oligonucleotide of formula VIII or a salt thereof, wherein the $L^P$ bonded to

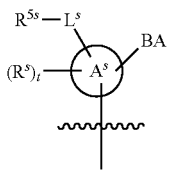

is an internucleotidic linkage of formula VII or a salt form thereof, wherein $P^L$ is P; and providing a modification product composition comprising a plurality of modification product oligonucleotides, each of which is independently an oligonucleotide of formula VIII or a salt thereof, wherein the $L^P$ bonded to

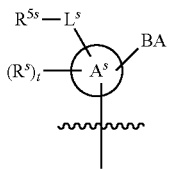

is an internucleotidic linkage of formula VII or a salt form thereof, wherein $P^L$ is not P.

190. The method of any one of the preceding embodiments, wherein a modification step comprises oxidation.

191. The method of any one of the preceding embodiments, wherein a modification step comprises oxidation, which oxidation converts a —P(-)— linkage phosphorus atom into a —P(=O)(-)— linkage phosphorus atom.

192. The method of any one of the preceding embodiments, wherein a modification reagent system is an oxidation reagent system comprising one or more oxidation reagent.

193. The method of any one of the preceding embodiments, wherein a modification reagent system comprises TBHP.

194. The method of any one of the preceding embodiments, wherein a modification reagent system comprises TBHP/Decane/DCM.

195. The method of any one of the preceding embodiments, wherein a modification reagent system comprises TBHP/Decane/DCM wherein the concentration of TBHP is about 1.1 M.

196. The method of any one of the preceding embodiments, wherein a modification reagent system comprises $I_2$.

197. The method of any one of the preceding embodiments, wherein a modification reagent system comprises $I_2$/Water/Pyridine.

198. The method of any one of the preceding embodiments, wherein a modification reagent system comprises $I_2$/Water/Pyridine, wherein the concentration of $I_2$ is about 0.05 M.

199. The method of any one of the preceding embodiments, wherein a modification step comprises sulfurization, which sulfurization comprises converting a —P(-)— linkage phosphorus atom into a —P(=S)(-)— linkage phosphorus atom.

200. The method of any one of the preceding embodiments, wherein a modification step comprises sulfurization, which sulfurization comprises converting an internucleotidic linkage of formula VII-b or a salt form thereof, wherein each of X, Y, and Z is —O—, into an internucleotidic linkage of formula VII or a salt thereof, wherein $P^L$ is P(=S), and each of X, Y, and Z is —O—.

201. The method of any one of the preceding embodiments, wherein a modification step comprises sulfurization, which sulfurization comprises converting a —P(-)— linkage phosphorus atom into a —P(=O)(—X-$L^s$-$R^5$)— linkage phosphorus atom, wherein X is —S—.

202. The method of any one of the preceding embodiments, wherein a modification step comprises sulfurization, which sulfurization comprises converting an internucleotidic linkage of formula VII-b or a salt form thereof, wherein each of X, Y, and Z is —O—, into an internucleotidic linkage of formula VII or a salt thereof, wherein $P^L$ is P(=O), and X is —S—, Y is —O—, and Z is —O—.

203. The method of any one of the preceding embodiments, wherein a modification step comprises sulfurization, which sulfurization comprises converting an internucleotidic linkage of formula VII-b or a salt form thereof, wherein each of X, Y, and Z is —O—, and —X-$L^s$-$R^5$ comprises a —Si(R)$_3$ group, into an internucleotidic linkage of formula VII or a salt thereof, wherein $P^L$ is P(=O), and X is —S—, Y is —O—, and Z is —O—.

204. The method of any one of the preceding embodiments, wherein a modification reagent system is a sulfurization reagent system comprising one or more sulfurization reagent.

205. The method of any one of the preceding embodiments, wherein a sulfurization reagent system comprises a sulfurization reagent selected from POS (3-phenyl-1,2,4-dithiazolin-5-one), DDTT (((dimethylamino-methylidene)amino)-3H-1,2,4-dithiazoline-3-thione), DTD (dimethylthiarum disulfide), xanthane hydride (XH), S-(2-cyanoethyl) methanesulfonothioate (MTS-CNE), or phenylacetyl disulfide.

206. The method of embodiment 205, wherein a sulfurization reagent is POS.

207. The method of embodiment 205, wherein a sulfurization reagent is DDTT.

208. The method of embodiment 205, wherein a sulfurization reagent is DTD.
209. The method of embodiment 205, wherein a sulfurization reagent is xanthane hydride.
210. The method of any one of the preceding embodiments, wherein a modification reagent system is or comprises POS in acetonitrile.
211. The method of any one of the preceding embodiments, wherein a modification reagent system is or comprises POS in acetonitrile, wherein the concentration of POS is about 0.1 M.
212. The method of any one of the preceding embodiments, wherein a modification reagent system is or comprises xanthane hydride in pyridine.
213. The method of any one of the preceding embodiments, wherein a modification reagent system is or comprises xanthane hydride in pyridine, wherein the concentration of xanthane hydride is about 0.2 M.
214. The method of embodiment 209, wherein the concentration of xanthane hydride is about 0.05-0.5 M.
215. The method of embodiment 209, wherein the concentration of xanthane hydride is about 0.1 M.
216. The method of embodiment 209, wherein the concentration of xanthane hydride is about 0.15 M.
217. The method of embodiment 209, wherein the concentration of xanthane hydride is about 0.2 M.
218. The method of embodiment 209, wherein the concentration of xanthane hydride is about 0.25 M.
219. The method of any one of embodiments 214-218, wherein the solvent is or comprises pyridine.
220. The method of any one of embodiments 214-219, wherein the solvent is or comprises acetonitrile.
221. The method of any one of embodiments 214-220, wherein the solvent comprises pyridine and acetonitrile, and the ratio of pyridine:acetonitrile is about 5:1 to 1:5 v/v, or is about 5:1, 4:1, 3:1, 2:1, 1:1, 1:2, 1:3, 1:4, or 1:5.
222. The method of embodiment 221, wherein the ratio of pyridine:acetonitrile is about 1:1 v/v.
223. The method of any one of the preceding steps, wherein a modification step provides a modification composition comprising a plurality of modification product oligonucleotides, each of which is independently an oligonucleotide of formula VIII or a salt thereof.
224. The method of any one of the preceding steps, wherein each modification step provides a modification product composition comprising a plurality of modification product oligonucleotides, each of which is independently an oligonucleotide of formula VIII or a salt thereof.
225. The method of any one of embodiments 218-224, wherein for a modification step, z of formula VIII for a modification product oligonucleotide ($z^{MD}$) is the same as z of formula VIII for a corresponding coupling product oligonucleotide ($z^{CP}$) or pre-modification capping product oligonucleotide ($z^{PR}$).
226. The method of any one of the preceding steps, wherein a modification product composition comprises a plurality of modification product oligonucleotides, each of which is independently of formula VIII or a salt thereof, wherein each $L^P$ bonded to

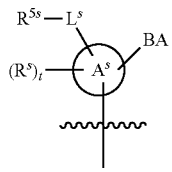

in formula VIII is independently an internucleotidic linkage of formula VII or a salt form thereof, wherein $P^L$ is not P.
227. The method of any one of the preceding steps, wherein a modification product composition comprises a plurality of modification product oligonucleotides, each of which is independently of formula VIII or a salt thereof, wherein each $L^P$ bonded to

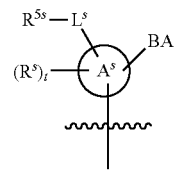

in formula VIII is independently an internucleotidic linkage of formula VII or a salt form thereof, wherein each $P^L$ is independently P(=W), wherein W is O or S.
228. The method of any one of the preceding steps, wherein a modification product composition comprises a plurality of modification product oligonucleotides, each of which is independently of formula VIII or a salt thereof, wherein each $L^P$ bonded to

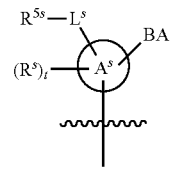

in formula VIII is independently an internucleotidic linkage of formula VII or a salt form thereof, wherein each $P^L$ is independently P(=W), wherein W is O or S, and wherein each —X-$L^s$-$R^5$ is independently -$L^7$-R', or of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.
229. The method of any one of the preceding steps, wherein a modification product composition comprises a plurality of modification product oligonucleotides, each of which is independently of formula VIII or a salt thereof, wherein each $L^P$ bonded to

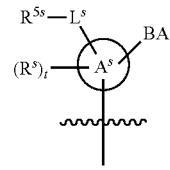

in formula VIII is independently an internucleotidic linkage of formula VII or a salt form thereof, wherein each $P^L$ is independently P(=S), and wherein each —X-$L^s$-$R^5$ is of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.
230. The method of any one of the preceding steps, wherein a modification product composition comprises a plurality of modification product oligonucleotides, each of which is independently of formula VIII or a salt thereof, wherein each $L^P$ bonded to

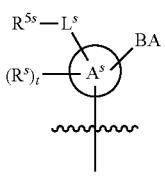

in formula VIII is independently an internucleotidic linkage of formula VII or a salt form thereof, wherein each $P^L$ is independently $P(=O)$, and wherein each —X-$L^s$-$R^5$ is —S-$L^s$-$R^5$.

231. The method of any one of the preceding steps, wherein a modification product composition comprises a plurality of modification product oligonucleotides, each of which is independently of formula VIII or a salt thereof, wherein each $L^P$ bonded to

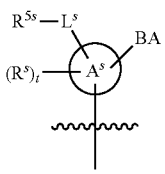

in formula VIII is independently an internucleotidic linkage of formula VII or a salt form thereof, wherein each $P^L$ is independently $P(=O)$, and wherein each —X-$L^s$-$R^5$ is independently -$L^7$-$R^5$.

232. The method of any one of the preceding embodiments, wherein a modification product composition comprises a plurality of modification product oligonucleotides, each of which is independently of formula VIII or a salt thereof, wherein each $L^P$ is independently of formula VII or a salt form thereof and contains no free primary or secondary amino groups.

233. The method of any one of the preceding embodiments, wherein a modification product composition comprises a plurality of modification product oligonucleotides, each of which is independently of formula VIII or a salt thereof, wherein each $L^P$ is independently of formula VII or a salt form thereof, wherein each of Y and Z is —O—.

234. The method of any one of the preceding embodiments, wherein the modification step provides a modification product composition comprises a plurality of modification product oligonucleotides, each of which is independently an oligonucleotide loaded on a support.

235. The method of any one of the preceding embodiments, wherein each modification step independently provides a modification product composition comprises a plurality of modification product oligonucleotides, each of which is independently an oligonucleotide loaded on a support.

236. The method of any one of the preceding embodiments, wherein a modification product composition comprising a plurality of modification product oligonucleotides is a chirally controlled oligonucleotide composition.

237. The method of any one of the preceding embodiments, wherein a modification product composition comprising a plurality of modification product oligonucleotides is a chirally controlled oligonucleotide composition wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least $((DS)^{Nc}*100)\%$ of all oligonucleotides sharing the same base sequence in the modification product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

238. The method of any one of the preceding embodiments, wherein a modification product composition comprises a plurality of oligonucleotides, each of which independently comprises a free —OH.

239. The method of any one of the preceding embodiments, wherein each modification product composition comprises a plurality of oligonucleotides, each of which independently comprises a free —OH.

240. The method of any one of the preceding embodiments, wherein a modification product composition comprises a plurality of de-blocked oligonucleotides or nucleosides, each of which independently comprises a free —OH.

241. The method of any one of the preceding embodiments, wherein each modification product composition comprises a plurality of de-blocked oligonucleotides or nucleosides, each of which independently comprises a free —OH.

242. The method of any one of embodiments 238-241, wherein the free —OH is a free 5'-OH.

243. The method of any one of the preceding embodiments, wherein a modification step comprising repeating the contacting, each time independently with the same or different modification reagent systems.

244. The method of any one of the preceding embodiments, wherein a post-modification capping step caps a plurality of hydroxyl groups.

245. The method of any one of the preceding embodiments, wherein a post-modification capping step, which caps a plurality of 5'-OH groups.

246. The method of any one of the preceding embodiments, wherein a post-modification capping reagent system comprises an acylating agent.

247. The method of any one of the preceding embodiments, wherein a post-modification capping reagent system comprises an acylating agent, wherein the acylating agent is of formula R'—C(O)-$L^s$-$R^s$.

248. The method of any one of the preceding embodiments, wherein a post-modification capping reagent system comprises an acylating agent, wherein the acylating agent is of formula R'—C(O)-$L^s$-$R^s$, wherein R'—C(O)— is bonded to a heteroatom of -$L^s$-$R^s$.

249. The method of any one of the preceding embodiments, wherein a post-modification capping reagent system comprises an acylating agent, wherein the acylating agent is of formula R'—C(O)-$L^s$-$R^s$, wherein R'—C(O)— is bonded to an oxygen, nitrogen, halogen, or sulfur, of -$L^s$-$R^s$.

250. The method of any one of the preceding embodiments, wherein a post-modification capping reagent system comprises an acylating agent, wherein the acylating agent is an anhydride.

251. The method of any one of the preceding embodiments, wherein a post-modification capping reagent system comprises an acylating agent, wherein the acylating agent is R—NCO.

252. The method of any one of the preceding embodiments, wherein a post-modification capping reagent system comprises an acylating agent, wherein the acylating agent is Ph-NCO.

253. The method of any one of the preceding embodiments, wherein a post-modification capping reagent system comprises a base.
254. The method of embodiment 253, wherein a base is of formula N(R³), wherein the nitrogen atom has no alpha-substitution.
255. The method of embodiment 253, wherein a base is optionally substituted pyridine.
256. The method of embodiment 253, wherein a base is substituted pyridine, comprising substituents at 2'- and 6'-positions.
257. The method of embodiment 253, wherein a base is pyridine.
258. The method of embodiment 253, wherein a base is 2,6-lutidine.
259. The method of embodiment 253, wherein a base is 2,6-lutidine.
260. The method of embodiment 253, wherein a base is triethylamine.
261. The method of embodiment 253, wherein a base is DIEA.
262. The method of embodiment 253, wherein a base is N-methyl morpholine.
263. The method of embodiment 253, wherein a base is 2-(dimethylamino)acetonitrile.
264. The method of any one of the preceding embodiments, wherein a post-modification capping reagent system comprises a strong nucleophile, or a reagent that when contacted with a coupling product composition, can provide a strong nucleophile.
265. The method of any one of the preceding embodiments, wherein a post-modification capping reagent system comprises an esterification catalyst, or a reagent that when contacted with a coupling product composition, can provide a strong nucleophile.
266. The method of any one of the preceding embodiments, wherein a strong nucleophile or an esterification catalyst is DMAP or NMI.
267. The method of any one of the preceding embodiments, wherein a strong nucleophile or an esterification catalyst is NMI.
268. The method of any one of the preceding embodiments, wherein a strong nucleophile or an esterification catalyst is DMAP.
269. The method of any one of embodiments 130-134, wherein the post-modification capping reagent system comprises one or more reagents selected from strong nucleophiles, one or more reagents that when contacted with a coupling product composition can provide one or more strong nucleophiles, one or more esterification catalysts, and one or more reagents that when contacted with a coupling product composition can provide one or more esterification catalysts, wherein level of such one or more reagents combined are at least 0.2, 0.5, 1, 1.1, 1.2, 1.5, or 2 equivalents relative to the acylating agent, the base, or the plurality of product oligonucleotides of the modification product composition.
270. The method of embodiment 269, wherein the level is at least 0.2, 0.5, 1, 1.1, 1.2, 1.5, or 2 equivalents relative to all acylating agents of the post-modification capping reagent system.
271. The method of embodiment 269, wherein the level is at least 1, 1.1, 1.2, 1.5, or 2 equivalents relative to the plurality of product oligonucleotides of the modification product composition.
272. The method of any one of the preceding embodiments, wherein a post-modification capping step is efficient for amidation and esterification.
273. The method of any one of the preceding embodiments, wherein a post-modification capping step is efficient for capping primary and secondary amino groups and for capping of free hydroxyl groups in that the post-modification capping step caps at least 80%, 85%, 90%, 91%, 92%, 93%, 94%, 95%, 96%, 97%, 98%, or 99% primary and secondary amino groups and at least 80%, 85%, 90%, 91%, 92%, 93%, 94%, 95%, 96%, 97%, 98%, or 99% free hydroxyl groups in the modification product composition.
274. The method of any one of the preceding embodiments, wherein a post-modification capping step caps at least 90%, 91%, 92%, 93%, 94%, 95%, 96%, 97%, 98%, or 99% of free hydroxyl groups of a modification product composition.
275. The method of any one of the preceding embodiments, wherein a post-modification capping step caps at least 90%, 91%, 92%, 93%, 94%, 95%, 96%, 97%, 98%, or 99% of free 5'-OH groups of a modification product composition.
276. The method of any one of the preceding embodiments, wherein the post-modification capping step caps one or more amino groups.
277. The method of any one of the preceding embodiments, wherein a post-modification capping step caps at least 90%, 91%, 92%, 93%, 94%, 95%, 96%, 97%, 98%, or 99% of free primary and secondary amino groups of a coupling product composition.
278. The method of any one of the preceding embodiments, wherein a post-modification capping step comprises:
    contacting a coupling product composition with a first post-modification capping system; and
    contacting a coupling product composition with a second post-modification capping system.
279. The method of embodiment 148, wherein the first and second post-modification capping systems are different.
280. The method of embodiment 279, wherein the first post-modification capping reagent system is selective for capping of amino groups over hydroxyl groups, and the second post-modification capping reagent system caps both amino and hydroxyl groups efficiently.
281. The method of any one of the preceding embodiments, wherein a post-modification capping reagent system comprises:
    Pyridine/DMAP/Ac$_2$O;
    2,6-Lutidine/NMI/Ac$_2$O;
    2,4,6-Collidine/Ac$_2$O;
    Triethylamine/Ac$_2$O;
    DIEA/Ac$_2$O;
    N-Methyl morpholine/Ac$_2$O;
    2,6-Lutidine, then after a period of time, NMI/Ac$_2$O;
    2,6-Lutidine/Ac$_2$O;
    PhNCO/2,6-Lutidine; or
    2-(dimethylamino)acetonitrile/Ac$_2$O.
282. The method of any one of the preceding embodiments, wherein a post-modification capping reagent system comprises:
    Pyridine (2 equiv.)/DMAP (cat.)/Ac$_2$O(4 equiv.);
    2,6-Lutidine (2 equiv.)/NMI (0.25 equiv.)/Ac$_2$O(4 equiv.);
    2,4,6-Collidine/Ac$_2$O(4 equiv.);
    Triethylamine/Ac$_2$O(4 equiv.);
    DIEA/Ac$_2$O(4 equiv.);
    N-Methyl morpholine/Ac$_2$O(4 equiv.);
    2,6-Lutidine (2 equiv.) then after 5 min. NMI (1 equiv.)/ Ac$_2$O(4 equiv.);
    2,6-Lutidine/Ac$_2$O(4 equiv.);
    PhNCO/2,6-Lutidine; or 2-(dimethylamino)acetonitrile/Ac$_2$O.

283. The method of any one of the preceding embodiments, wherein a post-modification capping reagent system is a solution of 2,6-Lutidine/NMI/Ac$_2$O.

284. The method of any one of embodiments 281-283, wherein a post-modification capping reagent system is a solution in acetonitrile.

285. The method of any one of the preceding steps, wherein a post-modification capping step provides a post-modification capping composition comprising a plurality of post-modification capping product oligonucleotides, each of which is independently an oligonucleotide of formula VIII or a salt thereof.

286. The method of any one of the preceding steps, wherein each post-modification capping step provides a post-modification capping product composition comprising a plurality of post-modification capping product oligonucleotides, each of which is independently an oligonucleotide of formula VIII or a salt thereof.

287. The method of any one of embodiments 285-286, wherein for a post-modification capping step, z of formula VIII for a post-modification capping product oligonucleotide ($z^{PT}$) is the same as z of formula VIII for a corresponding modification product oligonucleotide ($z^{MD}$).

288. The method of any one of the preceding steps, wherein a post-modification capping product composition comprises a plurality of post-modification capping product oligonucleotides, each of which is independently of formula VIII or a salt thereof, wherein each $L^P$ in formula VIII is independently an internucleotidic linkage of formula VII, or a salt form thereof, wherein $P^L$ is not P.

289. The method of any one of the preceding steps, wherein a post-modification capping product composition comprises a plurality of post-modification capping product oligonucleotides, each of which is independently of formula VIII or a salt thereof, wherein each $L^P$ in formula VIII is independently an internucleotidic linkage of formula VII, or a salt form thereof, wherein each $P^L$ independently P(=O) or P(=S).

290. The method of any one of the preceding embodiments, wherein a post-modification capping product composition comprises a plurality of post-modification capping product oligonucleotides, each of which is independently of formula VIII or a salt thereof, wherein each $L^P$ in formula VIII is independently of formula VII or a salt form thereof, wherein each —X-L$^s$-R$^5$ is independently -L$^7$-R$^1$, or of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R.

291. The method of any one of the preceding embodiments, wherein a post-modification capping product composition comprises a plurality of post-modification capping product oligonucleotides each of which is independently an oligonucleotide of formula VIII or a salt thereof, comprising one or more $L^P$ wherein $P^L$ is O, and —X-L$^s$-R$^5$ is -L$^7$-R$^1$.

292. The method of any one of the preceding embodiments, wherein a post-modification capping product composition comprises a plurality of post-modification capping product oligonucleotides each of which is independently an oligonucleotide of formula VIII or a salt thereof, comprising one or more $L^P$ wherein $P^L$ is O, and —X-L$^s$-R$^5$ is —S-L$^s$-R$^5$.

293. The method of any one of the preceding embodiments, wherein a post-modification capping product composition comprises a plurality of post-modification capping product oligonucleotides each of which is independently an oligonucleotide of formula VIII or a salt thereof, comprising one or more $L^P$ wherein $P^L$ is S, and of such a structure that H—X-L$^s$-R$^5$ is a compound of formula I, I-a, I-a-1, I-a-2, I-b, I-c, I-d, I-e, II, II-a, II-b, III, III-a, or III-b, wherein at least one of R$^5$ or R$^6$ is —C(O)R.

294. The method of any one of the preceding embodiments, wherein a post-modification capping product composition comprises a plurality of post-modification capping product oligonucleotides, each of which is independently of formula VIII or a salt thereof, wherein each $L^P$ is independently of formula VII or a salt form thereof, wherein each of Y and Z is —O—.

295. The method of any one of the preceding embodiments, wherein the post-modification capping step provides a post-modification capping product composition comprises a plurality of post-modification capping product oligonucleotides, each of which is independently an oligonucleotide loaded on a support.

296. The method of any one of the preceding embodiments, wherein each post-modification capping step independently provides a post-modification capping product composition comprises a plurality of post-modification capping product oligonucleotides, each of which is independently an oligonucleotide loaded on a support.

297. The method of any one of the preceding embodiments, wherein a post-modification capping product composition comprising a plurality of post-modification capping product oligonucleotides is a chirally controlled oligonucleotide composition.

298. The method of any one of the preceding embodiments, wherein a post-modification capping product composition comprising a plurality of post-modification capping product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least ((DS)$^{Nc}$*100)% of all oligonucleotides sharing the same base sequence in the post-modification capping product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

299. The method of any one of the preceding embodiments, wherein a post-modification capping step comprising repeating the contacting, each time independently with the same or different post-modification capping reagent systems.

300. The method of any one of the preceding embodiments, wherein the strong nucleophile and/or esterification catalyst is a compound that provides at least 60%, 70%, 80%, 90%, 95%, 96%, 97%, 98%, 99%, or 99.5% completion of esterification of 5'-OH of a plurality of oligonucleotides when used in a capping reagent system at 3-10% (volume/volume for liquid compounds; weight/volume for solid compounds) concentration, together with 5-10% Ac$_2$O (v/v), 5-15% 2,6-lutidine (v/v), in ACN or THF as solvent, and more than 10 equivalents relative to all oligonucleotides in contact with the capping reagent system for 0.1, 0.2, 0.3, 0.4, 0.5, 1, 2, 3, 4, 5, 6, 7, 8, 9, or 10 minutes.

301. The method of any one of the preceding embodiments, wherein the post-modification capping step is comparable or identical to a capping condition of traditional oligonucleotide synthesis based on phosphoramidite chemistry with respect to efficiency of capping hydroxyl groups to be capped.

302. The method of any one of the preceding embodiments, comprising a de-blocking step, wherein a de-blocking reagent system comprises a de-blocking reagent, wherein the de-blocking reagent is an acid.

303. The method of embodiment 299, wherein the acid is DCA (dichloroacetic acid).

304. The method of embodiment 299, wherein the de-blocking reagent system is 3% DCA in toluene.

305. The method of any one of the preceding embodiments, comprising a de-blocking step, wherein:
a modification product composition being contacted comprises a plurality of modification product oligonucleotides, each of which is independently an oligonucleotide; or
a post-modification capping product composition being contacted comprises a plurality of post-modification capping product oligonucleotides, each of which is independently an oligonucleotide; and
the de-blocking group converts a plurality of blocked hydroxyl groups of oligonucleotides of the modification or post-modification capping plurality into a plurality of free hydroxyl groups.

306. The method of embodiment 305, wherein the de-blocking group converts a plurality of 5'-blocked hydroxyl groups of oligonucleotides of the modification or post-modification capping plurality into a plurality of 5'-free hydroxyl groups.

307. The method of embodiment 305, wherein the de-blocking step converts a plurality of DMTr-blocked 5'-blocked hydroxyl groups of oligonucleotides of the modification or post-modification capping plurality into a plurality of 5'-free hydroxyl groups.

308. The method of any one of the preceding embodiments, comprising a de-blocking step, wherein:
a modification product composition being contacted comprises a plurality of modification product oligonucleotides, each of which is independently an oligonucleotide of formula VIII or a salt thereof, wherein $R^{5s}$ is —OR where R is not —H, and each $L^P$ is an internucleotidic linkage of formula VII or a salt form thereof, wherein $P^L$ is not P; or
a post-modification capping product composition being contacted comprises a plurality of post-modification capping product oligonucleotides, each of which is independently an oligonucleotide of formula VIII or a salt thereof, wherein $R^{5s}$ is —OR where R is not —H, and each $L^P$ is an internucleotidic linkage of formula VII or a salt form thereof, wherein $P^L$ is not P; and
the de-blocking step converts $R^{5s}$ from —OR, wherein R is not —H, into —OH.

309. The method of any one of the preceding embodiments, wherein the de-blocking group only de-block a blocked hydroxyl group in a nucleoside unit that corresponds to a nucleoside unit of the coupled partner compound of the immediately preceding coupling step.

310. The method of any one of the preceding steps, wherein a de-blocking step provides a post-modification capping composition comprising a plurality of post-modification capping product oligonucleotides, each of which is independently an oligonucleotide of formula VIII or a salt thereof.

311. The method of any one of the preceding steps, wherein each deblocking step provides a deblocking product composition comprising a plurality of deblocking product oligonucleotides, each of which is independently an oligonucleotide of formula VIII or a salt thereof.

312. The method of any one of the preceding embodiments, wherein for a deblocking step, z of formula VIII for a deblocking product oligonucleotide ($z^{DB}$) is the same as z of formula VIII for a corresponding modification product oligonucleotide ($z^{MD}$) or post-modification capping product oligonucleotide ($2^{PT}$).

313. The method of any one of the preceding steps, wherein a de-blocking product composition comprises a plurality of de-blocking product oligonucleotides, each of which is independently of formula VIII or a salt thereof, wherein $R^{5s}$ is —OH.

314. The method of any one of the preceding steps, wherein a de-blocking product composition comprises a plurality of de-blocking product oligonucleotides, each of which is independently of formula VIII or a salt thereof, wherein $R^{5s}$ is 5'-OH.

315. The method of any one of the preceding steps, wherein a de-blocking product composition comprises a plurality of de-blocking product oligonucleotides, each of which is independently of formula VIII or a salt thereof, wherein each $L^P$ in formula VIII is independently an internucleotidic linkage of formula VII, or a salt form thereof, wherein $P^L$ is not P.

316. The method of any one of the preceding steps, wherein a de-blocking product composition comprises a plurality of de-blocking product oligonucleotides, each of which is independently of formula VIII or a salt thereof, wherein each $L^P$ in formula VIII is independently an internucleotidic linkage of formula VII, or a salt form thereof, wherein each $P^L$ independently P(=O) or P(=S).

317. The method of any one of the preceding embodiments, wherein a de-blocking product composition comprises a plurality of de-blocking product oligonucleotides, each of which is independently of formula VIII or a salt thereof, wherein each $L^P$ in formula VIII is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.

318. The method of any one of the preceding embodiments, wherein a de-blocking product composition comprises a plurality of de-blocking product oligonucleotides each of which is independently an oligonucleotide of formula VIII or a salt thereof, comprising one or more $L^P$ wherein $P^L$ is O, and —X-$L^s$-$R^5$ is -$L^7$-$R^1$.

319. The method of any one of the preceding embodiments, wherein a de-blocking product composition comprises a plurality of de-blocking product oligonucleotides each of which is independently an oligonucleotide of formula VIII or a salt thereof, comprising one or more $L^P$ wherein $P^L$ is O, and —X-$L^s$-$R^5$ is —S-$L^s$-$R^5$.

320. The method of any one of the preceding embodiments, wherein a de-blocking product composition comprises a plurality of de-blocking product oligonucleotides each of which is independently an oligonucleotide of formula VIII or a salt thereof, comprising one or more $L^P$ wherein $P^L$ is S, and of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.

321. The method of any one of the preceding embodiments, wherein a de-blocking product composition comprises a plurality of de-blocking product oligonucleotides, each of which is independently of formula VIII or a salt thereof, wherein each $L^P$ is independently of formula VII or a salt form thereof, wherein each of Y and Z is —O—.

322. The method of any one of the preceding embodiments, wherein the de-blocking step provides a de-blocking product composition comprises a plurality of de-blocking product oligonucleotides, each of which is independently an oligonucleotide loaded on a support.

323. The method of any one of the preceding embodiments, wherein each de-blocking step independently provides a de-blocking product composition comprises a plurality of de-blocking product oligonucleotides, each of which is independently an oligonucleotide loaded on a support.

324. The method of any one of the preceding embodiments, wherein a de-blocking product composition comprising a plurality of de-blocking product oligonucleotides is a chirally controlled oligonucleotide composition.

325. The method of any one of the preceding embodiments, wherein a de-blocking product composition comprising a plurality of de-blocking product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the de-blocking product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

326. The method of any one of the preceding embodiments, wherein a de-blocking step comprising repeating the contacting, each time independently with the same or different de-blocking reagent systems.

327. The method of any one of the preceding embodiments, comprising repeating steps b) through e) a number of times until the desired length of a plurality of oligonucleotides is achieved to provide a post-cycle product composition comprising a plurality of post-cycle product oligonucleotides.

328. The method of any one of the preceding embodiments, wherein each post-cycle product oligonucleotide is independently an oligonucleotide of formula VIII or a salt thereof.

329. The method of any one of the preceding embodiments, wherein each post-cycle product oligonucleotide is independently an oligonucleotide of formula VIII or a salt thereof, wherein each $L^P$ is independently of formula VII or a salt form thereof.

330. The method of any one of the preceding embodiments, wherein each post-cycle product oligonucleotide is independently an oligonucleotide of formula VIII or a salt thereof, wherein each $L^P$ is independently of formula VII or a salt form thereof, wherein $P^L$ is not P.

331. The method of any one of the preceding steps, wherein a post-cycle product composition comprises a plurality of post-cycle product oligonucleotides, each of which is independently of formula VIII or a salt thereof, wherein each $L^P$ in formula VIII is independently an internucleotidic linkage of formula VII, or a salt form thereof, wherein each $P^L$ independently P(=O) or P(=S).

332. The method of any one of the preceding embodiments, wherein a post-cycle product composition comprises a plurality of post-cycle product oligonucleotides, each of which is independently of formula VIII or a salt thereof, wherein each $L^P$ in formula VIII is independently of formula VII or a salt form thereof, wherein each —X-$L^s$-$R^5$ is independently -$L^7$-$R^1$, or of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.

333. The method of any one of the preceding embodiments, wherein a post-cycle product composition comprises a plurality of post-cycle product oligonucleotides each of which is independently an oligonucleotide of formula VIII or a salt thereof, comprising one or more $L^P$ wherein $P^L$ is O, and —X-$L^s$-$R^5$ is -$L^7$-$R^1$.

334. The method of any one of the preceding embodiments, wherein a post-cycle product composition comprises a plurality of post-cycle product oligonucleotides each of which is independently an oligonucleotide of formula VIII or a salt thereof, comprising one or more $L^P$ wherein $P^L$ is O, and —X-$L^s$-$R^5$ is —S-$L^s$-$R^5$.

335. The method of any one of the preceding embodiments, wherein a post-cycle product composition comprises a plurality of post-cycle product oligonucleotides each of which is independently an oligonucleotide of formula VIII or a salt thereof, comprising one or more $L^P$ wherein $P^L$ is S, and of such a structure that H—X-$L^s$-$R^5$ is a compound of formula I, I-a, I-a-I, I-a-2, I-b, I-c, I-d, I-e, II, II-a, II-b, III, III-a, or III-b, wherein at least one of $R^5$ or $R^6$ is —C(O)R.

336. The method of any one of the preceding embodiments, wherein a post-cycle product composition comprises a plurality of post-cycle product oligonucleotides, each of which is independently of formula VIII or a salt thereof, wherein each $L^P$ is independently of formula VII or a salt form thereof, wherein each of Y and Z is —O—.

337. The method of any one of the preceding embodiments, wherein the post-cycle step provides a post-cycle product composition comprises a plurality of post-cycle product oligonucleotides, each of which is independently an oligonucleotide loaded on a support.

338. The method of any one of the preceding embodiments, wherein each post-cycle step independently provides a post-cycle product composition comprises a plurality of post-cycle product oligonucleotides, each of which is independently an oligonucleotide loaded on a support.

339. The method of any one of the preceding embodiments, wherein a post-cycle product composition comprising a plurality of post-cycle product oligonucleotides is a chirally controlled oligonucleotide composition.

340. The method of any one of the preceding embodiments, wherein a post-cycle product composition comprising a plurality of post-cycle product oligonucleotides is a chirally controlled oligonucleotide composition wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the post-cycle product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

341. The method of any one of the preceding embodiments, comprising further modifying a plurality of post-cycle product oligonucleotides.

342. The method of any one of the preceding embodiments, comprising conjugating a plurality of post-cycle product oligonucleotides with lipid moieties.

343. The method of any one of the preceding embodiments, comprising conjugating a plurality of post-cycle product oligonucleotides with targeting moieties.

344. The method of any one of the preceding embodiments, comprising conjugating a plurality of post-cycle product oligonucleotides with targeting moieties, which targeting moieties are cell receptor ligands.

345. The method of any one of the preceding embodiments, comprising conjugating a plurality of post-cycle product oligonucleotides with targeting moieties, which targeting moieties are carbohydrate moieties 346. The method of any one of the preceding embodiments, comprising conjugating a plurality of post-cycle product oligonucleotides with carbohydrate moieties.

347. The method of any one of the preceding embodiments, comprising a post-cycle modification step, comprising:
providing a composition comprising a plurality of oligonucleotides with a post-cycle modification reagent system;
removing one or more chiral auxiliary moieties from the plurality of oligonucleotides.

348. The method of any one of the preceding embodiments, comprising a post-cycle modification step, wherein the post-cycle modification step comprises:
providing a composition comprising a plurality of oligonucleotides with a post-cycle modification reagent system;
converting one or more internucleotidic linkages of formula VII or a salt form thereof, wherein $P^L$ is P(=S), into phosphorothioate internucleotidic linkages (—O—P(=O)(—SH)—O— or a salt form thereof).

349. The method of any one of the preceding embodiments, comprising a post-cycle modification step, wherein the post-cycle modification step comprises:
providing a composition comprising a plurality of oligonucleotides with a post-cycle modification reagent system;
converting one or more internucleotidic linkages of formula VII or a salt form thereof, wherein $P^L$ is P(=S), and —X-$L^s$-$R^5$ comprises a —Si(R)$_3$ moiety, into phosphorothioate internucleotidic linkages (—O—P(=O)(—SH)—O— or a salt form thereof).

350. The method of any one of the preceding embodiments, wherein an X-$L^s$-$R^5$ comprises a —Si(R)$_3$ moiety is

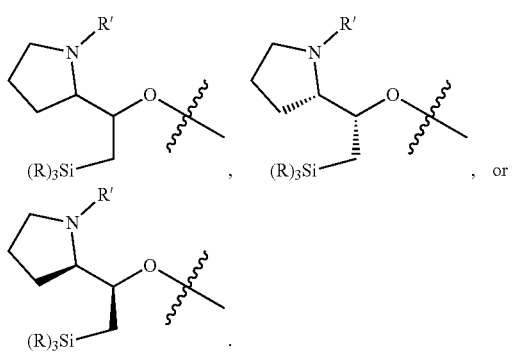

351. The method of embodiment 350, wherein R' is —H.
352. The method of embodiment 350, wherein R' is —C(O)R.
353. The method of embodiment 350, wherein R' is —C(O)CH$_3$.

354. The method of any one of the preceding embodiments, wherein the post-cycle modification reagent system comprises F$^-$.

355. The method of any one of the preceding embodiments, wherein the post-cycle modification reagent system comprises HF-Pyridine.

356. The method of any one of the preceding embodiments, wherein the post-cycle modification reagent system comprises 3HF-TEA.

357. The method of any one of the preceding embodiments, wherein the post-cycle modification reagent system comprises tetrabutylammonium fluoride.

358. The method of any one of the preceding embodiments, wherein the post-cycle modification reagent system comprises tetrabutylammonium difluorotriphenylsilicate.

359. The method of any one of the preceding embodiments, comprising a cleavage/deprotection step that comprises:
contacting a plurality of oligonucleotides with one or more cleavage/deprotection reagent systems;
wherein the cleavage/deprotection step provides a final product composition comprising a plurality of final product oligonucleotides.

360. The method of any one of the preceding embodiments, comprising a cleavage/deprotection step that comprises:
contacting a plurality of oligonucleotides, each of which is independently loaded on a support, with one or more cleavage/deprotection reagent systems;
wherein the cleavage/deprotection step provides a final product composition comprising a plurality of final product oligonucleotides, each of which is cleaved from a solid support.

361. The method of any one of the preceding embodiments, wherein a cleavage/deprotection step comprises:
contacting a plurality of oligonucleotides, each of which is independently loaded on a support, with one or more cleavage/deprotection reagent systems;
de-protecting one or more blocking groups of the oligonucleotides;
cleaving the oligonucleotides from a support; and
wherein the cleavage/deprotection step provides a final product composition comprising a plurality of final product oligonucleotides.

362. The method of any one of the preceding embodiments, wherein a cleavage/deprotection reagent system comprises a base.

363. The method of any one of the preceding embodiments, wherein a cleavage/deprotection reagent system comprises concentrated NH$_4$OH.

364. The method of any one of the preceding embodiments, wherein a cleavage/deprotection reagent system comprises a metal chelator.

365. The method of any one of the preceding embodiments, wherein a cleavage/deprotection reagent system comprises mercaptoethanol, 1-dodecanthiol, dithiothreitol (DTT), thiophenol, 1,2-diaminoethane,1,3-diaminopropane, 2,3-mercapto 1-propanesulfonic acid, 2,3-mercapto propane-1-ol, or meso 2,3-dimercapto succinic acid.

366. The method of any one of the preceding embodiments, wherein a cleavage/deprotection reagent system comprises EDTA.

367. The method of any one of the preceding embodiments, wherein a cleavage/deprotection step comprises elevated temperature.

368. The method of any one of the preceding steps, wherein a final product composition comprising a plurality of final product oligonucleotides, each of which is independently an oligonucleotide of formula VIII or a salt thereof.

369. The method of any one of the preceding steps, wherein a final product composition comprising a plurality of final product oligonucleotides, each of which is independently an oligonucleotide of formula VIII or a salt thereof, wherein each $L^P$ in formula VIII is independently an internucleotidic linkage of formula VII, or a salt form thereof, wherein $P^L$ is not P.

370. The method of any one of the preceding steps, wherein a final product composition comprising a plurality of final product oligonucleotides, each of which is independently an oligonucleotide of formula VIII or a salt thereof, wherein each $L^P$ in formula VIII is independently an internucleotidic linkage of formula VII, or a salt form thereof, wherein each $P^L$ independently P(=O).

371. The method of any one of the preceding steps, wherein a final product composition comprising a plurality of final product oligonucleotides, each of which is independently an oligonucleotide of formula VIII or a salt thereof, wherein each $L^P$ in formula VIII is independently an internucleotidic linkage of formula VII, or a salt form thereof, wherein each X is independently —O— or —S—.

372. The method of any one of the preceding steps, wherein a final product composition comprising a plurality of final product oligonucleotides, each of which is independently an oligonucleotide of formula VIII or a salt thereof, wherein each $L^P$ in formula VIII is independently an internucleotidic linkage of formula VII, or a salt form thereof, wherein each of Y and Z is —O—.

373. The method of any one of the preceding steps, wherein a final product composition comprising a plurality of final product oligonucleotides, each of which is independently an oligonucleotide of formula VIII or a salt thereof, wherein each $L^P$ in formula VIII is independently a natural phosphate linkage (—O—P(=O)(—OH)—O— or a salt form thereof) or phosphorothioate linkage (—O—P(=O)(—SH)—O— or a salt form thereof).

374. The method of any one of the preceding steps, wherein a final product composition comprising a plurality of final product oligonucleotides, each of which is not loaded on a support.

375. The method of any one of the preceding embodiments, wherein a final product composition comprising a plurality of final product oligonucleotides is a chirally controlled oligonucleotide composition.

376. The method of any one of the preceding embodiments, wherein a final product composition comprising a plurality of final product oligonucleotides is a chirally controlled oligonucleotide composition wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least ((DS)$^{Nc}$*100)% of all oligonucleotides sharing the same base sequence in the final product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

377. The method of any one of the preceding embodiments, wherein the method provides a final product composition with at least 40%, 45%, 50%, 55%, 60%, 65%, 70% or 75% crude purity.

378. The method of any one of the preceding embodiments, wherein the crude purity is % full-length product.

379. The method of any one of the preceding embodiments, wherein the crude purity is % full-length product as assessed by LC-UV monitored at UV 260 nm.

380. The method of any one of the preceding embodiments, comprising purifying the final product composition using chromatography or electrophoresis.

381. The method of any one of the preceding embodiments, comprising purifying the final product composition using HPLC.

382. A crude chirally controlled oligonucleotide composition comprising a plurality of oligonucleotides, wherein:
oligonucleotides of the plurality share the same base sequence;
oligonucleotides of the plurality share the same pattern of backbone linkages; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least ((DS)$^{Nc}$*100)% of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

383. A crude chirally controlled oligonucleotide composition comprising a plurality of oligonucleotides, wherein:
oligonucleotides of the plurality share the same constitution; and
oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
wherein at least ((DS)$^{Nc}$*100)% of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage;
wherein the crude chirally controlled oligonucleotide composition has a crude purity of at least 40%, 45%, 50%, 55%, 60%, 65%, 70%, or 75%.

384. The composition of any one of embodiments 381-383, wherein the crude chirally controlled oligonucleotide composition is cleaved from a support, and before any further purification.

385. The composition of any one of embodiments 381-383, wherein the crude chirally controlled oligonucleotide composition is cleaved from a support, after de-salting, and before any further purification.

386. The composition of any one of the preceding embodiments, wherein the crude chirally controlled oligonucleotide composition is before any chromatograph or gel purification.

387. The method or composition of any one of the preceding embodiments, wherein the crude purity is % full-length product.

388. The method or composition of any one of the preceding embodiments, wherein the crude purity is % full-length product as assessed by LC-UV monitored at UV 260 nm.

389. A composition, comprising a plurality of oligonucleotides and a reagent of a reagent system, wherein:

the plurality of oligonucleotides is a plurality of oligonucleotides of a modification product composition of any one of the preceding embodiments;

the reagent system is a pre-modification or post-modification capping reagent system of any one of the preceding embodiments; and the post-modification capping reagent system is in contact with the plurality of oligonucleotides.

390. The composition of embodiment 389, wherein the plurality of oligonucleotides are loaded on a support.

391. The composition of any one of embodiments 389-390, wherein:

oligonucleotides of the plurality share the same base sequence;

oligonucleotides of the plurality share the same pattern of backbone linkages; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

392. The composition of any one of embodiments 389-390, wherein:

oligonucleotides of the plurality share the same constitution; and oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;

wherein at least $((DS)^{Nc}*100)\%$ of all oligonucleotides sharing the same base sequence in the crude composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

393. The method of any one of the preceding embodiments, wherein DS is at least 90%.

394. The method of any one of the preceding embodiments, wherein DS is at least 92%.

395. The method of any one of the preceding embodiments, wherein DS is at least 95%.

396. The method of any one of the preceding embodiments, wherein DS is at least 98%.

397. The method or composition of any one of the preceding embodiments, wherein a support is a solid support.

398. The method or composition of any one of the preceding embodiments, wherein a support is a polystyrene support.

399. The method or composition of any one of embodiments 1-393, wherein a support is a CPG support.

400. The method or composition of any one of the preceding embodiments, wherein a support has a unit loading capacity of about 50-300 umol/g.

401. The method or composition of any one of the preceding embodiments, wherein a support has a unit loading capacity of about 50-80, 80-100, 100-120, 120-140, 140-160, 160-180, 180-210, or 210-250 umol/g.

402. The method or composition of any one of the preceding embodiments, wherein the oligonucleotides or nucleosides are connected to a solid support through a linker.

403. The method or composition of any one of the preceding embodiments, wherein oligonucleotides of a plurality have a length of at least 10, 11, 12, 13, 14, 15, 16, 17, 18, 19, 20, 21, 22, 23, 24, or 25 nucleobases.

404. The method or composition of any one of the preceding embodiments, wherein each nucleobase or BA is independently an optionally substituted or protected nucleobase selected from A, T, C, G, and U.

405. The method or composition of any one of the preceding embodiments, wherein oligonucleotides of a plurality independently comprise one or more modified sugar moieties.

406. The method or composition of any one of the preceding embodiments, wherein oligonucleotides of a plurality independently comprise one or more sugar moieties having the structure of

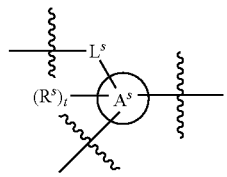

407. The method or composition of any one of the preceding embodiments, wherein oligonucleotides of a plurality independently comprise one or more sugar moieties having the structure of

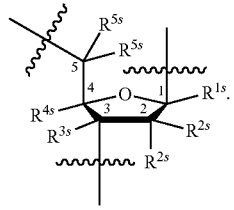

408. The method or composition of any one of the preceding embodiments, wherein oligonucleotides of a plurality independently comprise one or more sugar moieties having the structure of

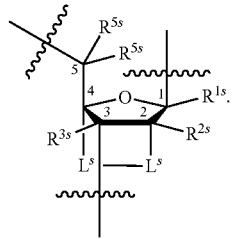

409. The method or composition of any one of the preceding embodiments, wherein oligonucleotides of a plurality independently comprise one or more sugar moieties having the structure of

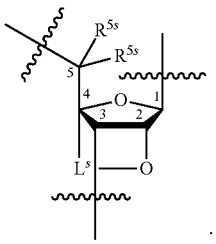

410. The method or composition of any one of the preceding embodiments, wherein oligonucleotides of a plurality independently comprise one or more sugar moieties having the structure of

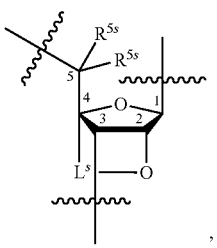

, wherein -$L^s$- is —$CH_2$—.

411. The method or composition of any one of the preceding embodiments, wherein oligonucleotides of a plurality independently comprise one or more sugar moieties having the structure of

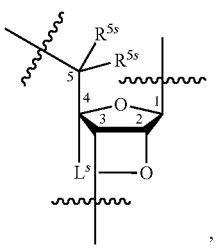

, wherein -$L^s$- is —(S)—CHR—, wherein R is not —H.

412. The method or composition of any one of the preceding embodiments, wherein oligonucleotides of a plurality independently comprise one or more sugar moieties having the structure of

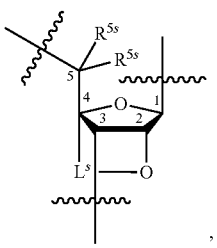

, wherein -$L^s$- is —(R)—CHR—, wherein R is not —H.

413. The method or composition of any one of the preceding embodiments, wherein oligonucleotides of a plurality independently comprise one or more sugar moieties having the structure of

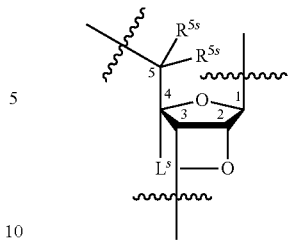

, wherein -$L^s$- is —CHR—.

414. The method or composition of any one of the preceding embodiments, wherein oligonucleotides of a plurality independently comprise one or more sugar moieties having the structure of

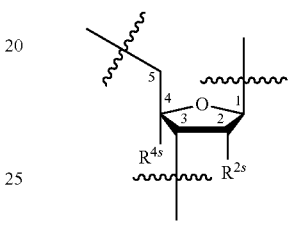

415. The method or composition of any one of the preceding embodiments, wherein oligonucleotides of a plurality independently comprise one or more sugar moieties having the structure of

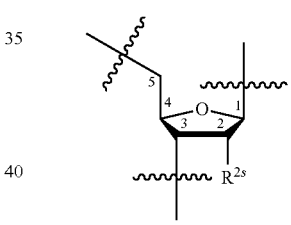

416. The method or composition of any one of the preceding embodiments, wherein C1 is connected to a nucleobase or BA.

417. The method or composition of any one of the preceding embodiments, wherein for at least one sugar moiety, $R^{2s}$ is —H.

418. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is —H.

419. The method or composition of any one of the preceding embodiments, wherein for at least one sugar moiety, $R^{2s}$ is not —H.

420. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is not —H.

421. The method or composition of any one of the preceding embodiments, wherein for at least one sugar moiety, $R^{2s}$ is —F.

422. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is —F.

423. The method or composition of any one of the preceding embodiments, wherein for at least one sugar moiety, $R^{2s}$ is —OR.
424. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is —OR.
425. The method or composition of any one of the preceding embodiments, wherein for at least one sugar moiety, $R^{2s}$ is —OMe.
426. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is —OMe.
427. The method or composition of any one of the preceding embodiments, wherein for at least one sugar moiety, $R^{2s}$ is -MOE.
428. The method or composition of any one of the preceding embodiments, wherein for at least 2-20, or at least 2, 3, 4, 5, 6, 7, 8, 9, 10, 11, 12, 13, 14, 15, 16, 17, 18, 19, or 20 sugar moieties, $R^{2s}$ is -MOE.
429. The method or composition of any one of the preceding embodiments, wherein the at least 2-20, or at least 2, 3, 4, 5, 6, 7, 8, 9, 10, 11, 12, 13, 14, 15, 16, 17, 18, 19, or 20 sugar moieties are consecutive.
430. The method or composition of any one of the preceding embodiments, wherein oligonucleotides of a plurality comprise 1-20, or at least 1, 2, 3, 4, 5, 6, 7, 8, 9, 10, 11, 12, 13, 14, 15, 16, 17, 18, 19, or 20 chirally controlled internucleotidic linkages (Nc is 1-20, or at least 1, 2, 3, 4, 5, 6, 7, 8, 9, 10, 11, 12, 13, 14, 15, 16, 17, 18, 19, or 20).
431. The method or composition of any one of the preceding embodiments, wherein oligonucleotides of a plurality comprise 1-20, or at least 1, 2, 3, 4, 5, 6, 7, 8, 9, 10, 11, 12, 13, 14, 15, 16, 17, 18, 19, or 20 chirally controlled phosphorothioate linkages (Nc is 1-20, or at least 1, 2, 3, 4, 5, 6, 7, 8, 9, 10, 11, 12, 13, 14, 15, 16, 17, 18, 19, or 20).
432. The method or composition of any one of the preceding embodiments, wherein oligonucleotides of a plurality comprise 1-20, or at least 1, 2, 3, 4, 5, 6, 7, 8, 9, 10, 11, 12, 13, 14, 15, 16, 17, 18, 19, or 20 natural phosphate linkages.
433. The method or composition of any one of the preceding embodiments, wherein the 1-20, or at least 1, 2, 3, 4, 5, 6, 7, 8, 9, 10, 11, 12, 13, 14, 15, 16, 17, 18, 19, or 20 chirally controlled internucleotidic linkages are consecutive.
434. The method or composition of any one of the preceding embodiments, wherein the 1-20, or at least 1, 2, 3, 4, 5, 6, 7, 8, 9, 10, 11, 12, 13, 14, 15, 16, 17, 18, 19, or 20 natural phosphate linkages are consecutive.
435. The method or composition of any one of the preceding embodiments, wherein oligonucleotides of a plurality comprise a pattern of backbone chiral centers comprising (Rp)n(Sp)p, wherein n is 1-10, and each of p and m is independently 1-50.
436. The method or composition of any one of the preceding embodiments, wherein oligonucleotides of a plurality comprise a pattern of backbone chiral centers comprising (Sp)m(Rp)n(Sp)p, wherein n is 1-10, and each of p and m is independently 1-50.
437. The method or composition of any one of the preceding embodiments, wherein oligonucleotides of a plurality comprise a pattern of backbone chiral centers comprising (Rp)n(Sp)p, wherein n is 1, m is 2-50, and p is 2-50.
438. The method or composition of any one of the preceding embodiments, wherein oligonucleotides of a plurality comprise a pattern of backbone chiral centers comprising (Sp)m(Rp)n(Sp)p, wherein n is 1, m is 2-50, and p is 2-50.
439. The method or composition of any one of the preceding embodiments, wherein oligonucleotides of a plurality comprise a pattern of backbone chiral centers comprising (Op)n(Sp)p, wherein n is 1-10, and each of p and m is independently 1-50.
440. The method or composition of any one of the preceding embodiments, wherein oligonucleotides of a plurality comprise a pattern of backbone chiral centers comprising (Sp)m(Op)n(Sp)p, wherein n is 1-10, and each of p and m is independently 1-50.
441. The method or composition of any one of the preceding embodiments, wherein oligonucleotides of a plurality comprise a pattern of backbone chiral centers comprising (Op)n(Sp)p, wherein n is 1, m is 2-50, and p is 2-50.
442. The method or composition of any one of the preceding embodiments, wherein oligonucleotides of a plurality comprise a pattern of backbone chiral centers comprising (Sp)m(Op)n(Sp)p, wherein n is 1, m is 2-50, and p is 2-50.
443. The method or composition of any one of the preceding embodiments, wherein oligonucleotides of a plurality comprise a pattern of backbone chiral centers comprising two or more units independently selected from (Rp)n(Sp)p or (Op)n(Sp)p, wherein n is 1 and each p is independently 2-50.
444. The method or composition of any one of the preceding embodiments, wherein oligonucleotides of a plurality comprise a pattern of backbone chiral centers comprising two or more (Rp)n(Sp)p, wherein n is 1 and each p is independently 2-50.
445. The method of any one of embodiments 435-444, wherein oligonucleotides of a plurality each comprise a region comprising the pattern of backbone chiral centers.
446. The method of embodiments 445, wherein each sugar moiety of the region independently has two 2'-H.
447. The method of any one of embodiments 445-446, wherein the region is flanked by a 5'-region comprising one or more sugar modifications.
448. The method of embodiment 447, wherein each sugar moiety of the 5'-region independently comprises a sugar modification.
449. The method of any one of embodiments 445-448, wherein the region is flanked by a 3'-region comprising one or more sugar modifications.
450. The method of embodiment 449, wherein each sugar moiety of the 3'-region independently comprises a sugar modification.
451. The method or composition of any one of the preceding embodiments, wherein oligonucleotides of a plurality share a base sequence identical or complementary to a portion of a DMD sequence.
452. The method or composition of any one of the preceding embodiments, wherein oligonucleotides of a plurality share a base sequence identical or complementary to a portion of a HTT sequence.
453. The method or composition of any one of the preceding embodiments, wherein oligonucleotides of a plurality share a base sequence identical or complementary to a portion of a HTT sequence containing a SNP.
454. The method of any one of the preceding embodiments, wherein the final oligonucleotide product is a solid.
455. The method of any one of the preceding embodiments, wherein the final oligonucleotide product is an oligonucleotide solution.
456. The method or composition of any one of the preceding embodiments, wherein oligonucleotides of a plurality share a base sequence which is or comprises a base sequence of US20150211006, US20170037399, WO2017/015555, WO2017/015575, WO2017/062862, WO2017/160741, WO2017/192664, WO2017/192679, WO2017/210647, WO2018/022473, WO2018/067973, or WO2018/098264.
457. The method or composition of any one of the preceding embodiments, wherein oligonucleotides of a plurality share a pattern of backbone chiral centers which is or comprising a pattern of backbone chiral centers of US20150211006, US20170037399, WO2017/015555, WO2017/015575, WO2017/062862, WO2017/160741, WO2017/192664, WO2017/192679, WO2017/210647, WO2018/022473, WO2018/067973, or WO2018/098264.

458. The method or composition of any one of the preceding embodiments, wherein oligonucleotides of a plurality are the same and are an oligonucleotide of US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264.

459. The method or composition of any one of the preceding embodiments, wherein a product composition is a chirally controlled oligonucleotide composition of an oligonucleotide of US20150211006, US20170037399, WO2017/015555, WO2017/015575, WO2017/062862, WO2017/160741, WO2017/192664, WO2017/192679, WO2017/210647, WO2018/022473, WO2018/067973, WO2018/098264.

460. The method or composition of any one of the preceding embodiments, wherein a final product composition is a chirally controlled oligonucleotide composition of an oligonucleotide of US20150211006, US20170037399, WO2017/015555, WO2017/015575, WO2017/062862, WO2017/160741, WO2017/192664, WO2017/192679, WO2017/210647, WO2018/022473, WO2018/067973, or WO2018/098264.

461. The method of any one of the preceding embodiments, wherein the final product composition is a chirally controlled oligonucleotide composition of an oligonucleotide of US20150211006, US20170037399, WO2017/015555, WO2017/015575, WO2017/062862, WO2017/160741, WO2017/192664, WO2017/192679, WO2017/210647, WO2018/022473, or WO2018/067973, WO2018/098264.

462. The method of any one of the preceding embodiments, wherein the selection is from US20150211006, US20170037399, WO2017/015555, WO2017/015575, and WO2017/062862.

463. The method of any one of the preceding embodiments, wherein the final product composition is a chirally controlled oligonucleotide composition of WV-887, WV-892, WV-896, WV-1714, WV-2444, WV-2445, WV-2526, WV-2527, WV-2528, WV-2530, WV-2531, WV-2578, WV-2580, WV-2587, WV-3047, WV-3152, WV-3472, WV-3473, WV-3507, WV-3508, WV-3509, WV-3510, WV-3511, WV-3512, WV-3513, WV-3514, WV-3515, WV-3545, or WV-3546.

464. The method of any one of the preceding embodiments, wherein the final product composition is a chirally controlled oligonucleotide composition of WV-2603, WV-2595, WV-1510, WV-2378, WV-2380, WV-1092, WV-1497, WV-1085, WV-1086, or WV-2623.

EXEMPLIFICATION

Non-limiting examples were provided below. A person of ordinary skill in the art appreciates that other compounds and compositions, e.g., chiral auxiliaries of formula I, I-a, I-a-1, I-a-2, I-b, I-c, I-d, I-e, II, II-a, II-b, III, III-a, or III-b, or salts thereof, phosphoramidites of formula IV, IV-a, IV-b, IV-c-1, IV-c-2, IV-d, IV-e, IVa, IVa-a, IVa-b, IVa-c-1, IVa-c-2, IVa-d, IVa-e, V, V-a, V-b, V-c-1, V-c-2, V-d, V-e, VI, VI-a, VI-b, VI-c, VI-c-1, VI-c-2, VI-d, or VI-e, or salts thereof, oligonucleotides of formula VIII or salts thereof, oligonucleotides comprising one or more internucleotidic linkages each independently of formula VII, VII-a-1, VII-a-2, VII-b, VII-c, VII-d, or VII-e, or a salt form thereof, compositions of provided compounds, e.g., compositions of provided oligonucleotides (including various chirally controlled compositions), etc. can be similarly prepared and utilized in accordance with the present disclosure.

Example 1. Example Reagents and/or Oligonucleotides

As appreciated by those skilled in the art, many supports, chiral auxiliaries, phosphoramidites, coupling reagents, capping reagents (both pre-modification capping and post-modification capping), modification reagents (e.g., oxidation reagents, sulfurization reagents, etc.), de-blocking reagents, post-cycle modification reagents, cleavage reagents, deprotection reagents, etc., can be utilized in accordance with the present disclosure to provide a variety of oligonucleotides and compositions thereof. Example reagents and/or product oligonucleotides and compositions thereof include those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, etc. and, as demonstrated in the examples, may be utilized in technologies of the present disclosure. As readily appreciated by those skilled in the art, example conditions described herein may be adjusted in accordance with the present disclosure. In some embodiments, a step of a provided method uses a condition described herein, or a variant thereof.

Example 2. Example Support and Linkers

Many supports and/or linkers can be utilized in accordance with the present disclosure. In some embodiments, certain supports and/or linkers are commercially available from various vendors, e.g., Prime Synthese, GE, etc. Among other things, the present disclosure provides modified support and linkers for loading oligonucleotides/nucleosides onto solid support. As those skilled in the art readily appreciate, support and/or linkers described herein may be additionally and/or alternatively utilized with other support and/or linkers.

Scheme 1: Preparation of 1,3-bis(17-amino-3,6,9,12,15-pentaoxaheptadecyl)urea (3).

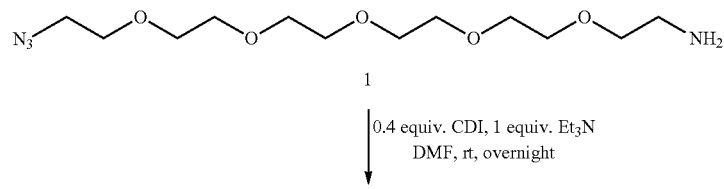

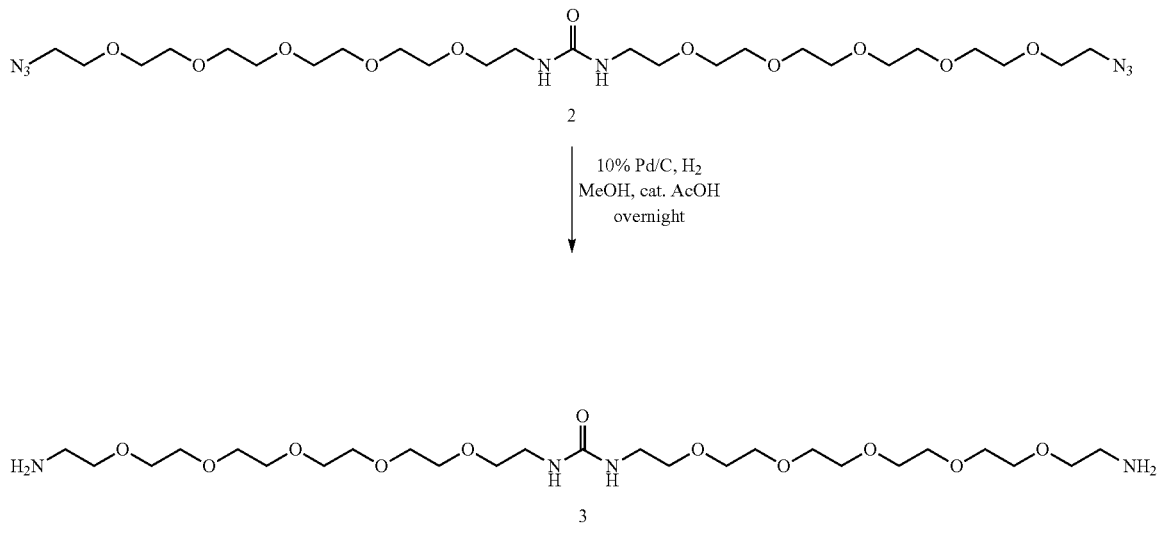

Preparation of 1,3-bis(17-azido-3,6,9,12,15-pentaoxaheptadecyl)urea (2): To a solution of 17-azido-3,6,9,12,15-pentaoxaheptadecan-1-aminium (1) (30 g, 97.73 mmol) in DMF (100 mL), triethyl amine (TEA) (9.89 g, 97.73 mmol) and 1,1-carbonyldiimidazole (7.80 g, 0.22 mmol) were added sequentially at room temperature under Argon. The reaction mixture was stirred at room temperature overnight. The solvent was evaporated under reduced pressure to give 2, as slightly yellow oil (24 g, 75% yield), which was used further without purification. MS (ESI$^+$) calculated for $C_{25}H_{50}N_8O_{11}$: 638.4; found: 639.3 (M+H$^+$).

Preparation of 1,3-bis(17-azido-3,6,9,12,15-pentaoxaheptadecyl)urea (3): To a solution of 1,3-bis(17-amino-3,6,9, 12,15-pentaoxaheptadecyl)urea (24 g, 37.57 mmol) in MeOH (80 mL), were added 10% wet Pd/C (2 g) and acetic acid (~2 equiv.). The reaction mixture was de-gassed with help of vacuum and purged with 1 atmosphere H$_2$ gas balloon (this procedure was repeated 3 times) and stirred under H$_2$ gas overnight. TLC showed starting material was disappeared and then filtered over celite pad. Filtrate was concentrated, and co-evaporated with toluene (3×80 mL) to give 3, as yellow syrup (21.5 g, 98% yield), which was used for the next step without purification. MS (ESI$^+$) calculated for $C_{25}H_{54}N_4O_{11}$: 586.4 found: 587.3 (M+H$^+$).

Preparation of Example CPG Solid Supports.

Scheme 2: Example Aminopropyl-CPG Solid Supports.

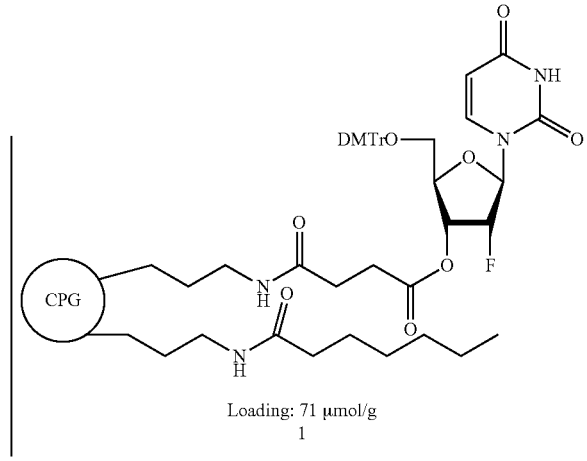

Loading: 71 µmol/g
1

-continued
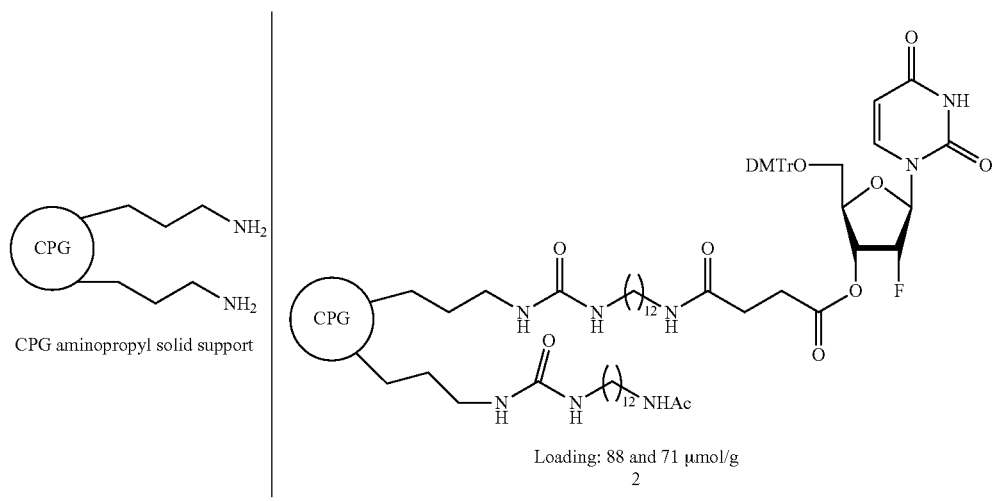
CPG aminopropyl solid support
Loading: 88 and 71 μmol/g
2
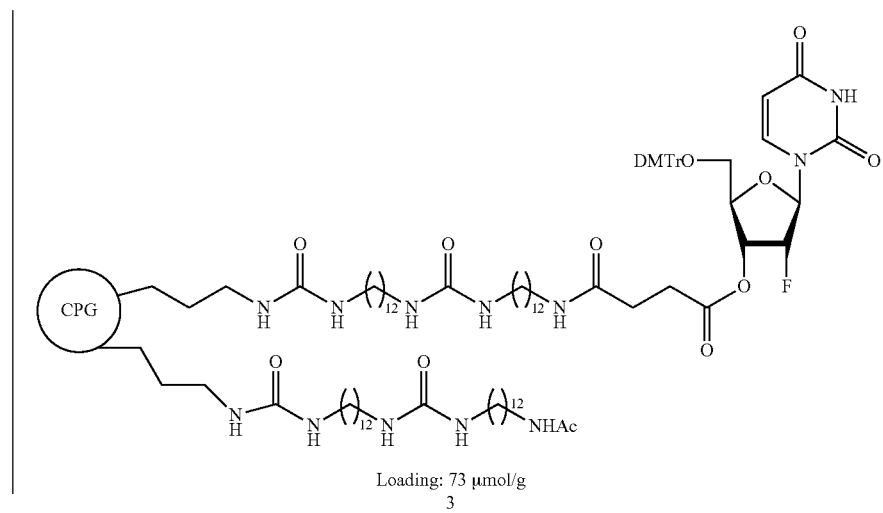
Loading: 73 μmol/g
3
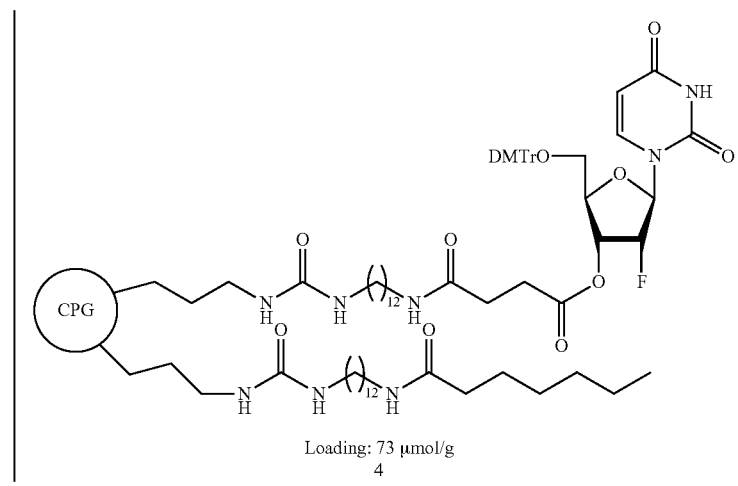
Loading: 73 μmol/g
4

-continued
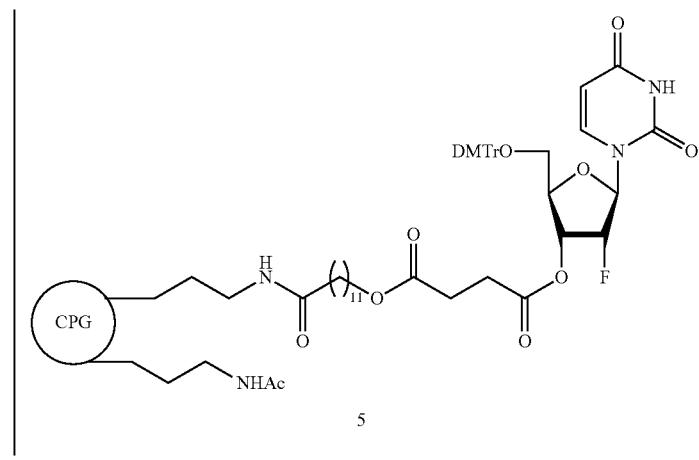
5
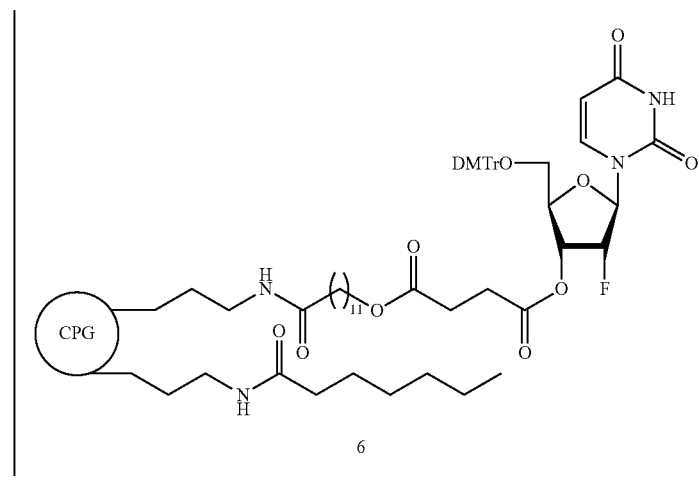
6
Scheme 3: Example Aminopropyl-CPG Solid Supports.
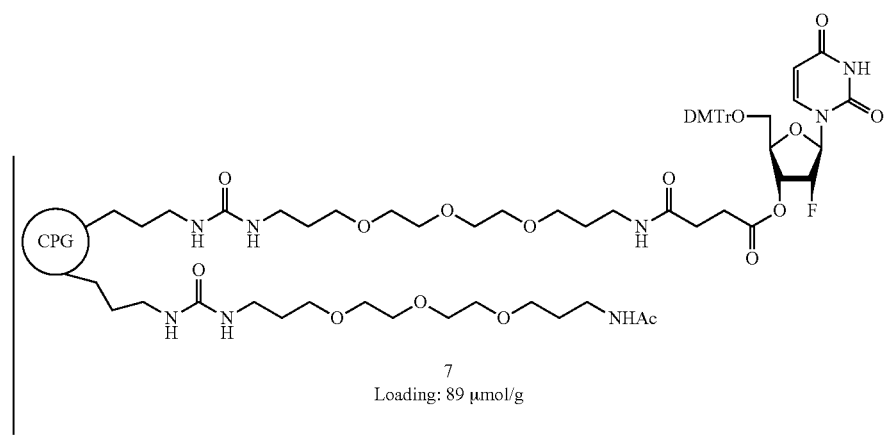
7
Loading: 89 μmol/g

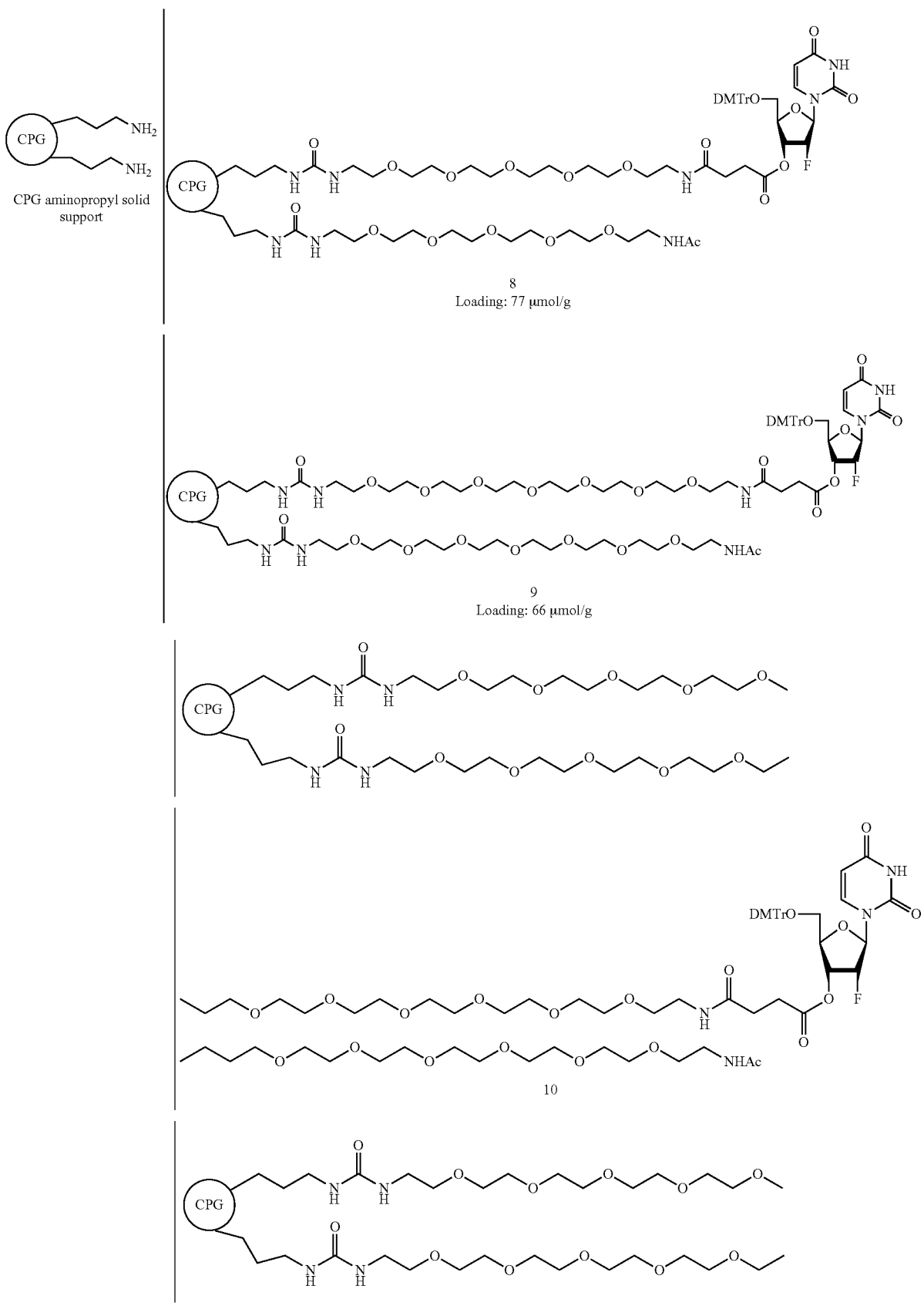

-continued
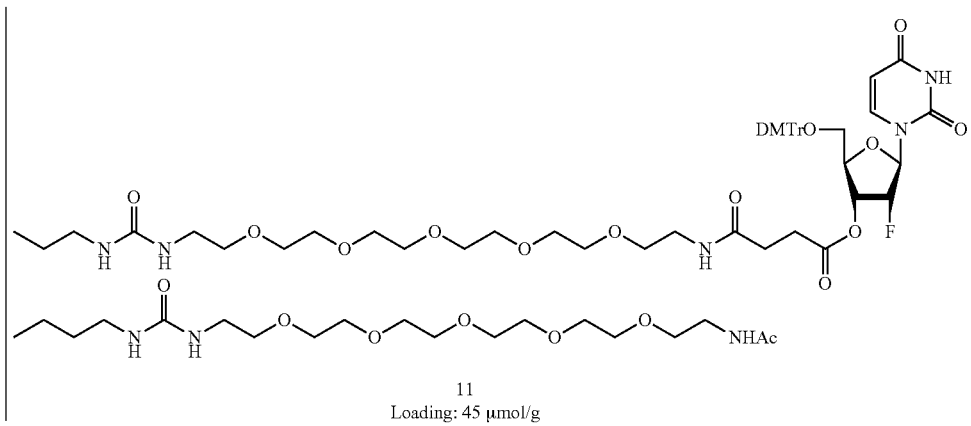
11
Loading: 45 µmol/g
Scheme 4: Amino-nonyl-CPG Solid Supports.
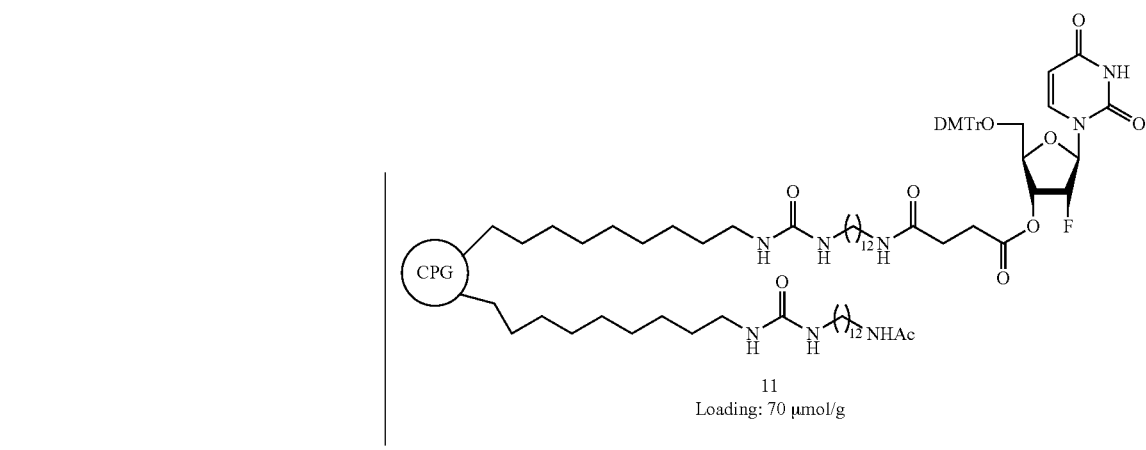
11
Loading: 70 µmol/g
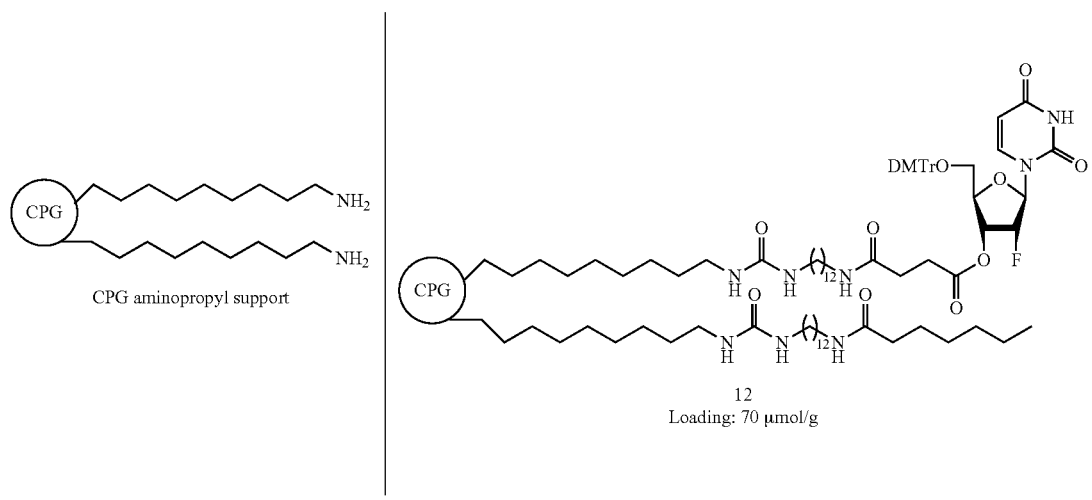
CPG aminopropyl support
12
Loading: 70 µmol/g -continued

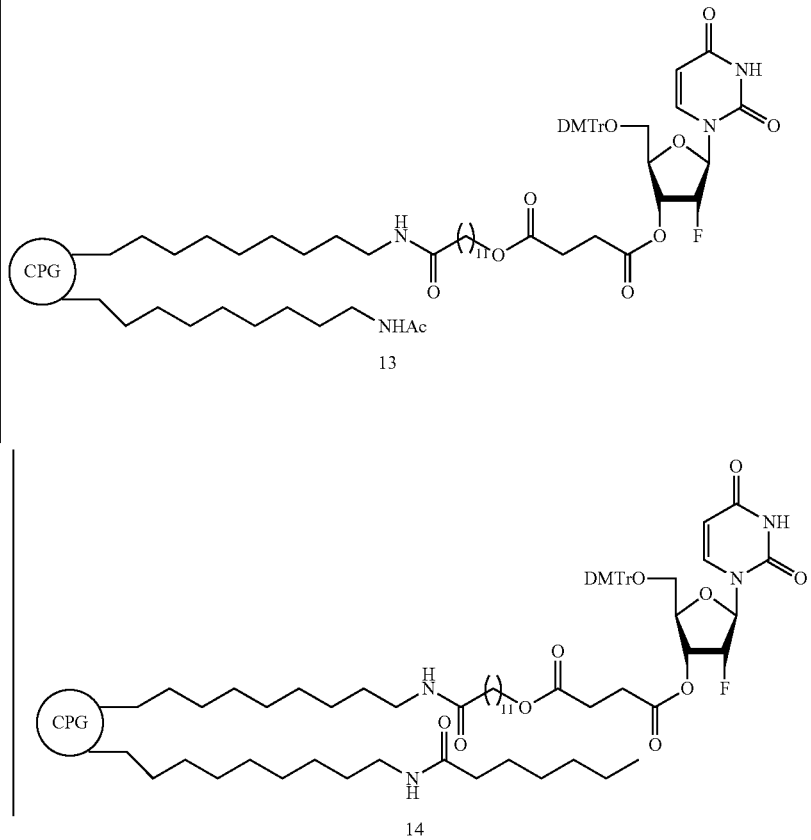

13

14

Scheme 5: Amino-nonyl-CPG Solid Support.

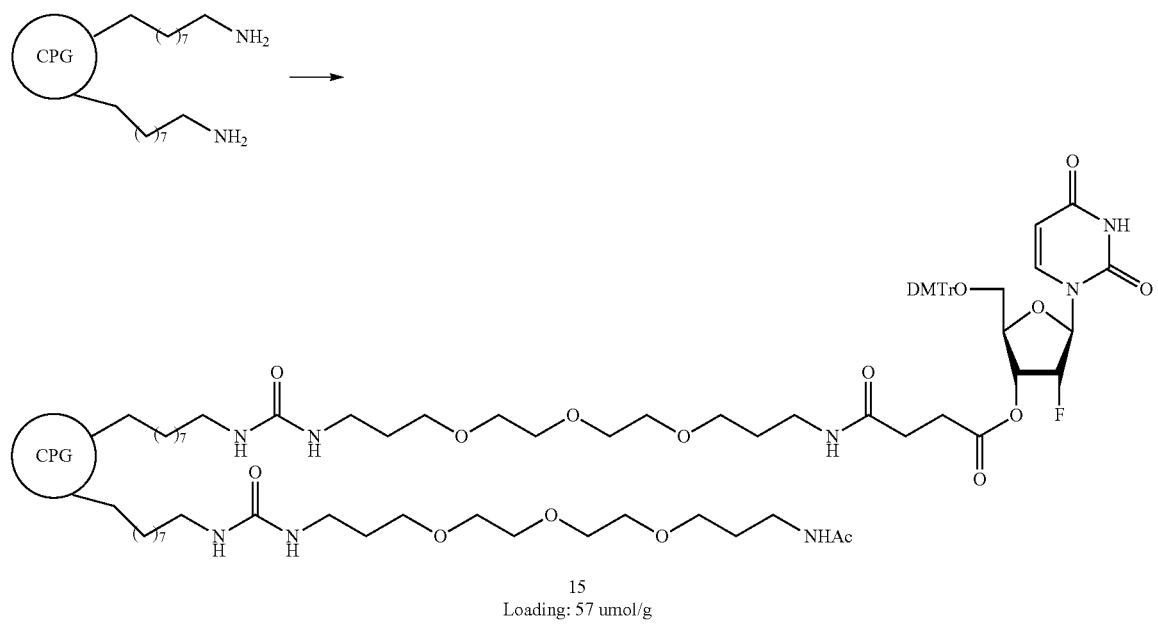

15
Loading: 57 umol/g

General procedure for CPG-p-nitrophenyl carbamate I: An dried 2 L RB flask was cooled under vacuum then filled with Argon. Then DCM (375 mL, 7.5 mL per g of CPG) and p-Nitrophenyl chloroformate (12 g, 0.24 g per g of CPG) were added under Argon and shaken the flask for 3 min, and once p-Nitrophenyl chloroformate was dissolved then pyridine (50 mL, 1 mL per g of CPG) was added, at this stage a white solid was formed with a slightly exothermic reaction. Then immediately an amino functionalized support (Aminopropyl-CPG or amino-nonyl-CNA-CPG) was added and the reaction mixture was shaken 5 min, and mechanical wrist shaker for overnight. Filtered and washed with DCM (3×350 mL) and followed by THF (3×350 mL), and solids (Aminopropyl-CPG- or CNA-p-nitrophenyl carbamate) were taken into 1 L RB flask and dried under vacuum for around 4 hr. Pyridine (200 mL) and Ac$_2$O (50 mL) were added into the dried Aminopropyl-CPG- or CNA-p-nitrophenyl carbamate and overhead shaker for 1 h. CPG was filtered and washed with THF (350 mL×3) and CH$_3$CN (350 mL×3) and dried under vacuum overnight to give Aminopropyl-CPG- or Amino-nonyl-CPG-p-nitrophenyl carbamate. Loading: 130-201 μmol/g.

General procedure for CPG urea derivatives II: To an over dried 1 L RB flask cooled under vacuum and plugged with Argon. NH$_2$—(CH$_2$)$_n$—NH$_2$ or NH$_2$-(PEG)$_n$-NH$_2$ (20 equiv.) was dissolved in DCM (10 mL per g of CPG), and followed by Pyridine (1 ml per g of CPG) was added. Then immediately CPG-p-nitrophenyl carbamate was added to the reaction mixture and overhead shaker for overnight. Filtered and washed with MeOH (3×300 mL), and followed by DCM (3×300 mL), and solids (CPG-NH$_2$—CO—NH$_2$—(CH$_2$)$_n$—NH$_2$ or CPG-NH$_2$—CO—NH$_2$—(PEG)$_n$-NH$_2$) was taken into L RB flask and dried under vacuum overnight.

General Procedure for nucleoside loading III: To an over dried 500 mL RB flask cooled under vacuum and plugged with Argon. Then 5'-DMTr-2'-F-dU-3'-Triethylammonium-succinate (1 equiv.), and HBTU (2.5 equiv.) were added into the flask, and followed by CH$_3$CN (10 mL per g of CPG). To this suspension, DIPEA (5.0 equiv.) was added and immediately, CPG-NH$_2$—CO—NH$_2$—NH$_2$—(CH$_2$)$_n$—NH$_2$ or CPG-NH$_2$—CO—NH$_2$—(PEG)$_n$-NH$_2$ or Appropriate amino-linker added and mechanical wrist shaker for overnight. At this stage, small amount of CPG washed with DCM/MeOH and dried and checked CPG loading, it was 60-90 μm/g. Then CPG was filtered and washed with MeOH and DCM and solids were taken into 500 mL RB flask and dried under vacuum for around 4 h, and capped with Pyridine/Ac$_2$O (3:1) or heptanoic acid/Ac$_2$O (3:1) and followed by overhead shaker for 1-4 h. The CPG was filtered and washed with MeOH and DCM and dried under vacuum overnight to give a CPG-linker-Succinyl-Urea-2'-F-dU (Loading: 60-90 μmol/g).

Procedure for CPG solid support (3, Scheme 2): To make CPG support 3 (Scheme 2), as sequentially followed the following steps: general procedure for CPG-p-nitrophenyl carbamate I, then general procedure for CPG urea derivatives II, and again general procedure for CPG-p-nitrophenyl carbamate I, and general procedure for CPG urea derivatives II and finally general procedure for nucleoside loading III.

Procedure for CPG Solid supports (5,6,13,14): An amino functionalized support (Aminopropyl-CPG or amino-nonyl-CPG) (2 g), 12-dimethoxytritylhydroxy-dodecanoic acid (0.8 mmol), 4-dimethylaminopyridine (0.4 mmol), HBTU (2.4 mmol), triethylamine (0.4 mL), and pyridine (30 mL) were shaken at room temperature (16 h). The support was filtered off, washed, and dried. Linker loading was determined by trityl analysis. After deprotecting trityl group, nucleoside succinate was loaded following the above general procedure for nucleoside loading III.

Example supports and/or linkers can be utilized for preparation of compositions, including chirally controlled oligonucleotide compositions, of oligonucleotides of various, e.g., base sequences, modifications, patterns of backbone chiral centers, etc. For example, example supports and/or linkers were utilized to prepare chirally controlled oligonucleotide compositions with crude purities of over 50%, and in many cases, over 60% or 65%.

Example 3. Example Post-Cycle Modification and Cleavage/Deprotection Conditions In some embodiments, the present disclosure provides a variety of conditions for use in provided technologies to, e.g., to remove chiral auxiliaries, to de-protect blocked nucleobases, and to cleave oligonucleotide from support, etc. Example conditions are described herein. Those skilled in the art appreciate that other conditions may be utilized in accordance with the present disclosure.

AMA Condition (e.g., 1 μmol scale): After synthesis, the resin was treated with AMA (conc. NH$_3$-40% MeNH$_2$ (1:1, v/v)) (1 mL) for 45 min at 50° C. (if an oligonucleotide contains 2'F-nucleoside, 35° C. for 2 h can be beneficial and was typically used). Afterwards, in some embodiments, the mixture was cooled to room temperature and the resin was removed by membrane filtration (washed with H$_2$O for 2 mL). In some embodiments, the filtrate was concentrated under reduced pressure until it becomes about 1 mL. In some embodiments, the residue was diluted with 1 mL of H$_2$O and analyzed by RP-UPLC-MS.

TBAF Condition (e.g., SP-linker, 1 μmol scale): After synthesis, the resin was treated with 0.1 TBAF in MeCN (1 mL) for 2 h (generally, 30 min is enough) at room temperature, washed with MeCN, dried, and add conc. NH$_3$ (1 mL) for 12 h at 55° C. (which, among other things, may deprotect blocked nucleobases and cleave oligonucleotides from support). Afterwards, in some embodiments, the mixture was cooled to room temperature and the resin was removed by membrane filtration. In some embodiments, the filtrate was concentrated under reduced pressure until it becomes about 1 mL. In some embodiments, the residue was diluted with 1 mL of H$_2$O. In some embodiments, the crude product was optionally de-salted before analysis. In some embodiments, the crude product was analyzed by RP-UPLC-MS.

TEA-HF Condition (suc.-linker, 1 μmol scale): After synthesis, the resin was treated with 1 M TEA-HF in DMF-H$_2$O (3:1, v/v; 1 mL) for 2 h at 50° C. Support, e.g., PS5G, CPG, etc., was washed with MeCN, and H$_2$O and add AMA (conc. NH$_3$-40% MeNH$_2$ (1:1, v/v)) (1 mL) (which, among other things, may deprotect blocked nucleobases and cleave oligonucleotides from support) for 45 min at 50° C. (if oligonucleotide contains 2'F-nucleoside, 35° C. for 2 h can be beneficial). Afterwards, in some embodiments, the mixture was cooled to room temperature and the resin was removed by membrane filtration (washed with H$_2$O for 2 mL). In some embodiments, the filtrate was concentrated under reduced pressure until it becomes about 1 mL. In some embodiments, the residue was diluted with 1 mL of H$_2$O. In some embodiments, the crude product was optionally de-salted before analysis. In some embodiments, the crude product was analyzed by RP-UPLC-MS. In some embodiments, TEA-HF provided better yields and/or purities compared to other conditions when certain chiral auxiliaries were used.

In some embodiments, example post-cycle modification and/or cleavage/deprotection conditions are as described below:

| No. | 1$^{st}$ Treatment | 2$^{nd}$ Treatment | 3$^{rd}$ Treatment |
|---|---|---|---|
| 1 | Aq. MA, 40° C., 45 min | TEA•3HF, pH 5, 50° C., 2 h | N/A |
| 2 | Aq. MA, RT, 5 min | TEA•3HF, pH 5, 50° C., 1 h | Aq. MA, pH > 10, RT, 2 h, |

-continued

| No. | 1st Treatment | 2nd Treatment | 3rd Treatment |
|---|---|---|---|
| 3 | TEA•HF in DMF/H₂O, pH 6.7, 50° C., 1 h | a. Filtrate, AMA, pH > 10, RT, 2 h b. CPG, AMA, RT, 2 h | N/A |
| 4 | 1M KF in H₂O, 50° C., 1.5 h | CPG, AMA, RT, 2h | N/A |
| 5 | Conc. NH4OH, RT, 10 min | TEA•3HF, pH 5, 50° C., 1 h | AMA, pH > 10, RT, 2.5 h, overnight |
| 6 | a. Conc. NH4OH, RT, 10 min, b. To Filtrate, Aq. MA added | TEA•3HF, pH 5, 50° C., 1 h | AMA, pH > 10, RT, 2 h, overnight |
| 7 | AMA, RT, 2 h | TEA•3HF, pH 5, 50° C., 1 h, 1.5 h | N/A |
| 8 | AMA, RT, 15 min | TEA•3HF, pH 5, 50° C., 1 h | AMA, pH > 10, RT, 2 h, overnight |
| 9 | Conc. NH4OH, RT, overnight | TEA•3HF, pH 5, 50° C., 2 h | N/A |
| 10 | AMA (Aq. NH3/MA = 9/1, v/v), RT, overnight | TEA•3HF, pH 5, 50° C., 2 h | N/A |
| 11 | AMA (Aq. NH3/MA = 3/1, v/v), RT, overnight | TEA•3HF, pH 5, 50° C., 2 h | N/A |
| 12 | Aq. NH3/EtOH = 3/1, v/v, 40° C., overnight | TEA•3HF, pH 5, 50° C., 2 h | N/A |
| 13 | Conc. NH4OH, 40° C., overnight | TEA•3HF, pH 5, 50° C., 2 h | N/A |
| 14 | 1X Conc of TEA•HF, 5 h, RT | Conc. NH4OH, 35° C., 24 h | N/A |
| 15 | 2.5X Conc of TEA•HF, 5 h, RT | Conc. NH4OH, 35° C., 24 h | N/A |
| 16 | 5X Conc of TEA•HF, 5 h, RT | Conc. NH4OH, 35° C., 24 h | N/A |
| 17 | 1X Conc of TEA•HF, 5 h, RT | AMA, RT, 3-10 h | N/A |
| 18 | 1X Conc of TEA•HF, 5 h, RT | Aq. MeNH2, RT, 3-10 h | N/A |
| 19 | 1X Conc of TEA•HF/metal chelating agent, 5 h, RT | Conc. NH4OH, 35° C., 24 h | N/A |
| 20 | 2.5X Conc of TEA•HF/-metal chelating agent, 5 h, RT | Conc. NH4OH, 35° C., 24 h | N/A |
| 21 | 5X Conc of TEA•HF/metal chelating agent, 5 h, RT | Conc. NH4OH, 35° C., 24 h | N/A |
| 22 | 1X Conc of TEA•HF, 5 h, RT | AMA/metal chelating agent, RT, 3-10 h | N/A |
| 23 | 2.5X Conc of TEA•HF, 5 h, RT | Aq. MeNH2/metal chelating agent, RT, 2-3 h | N/A |
| 24 | 5X Conc of TEA•HF, 3-12 h, RT | Conc. NH4OH/-thiol, 9/1, v/v, 35° C., 24 h | N/A |
| 25 | 1X Conc of TEA•HF/EDTA, 5 h, RT | Conc. NH4OH, 35° C., 24 h | N/A |
| 26 | 2.5X Conc of TEA•HF/EDTA, 5 h, RT | Conc. NH4OH, 35° C., 24 h | N/A |
| 27 | 5X Conc of TEA•HF/EDTA, 5 h, RT | Conc. NH4OH, 35° C., 24 h | N/A |
| 28 | 1X Conc of TEA•HF, 5 h, RT | Conc. NH4OH/EDTA, 35° C., 24 h | N/A |
| 24 | 2.5X Conc of TEA•HF, 3-12 h, RT | Conc. NH4OH/EDTA, 35° C., 24 h | N/A |
| 25 | 5X Conc of TEA•HF, 3-5 h, RT | Conc. NH4OH/EDTA, 35° C., 24 h | N/A |
| 26 | TBAF, DMF or DMSO or ACN | Conc. NH4OH, 35° C., 24 h or AMA, RT, 3-8 h | N/A |
| 27 | Tetrabutylammonium difluorotriphenylsilicate, DMF or DMSO or ACN | Conc. NH4OH, 35° C., 24 h or AMA, RT, 3-8 h | N/A |
| 28 | Tetrabutylammonium difluorotriphenylsilicate/Acetic acid (1/1), DMF or DMSO or ACN | Conc. NH4OH, 35° C., 24 h or AMA, RT, 3-8 h | N/A |
| 29 | Tetrabutylammonium difluorotriphenylsilicate/Acetic acid (1/1), DMF or DMSO or ACN | Conc. NH4OH, 35° C., 24 h or AMA, RT, 3-8 h | N/A |
| 30 | Pyridine•HF, DMF or DMSO or ACN | Conc. NH4OH, 35° C., 24 h or AMA, RT, 3-8 h | N/A |
| 31 | 1M TEA•HF in DMF/Water, 50 deg C., 1-2.5 h | Conc. NH4OH, 40-55° C., 16-24 h | N/A |

In some embodiments, a metal chelating agent (metal chelator) is mercaptoethanol, 1-dodecanthiol, dithiothreitol (DTT), thiophenol, 1,2-diaminoethane,1,3-diaminopropane, 2,3-mercapto 1-propanesulfonic acid, 2,3-mercapto propane-1-ol, or meso 2,3-dimercapto succinic acid.

In some embodiments, post-cycle modification (e.g., a TBAF or TEA-HF condition, and cleavage/deprotection steps were performed in one pot. In some embodiments, a one-pot reaction generated a large amount of salts. In some embodiments, crude products of a one-pot process were first de-salted before analysis of crude oligonucleotide purity.

In some embodiments, a post-cycle modification, and/or cleavage/deprotection condition is or comprises an AMA condition. In some embodiments, a post-cycle modification, and/or cleavage/deprotection condition is or comprises a TBAF condition. In some embodiments, a post-cycle modification, and/or cleavage/deprotection condition is or comprises a TEA-HF condition. In some embodiments, a post-cycle modification, and/or cleavage/deprotection condition is or comprises a combination of an AMA condition, a TBAF condition, and/or a TEA-HF condition. As those skilled in the art appreciates, conditions for various steps, e.g., coupling, pre-modification capping, modification, post-modification capping, de-blocking, post-cycle modification, cleavage/deprotection, etc. can be each individually optimized, including adjusting example conditions provided in the present disclosure, in accordance with the present disclosure.

Among other things, the present disclosure provides compounds with diverse properties for use as chiral auxiliaries, and various deprotection conditions which can effectively remove certain types of chiral auxiliaries according to their properties while being compatible with the overall oligonucleotide preparation schemes, thereby providing enormous flexibility and options so that oligonucleotides can be prepared with desired yield, purity, and/or selectivity.

Example 4. Provided Technologies Deliver Greatly Improved Results

Among other things, the present disclosure provides technologies that can achieve greatly improved results, e.g., unexpectedly high crude purity and yield compared to an appropriate reference technology, e.g., one using capping steps as in traditional oligonucleotide synthesis based on phosphoramidite chemistry. Provided technologies were utilized to prepare oligonucleotide compositions, including chirally controlled oligonucleotide compositions, of oligonucleotides comprising various sequence lengths, base sequences, base modifications, sugar modifications, internucleotidic linkages (including natural phosphate linkages and modified internucleotidic linkages, including chirally controlled chiral modified internucleotidic linkages), patterns of modifications, patterns of back bone chiral centers, etc. Provided technologies can provide oligonucleotide compositions, particularly chirally controlled oligonucleotide composition, with high efficiency independently of base sequence, chemical modifications, stereochemistry, etc. The present example describes certain procedures and results from preparation of WV-3473.

Example runs using DPSE as chiral auxiliary for preparation of WV-3473, 5'-fU*SfC*SfA*SfA*SfG*SfG*SmAfA*SmGmA*SfU*SmGmGfC*SfA*SfU*SfU*SfU*SfC*Sf U -3' (SEQ ID NO: 2) (m: 2'-OMe, f: 2'-F; *: phosphorothioate linkage; *S: Sp phosphorothioate linkage; no * between bases represents natural phosphate linkage), which has a Molecular Weight of 6732.82 (free acid), and Extinction Coefficient ($M^{-1}$ $cm^{-1}$) of 204,500, were described below demonstrating various advantages of provided technologies, e.g., unexpectedly high crude purity and yield, increased flexibility with reaction conditions, etc. See also FIG. 5.

Example Cycles for Synthesis

| Batch | B6 | B19 | B56 | B110 |
|---|---|---|---|---|
| Process Step | Detritylation<br>Coupling<br>Pre-Cap B<br>Cap<br>Thiolation<br>N/A | Detritylation<br>Coupling<br>Pre-Cap B<br>N/A<br>Thiolation<br>Post-Thio-Cap | Detritylation<br>Coupling<br>Pre-Cap B<br>N/A<br>Thiolation<br>Post-Thio-Cap | Detritylation<br>Coupling<br>Pre-Cap B<br>N/A<br>Thiolation<br>Post-Thio-Cap |

In some embodiments, Detritylation is a de-blocking step. In some embodiments, coupling is a coupling step. In some embodiments, pre-Cap B is a pre-modification capping step, or uses conditions of a pre-modification capping step. In some embodiments, Cap is a post-modification capping step, or uses conditions of a post-modification capping step. In some embodiments, Thiolation is a modification step comprising sulfurization (thiolation). In some embodiments, Post-Thio-Cap is a post-modification capping step.

Example Conditions

| Process Step | Parameter | B6 | B19 | B56 | B110 |
|---|---|---|---|---|---|
| Synthesis Column and Synthesizer | Scale | 0.315 mmol | 0.315 mmol | 0.430 mmol | 0.396 mmol |
| | Solid Support | PS 5G | PS 5G | NittoPhase HL | CPG |
| | Support Loading | 149 μmol/g | 149 μmol/g | 205 μmol/g | 73 μmol/g |
| | Support density | 0.11 g/mL | 0.11 g/mL | 0.109 g/mL | 0.24 g/mL |
| | Column Diameter | 3.5 cm | 3.5 cm | 3.5 cm | 2.0 cm |
| | Column Volume | 19.2 mL | 19.2 mL | 19.2 mL | 22.0 mL |
| | Column Height | 2.0 cm | 2.0 cm | 2.0 cm | 7.0 cm |
| | Synthesizer | Akta100 | Akta100 | Akta100 | Akta100 |
| | Loop Volume | 8 mL | 8 mL | 8 mL | 8 mL |
| Pre-Synthesis Wash | Pre-Synthesis Wash Solvent | Acetonitrile | Acetonitrile | Acetonitrile | Acetonitrile |
| | Pre-Synthesis Wash Flow Rate | (424 cm/hr) | (424 cm/hr) | (424 cm/hr) | (424 cm/hr) |
| | Pre-Synthesis Wash Volume | 2 CV | 2 CV | 2 CV | 2 CV |
| UV Watch Command | Reagent | 3% DCA/toluene | 3% DCA/toluene | 3% DCA/toluene | 3% DCA/toluene |
| Detritylation | Control Mode | UV Watch Command | UV Watch Command | UV Watch Command | UV Watch Command |
| | Watch Command Wavelength | 436 nm | 436 nm | 436 nm | 436 nm |
| | UV Autozero | Autozero on 3% DCA in bypass prior to the 1st detrit. | Autozero on 3% DCA in bypass prior to the 1st detrit. | Autozero on 3% DCA in bypass prior to the 1st detrit. | Autozero on 3% DCA in bypass prior to the 1st detrit. |
| | Watch Command setting | 250 mAU | 250 mAU | 250 mAU | 500 mAU |
| | Watch Command Initiation | 1.2 CV | 1.2 CV | 1.2 CV | 1.2 CV |
| | Detrit Flow Rate | 220 and 260 cm/hr | 220 and 260 cm/hr | 300 cm/hr | 424 cm/hr |
| | ACN Wash after Detrit | (212 cm/hr) 2 CV (424 cm/hr) 2 CV | (212 cm/hr) 2 CV (424 cm/hr) 2 CV | (212 cm/hr) 2 CV (424 cm/hr) 2 CV | (212 cm/hr) 2 CV (424 cm/hr) 2 CV |
| Coupling | Stereo Amidite Eq | 4 eq. | 4 eq. | 4 eq. | 2.5 eq. |
| | Diluent for Stereo DPSE Amidite | Acetonitrile for 2'-F-A-L, 2'-F-C-L, 2'-F-G-L<br>20% IBN/80% ACN for 2'-F-U-L, 2'-OMe-A-L | | | |
| | Concentration of Stereo DPSE Amidite | 0.175M | 0.2M | 0.2M | 0.2M |
| | Stereo DNA-Activator | CMIMT | | | |
| | CMIMT Concentration | 0.6M | | | |
| | CMIMT Solvent | Acetonitrile | | | |
| | CMIMT Eq/Support | 20.60 | 28.00 | 28.00 | 15.25 |

-continued

| Process Step | Parameter | B6 | B19 | B56 | B110 |
|---|---|---|---|---|---|
| | CMIMT/DPSE Amidite Molar ratio | 5.2:1 | 7.0:1 | 7.0:1 | 6.1:1 |
| | % Volume of CMIMT Activator | 60% | 70% | 70% | 67% |
| | Standard Amidite Eq | 3.5 eq. | 3.5 eq. | 3.5 eq. | 2.5 eq. |
| | Standard Amidite Solvent | Acetonitrile | | | |
| | Standard Amidite Concentration | 0.175M | 0.2M | 0.2M | 0.2M |
| | Standard amidite-Activator | ETT | | | |
| | ETT Concentration | 0.6M | | | |
| | ETT Solvent | Acetonitrile | | | |
| | ETT Eq/Support | 18.0 eq. | 15.75 | 15.75 | 11.25 |
| | ETT:Standard Amidite Molar Ratio | 5.1:1 | 4.5:1 | 4.5:1 | 4.5:1 |
| | % Volume ETT Activator | 60% | | | |
| | Push Volume | Amidite/activator port-dependent to fully deliver coupling charge to recycle loop | | | |
| | Recycle Flow Rate | 300 cm/hr | 300 cm/hr | 300 cm/hr | 212 cm/hr |
| | Stereo DPSE amidite Recycle Time | 10 min | 15 min | 15 min | 10 min |
| | Standard amidite-Recycle Time | 8 min | | | |
| | Coupling ACN Wash Flow Rate (LFlow_AB) | 424 cm/hr | 424 cm/hr | 424 cm/hr | 424 cm/hr |
| | Coupling ACN Wash Volume | 2 CV | 2 CV | 2 CV | 2 CV |
| Pre-Cap B | Mode | Flow-Through | | | |
| | Reagent | 20%:30%:50% = $Ac_2O$:2,6-Lutidine:ACN (v/v/v) | | | |
| | Charge Volume | 1 CV | 2 CV | 2 CV | 1 CV |
| | Contact Time | 1.2 min | 2 min | 2 min | 4 min |
| | ACN Wash Volume | 1.2 CV | 1.2 CV | 1 CV | 2 CV |
| | ACN Wash Flow rate (LFlow_AB) | 424 cm/hr | | | |
| Cap | Mode | Flow-Through | | | |
| | Reagent | Cap A = 20%:80% = NMI:ACN (v/v) Cap B = 20%:30%:50% = $Ac_2O$:2,6-Lutidine:ACN (v/v/v) | | | |
| | Charge Volume (1:1 mix of Cap A & Cap B) | 1.2 CV | N/A | N/A | N/A |
| | Contact Time | 1.5 min | N/A | N/A | N/A |
| | ACN Push Flow Rate | Same As Capping Charge Flow Rate | N/A | N/A | N/A |
| | CV_CT_contactime | 1.3 CV | N/A | N/A | N/A |
| | ACN Push Flow Rate | 424 cm/hr | N/A | N/A | N/A |
| | ACN Wash Volume | 1.2 CV | N/A | N/A | N/A |
| Thiolation | Mode | Flow-Through | | | |
| | Reagent | POS in Acetonitrile | POS in Acetonitrile | POS in Acetonitrile | XH in Pyridine |
| | Concentration | 0.1M | 0.1M | 0.1M | 0.2M |
| | Eq Thio/Support | 12.2 eq. | 12.2 eq. | 12.2 eq. | 6.7 eq. |
| | Charge Volume | 2 CV | 2 CV | 2 CV | 0.6 CV |
| | Contact Time | 6 min | 6 min | 6 min | 6 min |
| | CV_CT_contactime | 1.3 CV | 1.3 CV | 1.3 CV | 1.3 CV |
| | ACN Wash Flow rate (LFlow_AB) | | 424 cm/hr | | 424 cm/hr |
| | ACN Wash Volume | | 2.0 CV | | 2.0 CV |
| Oxidation | Mode | Flow-Through | | | |
| | Ox Reagent | TBHP/Decane/DCM | TBHP/Decane/DCM | TBHP/Decane/DCM | Iodine/Water/Pyridine |
| | Concentration of Ox Solution | 1.1M | 1.1M | 1.1M | 0.05M |
| | Eq Ox/Support | 77 eq. | 77 eq. | 77 eq. | 3.5 eq. |
| | Contact Time | 2 min | 2 min | 2 min | 2 min |
| | ACN Push Volume | 1.3 CV | 1.3 CV | 1.3 CV | 1.3 CV |

-continued

| Process Step | Parameter | B6 | B19 | B56 | B110 |
|---|---|---|---|---|---|
| | ACN Wash Flow rate (LFlow_AB) | 424 cm/hr | 424 cm/hr | 424 cm/hr | 424 cm/hr |
| | ACN Wash Volume | 2.0 CV | 2.0 CV | 2.0 CV | 2.0 CV |
| Post Thio/Ox Cap | Mode | | Flow-Through | | |
| | | | Cap A = 20%:80% = NMI:ACN (v/v) | | |
| | | | Cap B = 20%:30%:50% = Ac$_2$O:2,6-Lutidine:ACN (v/v/v) | | |
| | Charge Volume (1:1 mix of Cap A & Cap B) | N/A | 0.5 CV | 0.5 CV | 0.4 CV |
| | Contact Time | N/A | 0.5 min | 0.5 min | 0.8 min |
| | ACN Push Flow Rate | N/A | Same As Capping Charge Flow Rate | Same As Capping Charge Flow Rate | Same As Capping Charge Flow Rate |
| | CV_CT_contactime | N/A | 1.3 CV | 1.3 CV | 1.3 CV |
| | ACN Wash Flow rate (LFlow AB) | N/A | 424 cm/hr | 424 cm/hr | 424 cm/hr |
| | ACN Wash Volume | N/A | 1.2 CV | 1.2 CV | 1.2 CV |
| Final Column Wash with ACN | Mode | | Flow Through | | |
| | ACN Wash Volume | 2 CV | 2 CV | 2 CV | 2 CV |
| | ACN Wash Flow rate (LFlow_AB) | 424 cm/hr | 424 cm/hr | 424 cm/hr | 424 cm/hr |

Example Post-Cycle Modification, Cleavage and Deprotection Conditions. Example 2 steps cleavage and deprotection process parameters were described in this section.

| Process Step | Parameter | Examples |
|---|---|---|
| Drying Solid Support with Nitrogen | Temperature | R.T. |
| | Argon Pressure | LT 30 psi |
| | Drying Time | NLT 30 min |
| 1M TEA-HF Treatment | Reaction Vessel | High pressure rated bottle |
| | Reagents | 1.0M TEA-HF in DMF/H$_2$O, 3/1, v/v |
| | Volume | 80 ± 5 mL/mmol |
| | Reaction Temp | 50 ± 2.5° C. |
| | Reaction Time | 2.0-2.5 hrs |
| | Solid Support Wash Solvent | WFI and ACN |
| | Wash Volume | WFI: 200-250 mL/mmol ACN: 200-250 mL/mmol |
| Cleavage and Deprotection | Vessel | High pressure rated bottle |
| | Reagent | Conc. NH$_4$OH (28-30%): Ethanol = 3/1, v/v |
| | Reagent Volume | 80 ± 5 mL/mmol |
| | Reaction Time | 16-18 hrs |
| | Reaction Temperature | 55 ± 2.5° C. |
| | Filtration | Bio-automation or Nalgene Filter |
| | Support Wash Solution | WFI |
| | Support Wash Volume | 200-350 mL/mmole |

1M TEA-HF (triethylamine hydrofluoride) in DMF/water removes DPSE auxiliary group from internucleotidic linkages of the stereodefined nucleotides. Crude material was released from the solid support with aqueous conc. ammonium hydroxide/ethanol under a heated condition.

For B110, which used a CPG support, a one-pot process was utilized.

Example Post-Cycle Modification, Cleavage and Deprotection Conditions

| Process Step | Parameter | Examples |
|---|---|---|
| Drying Solid Support with Nitrogen | Temperature | R.T. |
| | Argon Pressure | LT 30 psi |
| | Drying Time | NLT 30 min |
| C&D 1 | Reaction Vessel | High pressure rated bottle |
| | Reagents | (5X) TEA-HF in DMSO/H$_2$O, 5/1, v/v |
| | Volume | 100 ± 5 mL/mmol |
| | Reaction Temp | 27 ± 2.5° C. |
| | Reaction Time | 3.0-4.0 hrs |
| | Reaction Mixture | Ice Bath |
| | Cooling after C&D 1 | |
| | Cooling Time | NLT 30 min |
| C&D 2 | Vessel | High pressure rated bottle |
| | Mode | One Pot Reaction |
| | Reagent | Conc. NH$_4$OH (28-30%) |
| | Reagent Volume | 200 ± 10 mL/mmol |
| | Reaction Time | 24 ± 0.5 hrs |
| | Reaction Temperature | 35 ± 2.5° C. |
| | Filtration | Bio-automation or Nalgene Filter, 0.2 μm |
| | Support Wash Solution | WFI |
| | Support Wash Volume | 200-350 mL/mmole |

Example Recipe for 1M TEA.HF Solution in DMF/Water, 3/1, v/v

| Reagent | Solvents/Reagents | Volume (mL) | Total Volume (mL) |
|---|---|---|---|
| 1M TEA•HF in DMF/Water, 3/1, v/v | DMF | 64.3 | 100 |
| | Water | 21.4 | |
| | Triethylamine (TEA) | 9.0 | |
| | Triethylamine trihydrofluoride (TEA•3HF) | 5.3 | |

Recipe for 5× Solution of TEA.HF in DMSO/Water, 5/1, v/v

| Reagent | Solvents/Reagents | Volume (mL) | Total Volume (mL) |
|---|---|---|---|
| (5X) TEA•HF in DMSO/Water, 5/1, v/v | DMSO<br>Water<br>Triethylamine (TEA)<br>Triethylamine trihydrofluoride (TEA•3HF) | 55.0<br>11.0<br>9.0<br>25.0 | 100 |

Example Results

| Batch# | Solid Support | Crude Purity (% FLP) |
|---|---|---|
| B6 | PS 5G | 34.0 |
| B19 | PS 5G | 47.6 |
| B56 | NittoPhaseHL | 44.3 |
| B110 | CPG | 75.2 (59.0) |

Figure 2:
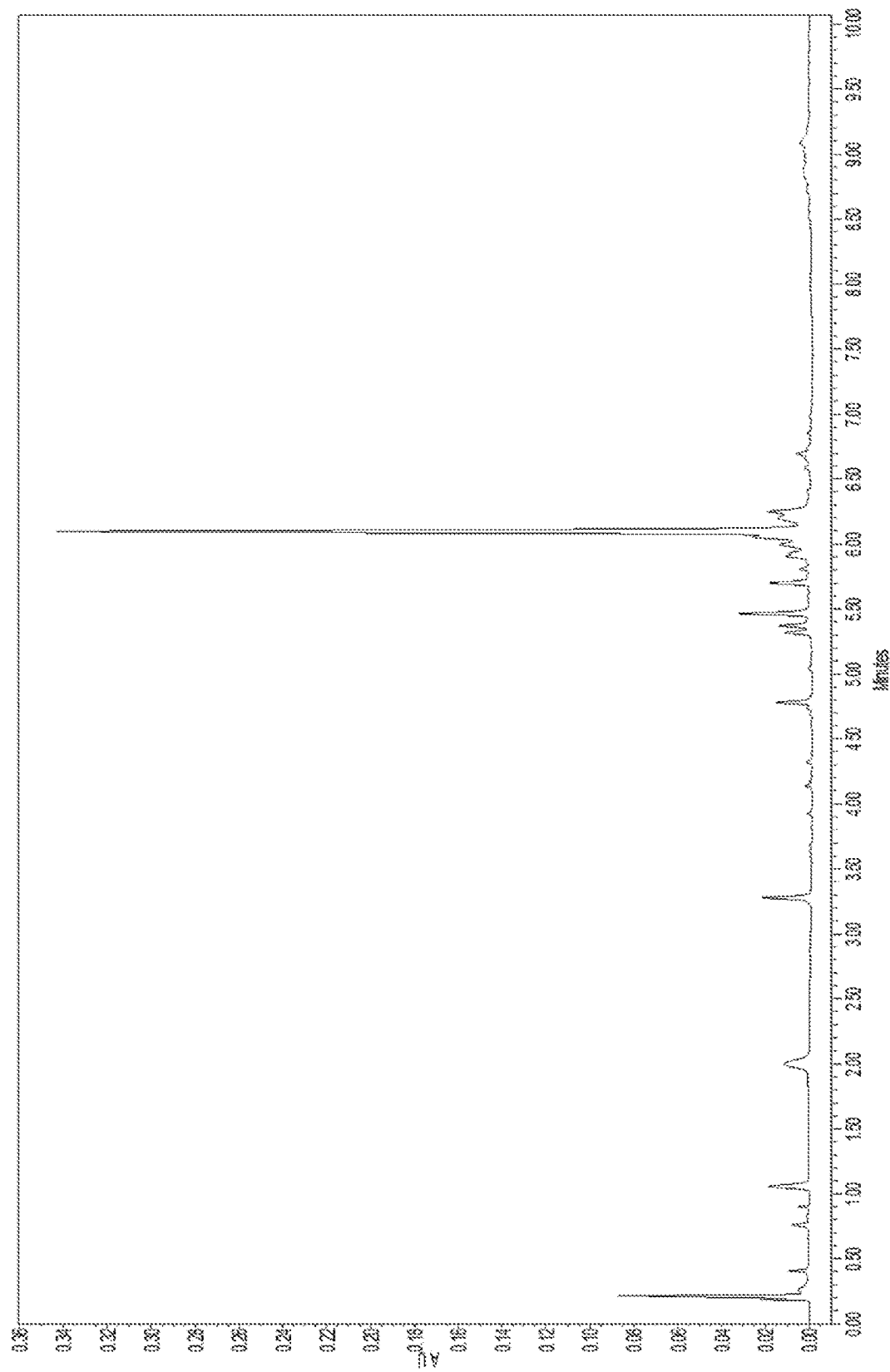
FIG. 2. Crude UPLC chromatogram for B19.
Figure 3:
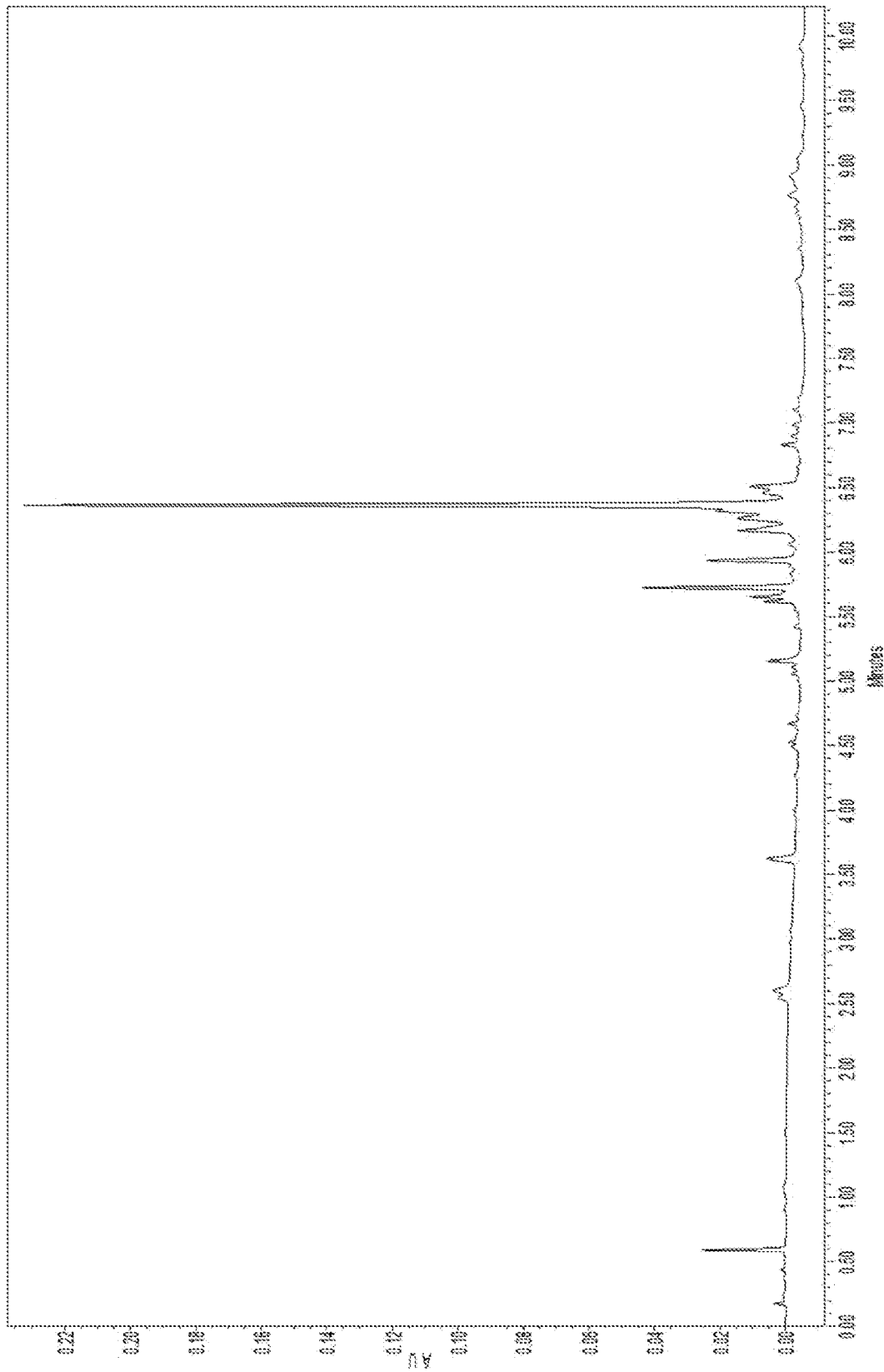
FIG. 3. Crude UPLC chromatogram for B56.
Figure 5:
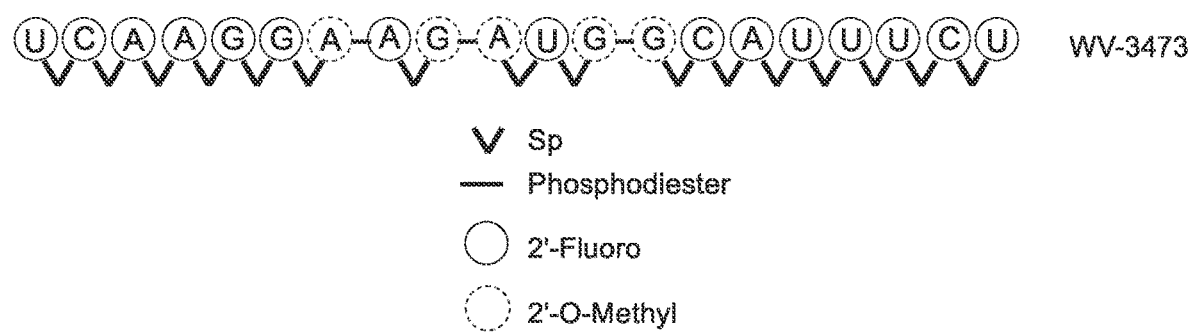
FIG. 5. WV-3473. Sp: Sp phosphorothioate linkage (acid form is —O—P(O)(SH)—(O)— wherein P is in Sp form); —: phosphodiester linkage (natural phosphate linkage, acid form is —O—P(O)(OH)—(O)—). WV-3473 sequence disclosed as SEQ ID NO: 2.

( ) indicates the purity of the crude sample as is injected into UPLC. 75.2% is after de-salting and before any other purification methods (e.g., NAP). Example results were depicted in FIGS. 1-4. An example NAP-10 used was as follows:

Excess storage solution was allowed to flow through the column;

Column was equilibrated with MILLIQ® water (3 mL×2);

25 OD in 1 mL water (~1 mg) was applied into the column;

Desalted oligonucleotide was eluted from the column with 1.5 mL of water;

Eluted oligonucleotide was injected into the UPLC to assess the crude purity.

An example UPLC analytical process was as follows. Applicant notes that retention time might shift due to running conditions, e.g., batches of buffers, gradients, sample compositions, etc.

A: 100 mM HFIP, 10 mM TEA in Water
B: 100% Acetonitrile
Flow rate: 0.8 mL/min
Temp: 55 degC
Column: Waters Acquity BEH C18 1.7 um 2.1×50 mm
Gradient: 3-13% in 10 min As demonstrated, provided technologies can, among other things, produce unexpectedly high crude purity and/or yield (e.g., 47.6% for B19, 44.3% for B56, and 75.2% (59%) for B110, compared to 34% for B6). Hundreds grams of therapeutic oligonucleotide agents were produced using provided technologies.

Those skilled in the art appreciate that described technologies (e.g., reagents, concentrations, conditions, solvents, etc.) may be adjusted to achieve improved results (e.g., yield, purify, etc.) For example, in some embodiments, XII may be utilized at a lower concentration than described above (e.g., less than 0.2 M). In some embodiments, XH was utilized at about 0.1 M. In some embodiments, XH was utilized at about 0.1 M in a solution comprising a base, e.g., a pyridine-acetonitrile solution (e.g., 1:1 v/v 0.2 M XH in pyridine and acetonitrile). In some embodiments, a lower concentration provides improved product yield and/or purity (e.g., in term of certain undesired product (e.g., by-product having a phosphate linkage in place of a desired phosphorothioate linkage), 1.5, 2, 3, 4, 5 or more fold of improvement). In some embodiments, a sulfurization reagent composition comprises less than or about 90%, 80%, 70%, 60%, 50%, 40%, 30%, 20%, 10% of a base, e.g., pyridine (v/v). In some embodiments, a thiolation process is very robust; for example, no additional drying step was necessary if fresh, anhydrous acetonitrile and pyridine were used directly from new bottles. In some embodiments, the contact time was kept at the same length, e.g., 6 minutes. In some embodiments, the total amount of solution may be increased to maintain the equivalents of a reagent, e.g., XII at a lower concentration. In some embodiments, oxidation was performed using iodine in pyridine/water, which is safer and provides increased purity and/or yield. In some embodiments, solid support, e.g., CPG, may be optimized; for example, in some embodiments, CPG with loading of first base at around e.g., 50-90, 60-70, 60-80, 60-90, 70-80, 70-90 umole/g etc., and/or bulk density of e.g., 0.1-0.3, 0.1-0.15, 0.1-0.2, 0.1-0.25, 0.15-0.2, 0.15-0.25, 0.15-0.3, 0.20-0.21, 0.20-0.22, 0.20-0.23, 0.20-0.24, 0.20-0.25, 0.20-0.26, 0.20-0.27, 0.20-0.28, 0.20-0.29, 0.20-0.30, 0.22-0.23, 0.22-0.24, 0.22-0.25, 0.22-0.26, 0.22-0.27, 0.22-0.28, 0.22-0.29, 0.22-0.30, 0.25-0.26, 0.25-0.27, 0.25-0.28, 0.25-0.29, 0.25-0.30, 0.26-0.27, 0.26-0.28, 0.26-0.29, 0.27-0.28, 0.27-0.29, 0.27-0.3, 0.28-0.29, 0.28-0.3, 0.29-0.3 cc/g etc.

Crude oligonucleotides, in some cases, were purified using various chromatography technologies, e.g., those described in US2015100197, U.S. Pat. Nos. 9,744,183, 9,605,019, 9,394,333, 8,859,755, US20130178612, U.S. Pat. Nos. 8,470,987, 8,822,671, US20150211006, US20170037399, WO2017/015555, WO2017/015575, WO2017/062862, etc.

Example 5. Provided Technologies can Provide Oligonucleotides with High Efficiency Among other things, provided technologies are particularly useful for highly efficient synthesis of oligonucleotides with high yields and/or purity, and optionally with precise control of chemistry and stereochemistry for each oligonucleotide. In some embodiments, the present disclosure provides methods for preparing collections of oligonucleotides in plate formats. Described below is an example procedure for oligonucleotide synthesis in parallel at scales useful for plate formats. In some embodiments, the present disclosure provides technologies for high-throughput preparation of oligonucleotides optionally with independent control of chemical modifications and stereochemistry of each oligonucleotide. Those skilled in the art appreciate that exact conditions, e.g., solvents, concentrations, reaction times, etc., may be further adjusted.

DPSE (for chirally controlled internucleotidic linkages) and cyanoethyl amidites (for stereorandom or phosphate internucleotidic linkages) were prepared at 0.1 M in isobutyronitrile, acetonitrile or combinations thereof. Typically isobutyronitrile was used. In some embodiments, a combination of isobutyronitrile and acetonitrile was utilized. In some embodiments, dichloromethane or tetrahydrofuran, e.g., at about 10%, 15%, 20%, etc., was utilized for certain amidites. 1 umol standard CPG columns were used. Other supports, e.g., Nittophase (e.g., NITTOPHASE® solid support, NITTOPHASE® HL solid support, etc.), Universal support, etc., can also be utilized. In some embodiments, plates of 96 1-umol columns were used for synthesis, wherein each column can be independently and optionally utilized to prepare a designed oligonucleotide with control of its structural elements as desired. In some embodiments, the synthesis was performed as DMT-on if C18 cartridge purification was to be used for purification. Example reagents used were:

Deblocking solution—3% trichloroacetic acid in dichloromethane

Activator 1—0.25M ETT in acetonitrile

Activator 2—0.5M CMIMT in acetonitrile

Cap A—tetrahydrofuran/2,6-lutidine/acetic anhydride (80/10/10)

Oxidation—0.02M iodine in THF/pyridine/$H_2O$ (70/20/10)

Thiolation reagent—0.2M xanthane hydride in pyridine

Cap B—16% n-methylimidazole in THF

A typical cycle was as follows:

Deblock; then Double coupling; then Cap A only; then Oxidation or Thiolation; then Cap A and B (typically 1:1)

All amidites were typically double coupled. Each coupling was 9.5 equivalents of amidite to growing chain. Activator 1 was typically used with cyanoethyl amidites. Activator 2 was typically used with DPSE amidites. The activator 1/cyanoethyl amidite ratio was typically 2.9. The activator 2/DPSE amidite ratio was typically 5.8. Coupling time ranges from approximately 2 to 6 minutes depending on the amidite.

After synthesis of the oligonucleotide chain, the first step of deprotection was typically a diethylamine wash: 400 uL of 20% DEA was added to each column and allowed to drain through over 5 min, then pulled completely through. The wash was repeated twice more for a total of 1200 uL and 15 min. The oligonucleotide/solid support was then washed with 5×200 uL of acetonitrile and dried by pulling vacuum. In some embodiments, a step utilizes reagents and/or conditions that keep 5'-protection groups on; for example, in some embodiments, a second step keeps DMT on. In some embodiments, provided technologies comprise additional bases. Those skilled in the art appreciate that conditions and/or reagents may be adjusted in view of types of support, 2'-modifications, 5'-protection (e.g., DMT) on or off, etc. in accordance with the present disclosure. In some embodiments, the second deprotection step was a treatment with DMF/water/TEA/TEA.3HF followed by ammonium hydroxide: Dimethylformamide/water/triethylamine/triethylamine-trihydrofluoride solution was prepared in the ratio: TEA.3HF 0.5 mL; TEA 0.877 mL; DMF 7.77 mL; and Water 1.55 mL. 250 uL of this fluoride solution was added to the solid support, e.g., CPG, and incubated at room temperature for a suitable period of time, e.g., 5 h. Then 375 uL of $NH_4OH$ was added directly and incubated 24 h at 35° C. The samples were filtered using a 96 well plate filter (PTFE 0.45 uM). They were then washed with 4×250 uL of water. The products were then optionally purified through cartridge purification and/or other purification methods. In some embodiments, DMT can be removed during one or more purification processes. Alternatively, 5'-protection groups, e.g., DMT, can be removed before purification (e.g., HPLC, UPLC, etc.).

Example 6. Provided Technologies Can Significantly Simplify Operations

Among other things, provided technologies can greatly improve operations particularly for large scale oligonucleotide synthesis. As those skilled in the art appreciate, transferring solid support from containers to containers for different steps can significantly lower efficiency and increase cost. In some embodiments, the present disclosure provides technologies for performing certain processes that are typically performed off-column in traditional oligonucleotide synthesis on-column, thereby improving efficiency and/or reducing cost. In some embodiments, the present disclosure provides technologies for on-column deprotection and/or cleavage. In some embodiments, provided technologies improve scalability. An example was described below.

On-Column Removal of Chiral Auxiliary.

In some embodiments, the present disclosure provides technologies for removing chiral auxiliaries on column. For example, in some embodiments, DPSE auxiliaries were removed on column. In some embodiments, a TEA-HF cocktail was charged into a reaction vessel (100 mL/mmole). The reaction vessel was connected to the column in an up flow orientation. A suitable pump was used to circulate the TEA-HF cocktail for 6+/−0.5 hours at a suitable temperature (in some embodiments, room temperature) to complete the removal of the DPSE chiral auxiliary. There can be some product cleaved from the support during this step at e.g., approximately 80%. Deprotection of the chiral auxiliary was typically complete after 6+/−0.5 hours. The TEA-HF cocktail was flushed from the column with a DMSO:Water (5:1) solution at a suitable amount, e.g., 1 cv, to remove the TEA-HF cocktail from the column, which step can prevent precipitation upon the addition of ammonium hydroxide in the next step. In some embodiments, the reaction and/or vessel were cooled, e.g., to 0° C.

On-Column Cleavage of Product from Support.

In some embodiments, the remaining product is cleaved from the support by treatment with ammonium hydroxide (200 mL/mmole) at room temperature for 30 minutes. The column is flushed with 1 cv of fresh ammonium hydroxide to complete recovery of product from the column. In some embodiments, product solution from the cleavage step were collected in a separate vessel different from the vessel containing the product solution of on-column removal of chiral auxiliaries.

Deprotection.

The ammonium hydroxide product solution was transferred with stirring to the TEA-HF product vessel. Temperature was increased and maintained at 37+/−2° C. for 24 hrs. In some embodiments, maintaining an increased temperature was crucial for complete removal of certain protecting groups, e.g., iBu on the exocyclic ring of a guanosine base. Applicant notes that the temperature cannot be too high. In some embodiments, it was observed that if the reaction temperature was high (e.g., 45° C.), the phosphate contents (instead of the desired phosphorothioate internucleotidic linkage) in the crude sample may increased.

Filtration.

The crude deprotected material was filtered with a 10 uM filter followed by a 0.45 uM filter. In some embodiments, a second filtration protects purification equipment (e.g., pumps, columns, etc.) and/or facilitates a purification process.

Example Recipe for Preparation of a 1× Solution of TEA.HF (1 L)

| Solvent/Reagents | Required Volume (mL) | Total Volume of Prep (mL) |
|---|---|---|
| DMSO | 777 ± 39 | 1000 |
| Water | 155 ± 7.8 | |
| Triethylamine (TEA) | 18 ± 0.9 | |
| Triethylamine trihydrofluoride (TEA•3HF) | 50 ± 2.5 | |

Example WV-3473 Cleavage and Deprotection Parameters

| Process Step | Parameter | PD campaign |
|---|---|---|
| Drying Solid Support with Nitrogen | Temperature | R.T. |
| | Nitrogen or Argon Pressure | LT 30 psi |
| | Drying Time | NLT 30 min |
| 1× TEA-HF Treatment (1st C&D) | Reaction Vessel | Appropriate for TEA-HF solution |
| | Reagents | 1.0 × TEA-HF in DMSO/H$_2$O, 5/1, v/v |
| | Volume | 100 ± 5 mL/mmol |
| | Reaction Temp | 27 ± 2.5° C. |
| | Flow rate | 400 cm/hr |
| | Reaction Time | 6 +/− 0.5 hrs |
| | Column Flush | DMSO:Water 5:1 |
| | Column Flush Volume | 1 cv |
| Cleavage from support On-Column | Vessel | Appropriate for TEA-HF/Ammonium Hydroxide solution |
| | Reagent | Conc. NH$_4$OH (28-30%) |
| | Reagent Volume | 200 ± 5 mL/mmol |
| | Reaction Time | 24 ± 1 hrs |
| | Reaction Temperature | 37 +/− 2° C. |
| | Column Flush | Ammonium hydroxide |
| | Column Flush Volume | 1 cv |
| Removal of Protecting groups | Vessel | Appropriate for TEA-HF/Ammonium Hydroxide solution |
| | Reagent | Conc. NH$_4$OH (28-30%) |
| | Reagent Volume | 200 ± 5 mL/mmol |
| | Reaction Time | 24 ± 1 hrs |
| | Reaction Temperature | 37 +/− 2° C. |
| Filtration | Course Filtration | 10-40 μm filter |
| | Fine Filtration | 0.45-0.2 μm filter |
| | Support Wash Solution | WFI |
| | Support Wash Volume | 200-350 mL/mmole |

Example 7. Oligonucleotide Products as Solids or Solutions

The present disclosure can provide oligonucleotide products in various forms. In some embodiments, products were provided as solid. In some embodiments, products were provided as solutions, e.g., in water, a salt solution, or a buffer.

In some embodiments, for example, a product, e.g., WV-3473 from Examples above, was lyophilized and packaged in, e.g., HDPE bottles. A drug product for administration may made by reconstituting the lyophilized solid in an appropriate vehicle (e.g., water, a salt solution, a saline, etc.) to a suitable target concentration.

In some embodiments, a product, e.g., WV-3473 from Examples above, were provided as a solution, typically of a high concentration compared to the concentration used for administration to a subject. Various solvent can be utilized in accordance with the present disclosure. For example, in some embodiments, a solvent is water (e.g., injection grade water). In some embodiments, a solvent is a salt solution, e.g., a saline solution which is used in drug formulation, injection, etc. In some embodiments, a solvent is a buffer, e.g., PBS, DPBS, etc. Before administration to a subject, a product can be reconstituted using an appropriate vehicle (e.g., water, a salt solution, a saline, etc.) to a suitable target concentration. In some embodiments, liquid formulations provide certain benefits, for example, in some embodiments, elimination of a lyophilization process and related operations provide high product purity and/or yield. In some embodiments, liquid formulation (liquid drug substance) simplifies drug product vialing steps, improves efficiency, and/or lowers cost.

Described below was a procedure using DPBS as a diafiltration (DF) buffer during the final DF step. As appreciated by those skilled in the art, various other solutions, e.g., salt solutions, buffers (e.g., PBS), etc., may be utilized. The oligonucleotide was WV-3473 which were a test oligonucleotide for various process chemistry technologies.

Certain Equipment, Raw Materials and Process Aids

| Equipment/Material | Description/Amount | Asset ID/Lot # | Vendor |
|---|---|---|---|
| Equipment | SARTOFLOW ® Smart TFF System (crossflow filtration system) | 100368-703-TFF-001 | Sartorius |
| Cassette | 2K SARTOCON ® CELL (slice microfiltration set) | 71146123 | Sartorius |
| Sample | WV-3473 Purified Pool | PD_1821020101_Pool | N/A |
| Water for Injection (WFI) | 20 L | 1959059 | Gibco |
| DPBS 1× | 6 L | 1967621 | Gibco |
| 500 mL Corning Storage bottle | 1 | 430282 | Corning |
| 150 mL Corning Storage bottle | 3 | 431175 | Corning |
| pH/Conductivity meter | Mettler-Toledo | 100317-204-PCM-001 | Mettler-Toledo |

DPBS 1× (No Calcium, No Magnesium) Media Formulation

| Components | MW | Conc (mg/L) | mM |
|---|---|---|---|
| Potassium Chloride (KCl) | 75.0 | 200.0 | 2.6666667 |
| Potassium Phosphate monobasic (KH$_2$PO$_4$) | 136.0 | 200.0 | 1.4705882 |
| Sodium Chloride (NaCl) | 58.0 | 8000.0 | 137.93103 |
| Sodium Phosphate dibasic (Na$_2$HPO$_4$—7H$_2$O) | 268.0 | 2160.0 | 8.059702 |

Example Ultrafiltration (UF)/DF Unit Operations Flow: Initial Concentration (UF) (Target 20 mg/mL), then 1st Diafiltration (DF) (Permeate cond: ≤1 mS/cm), then 2nd Diafiltration (DF) (DPBS, ≥10 DV, pH 7), then Final conc & Rinse (DPBS) (Target ≥36 mg/mL).

Initial Concentration of WV-3473 (UF)

2×0.1 M$^2$ 2K SARTOCON® Slice Cellulose membranes were installed on the SARTOFLOW® Smart TFF system and the unit cleaned with 0.5 N NaOH and WFI. The pooled sample from the purification step (13.8 L, 362,112 OD) in a 20 L LDPE bottle was then attached to the external peristaltic pump which was connected to the system.

Targeting a concentration of 600 OD/mL, the recirculation feed tank weight was set to 600 g (600 mL) using a WIRC2100 load cell module in the 'auto' mode. The permeate control valve was then fully opened by turning the knob counterclockwise. With a circulation pump setting of 30% and targeting a TMP of 2.5-3.0 bar, the retentate pressure control valve was carefully turned clockwise until PIR2600 recorded a value of 2.5-3.0 bar. With these settings, an initial permeate flowrate of up to 77 g/min was recorded. The initial ultrafiltration was then performed as summarized below:

Initial UF:

| Parameter | Set Point |
|---|---|
| Cassette | 2K SARTOCON ® CELL |
| Sample Amount | 362,112 OD |
| Cassette Area | 2 × 0.1M$^2$ |
| Sample Volume | 13,800 mL |
| Target UF Volume | 600 mL |
| Target UF concentration | 600 OD/mL |
| Circulation Pump Setting | 30% |
| TMP | 2.5-3.0 bar |
| Initial Permeate Flux | 77 mL/min |
| Final Permeate Flux | 60 mL/min |
| Retentate pH | 9.75 |
| Initial Permeate Cond | 103.1 mS/cm |

1st Diafiltration (DF) with Water: After the sample was concentrated to 600 mL, 600 OD/mL in the feed tank, the 20 L LDPE bottle was replaced with a 20 L bag of WFI and attached to the external peristaltic pump. Using the same conditions set above, diafiltration (DF) was performed until the permeate conductivity was ≤1000 μS/cm as summarized below:

| Parameter | Set Point |
|---|---|
| Cassette | 2K SARTOCON ® CELL |
| Sample Amount | 362,112 OD |
| Cassette Area | 2 × 0.1M$^2$ |
| Feed Tank Volume | 600 mL |
| Feed Tank concentration | 600 OD/mL |
| Circulation Pump Setting | 30% |
| TMP | 2.5-3.0 bar |
| Permeate Flux | 60-77 mL/min |
| Initial Retentate pH | 9.75 |
| Final Retentate pH | 8.65 |
| Initial Permeate Cond | 103.1 mS/cm |
| Final Permeate Cond | 866 μS/cm |

2$^{nd}$ Diafiltration (DF) with DPBS: Following DF as described above, the WFI bag was replaced with 6 L of DPBS and attached to the external peristaltic pump. Using the same conditions set above, the final diafiltration (DF) was performed using DPBS until 10 DVs had been exchanged. During this step, the pH dropped from 8.65 to 7.03. The final permeate conductivity measured was ≥13 mS/cm. An example set of parameters were summarized below:

| Parameter | Set Point |
|---|---|
| Cassette | 2K SARTOCON ® CELL |
| Sample Amount | 362,112 OD |
| Cassette Area | 2 × 0.1M$^2$ |
| Feed Tank Volume | 600 mL |
| Feed Tank concentration | 600 OD/mL |
| Circulation Pump Setting | 30% |
| TMP | 2.5-3.0 bar |
| Permeate Flux | 60-77 mL/min |
| Initial Retentate pH | 8.65 |
| Final Retentate pH | 7.03 |
| Initial Permeate Cond | 866 mS/cm |
| Final Permeate Cond | 13.65 μS/cm |

Final Concentration and Rinse: After the completion of the DPBS DF step, the external peristaltic pump was stopped by setting the WIRC2100 load cell module to the "off" mode. Keeping all the other parameters as described above, the sample was concentrated until the feed tank weight was 100 g (100 mL). The 1 retentate pressure control valve was then fully opened by turning the knob counterclockwise. The 1 permeate control valve was then fully closed by turning the knob clockwise. With a circulation pump setting of 70% the product was then drained into a 500 mL sterile Corning bottle. The feed tank was rinsed with 2×50 mL of DPBS and the rinsates drained into two separate 150 mL sterile Corning bottles. The ODs of the three bottles was then measured to determine the yield and recovery. The bulk product and the two rinses were then combined to obtain a product with a concentration of 1523 OD/mL. Example results were summarized below:

| Parameter | Set Point |
|---|---|
| Cassette | 2K SARTOCON ® CELL |
| Sample Amount | 362,112 OD |
| Cassette Area | 2 × 0.1M$^2$ |
| Initial Feed Tank Volume | 600 mL |
| Final Feed Tank Volume | 100 mL |
| Circulation Pump Setting | 70% |
| TMP | 0.0-3.5 bar |
| Bulk Volume | 140 mL |
| Bulk OD | 273,700 |
| Rinse 1 Volume | 50 |
| Rinse 1 OD | 55,050 |
| Rinse 2 Volume | 50 mL |
| Rinse 2 OD | 36,750 |
| Final Product conc. | 1523 OD/mL |

| Parameter | Set Point |
|---|---|
| Recovery | 365,500 |
| % Recovery | 100.9% |

Example 8. UF/DF of Crude Product

In some embodiments, provided technologies comprise removal of reagents, by-products, salts, etc. before one or more purification steps. In some embodiments, removal of such chemicals help to protect instruments, facilitate operations, improve efficiency and results, and/or lower cost. An example using UF/DF was described below.

Crude WV-3473 was filtered (0.22 uM) and stored at 2° C. In some embodiments, upon storage, precipitation occurs and the solution may turn into a turbid cloudy mixture, e.g., without the intention to be limited by any theory, due to salts, organic solvent, etc. that were in the crude solution. Typically, when a sample of the mixture was diluted with water (e.g., ×5), a clear solution was formed. The cloudy material can also be filtered (0.22 uM) resulting in a clear solution.

In one example procedure, a filtered crude material (600 mL, 61,200 OD) was diluted ×5 with water into a 5 L media bottle. Using a SARTOFLOW® Smart TFF system with a 0.1 $M^2$ 2K SARTOCON® Slice Cellulose membrane, example sample UF/DF parameters and data were summarized below:

| Parameter | PD Set Point |
|---|---|
| Cassette | 2K SARTOCON ® Slice Cassette Cellulose Membrane |
| Sample Amount | 61,200 OD |
| Cassette Area | 1 × 0.1$M^2$ |
| Sample Volume | 600 mL |
| Sample Vol after Dilution | 3000 mL |
| Target UF Volume | 200 mL |
| Target UF concentration | 300 OD/mL |
| DF Volume | NLT 7 DVs |
| Circulation Pump Setting | 30% |
| TMP | 3.0 bar |
| Permeate Flux | 45 mL/min |
| Initial Retentate pH | 11.5 |
| Final Retentate pH | 9.4 |
| Initial Retentate Cond | 3.1 mS/cm |
| Final Retentate Cond | 1.037 mS/cm |
| Recovery | 58,000 OD |
| % Recovery | 95% |
| Crude Purity before UF/DF | 60.1% |
| Crude Purity after UF/DF | 62.6% |

Example 9. Example Post-Synthesis Processes

Various technologies can be utilized to purify, formulate, etc., oligonucleotides. Described below are certain example processes useful for post-synthesis processing of oligonucleotides, including purification, UF/DF, lyophilization, etc. In some embodiments, provided technologies comprise anion exchange resin purification. In some embodiments, provided technologies comprise AEX purification. In some embodiments, AEX purification is performed on TSKgel SuperQ 5PW (20 μm) targeting a loading of 20 mg/mL using LEWA purification skid. In some embodiments, anion exchange resin provides improved purification purify and yield. In some embodiments, UF/DF was performed on the SARTO-FLOW® Advanced system while lyophilization was performed on the VirTis Lyo system. In some embodiments, an oligonucleotide, e.g., WV-3473, was prepared on CPG solid support at e.g., 1.26 mmol. As an example, in some embodiments, a preparation comprises solid phase synthesis (1.26 mmol), then desilylation (1× solution) (removal of DPSE auxiliary), then cleavage and deprotection (conc. $NH_4OH$), then purification (TSKgel SuperQ 5PW), then UF/DF (SARTOCON® 2K), then lyophilization (which can be optionally replaced with UF/DF if product oligonucleotides are to be provided as high concentration solutions, e.g., as described in Examples above).

Certain Abbreviations

| | |
|---|---|
| ACN | Acetonitrile |
| AEX | Anion Exchange Chromatography |
| C&D | Cleavage and Deprotection |
| cGMP | Current Good Manufacturing Practices |
| DNA | Deoxyribonucleic acid |
| DPSE | (S)-2-(methyldiphenylsilyl)-1-((S)-Pyrrolidin-2-yl)-ethan-1-ol |
| HDPE | High density polyethylene |
| LC/MS | Liquid chromatography/mass spectroscopy |
| MP | Mock Pool |
| MWCO | Molecular weight cut off |
| NA | Not applicable |
| NLT | Not less than |
| NMT | Not more than |
| OD | Optical Density |
| OP 400 | Oligo Pilot 400 Synthesizer |
| TFF | Tangential flow filtration |
| UF/DF | Ultrafiltration/Diafiltration |
| UPLC | Ultra-High Pressure Liquid Chromatography |
| UV | Ultra-violet |

Example Chromatography

Example TSKgel SuperQ 5PW (20 μm) Column Packing Conditions

Compression Factor: 1.20

Target≥10 Bar (150 psi) to pack the column

De-fine 2-3 times prior to packing

Slurry concentration prior to packing: 65-70%

Packing buffer: 20% Ethanol

Leave column under pressure (DAC mode) overnight for the bed to settle

At 20 mg/mL loading, precipitation is observed in neutralized fractions upon storage at 2 to 8° C.

Example Column Efficiency Testing

| Process Step | Parameter | PD Set Point | MFG Set Point |
|---|---|---|---|
| Equilibration | Flow Rate | 60 cm/hr | 60 cm/hr |
| | Temperature | Ambient | Ambient |
| | Equilibration Solution | 0.4M NaCl/Water | 0.4M NaCl/Water or 0.4M NaCl/15% EtOH |
| | Equilibration Volume | NLT 3 CV | NLT 3 CV |
| Injection | Injection Solution | 0.8M NaCl/Water | 0.8M NaCl/Water or 0.8M NaCl/15% EtOH/7% Acetone |
| | Injection Volume | 1-3% CV | 1-3% CV |

-continued

| Process Step | Parameter | PD Set Point | MFG Set Point |
|---|---|---|---|
| Elution | Elution Solution | 0.4M NaCl/Water | 0.4M NaCl/Water or 0.4M NaCl/15% EtOH |
|  | Elution Volume | NLT 1.5 CV | NLT 1.5 CV |
| Rinse | Rinse Volume | Water | Water |
|  | Rinse Solution | NLT 2 CV | NLT 2 CV |
| Storage | Storage Solution | 20% EtOH/Water | 20% EtOH/Water |
|  | Storage Volume | NLT 2 CV | NLT 2 CV |
| Acceptance Criteria | Asymmetry | 0.8-3.5 | 0.8-3.5 |

Example Chromatography Process Parameters

| Process Step | Parameter | PD Set Point | MFG Set Point |
|---|---|---|---|
| Crude Preparation | Temperature | Ambient | Ambient |
|  | Filtration | 0.2-1.2 μm Filter unit | 0.2-1.2 μm Filter unit |
|  | Crude Dilution with WFI | Dilute to Cond ≤ 12 mScm$^{-1}$ if required | Dilute to Cond ≤ 12 mScm$^{-1}$ if required |
| Chromatography Column | Scale | 0.4-1 mmol | 10 mmol |
|  | Media | TSKgel SuperQ 5PW | TSKgel SuperQ 5PW |
|  | Diameter | 2.5 cm | 10 cm |
|  | Bed Height | 30 ± 2 cm | 30 ± 2 cm |
|  | CV | Target 147.3 mL | Target 2.4 L |
|  | Loading Range (mg/mL) | 10 to 20 mg/mL | 10 to 20 mg/mL |
|  | Loading Range (OD/mL) | 300 to 600 OD/mL | 300 to 600 OD/mL |
|  | Column Temperature | Ambient | Ambient |
|  | Mobile Phase Eluent A | 20 mM NaOH | 20 mM NaOH |
|  | Eluent B | 20 mM NaOH + 2.5M NaCl | 20 mM NaOH + 2.5M NaCl |
|  | Eluent B Target Cond | 168 ± 5 mScm-1 | 168 ± 5 mScm-1 |
|  | CIP A Solution | 20 mM NaOH | 20 mM NaOH |
|  | CIP B Solution | 20 mM NaOH, 2.5M NaCl with 7% ACN | 20 mM NaOH, 2.5M NaCl with 7% ACN |
|  | SIP Solution | 0.5M NaOH | 0.5M NaOH |
| Column CIP/Sanitization | Rinse Solution | WFI | WFI |
|  | High pH Wash I (column wash) Composition | 100% SIP Solution | 100% SIP Solution |
|  | Volume | 1 CV | 1 CV |
|  | Flow Rate | 200 cm/hr | 200 cm/hr |
|  | Eluent B Equilibration (column wash) Composition | 100% CIP B Solution | 100% CIP B Solution |
|  | Volume | 2 CV | 2 CV |
|  | Flow Rate | 200 cm/hr | 200 cm/hr |
|  | Eluent A Equilibration (column wash) Composition | 100% Eluent A | 100% Eluent A |
|  | Volume | 1 CV | 1 CV |
|  | Flow Rate | 200 cm/r | 200 cm/r |
|  | A/B Gradient CIP Flow rate | 200 cm/hr | 200 cm/hr |
|  | Composition | 100% A --> 0% A; 0% B --> 100% B | 100% A --> 0% A; 0% B --> 100% B |
|  | Volume (CV) | 0.5 | 0.5 |
|  | Composition | 0% A; 100% B (Isocratic hold) | 0% A; 100% B (Isocratic hold) |
|  | Volume (CV) | 0.4 | 0.4 |
|  | Composition | 0% A --> 100% A; 100% B --> 0% B | 0% A --> 100% A; 100% B --> 0% B |
|  | Volume (CV) | 0.1 | 0.1 |
|  | Composition | 100% A; 0% B (Isocratic hold) | 100% A; 0% B (Isocratic hold) |
|  | Volume (CV) | 0.5 | 0.5 |
|  | Composition | 100% A --> 0% A; 0% B --> 100% B | 100% A --> 0% A; 0% B --> 100% B |
|  | Volume (CV) | 0.5 | 0.5 |
|  | Composition | 0% A; 100% B (Isocratic hold) | 0% A; 100% B (Isocratic hold) |
|  | Volume (CV) | 0.4 | 0.4 |
|  | Composition | 0% A --> 100% A; 100% B --> 0% B | 0% A --> 100% A; 100% B --> 0% B |
|  | Volume (CV) | 0.1 | 0.1 |
|  | Composition | 100% A; 0% B (Isocratic hold) | 100% A; 0% B (Isocratic hold) |
|  | Volume (CV) | 0.5 | 0.5 |
|  | Composition | 100% A --> 0% A; 0% B --> 100% B | 100% A --> 0% A; 0% B --> 100% B |
|  | Volume (CV) | 0.5 | 0.5 |
| Column CIP/Sanitization | Composition | 0% A; 100% B (Isocratic hold) | 0% A; 100% B (Isocratic hold) |
|  | Volume (CV) | 0.4 | 0.4 |
|  | Composition | 0% A --> 100% A; 100% B --> 0% B | 0% A --> 100% A; 100% B --> 0% B |

-continued

| Process Step | Parameter | | PD Set Point | |
|---|---|---|---|---|
| | | Volume (CV) | 0.1 | 0.1 |
| | | Composition | 100% A; 0% B (Isocratic hold) | 100% A; 0% B (Isocratic hold) |
| | | Volume (CV) | 0.5 | 0.5 |
| | | Composition | 100% A --> 0% A; 0% B --> 100% B | 100% A --> 0% A; 0% B --> 100% B |
| | | Volume (CV) | 0.5 | 0.5 |
| | | Composition | 0% A; 100% B (Isocratic hold) | 0% A; 100% B (Isocratic hold) |
| | | Volume (CV) | 0.4 | 0.4 |
| | High pH Wash (Column Sanitization) | Composition | 100% SIP Solution | 100% SIP Solution |
| | | Volume | 0.6 CV | 0.6 CV |
| | | Flow Rate | 115 cm/hr | 115 cm/hr |
| | High pH Wash (Column Sanitization) | Composition | 100% SIP Solution | 100% SIP Solution |
| | | Volume | 0.4 CV | 0.4 CV |
| | | Flow Rate | 200 cm/hr | 200 cm/hr |
| | High pH Wash (Column Sanitization) | Composition | 100% SIP Solution | 100% SIP Solution |
| | | Volume | 0.5 CV | 0.5 CV |
| | | Flow Rate | 200 cm/hr | 200 cm/hr |
| | High pH Hold | Hold time | NLT 60 min | NLT 60 min |
| | Water Wash (Column Sanitization) | Composition | 100% Water | 100% Water |
| | | Volume | NLT 4.5 CV or until pH ≤ 9 | NLT 4.5 CV or until pH ≤ 9 |
| | | Flow Rate | 200 cm/hr | 200 cm/hr |
| | Water Sampling (Column Sanitization) | Composition | 100% Water | 100% Water |
| | | Volume | 1.3 CV | 1.3 CV |
| | | Flow Rate | NLT 40 cm/hr | NLT 40 cm/hr |
| | QC Testing | Endotoxin | <0.25 EU/mL | <0.25 EU/mL |
| | | UV | <0.05 AU | <0.05 AU |
| Pre-Load/ Equilibration | A Wash 1 | Composition | 200 cm/hr | 200 cm/hr |
| | | Volume | NLT 2 CV | NLT 2 CV |
| | | Flow rate | 200 cm/hr | 200 cm/hr |
| | B Wash | Composition | N/A | N/A |
| | | Volume | N/A | N/A |
| | | Flow Rate | N/A | N/A |
| | A Wash 2 | Composition | N/A | N/A |
| | | Volume | N/A | N/A |
| | | Flow Rate | N/A | N/A |
| Loading/Post-Load Washes | Sample Loading | Composition | N/A | N/A |
| | | Temperature | Ambient | Ambient |
| | | Flow Rate | 200 cm/hr | 200 cm/hr |
| | Post Loading Wash/Re-equilibration | Composition | 100% Eluent A | 100% Eluent A |
| | | Volume | NLT 2 CV | NLT 2 CV |
| | | Flow Rate | 200 cm/hr | 200 cm/hr |
| Gradient Elution | Mixing loop through bypass | Equilibration | N/A | N/A |
| | | Isocratic Step | N/A | N/A |
| | | Isocratic Step Volume | N/A | N/A |
| | | Gradient Start Point | 0% B | 0% B |
| | | Conductivity Start | TBA | TBA |
| | | Gradient 1 End Point | 25% B | 25% B |
| | | Conductivity End | TBA | TBA |
| | | Gradient 1 Duration | 5 CV (0-25%) | 5 CV (0-25%) |
| | | Isocratic Hold | 25% B | 25% B |
| | | Isocratic Hold Volume | 1 CV | 1 CV |
| | | Gradient 2 Start Point | 25% | 25% |
| | | Conductivity Start | TBA | TBA |
| | | Gradient 2 End Point | 90% B | 90% B |
| | | Conductivity End | TBA | TBA |
| | | Gradient 2 Duration | 15 CV (25-90%) | 15 CV (25-90%) |
| | | Flow Rate | 200 cm/hr | 200 cm/hr |
| | | Fractionation UV watch 280 nm | ≥1000 mAU | ≥1000 mAU |
| | | Fraction Size | Target 20% CV | Target 20% CV |
| | | Fraction Volume | 30 mL | 500 mL |
| | Fraction Neutralization & Storage | Reagent | 2M sodium phosphate monobasic buffer | 2M sodium phosphate monobasic buffer |
| | | Volume | NLT 10 µL per 1 mL of Fraction | NLT 10 µL per 1 mL of Fraction |
| | | Target pH | 7.0-8.0 | 7.0-8.0 |
| | | Estimated Frac Concentration | N/A | |
| | | Estimated # of Fracs | N/A | |
| | | Frac Storage Conditions | 2-8° C. | 2-8° C. |

-continued

| Process Step | Parameter | PD Set Point | |
|---|---|---|---|
| Post-Elution Wash & Column Equilibration | Wash B Composition | 100% Solution B | 100% Solution B |
| | Wash B Volume | NLT 3 CV | NLT 3 CV |
| | Flow Rate | 200 cm/hr | 200 cm/hr |
| | Wash A Composition | 100% Solution A | 100% Solution A |
| | Wash A Volume | NLT 3 CV | NLT 3 CV |
| Expected Recovery | FLP Recovery | ≥80% | ≥80% |
| Expected Pool Purity | % FLP | ≥85% | ≥85% |

Ultrafiltration (UF)/Diafiltration (DF)

UF/DF Process Parameters. In some embodiments, membranes can be re-used if they pass reuse tests.

| Process Step | Parameter | PD Set Point | MFG Set Point |
|---|---|---|---|
| Setup | Cassette | SARTOCON ® Slice Cassette Cellulose Membrane | SARTOCON ® Slice Cassette Cellulose Membrane |
| | Scale | 0.5-2.0 mmol | 10 mmol |
| | Cassette Area | 2 × 0.1M$^2$ | 1 × 0.6M$^2$ |
| | CIP Solution | 100% HPW or WFI | 100% HPW or WFI |
| | CIP Circulation Pump Setting | 30-70% | 30-70% |
| | CIP Solution | 100% WFI | 100% WFI |
| | CIP Volume | NLT 2 L | NLT 4 |
| | SIP Solution | 0.5N NaOH | 0.5N NaOH |
| | SIP Circulation Pump Setting | 30-70% | 30-70% |
| | SIP Solution | 0.5N NaOH | 0.5N NaOH |
| | SIP Volume | NLT 2 L | NLT 4 L |
| | SIP Hold Time | NLT 60 min | NLT 60 min |
| | Membrane Rinse Solution | 100% HPW or WFI | 100% HPW or WFI |
| | Membrane Rinse End Point | Permeate Cond. ≤ 1.0 mS/cm | Permeate Cond. ≤ 1.0 mS/cm |
| | Membrane Rinse End Point | Permeate pH 5-7 | Permeate pH 5-7 |
| Acceptance Criteria | Endotoxin | <0.25 EU/mL | <0.25 EU/mL |
| | UV | ≤0.050 AU | ≤0.050 AU |
| Membrane Conditioning | Membrane Conditioning Solution | 25 mM HCl | 25 mM HCl |
| | Membrane Conditioning End Point | Permeate pH 2-4 | Permeate pH 2-4 |
| Membrane Wash | Membrane Wash Solution | 100% HPW or WFI | 100% HPW or WFI |
| | Membrane Wash Volume | NLT 2 L | NLT 10 L |
| Pool Neutralization | Reagent | 0.1M HCl and 0.1N NaOH | 0.1M HCl and 0.1N NaOH |
| | pH | 6.7-7.3 | 6.7-7.3 |
| Initial Concentration | Target Concentration | NMT 600 OD/mL | NMT 600 OD/mL |
| | Target Volume | 200-100 mL | Calculate in MBR |
| | Circulation Pump Setting | 30-70% | 30-70% |
| | Target TMP | Target 1.5-3.5 bar | Target 1.5-3.5 bar |
| Salt Exchange | Diafiltration Solution | | |
| | Number of Exchanges | | |
| | Permeate Conductivity Post-Diafiltration | | |
| Diafiltration | Diafiltration Solution | WFI | WFI |
| | Number of Exchanges | NLT 7 | NLT 7 |
| | Target TMP | 1.5-3.5 bar | 1.5-3.5 bar |
| | Circulation Pump Setting | 30-70% | 30-70% |
| | Target TMP | 1.5-3.5 bar | 1.5-3.5 bar |
| | Conductivity before final pH verification | NMT 1000 μScm$^{-1}$ | NMT 1000 μScm−1 |
| | Final pH Verification (Retentate) | 0.1M HCl if needed. 0.1N NaOH only if pH ≤ 6.7 | 0.1M HCl if needed. 0.1N NaOH only if pH ≤ 6.7 |
| | Post-Diafiltration Permeate Conductivity | NMT 50 μS/cm | NMT 50 μS/cm |
| Final Concentration | Target Concentration | NLT 1500 OD/mL unless limited by system capacity | NLT 1500 OD/mL unless limited by system capacity (contact managment) |
| | Target Volume | Calculate based on Yield | Calculate in MBR |

-continued

| Process Step | Parameter | PD Set Point | MFG Set Point |
|---|---|---|---|
| | Final retentate pH | 6.7-7.3 | 6.7-7.3 |
| | Circulation Pump Setting | 30-70%. | 30-70% |
| | Target TMP | 1.5-3.5 bar | 1.5-3.5 bar |
| Retentate Recovery | Water for Rinse | 25-30 mL | 250-500 mL |
| | Target Water Rinses 3-6 | Recirculate for 5 min each | Recirculate for 5 min each |
| Cassette Storage | Storage Wash | Purified water to NMT 0.050 OD/mL | Purified water to NMT 0.050 OD/mL |
| | Storage Wash | 0.1N NaOH | 0.1N NaOH |
| Storage Conditions | Storage Temperature | 2-8° C. | 2-8 ° C. |
| Expected Recovery | OD Recovery | >95% | >95% |

Freeze Drying

Example Freeze Drying Parameters

| | | | PD Set Point | | |
|---|---|---|---|---|---|
| # | Operation | | Temp. (° C.) | Pressure (mTorr) | Time (min) |
| 1 | Loading | Loading shelf temp. | R.T. | atm | |
| 2 | Freezing | Shelf temp. | −40 | | 120 |
| 3 | Evacuation | Shelf temp. | −40 | 400 | 30 |
| 4 | Primary Drying | Shelf temp. | −10 | 300 | 480 |
| 5 | Primary Drying | Shelf temp. | −5 | 300 | 480 |
| 6 | Primary Drying | Shelf temp. | 0 | 300 | 480 |
| 7 | Primary Drying | Shelf temp. | 10 | 300 | 480 |
| 8 | Primary Drying | Shelf temp. | 20 | 300 | 480 |
| 9 | Primary Drying | Shelf temp. | 25 | 300 | 480 |
| 10 | Secondary Drying | Shelf temp. | 25 | 100 | 480 |
| 11 | Aeration | Gas type Dry N$_2$ | 25 | atm | — |
| 12 | Unloading | Shelf temp. | R.T. | atm | — |

EQUIVALENTS

Having described some illustrative embodiments of the disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the following claims, the means are not intended to be limited to the means disclosed herein for performing the recited function, but are intended to cover in scope any means, known now or later developed, for performing the recited function.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present disclosure is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method for preparing an oligonucleotide, comprising one or more cycles, each of which independently comprises the following steps:
   (1) coupling;
   (2) a pre-modification capping;
   (3) a modification step;
   (4) a post-modification capping; and
   (5) de-blocking;
   wherein the capping condition of each pre-modification capping step after a coupling step and before the next modification step is independently selective or specific for amidation over esterification.

2. The method of claim 1, wherein each pre-modification capping step after a coupling step and before the next modification step independently comprises no strong nucleophile, or if it comprises one or more strong nucleophiles, the level of each of the one or more strong nucleophiles is independently no more than about 0.1, equivalent relative to the first incorporated nucleoside of the oligonucleotide.

3. The method of claim 1, wherein each pre-modification capping step after a coupling step and before the next modification step independently comprises no esterification catalyst, or if it comprises one or more esterification catalysts, the level of each of the one or more esterification catalysts is independently no more than about 0.01, 0.02, 0.05, 0.1, 0.2, 0.5, or 1 equivalent relative to the first incorporated nucleoside of the oligonucleotide.

4. The method of claim 1, wherein each coupling step independently forms an internucleotidic linkage of formula VII-b:

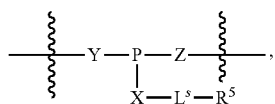

or a salt form thereof, wherein:
   each of $R^1$ and $R^5$ is independently —H, -$L^s$-R, halogen, —CN, —$NO_2$, -$L^s$-Si(R)$_3$, —OR, —SR, or —N(R)$_2$;
   each of X, Y and Z is independently —O—, —S—, —N(-$L^s$-$R^1$)—, or $L^s$;
   each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
   each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
   each Cy$^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
   each R' is independently —R, —C(O)R, —C(O)OR, or —S(O)$_2$R;
   each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

5. The method of claim 4, wherein a pre-modification capping step comprises utilization of a pre-modification capping reagent system which comprises an acylating agent and a base.

6. The method of claim 5, wherein a pre-modification capping reagent system comprises an acylating agent, wherein the acylating agent is of formula R'—C(O)-$L^s$-$R^s$, wherein:

each $R^s$ is independently —H, halogen, —CN, —$N_3$, —NO, —$NO_2$, -$L^s$-R', -$L^s$-Si(R)$_3$, -$L^s$-OR', -$L^s$-SR', -$L^s$-N(R')$_2$, —O-$L^s$-R', —O-$L^s$-Si(R)$_3$, —O-$L^s$-OR', —O-$L^s$-SR', or —O-$L^s$-N(R')$_2$;

each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

7. The method of claim 6, wherein a base is of formula N(R)$_3$, wherein the nitrogen atom has no alpha-substitution, wherein:

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

8. The method of claim 7, wherein a pre-modification capping reagent system is a solution of 2,6-Lutidine/Ac$_2$O.

9. The method of claim 5, comprising a modification step which comprises modifying an internucleotidic linkage formed in the immediate preceding coupling step.

10. The method of claim 4, wherein a modification step comprises modifying an internucleotidic linkage of formula VII-b or a salt form thereof to provide an internucleotidic linkage of formula VII:

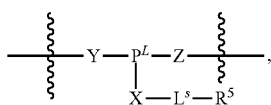

or a salt form thereof, wherein:
P$^L$ is P(=W) or P→B(R')$_3$;
W is O, S or Se;
each of R$^1$ and R$^5$ is independently —H, -L$^s$-R, halogen, —CN, —NO$_2$, -L$^s$-Si(R)$_3$, —OR, —SR, or —N(R)$_2$;
each of X, Y and Z is independently —O—, —S—, —N(-L$^s$-R$^1$)—, or L$^s$;
each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms independently selected from oxygen, nitrogen, sulfur, phosphorus and silicon, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O) O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —C(O)OR, or —S(O)$_2$R;
each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

11. The method of claim 4, wherein a modification step comprises sulfurization, which sulfurization comprises converting a —P(-)— linkage phosphorus atom in an internucleotidic linkage of formula VII-b or a salt form thereof into —P(=S)(-)—.

12. The method of claim 11, wherein a modification reagent system is a sulfurization reagent system comprising one or more sulfurization reagent, wherein a sulfurization reagent system comprises a sulfurization reagent selected from POS (3-phenyl-1,2,4-dithiazolin-5-one), DDTT (((dimethylamino-methylidene)amino)-3H-1,2,4-dithiazaoline-3-thione), DTD (dimethylthiarum disulfide), xanthane hydride (XH), S-(2-cyanoethyl) methanesulfonothioate (MTS-CNE), or phenylacetyl disulfide.

13. The method of claim 11, comprising a post-modification capping step which caps a plurality of hydroxyl groups.

14. The method of claim 13, wherein a post-modification capping reagent system is a solution of 2,6-Lutidine/NMI/Ac$_2$O.

15. The method of claim 13, comprising a de-blocking step, wherein a de-blocking reagent system comprises a de-blocking reagent, wherein the de-blocking reagent is an acid.

16. The method of claim 15, comprising a cleavage/deprotection step that comprises:
contacting a plurality of oligonucleotides with one or more cleavage/deprotection reagent systems;
wherein the cleavage/deprotection step provides a final product composition comprising a plurality of final product oligonucleotides.

17. The method of claim 16, wherein a final product composition comprising a plurality of final product oligonucleotides is a chirally controlled oligonucleotide composition wherein:
   oligonucleotides of the plurality share the same constitution; and
   oligonucleotides of the plurality comprise at least one chirally controlled internucleotidic linkage, which internucleotidic linkage is chirally controlled in that oligonucleotides of the plurality share the same stereochemical configuration at the chiral linkage phosphorus of the internucleotidic linkage;
   wherein at least $((DS)^{Nc}*100)\%$ of all oligonucleotides sharing the same base sequence in the final product composition are oligonucleotides of the plurality, wherein DS is at least 80%, 85%, 90%, 91%, 92%, 93%, 94%, 95%, 96%, 97%, 98% or 99%, and Nc is the number of chirally controlled internucleotidic linkage.

18. The method of claim 17, wherein the method provides a final product composition with at least 40%, 45%, 50%, 55%, 60%, 65%, 70% or 75% crude purity, wherein the crude purity is % full-length product.

19. The method of claim 4, wherein —X-$L^s$-$R^5$ is of such a structure that H—X-$L^s$-$R^5$ is a compound of formula I-a:

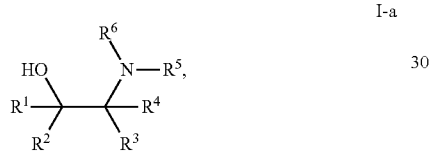

I-a or a salt thereof, wherein:
   each of $R^1$ and $R^2$ is independently —H, -$L^s$-R, halogen, —CN, —NO$_2$, -$L^s$-Si(R)$_3$, —OR, —SR, or —N(R)$_2$;
   $R^3$ is —H;
   $R^4$ and $R^5$ are taken together with their intervening atoms to form an optionally substituted 3-20 membered heterocyclyl ring having 1-5 heteroatoms;
   $R^6$ is —H;
   each $L^s$ is independently a covalent bond, or a bivalent, optionally substituted, linear or branched group selected from a $C_{1-30}$ aliphatic group and a $C_{1-30}$ heteroaliphatic group having 1-10 heteroatoms, wherein one or more methylene units are optionally and independently replaced by an optionally substituted group selected from $C_{1-6}$ alkylene, $C_{1-6}$ alkenylene, —C≡C—, a bivalent $C_1$-$C_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with $Cy^L$;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each $Cy^L$ is independently an optionally substituted tetravalent group selected from a $C_{3-20}$ cycloaliphatic ring, a $C_{6-20}$ aryl ring, a 5-20 membered heteroaryl ring having 1-10 heteroatoms, and a 3-20 membered heterocyclyl ring having 1-10 heteroatoms;

each R' is independently —R, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

20. The method of claim 19, wherein $R^1$ is —H and $R^2$ is —CH$_2$—Si(R)$_3$ wherein each R of —Si(R)$_3$ is independently not —H.

21. The method of claim 20, wherein H—X-$L^s$-$R^5$ is

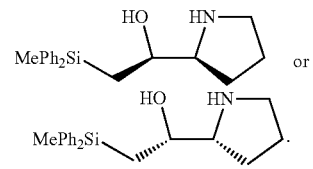

22. The method of claim 19, wherein a modification step comprises modifying an internucleotidic linkage to provide an internucleotidic linkage of formula VII:

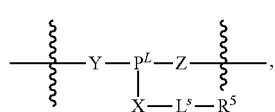

VII or a salt form thereof, wherein:
   $P^L$ is P(=W) or P→B(R')$_3$;
   W is O, S or Se;
   each of Y and Z is independently —O—, —S—, —N(-$L^s$-$R^1$)—, or $L^s$;

—X-L$^s$-R$^5$ is of such a structure that H—X-L$^s$-R$^5$ is a compound of formula I-a:

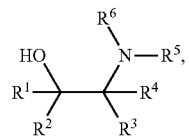

I-a or a salt thereof, wherein:
wherein:
   each of R$^1$ and R$^2$ is independently —H, -L$^s$-R, halogen, —CN, —NO$_2$, -L$^s$-Si(R)$_3$, —OR, —SR, or —N(R)$_2$;
   R$^3$ is —H;
   R$^4$ and R$^5$ are taken together with their intervening atoms to form an optionally substituted 3-20 membered heterocyclyl ring having 1-5 heteroatoms;
   R$^6$ is —C(O)R;
   each L$^s$ is independently a covalent bond, or a bivalent, optionally substituted, linear or branched group selected from a C$_{1-30}$ aliphatic group and a C$_{1-30}$ heteroaliphatic group having 1-10 heteroatoms, wherein one or more methylene units are optionally and independently replaced by an optionally substituted group selected from C$_{1-6}$ alkylene, C$_{1-6}$ alkenylene, —C≡C—, a bivalent C$_1$-C$_6$ heteroaliphatic group having 1-5 heteroatoms, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—, and one or more carbon atoms are optionally and independently replaced with Cy$^L$;
   each -Cy- is independently an optionally substituted bivalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
   each Cy$^L$ is independently an optionally substituted tetravalent group selected from a C$_{3-20}$ cycloaliphatic ring, a C$_{6-20}$ aryl ring, a 5-20 membered heteroaryl ring having 1-10 heteroatoms, and a 3-20 membered heterocyclyl ring having 1-10 heteroatoms;
   each R' is independently —R, —C(O)R, —C(O)OR, or —S(O)$_2$R;
   each R is independently —H, or an optionally substituted group selected from C$_{1-30}$ aliphatic, C$_{1-30}$ heteroaliphatic having 1-10 heteroatoms, C$_{6-30}$ aryl, C$_{6-30}$ arylaliphatic, C$_{6-30}$ arylheteroaliphatic having 1-10 heteroatoms, 5-30 membered heteroaryl having 1-10 heteroatoms, and 3-30 membered heterocyclyl having 1-10 heteroatoms, or
   two R groups are optionally and independently taken together to form a covalent bond, or:
   two or more R groups on the same atom are optionally and independently taken together with the atom to form an optionally substituted, 3-30 membered, monocyclic, bicyclic or polycyclic ring having, in addition to the atom, 0-10 heteroatoms; or
   two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms.

23. The method of claim 22, wherein R$^1$ is —H and R$^2$ is —CH$_2$—Si(R)$_3$ wherein each R of —Si(R)$_3$ is independently not —H.

24. The method of claim 23, wherein H—X-L$^s$-R$^5$ is

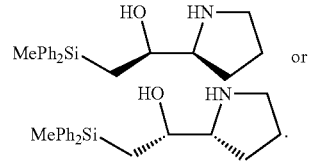

25. The method of claim 1, comprising a cycle consisting of the steps of 1) coupling; 2) capping; 3) modification; and 4) deblocking.

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 1
agcuucttgt ccagcuuuau                                              20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ucaaggaaga uggcauuucu                                              20
```